US006534631B1

(12) United States Patent
Ruben et al.

(10) Patent No.: US 6,534,631 B1

(45) Date of Patent: Mar. 18, 2003

(54) SECRETED PROTEIN HT5GJ57

(75) Inventors: Steven M. Ruben, Olney, MD (US); George Komatsoulis, Silver Spring, MD (US); Roxanne D. Duan, Bethesda, MD (US); Craig A. Rosen, Laytonsville, MD (US); Paul A. Moore, Germantown, MD (US); Yanggu Shi, Gaithersburg, MD (US); David W. LaFleur, Washington, DC (US); Reinhard Ebner, Gaithersburg, MD (US); Henrik Olsen, Gaithersburg, MD (US); Laurie A. Brewer, St. Paul, MN (US); Kimberly A. Florence, Rockville, MD (US); Paul Young, Gaithersburg, MD (US); Michael Mucenski, Cincinnati, OH (US); Gregory A. Endress, Potomac, MD (US); Daniel R. Soppet, Centreville, VA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/482,273

(22) Filed: Jan. 13, 2000

Related U.S. Application Data

(63) Continuation-in-part of application No. PCT/US99/15849, filed on Jul. 14, 1999.

(60) Provisional application No. 60/092,956, filed on Jul. 15, 1998, provisional application No. 60/092,922, filed on Jul. 15, 1998, and provisional application No. 60/092,921, filed on Jul. 15, 1998.

(51) Int. Cl.[7] ........................ C07K 1/100; C07K 14/00; C07K 17/00; A61K 38/00; C12N 15/00; C12N 15/09; C12N 5/00

(52) U.S. Cl. ..................... 530/350; 536/23.1; 536/24.1; 435/320.1; 435/325; 530/300

(58) Field of Search .............................. 435/320.1, 325; 530/350, 300, 324; 536/23.1, 24.1; 424/185.1, 192.1

(56) References Cited

U.S. PATENT DOCUMENTS

| | | | |
|---|---|---|---|
| 5,670,367 A | 9/1997 | Dorner et al. .............. | 510/224 |
| 5,849,498 A | 12/1998 | Bandman et al. .............. | 435/6 |

FOREIGN PATENT DOCUMENTS

| | | |
|---|---|---|
| WO | 00/00610 | 1/2000 |
| WO | WO00/04140 A1 | 1/2000 |
| WO | WO01/51504 A1 | 7/2001 |

OTHER PUBLICATIONS

Setni et al., Human Immunology, vol. 46, pp. 69–81, 1996.*

Geneseq Accession No. AAY11487 (Feb. 11, 1999).

"Toward a complete human genome sequence", Genome Res., 8(11):1097–2108 (Nov. 1998)—Abstract only.

Genbank Accession No. AC005081 (Jun. 12, 1998).

Auffray et al., Genbank Accession No. Z39117 (Oct. 31, 1994).

Genbank Accession No. AA807717 (Feb. 18, 1998).

Hillier et al., Genbank Accession No. N48658 (Feb. 14, 1996).

Sohn et al., Genbank Accession No. T25945 (Mar. 10, 1998).

Adams et al., Genbank Accession No. T30849 (Sep. 6, 1995).

Genbank Accession No. AA731435 (Jan. 23, 1998).

Genbank Accession No. AA810638 (Feb. 13, 1998).

Hillier et al., Genbank Accession No. AA166766 (Dec. 19, 1996).

Genbank Accession No. AA975334 (May 22, 1998).

Hillier et al., Genbank Accession No. N48728 (Feb. 14, 1996).

Genbank Accession No. AA648496 (Oct. 29, 1997).

Adams et al., Genbank Accession No. AA361096 (Apr. 21, 1997).

Genbank Accession No. AA594614 (Sep. 18, 1997).

Hillier et al., Genbank Accession No. T61448 (Feb. 13, 1995).

Hillier et al., Genbank Accession No. N34423 (Jan. 16, 1996).

Genbank Accession No. AA765412 (Feb. 19, 1998).

Hillier et al., Genbank Accession No. H23560 (Jul. 6, 1995).

Hillier et al., Genbank Accession No. AA722908 (Jan. 2, 1998).

Hillier et al., Genbank Accession No. W58075 (Oct. 15, 1996).

Hillier et al., Genbank Accession No. AA723128 (Jan. 2, 1998).

Genbank Accession No. AA633095 (Oct. 31, 1997).

Hillier et al., Genbank Accession No. W57991 (Oct. 15, 1996).

Genbank Accession No. AA604586 (Sep. 29, 1997).

Genbank Accession No. AA827120 (Mar. 5, 1998).

Genbank Accession No. AA811488 (Feb. 19, 1998).

(List continued on next page.)

*Primary Examiner*—Michael Borin
*Assistant Examiner*—Shubo (Joe) Zhou
(74) *Attorney, Agent, or Firm*—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating diseases, disorders, and/or conditions related to these novel human secreted proteins.

12 Claims, 3 Drawing Sheets

OTHER PUBLICATIONS

Figure 2:
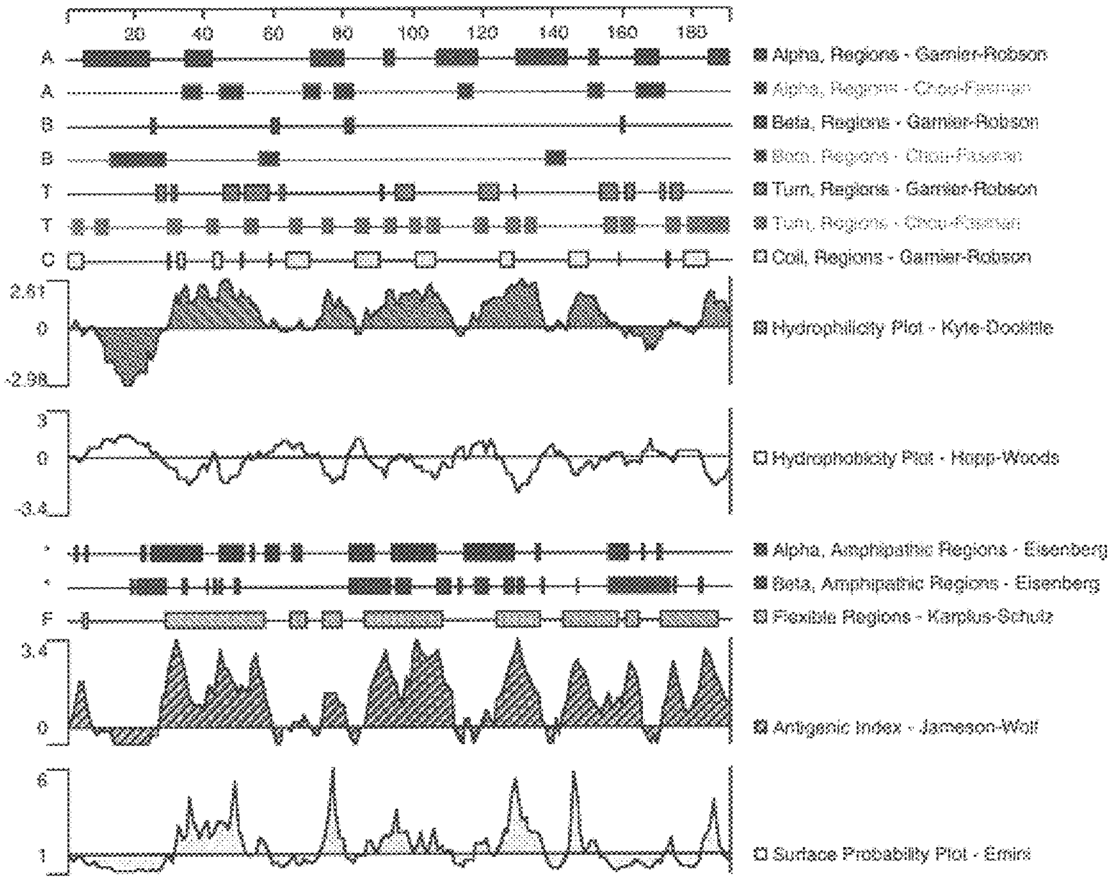

Genbank Accession No. AA593214 (Sep. 25, 1997).

GIBCO BRL, "Random Printers DNA Labeling System", GIBCO BRL Catalogue and Reference Guide, Life Technologies, Inc., Gaithersburg, MD, USA, p. 404, (1990).

Watson et al., "Methods of Creating Recombinant DNA Molecules", Recombinant DNA, Chapter 5, pp. 63–77, Scientific American Books, (1994).

Ikeda et al., "Epitope Mapping of Anti–recA Protein IgGs by Region Specified Polymerase Chain Reaction Mutagenesis", Journal of Biological Chemistry, vol. 267, No. 9, pp. 6291–6296, (1992).

Stuurman et al., "Interphase phosphorylation of the Drosophila nuclear lamin: site–mapping using a monoclonal antibody", Journal of Cell Science, 108:3137–3144, (1995).

* cited by examiner

Figure 1A

```
  1  GGTCGACGGTATCGATAAGCTTGATATCGAATTCCTGCAACAGTTCTTGGAAACCCACTC   60

 61  GAGAGGGCCACGCCTCCATTCACCAGGCCACGCATCACAAGAGGCAACACCAGGAGCCAA  120

121  CATGAGCTCGGGGACTGAACTGCTGTGGCCCGGAGCAGCGCTGCTGGTGCTGTTGGGGGT  180
  1   M  S  S  G  T  E  L  L  W  P  G  A  A  L  L  V  L  L  G  V   20

181  GGCAGCCAGTCTGTGTGTGCGCTGCTCACGCCCAGGTGCAAAGAGGTCAGAGAAAATCTA  240
 21   A  A  S  L  C  V  R  C  S  R  P  G  A  K  R  S  E  K  I  Y   40

241  CCAGCAGAGAAGTCTGCGTGAGGACCAACAGAGCTTTACGGGGTCCCGGACCTACTCCTT  300
 41   Q  Q  R  S  L  R  E  D  Q  Q  S  F  T  G  S  R  T  Y  S  L   60

301  GGTCGGGCAGGCATGGCCAGGACCCCTGGCGGACATGGCACCCACAAGGAAGGACAAGCT  360
 61   V  G  Q  A  W  P  G  P  L  A  D  M  A  P  T  R  K  D  K  L   80

361  GTTGCAATTCTACCCCAGCCTGGAGGATCCAGCATCTTCCAGGTACCAGAACTTCAGCAA  420
 81   L  Q  F  Y  P  S  L  E  D  P  A  S  S  R  Y  Q  N  F  S  K  100

421  AGGAAGCAGACACGGGTCGGAGGAAGCCTACATAGACCCCATTGCCATGGAGTATTACAA  480
101   G  S  R  H  G  S  E  E  A  Y  I  D  P  I  A  M  E  Y  Y  N  120

481  CTGGGGGCGGTTCTCGAAGCCCCCAGAAGATGATGATGCCAATTCCTACGAGAATGTGCT  540
121   W  G  R  F  S  K  P  P  E  D  D  D  A  N  S  Y  E  N  V  L  140

541  CATTTGCAAGCAGAAAACCACAGAGACAGGTGCCCAGCAGGAGGGCATAGGTGGCCTCTG  600
141   I  C  K  Q  K  T  T  E  T  G  A  Q  Q  E  G  I  G  G  L  C  160

601  CAGAGGGGACCTCAGCCTGTCACTGGCCCTGAAGACTGGCCCCACTTCTGGTCTCTGTCC  660
161   R  G  D  L  S  L  S  L  A  L  K  T  G  P  T  S  G  L  C  P  180

661  CTCTGCCTCCCCGGAAGAAGATGAAGGAATCTGAGGATTATCAGAACTTCAGCATTCCAT  720
181   S  A  S  P  E  E  D  E  G  I  *                              191

721  CCATTCAGTGGCGCGAGTCCAGGAAGGTCATGGGGCAACTCCAGAGAAGAAAGCATCCCC  780

781  TGGCCCGGTGGGAAGCCCAGACGAGGAGGACGGGGAACCGGATTACGTGAATGGGGAGGT  840

841  GGCAGCCACAGAAGCCTAGGGCAGACCAAGAAGAAAGGAGCCAAGGCAAAGAGGGACCAC  900
```

Figure 1B

```
 901  TGTGCTCATGGACCCATCGCTGCCTTCCAAGGACCATTTCCCAGAGCTACTCAACTTTTA   960
 961  AGCCCCTGCCATGGTTGCTCCTGGAAGGAGAACCAGCCACCCTGAGGACCACCTGGCCAT  1020
1021  GCGTGCACAGCCTGGGAAAAGACAGTTACTCACGGGAGCTGCAGGCCCCGTCACCAAGCC  1080
1081  CTCTCCCGACCCAGGCTTTGTGGGGCAGGCACCTGGTACCAAGGGTAACCCGGCTCCTGG  1140
1141  TATGGACGGATGCGCAGGATTTAGGATAAGCTGTCACCCAGTCCCCATAACAAAACCACT  1200
1201  GTCCAACACTGGTATCTGTGTTCTTTTGTGCTATGAATTTGGATTCCTAATTGCTATTGT  1260
1261  TGGTTGCTGGGGTTTTAAATGATTGATAAGCTTGTACAGTTAACTTATAGAGGGGGAGCC  1320
1321  ATATTTAACATTCTGGATTTCAGAGTAGAGATTTCTGTGTTGTCTCCTAGAAAGCATTAC  1380
1381  ATGTAGTTTATTTCAGCATCCTTGTTGGGTGGGGCCCTGGCTCTCTTCCCCTTTGGTGGG  1440
1441  ACCTCCCCTTTCTTTGGGCTTCAGTTCACTCAGGAAGAAATGAGGCTGTCGCCATCTTTA  1500
1501  TGTGCTTCCAGTGGAAATGTCACTTGCTACAGACAATAGTGCATGAGAGTCTAGAGAAGT  1560
1561  AGTGACCAGAACAGGGCAGAGTAGGTCCCCTCCATGGCCCTGAATCCTCCTCTGCTCCAG  1620
1621  GGCTGGCCTCTGCAGAGCTGATTAAACAGTGTTGTGACTGTCTCATGGGAAGAGCTGGGG  1680
1681  CCCAGAGGGACCTTGAGTCAGAAATGTTGCCAGAAAAAGTATCTCCTCCAACCAAAACAT  1740
1741  CTCAATAAAACCATTTTAGTTGAAAAAAAAAAAAAAAAAAAAAAAAAAAAAAAAAAAA  1797
```

SECRETED PROTEIN HT5GJ57

This application is a continuation-in-part of, and claims benefit under 35 U.S.C. §120 of copending U.S. patent application Ser. No: PCT/US99/15849 filed Jul. 14, 1999, which is hereby incorporated by reference, which claims benefit under 35 U.S.C. §119(e) based on U.S. Provisional Applications:

| Appln Serial No. | Filing Date |
|---|---|
| 60/092,921 | 15 Jul. 1998 |
| 60/092,922 | 15 Jul. 1998 |
| 60/092,956 | 15 Jul. 1998 |

FIELD OF THE INVENTION

This invention relates to newly identified polynucleotides and the polypeptides encoded by these polynucleotides, uses of such polynucleotides and polypeptides, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical diseases, disorders, and/or conditions by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant and synthetic methods for producing the polypeptides and polynucleotides. Also provided are diagnostic methods for detecting diseases, disorders, and/or conditions related to the polypeptides and polynucleotides, and therapeutic methods for treating such diseases, disorders, and/or conditions. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42 degree C. in a solution comprising 50% formamide, 5×SSC (750 mM NaCI, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50 degree C with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched , for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann Ny Acad Sci 663:48–62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention

Features of Protein Encoded by Gene No: 1

This gene is expressed primarily in pancreas islet cell tumors.

In another embodiment, polypeptides comprising the amino acid sequence of the open reading frame upstream of the predicted signal peptide are contemplated by the present invention. Specifically, polypeptides of the invention comprise the following amino acid sequence: PFCSGFFPSL WIYLPFIFNVSDLWMGSLSGCALPFCLXVFFLTVS PSAVGLLXFAGGPLQTLFAWVSPVEAAEQQRLLPV LSSGSFVSEGTCQMPARALLYEVSVGAYWEI PPSQDTRRSGTYLRRQSDP (SEQ ID NO: 195). Polynucleotides encoding these polypeptides are also provided.

Therefore, polynucleotides and polypeptides of the invention are useful as reagents for differential identification of the tissue(s) or cell type(s) present in a biological sample and for diagnosis of diseases and conditions which include, but are not limited to, disorders of the pancreas, including cancer and diabetes. Similarly, polypeptides and antibodies directed to these polypeptides are useful in providing immunological probes for differential identification of the tissue(s) or cell type(s). For a number of disorders of the above tissues or cells, particularly of the pancreas, expression of this gene at significantly higher or lower levels may be routinely detected in certain tissues or cell types (e.g., endocrine, cancerous, or wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in tumors of pancreatic islet cells indicates that polynucleotides and polypeptides corresponding to this gene are useful for diagnosis, treatment and intervention of such tumors, in addition to other endocrine or gastrointestinal tumors where expression has been indicated. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1099 of SEQ ID NO:11, b is an integer of 15 to 1113, where both a and b correspond to the positions of nucleotide residues shown in SEQ ID NO:11, and where b is greater than or equal to a+14.

Features of Protein Encoded by Gene No: 2

This gene is expressed equally in hemangiopericytoma cells, breast lymph node tissue, and bone marrow.

In another embodiment, polypeptides comprising the amino acid sequence of the open reading frame upstream of the predicted signal peptide are contemplated by the present invention. Specifically, polypeptides of the invention comprise the following amino acid sequence: HEGSCRAPGF SAHKGRGCPSPRMTLPSRALASLGVGVWGMLRLN QVTVSCGGSRWSSRVALGAFSWVCGVALVLQP SGGGLGLTSPSEGCWEGELALAVLRAPGGSPS (SEQ ID NO: 196). Polynucleotides encoding these polypeptides are also provided.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic disorders, particularly leukemia. Similarly, polypeptides and antibodies directed to these polypeptides are useful in providing immunological probes for differential identification of the tissue(s) or cell type(s). For a number of disorders of the above tissues or cells, particularly of the vascular and immune systems, expression of this gene at significantly higher or lower levels may be routinely detected in certain tissues or cell types (e.g., immune, hemolymphoid, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 104 as residues: Gly-29 to Ser-35, Ser-63 to Cys-68. Polynucleotides encoding said polypeptides are also provided.

The tissue distribution in hemangiopericytoma, breast lymph node, and bone marrow indicates that polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the "Immune Activity" and "Infectious Disease" sections below, in Example 11, 13, 14, 16, 18, 19, 20, and 27, and elsewhere herein. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 969 of SEQ ID NO:12, b is an integer of 15 to 983, where both a and b correspond to the positions of nucleotide residues shown in SEQ ID NO:12, and where b is greater than or equal to a+14.

Features of Protein Encoded by Gene No: 3

The protein product of this gene shares homology with Drosophila, mouse, and human Slit proteins (See Genbank Accession Numbers (protein) AAD25539 and AAD38940; all references available through this accession are hereby incorporated herein by reference; for example Rothberg et al., Genes Dev. 4:2169–87 (1990), Brose K., et al., Cell 1999 Mar. 19;96(6):795–806, and Liang Y., et al., J. Biol. Chem. 1999 Jun 18;274(25):17885–92). Slit gene products are secreted proteins that contain both EGF domain and Leucine Rich Repeat domains; and function as ligands for cell-surface receptors. In Drosophilia, Slits are important in the development of midline glia and commissural axon pathways. In vertebrates, Slit family proteins have been shown to function as ligands of receptors in nervous system tissue. Slit proteins are thought to be critical for certain stages of central nervous system histogenesis and to have evolutionarily conserved roles in axon guidance (Brose K., et al., Cell 1999 Mar 19;96(6):795–806 and Liang Y., et al., J. Biol. Chem. 1999 Jun 18;274(25):17885–92). Based on the sequence similarity, the translation product of this gene is expected to share at least some biological activities with Slit proteins. Such activities are known in the art, some of which are described elsewhere herein.

This gene is expressed primarily in human hippocampus.

Therefore, polynucleotides and polypeptides of the invention are useful as reagents for differential identification of the tissue(s) or cell type(s) present in a biological sample and for diagnosis of diseases and conditions which include, but are not limited to, neurological, and developmental disorders. Similarly, polypeptides and antibodies directed to these polypeptides are useful in providing immunological probes for differential identification of the tissue(s) or cell type(s). For a number of disorders of the above tissues or cells, particularly of the neurological system, expression of this gene at significantly higher or lower levels may be routinely detected in certain tissues or cell types (e.g., neurological, cancerous, or wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution within human hippocampus combined with the homology to the Drosophila slit protein, indicates that polynucleotides and polypeptides corresponding to this gene are useful for the detection, treatment and/or prevention of neurodegenerative disease states, behavioral disorders, or inflammatory conditions. Representative uses are described in the "Regeneration" and "Hyperproliferative Disorders" sections below, in Example 11, 15, and 18, and eglsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, panic disorder, learning disabilities, ALS, psychoses, autism, and altered behaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 959 of SEQ ID NO:13, b is an integer of 15 to 973, where both a and b correspond to the positions of nucleotide residues shown in SEQ ID NO:13, and where b is greater than or equal to a+14.

Features of Protein Encoded by Gene No: 4

In another embodiment, polypeptides comprising the amino acid sequence of the open reading frame upstream of the predicted signal peptide are contemplated by the present invention. Specifically, polypeptides of the invention comprise the following amino acid sequence: IPLTLPGIFL LIRLFWRLGQSICGPGKLVLWPQFCCGCAVISG HCVPRGMPSSW LPGCFVLLCLVAVGCQLREWGVG GVSAVGLLALPHLQVLGMRGRGLISGG (SEQ ID NO: 197). Polynucleotides encoding these polypeptides are also provided.

The gene encoding the disclosed cDNA is believed to reside on chromosome 16. Accordingly, polynucleotides related to this invention are useful as a marker in linkage analysis for chromosome 16.

This gene is expressed in KMH2 cells, osteoblasts, fetal spleen, Jurkat membrane bound polysomes, breast, and cerebellum.

Therefore, polynucleotides and polypeptides of the invention are useful as reagents for differential identification of the tissue(s) or cell type(s) present in a biological sample and for diagnosis of diseases and conditions which include, but are not limited to, cancer, immune, and skeletal disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, skeletal, cancerous, or wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in KMH2 cells, osteoblasts, and fetal spleen indicates that polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Expression of this gene product in fetal spleen and T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1444 of SEQ ID NO:14, b is an integer of 15 to 1458, where both a and b correspond to the positions of nucleotide residues shown in SEQ ID NO:14, and where b is greater than or equal to a+14.

Features of Protein Encoded by Gene No: 5

The translation product of this gene shares sequence homology with phospholipase A2 which cleaves fatty acids from carbon 2 of glycerol (ref. Prosite pattern documentation for PS2—HIS). Many snake venoms contain phospolipase A2, which prevents transmission of nerve impulses to muscles by blocking the release of acetylcholine from the neuron. Therefore, included in this invention as preferred domains are Phospholipase A2 histidine active site domains, which were identified using the ProSite analysis tool (Swiss Institute of Bioinformatics). Phospholipase A2 is an enzyme which releases fatty acids from the second carbon group of glycerol. Structurally, PA2's are small and rigid proteins of 120 amino-acid residues that have four to seven disulfide bonds. PA2 binds a calcium ion which is required for activity. The side chains of two conserved residues, a histidine and an aspartic acid, participate in a 'catalytic network'. Two different signature patterns for PA2's were developed. The first is centered on the active site histidine and contains three cysteines involved in disulfide bonds. The consensus pattern is as follows: C-C-x(2)-H-x(2)-C [H is the active site residue].

Preferred polypeptides of the invention comprise a Phospholipase A2 histidine active site domain selected from the following amino acid sequences: CCNQHDRC (SEQ ID NO: 199), SLTKCCNQHDRCYET (SEQ ID NO: 200), and/or LTKCCNQHDRCYETCG (SEQ ID NO: 201). Polynucleotides encoding these polypeptides are also provided. Further preferred are polypeptides comprising the Phospholipase A2 histidine active site domain of the sequence listed in Table 1 for this gene, and at least 5, 10, 15, 20, 25, 30, 50, or 75 additional contiguous amino acid residues of this referenced sequence. The additional contiguous amino acid residues may be N-terminal or C-terminal to the Phospholipase A2 histidine active site domain. Alternatively, the additional contiguous amino acid residues may be both N-terminal and C-terminal to the Phospholipase A2 histidine active site domain, wherein the total N- and C-terrminal contiguous amino acid residues equal the specified number. The above preferred polypeptide domain is characteristic of a signature specific to Phospholipase A2 proteins. Based on the sequence similarity, the translation product of this gene is expected to share at least some biological activities with Phospholipase A2 proteins. Such activities are known in the art, some of which are described elsewhere herein, or see, for example, McIntosh, et al. J. Biol. Chem. 270 (8), 3518–3526 (1995), incorporated herein by reference.

In another embodiment, polypeptides comprising the amino acid sequence of the open reading frame upstream of the predicted signal peptide are contemplated by the present invention. Specifically, polypeptides of the invention comprise the following amino acid sequence: GPAGKEAWI WSWLLPSPGPAPLPSASWGLCGDAPRAAARGPVEP GAARMALLSRPALTLLLLLMAAVVRCQEQAQTTD WRATLKTIRNGVHKIDTYLNAALDLLGGEDGLC QYKCSDGSKPFPRYGYKPSPPNGCGSPLFGXHLNI GIPSLTKCCNQHDRCYETCGKSKNDCDEEFQYCLS KICRDVQKTLGLTQHVQACETTVELLFDSVIHLGCK PYLDSQRAAC RCHYEEKTDL (SEQ ID NO: 198). Polynucleotides encoding these polypeptides are also provided.

The gene encoding the disclosed cDNA is believed to reside on chromosome 4. Accordingly, polynucleotides related to this invention are useful as a marker in linkage analysis for chromosome 4.

This gene is expressed in a diverse variety of cell types.

Therefore, polynucleotides and polypeptides of the invention are useful as reagents for differential identification of the tissue(s) or cell type(s) present in a biological sample and for diagnosis of diseases and conditions which include, but are not limited to, neurological disorders, or metabolism disorders, specifically phospholipase A2 deficiencies. Similarly, polypeptides and antibodies directed to these polypeptides are useful in providing immunological probes for differential identification of the tissue(s) or cell type(s). For a number of disorders of the above tissues or cells, particularly of the neuromuscular system, expression of this gene at significantly higher or lower levels may be routinely detected in certain tissues or cell types (e.g., pancreas, cancerous and wounded tissues) or bodily fluids (e.g., bile, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 107 as residues: Gln-23 to Asp-30, Lys-66 to Cys-87. Polynucleotides encoding said polypeptides are also provided.

The ubiquitous tissue distribution and homology to phospholipase A2 indicates that polynucleotides and polypeptides corresponding to this gene are useful for diagnosis and treatment of neuromuscular disorders. Alternatively, considering the activity of phospholipase A2 as a block for neuro-transmission may suggest that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Alternatively, the homology to Phospholipase A2 proteins may indicate a potential use for the protein product of this gene in diagnosis, treatment and/or prevention of metabolism disorders, specifically deficiencies in Phospholipase A2. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO: 15 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1991 of SEQ ID NO:15, b is an integer of 15 to 2005, where both a and b correspond to the positions of nucleotide residues shown in SEQ ID NO:15, and where b is greater than or equal to a +14.

Features of Protein Encoded by Gene No 6

In a specific embodiment polypeptides of the invention comprise the following amino acid sequence: GTSSAR PRGALPGGSAPSAPHGQLPGRAQPAPVSGPPPTS GLCHFDPAAPWPLWPGPWQLPPHPQDWPAHPDI PQDWVSFLRSFGQLTLCPRNGTVTGKWRGSHVVGL LTTLNFGDGPDRNKTRTFQATVLGSQMGLKGSS AGQLVLITARVTTERTAGTCLYFSAVPGILPSSQP PISC SEEGAGNATLSPRMGEECVSVWSHEGLVLTKLLTSE ELALCGSRLLVLGSFLLLFCGLLCCVTAMCFHPRR ESHWSRTRL (SEQ ID NO: 202). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: ARAPPGPEGL SPEAQPPLLPMGNCQAGHNLHLCLAHHPPLVCAT LILLLLGLSGLGLGSFLLTHRTGLRTLTSPRTGSLF (SEQ ID NO: 203). Polynucleotides encoding these polypeptides are also provided.

This gene is expressed in a wide variety of tissue types including testes, cerebellum, dendritic cells, breast cancer, umbilical vein endothelial cells, epididymus, corpus colosum, chronic synovitis, liver hepatome, normal breast, osteoblasts, melanocytes, B cell lymphomas, and to a lesser extent in other tissues.

Therefore, polynucleotides and polypeptides of the invention are useful as reagents for differential identification of the tissue(s) or cell type(s) present in a biological sample and for diagnosis of diseases and conditions which include, but are not limited to, cancer, particularly of endothelial tissues. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., endothelial, cancerous, or wounded tissues) or bodily fluids (e.g., lymph, seminal fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 108 as residues: Thr-52 to Gly-57. Polynucleotides encoding said polypeptides are also provided.

Expression within embryonic tissue and other cellular sources marked by proliferating cells indicates that the protein product of this gene may play a role in the regulation of cellular division and may show utility in the diagnosis, treatment, and/or prevention of developmental diseases and disorders, cancer, and other proliferative conditions. Representative uses are described in the "Hyperproliferative Disorders" and "Regeneration" sections below and elsewhere herein. Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also relies on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 929 of SEQ ID NO:16, b is an integer of 15 to 943, where both a and b correspond to the positions of nucleotide residues shown in SEQ ID NO:16, and where b is greater than or equal to a +14.

Features of Protein Encoded by Gene No: 7

In another embodiment, polypeptides comprising the amino acid sequence of the open reading frame upstream of the predicted signal peptide are contemplated by the present invention. Specifically, polypeptides of the invention comprise the following amino acid sequence: RFLSVXPQX EVPFLLHPCVCFXGGHPSLLPDPCRAVGGGWEAPR CCLHEALCQSLGCKAEEIVSVSESSSAQRCWYLLR GRKAGGRGPASPVLFALMRLESLCHLCLACLFFRL PATRTVYCMNEAEIVDVALGILIESRKQXKACE QPALAGADNPEHSPPCSVSPHTSSGSSSEEEDS GKQALXPGLSPSQRPGGSSSACSRSPEEEEEEDV LKYVREIFFS (SEQ ID NO: 204). Polynucleotides encoding these polypeptides are also provided. Polynucleotides of the invention do not consist of the nucleic acid sequences shown as GeneSeq Accession Nos: V59595 and V59744, which are hereby incorporated herein by reference.

This gene is expressed primarily in a variety of immune cell types, including stromal cells, dendritic cells, leukocytes, activated T-cells, macrophages, monoctyes, neutrophils and to a lesser extent in a variety of other adult and fetal tissues.

Therefore, polynucleotides and polypeptides of the invention are useful as reagents for differential identification of the tissue(s) or cell type(s) present in a biological sample and for diagnosis of diseases and conditions which include, but are not limited to, cancer and other proliferative disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous, or wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in immune cells indicates that polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Expression of this gene product in fetal tissue and various hematopoietic cancers indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues.

Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence is umbersome. Accordingly, preferably excluded from the present invention are one or more polynucleotides comprising a nucleotide sequence described by the general formula of a–b, where a is any integer between 1 to 1489 of SEQ ID NO:17, b is an integer of 15 to 1503, where both a and b correspond to the positions of nucleotide residues shown in SEQ ID NO:17, and where b is greater than or equal to a+14.

Features of Protein Encoded by Gene No: 8

When tested against Jurkat T-cell lines. supernatants removed from cells containing this gene activated the NF-kB (Nuclear Factor kB) pathway. Thus, it is likely that this gene activates T-cells through the NF-kB signal transduction pathway. NF-kB is a transcription factor activated by a wide variety of agents, leading to cell activation, differentiation, or apoptosis. Reporter constructs utilizing the NF-kB promoter element are used to screen supernatants for such activity. In a specific embodiment polypeptides of the invention comprise the following amino acid sequence: VPGWPRACSPCQADSPRAHPPKLRGILRWAPVPLX CAALCPPLDSGMSMAACPEAPEPSFLREVPSS PASTQWHRPCNFRQVEANPRKEPKNLVWRDVS LGQXSRTPRGSGLELVRVCGGGMQRDKTVVEE RVGEERERERERESLGGAGKHGEMRCVYVRESV GAPGRAGGGGNGVNSVGCVRTVHSGSXPPPSAGVS (SEQ ID NO: 205). Also preferred are the polynucleotides encoding these polypeptides.

This gene is expressed primarily in parts of the brain such as cerebellum and frontal lobe.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, cancerous, or wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in cerebellum and frontal lobe indicates that polynucleotides and polypeptides corresponding to this gene are useful for the detection, prevention and/or treatment of neurodegenerative disease states and behavioural disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1498 of SEQ ID NO:18, b is an integer of 15 to 1512, where both a and b correspond to the positions of nucleotide residues shown in SEQ ID NO:18, and where b is greater than or equal to a +14.

Features of Protein Encoded by Gene No: 9

In a specific embodiment, polypeptides comprising the amino acid sequence of the open reading frame upstream of the predicted signal peptide are contemplated by the present invention. Specifically, polypeptides of the invention comprise the following amino acid sequence: TRPGKELNLVF GLQLSMARIGSTVNMNLMGWLYSKIEALLGSAGHT TLGITLMIGGITCILSLICALALAYLDQRAERIL HKEQGKTGEVIKLTDVKDFSLPLWLIFIICVCYY VAVFPFIGLGKVFFTEKFGFSSQAASAINSV VYVISAPMSPVFGLLVDKTGKNIIWVLCA (SEQ ID NO: 206). Polynucleotides encoding these polypeptides are also provided.

The gene encoding the disclosed cDNA is believed to reside on chromosome 3. Accordingly, polynucleotides related to this invention are useful as a marker in linkage analysis for chromosome 3.

This gene is expressed primarily in fetal tissue, and to a lesser extent in a variety of adult human tissues.

Therefore, polynucleotides and polypeptides of the invention are useful as reagents for differential identification of the tissue(s) or cell type(s) present in a biological sample and for diagnosis of diseases and conditions which include, but are not limited to, fetal abnormalities, particularly developmental disorders. Similarly, polypeptides and antibodies directed to these polypeptides are useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., developing, or cancerous and wounded tissues) or bodily fluids (e.g., amniotic fluid, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 111 as residues: Lys-30 to Thr-35. Polynucleotides encoding said polypeptides are also provided.

The tissue distribution in fetal tissue indicates that polynucleotides and polypeptides corresponding to this gene are useful for the diagnosis and treatment of cancer and other proliferative disorders. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Expression within embryonic tissue and other cellular sources marked by proliferating cells indicates that this protein may play a role in the regulation of cellular division. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between I to 1641 of SEQ ID NO: 19, b is an integer of 15 to 1655, where both a and b correspond to the positions of nucleotide residues shown in SEQ ID NO:19, and where b is greater than or equal to a+14.

Features of Protein Encoded by Gene No: 10

The translation product of this gene shares sequence homology with human histiocyte-secreted factor (HSF) which is a novel cytokine that shows in vivo antitumour activity without the cytotoxicity associated with tumour necrosis factor. Furthermore, the translation product of this gene also shares sequence homology with the human endogenous virus S71 gag polyprotein, the sequence of which is believed to represent a transformation locus for several cancers (See Genbank Accession No. pirlA46312lA46312; all references available through this accession are hereby incorporated by reference herein). Similarly, the translation product of this gene also shares homology with B219, a sequence that is expressed in at least four isoforms in very primitive hematopoietic cell populations which may represent a novel hemopoietin receptor (See, e.g., Cioffi, et al. Nat. Med. 2:585–589 (1996), which is hereby incorporated by reference herein). In a preferred embodiment polypeptides of the invention comprise the following amino acid sequence: CKDLCSRVYLLTLSPLLSYDPATSHSPRNTQ (SEQ ID NO: 207). Also preferred are the polynucleotides encoding these polypeptides.

This gene is expressed primarily in tonsil, and colon, and to a lesser extent in a wide variety of human tissues.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, and gastrointestinal disorders, particularly tumors of the colon and tonsil. Similarly, polypeptides and antibodies directed to these polypeptides are useful in providing immunological probes for differential identification of the tissue(s) or cell type(s). For a number of disorders of the above tissues or cells, particularly of the hematopoietic, digestive and immune systems, expression of this gene at significantly higher or lower levels may be routinely detected in certain tissues or cell types (e.g., immune, hematopoietic, gastrointestinal, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 112 as residues: Met-1 to Cys-6. Polynucleotides encoding said polypeptides are also provided.

The tissue distribution in tonsil and colon, combined with the homology to human histiocyte growth factor, the human endogenous viral protein, and B219 strongly indicate that polynucleotides and polypeptides corresponding to this gene are useful for the diagnosis, treatment and/or prevention, of a variety of hematopoietic and immune system disorders such as anemia, pancytopenia, leukopenia, thrombocytopenia or leukemia. Representative uses are described in the "Immune Activity" and "Infectious Disease" sections below, in Example 11, 13, 14, 16, 18, 19, 20, and 27, and elsewhere herein.

Expression of this gene product in tonsils indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues.

Moreover, the protein may represent a secreted factor that influences the differentiation or behavior of other blood cells, or that recruits hematopoietic cells to sites of injury. In addition, this gene product may have commercial utility in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2511 of SEQ ID NO:20, b is an integer of 15 to 2525, where both a and b correspond to the positions of nucleotide residues shown in SEQ ID NO:20, and where b is greater than or equal to a+14.

Features of Protein Encoded by Gene No: 11

The gene encoding the disclosed cDNA is believed to reside on chromosome 7. Accordingly, polynucleotides related to this invention are useful as a marker in linkage analysis for chromosome 7.

In another embodiment, polypeptides comprising the amino acid sequence of the open reading frame upstream of the predicted signal peptide are contemplated by the present invention. Specifically, polypeptides of the invention comprise the following amino acid sequence: IICECWEEEC QSCRLKITQPREICRMDFLVLFLFYLASVLMGLVLI CVCSKTHSLKGLARGGAQIFSCIIPECLQRAXHGLL HYLFHTRNHTFIVLHLVLQGMVYTEYTWEVFGYC QELELSLHYLLLPYLLLGVNLFFFTLTCGTNPGIIT KANELLFLHVYEFDEVMFPKNVRCSTCDLRKPAR SKHCSVCNWCVHRFDHHCVWVNNCIGAWNIRY FLIYVLTLTASAATVAIVSTTFLVHLVVMSDLYQETY IDDLGHLHVMDTVFLIQYLFLTFPRIVFMLGFVVV LSFLLGGYLLFVLYLAATNQTTNEWYRGDWAWC QRCPLVAWPPSAEPQVHRNIHSHGLRSNLQEIFLP AFPCHERKKQE (SEQ ID NO: 208). Polynucleotides encoding these polypeptides are also provided.

This gene is expressed primarily in colon and brain and to some extent in all tissues.

Therefore, polynucleotides and polypeptides of the invention are useful as reagents for differential identification of the tissue(s) or cell type(s) present in a biological sample and for diagnosis of diseases and conditions which include, but are not limited to, neurological and digestive disorders. Similarly, polypeptides and antibodies directed to these polypeptides are useful in providing immunological probes for differential identification of the tissue(s) or cell type(s). For a number of disorders of the above tissues or cells, particularly of the central nervous system and digestive system, expression of this gene at significantly higher or lower levels may be routinely detected in certain tissues or cell types (e.g., neurological, gastrointestinal, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Alternatively, expression of this gene in colon may indicate a role in the detection, prevention and/or treatment of colon disorders such as colon cancer, Crohn's disease, ulcers, and digestive tract disorders in general. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are elated to SEQ ID NO:21 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1382 of SEQ ID NO:21, b is an integer of 15 to 1396, where both a and b correspond to the positions of nucleotide residues shown in SEQ ID NO:21, and where b is greater than or equal to a+14.

Features of Protein Encoded by Gene No: 12

When tested against Reh cell lines, supernatants removed from cells containing this gene activated the GAS (gamma activation site) pathway. Thus, it is likely that this gene activates B-cells through the Jak-STAT signal transduction pathway. GAS is a promoter element found upstream in many genes which are involved in the Jak-STAT pathway. The Jak-STAT pathway is a large, signal transduction pathway involved in the differentiation and proliferation of cells. Therefore, activation of the Jak-STATs pathway, reflected by the binding of the GAS element, can be used to indicate proteins involved in the proliferation and differentiation of cells.

This gene maps to chromosome 7, and therefore, may be used as a marker in linkage analysis for chromosome 7.

This gene is expressed primarily in brain, and in the developing embryo.

Therefore, polynucleotides and polypeptides of the invention are useful as reagents for differential identification of the tissue(s) or cell type(s) present in a biological sample and for diagnosis of diseases and conditions which include, but are not limited to, neurological, behavioral, immune, and developmental disorders. Similarly, polypeptides and antibodies directed to these polypeptides are useful in providing immunological probes for differential identification of the tissue(s) or cell type(s). For a number of disorders of the above tissues or cells, particularly of the nervous and developmental systems, expression of this gene at significantly higher or lower levels may be routinely detected in certain tissues or cell types (e.g., neural, developing, immune, or cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 114 as residues: Lys-60 to Asn-67. Polynucleotides encoding said polypeptides are also provided.

The tissue distribution in brain indicates that polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, the tissue distribution in developing embryo indicates that the gene or gene product may also play a role in the treatment and/or detection of developmental disorders associated with the developing embryo, sexually-linked disorders, or disorders of the cardiovascular system. Alternatively, the biological activity within B-cells indicates that polynucleotides and polypeptides corresponding to this gene are useful for the diagnosis and treatment of a variety of immune system disorders. Activation of genes within B-cells indicates a role for this protein in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions.

Therefore it may be also used as an agent for immunological disorders including arthritis, asthma, immune deficiency diseases such as AIDS, leukemia, rheumatoid arthritis, inflammatory bowel disease, sepsis, acne, and psoriasis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1055 of SEQ ID NO:22, b is an integer of 15 to 1069, where both a and b correspond to the positions of nucleotide residues shown in SEQ ID NO:22, and where b is greater than or equal to a+14.

Features of Protein Encoded by Gene No: 13

This gene maps to chromosome 6, and therefore, may be used as a marker in linkage analysis for chromosome 6.

In another embodiment, polypeptides comprising the amino acid sequence of the open reading frame upstream of the predicted signal peptide are contemplated by the present invention. Specifically, polypeptides of the invention comprise the following amino acid sequence: LLSFKIRGLRT EDAGWAQSSSGGLCVRGDAFWMPSSSSGLGSPSR PPSSFLCLLLLLLPPAALALLLFFLDFFPPRAAVSP FLPDHCSARQPRVWRRETLNRSASGLGCWARSTEQ GAVGVATGTVLDI SLPASCLSLWPPGPSGGI (SEQ ID NO: 209). Polynucleotides encoding these polypeptides are also provided.

In a specific embodiment polypeptides of the invention comprise the following amino acid sequence: QLGLCLT SASLPPASRCGHQAPLGASDLSAHHSAPGFSDSYF TMSCQSSLSRA EILQCPLVPSVSPPTHLPQGRANKSS RASLPLLPQTHWCLFPSARGWRRGIQSGLPPGGSC TSPRSPPQTLHQHITLVNHNTSYWQSPST (SEQ ID NO: 210), HQPPCLLPLAVATRPLWGHLTCLPIILHLV SVTLTSPCLANQAFQGQRSYNALWCPLFLLLPTSP KGEQTNHPEPACPCFPKLTGVFSLQHVVGAEEFSQV FLLVDPVPVLDHLLKLFTSTSHLLIIIPHIGKAPAPD SLL EELSLSLATHCKVAVARFT (SEQ ID NO: 211). Also preferred are the polynucleotides encoding these polypeptides.

Polynucleotides of the invention do not consist of the nucleic acid sequence shown as GeneSeq Accession No. X04377, which is hereby incorporated herein by reference.

This gene is expressed primarily in brain.

Therefore, polynucleotides and polypeptides of the invention are useful as reagents for differential identification of the tissue(s) or cell type(s) present in a biological sample and for diagnosis of diseases and conditions which include, but are not limited to, behavioral and neurological disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 115 as residues: Pro-2 to Gly-7, Ser-10 to Ser-16, Pro-52 to Val-62, Arg-64 to Ser-73. Polynucleotides encoding said polypeptides are also provided.

The tissue distribution in brain indicates that polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1644 of SEQ ID NO:23, b is an integer of 15 to 1658, where both a and b correspond to the positions of nucleotide residues shown in SEQ ID NO:23, and where b is greater than or equal to a+14.

Features of Protein Encoded by Gene No: 14

The translation product of this gene was shown to have homology to the lysosomal mannosidase alpha-B protein (See Genebank Accession No. P34098) which is thought to be important in protein metabolism. One embodiment of this gene comprises polypeptides of the following amino acid sequence: MAAEGSRFSSQSPGLVDRQGPKCDPSR LVSPWGRHGLRILQIGHHHGRDGQHEATHHLLRVL RAPRVGKADEGAVDSDPSTPLQLKHEAAHAEDH AQQVHVVRRRVVQGRVTFARRGLVPQHFVRPPWV RHIVSGHSESKARSRLFRCRNRSFRR AS (SEQ ID NO: 212), and/or RLVSPWGRHGLRILQIGHHHGRDGQH EATHHLLRVLRA (SEQ ID NO: 213). An additional embodiment is the polynucleotides encoding these polypeptides.

This gene maps to chromosome 19, and therefore, may be used as a marker in linkage analysis for chromosome 19.

This gene is expressed primarily in brain, placenta, fetal liver, and to a lesser extent in most tissues.

Therefore, polynucleotides and polypeptides of the invention are useful as reagents for differential identification of the tissue(s) or cell type(s) present in a biological sample and for diagnosis of diseases and conditions which include, but are not limited to, neurological, reproductive, and hepatic disorders. Similarly, polypeptides and antibodies directed to these polypeptides are useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., neural, hepatic, or cancerous and wounded tissues) or bodily fluids (e.g., bile, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 116 as residues: Asn-34 to Lys-42, Leu-60 to Trp-70. Polynucleotides encoding said polypeptides are also provided.

The tissue distribution predominantly in brain indicates a role in the detection/treatment of neurodegenerative disease states and behavioural disorders such as Alzheimer's Disease, Parkinson's Disease, Huntington's Disease, schizophrenia, mania, dementia, paranoia, obsessive compulsive disorder and panic disorder. Alternatively, the tissue distribution in liver indicates that polynucleotides and polypeptides corresponding to this gene are useful for the detection and treatment of liver disorders and cancers (e.g., hepatoblastoma, jaundice, hepatitis, liver metabolic diseases and conditions that are attributable to the differentiation of hepatocyte progenitor cells). In addition the expression in fetus would suggest a useful role for the protein product in developmental abnormalities, fetal deficiencies, pre-natal disorders and various would-healing models and/or tissue trauma.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1063 of SEQ ID NO:24, b is an integer of 15 to 1077, where both a and b correspond to the positions of nucleotide residues shown in SEQ ID NO:24, and where b is greater than or equal to a+14.

Features of Protein Encoded by Gene No: 15

This gene is expressed primarily in spinal cord, Merkel cells, and adipose tissues.

Therefore, polynucleotides and polypeptides of the invention are useful as reagents for differential identification of the tissue(s) or cell type(s) present in a biological sample and for diagnosis of diseases and conditions which include, but are not limited to, disorders of the nervous and immune systems, particularly those disorders relating to the CNS involving lipid metabolism disorders. Similarly, polypeptides and antibodies directed to these polypeptides are useful in providing immunological probes for differential identification of the tissue(s) or cell type(s). For a number of disorders of the above tissues or cells, particularly of the nervous and immune systems and adipose tissue, expression of this gene at significantly higher or lower levels may be routinely detected in certain tissues or cell types (e.g., neural, immune, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in spinal cord, Merkel cells and adipose tissue indicates that polynucleotides and polypeptides corresponding to this gene are useful for the treatment and/or diagnosis of diseases the nervous systems, such as spinal cord injury, neurodegenerative diseases, muscular dystrophy or obesity. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1191 of SEQ ID NO:25, b is an integer of 15 to 1205, where both a and b correspond to the positions of pucleotide residues shown in SEQ ID NO:25, and where b is greater than or equal to a+14.

Features of Protein Encoded by Gene No: 16

The translation product of this gene shares sequence homology with the human uncoupling protein-2 which is thought to be important in energy metabolism, obesity, and the predisposition of hyperinsulinemia (See Genbank Accession No. gil1857278). Recently, another group published on this gene, designating it brain mitochondrial carrier protein-1 (BCMP1) (J Biol Chem 1998 Dec 18;273(51):34611-5). One embodiment of this gene comprises polypeptides of the following amino acid sequence: PTDVLKIRMQAQ (SEQ ID NO: 214), and/or TYEQLKR (SEQ ID NO: 215). An additional embodiment is the polynucleotides encoding these polypeptides.

This gene maps to the X chromosome, and therefore, may be used as a marker in linkage analysis for the X chromosome.

This gene is expressed primarily in manic depression brain tissue, epileptic frontal cortex, human erythroleukemia cell line, T-helper cells, and to a lesser extent in endothelial and amygdala cells.

Therefore, polynucleotides and polypeptides of the invention are useful as reagents for differential identification of the tissue(s) or cell type(s) present in a biological sample and for diagnosis of diseases and conditions which include, but are not limited to, disorders of the central nervous system or hematopoietic/immune disorders. Similarly, polypeptides and antibodies directed to these polypeptides are useful in providing immunological probes for differential identification of the tissue(s) or cell type(s). For a number of disorders of the above tissues or cells, particularly of the central nervous system or hematopoietic/immune systems, expression of this gene at significantly higher or lower levels may be routinely detected in certain tissues or cell types (e.g., neural, hemolymphoid, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 118 as residues: Ser-34 to Thr-39, Gln-198 to Leu-205. Polynucleotides encoding said polypeptides are also provided.

The tissue distribution in neural tissues combined with the homology to the human uncoupling protein indicates that polynucleotides and polypeptides corresponding to this gene are useful for the detection and/or treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and preception. In addition, the gene or gene product may also play a role in the treatment and/or detection of developmental disorders associated with the developing embryo, sexually-linked disorders, or disorders of the cardiovascular system. Protein, as well as, antibodies directed against the protein may show utility as a tumor marker and/or immunotherapy targets for the above listed tissues. Alternatively, given the homology to uncoupling proteins, the gene and/or its translation product may also be used in the diagnosis, treatment, and/or prevention of thermogenesis disorders such as obesity, cachexia, and hyperinsulinemia. Uncoupling proteins dissipate the proton gradient created from the oxidation of fuels by the electron transport chain, thus releasing stored energy as heat. Dysfunction of thermogenesis can induce disorders such as obesity and cachexia. It is thought that obesity may result from decreased thermogenesis in humans. Alternatively, cachexia is a metabolic state in which energy expenditure exceeds food intake, for example in anorexia nervosa. Uncoupling proteins may be useful for the treatment and/or prevention of diseases and/or disorders involved with aberrant metabolic and thermogenic pathways. The following method provides for the determination of respiration uncoupling activity of the polypeptides of the present invention, including fragments and variants of the full length proteins. Briefly, yeast are transfected with an expression vector expressing polypeptide of the present invention as previously described by Bouillaud et al., EMBO J., 13:1990 (1994) (incorporated by reference herein in its entirety). Rates of growth in liquid medium of transformed yeast are measured in the presence of galactose, which induces expression, as described in International Publication No. WO 98/31396 (incorporated by reference herein in its entirety). Instantaneous generation times are compared between the polypeptide of the present invention and appropriate controls. An in vivo decrease of membrane potential associated with uncoupling of respiration is analyzed by flow cytometry of yeast labeled with the potential sensitive probe DiOC6 (3) (3,3'-dihexyloxacarbocyanine iodine, Molecular Probes, Eugene, OR). The ability of a polypeptide of the present invention to influence mitochondrial activity and uncouple respiration is thus determined.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1660 of SEQ ID NO:26, b is an integer of 15 to 1674, where both a and b correspond to the positions of nucleotide residues shown in SEQ ID NO:26, and where b is greater than or equal to a+14.

Features of Protein Encoded by Gene No: 17

The translation product of this gene shares sequence homology with 55 kD deglycosylated zona pellucida protein which is known to be important in egg fertilization (See Genebank Accession No.R39356). One embodiment of this gene comprises polypeptides of the following amino acid sequence: RPRPSASSLARSASLLPAAHGXGVG GAGGGSSXLRSRYQQLQNEEESGEPEQAAGDAPPP YSSISAESAHXFDYKDESGFPKPPSYNVATTLPSYDE AERTKAEATIPLVPGRDEDFVGRDDFDDADQL RIGNDGIF (SEQ ID NO: 216), RYQQLQNEEES GEPEQAAGD (SEQ ID NO: 217), and/or PGRDED FVGRDDFDDADQLRIG (SEQ ID NO: 218). An additional embodiment is the polynucleotides encoding these polypeptides.

Preferred polypeptide fragments of the invention comprise the following amino acid sequence: MLTFFMAFLFN WIGFFLSFCLTTSAAGRYGAISGFGLSLIKWILIVRFS TYFPGYFDGQYWLWWVFLVLGFLLFLRGFINY AKVRKMPET FSNLPRTRVLFIY (SEQ ID NO: 219). Polynucleotides encoding these polypeptides are also provided.

Preferred polypeptide variants of the invention comprise the following amino acid sequence: MKKSLENLNR LQVMLLHLTAAFLQRAQHXFDYKDESGFPKPPSYN VATTLPSYDEAERTKAEATIPLVPGRDEDFVGRD DFDDADQLRIGNDGIFMLTFFMAFLFNWIGFFLSF CLTTSAAGRYGAISGFGLSLIKWILIVRFSTYFPGYFD GQYWLW WVFLVLGFLLFLRGFINYAKVRKMPETF SNLPRTRVLFIY (SEQ ID NO: 220), MLLHLTAAFLQ RAQFSTYFPGYFDGQYWLWWVFLVLGFLLFLRGFIN YAKVRKMPETFSNLPRTRVLFIY (SEQ ID NO: 221), MLTFFMAFLFNWIGFFLSFCLTTSAAGRYGAIS GFGLSLIKWILIVRFSTYFPAF MNSLSRSKRTPAGSES RCRTQRNNHLL (SEQ ID NO: 222), and/or MKKSLEN LNRLQVMLLHLTAAFLQRAHXILTTRMSLGFQ SPHLTM (SEQ ID NO: 223). Polynucleotides encoding these polypeptides are also provided.

When tested against U937 cell lines, supernatants removed from cells containing this gene activated the GAS (gamma activating sequence) promoter element. Thus, it is likely that this gene activates myeloid cells, and to a lesser extent, other immune and hematopoietic cells and JAK-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in adult kidney, colon adenocarcinoma, and fetal brain, and to a lesser extent, ubiquitously expression in many tissues.

Therefore, polynucleotides and polypeptides of the invention are useful as reagents for differential identification of the tissue(s) or cell type(s) present in a biological sample and for diagnosis of diseases and conditions which include, but are not limited to, disorders of kidney, colon cancers, and central nervous system. Similarly, polypeptides and antibodies directed to these polypeptides are useful in providing immunological probes for differential identification of the tissue(s) or cell type(s). For a number of disorders of the above tissues or cells, particularly of the renal and neural systems, and cancers, expression of this gene at significantly higher or lower levels may be routinely detected in certain tissues or cell types (e.g., renal, neural, urogenital, or cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 119 as residues: Cys-15 to Gly-36. Polynucleotides encoding said polypeptides are also provided.

The tissue distribution adult kidney, colon adenocarcinoma, and fetal brain indicates that polynucleotides and polypeptides corresponding to this gene are useful for diagnosis and treatment of kidney diseases, colon cancers, and disorders of the central nervous system. Additionally, the homology to the zona pellucida protein indicates that the gene product may be used for male contraceptive development, and infertility diagnosis etc. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1951 of SEQ ID NO:27, b is an integer of 15 to 1965, where both a and b correspond to the positions of nucleotide residues shown in SEQ ID NO:27, and where b is greater than or equal to a+14.

Features of Protein Encoded by Gene No: 18

The translation product of this gene shares sequence homology with the chicken transferrin receptor in addition to a human prostate-specific protein homolog (See Genebank Accession Nos.pirlJH0570lJH0570 and gil2565338 (AF026380), respectively). This gene also shares significant homology with both the murine and the rat hematopoietic lineage switch 2 proteins (See Genbank Accession Nos. g3169729 and g3851632, respectively), which are induced during an erythroid to myeloid lineage switch.

A preferred polypeptide fragment of the invention comprises the following amino acid sequence: MTVMDPKQM-NVAAAVWAVVSYVVADMEEML PRS (SEQ ID NO: 224). Polynucleotides encoding these polypeptides are also provided.

This gene is expressed primarily in fetal tissues, such as liver/spleen and brain.

Therefore, polynucleotides and polypeptides of the invention are useful as reagents for differential identification of the tissue(s) or cell type(s) present in a biological sample and for diagnosis of diseases and conditions which include, but are not limited to, pre-natal disorders, anomalies, deficiencies. Similarly, polypeptides and antibodies directed to these polypeptides are useful in providing immunological probes for differential identification of the tissue(s) or cell type(s). For a number of disorders of the above tissues or cells, particularly of the developing fetus, expression of this gene at significantly higher or lower levels may be routinely detected in certain tissues or cell types (e.g., developing, cancerous and wounded tissues) or bodily fluids (e.g., amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 120 as residues: Arg-31 to Lys-37, Lys-58 to Glu-65, Asp-157 to Gly-168, Ile-219 to Gly-225, Ala-260 to Ser-268, Thr-276 to Glu-282. Polynucleotides encoding said polypeptides are also provided.

The tissue distribution indicates that polynucleotides and polypeptides corresponding to this gene are useful for treatment and diagnosis of pre-natal disorders, anomalies and deficiencies.

The homology to the hematopoietic lineage switch 2 proteins also indicates that the translation product of this gene is useful for the detection and/or treatment of immune system disorders. In addition, the homology to the transferrin receptor indicates that the translation product of the present invention may have utility in the regulation of iron metabolism as well as the numerous genes under the stringent control of physiologic iron levels. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1849 of SEQ ID NO:28, b is an integer of 15 to 1863, where both a and b correspond to the positions of nucleotide residues shown in SEQ ID NO:28, and where b is greater than or equal to a+14.

Features of Protein Encoded by Gene No: 19

In another embodiment, polypeptides comprising the amino acid sequence of the open reading frame upstream of the predicted signal peptide are contemplated by the present invention. Specifically, polypeptides of the invention comprise the following amino acid sequence: PRVRSREPVAGAPGCGTAGPPAMATLWGGLLRLGSLLSLSCLALSVLLLAHCQTPPSDCLHVVEPMPVRGPDVEAYCLRCECKYEERSSVTIKVTIIIYLSILGLLLLYMVYLTLVEPILKRRLFGHAQLIQSDDDIGDHQPFANAHDVLARSRSRANV LNKVEYAQQRWKLQVQEQRKSVFDRHVVLS (SEQ ID NO: 225). Polynucleotides encoding these polypeptides are also provided.

The polypeptide of this gene has been determined to have a transmembrane domain at about amino acid position 72–88 of the amino acid sequence referenced in Table 1 for this gene. Moreover, a cytoplasmic tail encompassing amino acids 89 to 167 of this protein has also been determined. Based upon these characteristics, it is believed that the protein product of this gene shares structural features to type Ia membrane proteins.

A preferred polypeptide variant of the invention comprise the following amino acid sequence: MATLWGGLLRLGSLLSLSCLALSVLLLAHCQTPPRISRMSDVNVSALPIKKNSGHYNKNISQKDCDCLHVVEPMPVRGPDVEAYCLRCECKYEERSSVTIKVTIIIYLSILGLLLLYMVYLTLVEPILKRRLFGHAQLIQSDDDIGDHQPFANAHDVLARSRSRANVLNKVEYGTAALEASSPRAAKSLSLTGMLSSANWGIEFKVTRKKQADNWKGTDWVLLGFILIPC (SEQ ID NO: 226). Polynucleotides encoding these polypeptides are also provided.

This gene is expressed primarily in infant brain tissue, and to a lesser extent in other cell types and tissues.

Therefore, polynucleotides and polypeptides of the invention are useful as reagents for differential identification of the tissue(s) or cell type(s) present in a biological sample and for diagnosis of diseases and conditions which include, but are not limited to, developmental and neurodegenerative diseases of the brain and nervous system, such as depression, schizophrenia, Alzheimer's disease, Parkinson's disease, Huntington's disease, mania, dementia, paranoia, addictive behavior, sleep disorders, epilepsy, transmissible spongiform encephalopathy (TSE), Creutzfeldt-Jakob disease (CJD). Similarly, polypeptides and antibodies directed to these polypeptides are useful in providing immunological probes for differential identification of the tissue(s) or cell type(s). For a number of disorders of the above tissues or cells, particularly of the brain, expression of this gene at significantly higher or lower levels may be routinely detected in certain tissues or cell types (e.g., neural, developmental, or cancerous and wounded tissues) or bodily fluids (e.g., amniotic fluid, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 121 as residues: Gln-110 to Pro-120, Val-152 to Val-159. Polynucleotides encoding said polypeptides are also provided.

The tissue distribution in infant brain tissue indicates that polynucleotides and polypeptides corresponding to this gene are useful for the treatment and/or diagnosis of developmental, degenerative and behavioral conditions of the brain and nervous system. Representative uses are described in the "Regeneration" and "Hyperproliferative Disorders" sections below, in Example 11, 15, and 18, and elsewhere herein. Briefly, the uses include, but are not limited to the detection, treatment, and/or prevention of schizophrenia, Alzheimer's disease, Parkinson's disease, Huntington's disease, Tourette Syndrome, transmissible spongiform encephalopathy (TSE), Creutzfeldt-Jakob disease (CJD), mania, depression, dementia, paranoia, addictive behavior, obsessive-compulsive disorder and sleep disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1612 of SEQ ID NO:29, b is an integer of 15 to 1626, where both a and b correspond to the positions of nucleotide residues shown in SEQ ID NO:29, and where b is greater than or equal to a+14.

Features of Protein Encoded by Gene No: 20

The translation product of this gene shares sequence homology with a recently published gene Dysferlin, which is thought to be a skeletal muscle gene that is mutated in Miyoshi myopathy and limb girdle muscular dystrophy (See Genbank Accession No. g3600028, and Nat. Genet. 20 (1), 31–36 (1998); all references available through this accession are hereby incorporated by reference herein.)).

This gene is expressed primarily in fetal liver, fetal heart tissue, and T-cells.

Therefore, polynucleotides and polypeptides of the invention are useful as reagents for differential identification of the tissue(s) or cell type(s) present in a biological sample and for diagnosis of diseases and conditions which include, but are not limited to, immunodeficiency, tumor necrosis, lymphomas, auto-immunities, cancer, inflammation, anemias (leukemia) and liver disorders, vascular disorders, and cancers (e.g., hepatoblastoma, hepatitis, liver metabolic diseases and conditions that are attributable to the differentiation of hepatocyte progenitor cells). Similarly, polypeptides and antibodies directed to these polypeptides are useful in providing immunological probes for differential identification of the tissue(s) or cell type(s). For a number of disorders of the above tissues or cells, particularly of the liver and immune system, expression of this gene at significantly higher or lower levels may be routinely detected in certain tissues or cell types (e.g., hepatic, developmental, vascular, or cancerous and wounded tissues) or bodily fluids (e.g., amniotic fluid, bile, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for the diagnosis and treatment of immune disorders including: leukemias, lymphomas, auto-immunities, immunodeficiencies (e.g., AIDS), immuno-supressive conditions (transplantation) and hematopoeitic disorders. In addition this gene product may be applicable in conditions of general microbial infection, inflammation or cancer.

Expression in liver may suggest a role for this gene product in the treatment and detection of liver disorders and cancers (e.g., hepatoblastoma, jaundice, hepatitis, liver metabolic diseases and conditions that are attributable to the differentiation of hepatocyte progenitor cells).

Alternatively, the tissue distribution in fetal heart tissue indicates that the protein product of this gene is useful for the diagnosis and treatment of conditions and pathologies of the cardiovascular system, such as heart disease, restenosis, atherosclerosis, stoke, angina, thrombosis, and wound healing. Protein, as well as, antibodies directed against the protein may show utility as a tumor marker and/or immunotherapy targets for the above listed tissues. Additionally, the homology to the dysferlin gene indicates that polynucleotides and polypeptides corresponding to this gene are useful for diseases related to degenerative myopathies that are characterized by the weakness and atrophy of muscles without neural degradation; such as Duchenne and Becker's muscular dystropies. Protein, as well as, antibodies directed against the protein may show utility as a tumor marker and/or immunotherapy targets for the above listed tissues Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 591 of SEQ ID NO:30, b is an integer of 15 to 605, where both a and b correspond to the positions of nucleotide residues shown in SEQ ID NO:30, and where b is greater than or equal to a+14.

Features of Protein Encoded by Gene No: 21

This gene is expressed primarily in haemopoietic cels and tumor cells, such as pancreatic tumor tissue, and to a lesser extent in bladder cells.

Therefore, polynucleotides and polypeptides of the invention are useful as reagents for differential identification of the tissue(s) or cell type(s) present in a biological sample and for diagnosis of diseases and conditions which include, but are not limited to, haemopoietic disorders, diseases of the renal and pancreatic systems, and cancer. Similarly, polypeptides and antibodies directed to these polypeptides are useful in providing immunological probes for differential identification of the tissue(s) or cell type(s). For a number of disorders of the above tissues or cells, particularly of the haemopoietic, pancreatic, and renal systems, expression of this gene at significantly higher or lower levels may be routinely detected in certain tissues or cell types (e.g., pancreas, renal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for the treatment and/or diagnosis of disorders of the renal, pancreatic and haemopoietic systems, and cancers thereof. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 917 of SEQ ID NO:3 1, b is an integer of 15 to 931, where both a and b correspond to the positions of nucleotide residues shown in SEQ ID NO:31, and where b is greater than or equal to a+14.

Features of Protein Encoded by Gene No: 22

This gene is expressed primarily in liver tissue, cancer cells and fetal lung tissue, and to a lesser extent in dendritic cells.

Therefore, polynucleotides and polypeptides of the invention are useful as reagents for differential identification of the tissue(s) or cell type(s) present in a biological sample and for diagnosis of diseases and conditions which include, but are not limited to, metabolic disorders, diseases of developing systems and cancers. Similarly, polypeptides and antibodies directed to these polypeptides are useful in providing immunological probes for differential identification of the tissue(s) or cell type(s). For a number of disorders of the above tissues or cells, particularly of the fetus, metabolic systems and cancers, expression of this gene at significantly higher or lower levels may be routinely detected in certain tissues or cell types (e.g., developing, metabolic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 124 as residues: His-44 to Gly-49. Polynucleotides encoding said polypeptides are also provided.

The tissue distribution indicates that polynucleotides and polypeptides corresponding to this gene are useful for the treatment and/or diagnosis of disorders of the fetus, metabolic systems and cancers.

The tissue distribution also indicates that polynucleotides and polypeptides corresponding to this gene are useful for the detection and treatment of liver disorders and cancers (e.g. hepatoblastoma, jaundice, hepatitis, liver metabolic diseases and conditions that are attributable to the differentiation of hepatocyte progenitor cells). In addition the expression in fetus would suggest a useful role for the protein product in developmental abnormalities, fetal deficiencies, pre-natal disorders and various would-healing models and/or tissue trauma. Protein, as well as, antibodies directed against the protein may show utility as a tumor marker and/or irnmunotherapy targets for the above listed tissues.

Many polynucleotide sequences, such as FST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1393 of SEQ ID NO:32, b is an integer of 15 to 1407, where both a and b correspond to the positions of nucleotide residues shown in SEQ ID NO:32, and where b is greater than or equal to a+14.

Features of Protein Encoded by Gene No: 23

This gene is expressed primarily in central nervous system tissues and cancers, such as endometrial tumors, and to a lesser extent in other tissues and organs.

Therefore, polynucleotides and polypeptides of the invention are useful as reagents for differential identification of the tissue(s) or cell type(s) present in a biological sample and for diagnosis of diseases and conditions which include, but are not limited to, disorders of the CNS and cancers. Similarly, polypeptides and antibodies directed to these polypeptides are useful in providing immunological probes for differential identification of the tissue(s) or cell type(s). For a number of disorders of the above tissues or cells, particularly of the central nervous system and cancerous tissues, expression of this gene at significantly higher or lower levels may be routinely detected in certain tissues or cell types (e.g., neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 125 as residues: Tyr-16 to Ser-22, Asp-209 to Leu-215. Polynucleotides encoding said polypeptides are also provided.

The tissue distribution in central nervous system tissues indicates that polynucleotides and polypeptides corresponding to this gene are useful for the treatment and/or diagnosis of diseases of the central nervous system, as well as cancers of tissues where expression of this gene has been observed, such as in endometrial tumors.

The tissue distribution in central nervous system tissues indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1512 of SEQ ID NO:33, b is an integer of 15 to 1526, where both a and b correspond to the positions of nucleotide residues shown in SEQ ID NO:33, and where b is greater than or equal to a+14.

Features of Protein Encoded by Gene No: 24

The translation product of this gene shares sequence homology with low-density lipoprotein receptor (See, e.g., Genbank Accession No. >dbj|BAA24580.1; all references available through this accession are hereby incorporated by reference herein).

The translation product of this gene also shares sequence homology with a rat homolog of the human CD94 (See, e.g., Genbank Accession No. gb|AAC10220.1; all references available through this accession are hereby incorporated by reference herein).

This gene is expressed primarily in macrophages, eosinophils, neutrophil and other cells of the haemopoietic and immune system.

Therefore, polynucleotides and polypeptides of the invention are useful as reagents for differential identification of the tissue(s) or cell type(s) present in a biological sample and for diagnosis of diseases and conditions which include, but are not limited to, disorders of the immune and haemopoietic systems and diseases of the endothelial and vascular system. Similarly, polypeptides and antibodies directed to these polypeptides are useful in providing immunological probes for differential identification of the tissue(s) or cell type(s). For a number of disorders of the above tissues or cells, particularly of the immune, haemopoietic and vascular system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 126 as residues: Lys-9 to Ala-17, Met-55 to Leu-61, Tyr-105 to Cys-127, Asp-132 to Lys-141, Ser-165 to Tyr-172, Pro-178 to Met-186, His-222 to Gln-227. Polynucleotides encoding said polypeptides are also provided.

The tissue distribution and homology to LDL receptor and rat CD94 homolog indicates that polynucleotides and polypeptides corresponding to this gene are useful for the treatment and/or diagnosis of disorders of the immune, haemopoietic and vascular systems.

Moreover, the tissue distribution indicates that polynucleotides and polypeptides corresponding to this gene are useful for the diagnosis and/or treatment of hematopoietic disorders. This gene product is primarily expressed in hematopoietic cells and tissues, suggesting that it plays a role in the survival, proliferation, and/or differentiation of hematopoieitic lineages. Expression of this gene product in eosinophils and macrophage also strongly indicates a role for this protein in immune function and immune surveillance. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1723 of SEQ ID NO:34, b is an integer of 15 to 1737, where both a and b correspond to the positions of nucleotide residues shown in SEQ ID NO:34, and where b is greater than or equal to a+14.

Features of Protein Encoded by Gene No: 25

A preferred polypeptide fragment of the invention comprises the following amino acid sequence: MAAAGRLPSSWALFSPLLAGLALLGVGPVPARALHNVTAELFGAEAWGTLAAFGDLNSDKQTDLFVLRERNDLIVFLADQNAPYFKPKVKVSFKNHSALITSVVPGDYDGDSQMDVLLTYLPKNYAKSELGAVIFWGQNQTLDPNNMTILNRTFQDEPLIMDFNGDLIPDIFGITNESNQPQILLGGNLSWHPALTTTSKMRIPHSHAFIDLTEDFTADLFLTTLNATTSTFQFEIWENLDGNFSVSTILEKPQNMMVVGQSAFADFDGDGHMDHLLPGCEDKNCQKSTIYLVRSGMKQWVPVLQDFSNKGTLWGFVPFVDEQQPTEIPIPITLHIGDYNMDGYPDALVILKNTSGSNQQAFLLENVPCNNASCEEARRMFKVYWELTDLNQIKDAMVATFFDIYEDGILDIVVLSKGYTKNDFAIHTLKNNFEADAYFVKVIVLSGLCSNDCPRR (SEQ ID NO: 227). Polynucleotides encoding these polypeptides are also provided.

When tested against U937 cell lines, supernatants removed from cells containing this gene activated the GAS (gamma activating sequence) promoter element. Thus, it is likely that this gene activates myeloid cells, and to a lesser extent, other immune and hematopoietic cells and tissue cell types, through the JAK-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in infant brain and placental tissues, and to a lesser extent in several other tissues including cancers.

Therefore, polynucleotides and polypeptides of the invention are useful as reagents for differential identification of the tissue(s) or cell type(s) present in a biological sample and for diagnosis of diseases and conditions which include, but are not limited to, brain disorders and diseases of developing systems and cancers. Similarly, polypeptides and antibodies directed to these polypeptides are useful in providing immunological probes for differential identification of the tissue(s) or cell type(s). For a number of disorders of the above tissues or cells, particularly of the central nervous system and fetal systems, expression of this gene at significantly higher or lower levels may be routinely detected in certain tissues or cell types (e.g., neural, developing, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 127 as residues: Leu-56 to Thr-62, Gln-80 to Pro-87, Gly-106 to Gln-113, Pro-122 to Lys-127, Gln-138 to Asn-146. Polynucleotides encoding said polypeptides are also provided.

The tissue distribution in neural tissues and developing tissues indicates that polynucleotides and polypeptides corresponding to this gene are useful for the treatment and/or diagnosis of disorders of the central nervous system, disorders of developing systems, and cancers. The tissue distribution in infant brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders.

The tissue distribution indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product may be produced by the placenta and then transported to the embryo, where it may play a crucial role in the development and/or survival of the developing embryo or fetus. Expression of this gene product in a vascular-rich tissue such as the placenta also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2228 of SEQ ID NO:35, b is an integer of 15 to 2242, where both a and b correspond to the positions of nucleotide residues shown in SEQ ID NO:35, and where b is greater than or equal to a+14.

Features of Protein Encoded by Gene No: 26

Preferred polypeptides encoded by this gene comprise the following amino acid sequence: MTKREDGGYTFTAT PEDFPKKHKAPVIDIGIANTGKFIMTASSDTTVLIWS LKGQVLSTINTNQMNNTHAAVSPCGRFVASCGFTP DVKVWEVCFGKKGEFQEVVRAFELKGHSAAVHS FAFSNDSRRMASVSKDGTWKLWDTXVEYKKKQDPY LLKTGRFEEAAGAXPCRLALSPNAQVLALASGSSIH LYNTRRGEKEECFERVHGECIANLSFDITGRFLAS CGDRAVRLFHNTPGHRAMVEEMQGHLKRASNEST RQRLQQQLTQAQETLKSLGALKK (SEQ ID NO: 228). Polynucleotides encoding such polypeptides are also provided.

The gene encoding the disclosed cDNA is thought to reside on chromosome 7. Accordingly, polynucleotides related to this invention are useful as a marker in linkage analysis for chromosome 7.

When tested against U937 Myeloid cell lines, supernatants removed from cells containing this gene activated the GAS assay. Thus, it is likely that this gene activates myeloid cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

The polypeptide of this gene has been determined to have a transmembrane domain at about amino acid position 12–28 of the amino acid sequence referenced in Table 1 for this gene. Based upon these characteristics, it is believed that the protein product of this gene shares structural features to type Ib membrane proteins.

In another embodiment, polypeptides comprising the amino acid sequence of the open reading frame upstream of the predicted signal peptide are contemplated by the present invention. Specifically, polypeptides of the invention comprise the following amino acid sequence: VIRHEGST NMELSQMSXLMGLSVLLGLLALMATAAVXRGWL RAGEERSGRPACQKANGFPPDKSSGSKKQKQYQR IRKEKPQQHNFTHRLLAAALKSHSGNISCMDFSS NGKYLATCADDRTIRIWSTKDFLQREHRSMRA NVELDHATLVRFSPDCRAFIVWLANGDTLRVFKMT KREDGGYTFTATPEDFPKKHKAPVIDIGIANTGK FIMTASSDTTVLIWSLKGQVLSTINTNQMN NTHAAVSPCGRFVASCGFTPDVKVWEVCFGK KGEFQEVVRAFELKGHSAAVHSFAFSNDSRRMAS VSKDGTWKLWDTXVEYKKKQDPYLLKTGRFEEAA GAXPCRLALSPNAQVLALASGSSIHLYNTRRGE KEECFERVHGECIANLSFDITGRFLASCGDRAVR LFHNTPGHRAMVEEMQGHLKRASNESTRQR LQQQLTQAQETLKSLGALKK (SEQ ID NO: 229). Polynucleotides encoding these polypeptides are also provided.

This gene is expressed primarily in testes, synovial sarcoma and fetal tissues, and to a lesser extent in several other tissues.

Therefore, polynucleotides and polypeptides of the invention are useful as reagents for differential identification of the tissue(s) or cell type(s) present in a biological sample and for diagnosis of diseases and conditions which include, but are not limited to, disorders of the reproductive and developing systems and cancers. Similarly, polypeptides and antibodies directed to these polypeptides are useful in providing immunological probes for differential identification of the tissue(s) or cell type(s). For a number of disorders of the above tissues or cells, particularly of the reproductive and developing systems, expression of this gene at significantly higher or lower levels may be routinely detected in certain tissues or cell types (e.g., reproductive, testicular, and cancerous and wounded tissues) or bodily fluids (e.g., lymph, serum, plasma, seminal fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in testes tissue, synovial sarcoma, and fetal tissues, indicates that polynucleotides and polypeptides corresponding to this gene are useful for the treatment and/or diagnosis of disorders of the reproductive and developing systems, and cancers.

The tissue distribution also indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence.

This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

Furthermore, the tissue distribution indicates that polynucleotides and polypeptides corresponding to this gene are useful for the diagnosis and treatment of cancer and other proliferative disorders.

Expression within embryonic tissue and other cellular sources marked by proliferating cells indicates that this protein may play a role in the regulation of cellular division. Additionally, the expression in hematopoietic cells and tissues indicates that this protein may play a role in the proliferation, differentiation, and/or survival of hematopoietic cell lineages. In such an event, this gene may be useful in the treatment of lymphoproliferative disorders, and in the maintenance and differentiation of various hematopoietic lineages from early hematopoietic stem and committed progenitor cells. Similarly, embryonic development also involves decisions involving cell differentiation and/or apoptosis in pattern formation. Thus this protein may also be involved in apoptosis or tissue differentiation and could again be useful in cancer therapy. This protein is useful for the treatment, detection, and/or prevention of William's disease. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2221 of SEQ ID NO:36, b is an integer of 15 to 2235, where both a and b correspond to the positions of nucleotide residues shown in SEQ ID NO:36, and where b is greater than or equal to a+14.

Features of Protein Encoded by Gene No: 27

Preferred polypeptides encoded by this gene comprise amino acids 1–363, 2–363, 4–363, 5–363, 30–363, 31–363, 32–363, 75–363, 76–363 and 82–363 of the following amino acid sequence: MSVMVVRKKVTRKWEKLPGRNTFC CDGRVMMARQKGIFYLTLFLILGTCTLFFAFECRY LAVQLSPAIPVFAAMLFLFSMATLLRTSFSDPGV IPRALPDEAAFIEMEIEATNGAVPQGQRPPPRIKNF QINNQIVKLKYCYTCKIFRPPRASHCSICDNCVER FDHHCPWVGNCVGKRNYRYFYLFILSLSLLTIYV FAFNIVYVALKSLKI GFLETLKETPGTVLEVLICFFTL WSVVGLTGFHTFLVALNQTTNEDIKGSWTG KNRVQNPYSHGNIVKNCCEVLCGPLPPSVLDR RGILPLEESGSRPPSTQETSSSLLPQSPAPTELNSNEM PEDSSTPEEMPPPEPPEPPQEAAEAEK (SEQ ID NO: 230). Polynucleotides encoding such polypeptides are also provided.

A preferred polypeptide variant of the invention comprises the following amino acid sequence: MLFLFS MATLLRTSFSDPGVIPRALPDEAAFIEMEIEATN GAVPQGQRPPPRIKNFQINNQIVKLKYCYTCKIFRP PRASHCSICDNCVERFDHHCPWVGNCVGKRNYRY FYLFILSLSLLTIYVFAFNIVYVALKSLKIGFLETLK GNSWNCSRSPHLLLYTLVRRGTDWISYFPRGSQP DNQ (SEQ ID NO: 231). Polynucleotides encoding these polypeptides are also provided.

This gene is expressed primarily in ovarian and endometrial tumors, fetal liver, spleen and brain tissues, and to a lesser extent in several other tissues and organs.

Therefore, polynucleotides and polypeptides of the invention are useful as reagents for differential identification of the tissue(s) or cell type(s) present in a biological sample and for diagnosis of diseases and conditions which include, but are not limited to, disorders of the developing systems, and cancers of the female reproductive system. Similarly, polypeptides and antibodies directed to these polypeptides are useful in providing immunological probes for differential identification of the tissue(s) or cell type(s). For a number of disorders of the above tissues or cells, particularly of the developing, female reproductive and fetal systems, expression of this gene at significantly higher or lower levels may be routinely detected in certain tissues or cell types (e.g., reproductive, developing, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 129 as residues: Pro-44 to Lys-54, Cys-88 to His-95, Val-103 to Tyr-108, Gln-181 to Ser-190, Thr-192 to Ile-206, Glu-233 to Ser-245, Ser-252 to Ala-286. Polynucleotides encoding said polypeptides are also provided.

The tissue distribution in developing systems indicates that polynucleotides and polypeptides corresponding to this gene are useful for the treatment and/or diagnosis of disorders of developing and fetal systems and cancers. Furthermore, the tissue distribution in ovarian and endometrial tumor tissues indicates that the translation product of this gene is useful for the detection, diagnosis, and/or treatment of cancers of the female reproductive system. Accordingly, preferred are antibodies which specifically bind a portion of the translation product of this gene. Also provided is a kit for detecting these tumors. Such a kit comprises in one embodiment an antibody specific for the translation product of this gene bound to a solid support.

Also provided is a method of detecting these tumors in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2957 of SEQ ID NO:37, b is an integer of 15 to 2971, where both a and b correspond to the positions of nucleotide residues shown in SEQ ID NO:37, and where b is greater than or equal to a+14.

Features of Protein Encoded by Gene No: 28

This gene is expressed primarily in normal and cancerous colon tissue, macrophages, endothelial cells and placental tissue, and to a lesser extent in several other tissues and organs.

Therefore, polynucleotides and polypeptides of the invention are useful as reagents for differential identification of the tissue(s) or cell type(s) present in a biological sample and for diagnosis of diseases and conditions which include, but are not limited to, colon cancer and gastrointestinal disorders, immune disorders, vascular diseases and disorders of developing systems. Similarly, polypeptides and antibodies directed to these polypeptides are useful in providing immunological probes for differential identification of the tissue(s) or cell type(s). For a number of disorders of the above tissues or cells, particularly of the immune , vascular and developing systems, expression of this gene at significantly higher or lower levels may be routinely detected in certain tissues or cell types (e.g., immune, gastrointestinal, developmental, vascular, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 130 as residues: Thr-27 to Ser-33. Polynucleotides encoding said polypeptides are also provided.

The tissue distribution in macrophage, endothelial and placental tissues, and normal and cancerous colon tissues, indicates that polynucleotides and polypeptides corresponding to this gene are useful for the treatment and/or diagnosis of immune, gastrointestinal and vascular disorders and diseases. Expression of this gene product in colon tissue indicates involvement in digestion, processing, and elimination of food, as well as a potential role for this gene as a diagnostic marker or causative agent in the development of colon cancer, and cancer in general. Accordingly, preferred are antibodies which specifically bind a portion of the translation product of this gene.

Also provided is a kit for detecting colon cancer. Such a kit comprises in one embodiment an antibody specific for the translation product of this gene bound to a solid support. Also provided is a method of detecting colon cancer in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein.

Alternatively, the tissue distribution in placental tissue indicates that polynucleotides and polypeptides corresponding to this gene are useful for the diagnosis and/or treatment of disorders of the placenta. Specific expression within the placenta indicates that this gene product may play a role in the proper establishment and maintenance of placental function. Alternately, this gene product may be produced by the placenta and then transported to the embryo, where it may play a crucial role in the development and/or survival of the developing embryo or fetus. Expression of this gene product in a vascular-rich tissue such as the placenta and endothelial cells also indicates that this gene product may be produced more generally in endothelial cells or within the circulation. In such instances, it may play more generalized roles in vascular function, such as in angiogenesis. It may also be produced in the vasculature and have effects on other cells within the circulation, such as hematopoietic cells. It may serve to promote the proliferation, survival, activation, and/or differentiation of hematopoietic cells, as well as other cells throughout the body.

Additionally, expression of this gene product in macrophage also strongly indicates a role for this protein in immune function and immune surveillance. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1149 of SEQ ID NO:38, b is an integer of 15 to 1163, where both a and b correspond to the positions of nucleotide residues shown in SEQ ID NO:38, and where b is greater than or equal to a+14.

Features of Protein Encoded by Gene No: 29

The translation product of this gene shares homology with HNK-sulfotransferase, which directs glycan synthesis (see, e.g., Genbank Accession no. AF033827; all references available through this accession are hereby incorporated by reference herein).

This gene is expressed primarily in activated T cells, osteoclastoma, and glioblastoma, and to a lesser extent in various other normal and transformed cell types.

Therefore, polynucleotides and polypeptides of the invention are useful as reagents for differential identification of the tissue(s) or cell type(s) present in a biological sample and for diagnosis of diseases and conditions which include, but are not limited to, inflammation, immune defects, cancer.

Similarly, polypeptides and antibodies directed to these polypeptides are useful in providing immunological probes for differential identification of the tissue(s) or cell type(s). For a number of disorders of the above tissues or cells, particularly of the immune and hemopoietic systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 131 as residues: Pro-32 to Gly-48, Gln-63 to Thr-69, Pro-77 to Trp-84, Val-88 to Leu-94. Polynucleotides encoding said polypeptides are also provided.

The tissue distribution in T-cells and various types of neoplasms indicates that polynucleotides and polypeptides corresponding to this gene are useful for the detection, study and/or treatment of inflammatory and general immune defects, and various types of neoplasms. Expression of this gene product in T cells strongly indicates a role for this protein in immune function and immune surveillance. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types.

Alternatively, the tissue distribution in various cancerous tissues indicates that the translation product of the gene is useful for the detection, diagnosis, and/or treatment of these cancers, as well as cancers of other tissues where expression has been observed. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1918 of SEQ ID NO:39, b is an integer of 15 to 1932, where both a and b correspond to the positions of nucleotide residues shown in SEQ ID NO:39, and where b is greater than or equal to a+14.

Features of Protein Encoded by Gene No: 30

Preferred polypeptides of the invention comprise the following amino acid sequence: LHECLPGSISYLHPRTP WLCLPPQHLSFSTFSPPWQPAMSPVPGTGGPPCGL (SEQ ID NO: 232), and/or MLPLLIICLLPAIEGKNCL RCWPELSALIDYDLQILWVTPGPPTELSQSIHSLFLE DNNFLK PWYLDRDHLEEETAKFFTQVHQAIKTL RDDKTVLLEEIYTHKNLFTERLNKIS DGLKEKGAPPLHECLPGSISYLHPRTPWLCLP PQHLSFSTFSPPWQPAMSPVPGTGGPPCGL (SEQ ID NO: 233). Polynucleotides encoding these polypeptides are also provided.

This gene is expressed primarily in infant brain, testes and activated T cells, and to a lesser extent in various other normal and transformed cell types.

Therefore, polynucleotides and polypeptides of the invention are useful as reagents for differential identification of the tissue(s) or cell type(s) present in a biological sample and for diagnosis of diseases and conditions which include, but are not limited to, neurological, reproductive and inflammatory conditions. Simiarly, polypeptides and antibodies directed to these polypeptides are useful in providing immunological probes for differential identification of the tissue(s) or cell type(s). For a number of disorders of the above tissues or cells, particularly of the neural, immune and male reproductive systems, expression of this gene at significantly higher or lower levels may be routinely detected in certain tissues or cell types (e.g., neural, immune, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 132 as residues: Gly-41 to Leu-46, Asp-67 to Thr-75, Ile-114 to Ala-123. Polynucleotides encoding said polypeptides are also provided.

The tissue distribution in infant brain tissue, testes tissue, and activated T-cells, indicates that polynucleotides and polypeptides corresponding to this gene are useful for the study, diagnosis, and/or treatment of neurological, reproductive and immune system disorders. Expression of this gene product in T-cells indicates a role in the regulation of the proliferation; survival; differentiation; and/or activation of potentially all hematopoietic cell lineages, including blood stem cells. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell type.

Alternatively, the tissue distribution in testes tissue indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Furthermore, the tissue distribution in infant brain tissue indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 867 of SEQ ID NO:40, b is an integer of 15 to 881, where both a and b correspond to the positions of nucleotide residues shown in SEQ ID NO:40, and where b is greater than or equal to a+14.

Features of Protein Encoded by Gene No: 31

The translation product of this gene shares sequence homology with some human and rodent melanoma and leukocyte specific antigens (see, for example, Genbank accession nos: gil189384, gil205898 and gil180926).

In addition, the translation product of this gene shares sequence homology with Tetraspan protein (see, for example, Genbank accession number: GI 3152703). Therefore, it is likely that the polypeptide of this gene shares some biological functions, such as cell-to-cell signaling, adhesion, proliferation, and differentiation with Tetraspan.

The polypeptide of this gene has been determined to have two transmembrane domains at about amino acid position 52–68 and 197–213 of the amino acid sequence referenced in Table 1 for this gene. Based upon these characteristics, it is believed that the protein product of this gene shares structural features to type IIIa membrane proteins.

The transmembrane 4 superfamily (TM4SF) or tetraspan superfamily has at least 16 members (including CD9, CD20, CD37, CD53, CD63, CD81, CD82, A15, CO-029, Sm23, RDS, Uro B, Uro A, SAS, Rom-1, PETA3, and YKK8), is the second biggest subfamily among CD antigen superfamily. and activation antigen of T-cells. All TM4SF member contains four putative transmembrane domains, two extracellular loops, and two short cytoplasmic tails. They are variously expressed on Immature, early, mature, activated lymphocytes, monocytes, macrophages, granulocytes, platelets, eosinophils, basophils, certain leukemic and lymphoma cells, and a variety of other cells and tissues. CD9 cell surface protein is expressed by both hematopoietic and neural cells, and may play a role for CD9 in intercellular signaling in the immune and nervous system. CD63 is a 53-Kd lysosomal membrane glycoprotein that has been identified as a platelet activation molecule, which play important role in cell adhesion of platelets and endothelial cells. Increased mRNA for CD63 antigen was found in atherosclerotic lesions of Watanabe heritable hyperlipidemic rabbits, suggesting a potential role of CD63 in progression of atherosclerosis. CD63 is also a mast cell marker. CD82 was originally identified as the target of several mAbs inhibitory to syncytium formation induced by human T-cell leukemia virus type I (HTLV-I), the etiological agent of adult T-cell leukemia. Therefore, this gene could be a target for the development of a drug for this leukemia. CD81 is the target of an antiproliferative antibody. A diverse group of human cell lines, including hematolymphoid, neuroectodermal, and mesenchymal cells, express the CD81 protein. Many of the lymphoid cell lines, in particular those derived from large cell lymphomas, were susceptible to the antiproliferative effects of the antibody. CD81 may therefore play an important role in the regulation of lymphoma cell growth. CD9, CD20, CD37, CD63, CD81 and CD82 have been implicated in the regulation of cell growth, adhesion, and signal transduction of B, T lymphocytes and some other non-lymphoid cells. They associate with CD2, CD21 , CD4, CD8, MHC Class II molecules, integrins, function as co-receptor for T, B and other lymphoid cells.

Some TM4SF are leukocyte antigens, highly expressed in activated leukocytes, lymphocytes, are highly specific surface marker for lymphoblastic leukemia, lymphoma, melanoma, and neuroblastoma. CD9 has been show to be involved in cell motility and tumor metastasis. These antigen could be a valuable immunogen or target to implement active and passive immunotherapy in patients with cancer. Others have been shown to be involved in inhibition of prostate cancer metastasis. This gene has close homology to C33 antigen (CD82). which is a member of the transmembrane 4 superfamily (TMSF) and activation antigen of T-cells. C33 Ag (CD82 was originally identified as the target of several mAbs inhibitory to syncytium formation induced by human T-cell leukemia virus type I (HTLV-I), the etiological agent of adult T-cell leukemia. Therefore, this gene could be very important target for developing drug for leukemia. Other members of this family are Sm23, CO-029, R2, TAPA-1, CD9, CD37, CD53, and CD63. CD63 is a 53-Kd lysosomal membrane glycoprotein that has been identified as a platelet activation molecule. There are strong evidence indicating that CD63 and Pltgp40, a platelet membrane glycoprotein are the same molecule and that CD63/Pltgp40 is identical to the well-characterized, stage-specific melanoma-associated antigen ME491. These antigens could be valuable immunogens or target to implement active and passive immunotherapy in patients with cancer.

This gene is expressed primarily in fetal tissue (kidney, heart, liver, spleen, brain), macrophages, dendritic cells, retina and to a lesser extent in various other tissues, mostly of lymphoid origin or epithelial cell types. In addition This gene is expressed in cancerous tissues (e.g. breast).

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic diseases and/or disorders and cancers in a variety of organs and cell types. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., developmental, proliferating, immune, hematopoietic, integumentary, and cancerous and wounded tissues) or bodily fluids (e.g., lymph, serum, plasma, urine, synovial fluid, spinal fluid, or amniotic fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 133 as residues: Tyr-123 to Tyr-131, Cys-134 to Ser-145, Tyr-234 to Tyr-244. Polynucleotides encoding said polypeptides are also provided.

The tissue distribution fetal cells and tissues and homology to tumor antigens indicates that polynucleotides and polypeptides corresponding to this gene are useful for study, treatment and diagnosis of lymphoid and epithelial disorders and neoplasms. Additionally, tissue distribution in immune cells and other tissues indicates that polynucleotides and polypeptides corresponding to this gene are useful for the diagnosis and treatment of disorders affecting hematopoiesis, including cancers. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1918 of SEQ ID NO:41, b is an integer of 15 to 1932, where both a and b correspond to the positions of nucleotide residues shown in SEQ ID NO:41, and where b is greater than or equal to a+14.

Features of Protein Encoded by Gene No: 32

The translation product of this gene shares limited sequence homology with VEGF which is thought to be important in regulation of endothelial cell growth. Therefore, it is likely that the protein encoded by this gene would share some similar biological functions.

When tested against U937 Myeloid cell lines, supernatants removed from cells containing this gene activated the GAS assay. Thus, it is likely that this gene activates myeloid cells, and to a lesser extent, other immune and hematopoietic cells and tissue cell types, through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed in brain.

Therefore, polynucleotides and polypeptides of the invention are useful as reagents for differential identification of the tissue(s) or cell type(s) present in a biological sample and for diagnosis of diseases and conditions which include, but are not limited to, nervous system disease and/or disorders. Similarly, polypeptides and antibodies directed to these polypeptides are useful in providing immunological probes for differential identification of the tissue(Is) or cell type(s). For a number of disorders of the above tissues or cells, particularly of the central nervous system, expression of this gene at significantly higher or lower levels may be routinely detected in certain tissues or cell types (e.g., neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 134 as residues: Thr-25 to Pro-46. Polynucleotides encoding said polypeptides are also provided.

The tissue distribution in brain indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1150 of SEQ ID NO:42, b is an integer of 15 to 1164, where both a and b correspond to the positions of nucleotide residues shown in SEQ ID NO:42, and where b is greater than or equal to a+14.

Features of Protein Encoded by Gene No: 33

The translation product of this gene shares sequence homology with human p150 which is thought to be important in signal transduction in neuronal cells. Therefore, it is likely that the protein encoded by this polynucleotide would share some similar biological functions with p150.

This gene is expressed primarily in whole embryo and cerebellum.

Therefore, polynucleotides and polypeptides of the invention are useful as reagents for differential identification of the tissue(s) or cell type(s) present in a biological sample and for diagnosis of diseases and conditions which include, but are not limited to, neurological and growth defects/disorders. Similarly, polypeptides and antibodies directed to these polypeptides are useful in providing immunological probes for differential identification of the tissue(s) or cell type(s). For a number of disorders of the above tissues or cells, particularly of the CNS, expression of this gene at significantly higher or lower levels may be routinely detected in certain tissues or cell types (e.g., neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for study and treatment of central nervous system, neurodevelopmental, cognitive, and memory disorders. The tissue distribution also indicates that polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues. Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1091 of SEQ ID NO:43, b is an integer of 15 to 1105, where both a and b correspond to the positions of nucleotide residues shown in SEQ ID NO:43, and where b is greater than or equal to a+14.

Features of Protein Encoded by Gene No: 34

This gene is expressed primarily in PMA stimulated HL-60 cells and to a lesser extent in 6 week embryo.

Therefore, polynucleotides and polypeptides of the invention are useful as reagents for differential identification of the tissue(s) or cell type(s) present in a biological sample and for diagnosis of diseases and conditions which include, but are not limited to, disorders affecting cell differentiation, particularly hematopoietic disorders and/or defects. Similarly, polypeptides and antibodies directed to these polypeptides are useful in providing immunological probes for differential identification of the tissue(s) or cell type(s). For a number of disorders of the above tissues or cells, particularly of the metabolic system, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 136 as residues: Pro-61 to Asp-68. Polynucleotides encoding said polypeptides are also provided.

The tissue distribution indicates that polynucleotides and polypeptides corresponding to this gene are useful for the study of cellular differentiation and for the treatment and diagnosis of hematopoietic related disorders such as anemia, pancytopenia, leukopenia, thrombocytopenia or leukemia. The tissue distribution also indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses).

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types Additionally, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1248 of SEQ ID NO:44, b is an integer of 15 to 1262, where both a and b correspond to the positions of nucleotide residues shown in SEQ ID NO:44, and where b is greater than or equal to a+14.

Features of Protein Encoded by Gene No: 35

This gene is expressed primarily in colon.

Therefore, polynucleotides and polypeptides of the invention are useful as reagents for differential identification of the tissue(s) or cell type(s) present in a biological sample and for diagnosis of diseases and conditions which include, but are not limited to, disorders and/or defects of the digestive tract including but not limited to cancers of the gastrointestinal tract. Similarly, polypeptides and antibodies directed to these polypeptides are useful in providing immunological probes for differential identification of the tissue(s) or cell type(s). For a number of disorders of the above tissues or cells, particularly of the digestive system, expression of this gene at significantly higher or lower levels may be routinely detected in certain tissues or cell types (e.g., gastrointestinal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for treatment and diagnosis of disorders of the digestive system particularly disorders involving the colon. Further, expression of this gene product in colon tissue indicates involvement in digestion, processing, and elimination of food, as well as a potential role for this gene as a diagnostic marker or causative agent in the development of colon cancer, and cancer in general. Protein, as well as, antibodies directed against the protein may show utility as a tumor marker and/or immunotherapy targets for the colon and/or other gastrointestinal tissue including, but not limited to, stomach, small intestine, large intestine, and rectum.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 503 of SEQ ID NO:45, b is an integer of 15 to 517, where both a and b correspond to the positions of nucleotide residues shown in SEQ ID NO:45, and where b is greater than or equal to a+14.

Features of Protein Encoded by Gene No: 36

This gene is expressed primarily in blood cells.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic diseases. Similarly, polypeptides and antibodies directed to these polypeptides are useful in providing immunological probes for differential identification of the tissue(s) or cell type(s). For a number of disorders of the above tissues or cells, particularly of the immune and hematopoietic system, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 138 as residues: Pro-19 to Cys-29, Thr-35 to Glu-44, Val-72 to Lys-78. Polynucleotides encoding said polypeptides are also provided.

The tissue distribution indicates that polynucleotides and polypeptides corresponding to this gene are useful for treatment and diagnosis and/or treatment of disorders of the immune and hematopoietic system. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses).

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 844 of SEQ ID NO:46, b is an integer of 15 to 858, where both a and b correspond to the positions of nucleotide residues shown in SEQ ID NO:46, and where b is greater than or equal to a+14.

Features of Protein Encoded by Gene No: 37

This gene is expressed in multiple tissue systems such as brain, immune cells, prostate, uterus, testes, placenta, and fetal heart as well as in cancerous tissues such as ovarian tumors.

Therefore, polynucleotides and polypeptides of the invention are useful as reagents for differential identification of the tissue(s) or cell type(s) present in a biological sample and for diagnosis of diseases and conditions which include, but are not limited to, disorders of the immune, reproductive, urogenital, and central nervous system. Similarly, polypeptides and antibodies directed to these polypeptides are useful in providing immunological probes for differential identification of the tissue(s) or cell type(s). For a number of disorders of the above tissues or cells, particularly of the central nervous system and immune system, expression of this gene at significantly higher or lower levels may be routinely detected in certain tissues or cell types (e.g., immune, reproductive, urogenital, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 139 as residues: Tyr-33 to Lys-38. Polynucleotides encoding said polypeptides are also provided.

The tissue distribution indicates that polynucleotides and polypeptides corresponding to this gene are useful for treatment and diagnosis of disorders of the immune, urogenital, reproductive, and central nervous systems. The tissue distribution in central nervous system tissues indicates that polynucleotides and polypeptides corresponding to this gene are useful for the treatment and/or diagnosis of diseases of the central nervous system, as well as cancers of tissues where expression of this gene has been observed, such as in ovarian tumors.

The tissue distribution in central nervous system tissues also indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo.

Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues. The tissue distribution in uterus indicates that polynucleotides and polypeptides corresponding to this gene are useful for treating female infertility. The protein product is likely involved in preparation of the endometrium of implantation and could be administered either topically or orally. Alternatively, this gene could be transfected in gene-replacement treatments into the cells of the endometrium and the protein products could be produced. Similarly, these treatments could be performed during artificial insemination for the purpose of increasing the likelihood of implantation and development of a healthy embryo. In both cases this gene or its gene product could be administered at later stages of pregnancy to promote healthy development of the endometrium. Protein, as well as, antibodies directed against the protein may show utility as a tumor marker and/or immunotherapy targets for the above listed tissues. The tissue distribution in testes indicates that polynucleotides and polypeptides corresponding to this gene are useful for the treatment and diagnosis of conditions concerning proper testicular function (e.g. endocrine function, sperm maturation), as well as cancer. Therefore, this gene product is useful in the treatment of male infertility and/or impotence. This gene product is also useful in assays designed to identify binding agents, as such agents (antagonists) are useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 6093 of SEQ ID NO:47, b is an integer of 15 to 6107, where both a and b correspond to the positions of nucleotide residues shown in SEQ ID NO:47, and where b is greater than or equal to a+14.

Features of Protein Encoded by Gene No: 38

This gene is expressed in a wide range of tissue systems such as brain, immune cells, fetal liver, kidney, testes, breast, and pancreas as well as cancerous tissue such as ovarian tumors.

Therefore, polynucleotides and polypeptides of the invention are useful as reagents for differential identification of the tissue(s) or cell type(s) present in a biological sample and for diagnosis of diseases and conditions which include, but are not limited to, disorders of the central nervous system, immune system, urogenital, and reproductive system. Similarly, polypeptides and antibodies directed to these polypeptides are useful in providing immunological probes for differential identification of the tissue(s) or cell type(s). For a number of disorders of the above tissues or cells, particularly of the immune and central nervous system, expression of this gene at significantly higher or lower levels may be routinely detected in certain tissues or cell types (e.g., immune, CNS, urogenital, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 140 as residues: Met-I to Ser-7, Asp-32 to Pro-43, Ser-96 to Arg-102. Polynucleotides encoding said polypeptides are also provided.

The tissue distribution indicates that polynucleotides and polypeptides corresponding to this gene are useful for treatment and diagnosis of disorders of the immune, reproductive, urogenital and central nervous systems.

The tissue distribution in central nervous system tissues indicates that polynucleotides and polypeptides corresponding to this gene are useful for the treatment and/or diagnosis of diseases of the central nervous system, as well as cancers of tissues where expression of this gene has been observed, such as in ovarian tumors.

The tissue distribution in central nervous system tissues also indicates that polynucleotides and polypeptides corresponding to this gene are useful for the detection/treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

The tissue distribution indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement.

Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors to identify agents that modulate their interactions, in addition to its use as a nutritional supplement. Protein, as well as, antibodies directed against the protein may show utility as a tumor marker and/or immunotherapy targets for the above listed tissues. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 689 of SEQ ID NO:48, b is an integer of 15 to 703, where both a and b correspond to the positions of nucleotide residues shown in SEQ ID NO:48, and where b is greater than or equal to a+14.

Features of Protein Encoded by Gene No: 39

This gene is expressed primarily in macrophages and fetal cells and to a lesser extent in cancerous ovarian tissues.

Therefore, polynucleotides and polypeptides of the invention are useful as reagents for differential identification of the tissue(s) or cell type(s) present in a biological sample and for diagnosis of diseases and conditions which include, but are not limited to, immune diseases, disorders of developing tissues, and cancer. Similarly, polypeptides and antibodies directed to these polypeptides are useful in providing immunological probes for differential identification of the tissue(s) or cell type(s). For a number of disorders of the above tissues or cells, particularly of the fetal and immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene are useful for treatment and diagnosis of developmental abnormalities and disorders of the immune systems.

The tissue distribution cancerous ovaries indicates that polynucleotides and polypeptides corresponding to this gene are useful for the diagnosis and intervention of these tumors.

Expression of this gene product in macrophage cells strongly indicates a role for this protein in immune function and immune surveillance. This gene product may be involved in the regulation of cytokine production, antigen presentation, or other processes that may also suggest a usefulness in the treatment of cancer (e.g. by boosting immune responses). This gene product may have clinical utility in the treatment of immune dysfunction; in the correction of autoimmunity; in immune modulation; and in the control of inflammation.

The tissue distribution indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scieroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation.

The tissue distribution also indicates that polynucleotides and polypeptides corresponding to this gene are useful for the treatment, diagnosis, and/or prevention of various skin disorders such as melanomas. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 625 of SEQ ID NO:49, b is an integer of 15 to 639, where both a and b correspond to the positions of nucleotide residues shown in SEQ ID NO:49, and where b is greater than or equal to a+14.

Features of Protein Encoded by Gene No: 40

This gene is expressed primarily in neutrophils, bone marrow, brain, and fetal cells.

Therefore, polynucleotides and polypeptides of the invention are useful as reagents for differential identification of the tissue(s) or cell type(s) present in a biological sample and for diagnosis of diseases and conditions which include, but are not limited to, hematopoietic disorders, Limbic system dysfunction/defects and disorders of the immune system and developing systems. Similarly, polypeptides and antibodies directed to these polypeptides are useful in providing immunological probes for differential identification of the tissue(s) or cell type(s). For a number of disorders of the above tissues or cells, particularly of the immune, Limbic system and developing systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 142 as residues: Ala-84 to Gln-93. Polynucleotides encoding said polypeptides are also provided.

The tissue distribution indicates that polynucleotides and polypeptides corresponding to this gene are useful for treatment and diagnosis of disorders of the immune, Limbic system, CNS and developing systems. Expression of this gene product in bone marrow, eosinophils, and neutrophils strongly indicates a role for this protein in hematopoiesis and immune surveillance. This gene product may be involved in the regulation of cytokine production, antigen presentation, or other processes that may also suggest a usefulness in the treatment of cancer (e.g. by boosting immune responses). This gene product may have clinical utility in the treatment of immune dysfunction; in the correction of autoimmunity; in immune modulation; and in the control of inflammation.

The tissue distribution indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

Additionally, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 853 of SEQ ID NO:50, b is an integer of 15 to 867, where both a and b correspond to the positions of nucleotide residues shown in SEQ ID NO:50, and where b is greater than or equal to a+14.

Features of Protein Encoded by Gene No: 41

When tested against MVEC endothelial cell lines, supernatants removed from cells containing this gene activated the expression of ICAM-1. Thus, this gene activates signal transduction pathways which upregulate cell-surface expression and/or secretion of ICAM-1. ICAM-1—is found on the cell surface of endothelial cells, smooth muscle cells, epithelial cells, and fibroblasts. It binds to its ligand, LFA-1, a heterodimer complex that is a member of the leukocyte integrin family of cell adhesion receptors. Inflammatory mediators and cytokines, such as, IL-1, TNFa and IFNg, stimulate ICAM-1 expression on vascular cells, in addition to the aforementioned cells and tissue cell types. Polypeptides which increase ICAM expression are useful in the treatment of cancer, cardiovascular, autoimmune and inflammatory diseases and/or disorders.

This gene is expressed primarily in ovary and to a lesser extent in fetal tissue, colon, and immune cells.

Therefore, polynucleotides and polypeptides of the invention are useful as reagents for differential identification of the tissue(s) or cell type(s) present in a biological sample and for diagnosis of diseases and conditions which include, but are not limited to, ovarian cancer, gastrointestinal and immune system disorders. Similarly, polypeptides and antibodies directed to these polypeptides are useful in providing immunological probes for differential identification of the tissue(s) or cell type(s). For a number of disorders of the above tissues or cells, particularly of the female reproductive system, expression of this gene at significantly higher or lower levels may be routinely detected in certain tissues or cell types (e.g., reproductive, gastrointestinal, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 143 as residues: Ile-23 to Ala-29. Polynucleotides encoding said polypeptides are also provided.

The tissue distribution indicates that polynucleotides and polypeptides corresponding to this gene are useful for diagnosis and treatment of ovarian cancer and related metastases. The tissue distribution indicates that polynucleotides and polypeptides corresponding to this gene are also useful for treating female infertility. Additionally, the tissue distribution in colon tissues indicates that polynucleotides and polypeptides corresponding to this gene are useful for the diagnosis and/or treatment of disorders involving the gastrointestinal tract. This may include diseases associated with digestion and food absorption, as well as hematopoietic disorders involving the Peyer's patches of the small intestine, or other hematopoietic cells and tissues within the body. Similarly, expression of this gene product in colon tissue indicates again involvement in digestion, processing, and elimination of food, as well as a potential role for this gene as a diagnostic marker or causative agent in the development of colon cancer, and cancer in general.

Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1555 of SEQ ID NO:51, b is an integer of 15 to 1569, where both a and b correspond to the positions of nucleotide residues shown in SEQ ID NO:51, and where b is greater than or equal to a+14.

Features of Protein Encoded by Gene No: 42

The translation product of this gene shares sequence homology with retrovirus-related reverse transcriptase pseudogene. In addition, this gene shares homology with human interferon-beta (Genseq accession number T35524; all references available through this accession are hereby incorporated herein by reference), therefore, it is likely that this gene and the protein encoded by this gene shares some similar biological functions with this protein.

This gene is expressed primarily in frontal cortex.

Therefore, polynucleotides and polypeptides of the invention are useful as reagents for differential identification of the tissue(s) or cell type(s) present in a biological sample and for diagnosis of diseases and conditions which include, but are not limited to, neurodegenerative diseases and/or disorders. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in frontal cortex and homology to retrovirus-related reverse transcriptase pseudogene and human interferon-beta indicates that polynucleotides and polypeptides corresponding to this gene are useful for diagnosis and treatment of neurodegenerative diseases of the brain, particularly of the frontal cortex.

The tissue distribution indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, multiple sclerosis, cystic fibrosis, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1182 of SEQ ID NO:52, b is an integer of 15 to 1196, where both a and b correspond to the positions of nucleotide residues shown in SEQ ID NO:52, and where b is greater than or equal to a+14.

Features of Protein Encoded by Gene No: 43

This gene is expressed primarily in immune cells, brain, fetal tissue, and cancerous tissues (such as testes, stomach, lung, pancreas, ovaries) and to a lesser extent in other numerous tissues including, but not limited to, testes and kidney.

Therefore, polynucleotides and polypeptides of the invention are useful as reagents for differential identification of the tissue(s) or cell type(s) present in a biological sample and for diagnosis of diseases and conditions which include, but are not limited to, neurodegenerative diseases. Similarly, polypeptides and antibodies directed to these polypeptides are useful in providing immunological probes for differential identification of the tissue(s) or cell type(s). For a number of disorders of the above tissues or cells, particularly of the central nervous system and immune cells expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 145 as residues: Lys-23 to Lys-35, Met-46 to Tyr-52. Polynucleotides encoding said polypeptides are also provided.

The tissue distribution indicates that polynucleotides and polypeptides corresponding to this gene are useful for diagnosis and treatment of neurodegenerative disorders of the frontal cortex, as well as, cancer or a number of tissues including but not limited to testes, stomach, lung, pancreas, and ovaries.

The tissue distribution also indicates polynucleotides and polypeptides corresponding to this gene are useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

The tissue distribution indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 931 of SEQ ID NO:53, b is an integer of 15 to 945, where both a and b correspond to the positions of nucleotide residues shown in SEQ ID NO:53, and where b is greater than or equal to a+14.

Features of Protein Encoded by Gene No: 44

This gene is expressed primarily in epithelioid sarcoma and to a lesser extent in pancreatic carcinoma, aorta endothelial cells induced with TNF-alpha, and amniotic cells induced with TNF. This gene is also expressed, to a lesser extent, in cancerous lung and ovary tissue and fetal tissue.

Therefore, polynucleotides and polypeptides of the invention are useful as reagents for differential identification of the tissue(s) or cell type(s) present in a biological sample and for diagnosis of diseases and conditions which include, but are not limited to, epithelioid sarcoma and related cancers. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., cancerous and wounded tissues) or bodily fluids (e.g., amniotic, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 146 as residues: Tyr-39 to Arg-51. Polynucleotides encoding said polypeptides are also provided.

The tissue distribution indicates that polynucleotides and polypeptides corresponding to this gene are useful for diagnosis and treatment of certain cancers, including epithelioid sarcoma and pancreatic carcinoma.

The tissue distribution in tumors of lung, ovary, and pancreas origins indicates that polynucleotides and polypeptides corresponding to this gene are useful for the diagnosis and intervention of these tumors, in addition to other tumors where expression has been indicated.

Moreover, the expression within embryonic tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation.

The tissue distribution indicates polynucleotides and polypeptides corresponding to this gene are useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 474 of SEQ ID NO:54, b is an integer of 15 to 488, where both a and b correspond to the positions of nucleotide residues shown in SEQ ID NO:54, and where b is greater than or equal to a+14.

Features of Protein Encoded by Gene No: 45

In another embodiment, polypeptides comprising the amino acid sequence of the open reading frame upstream of the predicted signal peptide are contemplated by the present invention. Specifically, polypeptides of the invention comprise the following amino acid sequence: PPVPPWIS LPLTGSPPRPGFVPVSPFCFSPMTNGHQVLLLLL LTSAVAAGPWPQVHAGQWGWMCLPPGLPSVQARS GLGGLPGGPQWVPGGARGY (SEQ ID NO: 234). Polynucleotides encoding these polypeptides are also provided.

This gene is expressed primarily in fetal and infant tissue, particularly infant brain and fetal liver/spleen libraries, and to a lesser extent in breast, ovary tumor, pharynx carcinoma, endometrial stromal cells, thymus, islet cell tumors, and adult cerebellum.

Therefore, polynucleotides and polypeptides of the invention are useful as reagents for differential identification of the tissue(s) or cell type(s) present in a biological sample and for diagnosis of diseases and conditions which include, but are not limited to, cancer and other proliferative disorders. Similarly, polypeptides and antibodies directed to these polypeptides are useful in providing immunological probes for differential identification of the tissue(s) or cell type(s). For a number of disorders of the above tissues or cells, particularly of the brain and breast, expression of this gene at significantly higher or lower levels may be routinely detected in certain tissues or cell types (e.g., immune, developmental, hematopoietic, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in developing cells and tissues indicates that polynucleotides and polypeptides corresponding to this gene are useful for diagnosis and treatment of cancer and other proliferative disorders. The expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2846 of SEQ ID NO:55, b is an integer of 15 to 2860, where both a and b correspond to the positions of nucleotide residues shown in SEQ ID NO:55, and where b is greater than or equal to a+14.

Features of Protein Encoded by Gene No: 46

In another embodiment, polypeptides comprising the amino acid sequence of the open reading frame upstream of the predicted signal peptide are contemplated by the present invention. Specifically, polypeptides of the invention comprise the following amino acid sequence: IQQWGDSV LGRRCRDLLLQLYLQRPELRVPVPEVLLHSEGA ASSSVCKLDGLIHRFITLLADTSDSRALENRGADAS MACRKLAVAHPLLLLRHLPMIAALLHGRTHLNFQE FRQQNHLSCFLHVLGLLELLQPHVFRSEHQGAL WDCLLSFIRLLLNYRKSSRHLAAFINKFVQFIHKYI TYNAPAAISFLQKHADPLHDLSFDNSDLVMLKSLLA GLSLPSRDDRTDRGLDEEGEEESSAGSLPLVSVSLF TPLTAAEMAPYMKRLSRGQTVEDLLEVLSDIDEM SRRRPEILSFFSTNLQRLMSSAEECCRNLAFSLAL RSMQNSPSIAAAFLPTFMYCLGSQDFEVVQTALRN LPEYALLCQEHAAVLLHRAFLVGMYGQMDPSA QISEALRILHMEAVM (SEQ ID NO: 235). Polynucleotides encoding these polypeptides are also provided.

This gene is expressed primarily in breast cancer, and to a lesser extent in a variety of other cancers, including uterine cancer, synovial sarcoma, and pharynx carcinoma.

Therefore, polynucleotides and polypeptides of the invention are useful as reagents for differential identification of the tissue(s) or cell type(s) present in a biological sample and for diagnosis of diseases and conditions which include, but are not limited to, breast cancer; proliferative diseases and/or disorders. Similarly, polypeptides and antibodies directed to these polypeptides are useful in providing immunological probes for differential identification of the tissue(s) or cell type(s). For a number of disorders of the above tissues or cells, particularly of the breast, expression of this gene at significantly higher or lower levels may be routinely detected in certain tissues or cell types (e.g., reproductive, breast, proliferative, and cancerous and wounded tissues) or bodily fluids (e.g., lymph, serum, plasma, breast milk, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 148 as residues: Glu-35 to His-41, Ser-62 to Ala-67, Pro-145 to Leu-155, Glu-157 to Ser-163, Arg-190 to Val-197, Asp-208 to Pro-215, Ser-247 to Pro-252. Polynucleotides encoding said polypeptides are also provided.

The tissue distribution in breast cancer tissues indicates that polynucleotides and polypeptides corresponding to this gene are useful for the diagnosis and/or treatment of cancer. Elevated expression of this gene product in cancers, such as breast cancer, suggest that it may be involved in the abnormal proliferation of cells, dedifferentiation, angiogenesis, and other processes that accompany the development of cancer. Thus, therapeutics targeted against this gene product may be useful therapeutic products in and of themselves.

Alternately, expression of this gene product at elevated levels in breast tissue may be reflective of expression within breast lymph nodes, and may suggest a hematopoietic role for this protein. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1545 of SEQ ID NO:56, b is an integer of 15 to 1559, where both a and b correspond to the positions of nucleotide residues shown in SEQ ID NO:56, and where b is greater than or equal to a+14.

Features of Protein Encoded by Gene No: 47

The translation product of this gene shares limited sequence homology with cytochrome-c oxidase. An alternative embodiment is the polypeptide comprising the following amino acid sequence: MLLKHLQRMVS VPQVKASALKVVTLTANDKTSVSFSSLPGQGVIYN VIVWDPFLNTSAAYIPAHTYACSFEAGEGSCASL GRVSSKVFFTLFALLGFFICFFGHRFWKTELFFIGFI IMGFFFYILITRLTPIKYDVNLILTAVTGSVG GMFLVAVWWRFGILSICMLCVGLVLGFLISSVTFFT PLGNLKIFHDDGVFWVTFSCIAILIPVVFMGCL RILNILTCGVIGSYSVVLAIDSYWSTSLSYITL NVLKRALNKDFHRAFTNVPFQTNDFIILAVWGM LAVSGITLQIRRERGRPFFPPHPYKLWKQERERRVTNI LDPSYHIPPLRERLYGRLTQIKGLFQKEQPAGERT PLLL (SEQ ID NO: 236).

In another embodiment, polypeptides comprising the amino acid sequence of the open reading frame upstream of the predicted signal peptide are contemplated by the present invention. Specifically, polypeptides of the invention comprise the following amino acid sequence: WARLRGPGA HARTSPQPWRGPSPAQAAMGFLQLLVVXVLXSEHR VAGAAEVFGNSSEGLIEFSVGKFRYFELNRPFPEE AILHDISSNVTFLIFQIHSQYQNTTVSFSPRRRSPTM (SEQ ID NO: 237). Polynucleotides encoding these polypeptides are also provided.

This gene is expressed primarily in keratinocytes, brain, and spinal cord and to a lesser extent in hematopoietic cells and tissues.

Therefore, polynucleotides and polypeptides of the invention are useful as reagents for differential identification of the tissue(s) or cell type(s) present in a biological sample and for diagnosis of diseases and conditions which include, but are not limited to, neurodegenerative disorders; hematopoietic disorders; integumentary disorders; immune dysfunction; learning disabilities. Similarly, polypeptides and antibodies directed to these polypeptides are useful in providing immunological probes for differential identification of the tissue(s) or cell type(s). For a number of disorders of the above tissues or cells, particularly of the immune and nervous systems, expression of this gene at significantly higher or lower levels may be routinely detected in certain tissues or cell types (e.g., integumentary, neural, developmental, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain and spinal cord cells and tissues indicates that polynucleotides and polypeptides corresponding to this gene are useful for the diagnosis and treatment of a variety of neurological and hematopoietic disorders. For example, elevated levels of expression of this gene product in brain and spinal cord indicates that it may be involved in neurodegenerative disorders. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Alternately, expression of this gene product in hematopoietic cells indicates that it may be involved in the proliferation, differentiation, survival, and activation of all hematopoietic lineages, including stem and progenitor cells.

Expression of this gene product in keratinocytes indicates that it may be involved in normal skin function, and could be involved in skin disorders, dermatitis, and fibrosis. The protein is useful in detecting, treating, and/or preventing congenital disorders (i.e. nevi, moles, freckles, Mongolian spots, hemangiomas, port-wine syndrome), integumentary tumors (i.e. keratoses, Bowen's disease, basal cell carcinoma, squamous cell carcinoma, malignant melanoma, Paget's disease, mycosis fungoides, and Kaposi's sarcoma), injuries and inflammation of the skin (i.e., wounds, rashes, prickly heat disorder, psoriasis, dermatitis), atherosclerosis, uticaria, eczema, photosensitivity, autoimmune disorders (i.e. lupus erythematosus, vitiligo, dermatomyositis, morphea, scleroderma, pemphigoid, and pemphigus), keloids, striae, erythema, petechiae, purpura, and xanthelasma. In addition, such disorders may predispose increased susceptibility to viral and bacterial infections of the skin (i.e. cold sores, warts, chickenpox, molluscum contagiosum, herpes zoster, boils, cellulitis, erysipelas, impetigo, tinea, althletes foot, and ringworm).

Moreover, the protein product of this gene may also be useful for the treatment or diagnosis of various connective tissue disorders (i.e., arthritis, trauma, tendonitis, chrondomalacia and inflammation, etc.), autoimmune disorders (i.e., rheumatoid arthritis, lupus, scleroderma, dermatomyositis, etc.), dwarfism, spinal deformation, joint abnormalities, amd chondrodysplasias (i.e. spondyloepiphyseal dysplasia congenita, familial osteoarthritis, Atelosteogenesis type H, metaphyseal chondrodysplasia type Schmid). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2050 of SEQ ID NO:57, b is an integer of 15 to 2064, where both a and b correspond to the positions of nucleotide residues shown in SEQ ID NO:57, and where b is greater than or equal to a+14.

Features of Protein Encoded by Gene No: 48

In another embodiment, polypeptides comprising the amino acid sequence of the open reading frame upstream of the predicted signal peptide are contemplated by the present invention. Specifically, polypeptides of the invention comprise the following amino acid sequence: PRVRPASPPVR SPARWGSMAGSPLLWGPRAGGVGLLVLLLLGLFRP PPALCARPVKEPRGLSAASPPLARLALLAASG GQCPEVRRRGRCRPGAGAGASAGAERQERARAE AQRLRISRRASWRSCCASGAPPATLIRLWAWTTTP TRLQRSSLALCSAPALTLPP (SEQ ID NO: 238). Polynucleotides encoding these polypeptides are also provided.

This gene is expressed primarily in human pituitary and to a lesser extent in pineal gland, and other areas of the brain.

Therefore, polynucleotides and polypeptides of the invention are useful as reagents for differential identification of the tissue(s) or cell type(s) present in a biological sample and for diagnosis of diseases and conditions which include, but are not limited to, pituitary dysfunction; abnormal growth; neurological defects; insufficient milk secretion; abnormal smooth muscle contraction. Similarly, polypeptides and antibodies directed to these polypeptides are useful in providing immunological probes for differential identification of the tissue(s) or cell type(s). For a number of disorders of the above tissues or cells, particularly of the endocrine and nervous systems, expression of this gene at significantly higher or lower levels may be routinely detected in certain tissues or cell types (e.g., endocrine, developmental, reproductive, and cancerous and wounded tissues) or bodily fluids (e.g., lymph, serum, plasma, urine, amniotic fluid, breast milk, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 150 as residues: Pro-36 to Gly-42, Pro-64 to Ala-76, Gly-83 to Ala-90, Ser-100 to Cys-108, Thr-126 to Ser-135. Polynucleotides encoding said polypeptides are also provided.

The tissue distribution primarily in pituitary cells and tissues indicates that polynucleotides and polypeptides corresponding to this gene are useful for the diagnosis and/or treatment of a variety of disorders, particularly of the endocrine system.

Elevated expression of this gene product in the pituitary indicates that it may be possibly a hormone-like substance that either controls pituitary development itself, or various processes controlled by the pituitary. These include growth, milk secretion, smooth muscle contraction, diuresis, blood pressure, and homeostasis. Thus, this gene product may have numerous clinical applications.

Moreover, expression of this gene product in other regions of the brain indicates that it may be involved in normal neurological function, and may be useful in the treatment of a variety of neurological disorders. Representative uses are described in the "Biological Activity", "Hyperproliferative Disorders", and "Binding Activity" sections below, in Example 11, 17, 18, 19, 20 and 27, and elsewhere herein. Briefly, the protein can be used for the detection, treatment, and/or prevention of Addison's disease, Cushing's Syndrome, and disorders and/or cancers of the pancreas (e.g. diabetes mellitus), adrenal cortex, ovaries, pituitary (e.g., hyper-, hypopituitarism), thyroid (e.g. hyper-, hypothyroidism), parathyroid (e.g. hyper-, hypoparathyroidism), hypothallamus, and testes. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1036 of SEQ ID NO:58, b is an integer of 15 to 1050, where both a and b correspond to the positions of nucleotide residues shown in SEQ ID NO:58, and where b is greater than or equal to a+14.

Features of Protein Encoded by Gene No: 49

In another embodiment, polypeptides comprising the amino acid sequence of the open reading frame upstream of the predicted signal peptide are contemplated by the present invention. Specifically, polypeptides of the invention comprise the following amino acid sequence: PRVRLATPNI WDLSMLFAFISLLVMLPTWWIVSSWLVWGVILF VYLVIRALRLWRTAKLQVTLKKYSVHLEDMAT NSRAFTNLVRKALRLIQETEVISRGFTLVSAACPFNK AGQHPSQHLIGLRKAVYRTLRANFQAARLATLYM LKNYPLNSESDNVTNYICVVPFKELGLGLSEEQI SEEEAHNFTDGFSLPALKVLFQLWVAQSSEFFRRLA LLLSTANSPPGPLLTPALLPHRILSDVTQGLPHAH SACLEELKRSYE FYRYFETQHQSVPQCLSKTQQK SRELNNVHTAVRSLQLHLKALLNEVILEDELEK LVCTKETQELVSEAYPILEQKLKLIQPHVQAS NNCWEEAISQVDKLLRRNTDKKGKPEIACENPH CTVSTFEAAYSTHCRQRSNPRGAGIRSLCR (SEQ ID NO: 239). Polynucleotides encoding these polypeptides are also provided.

The polypeptide of this gene has been determined to have a transmembrane domain at about amino acid position 7–23 of the amino acid sequence referenced in Table 1 for this gene. Moreover, a cytoplasmic tail encompassing amino acids 24 to 390 of this protein has also been determined. Based upon these characteristics, it is believed that the protein product of this gene shares structural features to type Ib membrane proteins.

The gene encoding the disclosed cDNA is believed to reside on chromosome 12. Accordingly, polynucleotides related to this invention are useful as a marker in linkage analysis for chromosome 12.

This gene is expressed primarily in prostate and placenta and to a lesser extent in pancreatic tumors and hematopoietic cells.

Therefore, polynucleotides and polypeptides of the invention are useful as reagents for differential identification of the tissue(s) or cell type(s) present in a biological sample and for diagnosis of diseases and conditions which include, but are not limited to, prostate cancer; pancreatic cancer; prostate dysfunction; hematopoietic disorders; reproductive diseases and/or disorders, and pancreatitis. Similarly, polypeptides and antibodies directed to these polypeptides are useful in providing immunological probes for differential identification of the tissue(s) or cell type(s). For a number of disorders of the above tissues or cells, particularly of the endocrine and immune systems, expression of this gene at significantly higher or lower levels may be routinely detected in certain tissues or cell types (e.g., reproductive, prostate, pancreas, placental, vascular, and cancerous and wounded tissues) or bodily fluids (e.g., lymph, serum, seminal fluid, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 151 as residues: Pro-85 to Ser-94, Pro-127 to Thr-136, Glu-154 to Glu-160, Phe-240 to Ser-250, Leu-255 to Leu-265, Leu-341 to Lys-351, Thr-372 to Gly-384. Polynucleotides encoding said polypeptides are also provided.

The tissue distribution in prostate and placental cells and tissues indicates that polynucleotides and polypeptides corresponding to this gene are useful for the diagnosis and/or treatment of a variety of reproductive disorders. Elevated expression of this gene product in the prostate indicates that it may be involved in normal prostate function, and may be a diagnostic marker for prostate cancer.

Alternately, expression of this gene product in placenta indicates that it may play a role in normal vascular function, and may be involved in such processes as angiogenesis and endothelial cell chemotaxis. Thus, this gene product may be useful in the treatment of myocardial infarction, cancer, ischemia, and diabetic retinopathy. Expression of this gene product in placenta may also be indicative of fetal health and development. Similarly, expression of this gene product in hematopoietic cells indicates that it may be involved in the proliferation, differentiation, survival, or activation of all hematopoietic cell lineages. Finally, expression of this gene product in pancreatic cancers indicates that it may play a role in cancer in general, or in pancreatic function.

The secreted protein may also be used to determine biological activity, to raise antibodies, as tissue markers, to isolate cognate ligands or receptors, to identify agents that modulate their interactions, and as nutritional supplements. It may also have a very wide range of biological activities. Representative uses are described in the "Chemotaxis" and "Binding Activity" sections below, in Examples 11, 12, 13, 14, 15, 16, 18, 19, and 20, and elsewhere herein. Briefly, the protein may possess the following activities: cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating hemophilia, cardiac infarction etc.); anti-inflammatory activity (e.g. for treating septic shock, Crohn's disease); as antimicrobials; for treating psoriasis or other hyperproliferative diseases; for regulation of metabolism, and behavior. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2519 of SEQ ID NO:59, b is an integer of 15 to 2533, where both a and b correspond to the positions of nucleotide residues shown in SEQ ID NO:59, and where b is greater than or equal to a+14.

Features of Protein Encoded by Gene No: 50

When tested against Jurkat and K562 cell lines, supernatants removed from cells containing this gene activated the GAS (gamma activating sequence) and ISRE (interferon-sensitive responsive element) promoter elements, respectively. Thus, it is likely that this gene activates myeloid, leukemia, and to a lesser extent, other immune or hematopoietic cells and tissue cell-types, through the JAK-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells. ISRE is also a promoter element found upstream in many genes which are involved in the Jak-STAT pathway. The Jak-STAT pathway is a large, signal transduction pathway involved in the differentiation and proliferation of cells. Therefore, activation of the Jak-STAT pathway, reflected by the binding of the ISRE element, can be used to indicate proteins involved in the proliferation and differentiation of cells.

In another embodiment, polypeptides comprising the amino acid sequence of the open reading frame upstream of the predicted signal peptide are contemplated by the present invention. Specifically, polypeptides of the invention comprise the following amino acid sequence: AAPHPPLLR PLCLWCPLWPAWPLRGRPRSAWKRWPPLPVGPA KLGCSMTTRQPTAVSWPCWLMSSSLSTACLAW TLTGSLAREATRRARSLSPTWNCSARQVPPSPPHS GLGRRGWAHCHLTCLLVTQLFRVGRIHPILSLPLVT (SEQ ID NO: 240). Polynucleotides encoding these polypeptides are also provided.

This gene is expressed primarily in brain and placenta.

Therefore, polynucleotides and polypeptides of the invention are useful as reagents for differential identification of the tissue(s) or cell type(s) present in a biological sample and for diagnosis of diseases and conditions which include, but are not limited to, vascular diseases; aberrant angiogenesis; neurological disorders; learning disorders; placental insufficiency; and fetal distress. Similarly, polypeptides and antibodies directed to these polypeptides are useful in providing immunological probes for differential identification of the tissue(s) or cell type(s). For a number of disorders of the above tissues or cells, particularly of the vascular and neurological systems (CNS/PNS), expression of this gene at significantly higher or lower levels may be routinely detected in certain tissues or cell types (e.g., neural, reproductive, vascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 152 as residues: Met-1 to Thr-7, Glu-36 to Ser-43, Pro-46 to Gly-63. Polynucleotides encoding said polypeptides are also provided.

The tissue distribution in brain and placental cells and tissues, combined with the detected GAS and ISRE biological activities, indicates that the protein products of this gene are useful for the diagnosis and/or treatment of a variety of neural, reproductive, and vascular diseases and/or disorders. neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Expression of this gene product in placenta indicates that it may play a role in blood vessel development or function, as the placenta is a highly vascularized organ. Thus, this gene product may be involved in such processes as angiogenesis, endothelial cell chemotaxis, and vascular cord formation. Thus, it may be useful in the treatment of such conditions as myocardial infarction; ischemia; and cancer.

Alternately, expression of this gene product in the brain indicates that it may play a role in the survival, proliferation, or function of neurons, and thus may be useful in the diagnosis and treatment of such neurological disorders as ALS, schizophrenia, and Alzheimer's disease. It may likewise be involved in learning disorders as well. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 885 of SEQ ID NO:60, b is an integer of 15 to 899, where both a and b correspond to the positions of nucleotide residues shown in SEQ ID NO:60, and where b is greater than or equal to a+14.

Features of Protein Encoded by Gene No: 51

In another embodiment, polypeptides comprising the amino acid sequence of the open reading frame upstream of the predicted signal peptide are contemplated by the present invention. Specifically, polypeptides of the invention comprise the following amino acid sequence: LQLASQSAGIK GMSHCARPTFLTLLLASCFWAAAIPNRNVILSVSFR PLHMQFTLSILVFILRILILLRSFL (SEQ ID NO: 241). Polynucleotides encoding these polypeptides are also provided.

The polypeptide of this gene has been determined to have a transmembrane domain at about amino acid position 40-56 of the amino acid sequence referenced in Table 1 for this gene. Moreover, a cytoplasmic tail encompassing amino acids 57 to 60 of this protein has also been determined. Based upon these characteristics, it is believed that the protein product of this gene shares structural features to type Ia membrane proteins.

This gene is expressed primarily in spleen derived from patients with chronic lymphocytic leukemia.

Therefore, polynucleotides and polypeptides of the invention are useful as reagents for differential identification of the tissue(s) or cell type(s) present in a biological sample and for diagnosis of diseases and conditions which include, but are not limited to, chronic lymphocytic leukemia; hematopoietic disorders; impaired immune function; cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in spleen cells and tissues indicates that polynucleotides and polypeptides corresponding to this gene are useful for the diagnosis and/or treatment of a variety of hematopoietic disorders. Representative uses are described in the "Immune Activity" and "Infectious Disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Elevated expression of this protein in the spleens of patients with CLL indicates that it may be a useful marker for this disease. Alternately, it may be associated with the development and/or progression of the disease, and may be a useful target for therapeutic intervention. Additionally, this gene product may play more general roles in hematopoiesis, and may serve to control cellular decisions regarding proliferation, survival, activation, and/or differentiation of all hematopoietic cell lineages. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1065 of SEQ ID NO:61, b is an integer of 15 to 1079, where both a and b correspond to the positions of nucleotide residues shown in SEQ ID NO:61, and where b is greater than or equal to a+14.

Features of Protein Encoded by Gene No: 52

The translation product of this gene shares sequence homology with a putative protein tyrosine kinase from the Chilo iridescent virus. See, for example, Genbank accession no. gi|2738451 (AF003534). Based on the sequence similarity, the translation product of this gene is expected to share at least some biological activities with tyrosine kinases and signaling proteins. Such activities are known in the art, some of which are described elsewhere herein.

This gene is expressed in a variety of tissues, including microvascular endothelial cells, dendritic cells, and fetal tissues. as well as several tumors.

Therefore, polynucleotides and polypeptides of the invention are useful as reagents for differential identification of the tissue(s) or cell type(s) present in a biological sample and for diagnosis of diseases and conditions which include, but are not limited to, vascular, immune, and developmental diseases and/or disorders, particularly cancer. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., vascular, immune, developmental, proliferative, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 154 as residues: Ala-21 to Lys-3 1, Arg-41 to Cys-56, Thr-92 to Cys-102, Arg-132 to Val-137, Lys-152 to Ile-159, Pro-199 to Ser-205, Arg-210 to Asp-219, Ser-225 to Lys-230, Tyr-236 to Ala-241, Lys-243 to Leu-249, Thr-375 to Asp-381. Polynucleotides encoding said polypeptides are also provided.

The tissue distribution and homology to a tyrosine kinase indicates that polynucleotides and polypeptides corresponding to this gene are useful for diagnosis and treatment of cancer. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Alternatively, the protein is useful in the detection, treatment, and/or prevention of vascular conditions, which include, but are not limited to, microvascular disease, vascular leak syndrome, aneurysm, stroke, atherosclerosis, arteriosclerosis, or embolism. For example, this gene product may represent a soluble factor produced by smooth muscle that regulates the innervation of organs or regulates the survival of neighboring neurons. Likewise, it is involved in controlling the digestive process, and such actions as peristalsis. Similarly, it is involved in controlling the vasculature in areas where smooth muscle surrounds the endothelium of blood vessels. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1914 of SEQ ID NO:62, b is an integer of 15 to 1928, where both a and b correspond to the positions of nucleotide residues shown in SEQ ID NO:62, and where b is greater than or equal to a+14.

Features of Protein Encoded by Gene No: 53

The polypeptide of this gene has been determined to have a transmembrane domain at about amino acid position 2–18 of the amino acid sequence referenced in Table 1 for this gene. Based upon these characteristics, it is believed that the protein product of this gene shares structural features to type lb membrane proteins.

The translation product of this gene shares some homology with IL-6DPB, a nuclear, leucine-zipper containing, transcriptional regulator protein involved in interleukin-6 signal transduction (see e.g., GenBank Accession GI:204918; all references available through this accession are hereby incorporated herein by reference); for example, Roll, V. et al., Cell 63, 643–653 (1990). Therefore, this gene product is expected to have at least some biological activities in common with transcriptional regulatory proteins.

This gene is expressed primarily in neutrophils.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic diseases and/or disorders, particularly cancer and immune suppression. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 155 as residues: Gly-63 to Ser-72. Polynucleotides encoding said polypeptides are also provided.

The tissue distribution in neutrophils indicates that polynucleotides and polypeptides corresponding to this gene are useful as a marker for neutrophil monitoring in cancer and/or immune suppressed patients and/or during chemotherapy or radiation therapy. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:63 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 767 of SEQ ID NO:63, b is an integer of 15 to 781, where both a and b correspond to the positions of nucleotide residues shown in SEQ ID NO:63, and where b is greater than or equal to a+14.

Features of Protein Encoded by Gene No: 54

This gene is expressed primarily in IL-1 and LPS induced neutrophils, and to a lesser extent, in fetal brain.

Therefore, polynucleotides and polypeptides of the invention are useful as reagents for differential identification of the tissue(s) or cell type(s) present in a biological sample and for diagnosis of diseases and conditions which include, but are not limited to, immune, hematopoietic, and neural diseases and/or disorders, particularly cancer and immune suppression. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, neural, and cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 156 as residues: Ile-28 to Trp-37, Ser-68 to Lys-81. Polynucleotides encoding said polypeptides are also provided.

The tissue distribution in neutrophils indicates that polynucleotides and polypeptides corresponding to this gene are useful as a marker in neutrophils to monitor patients who are immune suppressed or cancer patients during chemotherapy or radiation therapy. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stein cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

Alternatively, polynucleotides and polypeptides corresponding to this gene are useful for the detection, treatment, and/or prevention of neurodegenerative disease states, behavioral disorders, or inflammatory conditions. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:64 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1180 of SEQ ID NO:64, b is an integer of 15 to 1194, where both a and b correspond to the positions of nucleotide residues shown in SEQ ID NO:64, and where b is greater than or equal to a+14.

Features of Protein Encoded by Gene No: 55

This gene is expressed primarily in prostate.

Therefore, polynucleotides and polypeptides of the invention are useful as reagents for differential identification of the tissue(s) or cell type(s) present in a biological sample and for diagnosis of diseases and conditions which include, but are not limited to, urogenital diseases and/or disorders, particularly prostate cancer. Similarly, polypeptides and antibodies directed to these polypeptides are useful in providing immunological probes for differential identification of the tissue(s) or cell type(s). For a number of disorders of the above tissues or cells, particularly of the urogenital system, expression of this gene at significantly higher or lower levels may be routinely detected in certain tissues or cell types (e.g., urogenital, prostate, renal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 157 as residues: Arg-30 to Gln-36. Polynucleotides encoding said polypeptides are also provided.

The tissue distribution in prostate cancer cells indicates that polynucleotides and polypeptides corresponding to this gene are useful for study, treatment and diagnosis of prostate cancer and other urogenital disorders. Moreover, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:65 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1663 of SEQ ID NO:65, b is an integer of 15 to 1677, where both a and b correspond to the positions of nucleotide residues shown in SEQ ID NO:65, and where b is greater than or equal to a+14.

Features of Protein Encoded by Gene No: 56

A preferred polypeptide of the invention comprises the following amino acid sequence: MVLVLRHPLCAR ERAFREPGRGLLTRTGQHDGAPAVTAVPGPLGAV AAAEGRRSAWGAGGSSPPRKVLWGDMRGR RAGVDVLGPALSSEAAGAEARGWGMPGMGVGV GASETRGALFLGREGVHGPCPMDGLGPWPWGPW (SEQ ID NO: 242). Polynucleotides encoding these polypeptides are also provided.

This gene is expressed primarily in rejected kidney.

Therefore, polynucleotides and polypeptides of the invention are useful as reagents for differential identification of the tissue(s) or cell type(s) present in a biological sample and for diagnosis of diseases and conditions which include, but are not limited to, diseases and/or disorders affecting the kidney. Similarly, polypeptides and antibodies directed to these polypeptides are useful in providing immunological probes for differential identification of the tissue(s) or cell type(s). For a number of disorders of the above tissues or cells, particularly of the urinary tract, expression of this gene at significantly higher or lower levels may be routinely detected in certain tissues or cell types (e.g., urogenital, renal, kidney, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 158 as residues: Ala-30 to Gly-36, Asp-45 to Trp-50, Lys-65 to Cys-71, Pro-80 to Cys-87. Polynucleotides encoding said polypeptides are also provided.

The tissue distribution in kidney indicates the protein product of this gene could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. The protein is useful for modulating the immune response to aberrant proteins, as may exist in proliferating cells and tissues. Such modulation of the immune response would also show utility in inhibiting the rejection of transplanted tissues, particularly of the renal system. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:66 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1223 of SEQ ID NO:66, b is an integer of 15 to 1237, where both a and b correspond to the positions of nucleotide residues shown in SEQ ID NO:66, and where b is greater than or equal to a+14.

Features of Protein Encoded by Gene No: 57

The translation product of this gene shares sequence homology with both human and mouse Fibulin polypeptides which is are extracellular matrix proteins found in heart tissue (See Genbank Accession Nos. emblCAA57876.1 and emblCAA53040.1, respectively; all references available through these accessions are hereby incorporated herein by reference; for example, J. Cell Biol. 123 (5), 1269–1277 (1993)).

Preferred polypeptides encoded by this gene comprise the following amino acid sequence: MGPAVKMWTNAWKGLDDCHYNQLCENTPGGHRCSCPRGYRMQGPSLPCLDVNECLQLPKACAYQCHNLQGSYRCLCPPGQTLLRDGKACTSLERNGQNVTTVSHRGPLLPWLRPWASIPGTSYHAWVSLRPGPMALSSVGRAWCPPGFIRQNGVCTDLDECRVRNLCQHACRNTEGSYQCLCPAGYRLLPSGKNCQDINECEEESIECGPGQMCFNTRGSYQCVDTPCPATYRQGPSPGTCFRRCSQDCGTGGPSTLQYRLLPLPLGVRAHHDVARLTAFSEVGVPANRTELSMLEPDPRSPFALRPLRAGLGAVYTRRALTRAGLYRLTVRAAAPRHQSVFVLLIAVSPYPY (SEQ ID NO: 243). Polynucleotides encoding these polypeptides are also provided.

A preferred polypeptide fragment of the invention comprises the following amino acid sequence: MRVLVVTIAPIYWALARESGEALNGHSLTGGKFRQSHTWSLLQGAAHDDPVARGLDPDGLLLLDVVVNGVVPGRAWLTQIFKCRTLKKHYVQTRAWPAVRGLHTALLPGRPPLVPTLQPQHPVQRGPGPPAPAGAAPAGLSYQLGL (SEQ ID NO: 244). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: HASGAFLVVRGEPQGSWGSMTGVINGRKFGVATLNTSVMQEAHSGVSSIHSSIRHVPANVGPLMRVLVVTIAPIYWALAREFSGEALNGHSLTGGKFRQESHVEFATGELLTMTQWPGVWIPMASCSSTWWSMALSPDSLADADLQVQDFEEHYVQTGPGQLFVGSTQRFFQGGLPSFLRCNHSIQYNAARGPQPQLVQHLRASAISSAFDPEAEALRFQLATALQAEENEVGCPEGFELDSQGAFCVDVDECAWDAHLCREGQRCVNLLGSYRCLPDCGPGFRVADGAGCEDVDECLEGLDDCHYNQLCENTPGGHRCSCPRGYRMQGPSLPCLDVNECLQLPKACAYQCHNLQGSYRCLCPPGQTLLRDGKACTSLERNGQNVTTVSHRGPLLPWLRPWASIPGTSYHAWVSLRPGPMALSSVGRAWCPPGFIRQNGVCTDLDECRVRNLCQHACRNTEGSYQCLCPAGYRLLPSGKNCQDINECEEESIECGPGQMCFNTRGSYQCVDTPCPATYRQGPSPGTCFRRCSQDCGTGGPSTLQYRLLPLPLGVRAHHDVARLTAFSEVGVPANRTELSMLEPDPRSPFALRPLRAGLGAVYTRRALTRAGLYRLTVRAAAPRHQSVFVLLIAVSPYPY (SEQ ID NO: 245). Polynucleotides encoding these polypeptides are also provided.

When tested against U937 and Jurkat cell lines, supernatants removed from cells containing this gene repeatedly activated the GAS (gamma activating sequence) promoter element. Thus, it is likely that this gene activates myeloid, T-cells, and to a lesser extent, other immune and hematopoietic cells and tissue cell types, through the JAK-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in kidney.

Therefore, polynucleotides and polypeptides of the invention are useful as reagents for differential identification of the tissue(s) or cell type(s) present in a biological sample and for diagnosis of diseases and conditions which include, but are not limited to, diseases and/or disorders affecting the kidney and renal system. Similarly, polypeptides and antibodies directed to these polypeptides are useful in providing immunological probes for differential identification of the tissue(s) or cell type(s). For a number of disorders of the above tissues or cells, particularly of the urinary tract, expression of this gene at significantly higher or lower levels may be routinely detected in certain tissues or cell types (e.g., renal, urogenital, kidney, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 159 as residues: Lys-32 to Ser-37, His-89 to Gly-94, Asn-124 to Gln-130, Ala-163 to Val-168, Cys-196 to Arg-201, Gln-244 to Gln-264, His-288 to Tyr-294, Leu-314 to Gln-319, Ala-392 to Ser-399, Pro-412 to Asp-419, Ala-452 to Pro-460, Arg-466 to Thr-473. Polynucleotides encoding said polypeptides are also provided.

The tissue distribution in rejected kidney, the homology to the conserved Fibulin-2 protein, in addition to the detected GAS biological activity, indicates that polynucleotides and polypeptides corresponding to this gene are useful for the diagnosis and treatment of disorders affecting kidneys, particularly proliferative disorders. Representative uses are described here and elsewhere herein.

The protein product of this gene could be used in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:67 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1920 of SEQ ID NO:67, b is an integer of 15 to 1934, where both a and b correspond to the positions of nucleotide residues shown in SEQ ID NO:67, and where b is greater than or equal to a+14.

Features of Protein Encoded by Gene No: 58

Preferred polypeptides encoded by this gene comprise the following amino acid sequence: MGEKFLLLAMKENHPECFCKILKILHCMDPGEWLPQTEHCVHLTPKEFLIWTMDIASNERSEIQSVALRLASKVISHHMQTCVENRELIAAELKQWVQLVILSCEDHLPTESRLAVVEVLTSTTPLFLTNPHPILELQDTLALWKCVLTLLQSEEQAVRDAATETVTTAMSQENTCQSTEFAFCQVDASIALALALAVLCDLLQQWDQLAPGLPILLGWLLGESDDLVACVESMHQVEEDYLFEKAEVNFWAETLIFVKYLCKHLFCLLSKSGWRPPSPEMLCHLQRMVSEQCHLLSQFFRELPPAAEFVKTVEFTRLRIQEERTLACLRLLAFLEGKEGEDTLVLSVWDSYAESRQLTLPRTEAAC (SEQ ID NO: 246). Polynucleotides encoding such polypeptides are also provided.

A preferred polypeptide fragment of the invention comprises the following amino acid sequence: MGEPNRHPSMFLLLLVLERLYASPMDGTSSALSMGPFVPFIMRCGHSPVYHSREMAARALVPFVMIDHIPNTIRTLLSTLPSCTDQCFRAKPHSWGHFSRFFHLLQAYSDSKTRNEFRLPARAD (SEQ ID NO: 247). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: MTGREFFSRFPELYPFLLKQLETVANTVDSDMGEPNRHPSMFLLLLVLERLYASPMDGTSSALSMGPFVPFIMRCGHSPVYHSREMAARALVPFVMIDHIPNTIRTLLSTLPSCTDQCFRQNHIHGTLLQVFHLLQAYSDSKHGTNSDFQHELTDITVCTKAKLWLAKRQNPCLVTRAVYIDILFLLTCCLNRSAKDNQPVLESLGFWEEVRGIISGSELITGFPWAFKVPGLPQYLQSLTRLAIAAVWAAAAKSGERETNVPISFSQLLESAFPEVRSLTLEALLEKFLAAASGLGEKGVPPLLCNMGEKFLLLAMKENHPECFCKILKILHCMDPGEWLPQTEHCVHLTPKEFLIWTMDIASNERSEIQSVALRLASKVISHHMQTCVENRELIAAELKQWVQLVILSCEDHLPTESRLAVVEVLTSTTPLFLTNPHPILELQDTLALWKCVLTLLQSEEQAVRDAATETVTTAMSQENTCQSTEFAFCQVDASIALALALAVLCDLLQQWDQLAPGLPILLGWLLGESDDLVACVESMHQVEEDYLFEKAEVNFWAETLIFVKYLCKHLFCLLSKSGWRPPSPEMLCHLQRMVSEQCHLLSQFFRELPPAAEFVKTVEFTRLRIQEERTLACLRLLAFLEGKEGEDTLVLSVWDSYAESRQLTLPRTEAAC (SEQ ID NO: 248). Polynucleotides encoding these polypeptides are also provided.

The polypeptide of this gene has been determined to have two transmembrane domains at about amino acid position 144-160, and 462-478 of the amino acid sequence referenced in Table 1 for this gene. Based upon these characteristics, it is believed that the protein product of this gene shares structural features to type IIIa membrane proteins.

Included in this invention as a preferred domain is the formate and nitrite transporters domain, which was identified using the ProSite analysis tool (Swiss Institute of Bioinformatics). A number of bacterial and archaebacterial proteins involved in transporting formate or nitrite have been shown [1] to be related: -focA and focB, from *Escherichia coli*, transporters involved in the bidirectional transport of formate. -fdhc, from *Methanobacterium formicicum* and thermoformicicum, a probable formate transporter. -nirC, from *Escherichia coli* and Salmonella typhimurium, a probable nitrite transporter. -*Bacillus subtilis* hypothetical protein yrhG. -*Bacillus subtilis* hypothetical protein ywcJ (ipa-48R). These transporters are proteins of about 280 residues and seem to contain six transmembrane regions. As signature patterns, we selected two conserved regions. The first one is located in what seems to be a cytoplasmic loop between the second and third transmembrane domains; the second is part of the fourth transmembrane region. The 70 Kd yeast hypothetical protein YHL008c is highly similar, in its N-terminal section, to the prokaryotic members of this family. The concensus pattern is as follows: [LIVMA]-[LIVMY]-x-G-[GSTA]-[DES]-L-[FI]-[TN]-[GS].

Preferred polypeptides of the invention comprise the following amino acid sequence: IISGSELITG (SEQ ID NO: 249). Polynucleotides encoding these polypeptides are also provided.

Further preferred are polypeptides comprising the formate and nitrite transporter domain of the sequence referenced in Table 1 for this gene, and at least 5, 10, 15, 20, 25, 30, 50, or 75 additional contiguous amino acid residues of this referenced sequence. The additional contiguous amino acid residues may be N-terminal or C-terminal to the formate and nitrite transporter domain. Alternatively, the additional contiguous amino acid residues may be both N-terminal and C-terminal to the formate and nitrite transporter domain, wherein the total N- and C-terminal contiguous amino acid residues equal the specified number. The above preferred polypeptide domain is characteristic of a signature specific to formate and nitrite transporter proteins. Based on the sequence similarity, the translation product of this gene is expected to share at least some biological activities with formate and nitrite transporter proteins. Such activities are known in the art, some of which are described elsewhere herein.

It is believed that this gene maps to chromosome 2. Accordingly, polynucleotides derived from this gene are useful in linkage analysis as markers for chromosome 2.

This gene is expressed primarily in cells of the immune system, primarily T-cells and to a lesser extent in spleen, liver, thymus, tonsils, and testis. Therefore, polynucleotides and polypeptides of the invention are useful as reagents for differential identification of the tissue(s) or cell type(s) present in a biological sample and for diagnosis of diseases and conditions which include, but are not limited to, immune and hematopoietic diseases and/or disorders, particularly disorders affecting hematopoiesis. Similarly, polypeptides and antibodies directed to these polypeptides are useful in providing immunological probes for differential identification of the tissue(s) or cell type(s). For a number of disorders of the above tissues or cells, particularly of hematopoetic cells, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 160 as residues: Gly-2 to Pro-8, Ser-82 to His-92, Tyr-107 to Asp-117, Arg-162 to Pro-169, Ser-224 to Thr-229, Leu-310 to His-315, Ser-333 to Glu-338, Glu-381 to Ser-388, Gln-428 to Ala-433, Met-446 to Thr-455, Ser-548 to Ser-554, Gly-613 to Asp-618, Ser-627 to Gln-633. Polynucleotides encoding said polypeptides are also provided.

The tissue distribution in immune cells and tissues indicates that polynucleotides and polypeptides corresponding to this gene are useful for the diagnosis and treatment of disorders affecting hematopoiesis, including cancers. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:68 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 3286 of SEQ ID NO:68, b is an integer of 15 to 3300, where both a and b correspond to the positions of nucleotide residues shown in SEQ ID NO:68, and where b is greater than or equal to a+14.

Features of Protein Encoded by Gene No: 59

This gene is expressed primarily in bone marrow, CD34 positive cells, and immune cells, including, neutrophils, T-cells, B-cells, macrophages, monocytes, and dendritic cells and to a lesser extent in brain and tonsils.

In one embodiments, polypeptides comprising the amino acid sequence of the open reading frame upstream of the predicted signal peptide are contemplated by the present invention. Specifically, polypeptides of the invention may comprise, or alternatively consist of the following amino acid sequence: VDGIDKLDIEFLQQFLETHSRGPRLH SPGHASQEATPGANMSSGTELLWPGAALLVLLG VAASLCVRCSRPGAKRSEKIYQQRSLREDQQSFTG SRTYSLVGQAW PGPLADMAPTRKDKLLQFYPSLE DPASSRYQNFSKGSRHGSEEAYIDPIAMEYYNWGRF SKPPEDDDANSYENVLICKQKTTETGAQQEG IGGLCRGDLSLSLAL KTGPTSGLCPSASPEEDEGI (SEQ ID NO: 250). Polynucleotides encoding these polypeptides are also provided.

Preferred polypeptide fragments may comprise or alternatively consist of one, two, three, four or more of the following amino acid sequence: ASSRYQNFSKGSRHG SEEAYIDPIA (SEQ ID NO: 251), MEYYNWGRF SKPPEDDDANSY (SEQ ID NO: 252), ENVLICKQKT TETGAQQEGIGGLCRGD (SEQ ID NO: 253), VRCSR PGAKRSEKIYQQRSLREDQQSFTGSRTYSLVGQA WPGPLADMAPTRKDKLLQ FYPSLEDPASS (SEQ ID NO: 255) and LSLSLALKTGPTSGLCPSASPEEDEGI (SEQ ID NO: 254). Polynucleotides encoding these polypeptide fragments (SEQ ID NOS:251, 252, 253, 254, and/or 255), polynucleotides that hybridize to the complementary strand of these polynucleotides (e.g., under the hybridization conditions described herein) are encompassed by the invention, as are the polypeptides encoded by these hybridizing polynucleotides.

Preferred polypeptides of the present invention comprise, or alternatively consist of one, two, three, four, five, or more of the immunogenic epitopes shown in SEQ ID NO: 161 as residues: Ser-29 to Thr-57, Pro-74 to Lys-79, Pro-85 to Glu-107, Tyr-118 to Tyr-136, Gln-144 to Gln-152, Ala-182 to Glu-188. Polynucleotides encoding these polypeptides are also provided.

Also preferred are polypeptides comprising the mature polypeptide which is predicted to consist of residues 26–190 of the foregoing sequence (SEQ ID NO: 161), and biologically active fragments of the mature polypeptide (e.g., fragments that stimulate the proliferation of bone marrow CD34+ cells).

FIGS. 1A–B show the nucleotide (SEQ ID NO:69) and deduced amino acid sequence (SEQ ID NO: 161) of this polypeptide.

FIG. 2 shows an analysis of the amino acid sequence (SEQ ID NO:161). Alpha, beta, turn and coil regions; hydrophilicity and hydrophobicity; amphipathic regions; flexible regions; antigenic index and surface probability are shown, and all were generated using the default settings. In the "Antigenic Index or Jameson-Wolf" graph, the positive peaks indicate locations of the highly antigenic regions of the protein, i.e., regions from which epitope-bearing peptides of the invention can be obtained. The domains defined by these graphs are contemplated by the present invention.

The data presented in FIG. 2 are also represented in tabular form in Table 3. The columns are labeled with the headings "Res", "Position", and Roman Numerals I–XIV. The column headings refer to the following features of the amino acid sequence presented in FIG. 2, and Table 3: "Res": amino acid residue of SEQ ID NO:161 and FIGS. 1A and 1B; "Position": position of the corresponding residue within SEQ ID NO: 161 and FIGS. 1A and 1B; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 2 and/or Table 3, as described above, was generated using the various modules and algorithms of the DNA*STAR set on default parameters. In a preferred embodiment, the data presented in columns VIII, IX, XIII, and XIV of Table 3 can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 2, but may, as shown in Table 3, be represented or identified by using tabular representations of the data presented in FIG. 2. The DNA*STAR computer algorithm used to generate FIG. 2 (set on the original default parameters) was used to present the data in FIG. 2 in a tabular format (See Table 3). The tabular format of the data in FIG. 2 is used to easily determine specific boundaries of a preferred region. The above-mentioned preferred regions set out in FIG. 2 and in Table 3 include, but are not limited to, regions of the aforementioned types identified by analysis of the amino acid sequence set out in FIGS. 1A–B (SEQ ID NO:161). As set out in FIG. 2 and in Table 3, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

The present invention is further directed to fragments of the isolated nucleic acid molecules described herein. By a fragment of an isolated DNA molecule having the nucleotide sequence of the deposited cDNA or the nucleotide sequence shown in SEQ ID NO:69 is intended DNA fragments at least about 15nt, and more preferably at least about 20 nt, still more preferably at least about 30 nt, and even more preferably, at least about 40 nt in length which are useful as diagnostic probes and primers as discussed herein. Of course, larger fragments 50–1500 nt in length are also useful according to the present invention, as are fragments corresponding to most, if not all, of the nucleotide sequence of the deposited cDNA or as shown in SEQ ID NO:69. By a fragment at least 20 nt in length, for example, is intended fragments which include 20 or more contiguous bases from the nucleotide sequence of the deposited cDNA or the nucleotide sequence as shown in SEQ ID NO:69. In this context "about" includes the particularly recited size, larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, and from about 601 to about 650, and from about 651 to about 700, and from about 701 to about 750, and from about 751 to about 800, and from about 801 to about 850, and from about 851 to about 900, and from about 901 to about 950, and from about 951 to about 1000, and from about 1001 to about 1050, and from about and from about 1051 to about 1100, and from about 1101 to about 1150, and from about 1151 to about 1200, and from about 1201 to about 1250, and from about 1251 to about 1300, and from about 1301 to about 1350, and from about 1351 to about 1400, and from about 1401 to about 1450, and from about 1451 to about 1500, and from about 1501 to about 1551, and from about 1551 to about 1600, and from about 1601 to about 1650, and from about 1651 to about 1700, and from about 1701 to about 1750, and from about 1751 to about 1797 of SEQ ID NO:69, or the complementary strand thereto, or the cDNA contained in the deposited gene. In this context "about" includes the particularly recited ranges, larger or smaller by several (5, 4, 3, 2, or 1) nucleotides, at either terminus or at both termini. In additional embodiments, the polynucleotides of the invention encode functional attributes of the corresponding protein.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotides encoding these polypeptide fragments are also preferred.

Preferably, the polynucleotide fragments of the invention encode a polypeptide which demonstrates a functional activity. By a polypeptide demonstrating a "functional activity" is meant to be a polypeptide capable of displaying one or more known functional activities associated with a full-length (complete) or mature-form of the protein. Such functional activities include, but are not limited to, biological activity (e.g., ability to regulate (e.g., stimulate) hematopoiesis in vitro or in vivo), antigenicity, and immunogenicity. The functional activity of polypeptides of the invention, and fragments, variants derivatives, and analogs thereof, can be assayed by various methods described herein.

In addition, assays described herein and otherwise known in the art may routinely be applied to measure biological activity of polypeptides and fragments of the invention, variants derivatives and analogs thereof (e.g., to regulate (e.g., to stimulate or inhibit) hematopoiesis in vitro or in vivo). For example, techniques known in the art (such as for example assaying for thymidine incorporation), may be applied or routinely modified to assay for the ability of the compositions of the invention to inhibit proliferation of hematopoietic cells. Other methods will be known to the skilled artisan and are within the scope of the invention.

Even if deletion of one or more amino acids from the N-terminus of a protein results in modification of loss of one or more biological functions of the protein, other functional activities (e.g., biological activities, ability to multimerize, etc.) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, the present invention further provides polypeptides having one or more residues deleted from the amino terminus of the amino acid sequence shown in FIG. 1 (i.e., SEQ ID NO:69), up to the Glu residue at position number 185 and polynucleotides encoding such polypeptides.

Particularly, N-terminal deletions of the polypeptide can be described by the general formula m-190, where m is an integer from 2 to 184, where m corresponds to the position of the amino acid residue identified in SEQ ID NO:161. More in particular, the invention provides polynucleotides encoding polypeptides comprising, or alternatively consisting of, an amino acid sequence selected from the group: V-26 to I-190; R-27 to I-190; C-28 to I-190; S-29 to I-190; R-30 to I-190; P-31 to I-190; G-32 to I-190; A-33 to I-190; K-34 to I-190; R-35 to I-190; S-36 to I-190; E-37 to I-190; K-38 to I-190; I-39 to I-190; Y-40 to I-190; Q-41 to I-190; Q-42 to I-190; R-43 to I-190; S-44 to I-190; L-45 to I-190; R-46 to I-190; E-47 to I-190; D-48 to I-190; Q-49 to I-190; Q-50 to I-190; S-51 to I-190; F-52 to I-190; T-53 to I-190; G-54 to I-190; S-55 to I-190; R-56 to I-190; T-57 to I-190; Y-58 to I-190; S-59 to I-190; L-60 to I-190; V-61 to I-190; G-62 to I-190; Q-63 to I-190; A-64 to I-190; W-65 to I-190; P-66 to I-190; G-67 to I-190; P-68 to I-190; L-69 to I-190; A-70 to I-190; D-71 to I-190; M-72 to I-190; A-73 to I-190; P-74 to I-190; T-75 to I-190; R-76 to I-190; K-77 to I-190; D-78 to I-190; K-79 to I-190; L-80 to I-190; L-81 to I-190; Q-82 to I-190; F-83 to I-190; Y-84 to I-190; P-85 to I-190; S-86 to I-190; L-87 to I-190; E-88 to I-190; D-89 to I-190; P-90 to I-190; A-91 to I-190; S-92 to I-190; S-93 to I-190; R-94 to I-190; Y-95 to I-190; Q-96 to I-190; N-97 to I-190; F-98 to I-190; S-99 to I-190; K-100 to I-190; G-101 to I-190; S-102 to I-190; R-103 to I-190; H-104 to I-190; G-105 to I-190; S-106 to I-190; E-107 to I-190; E-108 to I-190; A-109 to I-190; Y-110 to I-190; I-111 to I-190; D-112 to I-190; P-113 to I-190; I-114 to I-190; A-115 to I-190; M-116 to I-190; E-117 to I-190; Y-118 to I-190; Y-119 to I-190; N-120 to I-190; W-121 to I-190; G-122 to I-190; R-123 to I-190; F-124 to I-190; S-125 to I-190; K-126 to I-190; P-127 to I-190; P-128 to I-190; E-129 to I-190; D-130 to I-190; D-131 to I-190; D-132 to I-190; A-133 to I-190; N-134 to I-190; S-135 to I-190; Y-136 to I-190; E-137 to I-190; N-138 to I-190; V-139 to I-190; L-140 to I-190; I-141 to I-190; C-142 to I-190; K-143 to I-190; Q-144 to I-190; K-145 to I-190; T-146 to I-190; T-147 to I-190; E-148 to I-190; T-149 to I-190; G-150 to I-190; A-151 to I-190; Q-152 to I-190; Q-153 to I-190; E-154 to I-190; G-155 to I-190; I-156 to I-190; G-157 to I-190; G-158 to I-190; L-159 to I-190; C-160 to I-190; R-161 to I-190; G-162 to I-190; D-163 to I-190; L-164 to I-190; S-165 to I-190; L-166 to I-190; S-167 to I-190; L-168 to I-190; A-169 to I-190; L-170 to I-190; K-171 to I-190; T-172 to I-190; G-173 to I-190; P-174 to I-190; T-175 to I-190; S-176 to I-190; G-177 to I-190; L-178 to I-190; C-179 to I-190; P-180 to I-190; S-181 to I-190; A-182 to I-190; S-183 to I-190; P-184 to I-190; and E-185 to I-190, of SEQ ID NO:161. Polynucleotides encoding these polypeptides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind ligand) may still be retained. For example the ability of the shortened mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an mutein with a large number of deleted C-terminal amino acid residues may retain some biological or immunogenic activities. In fact, peptides composed of as few as six amino acid residues may often evoke an immune response. Accordingly, the present invention further provides polypeptides having one or more residues deleted from the carboxy terminus of the amino acid sequence of the polypeptide shown in FIGS. 1A–B (SEQ ID NO:161), as described by the general formula 1-n, where n is an integer from 6 to 184 where n corresponds to the position of amino acid residue identified in SEQ ID NO:161. More in particular, the invention provides polynucleotides encoding polypeptides comprising, or alternatively consisting of, an amino acid sequence selected from the group: V-26 to G-189; V-26 to E-188; V-26 to D-187; V-26 to E-186; V-26 to E-185; V-26 to P-184; V-26 to S-183; V-26 to A-182; V-26 to S-181; V-26 to P-180; V-26 to C-179; V-26 to L-178; V-26 to G-177; V-26 to S-176; V-26 to T-175; V-26 to P-174; V-26 to G-173; V-26 to T-172; V-26 to K-171; V-26 to L-170; V-26 to A-169; V-26 to L-168; V-26 to S-167; V-26 to L-166; V-26 to S-165; V-26 to L-164; V-26 to D-163; V-26 to G-162; V-26 to R-161; V-26 to C-160; V-26 to L-159; V-26 to G-158; V-26 to G-157; V-26 to I-156; V-26 to G-155; V-26 to E-154; V-26 to Q-153; V-26 to Q-152; V-26 to A-151; V-26 to G-150; V-26 to T-149; V-26 to E-148; V-26 to T-147; V-26 to T-146; V-26 to K-145; V-26 to Q-144; V-26 to K-143; V-26 to C-142; V-26 to I-141; V-26 to L-140; V-26 to V-139; V-26 to N-138; V-26 to E-137; V-26 to Y-136; V-26 to S-135; V-26 to N-134; V-26 to A-133; V-26 to D-132; V-26 to D-131; V-26 to D-130; V-26 to E-129; V-26 to P-128; V-26 to P-127; V-26 to K-126; V-26 to S-125; V-26 to F-124; V-26 to R-123; V-26 to G-122; V-26 to W-121; V-26 to N-120; V-26 to Y-119; V-26 to Y-118; V-26 to E-117; V-26 to M-116; V-26 to A-115; V-26 to I-114; V-26 to P-113; V-26 to D-112; V-26 to I-111; V-26 to Y-110; V-26 to A-109; V-26 to E-108; V-26 to E-107; V-26 to S-106; V-26 to G-105; V-26 to H-104; V-26 to R-103; V-26 to S-102; V-26 to G-101; V-26 to K-100; V-26 to S-99; V-26 to F-98; V-26 to N-97; V-26 to Q-96; V-26 to Y-95; V-26 to R-94; V-26 to S-93; V-26 to S-92; V-26 to A-91; V-26 to P-90; V-26 to D-89; V-26 to E-88; V-26 to L-87; V-26 to S-86; V-26 to P-85; V-26 to Y-84; V-26 to F-83; V-26 to Q-82; V-26 to L-81; V-26 to L-80; V-26 to K-79; V-26 to D-78; V-26 to K-77; V-26 to R-76; V-26 to T-75; V-26 to P-74; V-26 to A-73; V-26 to M-72; V-26 to D-71; V-26 to A-70; V-26 to L-69; V-26 to P-68; V-26 to G-67; V-26 to P-66; V-26 to W-65; V-26 to A-64; V-26 to Q-63; V-26 to G-62; V-26 to V-61; V-26 to L-60; V-26 to S-59; V-26 to Y-58; V-26 to T-57; V-26 to R-56; V-26 to S-55; V-26 to G-54; V-26 to T-53; V-26 to F-52; V-26 to S-51; V-26 to Q-50; V-26 to Q-49; V-26 to D-48; V-26 to E-47; V-26 to R-46; V-26 to L-45; V-26 to S-44; V-26 to R-43; V-26 to Q-42; V-26 to Q-41; V-26 to Y-40; V-26 to I-39; V-26 to K-38; V-26 to E-37; V-26 to S-36; V-26 to R-35; V-26 to K-34; V-26 to A-33; V-26 to G-32; and V-26 to P-31 of SEQ ID NO:161. Polynucleotides encoding these polypeptides are also encompassed by the invention.

In addition, any of the above listed N- or C-terminal deletions can be combined to produce a N- and C-terminal deleted polypeptide. The invention also provides polypeptides having one or more amino acids deleted from both the amino and the carboxyl termini, which may be described generally as having residues m-n of SEQ ID NO:161, where n and m are integers as described above. Polynucleotides encoding these polypeptides are also encompassed by the invention.

Also included are a nucleotide sequence encoding a polypeptide consisting of a portion of the complete amino acid sequence encoded by the cDNA clone contained in ATCC Deposit No.209889, where this portion excludes any integer of amino acid residues from 1 to about 180 amino acids from the amino terminus of the complete amino acid sequence encoded by the cDNA clone contained in ATCC Deposit No. 209889, or any integer of amino acid residues from 1 to about 180 amino acids from the carboxy terminus, or any combination of the above amino terminal and carboxy terminal deletions, of the complete amino acid sequence encoded by the cDNA clone contained in ATCC Deposit No. 209889. Polynucleotides encoding all of the above deletion mutant polypeptide forms also are provided.

The present application is also directed to proteins containing polypeptides at least 90%, 92%, 93%, 94%, 95%, 96%, 97%, 98% or 99% identical to the polypeptide sequence set forth herein m−n. In preferred embodiments, the application is directed to proteins containing polypeptides at least 90%, 95%, 96%, 97%, 98% or 99% identical to polypeptides having the amino acid sequence of the specific N- and C-terminal deletions recited herein. Polynucleotides encoding these polypeptides are also encompassed by the invention.

Polynucleotides and polypeptides of the invention are useful as reagents for differential identification of the tissue(s) or cell type(s) present in a biological sample and for diagnosis of diseases and conditions which include, but are not limited to, disorders affecting the immune and hematopoietic systems, particularly hematopoiesis. Similarly, polypeptides and antibodies directed to these polypeptides are useful in providing immunological probes for differential identification of the tissue(s) or cell type(s). For a number of disorders of the above tissues or cells, particularly of the immune system and hematopoeitic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

This gene has been found to stimulate the proliferation of bone marrow CD34+ cells. This assay which is described in Example 53 herein is based on the ability of human CD34+ to proliferate in presence of hematopoietic growth factors and evaluates the ability of the polypeptides of the invention, and agonists and antagonists thereof, to stimulate or inihibit this proliferation.

The tissue distribution in immune and hematopoietic cells and tissues and the ability to stimulate the proliferation of bone marrow CD34+ cells indicates that polynucleotides and polypeptides corresponding to this gene are useful for the diagnosis and treatment of disorders affecting the immune system and hematopoiesis. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. Moreover, the protein represents a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

The polynucleotides and/or polypeptides of the invention and/or agonists and/or antagonists thereof, can also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

The polynucleotides and/or polypeptides of the invention and/or agonists and/or antagonists thereof, may also be employed for the expansion of immature hematopoeitic progenitor cells, for example, granulocytes, macrophages or monocytes, by temporarily preventing their differentiation. These bone marrow cells may be cultured in vitro. Thus, polynucleotides and/or polypeptides of the invention, or agonists or antagonists thereof, may be useful as a modulator of hematopoietic stem cells in vitro for the purpose of bone marrow transplantation and/or gene therapy. Since stem cells are rare and are most useful for introducing genes into for gene therapy, polynucleotides and/or polypeptides of the invention can be used to isolate enriched populations of stem cells. Stem cells can be enriched by culturing cells in the presence of cytotoxins, such as 5-Fu, which kills rapidly dividing cells, where as the stem cells will be protected by polynucleotides and/or polypeptides of the invention. These stem cells can be returned to a bone marrow transplant patient or can then be used for transfection of the desired gene for gene therapy. In addition, this gene can be injected into animals which results in the release of stem cells from the bone marrow of the animal into the peripheral blood. These stem cells can be isolated for the purpose of autologous bone marrow transplantation or manipulation for gene therapy. After the patient has finished chemotherapy or radiation treatment, the isolated stem cells can be returned to the patient.

Polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

This gene product may also be involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

This gene may also have a very wide range of biological activities. Representative uses are described in the "Chemotaxis" and "Binding Activity" sections below, in Examples 11, 12, 13, 14, 15, 16, 18, 19, and 20, and elsewhere herein. Briefly, the protein may possess the following activities: cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating hemophilia, cardiac infarction etc.); anti-inflammatory activity (e.g. for treating septic shock, Crohn's disease); as antimicrobials; for treating psoriasis or other hyperproliferative diseases; for regulation of metabolism, and behavior. Also contemplated is the use of the corresponding nucleic acid in gene therapy procedures. Based upon the proteins immune cell specific message distribution, it may be involved in many aspects of the immune response, especially its initial stages, inflammation, allograft rejection, infectious disease response etc. It is frequently found in the hematopoietic cell cDNA libraries. Thus, this factor could be involved in the control of hematopoietic cell proliferation, differentiation, and function. Based on this one can postulate its use in the management of anemias, leukemias, neutropenia, thrombocytopenia, autoimmune iseases, blood tissue engraftment, and poikilothromerythromatosis. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The gene encoding the disclosed CDNA is believed to reside on chromosome 7. Accordingly, polynucleotides related to this invention are useful as a marker in linkage analysis for chromosome 7.

Many polynucleotide sequences, such as EST sequences, are publicly available and accessible through sequence databases. Some of these sequences are related to SEQ ID NO:69 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1783 of SEQ ID NO:69, b is an integer of 15 to 1797, where both a and b correspond to the positions of nucleotide residues shown in SEQ ID NO:69, and where b is greater than or equal to a+14.

Features of Protein Encoded by Gene No: 60

In another embodiment, polypeptides comprising the amino acid sequence of the open reading frame upstream of the predicted signal peptide are contemplated by the present invention. Specifically, polypeptides of the invention comprise the following amino acid sequence: VLWREASALV LSNRLSSGLLHDLLLQPAIHSRLFPRRSRGLSEG EGSSVSLQRSRVLSAMKHVLNLYLLGVVLTLLSI FVRVMESLEGLLESPSPGTSWTTRSQLANTEPT KGLPDHPSRSM (SEQ ID NO: 256). Polynucleotides encoding these polypeptides are also provided.

This gene is expressed primarily in immune cells including activated T cells, macrophages, jurkat cells, bone marrow cells, and osteoblasts and to a lesser extent in kidney cortex, brain, placenta and lung.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic diseases and/or disorders, particularly inflammation and diseases related to inflammatory activity. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 162 as residues: Pro-34 to Met-63. Polynucleotides encoding said polypeptides are also provided.

The tissue distribution in immune cells and tissues indicates that polynucleotides and polypeptides corresponding to this gene are useful for treating or diagnosing disease related to the normal or abnormal activation of T cells. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma.

Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1359 of SEQ ID NO:70, b is an integer of 15 to 1373, where both a and b correspond to the positions of nucleotide residues shown in SEQ ID NO:70, and where b is greater than or equal to a+14.

Features of Protein Encoded by Gene No: 61

In another embodiment, polypeptides comprising the amino acid sequence of the open reading frame upstream of the predicted signal peptide are contemplated by the present invention. Specifically, polypeptides of the invention comprise the following amino acid sequence: YTFHTQIFLDF PMIFLTVLPLAFLFLHSGFYHYISFSCLFSLSLALF FOFLDVATFRRPGQLFCERSVLFDMFHFGFVSLFL HEWIQAKHFWAGLFIVLPSDVFFSVHHLEAPDGSFP NIAKLSLIILLR (SEQ ID NO: 257). Polynucleotides encoding these polypeptides are also provided.

The polypeptide of this gene has been determined to have two transmembrane domains at about amino acid position 2–18 and 22–38 of the amino acid sequence referenced in Table 1 for this gene. Based upon these characteristics, it is believed that the protein product of this gene shares structural features to type IIIa membrane proteins.

This gene is expressed in many tissues including brain, liver, prostate, testes, cartilage, gall bladder. Expression is also seen in a number of tumors including colon carcinoma, pancreas tumor, osteoclastoma, ovarian cancer, B cell lymphoma and acute lymphocytic leukemias. Therefore, polynucleotides and polypeptides of the invention are useful as reagents for differential identification of the tissue(s) or cell type(s) present in a biological sample and for diagnosis of diseases and conditions which include, but are not limited to, tumors of various organs including the pancreas, colon, and bone. Similarly, polypeptides and antibodies directed to these polypeptides are useful in providing immunological probes for differential identification of the tissue(s) or cell type(s). For a number of disorders of the above tissues or cells, particularly of the major organs, expression of this gene at significantly higher or lower levels may be routinely detected in certain tissues or cell types (e.g., neural, hepatic, metabolic, reproductive, testicular, skeletal, and cancerous and wounded tissues) or bodily fluids (e.g., lymph, serum, amniotic fluid, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in tumors and proliferative tissues indicates that polynucleotides and polypeptides corresponding to this gene are useful for treating or diagnosing tumors of several major organs including the pancreas and large intestine. This protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:71 and may have been publicly available prior to conception of the present invention. Preferably, such related polynucleotides are specifically excluded from the scope of the present invention. To list every related sequence is cumbersome. Accordingly, preferably excluded firom the present invention are one or more polynucleotides comprising a nucleotide sequence described by the general formula of a–b, where a is any integer between 1 to 1565 of SEQ ID NO:71, b is an integer of 15 to 1579, where both a and b correspond to the positions of nucleotide residues shown in SEQ ID NO:71, and where b is greater than or equal to a+14.

Features of Protein Encoded by Gene No: 62

This gene is expressed primarily in dendritic cells and fetal liver/spleen and to a lesser extent in many tissues including tonsils, fetal lung, stromal cell lines, bone marrow cell lines, placenta and tumors including hepatocellular carcinoma, pancreas tumor and osteosarcoma.

Therefore, polynucleotides and polypeptides of the invention are useful as reagents for differential identification of the tissue(s) or cell type(s) present in a biological sample and for diagnosis of diseases and conditions which include, but are not limited to, diseases and/or disorders of the immune and hematopoietic system. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in dendritic cells and fetal liver/spleen indicates that polynucleotides and polypeptides corresponding to this gene are useful for diagnosing and treating disorders of the immune system particularly related to the control and generation of precursor cells. Polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the "Immune Activity" and "Infectious Disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:72 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1014 of SEQ ID NO:72, b is an integer of 15 to 1028, where both a and b correspond to the positions of nucleotide residues shown in SEQ ID NO:72, and where b is greater than or equal to a+14.

Features of Protein Encoded by Gene No: 63

This gene is expressed primarily in adrenal gland tumor and endothelial cells.

Therefore, polynucleotides and polypeptides of the invention are useful as reagents for differential identification of the tissue(s) or cell type(s) present in a biological sample and for diagnosis of diseases and conditions which include, but are not limited to, endocrine and vascular diseases and/or disorders, particularly diseases associated with the vascular endothelium. Similarly, polypeptides and antibodies directed to these polypeptides are useful in providing immunological probes for differential identification of the tissue(s) or cell type(s). For a number of disorders of the above tissues or cells, particularly of the vascular system, expression of this gene at significantly higher or lower levels may be routinely detected in certain tissues or cell types (e.g., endocrine, vascular, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in endothelial cells indicates that polynucleotides and polypeptides corresponding to this gene are useful for diagnosing and treating disorders that involve the vascular system including diseases such as athersclerosis, neoangiogenesis associated with tumor growth and conditions associated with inflammation. Moreover, the protein is useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Alternatively, the protein is useful in the treatment, detection, and/or prevention of metabolic disorders, particularly lethargy and depression. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:73 and may have been publicly available prior to conception of the present invention. Preferably, such related polynucleotides are specifically excluded from the scope of the present invention. To list every related sequence is cumbersome. Accordingly, preferably excluded from the present invention are one or ore polynucleotides comprising a nucleotide sequence described by the general formula of a–b, where a is any integer between 1 to 3660 of SEQ ID NO:73, b is an integer of 15 to 3674, where both a and b correspond to the positions of nucleotide residues shown in SEQ ID NO:73, and where b is greater than or equal to a+14.

Features of Protein Encoded by Gene No: 64

The translation product of this gene is related to bovine PAM precursor (See, e.g., Genbank accession gil 163482 incorporated herein by reference and also see the following patent publications, which are also incorporated herein by reference in their entirety: J04311386 and WO8902460). Many bioactive peptides terminate with an amino acid alpha-amide at their COOH terminus. The enzyme responsible for this essential posttranslational modification is known as peptidyl-glycine alpha-amidating monooxygenase or PAM. An NH2-terminal signal sequence and short propeptide precede the NH2 terminus of purified PAM. The sequences of several PAM cyanogen bromide peptides were localized in the NH2-terminal half of the predicted protein. The forms of PAM purified from bovine neurointermediate pituitary may be generated by endoproteolytic cleavage at a subset of the 10 pairs of basic amino acids in the precursor. High levels of PAM mRNA have been found in bovine pituitary and cerebral cortex. In corticotropic tumor cells, levels of PAM mRNA and pro-ACTH/endorphin mRNA are known to be regulated in parallel by glucocorticoids and CRF.

This gene is expressed primarily in endometrial tumors, dendritic cells, a multiple sclerosis library, kidney, hematopoietic cells, melanocytes, osteoblasts, the spleen, colon, ovary, stromal cells, fetal and adult brain, heart, and in tissues undergoing wound repair.

Therefore, polynucleotides and polypeptides of the invention are useful as reagents for differential identification of the tissue(s) or cell type(s) present in a biological sample and for diagnosis of diseases and conditions which include, but are not limited to, endometriosis, endometrial cancer, multiple sclerosis, hematopoietic diseases, bone disease, and wound healing. Similarly, polypeptides and antibodies directed to these polypeptides are useful in providing immunological probes for differential identification of the tissue(s) or cell type(s). For a number of disorders of the above tissues or cells, particularly the hematopoietic system and female reproduction. expression of this gene at significantly higher or lower levels may be routinely detected in certain tissues or cell types (e.g., reproductive, immune, hematopoieticm integumentary, skeletal, gastrointestinal, and cancerous and wounded tissues) or bodily fluids (e.g., lymph, serum, amniotic fluid, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in dendritic and hematopoietic cells and tissues indicates that polynucleotides and polypeptides corresponding to this gene are useful as a therapeutic or diagnostic agent is diseases of hematopoietic origin as well as the female reproductive track due to the gene's primary pattern of expression. Polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the "Immune Activity" and "Infectious Disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

The protein may also have a very wide range of biological activities. Representative uses are described in the "Chemotaxis" and "Binding Activity" sections below, in Examples 11, 12, 13, 14, 15, 16, 18, 19, and 20, and elsewhere herein. Briefly, the protein may possess the following activities: cytokine, cell proliferation/differentiation modulating activity or induction of other cytokines; immunostimulating/immunosuppressant activities (e.g. for treating human immunodeficiency virus infection, cancer, autoimmune diseases and allergy); regulation of hematopoiesis (e.g. for treating anemia or as adjunct to chemotherapy); stimulation or growth of bone, cartilage, tendons, ligaments and/or nerves (e.g. for treating wounds, stimulation of follicle stimulating hormone (for control of fertility); chemotactic and chemokinetic activities (e.g. for treating infections, tumors); hemostatic or thrombolytic activity (e.g. for treating hemophilia, cardiac infarction etc.); anti-inflammatory activity (e.g. for treating septic shock, Crohn's disease); as antimicrobials; for treating psoriasis or other hyperproliferative diseases; for regulation of metabolism, and behavior. Also contemplated is the use of the corresponding nucleic acid in gene therapy procedures. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:74 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2783 of SEQ ID NO:74, b is an integer of 15 to 2797, where both a and b correspond to the positions of nucleotide residues shown in SEQ ID NO:74, and where b is greater than or equal to a+14.

Features of Protein Encoded by Gene No: 65

The translation product of this gene shares sequence similarity with several G-protein coupled receptors (See Genbank Accession No. gblAAC77910.11 (AF061443); all references available through this accession are hereby incorporated herein by reference; for example, Mol. Endocrinol. 12, 1830–1845 (1998)). G-protein coupled receptors are well known in the are and affect a variety of functions.

In particular, the translation product of this gene shares similarity with Follical Stimulating Hormone Receptor. Preferred polypeptides encoded by this gene comprise the following amino acid sequence: GTRFPTGETPSLGFTV TLVLLNSLAFLLMAVIYTKLYCNLEKEDLSENSQS SMIKHVAWLIFTNCIFFCPVAFFSFAPLITAISISPE IMKSVTLIFFP (SEQ ID NO: 258). Polynucleotides encoding such polypeptides are also provided.

A preferred polypeptide fragment of the invention comprises the following amino acid sequence: MIKHVAWL-IFTNCIFFCP VAFFSFAPLITAISISPEIMKSVTLIFF-PCLLA (SEQ ID NO: 259). Polynucleotides encoding these polypeptides are also provided.

In another embodiment, polypeptides comprising the amino acid sequence of the open reading frame upstream of the predicted signal peptide are contemplated by the present invention. Specifically, polypeptides of the invention comprise the following amino acid sequence: GTRFPT GETPSLGFTVTLVLLNSLAFLLMAVIYTKLYCNLE KEDLSENSQSSMIKHVAWLIFTNCIFFCPVAFFSFA PLITAISISPEIMKSVTLIFFPLPACLNPVLYVFFNPK FKEDWKLLKRRVTKKSGSVSVSISSQGGCLEQD FYYDCGMYSHLQGNLTVCDCCESFLLTKPVSCKH LIKSHSCPALAVASCQRPEGYWSDCGTQSAHSDYAD EEDSFVSDSSDQVQACGRACFYQSRGFPLVRYAYNL PRVKD (SEQ ID NO: 260). Polynucleotides encoding these polypeptides are also provided.

The polypeptide of this gene has been determined to have a transmembrane domain at about amino acid position 43-59 of the amino acid sequence referenced in Table 1 for this gene. Moreover, a cytoplasmic tail encompassing amino acids 60 to 207 of this protein has also been determined. Based upon these characteristics, it is believed that the protein product of this gene shares structural features to type Ia membrane proteins.

Included in this invention as preferred domains are Zinc finger, C2H2 type domains, which were identified using the ProSite analysis tool (Swiss Institute of Bioinformatics). 'Zinc finger' domains [1–5] are nucleic acid-binding protein structures first identified in the Xenopus transcription factor TFIIIA. These domains have since been found in numerous nucleic acid-binding proteins.

A zinc finger domain is composed of 25 to 30 amino-acid residues. There are two cysteine or histidine residues at both extremities of the domain, which are involved in the tetrahedral coordination of a zinc atom. It has been proposed that such a domain interacts with about five nucleotides. A schematic representation of a zinc finger domain is shown below:

```
           x  x
         x      x
        x        x
        x        x
        x        x
        x        x
         C      H
        x   /    x
       x    Zn    x
        x   \    x
         C      H
 x x x x x        x x x x x
```

Many classes of zinc fingers are characterized according to the number and positions of the histidine and cysteine residues involved in the zinc atom coordination. In the first class to be characterized, called C2H2, the first pair of zinc coordinating residues are cysteines, while the second pair are histidines. A number of experimental reports have demonstrated the zinc-dependent DNA or RNA binding property of some members of this class. Some of the proteins known to include C2H2-type zinc fingers are listed below. We have indicated, between brackets, the number of zinc finger regions found in each of these proteins; a '+' symbol indicates that only partial sequence data is available and that additional finger domains may be present. In addition to the conserved zinc ligand residues it has been shown that a number of other positions are also important for the structural integrity of the C2H2 zinc fingers. The best conserved position is found four residues after the second cysteine; it is generally an aromatic or aliphatic residue. The concensus pattern is as follows: C-x(2,4)-C-x(3)-[LIVMFYWC]-x(8)-H-x(3,5)-H.

Preferred polypeptides of the invention comprise the following amino acid sequence: CDCCESFLLTKPVSCKH-LIKSH (SEQ ID NO: 261). Polynucleotides encoding these polypeptides are also provided.

Further preferred are polypeptides comprising the Zinc finger, C2H2 type domain of the sequence referenced in Table for this gene, and at least 5, 10, 15, 20, 25, 30, 50, or 75 additional contiguous amino acid residues of this referenced sequence. The additional contiguous amino acid residues may be N-terminal or C-terminal to the Zinc finger, C2H2 type domain. Alternatively, the additional contiguous amino acid residues may be both N-terminal and C-terminal to the Zinc finger, C2H2 type domain, wherein the total N- and C-terminal contiguous amino acid residues equal the specified number. The above preferred polypeptide domain is characteristic of a signature specific to zinc finger proteins. Based on the sequence similarity, the translation product of this gene is expected to share at least some biological activities with G-coupled proteins, their receptors, and zinc finger proteins. Such activities are known in the art, some of which are described elsewhere herein.

This gene is expressed primarily in adult and fetal liver, human placenta, colon carcinoma cell lines and fibroblasts and to a lesser extent in the fetal and adult brain, the developing nervous system, lung, pancreas, salivary gland, breast tissue, and dendritic cells.

Therefore, polynucleotides and polypeptides of the invention are useful as reagents for differential identification of the tissue(s) or cell type(s) present in a biological sample and for diagnosis of diseases and conditions which include, but are not limited to, diseases of the liver, developmental abnormalities, neurologic diseases, lung cancer, pancreatic cancer, and colon cancer. Similarly, polypeptides and antibodies directed to these polypeptides are useful in providing immunological probes for differential identification of the tissue(s) or cell type(s). For a number of disorders of the above tissues or cells, particularly of the neurological and hepatic origin, as well as the proliferation and/or differentiation of numerous types of tissues. expression of this gene at significantly higher or lower levels may be routinely detected in certain tissues or cell types (e.g., hepatic, immune, hematopoietic, neural, gastrointestinal, reproductive, and cancerous and wounded tissues) or bodily fluids (e.g., lymph, serum, amniotic fluid, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.Preferred polypeptides of the present invention comprise immunogenic epitopes shown in SEQ ID NO: 167 as residues: Pro-62 to Asp-67, Arg-74 to Gly-80, Gln-146 to Glu-168. Polynucleotides encoding said polypeptides are also provided.

The tissue distribution in fetal liver indicates that polynucleotides and polypeptides corresponding to this gene are useful for a diagnostic marker or therapeutic in a wide variety of disease states. Polynucleotides and polypeptides corresponding to this gene are useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the "Immune Activity" and "Infectious Disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types.

Alternatively, the protein expression in placental and brain tissue indicates the protein is useful in the detection, treatment, and/or prevention of vascular conditions, which include, but are not limited to, microvascular disease, vascular leak syndrome, aneurysm, stroke, atherosclerosis, arteriosclerosis, or embolism. For example, this gene product may represent a soluble factor produced by smooth muscle that regulates the innervation of organs or regulates the survival of neighboring neurons. Likewise, it is involved in controlling the digestive process, and such actions as peristalsis. Similarly, it is involved in controlling the vasculature in areas where smooth muscle surrounds the endothelium of blood vessels. The protein is useful in the treatment, detection, and/or prevention of bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; allergies; benign prostatic hypertrophy; and psychotic and neurological disorders, including anxiety, schizophrenia, manic depression, delirium, severe mental retardation and dyskinesias, such as Huntington's disease or Gilles de la Tourette's syndrome. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:75 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2689 of SEQ ID NO:75, b is an integer of 15 to 2703, where both a and b correspond to the positions of nucleotide residues shown in SEQ ID NO:75, and where b is greater than or equal to a+14.

Features of Protein Encoded by Gene No: 66

In another embodiment, polypeptides comprising the amino acid sequence of the open reading frame upstream of the predicted signal peptide are contemplated by the present invention. Specifically, polypeptides of the invention comprise the following amino acid sequence: ALENSG SPGLQDSARAHFNXSLRSFSFLRNQMYIFELSL YLEGTSFVVVLLFLL ISVSLDSPPTTKGWDSVLHI WVPLIVQ (SEQ ID NO: 262). Polynucleotides encoding these polypeptides are also provided.

This gene is expressed primarily in placenta and in hematopoietic cells, especially those of T-cell and monocyte origin and to a lesser extent in the brain, endothelial cells, and the lungs.

Therefore, polynucleotides and polypeptides of the invention are useful as reagents for differential identification of the tissue(s) or cell type(s) present in a biological sample and for diagnosis of diseases and conditions which include, but are not limited to, hematopoietic, vascular, and developmental diseases and/or disorders. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., vascular, immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 168 as residues: Ser-30 to Trp-37. Polynucleotides encoding said polypeptides are also provided.

The tissue distribution in hematopoietic cells indicates that polynucleotides and polypeptides corresponding to this gene are useful for therapeutic and/or diagnostic intervention in hematopoietic and developmental disorders. Representative uses are described in the "Immune Activity" and "Infectious Disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Alternatively, the protein is useful in the detection, treatment, and/or prevention of vascular conditions, which include, but are not limited to, microvascular disease, vascular leak syndrome, aneurysm, stroke, atherosclerosis, arteriosclerosis, or embolism. For example, this gene product may represent a soluble factor produced by smooth muscle that regulates the innervation of organs or regulates the survival of neighboring neurons. Likewise, it is involved in controlling the digestive process, and such actions as peristalsis. Similarly, it is involved in controlling the vasculature in areas where smooth muscle surrounds the endothelium of blood vessels. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 728 of SEQ ID NO:76, b is an integer of 15 to 742, where both a and b correspond to the positions of nucleotide residues shown in SEQ ID NO:76, and where b is greater than or equal to a+14.

Features of Protein Encoded by Gene No: 67

This gene is expressed primarily in the prostate and to a lesser extent in human B-cell lymphomas.

Therefore, polynucleotides and polypeptides of the invention are useful as reagents for differential identification of the tissue(s) or cell type(s) present in a biological sample and for diagnosis of diseases and conditions which include, but are not limited to, prostate cancer and diseases of hematopoietic origin, particularly of B-cells. Similarly, polypeptides and antibodies directed to these polypeptides are useful in providing immunological probes for differential identification of the tissue(s) or cell type(s). For a number of disorders of the above tissues or cells, particularly of the prostate and immune systems, expression of this gene at significantly higher or lower levels may be routinely detected in certain tissues or cell types (e.g., prostate, reproductive, hematopoietic, and cancerous and wounded tissues) or bodily fluids (e.g., lymph, serum, plasma, urine, seminal fluid, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 169 as residues: Asp-33 to Lys-42. Polynucleotides encoding said polypeptides are also provided.

The tissue distribution in prostate tissue indicates that polynucleotides and polypeptides corresponding to this gene are useful as a therapeutic or diagnostic marker for prostate cancer and disorders involving hematopoietic cells, especially those of B-cell origin. Moreover, the expression within cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus this protein may modulate apoptosis or tissue differentiation and is useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation. The protein is useful in modulating the immune response to aberrant proteins and polypeptides, as may exist in rapidly proliferating cells and tissues. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:77 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1811 of SEQ ID NO:77, b is an integer of 15 to 1825, where both a and b correspond to the positions of nucleotide residues shown in SEQ ID NO:77, and where b is greater than or equal to a+14.

Features of Protein Encoded by Gene No: 68

When tested against U937 cell lines, supernatants removed from cells containing this gene activated the GAS (gamma activating sequence) promoter element. Thus, it is likely that this gene activates myeloid cells through the JAK-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

In another embodiment, polypeptides comprising the amino acid sequence of the open reading frame upstream of the predicted signal peptide are contemplated by the present invention. Specifically, polypeptides of the invention comprise the following amino acid sequence: GHESICGSCR SWIYFSIRCRRRMRPWWSLLLEACATCAQTGPT RSTSCTQEVSHSSSTAYPAPMRRRCCLPSPRSCT (SEQ ID NO: 263). Polynucleotides encoding these polypeptides are also provided.

The gene encoding the disclosed cDNA is believed to reside on chromosome 17. Accordingly, polynucleotides related to this invention are useful as a marker in linkage analysis for chromosome 17.

This gene is expressed primarily in the brain and the developing embryo and to a lesser extent in the heart, colon, adipose tissue, kidney, mammary tissue, activated T-cells and dendritic cells.

Therefore, polynucleotides and polypeptides of the invention are useful as reagents for differential identification of the tissue(s) or cell type(s) present in a biological sample and for diagnosis of diseases and conditions which include, but are not limited to, neurological diseases, developmental conditions, colon cancer, and hematopoietic diseases, especially of T-cell origin. Similarly, polypeptides and antibodies directed to these polypeptides are useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, developmental, cardiovascular, adipose, immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 170 as residues: Thr-18 to Cys-26, Glu-29 to Thr-36, Ser-50 to Thr-55. Polynucleotides encoding said polypeptides are also provided.

The tissue distribution in brain, combined with the detected GAS biological activity, indicates that polynucleotides and polypeptides corresponding to this gene are useful for therapeutic and/or diagnostic agents in neurological diseases, developmental abnormalities, colon cancer, and hematopoietic diseases, especially those of T-cell origin. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:78 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1660 of SEQ ID NO:78, b is an integer of 15 to 1674, where both a and b correspond to the positions of nucleotide residues shown in SEQ ID NO:78, and where b is greater than or equal to a+14.

Features of Protein Encoded by Gene No: 69

The polypeptide of this gene has been determined to have a transmembrane domain at about amino acid position 2–18 of the amino acid sequence referenced in Table 1 for this gene. Based upon these characteristics, it is believed that the protein product of this gene shares structural features to type II membrane proteins.

In another embodiment, polypeptides comprising the amino acid sequence of the open reading frame upstream of the predicted signal peptide are contemplated by the present invention. Specifically, polypeptides of the invention comprise the following amino acid sequence: KRAGVEVG GLVMALAGSVFVLGGVLVLCVERNGEGEMG WPQHLPKSQPLS PPVAVRRCSFERSWIDLLVETSSSM VTCRQQVGTPNGMEGRGGGPKTTFPIRLQLSGA CAVRPEIQWEV (SEQ ID NO: 264). Polynucleotides encoding these polypeptides are also provided.

This gene is expressed primarily in activated monocytes, dendritic cells, and in the tonsils.

Therefore, polynucleotides and polypeptides of the invention are useful as reagents for differential identification of the tissue(s) or cell type(s) present in a biological sample and for diagnosis of diseases and conditions which include, but are not limited to, immune and hematopoietic diseases and/or disorders, particularly leukemia, lymphomas, tumors of hematopoietic origin. Similarly, polypeptides and antibodies directed to these polypeptides are useful in providing immunological probes for differential identification of the tissue(s) or cell type(s). For a number of disorders of the above tissues or cells, particularly of the hematopoietic system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 171 as residues: Gln-30 to Leu-38, Asn-75 to Thr-86. Polynucleotides encoding said polypeptides are also provided.

The tissue distribution in activated monocytes, dendritic cells, and tonsils indicates that polynucleotides and polypeptides corresponding to this gene are useful as a therapeutic and/or diagnostic agent for leukemias, lymphomas, and other diseases associated with cells of hematopoietic origin. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:79 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 2177 of SEQ ID NO:79, b is an integer of 15 to 2191, where both a and b correspond to the positions of nucleotide residues shown in SEQ ID NO:79, and where b is greater than or equal to a+14.

Features of Protein Encoded by Gene No: 70

When tested against U937 cell lines, supernatants removed from cells containing this gene activated the GAS (gamma activating sequence) promoter element. Thus, it is likely that this gene activates myeloid cells, and to a lesser extent, other immune cells and tissue cell types, through the JAK-STAT signal transduction pathway. GAS is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

The gene encoding the disclosed cDNA is believed to reside on chromosome 12. Accordingly, polynucleotides related to this invention are useful as a marker in linkage analysis for chromosome 12.

This gene is expressed primarily in the placenta, brain, and liver and to a lesser extent in most other tissues.

Therefore, polynucleotides and polypeptides of the invention are useful as reagents for differential identification of the tissue(s) or cell type(s) present in a biological sample and for diagnosis of diseases and conditions which include, but are not limited to, hematopoietic, neurological, vascular, and developmental diseases and/or disorders, particularly cancers. Similarly, polypeptides and antibodies directed to these polypeptides are useful in providing immunological probes for differential identification of the tissue(s) or cell type(s). For a number of disorders of the above tissues or cells, particularly of the immune and nervous systems, expression of this gene at significantly higher or lower levels may be routinely detected in certain tissues or cell types (e.g., hematopoietic, neurological, vascular, developmental, and cancerous and wounded tissues) or bodily fluids (e.g., lymph, serum, amniotic fluid, bile, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in brain tissue indicates that polynucleotides and polypeptides corresponding to this gene are useful therapeutic and/or diagnostic agent in a multitude of disease states, particularly those involving the immune and neurologic systems. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Moreover, the protein is useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:80 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1321 of SEQ ID NO:80, b is an integer of 15 to 1335, where both a and b correspond to the positions of nucleotide residues shown in SEQ ID NO:80, and where b is greater than or equal to a+14.

Features of Protein Encoded by Gene No: 71

The translation product of this gene shares sequence homology with the murine FIG. 1 (interleukin-four induced gene 1) (See Genbank Accession No AAB51353; all references available through this accession are hereby incorporated herein by reference; for example Chu,C. C. and Paul,W. E., Proc. Natl. Acad. Sci. U.S.A. 94 (6), 2507–2512 (1997)). which shares homology to the monoamine oxidases, particularly in domains responsible for FAD binding.

Preferred polypeptides encoded by this gene comprise the following amino acid sequence: QDWKAERSQDPFEKC MQDPDYEQLLKVTILEADNRIGGRIFTYRDQX TGWIGELGAMRMPSSHRILHKLCQGLGLNLTK FTQYDKNTWTEVHEXKLRNYVVEKVPEKLGYALR PQEKGHSPEDIYQMALNQALKDLKALGCRKA MKKFERHTLLEYLLGEGNLSRPAVQLLGDVMSEDG FFYLSFAEALRAXSCLSDRLQYSRIVGGWDLL PRALLSSLSGLVLLNAPVVAMTQGPHDVHVQIETSP PARNLKVLKAD VVLLTASGPAVKRITFS (SEQ ID NO: 265), and/or LPRHMQEALRRLHYVPATKVFLSFRRPF WREEHIEGGHSNTDRPSRMIFYPPPREGALL LASYTWSDAAAAFAGLSREEALRLALDDVAALH GPVVRQLWDGT GVVKRWAEDQHSQGGFVVQXPAL WQTEKDDWTVPYGRIYFAGEHTAYPHGWVETAVK SALRAAIKINSRKGPASDTASPEGHASDMEGQG HVHGVASSPSH DLAKEEGS (SEQ ID NO: 266). Polynucleotides encoding such polypeptides are also provided.

A preferred polypeptide fragment of the invention comprises the following amino acid sequence: MAPLALHLLV LVPILLSLVASQDWKAERSQDPFEKCMQDPDYE QLLKVTILEADNRIGGRIFTYRDQXTGWIGELGAM RMPSSHRILHKLCQGLGLNLTKFTQYDKNTW TEVHEXKLRNYVVEKVPEKLGYALRPQEKG HSPEDIYQMALNQALKDLKALGCRKAMKKFER HTLLEYLLGEGNLSRPAVQLLGDVMSEDGFFYL SFAEALRAXSCLSDRLQYSRIVGGWDLLPR ALLSSLSGLVLLNAPVVAMTQGPHDVHVQIETSP PARNLKVLKADVVLLTASGPAVKRITFSPRCPATCR RRCGG CTTCRPPRCS (SEQ ID NO: 267).

Based on the sequence similarity, the translation product of this gene is expected to share at least some biological activities with monoamine oxidases, disintegrins, metalloproteinases, and apoptosis modulating proteins. Such activities are known in the art, some of which are described elsewhere herein. Polynucleotides encoding these polypeptides are also provided.

The polypeptide of this gene has been determined to have a transmembrane domain at about amino acid position 235–251 of the amino acid sequence referenced in Table 1 for this gene. Moreover, a cytoplasmic tail encompassing amino acids 252 to 319 of this protein has also been determined. Based upon these characteristics, it is believed that the protein product of this gene shares structural features to type Ia membrane proteins.

This gene is expressed primarily in hematopoietic cells, particularly in dendritic cells, and activated monocytes and to a lesser extent in T-cells, endothelial cells, and cells associated with ulcerative colitis.

Therefore, polynucleotides and polypeptides of the invention are useful as reagents for differential identification of the tissue(s) or cell type(s) present in a biological sample and for diagnosis of diseases and conditions which include, but are not limited to, leukemias, lymphomas, and diseases associated with antigen presenting cells, in addition to apoptosis dependant events. Similarly, polypeptides and antibodies directed to these polypeptides are useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 173 as residues: Gln-22 to Gln-44, Ala-90 to Gly-95, Lys-137 to Trp-146, Arg-171 to Asp-181, Glu-370 to Ser-380, Asp-447 to Gly-452, Gln-463 to Trp-469, Asn-504 to Ala-510, Asp-512 to His-519, Ala-541 to Val-550, Asn-558 to His-566. Polynucleotides encoding said polypeptides are also provided.

The tissue distribution immune and hematopoietic cells and tissues, combined with the homology to the murine FIG. 1 gene indicates that polynucleotides and polypeptides corresponding to this gene are useful as a therapeutic and/or diagnostic agent for hematopoietic diseases, especially those associated with antigen presenting cells. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune functions. Therefore it is also useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:81 and may have been publicly available prior to conception of the present invention. Preferably, such related polynucleotides are specifically excluded from the scope of the present invention. To list every related sequence is cumbersome. Accordingly, preferably excluded from the present invention are one or more polynucleotides comprising a nucleotide sequence described by the general formula of a–b, where a is any integer between 1 to 1853 of SEQ ID NO:81, b is an integer of 15 to 1867, where both a and b correspond to the positions of nucleotide residues shown in SEQ ID NO:81, and where b is greater than or equal to a+14.

TABLE 1

| Gene No. | cDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HISCN02 | 209878<br>May 18, 1998 | pSport1 | 11 | 1113 | 1 | 1113 | 232 | 232 | 103 | 1 | 26 | 27 | 106 |
| 2 | HHGDM70 | 209878<br>May 18, 1998 | Lambda ZAP II | 12 | 983 | 102 | 983 | 69 | 69 | 104 | 1 | 57 | 58 | 86 |
| 3 | HHPGO40 | 209878<br>May 18, 1998 | Uni-ZAP XR | 13 | 973 | 1 | 973 | 68 | 68 | 105 | 1 | 37 | 38 | 302 |
| 3 | HHPGO40 | 209878<br>May 18, 1998 | Uni-ZAP XR | 82 | 984 | 1 | 984 | 74 | 74 | 174 | 1 | 37 | 38 | 224 |
| 4 | HAMGG68 | 209878<br>May 18, 1998 | pCMVSport 3.0 | 14 | 1458 | 1 | 1458 | 312 | 312 | 106 | 1 | 20 | 21 | 55 |
| 5 | HAPOM49 | 209878<br>May 18, 1998 | Uni-ZAP XR | 15 | 2005 | 1 | 2005 | 251 | 251 | 107 | 1 | 22 | 23 | 189 |
| 5 | HAPOM49 | 209878<br>May 18, 1998 | Uni-ZAP XR | 83 | 2664 | 1 | 2664 | 448 | 448 | 175 | 1 | 1 | 2 | 123 |
| 6 | HBGBA69 | 209878<br>May 18, 1998 | Uni-ZAP XR | 16 | 943 | 1 | 933 | 62 | 62 | 108 | 1 | 38 | 39 | 60 |
| 7 | HBJFJ26 | 209878<br>May 18, 1998 | Uni-ZAP XR | 17 | 1503 | 588 | 1480 | 290 | 290 | 109 | 1 | 26 | 27 | 128 |
| 7 | HBJFJ26 | 209878<br>May 18, 1998 | Uni-ZAP XR | 84 | 1328 | 413 | 1305 | 591 | 591 | 176 | 1 | 20 | 21 | 59 |
| 8 | HCEDH38 | 209878<br>May 18, 1998 | Uni-ZAP XR | 18 | 1512 | 1 | 1438 | 222 | 222 | 110 | 1 | 26 | 27 | 68 |
| 9 | HDPOJ08 | 209878<br>May 18, 1998 | pCMVSport 3.0 | 19 | 1655 | 1 | 1655 | 159 | 159 | 111 | 1 | 18 | 19 | 122 |
| 10 | HDPRX82 | 209878<br>May 18, 1998 | pCMVSport 3.0 | 20 | 2525 | 1 | 2525 | 128 | 128 | 112 | 1 | 32 | 33 | 82 |
| 11 | HELGK31 | 209878<br>May 18, 1998 | Uni-ZAP XR | 21 | 1396 | 25 | 1334 | 209 | 209 | 113 | 1 | 29 | 30 | 344 |
| 11 | HCNUA40 | 97898<br>Feb. 26, 1997<br>209044<br>May 15, 1997 | pBluescript | 85 | 1342 | 949 | 1237 | 960 | 960 | 177 | 1 | 33 | 34 | 105 |
| 12 | HFPCX64 | 209878<br>May 18, 1998 | Uni-ZAP XR | 22 | 1069 | 1 | 1069 | 181 | 181 | 114 | 1 | 28 | 29 | 181 |
| 12 | HFPCX64 | 209878<br>May 18, 1998 | Uni-ZAP XR | 86 | 1154 | 84 | 1154 | 257 | 257 | 178 | 1 | 28 | 29 | 87 |
| 12 | HCEBW71 | 209225<br>Aug. 28, 1997 | Uni-ZAP XR | 87 | 1197 | 141 | 1197 | 257 | 257 | 179 | 1 | 28 | 29 | 87 |
| 13 | HFXDO60 | 209878<br>May 18, 1998 | Lambda ZAP II | 23 | 1658 | 1 | 1658 | 131 | 131 | 115 | 1 | 46 | 47 | 115 |
| 14 | HHEPG41 | 209878<br>May 18, 1998 | pCMVSport 3.0 | 24 | 1077 | 385 | 1043 | 514 | 514 | 116 | 1 | 35 | 36 | 70 |
| 14 | HAUAI83 | 209072<br>Feb. 12, 1998 | Uni-ZAP XR | 88 | 910 | 1 | 886 | 253 | 253 | 180 | 1 | 37 | 38 | 49 |
| 14 | HJPAZ83 | 209072<br>Feb. 12, 1998 | Uni-ZAP XR | 89 | 1076 | 398 | 1076 | | 575 | 181 | 1 | 11 | 12 | 23 |
| 15 | HKGAH42 | 209878<br>May 18, 1998 | pSport1 | 25 | 1205 | 1 | 1205 | 143 | 143 | 117 | 1 | 21 | 22 | 63 |
| 16 | HMIAP86 | 209878<br>May 18, 1998 | Uni-ZAP XR | 26 | 1674 | 13 | 1674 | 182 | 182 | 118 | 1 | 19 | 20 | 334 |
| 17 | HMUAP70 | 209878<br>May 18, 1998 | pCMVSport 3.0 | 27 | 1965 | 531 | 1914 | 183 | 183 | 119 | 1 | 16 | 17 | 221 |
| 17 | HMUAP70 | 209878<br>May 18, 1998 | pCMVSport 3.0 | 90 | 1842 | 407 | 1783 | 413 | 413 | 182 | 1 | 25 | 26 | 103 |
| 17 | HAGFY16 | 97923<br>Mar. 7, 1997<br>209071<br>May 22, 1997 | Uni-ZAP XR | 91 | 1963 | 209 | 1922 | 251 | 251 | 183 | 1 | 28 | 29 | 198 |
| 17 | HBMCF37 | 209683<br>Mar. 20, 1998 | pBluescript | 92 | 1487 | 79 | 1487 | 170 | 170 | 184 | 1 | 44 | 45 | 70 |
| 17 | HFLQB16 | 209641<br>Feb. 25, 1998 | Uni-ZAP XR | 93 | 1653 | 394 | 1637 | 413 | 413 | 185 | 1 | 25 | 26 | 82 |
| 17 | HAGFY16 | 97923<br>Mar. 7, 1997<br>209071<br>May 22, 1997 | Uni-ZAP XR | 94 | 1830 | 87 | 1786 | 128 | 128 | 186 | 1 | 26 | 27 | 45 |

TABLE 1-continued

| Gene No. | cDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 18 | HRACJ35 | 209878 May 18, 1998 | pCMVSport 3.0 | 28 | 1863 | 8 | 1863 | 99 | 99 | 120 | 1 | 24 | 25 | 472 |
| 18 | HAWAZ34 | 209141 July 9, 1997 | pBluescript SK- | 95 | 1134 | 472 | 1132 | 687 | 687 | 187 | 1 | | | 33 |
| 19 | HTWDE26 | 209878 May 18, 1998 | pSport1 | 29 | 1626 | 1 | 1626 | 68 | 68 | 121 | 1 | 30 | 31 | 167 |
| 19 | HMHBN40 | 97901 Feb. 26, 1997 209047 May 15, 1997 | Uni-ZAP XR | 96 | 1772 | 69 | 1772 | 129 | 129 | 188 | 1 | 30 | 31 | 231 |
| 20 | HUSIB13 | 209878 May 18, 1998 | pSport1 | 30 | 605 | 1 | 605 | 172 | 172 | 122 | 1 | 32 | 33 | 46 |
| 21 | HBAFA02 | 209877 May 18, 1998 | pSport1 | 31 | 931 | 359 | 931 | 46 | 46 | 123 | 1 | 21 | 22 | 108 |
| 22 | H2CBT75 | 209877 May 18, 1998 | pBluescript SK- | 32 | 1407 | 1 | 1407 | 32 | 32 | 124 | 1 | 23 | 24 | 60 |
| 23 | HAGDQ42 | 209877 May 18, 1998 | Uni-ZAP XR | 33 | 1526 | 1 | 1526 | 126 | 126 | 125 | 1 | 18 | 19 | 248 |
| 24 | HBMCJ42 | 209877 May 18, 1998 | pBluescript | 34 | 1737 | 41 | 1580 | 244 | 244 | 126 | 1 | 44 | 45 | 248 |
| 25 | HDPBQ71 | 209877 May 18, 1998 | pCMVSport 3.0 | 35 | 2242 | 6 | 2242 | 24 | 24 | 127 | 1 | 33 | 34 | 612 |
| 25 | HDPFQ90 | PTA-499 Aug. 11, 1999 | pCMVSport 3.0 | 97 | 2381 | 162 | 2381 | 165 | 165 | 189 | 1 | 33 | 34 | 456 |
| 26 | HCEJG71 | 209877 May 18, 1998 | Uni-ZAP XR | 36 | 2235 | 2 | 2235 | 28 | 28 | 128 | 1 | 25 | 26 | 447 |
| 27 | HELHL48 | 209877 May 18, 1998 | Uni-ZAP XR | 37 | 2971 | 560 | 2557 | 629 | 629 | 129 | 1 | 16 | 17 | 291 |
| 27 | HSKCT36 | 209580 Jan. 14, 1998 | Uni-ZAP XR | 98 | 1955 | 1 | 1955 | 31 | 31 | 190 | 1 | 18 | 19 | 184 |
| 28 | HISAQ04 | 209877 May 18, 1998 | pSport1 | 38 | 1163 | 1 | 1163 | 61 | 61 | 130 | 1 | 21 | 22 | 78 |
| 29 | HJACB89 | 209877 May 18, 1998 | pBluescript SK- | 39 | 1932 | 28 | 1930 | 95 | 95 | 131 | 1 | 23 | 24 | 333 |
| 30 | HTECC05 | 209877 May 18, 1998 | Uni-ZAP XR | 40 | 881 | 1 | 881 | 27 | 27 | 132 | 1 | 15 | 16 | 164 |
| 31 | HBJLF01 | 209877 May 18, 1998 | Uni-ZAP XR | 41 | 1932 | 201 | 1931 | 217 | 217 | 133 | 1 | 46 | 47 | 244 |
| 32 | HBXGP60 | 209877 May 18, 1998 | ZAP Express | 42 | 1164 | 1 | 1164 | 143 | 143 | 134 | 1 | 22 | 23 | 55 |
| 33 | HCE5B20 | 209877 May 18, 1998 | Uni-ZAP XR | 43 | 1105 | 1 | 1105 | 237 | 237 | 135 | 1 | 25 | 26 | 54 |
| 34 | HCMSQ56 | 209877 May 18, 1998 | Uni-ZAP XR | 44 | 1262 | 1 | 1262 | 148 | 148 | 136 | 1 | 19 | 20 | 88 |
| 35 | HCNAH57 | 209877 May 18, 1998 | Lambda ZAP II | 45 | 517 | 1 | 517 | 35 | 35 | 137 | 1 | 33 | 34 | 61 |
| 36 | HCUEP91 | 209877 May 18, 1998 | ZAP Express | 46 | 858 | 2 | 858 | 266 | 266 | 138 | 1 | 20 | 21 | 105 |
| 37 | HDPCJ91 | 209877 May 18, 1998 | pCMVSport 3.0 | 47 | 6107 | 1 | 6107 | 131 | 131 | 139 | 1 | 28 | 29 | 51 |
| 38 | HDPGK25 | 209877 May 18, 1998 | pCMVSport 3.0 | 48 | 703 | 1 | 703 | 345 | 345 | 140 | 1 | 33 | 34 | 119 |
| 39 | HE2DY70 | 209877 May 18, 1998 | Uni-ZAP XR | 49 | 639 | 1 | 639 | 137 | 137 | 141 | 1 | 45 | 46 | 58 |
| 40 | HE2NV57 | 209877 May 18, 1998 | Uni-ZAP XR | 50 | 867 | 1 | 867 | 99 | 99 | 142 | 1 | 36 | 37 | 99 |
| 41 | HETBR16 | 209877 May 18, 1998 | Uni-ZAP XR | 51 | 1569 | 1 | 1569 | 161 | 161 | 143 | 1 | 21 | 22 | 64 |
| 42 | HFXDG13 | 209877 May 18, 1998 | Lambda ZAP II | 52 | 1196 | 1 | 1196 | 43 | 43 | 144 | 1 | 37 | 38 | 66 |
| 43 | HFXKY27 | 209877 May 18, 1998 | Lambda ZAP II | 53 | 945 | 1 | 945 | 44 | 44 | 145 | 1 | 19 | 20 | 58 |
| 44 | HHPEC09 | 209877 May 18, 1998 | Uni-ZAP XR | 54 | 488 | 1 | 488 | 71 | 71 | 146 | 1 | 19 | 20 | 55 |
| 45 | HISAD54 | 209877 May 18, 1998 | pSport1 | 55 | 2860 | 1 | 2860 | 172 | 172 | 147 | 1 | 19 | 20 | 65 |
| 46 | HJBCY35 | 209877 May 18, 1998 | pBluescript SK- | 56 | 1559 | 93 | 1272 | 232 | 232 | 148 | 1 | 23 | 24 | 327 |
| 47 | HKAEA19 | 209877 May 18, 1998 | pCMVSport 2.0 | 57 | 2064 | 1 | 1909 | 83 | 83 | 149 | 1 | 21 | 22 | 89 |
| 48 | HKGDL36 | 209877 May 18, 1998 | pSport1 | 58 | 1050 | 1 | 1050 | 55 | 55 | 150 | 1 | 33 | 34 | 148 |

TABLE 1-continued

| Gene No. | cDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 49 | HLDBS43 | 209877 May 18, 1998 | pCMVSport 3.0 | 59 | 2533 | 1 | 2533 | 73 | 73 | 151 | 1 | 26 | 27 | 390 |
| 50 | HLWAD92 | 209877 May 18, 1998 | pCMVSport 3.0 | 60 | 899 | 1 | 899 | 197 | 197 | 152 | 1 | 34 | 35 | 98 |
| 51 | HLYBI15 | 209877 May 18, 1998 | pSport1 | 61 | 1079 | 1 | 1079 | 92 | 92 | 153 | 1 | 22 | 23 | 60 |
| 52 | HMEJE05 | 209889 May 22, 1998 | Lambda ZAP II | 62 | 1928 | 1 | 1928 | 25 | 25 | 154 | 1 | 30 | 31 | 392 |
| 53 | HNGIX55 | 209889 May 22, 1998 | Uni-ZAP XR | 63 | 781 | 1 | 781 | 121 | 121 | 155 | 1 | 19 | 20 | 74 |
| 54 | HNHEX30 | 209889 May 22, 1998 | Uni-ZAP XR | 64 | 1194 | 1 | 1194 | 138 | 138 | 156 | 1 | 15 | 16 | 81 |
| 55 | HPJBI33 | 209889 May 22, 1998 | Uni-ZAP XR | 65 | 1677 | 1 | 1677 | 236 | 236 | 157 | 1 | 31 | 32 | 53 |
| 56 | HRABA80 | 209889 May 22, 1998 | pCMVSport 3.0 | 66 | 1237 | 1 | 1237 | 130 | 130 | 158 | 1 | 28 | 29 | 102 |
| 57 | HRACD80 | 209889 May 22, 1998 | pCMVSport 3.0 | 67 | 1934 | 1 | 1934 | 191 | 191 | 159 | 1 | 16 | 17 | 575 |
| 57 | HRACD80 | 209889 May 22, 1998 | pCMVSport 3.0 | 99 | 1958 | 1 | 1958 | 191 | 191 | 191 | 1 | 16 | 17 | 146 |
| 58 | HSLCX03 | 209889 May 22, 1998 | Uni-ZAP XR | 68 | 3300 | 984 | 2729 | 677 | 677 | 160 | 1 | 22 | 23 | 643 |
| 58 | HSLCX03 | 209889 May 22, 1998 | Uni-ZAP XR | 100 | 2444 | 1 | 2444 | 392 | 392 | 192 | 1 | 22 | 23 | 124 |
| 59 | HT5GJ57 | 209889 May 22, 1998 | Uni-ZAP XR | 69 | 1797 | 92 | 1797 | 122 | 122 | 161 | 1 | 25 | 26 | 190 |
| 60 | HTACS42 | 209889 May 22, 1998 | Uni-ZAP XR | 70 | 1373 | 1 | 1373 | 213 | 213 | 162 | 1 | 29 | 30 | 63 |
| 61 | HTEKE40 | 209889 May 22, 1998 | Uni-ZAP XR | 71 | 1579 | 1 | 1579 | 173 | 173 | 163 | 1 | 47 | 48 | 117 |
| 62 | HTOBX69 | 209889 May 22, 1998 | Uni-ZAP XR | 72 | 1028 | 1 | 1028 | 28 | 28 | 164 | 1 | 20 | 21 | 42 |
| 63 | HUVEO77 | 209889 May 22, 1998 | Uni-ZAP XR | 73 | 3674 | 1 | 3674 | 55 | 55 | 165 | 1 | 27 | 28 | 47 |
| 64 | H2CBG48 | 209889 May 22, 1998 | pBluescript SK- | 74 | 2797 | 1 | 2797 | 125 | 125 | 166 | 1 | 25 | 26 | 45 |
| 65 | H2CBU83 | 209889 May 22, 1998 | pBluescript SK- | 75 | 2703 | 1 | 2703 | 157 | 157 | 167 | 1 | 30 | 31 | 207 |
| 65 | H2CBU83 | 209889 May 22, 1998 | pBluescript SK- | 101 | 2709 | 1 | 2709 | 157 | 157 | 193 | 1 | 30 | 31 | 51 |
| 66 | HAPNY94 | 209889 May 22, 1998 | Uni-ZAP XR | 76 | 742 | 1 | 742 | 94 | 94 | 168 | 1 | 29 | 30 | 50 |
| 67 | HBJHZ58 | 209889 May 22, 1998 | Uni-ZAP XR | 77 | 1825 | 1 | 1825 | 102 | 102 | 169 | 1 | 29 | 30 | 42 |
| 68 | HCE2B33 | 209889 May 22, 1998 | Uni-ZAP XR | 78 | 1674 | 1 | 1668 | 67 | 67 | 170 | 1 | 18 | 19 | 55 |
| 69 | HDPBQ02 | 209889 May 22, 1998 | pCMVSport 3.0 | 79 | 2191 | 291 | 2191 | 460 | 460 | 171 | 1 | 24 | 25 | 108 |
| 70 | HFIYI70 | 209889 May 22, 1998 | pSport1 | 80 | 1335 | 1 | 1335 | 43 | 43 | 172 | 1 | 15 | 16 | 50 |
| 71 | HDPOZ56 | 209889 May 22, 1998 | pCMVSport 3.0 | 81 | 1867 | 415 | 1867 | 103 | 103 | 173 | 1 | 21 | 22 | 566 |
| 71 | HDPOZ56 | 209889 May 22, 1998 | pCMVSport 3.0 | 102 | 1722 | 1 | 1722 | 59 | 59 | 194 | 1 | 21 | 22 | 319 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X, SEQ ID NO:Y, or a deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using techniques described herein or otherwise known in the art, such as, for example, antibodies of the invention raised against the secreted protein.

The present invention provides a polynucleotide comprising, or alternatively consisting of, the nucleic acid sequence of SEQ ID NO:X, and/or a cDNA contained in ATCC deposit Z. The present invention also provides a polypeptide comprising, or alternatively, consisting of, the polypeptide sequence of SEQ ID NO:Y and/or a polypeptide encoded by the cDNA contained in ATCC deposit Z. Polynucleotides encoding a polypeptide comprising, or alternatively consisting of the polypeptide sequence of SEQ ID NO:Y and/or a polypeptide sequence encoded by the CDNA contained in ATCC deposit Z are also encompassed by the invention.

Signal Sequences

The present invention also encompasses mature forms of the polypeptide having the polypeptide sequence of SEQ ID NO:Y and/or the polypeptide sequence encoded by the cDNA in a deposited clone. Polynucleotides encoding the mature forms (such as, for example, the polynucleotide sequence in SEQ ID NO:X and/or the polynucleotide sequence contained in the cDNA of a deposited clone) are also encompassed by the invention. According to the signal hypothesis, proteins secreted by mammalian cells have a signal or secretary leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1–6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., +or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as desribed below). These polypeptides, and the polynucleotides encoding such polypeptides, are contemplated by the present invention.

Polynucleotide and Polypeptide Variants

The present invention is directed to variants of the polynucleotide sequence disclosed in SEQ ID NO:X, the complementary strand thereto, and/or the cDNA sequence contained in a deposited clone.

The present invention also encompasses variants of the polypeptide sequence disclosed in SEQ ID NO:Y and/or encoded by a deposited clone. "Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:X or the complementary strand thereto, the nucleotide coding sequence contained in a deposited cDNA clone or the complementary strand thereto, a nucleotide sequence encoding the polypeptide of SEQ ID NO:Y, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions or lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:Y, the polypeptide sequence encoded by the cDNA contained in a deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown inTable 1, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, an amino acid sequences shown in Table 1 (SEQ ID NO:Y) or to the amino acid sequence encoded by cDNA contained in a deposited clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5. Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1 a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. in contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is -5, 5–10, 5–25, 5–50, 10–50 or 50–150, conservative amino acid substitutions are preferable.

Polynucleotide and Polypeptide Fragments

The present invention is also directed to polynucleotide fragments of the polynucleotides of the invention.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:X. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1001, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

In the present invention, a "polypeptide fragment" refers to an amino acid sequence which is a portion of that contained in SEQ ID NO:Y or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

Preferably, the polynucleotide fragments of the invention encode a polypeptide which demonstrates a functional activity. By a polypeptide demonstrating a "functional activity" is meant, a polypeptide capable of displaying one or more known functional activities associated with a full-length (complete) polypeptide of invention protein. Such functional activities include, but are not limited to, biological activity, antigenicity [ability to bind (or compete with a polypeptide of the invention for binding) to an antibody to the polypeptide of the invention], immunogenicity (ability to generate antibody which binds to a polypeptide of the invention), ability to form multimers with polypeptides of the invention, and ability to bind to a receptor or ligand for a polypeptide of the invention.

The functional activity of polypeptides of the invention, and fragments, variants derivatives, and analogs thereof, can be assayed by various methods.

For example, in one embodiment where one is assaying for the ability to bind or compete with full-length polypeptide of the invention for binding to an antibody of the polypeptide of the invention, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand for a polypeptide of the invention identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94–123. In another embodiment, physiological correlates of binding of a polypeptide of the invention to its substrates (signal transduction) can be assayed.

In addition, assays described herein (see Examples) and otherwise known in the art may routinely be applied to measure the ability of polypeptides of the invention and fragments, variants derivatives and analogs thereof to elicit related biological activity related to that of the polypeptide of the invention (either in vitro or in vivo). Other methods will be known to the skilled artisan and are within the scope of the invention.

Epitopes and Antibodies

The present invention encompasses polypeptides comprising, or alternatively consisting of, an epitope of the polypeptide having an amino acid sequence of SEQ ID NO:Y, or an epitope of the polypeptide sequence encoded by a polynucleotide sequence contained in ATCC deposit No. Z or encoded by a polynucleotide that hybridizes to the complement of the sequence of SEQ ID NO:X or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:X), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 pg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH 1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-tenrinal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $^{10-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85 %, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferrably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15) :3209–3214 (1998); Yoon et al., J. Immunol. 160(7) :3170–3179 (1998); Prat et al., J. Cell. Sci. 111(Pt2) :237–247 (1998); Pitard et al., J. Immunol. Methods 205(2) :177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bioltechnology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to deterrnine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5) :155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art. Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved phannacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0. 1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 1251) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 1251) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $^{10-12}$ M, $5\times10^{-13}$ M, $10^{-13}$ M, $5\times10^{-14}$ M, $10^{-14}$ M, $5\times10^{-15}$ M, or $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem.

262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; W092/20316; W093/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication W094/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed. Therapeutic/Prophylactic Administration and Composition The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. Diagnosis and Imaging Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest.

Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit-generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for a-example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ,pGAPZ, pGAPZalph, pPIC9, pPIC3.5, pHIL-D2, pHIL-S1, pPIC3.5K, pPIC9K, and PA0815 (all available from Invitrogen, Carlbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O^2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., etal., *Mol. Cell. Biol.* 5:1111–21 (1985); Koutz, P.J, etaL, *Yeast* 5:167–77 (1989); Tschopp, J. F., et aL, Nucl. Acids Res. 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOXI promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PA0815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., *Nature*, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-termiinal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. NO: 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478, 925, which is herein incorporated by reference in its entirety).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31' mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferrably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. No. 5,858,659 and 5,856,104. The U.S. Pat.s referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Eghoim, R. H. Berg and O. Buchardt, Science 254, 1497 (1991); and M. Egholm, O. Buchardt, L.Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative diseases, disorders, and/or conditions are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra) For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative diseases, disorders, and/or conditions of hematopoietic cells and tissues, in light of the numerous cells and cell types of varying origins which are known to exhibit proliferative phenotypes.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression,CRCPress, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant,urine,fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making -oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (1251, 1211), carbon (14C), sulfur (35S), tritium (3H), indium (1121n), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 1311, 1121n, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "lmmunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treatingor preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term “naked” polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT : promoter, the metallothionein promoter; heat shock promoters; the albumin promoter; the ApoAl promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the nakednucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc. Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Feigner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolarnine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10: 1 to about 1:10. Preferably, the ration will be from about 5:1 to about 1:5. More preferably, the ration will be about 3:1 to about 1:3. Still more preferably, the ratio will be about 1:1.

U.S. Pat. No: 5,676,954 (which is herein incorporated by reference) reports on the injection of genetic material, complexed with cationic liposomes carriers, into nmice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19–14X, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al.,Science , 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell , 68:143–155 (1992); Engelhardt et al., Human Genet. Ther., 4:759–769 (1993); Yang et al., Nature Genet., 7:362–369 (1994); Wilson et al., Nature, 365:691–692 (1993); and U.S. Pat. No. : 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. : 5,641,670, issued Jun. 24, 1997; International Publication NO: WO 96/29411, published September 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding other angiongenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders,and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgamnmaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. These molecules could be important in the treatment or prevention of heart attacks (infarction), strokes, or scarring.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferrably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragements thereof, of the present invention. Such antibodies, fragments, or regions, will preferably have an affinity for polynucleotides or polypeptides, including fragements thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$ M, $5\times10^{-12}$M, $10^{-12}$M, $5\times10^{-13}$M, $10^{-13}$M, $5\times10^{-14}$M, $10^{-14}$M, $5\times10^{15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph IB, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et.al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses.50(5):423–33 (1998), Chem Biol Interact. Apr 24; 111–112:23–34 (1998), J Mol Med.76(6):402–12 (1998), Int J Tissue React;20(1): 3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol Immunol 1998;231:125–41, which is hereby incorporated by reference). Such thereapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or prodrugs) to targeted cells expressing the polypeptide of the present invention. Polypeptides or polypeptide antibodes of the invention may be associated with with heterologous polypeptides, heterologous nucleic acids, toxins, or prodrugs via hydrophobic, hydrophilic, ionic and/or covalent interactions. Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, ulmonary subvalvular stenosis, restrictive cardiomyopathy, Chagas cardiomyopathy, ndocardial fibroelastosis, endomyocardial fibrosis, Kearns Syndrome, myocardial eperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., *Biotech.* 9:630–634 (1991); Folkman etal., *N. Engl. J. Med.*, 333:1757–1763 (1995); Auerbach et al., *J. Microvasc. Res.* 29:401–411 (1985);

Folkman, Advances in Cancer Research, eds. Klein and Weinhouse, Academic Press, New York, pp. 175–203 (1985); Patz, *Am. J. Opthalmol.* 94:715–743 (1982); and Folkman et aL, Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et aL, Medicine, 2d Ed., J. B. Lippincott Co., Philadelphia (1985)) .Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treator prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al, *Am. J. Ophthal.* 85:704–710 (1978) and Gartner et al., *Surv. Ophthal.* 22:291–312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-i, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4): 1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intesting, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B 12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), Cryptococcus neoformans, Aspergillosis, Bacillaceae (e.g., Anthrax, Clostridium), Bacteroidaceae, Blastomycosis, Bordetella, Borrelia (e.g., Borrelia burgdorferi), Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi*, and *Salmonella paratyphi*), Serratia, Yersinia), Erysipelothrix, Helicobacter, Legionellosis, Leptospirosis, Listeria, Mycoplasmatales, *Mycobacterium leprae, Vibrio cholerae*, Neisseriaceae (e.g., Acinetobacter, Gonorrhea, Menigococcal), Meisseria meningitidis, Pasteurellacea Infections (e.g., Actinobacillus, Heamophilus (e.g., *Heamophilus influenza* type B), Pasteurella), Pseudomonas, Rickettsiaceae, Chlamydiaceae, Syphilis, Shigella spp., Staphylococcal, Meningiococcal, Pneumococcal and Streptococcal (e.g., Streptococcus pneumoniae and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., Plasmodium virax, Plasmodium falciparium, Plasmodium malariae and Plasmodium ovale). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used totreat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane.

Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support. chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be alterred by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity , and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense And Ribozyme (Antagonists)

In specific embodiments, antagonists according to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2×ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature*, 372:333–335 (1994). Thus, oligonucleotides complementary to either the 5'- or 3'-non-translated, non-coding regions of a polynucleotide sequence of the invention could be used in an antisense approach to inhibit translation of endogenous MRNA. Oligonucleotides complementary to the 5' untranslated region of the MRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methyiphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention. invention, and/or (b) a ribozyme directed to the polynucleotide of the present invention Other Activities The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, bums, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid Sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

In specific embodiments of the invention, for each "Contig ID" listed in the fourth column of Table 2, preferably excluded are one or more polynucleotides comprising, or alternatively consisting of, a nucleotide sequence referenced in the fifth column of Table 2 and described by the general formula of a–b, whereas a and b are uniquely determined for the corresponding SEQ ID NO:X referred to in column 3 of Table 2. Further specific embodiments are directed to polynucleotide sequences excluding one, two, three, four, or more of the specific polynucleotide sequences referred to in the fifth column of Table 2. In no way is this listing meant to encompass all of the sequences which may be excluded by the general formula, it is just a representative example. All references available through these accessions are hereby incorporated by reference in their entirety.

TABLE 2

| Gene No. | cDNA Clone ID | NT SEQ ID NO: X | Contig ID | Public Accession Numbers |
|---|---|---|---|---|
| 4 | HAMGG68 | 14 | 731859 | T50763, R53008, AA054732 |
| 5 | HAPOM49 | 15 | 769555 | R01247, R36924, N59290, N72014, N91904, N91912, N99466, W24077, W24089, W86920, AA235373, AA235784, AA417558, AA417671 |
| 5 | HAPOM49 | 83 | 722386 | R01247, R36924, H68902, N59290, N72014, N91904, N91912, N99466, W24077, W24089, W86920, AA235373, AA235784, AA417558, AA417671 |
| 7 | HBJFJ26 | 17 | 772348 | R02524, H14806, N53061, N73248, W93593, AA010653, AA037624, AA134768 |
| 7 | HBJFJ26 | 84 | 648583 | R02524, N53061, N73248, W93593, AA010653, AA037624, AA134768 |
| 8 | HCEDH38 | 18 | 730529 | T66539, R15913, R43424 |
| 11 | HELGK31 | 21 | 681138 | R09514, R09626, R09625, R54573, H11615, H18393, N79058, N94446, W30793, AA132746, AA132651, AA161264, AA161263, AA227183, AA426455, AA426587, AA424834 |
| 11 | HCNUA40 | 85 | 340352 | R09514, R09626, R09625, R54573, H11615, H18393, N79058, N94446, W24000, W30793, AA132746, AA132651, AA142878, AA143152, AA161264, AA161263 |
| 14 | HHEPG41 | 24 | 714102 | T52716, T61025, T61577, R09517, R09629, R24626, R26656, R68241, R68534, R70469, R70556, R71470, R71518, R77435, R77524, R79694, H01135, H01343, H01394, H03302, H03303, H03402, H18688, H18782, H18972, H19070, H20023, H20098, H20143, H20238, H21165, H22368, H22402, H23656, H27857, H40075, H40779, H46187, H46188, H46478, R86746, R87112, R91937, R92265, R94908, |

TABLE 2-continued

| Gene No. | cDNA Clone ID | NT SEQ ID NO: X | Contig ID | Public Accession Numbers |
|---|---|---|---|---|
| | | | | R94992, R99715, H50206, H50207, H59520, H60187, H60231, H60393, H67121, H71491, H71551, H71623, H75393, H81427, H84494, H84495, H84951, H93252, H99652, N23673, N24442, N24542, N25251, N33887, N33986, N38815, N58266, N58289, N70496, N71609, N71651, N72206, N76257, N77644, N77658, N77862, N94261, N95063, W01678, W04664, W31583, W32075, W37128, W37143, W38900, W40195, W58208, AA026633, AA026672, AA037789, AA129884, AA149944, AA150561, AA157861, AA159798, AA159902, AA164972, AA165011, AA186949, AA188345, AA419151, AA419096, AA427690 |
| 14 | HAUAI83 | 88 | 639009 | T52716, T61025, T61577, R09517, R26656, R70469, R71470, R77435, R79694, H03303, H03402, H18688, H18972, H21165, H22368, H27857, H46188, R87112, R91937, R94908, H60187, H60393, H67121, H81427, H84495, H84951, N70496, N71651, N72206, N95063, W31583, AA159798, AA164972, AA188345, AA419096 |
| 14 | HJPAZ83 | 89 | 383592 | T52716, T61025, T61577, R09517, R09629, R24626, R26656, R68241, R68534, R70469, R70556, R71470, R71518, R77435, R77524, R79694, H01135, H01343, H01394, H02789, H03302, H03303, H03402, H18688, H18782, H18972, H19070, H20023, H20098, H20143, H20238, H21165, H22368, H22402, H23656, H27857, H40075, H40779, H46187, H46188, H46478, R86746, R87112, R91937, R92265, R94908, R94992, R99715, H50206, H50207, H59520, H60187, H60231, H60393, H67121, H71491, H71551, H71623, H75393, H81427, H84494, H84495, H84951, H93252, H99652, N23673, N24442, N24542, N25251, N33887, N33986, N38815, N58266, N58289, N70496, N71609, N71651, N72206, N76257, N77644, N77658, N77862, N94261, N95063, W01678, W04664, W31583, W32075, W37128, W37143, W38900, W40195, W58208, AA026633, AA026672, AA037789, AA129884, AA149944, AA150561, AA157861, AA159798, AA159902, AA164972, AA165011, AA186949, AA188345 |
| 16 | HMIAP86 | 26 | 726831 | R19440, R44688, R44688, N48177, AA015735, AA015832, AA021119, AA035652, AA054548, AA056945, AA057005, AA142931 |
| 17 | HMUAP70 | 27 | 872208 | T54768, T63367, T63693, T91023, T84597, R12614, R13763, R18327, R20519, R25031, R32390, R32391, R42373, R43789, R53025, R20519, R43789, R42373, R55911, R56184, R63828, R64440, R81848, R81849, H13310, H15827, H16135, H23642, H41386, H38655, R90812, R90813, R90918, R90917, H53640, H53684, H86289, H97448, H99819, N22752, N25711, N27027, N30220, N34534, N35917, N36220, N40152, N43983, N57112, N59141, N59261, N75178, N76730, N78834, N92441, N94329, N94537, W17196, W23456, W30811, W31472, W31935, W33009, W35396, W46630, W56256, W92571, N89770, N89859, AA018416, AA019585, AA029562, AA029728, AA037122, AA055763, AA055962, AA056053, AA085090, AA112870, AA122341, AA161332, AA258388, AA258458, AA287736, AA287895, AA515285, AA521082, AA525839, AA565211, AA583521, AA602387, AA613126, AA577338, AA744564, AA744562, AA767024, AA807259, AA829478, AA831898, AA837702, AA857543, AA872758, AA872812, AA873496, AA876196, AA906972, AA907413, AA910558, AA910679, AA911982, AA918516, AA922986, AA931689, AA932624, AA935683, AA939289, AA953784, AA953789, |

TABLE 2-continued

| Gene No. | cDNA Clone ID | NT SEQ ID NO: X | Contig ID | Public Accession Numbers |
|---|---|---|---|---|
| | | | | AA973796, AA975996, AI028021, AI079727, D81853, N56132, C00677, R29165, C14582, AA092968, AA643728, AA283859, AA293329, AA293343, AA399445, AA399423, AA402367, AA410303, AA410485, AA421573, AA448868, AA452710, AA496466, AA664059, AA679878, AA447934, AA724357, AA725042, AA779099, AA781082, AA782100, AA782815, AA813278, AA843171, AA843277, AA843967, AA846407, AA861311, AA890689, AA984140, AA992894, AA993782, AA995135, AI027067, AI027113, AI027262, AI028088, AI042642, AI057601, AI041151, AI091181, AI091239, AI093012, AI093848, T24514, Z43644, Z45519, F02527, T54934, F06244, F04381, F04532, F08307, AI244846, AI245725, AI276792, AI279043, AI298862, AI307614, AI334644, AI343572, AI348509, AI348632, AI364763, AI202774, AI453449, AI446094, AI400913, AI401566, AI417788, AI418178, AI499779, AI566161, AI498899, AI419614, AI422091, AI570545, AI571822, AI582814, AI423417, AI423456, AI127285, AI128706, AI147786, AI148738, AI149386, AI167754, AI167826, AI168731, AI187434, AI652739, AI219638 |
| 17 | HMUAP70 | 90 | 723302 | T54768, T63367, T63693, T91023, T84597, R12614, R13763, R18327, R20519, R25031, R32390, R32391, R43789, R53025, R20519, R43789, R42373, R55911, R56184, R63828, R64440, R81848, R81849, H13310, H15827, H16135, H23642, H41386, H38655, R90812, R90813, R90918, R90917, H53640, H53684, H86289, H97448, H99819, N22752, N25711, N27027, N30220, N34534, N35917, N36220, N40152, N43983, N57112, N59141, N59261, N75178, N76730, N78834, N92441, N94329, N94537, W17196, W23456, W30811, W31472, W31935, W33009, W35396, W46630, W56256, W92571, N89770, N89859, AA018416, AA019585, AA029562, AA029728, AA037122, AA055763, AA055962, AA056053, AA085090, AA112870, AA122341, AA161332, AA258388, AA258458 |
| 17 | HAGFY16 | 91 | 778820 | T54768, T63367, T63693, T91023, T84597, R12614, R13763, R18327, R20519, R25031, R32390, R32391, R42373, R43789, R53025, R20519, R43789, R42373, R55911, R56184, R63828, R64440, R81848, R81849, H13310, H15827, H16135, H23642, H41386, H38655, R90812, R90813, R90918, R90917, H53640, H53684, H86289, H97448, H99819, N22752, N25711, N27027, N30220, N34534, N35917, N36220, N40152, N43983, N57112, N59141, N59261, N75178, N76730, N78834, N92441, N94329, N94537, W17196, W23456, W30811, W31472, W31935, W33009, W35396, W46630, W56256, W92571, N89770, N89859, AA018416, AA019585, AA029562, AA029728, AA037122, AA055763, AA055962, AA056053, AA085090, AA112870, AA122341, AA161332, AA258388, AA258458 |
| 17 | HBMCF37 | 92 | 674913 | T54768, T63367, T63693, T91023, T84597, R13763, R20519, R25031, R42373, R53025, R20519, R42373, R55911, R56184, R63828, R64440, R81848, R81849, H13310, H23642, R90812, R90813, R90918, R90917, H53640, H53684, H97448, H99819, N25711, N27027, N34534, N40152, N43983, N59141, N75178, N76730, N78834, N92441, N94537, W17196, W23456, W30811, W31472, W31935, W33009, W35396, W46630, W56256, N89770, AA019585, AA029562, AA029728, AA037122, AA055763, AA055962, AA056053, AA085090, AA122341, AA161332, AA258458 |

TABLE 2-continued

| Gene No. | cDNA Clone ID | NT SEQ ID NO: X | Contig ID | Public Accession Numbers |
|---|---|---|---|---|
| 17 | HFLQB16 | 93 | 646810 | T54768, T63367, T63693, T91023, T84597, R13763, R20519, R25031, R32391, R43789, R53025, R20519, R43789, R42373, R55911, R56184, R63828, R64440, R81849, H13310, H15827, H23642, H41386, H38655, R90812, R90813, R90918, R90917, H53640, H53684, H86289, H97448, H99819, N22752, N25711, N27027, N30220, N34534, N35917, N36220, N43983, N59141, N59261, N75178, N78834, N92441, N94329, N94537, W17196, W23456, W30811, W31472, W35396, W46630, W56256, N89770, N89859, AA018416, AA019585, AA029562, AA029728, AA037122, AA055763, AA055962, AA056053, AA085090, AA112870, AA122341, AA161332, AA258388, AA258458 |
| 17 | HAGFY16 | 94 | 381964 | T54768, T63367, T63693, T91023, T84597, R12614, R13763, R18327, R20519, R25031, R32390, R32391, R43789, R53025, R20519, R43789, R42373, R55911, R56184, R63828, R64440, R81848, R81849, H13310, H15827, H16135, H23642, H41386, H38655, R90812, R90813, R90918, R90917, H53640, H53684, H86289, H97448, H99819, N22752, N25711, N27027, N30220, N34534, N35917, N36220, N40152, N43983, N57112, N59141, N59261, N75178, N76730, N78834, N92441, N94329, N94537, W23456, W30811, W31472, W31935, W33009, W35396, W46630, W56256, W92571, N89770, N89859, AA018416, AA019585, AA029562, AA029728, AA037122, AA055763, AA055962, AA056053, AA085090, AA112870, AA122341, AA161332 |
| 18 | HRACJ35 | 28 | 730504 | R07660, T96591, T96696, R05716, R05717, R13864, R18560, R37006, R41427, R41427, H40140, H40189, N95081, W23483, W88670, W88683, AA016124, AA041196, AA041433, AA043329, AA043330, AA045134, AA045355, AA045610, AA054467, AA056673, AA126801, AA126627, AA127006, AA461136 |
| 18 | HAWAZ34 | 95 | 470546 | R07660, T96591, T96696, R05716, R05717, R37006, R41427, R41427, H40140, H40189, N95081, W23483, W88670, W88683, AA041196, AA041433, AA043329, AA043330, AA045134, AA045355, AA045610, AA054467, AA056673, AA126801, AA126627, AA127006, AA461136 |
| 21 | HBAFA02 | 31 | 679555 | W46460 |
| 24 | HBMCJ42 | 34 | 713345 | R19189 |
| 25 | HDPBQ71 | 35 | 727200 | T53666, T97552, T97598, R20695, R24935, R52737, R59440, R63901, R63983, R64175, R64256, R64291, H11513, H11875, H19041, H29405, H65681, H65682, N66596, N98627, W30696, AA081513, AA081567, AA233729, AA233772, AA233825, AA424168 |
| 26 | HCEJG71 | 36 | 715592 | T52089, R18534, R41523, R41523, H91883, W93789, W93790, W96217, W96311 |
| 27 | HELHL48 | 37 | 696945 | T39180, T58537, T58576, T64888, T74066, T87910, T88004, T84545, R00876, R01535, R22025, R24305, R44902, R47850, R44902, H04167, H08605, H08606, H30187, N26490, N31325, N47540, N47539, AA053180, AA053627, AA079475, AA079476, AA088551, AA100522, AA112746, AA136495, AA148445, AA148446, AA151938, AA152055, AA157827, AA179793, AA180517, AA180518, AA188708, AA232508, AA232607 |
| 29 | HJACB89 | 39 | 689899 | R35261, R50932, N57831, W24732, W94722, AA039350, AA039240 |
| 31 | HBJLF01 | 41 | 73211 | H86222, N51612, N53675, N53906, N73038, W89010, W95735, W95778, AA015836, AA016130, AA031919, AA032055, AA232951, AA233002 |
| 41 | HETBR16 | 51 | 703243 | N68223, AA127395 |

TABLE 2-continued

| Gene No. | cDNA Clone ID | NT SEQ ID NO: X | Contig ID | Public Accession Numbers |
|---|---|---|---|---|
| 46 | HJBCY35 | 56 | 719729 | R10335, R10855, R16895, R16949, R46300, R54656, R55419, H15972, H44330, W93021, AA136776, AA188015, AA186786, AA258242, AA259086 |
| 47 | HKAEA19 | 57 | 721489 | T56598, T57283, T90533, T82203, R53228, R84465, R85862, R87773, N23184, W94441, AA100812, AA126954, AA127163, AA172009, AA194102, AA236230, AA236296 |
| 58 | HSLCX03 | 68 | 889145 | T91232, R11114, T86015, R61399, R61444, N25312, N71736, AA463999, AA464700, AA515534, AA770594, AA971547, AA436445, AA436490, AA781889, AI005130, T20250, T20249, AI146546, AI350837, AI494424, AI569246, AI580715, AI123552, AI144206, AI240523, AI286226, AI610364 |
| 70 | HFIYI70 | 80 | 744906 | T63351, T63674, T87882, T87971, R39999, R48270, R51344, R51451, R49212, R39999, R59159, R64065, R66441, R76632, R80386, R80492, H03457, H03542, H05971, H20303, H20987, H25796, R89247, R89248, R98830, R99313, H48284, H50118, H56131, H64163, H78393, H93783, H93875, N23638, N26313, N29711, N32029, N33057, N34497, N39756, N42121, N42238, N47780, N57738, N58187, N58647, N64442, N67758, N70951, N71593, N94965, W19606, W48757, AA024815, AA024921, AA031973, AA053392, AA085909, AA129251, AA132937, AA132979, AA133081, AA146728, AA147067, AA147069, AA258537, AA424525, AA428935, AA429150, AA429385 |

Having generally described the invention, the same will be more readily understood by reference to the following examples, which are provided by way of illustration and are not intended as limiting.

EXAMPLES

Example 1

Isolation of a Selected cDNA Clone From the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ®2.1 | pCR ®2.1 |

Vectors Lambda Zap (U.S. Pat. Nos. 5,128,256 and 5,286,636), Uni-Zap XR (U.S. Pat. Nos. 5,128, 256 and 5,286,636), Zap Express (U.S. Pat. Nos. 5,128,256 and 5,286,636), pBluescript (pBS) (Short, J. M. et al., Nucleic Acids Res. 16:7583–7600 (1988); Alting-Mees, M. A. and Short, J. M., Nucleic Acids Res. 17:9494 (1989)) and pBK (Alting-Mees, M. A. et al., Strategies 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into *E. coli* strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P.O. Box 6009, Gaithersburg, Md. 20897. All Sport vectors contain an ampicillin resistance gene and may be transformed into *E. coli* strain DH10B, also available from Life Technologies. (See, for instance, Gruber, C. E., et al., Focus 15:59 (1993).)

Vector lafmid BA (Bento Soares, Columbia University, NY) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. (See, for instance, Clark, J. M., Nuc. Acids Res. 16:9677–9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C for 1 min; annealing at 55 degree C for 1 min; elongation at 72 degree C for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7): 1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT 1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT 1190-1. Following hybridization and washing, the blots are mounted and exposed to film at −70 degree C overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions : 30 seconds, 95 degree C; 1 minute, 56 degree C; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the laci repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacd repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4 degree C or frozen at −80 degree C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in *E coli* when it is present in the form of inclusion bodies. Unless otherwise specified, all of the following steps are conducted at 4–10 degree C.

Upon completion of the production phase of the *E. coli* fermentation, the cell culture is cooled to 4–10 degree C and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB 101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five pg of the expression plasmid pC6 a pC4 is cotransfected with 0.5 ug of the plasmid pSVneo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

GGGATCCGGAGCCCAAATCTTCTGACAAAAC
TCACACATGCCCACCGTGCCCAGCACCTGAAT
TCGAGGGTGCACCGTCAGTCTTCCTCT
TCCCCCCAAAACCCAAGGACACCCTCATGA
TCTCCCGGACTCCTGAGGTCACATGCGTGGT
GGTGGACGTAAGCCACGAAGACCCTGAG
GTCAAGTTCAACTGGTACGTGGACGGCG
TGGAGGTGCATAATGCCAAGACAAAGCCGCG
GGAGGAGCAGTA CAACAGCACGTACCGTGTG
GTCAGCGTCCTCACCGTCCTGCACCAGGACT
GGCTGAATGGCAAGGAGTACAAGTGCAAG
GTCTCCAACAAAGCCCTCCCAACCCCCATC
GAGAAAACCATCTCCAAAGCCAAAGG
GCAGCCCCGAGAACCACAGGTGTACACCCT
GCCCCCATCCCGGGATGAGCTGACCAAGAAC
CAGGTCAGCCTGACCTGCCTGGTCAAAGGCT
TCTATCCAAGCGACATCGCCGTGGAGTGG
GAGAGCAATGGGCAGCCGGAGAACAACTA
CAAGACCACGCCTCCCGTGCTGGACTC
CGACGGCTCCTTCTTCCTCTACAGCAAG
CTCACCGTGGACAAGAGCAGGTGGCAG
CAGGGGAACGTCTTCTCATGCTCCGTGATGCA
TGAGGCTCTGCACAACCACTACACGCAGAA
GAGCCTCTCCCTGTCTCCGGGTAAATGAGTGC
GACGGCCGCGACTCTAGAGGAT (SEQ ID NO:1)

Example 10

Production of an Antibody from a Polypeptide

The antibodies of the present invention can be prepared by a variety of methods. (See, Current Protocols, Chapter 2.) As one example of such methods, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the olypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production Of Secreted Protein For High-Throughput Screening Assays

The following protocol produces a supernatant containing a polypeptide to be tested. This supernatant can then be used in the Screening Assays described in Examples 13–20.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1×Penstrep(17–602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37 degrees C for 6 hours.

While cells are incubating, prepare appropriate media, either 1% BSA in DMEM with 1×penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$-$H_2O$; 71.02 mg/L of $Na_2HPO4$; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_20$; 6.65 mg/ml of L-Aspartic Acid; 29.56 mg/ml of L-Cystine-2HCL-$H_20$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_20$; 106.97 mg/ml of L-Isoleucine; 111.45 mg/mil of L-Leucine; 163.75 mg/mil of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_20$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1×penstrep. (BSA (81-068-3 Bayer) 100 gm dissolved in 1 L DMEM for a 10% BSA stock solution). Filter the media and collect 50 ul for endotoxin assay in 15ml polystyrene conical.

The transfection reaction is terminated, preferably by tag-teaming, at the end of the incubation period. Person A aspirates off the transfection media, while person B adds 1.5 ml appropriate media to each well. Incubate at 37 degrees C for 45 or 72 hours depending on the media used: 1 %BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13–20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| | JAKs | | | | | GAS (elements) |
|---|---|---|---|---|---|---|
| Ligand | tyk2 | Jak1 | Jak2 | Jak3 | STATS | or ISRE |
| IFN family | | | | | | |
| IFN-a/B | + | + | − | − | 1, 2, 3 | ISRE |
| IFN-g | | + | + | − | 1 | GAS (IRF1 > Lys6 > IFP) |
| Il-10 | + | ? | ? | − | 1,3 | |
| gp130 family | | | | | | |
| IL-6 (Pleiotrophic) | + | + | + | ? | 1, 3 | GAS (IRF1 > Lys6 > IFP) |
| Il-11(Pleiotrophic) | ? | + | ? | ? | 1, 3 | |
| OnM(Pleiotrophic) | ? | + | + | ? | 1, 3 | |
| LIF(Pleiotrophic) | ? | + | + | ? | 1, 3 | |
| CNTF(Pleiotrophic) | −/+ | + | + | ? | 1, 3 | |
| G-CSF(Pleiotrophic) | ? | + | ? | ? | 1, 3 | |
| IL-12(Pleiotrophic) | + | − | + | + | 1, 3 | |
| g-C family | | | | | | |
| IL-2 (lymphocytes) | − | + | − | + | 1, 3, 5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1, 3, 5 | |
| EPO | ? | − | + | − | 5 | GAS (B-CAS > IRF1 = IFP >> Ly6) |
| Receptor Tyrosine Kinases | | | | | | |
| EGF | ? | + | + | − | 1, 3 | GAS (IRF1) |
| PDGF | ? | + | + | − | 1, 3 | |
| CSF-1 | ? | + | + | − | 1, 3 | GAS (not IRF1) |

To construct a synthetic GAS containing promoter element, which is used in the Biological Assays described in Examples 13–14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:

5':GCGCCTCGAGATTTCCCCGAAATCTAGATTTC CCCGAAATGATTTCCCCGAAATGATTTC CCCGAAATATCTGCCATCTCAATTAG:3' (SEQ ID NO:3)

The downstream primer is complementary to the SV40 promoter and is flanked with a Hind III site: 5':GCGGCAAGCTTTTTGCAAAGCCTAGGC:3' (SEQ ID NO:4)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

5': CTCGAGATTTCCCCGAAATCTAGATTTCCCCGA AATGATTTCCCCGAAATGATTTCCCCGAA ATATCTGCCATCTCAATTAGTCAGCAACCAT AGTCCCGCCCCTAACTCCGCCCATCCCGC CCCTAACTCCGCCCAGTTCCGCCCATTCT CCGCCCCATGGCTGACTAATTTTTTTTATTTAT GCAGAGGCCGAGGCCGCC TCGGCCTCTGAGC TATTCCAGAAGTAGTGAGGAGGCTTTTTTG GAGGCCT AGGCTTTTGCAAAAAGCTT:3' (SEQ ID NO:5)

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13–14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, Il-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-cell Activity

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37 degrees C for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing polypeptides of the invention and/or induced polypeptides of the invention as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degrees C until SEAP assays are performed according to Example 17. The plates containing the remaining treated cells are placed at 4 degrees C and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by determining whether polypeptides of the invention proliferates and/or differentiates myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259–265) is used. First, harvest $2\times10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 degrees C for 45 min.

Wash the cells with RPMI 1640 medium containing 10% FBS and then resuspend in 10 ml complete medium and incubate at 37 degrees C for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 11. Incubate at 37 degrees C for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

5' GCGCTCGAGGGATGACAGCGATAGAACCCCGG -3' (SEQ ID NO:6)

5' GCGAAGCTTCGCGACTCCCCGGATCCGCCTC-3' (SEQ ID NO:7)

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat #08-115) in 30% ethanol (filter sterilized)) is added per one 10 cm plate or 50 ml per well of the 96-well plate, and allowed to air dry for 2 hr.

PC 12 cells are routinely grown in RPMI-1640 medium (Bio Whittaker) containing 10% horse serum (JRH BIOSCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 11. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:8), 18 bp of sequence complementary to the 5' end of the SV40 early promoter sequence, and is flanked with an XhoI site:

5':GCGGCCTCGAGGGGACTTTCCCGGGGACTTTCCGGGGACTTTCCGGGACTTTCCATCCTGCCATCTCAATTAG:3' (SEQ ID NO:9)

The downstream primer is complementary to the 3' end of the SV40 promoter and is flanked with a Hind III site:

5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

5':CTCGAGGGGACTTTCCCGGGGACTTTCCGGGGACTTTCCGGGACTTTCCATCTGCCATCTCAATTAGTCAGCAACCATAGTCCCGCCCCTAACTCCGCCCATCCCGCCCCTAACTCCGCCCAGTTCCGCCCATTCTCCGCCCCATGGCTGACTAATTTTTTTTATTTATGCAGAGGCCGAGGCCGCCTCGGCCTCTGAGCTATTCCAGAAGTAGTGAGGAGGCTTTTTTGGAGGCCTAGGCTTTTGCAAAAA GCTT:3' (SEQ ID NO:10)

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1, 1, 10 ng) is added to wells H9, H10, and H11, with a 5–10 fold activation typically observed.

Example 17

Assay for SEAP Activity

As a reporter molecule for the assays described in Examples 13–16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

Reaction Buffer Formulation:

| # of plates | Rxn buffer diluent (ml) | CSPD (ml) |
|---|---|---|
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |

-continued

| # of plates | Rxn buffer diluent (ml) | CSPD (ml) |
|---|---|---|
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C in a $C0_2$ incubator for 60 min. The plate is washed four times in the Biotek washer with HBSS leaving 100 ul of buffer.

For non-adherent cells, the cells are spun down from culture media. Cells are re-suspended to 2–5$\times10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C water bath for 30–60 min. The cells are washed twice with HBSS, resuspended to 1$\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular Ca++ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/mi), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P207 and a cocktail of protease inhibitors (#1836170) obtained from Boeheringer Mannheim (Indianapolis, Ind.) is added to each well and the plate is shaken on a rotating shaker for 5 minutes at 4 degrees C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degrees C at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 mM ATP/50 mM $MgCl_2$), then 10 ul of 5× Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate(1 mM), and then 5 ul of water. Mix the components gently and preincubate the reaction mix at 30 degrees C for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degrees C for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase(anti-P-Tyr-POD(0.5 u/ml)) to each well and incubate at 37 degrees C for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degrees C until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95 degrees C for 30 seconds; 60–120 seconds at 52–58 degrees C; and 60–120 seconds at 70 degrees C, using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genolic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5' -triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERI™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 24

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Gene Therapy Using Endogenous Genes Corresponding To Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., *Proc. Nati. Acad. Sci. USA*, 86:8932–8935 (1989); and Zijlstra et al., *Nature*, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 $\mu$g/ml. 0.5 ml of the cell suspension (containing approximately $1.5.\times10^6$ cells) is then added to the cuvette, and the cell suspension and DNA solutions are gently mixed. Electroporation is performed with a Gene-Pulser apparatus (Bio-Rad). Capacitance and voltage are set at 960 $\mu$F and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 28

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, W090/11092, W098/11779; U.S. Pat. No. 5693622, 5705151, 5580859; Tabata et al., Cardiovasc. Res. 35(3):470–479 (1997); Chao et al., Pharmacol. Res. 35(6):517–522 (1997); Wolff, Neuromuscul. Disord. 7(5):314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term “naked” polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 29

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (N.Y.) 11: 1263–1270 (1993); Wright et al., Biotechnology (N.Y.) 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 30

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (eg, lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, eg., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 31

Production of an Antibody a) Hybridoma Technology

The antibodies of the present invention can be prepared by a variety of methods. (See, Current Protocols, Chapter 2.) As one example of such methods, cells expressing XXX are administered to an animal to induce the production of sera containing polyclonal antibodies. In a preferred method, a preparation of XXX protein is prepared and purified to render it substantially free of natural contaminants. Such a preparation is then introduced into an animal in order to produce polyclonal antisera of greater specific activity.

Monoclonal antibodies specific for protein XXX are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with XXX polypeptide or, more preferably, with a secreted XXX polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 $\mu$g/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the XXX polypeptide.

Alternatively, additional antibodies capable of binding to XXX polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the XXX protein-specific antibody can be blocked by XXX. Such antibodies comprise anti-idiotypic antibodies to the XXX protein-specific antibody and are used to immunize an animal to induce formation of further XXX protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).)

b) Isolation Of Antibody Fragments Directed Against XXX From A Library Of scFvs

Naturally occurring V-genes isolated from human PBLs are constructed into a library of antibody fragments which contain reactivities against XXX to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 $\mu$g/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 $\mu$g/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 $\mu$g ampicillin/ml and 25 $\mu$g kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 $\mu$m filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 $\mu$g/ml or 10 $\mu$g/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 $\mu$g/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 32

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100U/ml penicillin, 10 ug/ml streptomycin, and $10_{-5}$ dilution of SAC) in a total volume of 150ul. Proliferation or inhibition is quantitated by a 20h pulse (luCi/well) with 3H-thymidine (6.7 Ci/mM) beginning 72h post factor addition. The positive and negative controls are IL2 and medium respectively.

In Vivo Assay—BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

The studies described in this example tested activity of a polypeptide of the invention. However, one skilled in the art could easily modify the exemplified studies to test the activity of polynucleotides of the invention (e.g., gene therapy), agonists, and/or antagonists of polynucleotides or polypeptides of the invention.

Example 33

T Cell Proliferation Assay

A CD3-induced proliferation assay is performed on PBMCs and is measured by the uptake of $^3$H-thymidine. The assay is performed as follows. Ninety-six well plates are coated with 100 $\mu$l/well of mAb to CD3 (HIT3a, Pharmingen) or isotype-matched control mAb (B33.1) overnight at 4 degrees C (1 $\mu$g/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C, plates are spun for 2 min. at 1000 rpm and 100 $\mu$l of supernatant is removed and stored -20 degrees C for measurement of IL-2 (or other cytokines) if effect on proliferation is observed. Wells are supplemented with 100 ul of medium containing 0.5 uCi of $^3$H-thymidine and cultured at 37 degrees C for 18–24 hr. Wells are harvested and incorporation of $^3$H-thymidine used as a measure of proliferation.

Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

The studies described in this example tested activity of polypeptides of the invention. However, one skilled in the art could easily modify the exemplified studies to test the activity of polynucleotides of the invention (e.g., gene therapy), agonists, and/or antagonists of polynucleotides or polypeptides of the invention.

Example 34

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Thl helper T-cell immune response, and induces cytotoxic T and NK cell function. An ELISA is used to measure the IL-12 release as follows. Dendritic cells ($10^6$/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degreesc. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 $\mu$g/ml, and then incubaed at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative burst. Purified monocytes are plated in 96-w plate at $2\text{-}1\times10^5$ cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 $\mu$l IN NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity of a polypeptide of the invention. However, one skilled in the art could easily modify the exemplified studies to test the activity of polypeptides, polynucleotides (e.g., gene therapy), agonists, and/or antagonists of the invention.

Example 35

Biological Effects of Polypeptides of the Invention Astrocyte and Neuronal Assays Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or polypeptides of the invention with or without IL-1$\alpha$ for 24 hours. The supernatants are collected and assayed for $PGE_2$ by EIA kit (Cayman, Ann Arbor, Minn.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1$\alpha$ for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10–2500 ng/ml which can be used to compare stimulation with polypeptides of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

The studies described in this example tested activity of a polypeptide of the invention. However, one skilled in the art could easily modify the exemplified studies to test the activity of polynucleotides (e.g., gene therapy), agonists, and/or antagonists of the invention.

Example 36

The Effect of Polypeptides of the Invention on the Growth of Vascular Endothelial Cells On day 1, human umbilical vein endothelial cells (HUVEC) are seeded at 2–5×$10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:Y, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

The studies described in this example tested activity of a polypeptide of the invention. However, one skilled in the art could easily modify the exemplified studies to test the activity of polynucleotides (e.g., gene therapy), agonists, and/or antagonists of the invention.

Example 37

Stimulatory Effect of Polypeptides of the Invention on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 niL serum-supplemented medium and are allowed to attach overnight. After serum-starvation for 12 hours in 0.5% FBS, conditions (bFGF, $VEGF_{165}$ or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example tested activity of a polypeptide of the invention. However, one skilled in the art could easily modify the exemplified studies to test the activity of polynucleotides (e.g., gene therapy), agonists, and/or antagonists of the invention.

Example 38

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36) :21985–21992 (1996).

The studies described in this example tested activity of a polypeptide of the invention. However, one skilled in the art could easily modify the exemplified studies to test the activity of polynucleotides (e.g., gene therapy), agonists, and/or antagonists of the invention.

Example 39

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, Md.; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5\times10^5$ cells suspended in 50 ul M199 containing 1% FBS are seeded in the upper compartment. The apparatus is then incubated for 5 hours at 37° C. in a humidified chamber with 5% C02 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity of a polypeptide of the invention. However, one skilled in the art could easily modify the exemplified studies to test the activity of polynucleotides (e.g., gene therapy), agonists, and/or antagonists of the invention.

Example 40

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

$2KNO_2+2KI+2H_2SO_46\ 2NO+I_2+2H_2O+2K_2SO4$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1\times10^6$ endothelial cells. All values reported are means of four to six measurements in each group (number of cell culture wells). See, Leak et al. *Biochem. and Biophys. Res. Comm.* 217:96–105 (1995).

The studies described in this example tested activity of polypeptides of the invention. However, one skilled in the art could easily modify the exemplified studies to test the activity of polynucleotides (e.g., gene therapy), agonists, and/or antagonists of the invention.

Example 41

Effect of Polypepides of the Invention on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity of a polypeptide of the invention. However, one skilled in the art could easily modify the exemplified studies to test the activity of polynucleotides (e.g., gene therapy), agonists, and/or antagonists of the invention.

Example 42

Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/ 5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 43

Angiogenesis Assay Using a Matrigel Implant in Mouse

In vivo angiogenesis assay of a polypeptide of the invention measures the ability of an existing capillary network to form new vessels in an implanted capsule of murine extracellular matrix material (Matrigel). The protein is mixed with the liquid Matrigel at 4 degree C and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C the Matrigel material is a liquid. The Matrigel is mixed with a polypeptide of the invention at 150 ng/ml at 4 degrees C and drawn into cold 3 ml syringes. Female C57Bl/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity of a polypeptide of the invention. However, one skilled in the art could easily modify the exemplified studies to test the activity of polynucleotides (e.g., gene therapy), agonists, and/or antagonists of the invention.

Example 44

Rescue of Ischemia in Rabbit Lower Limb Model

To study the in vivo effects of polynucleotides and polypeptides of the invention on ischemia, a rabbit hindlimb ischemia model is created by surgical removal of one femoral arteries as described previously (Takeshita et al., *Am J. Pathol* 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshitaet al. *Am J. Pathol* 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. *Hum Gene Ther*. 4:749–758 (1993); Leclerc et al. *J. Clin. Invest*. 90: 936–944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity of polynucleotides and polypeptides of the invention. However, one skilled in the art could easily modify the exemplified studies to test the agonists, and/or antagonists of the invention.

Example 45

Effect of Polvpeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13–14 week old spontaneously hypertensive rats (SHR). Data are expressed as the mean+/−SEM. Statistical analysis are performed with a paired t-test and statistical significance is defined as $p<0.05$ vs. the response to buffer alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 46

Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:

a) Ischemic skin
b) Ischemic skin wounds
c) Normal wounds

The experimental protocol includes:

a) Raising a 3×4 cm, single pedicle full-thickness random skin flap (myocutaneous flap over the lower back of the animal).
b) An excisional wounding (4–6 mm in diameter) in the ischemic skin (skin-flap).
c) Topical treatment with a polypeptide of the invention of the excisional wounds (day 0, 1, 2, 3, 4 post-wounding) at the following various dosage ranges: lmg to 100 mg.
d) Harvesting the wound tissues at day 3, 5, 7, 10, 14 and 21 post-wounding for histological, immunohistochemical, and in situ studies.

The studies described in this example tested activity of a polypeptide of the invention. However, one skilled in the art could easily modify the exemplified studies to test the activity of polynucleotides (e.g., gene therapy), agonists, and/or antagonists of the invention.

Example 47

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.
b) a polypeptide of the invention, in a dosage range of 20 mg–500 mg, is delivered intravenously and/or intramuscularly 3 times (perhaps more) per week for 2–3 weeks.
c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

The studies described in this example tested activity of a polypeptide of the invention. However, one skilled in the art could easily modify the exemplified studies to test the activity of polynucleotides (e.g., gene therapy), agonists, and/or antagonists of the invention.

Example 48

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:

a) The heart is exposed through a left-side thoracotomy in the rat. Immediately, the left coronary artery is occluded with a thin suture (6–0) and the thorax is closed.
b) a polypeptide of the invention, in a dosage range of 20 mg–500 mg, is delivered intravenously and/or intramuscularly 3 times (perhaps more) per week for 2–4 weeks.
c) Thirty days after the surgery, the heart is removed and cross-sectioned for morphometric and in situ analyzes.

The studies described in this example tested activity of a polypeptide of the invention. However, one skilled in the art could easily modify the exemplified studies to test the activity of polynucleotides (e.g., gene therapy), agonists, and/or antagonists of the invention.

Example 49

Rat Corneal Wound Healing Model

This animal model shows the effect of a polypeptide of the invention on neovascularization. The experimental protocol includes:

a) Making a 1–1.5 mm long incision from the center of cornea into the stromal layer.

b) Inserting a spatula below the lip of the incision facing the outer corner of the eye.

c) Making a pocket (its base is 1–1.5 mm form the edge of the eye).

d) Positioning a pellet, containing 50 ng–5 ug of a polypeptide of the invention, within the pocket.

e) Treatment with a polypeptide of the invention can also be applied topically to the corneal wounds in a dosage range of 20 mg–500 mg (daily treatment for five days).

The studies described in this example tested activity of a polypeptide of the invention. However, one skilled in the art could easily modify the exemplified studies to test the activity of polynucleotides (e.g., gene therapy), agonists, and/or antagonists of the invention.

Example 50

Diabetic Mouse and Glucocorticoid-Impaired Wound Healing Models

A. Diabetic db+/db+Mouse Model.

To demonstrate that a polypeptide of the invention accelerates the healing process, the genetically diabetic mouse model of wound healing is used. The full thickness wound healing model in the db+/db+mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et *Lab Invest.* 40(4):460–473 (1979); Coleman, D. L., *Diabetes* 31 (Suppl): 1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/nL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280–302 (1989); Wahlet al., J. Immunol. 115: 476–481 (1975); Werb et al., *J. Exp. Med.* 147:1684–1694 (1978)). Glucocorticoids retard wound healing by inhibiting angiogenesis, decreasing vascular permeability (Ebert et al., *An. Intern. Med.* 37:701–705 (1952)), fibroblast proliferation, and collagen synthesis (Beck et al., *Growth Factors*. 5.: 295–304 (1991); Haynes et al., *J. Clin. Invest.* 61: 703–797 (1978)) and producing a transient reduction of circulating monocytes (Haynes et al., *J. Clin. Invest.* 61: 703–797 (1978); Wahl, "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck et al., *Growth Factors*. 5: 295–304 (1991); Haynes et al., *J. Clin. Invest.* 61: 703–797 (1978); Wahl, "Glucocorticoids and wound healing", In: Antiinflammatory Steroid Action: Basic and Clinical Aspects, Academic Press, New York, pp. 280–302 (1989); Pierce et al., *Proc. Natl. Acad. Sci. USA* 86: 2229–2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methyipredniso-lone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

The studies described in this example tested activity of a polypeptide of the invention. However, one skilled in the art could easily modify the exemplified studies to test the activity of polynucleotides (e.g., gene therapy), agonists, and/or antagonists of the invention.

Example 51

Lymphadema Animal Model

The purpose of this experimental approach is to create an appropriate and consistent lymphedema model for testing the therapeutic effects of a polypeptide of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80EC until sectioning. Upon sectioning, the muscle is observed under fluorescent microscopy for lymphatics.

The studies described in this example tested activity of a polypeptide of the invention. However, one skilled in the art could easily modify the exemplified studies to test the activity of polynucleotides (e.g., gene therapy), agonists, and/or antagonists of the invention.

Example 52

Suppression of TNF Alpha-induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2;

Clonetics, San Diego, Calif.) supplemented with 10% FCS and 1% penicillin/streptomycin in a 37 degree C humidified incubator containing 5% $CO_2$.

HUVECs are seeded in 96-well plates at concentrations of 1×104 cells/well in EGM medium at 37 degree C for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C for either 5 h (selectin and integrin expression) or 24 h (integrin expression only). Plates are aspirated to remove medium and 100 μl of 0.1% paraformaldehyde-PBS(with Ca++and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 ||l of diluted primary antibody to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed ×3 with PBS (+Ca,Mg)+0.5% BSA.

Then add 20 μl of diluted ExtrAvidin-Alkaline Phosphotase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 μl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$ .5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity of a polypeptide of the invention. However, one skilled in the art could easily modify the exemplified studies to test the activity of polynucleotides (e.g., gene therapy), agonists, and/or antagonists of the invention.

Example 53

Assay for the Stimulation of Bone Marrow CD34+ Cell Proliferation

This assay is based on the ability of human CD34+ to proliferate in the presence of hematopoietic growth factors and evaluates the ability of isolated polypeptides expressed in mammalian cells to stimulate proliferation of CD34+ cells.

It has been previously shown that most mature precursors will respond to only a single signal. More immature precursors require at least two signals to respond. Therefore, to test the effect of polypeptides on hematopoietic activity of a wide range of progenitor cells, the assay contains a given polypeptide in the presence or absence of other hematopoietic growth factors. Isolated cells are cultured for 5 days in the presence of Stem Cell Factor (SCF) in combination with tested supernatant. SCF alone has a very limited effect on the proliferation of bone marrow (BM) cells, acting in such conditions only as a "survival" factor. However, combined with any factor exhibiting stimulatory effect on these cells (e.g., IL-3), SCF will cause a synergistic effect. Therefore, if the tested polypeptide has a stimulatory effect on a hematopoietic progenitors, such activity can be easily detected. Since normal BM cells have a low level of cycling cells, it is likely that any inhibitory effect of a given polypeptide, or agonists or antagonists thereof, might not be detected. Accordingly, assays for an inhibitory effect on progenitors is preferably tested in cells that are first subjected to in vitro stimulation with SCF+IL+3, and then contacted with the compound that is being evaluated for inhibition of such induced proliferation.

Briefly, CD34+cells are isolated using methods known in the art. The cells are thawed and resuspended in medium (QBSF 60 serum-free medium with I% L-glutamine (500 ml) Quality Biological, Inc., Gaithersburg, Md. Cat # 160–204–101). After several gentle centrifugation steps at 200×g, cells are allowed to rest for one hour. The cell count is adjusted to $2.5\times10^5$ cells/ml. During this time, 100 μl of sterile water is added to the peripheral wells of a 96-well plate. The cytokines that can be tested with a given polypeptide in this assay is rhSCF (R&D Systems, Minneapolis, Minn., Cat # 255-SC) at 50 ng/ml alone and in combination with rhSCF and rhIL-3 (R&D Systems, Minneapolis, Minn., Cat # 203-ML) at 30 ng/ml. After one hour, 10 μl of prepared cytokines, 50 μl SID (supernatants at 1:2 dilution=50 μl) and 20 μl of diluted cells are added to the media which is already present in the wells to allow for a final total volume of 100 μl. The plates are then placed in a 37° C./5% $CO_2$ incubator for five days.

Eighteen hours before the assay is harvested, 0.5 μCi/well of [3H] Thymidine is added in a 10 μl volume to each well to determine the proliferation rate. The experiment is terminated by harvesting the cells from each 96-well plate to a filtermat using the Tomtec Harvester 96. After harvesting, the filtermats are dried, trimmed and placed into OmniFilter assemblies consisting of one OmniFilter plate and one OmniFilter Tray. 60 μl Microscint is added to each well and the plate sealed with TopSeal-A press-on sealing film A bar code 15 sticker is affixed to the first plate for counting. The sealed plates is then loaded and the level of radioactivity determined via the Packard Top Count and the printed data collected for analysis. The level of radioactivity reflects the amount of cell proliferation.

The studies described in the above example test the activity of a given polypeptide to stimulate bone marrow CD34+ cell proliferation. One skilled in the art could easily modify the exemplified studies to test the activity of polynucleotides (e.g., gene therapy), antibodies, agonists, and/or antagonists and fragments and variants thereof. As a non-limiting example, potential antagonists tested in this assay would be expected to inhibit cell proliferation in the presence of cytokines and/or to increase the inhibition of cell proliferation in the presence of cytokines and a given polypeptide. In contrast, potential agonists tested in this assay would be expected to reduce the inhibition of cell proliferation in the presence of cytokines and a given polypeptide.

TABLE 3

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | — | — | — | — | — | — | C | 0.09 | 0.10 | — | — | — | 0.46 | 0.66 |
| Ser | 2 | — | — | — | — | — | T | C | 0.48 | 0.16 | — | — | — | 0.84 | 0.74 |
| Ser | 3 | — | — | — | — | — | T | C | 0.06 | −0.27 | * | — | — | 1.77 | 1.01 |
| Gly | 4 | — | — | — | — | — | T | C | −0.37 | −0.01 | — | — | — | 1.80 | 0.84 |
| Thr | 5 | — | — | — | — | — | T | C | −0.27 | 0.06 | — | — | F | 1.17 | 0.52 |
| Glu | 6 | A | — | — | — | — | — | — | 0.12 | 0.59 | * | — | F | 0.29 | 0.41 |
| Leu | 7 | A | — | — | — | — | — | — | 0.08 | 0.63 | — | — | — | −0.04 | 0.63 |
| Leu | 8 | A | — | — | — | — | — | — | −0.21 | 0.63 | — | — | — | −0.22 | 0.43 |
| Trp | 9 | A | — | — | — | — | T | — | −0.46 | 0.64 | — | — | — | −0.20 | 0.25 |
| Pro | 10 | A | — | — | — | — | T | — | −0.96 | 1.14 | — | — | — | −0.20 | 0.31 |
| Gly | 11 | A | — | — | — | — | T | — | −1.77 | 1.14 | — | — | — | −0.20 | 0.31 |
| Ala | 12 | A | — | — | — | — | T | — | −1.81 | 1.14 | — | — | — | −0.20 | 0.24 |
| Ala | 13 | A | — | — | B | — | — | — | −1.81 | 0.87 | — | — | — | −0.60 | 0.12 |
| Leu | 14 | A | — | — | B | — | — | — | −2.33 | 1.13 | — | — | — | −0.60 | 0.10 |
| Leu | 15 | A | — | — | B | — | — | — | −2.47 | 1.39 | — | — | — | −0.60 | 0.08 |
| Val | 16 | A | — | — | B | — | — | — | −2.98 | 1.31 | — | — | — | −0.60 | 0.08 |
| Leu | 17 | A | — | — | B | — | — | — | −2.98 | 1.46 | — | — | — | −0.60 | 0.07 |
| Leu | 18 | A | — | — | B | — | — | — | −2.98 | 1.27 | — | — | — | −0.60 | 0.09 |
| Gly | 19 | A | — | — | B | — | — | — | −2.47 | 1.09 | — | * | — | −0.60 | 0.12 |
| Val | 20 | A | — | — | B | — | — | — | −2.47 | 0.83 | — | — | — | −0.60 | 0.19 |
| Ala | 21 | A | — | — | B | — | — | — | −2.28 | 0.83 | — | * | — | −0.60 | 0.19 |
| Ala | 22 | A | — | — | B | — | — | — | −2.32 | 0.71 | * | * | — | −0.60 | 0.10 |
| Ser | 23 | A | — | — | B | — | — | — | −1.40 | 0.93 | * | * | — | −0.60 | 0.10 |
| Leu | 24 | A | — | — | B | — | — | — | −1.72 | 0.29 | — | * | — | −0.30 | 0.20 |
| Cys | 25 | — | — | B | B | — | — | — | −1.17 | 0.36 | * | * | — | −0.30 | 0.11 |
| Val | 26 | — | — | B | B | — | — | — | −0.47 | 0.24 | * | * | — | −0.30 | 0.11 |
| Arg | 27 | — | — | — | B | T | — | — | −0.09 | −0.14 | * | * | — | 1.04 | 0.25 |
| Cys | 28 | — | — | — | B | T | — | — | −0.13 | −0.40 | * | * | — | 1.38 | 0.73 |
| Ser | 29 | — | — | — | B | T | — | — | 0.09 | −0.54 | * | * | F | 2.17 | 0.97 |
| Arg | 30 | — | — | — | — | — | T | C | 0.80 | −0.69 | * | — | F | 2.71 | 0.50 |
| Pro | 31 | — | — | — | — | T | T | — | 1.77 | −0.69 | * | — | F | 3.40 | 1.86 |
| Gly | 32 | — | — | — | — | T | T | — | 1.36 | −1.26 | * | — | F | 3.06 | 2.72 |
| Ala | 33 | — | — | — | — | — | T | C | 2.02 | −1.26 | * | — | F | 2.52 | 1.86 |
| Lys | 34 | — | A | — | — | — | — | C | 2.37 | −1.26 | * | * | F | 1.78 | 2.08 |
| Arg | 35 | A | A | — | — | — | — | — | 1.37 | −1.69 | * | * | F | 1.24 | 4.21 |
| Ser | 36 | A | A | — | — | — | — | — | 1.33 | −1.43 | * | — | F | 0.90 | 2.92 |
| Glu | 37 | A | A | — | — | — | — | — | 1.68 | −1.17 | * | — | F | 0.90 | 2.29 |
| Lys | 38 | A | A | — | — | — | — | — | 2.27 | −0.77 | * | — | F | 0.90 | 2.02 |
| Ile | 39 | A | A | — | — | — | — | — | 2.33 | −0.37 | * | — | F | 0.60 | 2.62 |
| Tyr | 40 | A | — | — | — | — | — | — | 1.92 | −0.76 | — | — | F | 1.40 | 2.96 |
| Gln | 41 | A | — | — | — | — | T | — | 1.41 | −0.37 | — | * | F | 1.60 | 1.98 |
| Gln | 42 | A | — | — | — | — | T | — | 1.52 | 0.31 | — | — | F | 1.30 | 2.33 |
| Arg | 43 | — | — | — | — | — | T | C | 1.48 | −0.37 | — | * | F | 2.40 | 2.91 |
| Ser | 44 | — | — | — | — | — | T | C | 2.37 | −1.13 | — | — | F | 3.00 | 2.91 |
| Leu | 45 | — | A | — | — | — | — | C | 2.61 | −1.53 | * | * | F | 2.30 | 2.81 |
| Arg | 46 | — | A | — | — | T | — | — | 2.61 | −1.53 | * | — | F | 2.20 | 2.49 |
| Glu | 47 | — | A | — | — | T | — | — | 2.31 | −1.13 | * | — | F | 1.90 | 3.21 |
| Asp | 48 | — | A | — | — | T | — | — | 1.50 | −1.13 | * | — | F | 1.60 | 5.22 |
| Gln | 49 | — | A | — | — | T | — | — | 1.49 | −1.03 | * | * | F | 1.30 | 2.31 |
| Gln | 50 | — | A | — | — | T | — | — | 1.96 | −0.54 | * | * | F | 1.58 | 1.92 |
| Ser | 51 | — | A | — | — | — | — | C | 1.54 | −0.11 | * | — | F | 1.36 | 1.14 |
| Phe | 52 | — | — | — | — | T | T | — | 1.66 | 0.27 | — | — | F | 1.49 | 0.88 |
| Thr | 53 | — | — | — | — | T | T | — | 1.34 | −0.13 | — | — | F | 2.37 | 1.00 |
| Gly | 54 | — | — | — | — | T | T | — | 1.10 | −0.04 | * | — | F | 2.80 | 1.07 |
| Ser | 55 | — | — | — | — | T | T | — | 0.80 | 0.33 | — | — | F | 1.92 | 1.94 |
| Arg | 56 | — | — | — | B | T | — | — | 0.29 | −0.07 | — | — | F | 1.84 | 1.80 |
| Thr | 57 | — | — | — | B | T | — | — | 0.13 | 0.13 | — | — | F | 0.96 | 1.50 |
| Tyr | 58 | — | — | — | B | T | — | — | 0.10 | 0.34 | * | — | — | 0.38 | 0.83 |
| Ser | 59 | — | — | — | B | — | — | C | 0.44 | 0.39 | * | — | — | −0.10 | 0.42 |
| Leu | 60 | — | — | B | B | — | — | — | 0.16 | 0.79 | * | — | — | −0.60 | 0.50 |
| Val | 61 | — | — | B | B | — | — | — | −0.24 | 0.80 | * | — | — | −0.60 | 0.33 |
| Gly | 62 | — | — | — | — | T | — | — | −0.14 | 0.96 | — | — | — | 0.00 | 0.26 |
| Gln | 63 | — | — | — | — | T | — | — | −0.24 | 1.00 | — | — | — | 0.00 | 0.48 |
| Ala | 64 | — | — | — | — | — | — | C | −0.16 | 0.74 | — | — | — | −0.20 | 0.64 |
| Trp | 65 | — | — | — | — | — | T | C | −0.16 | 0.53 | — | — | F | 0.15 | 1.00 |
| Pro | 66 | — | — | — | — | — | T | C | 0.11 | 0.79 | * | — | F | 0.15 | 0.48 |
| Gly | 67 | — | — | — | — | — | T | C | 0.46 | 0.89 | * | — | F | 0.15 | 0.48 |
| Pro | 68 | — | — | — | — | — | T | C | −0.14 | 0.39 | * | — | F | 0.45 | 0.75 |
| Leu | 69 | — | A | — | — | — | — | C | −0.14 | 0.09 | — | — | F | 0.05 | 0.48 |
| Ala | 70 | — | A | — | — | — | — | C | −0.07 | 0.16 | — | — | — | −0.10 | 0.49 |
| Asp | 71 | A | A | — | — | — | — | — | −0.17 | 0.16 | — | — | — | −0.30 | 0.49 |
| Met | 72 | A | A | — | — | — | — | — | 0.29 | 0.21 | — | — | — | −0.30 | 0.86 |
| Ala | 73 | A | A | — | — | — | — | — | 0.54 | −0.47 | — | — | — | 0.45 | 1.67 |
| Pro | 74 | A | — | — | — | — | T | — | 1.36 | −0.97 | — | — | F | 1.30 | 2.00 |
| Thr | 75 | A | — | — | — | — | T | — | 1.99 | −0.97 | — | — | F | 1.30 | 3.38 |
| Arg | 76 | A | — | — | — | — | T | — | 1.18 | −1.59 | — | — | F | 1.30 | 6.69 |
| Lys | 77 | A | — | — | — | — | T | — | 0.97 | −1.40 | — | — | F | 1.30 | 3.57 |

TABLE 3-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 78 | A | A | — | — | — | — | — | 1.56 | −1.14 | — | — | F | 0.90 | 2.04 |
| Lys | 79 | A | A | — | — | — | — | — | 1.07 | −1.23 | — | — | F | 0.90 | 1.80 |
| Leu | 80 | A | A | — | — | — | — | — | 1.13 | −0.44 | — | — | — | 0.30 | 0.78 |
| Leu | 81 | — | A | B | — | — | — | — | 0.81 | 0.31 | — | — | — | −0.30 | 0.73 |
| Gln | 82 | — | A | B | — | — | — | — | 0.47 | 0.74 | * | * | — | −0.60 | 0.57 |
| Phe | 83 | — | A | B | — | — | — | — | −0.34 | 1.13 | * | * | — | −0.60 | 0.92 |
| Tyr | 84 | — | — | — | — | — | T | C | −0.39 | 1.13 | * | * | — | 0.00 | 0.92 |
| Pro | 85 | — | — | — | — | — | T | C | 0.42 | 0.44 | * | * | — | 0.00 | 0.92 |
| Ser | 86 | — | — | — | — | — | T | C | 1.02 | 0.04 | * | * | F | 0.60 | 1.78 |
| Leu | 87 | — | — | — | — | — | T | C | 0.43 | −0.31 | * | * | F | 1.50 | 1.75 |
| Glu | 88 | — | — | — | — | — | — | C | 0.83 | −0.57 | * | * | F | 1.90 | 1.14 |
| Asp | 89 | — | — | — | — | — | — | C | 0.78 | −0.61 | — | * | F | 2.20 | 1.14 |
| Pro | 90 | — | — | — | — | — | — | C | 1.10 | −0.61 | — | * | F | 2.50 | 1.86 |
| Ala | 91 | — | — | — | — | T | — | — | 1.16 | −1.30 | — | * | F | 3.00 | 2.10 |
| Ser | 92 | A | — | — | — | — | T | — | 1.97 | −0.54 | — | * | F | 2.50 | 1.97 |
| Ser | 93 | A | — | — | — | — | T | — | 1.97 | −0.14 | — | * | F | 1.90 | 2.21 |
| Arg | 94 | A | — | — | — | — | T | — | 1.27 | −0.17 | * | — | F | 1.60 | 3.52 |
| Tyr | 95 | — | — | — | — | T | T | — | 1.18 | 0.11 | * | * | F | 1.10 | 2.27 |
| Gln | 96 | — | — | — | — | T | — | — | 1.81 | 0.11 | * | * | F | 0.94 | 2.27 |
| Asn | 97 | — | — | — | — | T | — | — | 1.77 | −0.27 | * | * | F | 1.88 | 2.32 |
| Phe | 98 | — | — | — | — | T | — | — | 1.77 | 0.16 | * | * | F | 1.62 | 1.47 |
| Ser | 99 | — | — | — | — | T | T | — | 1.77 | −0.21 | * | * | F | 2.76 | 1.13 |
| Lys | 100 | — | — | — | — | T | T | — | 1.98 | −0.61 | * | — | F | 3.40 | 1.38 |
| Gly | 101 | — | — | — | — | — | T | C | 1.63 | −0.51 | * | — | F | 2.86 | 2.17 |
| Ser | 102 | — | — | — | — | — | T | C | 1.33 | −0.87 | * | — | F | 2.82 | 1.60 |
| Arg | 103 | — | — | — | — | — | — | C | 2.03 | −0.87 | * | — | F | 2.58 | 1.07 |
| His | 104 | — | — | — | — | — | T | C | 2.33 | −0.87 | * | — | F | 2.74 | 1.88 |
| Gly | 105 | — | — | — | — | — | T | C | 1.70 | −1.30 | * | — | F | 2.70 | 2.43 |
| Ser | 106 | — | — | — | — | — | T | C | 1.80 | −1.19 | * | — | F | 3.00 | 1.25 |
| Glu | 107 | A | — | — | — | — | T | — | 1.21 | −0.43 | — | * | F | 2.20 | 1.44 |
| Glu | 108 | A | — | — | — | — | — | — | 1.10 | −0.24 | — | * | F | 1.70 | 1.02 |
| Ala | 109 | A | — | — | — | — | — | — | 0.92 | −0.67 | — | * | — | 1.55 | 1.27 |
| Tyr | 110 | A | — | — | — | — | — | — | 0.38 | −0.63 | — | * | — | 1.25 | 1.14 |
| Ile | 111 | A | — | — | — | — | — | — | 0.09 | 0.06 | — | — | — | −0.10 | 0.46 |
| Asp | 112 | A | — | — | — | — | — | — | −0.51 | 0.56 | — | — | — | −0.40 | 0.46 |
| Pro | 113 | A | A | — | — | — | — | — | −0.51 | 0.67 | — | * | — | −0.60 | 0.29 |
| Ile | 114 | A | A | — | — | — | — | — | −0.17 | −0.09 | — | — | — | 0.30 | 0.72 |
| Ala | 115 | A | A | — | — | — | — | — | −0.17 | −0.01 | * | — | — | 0.30 | 0.67 |
| Met | 116 | A | A | — | — | — | — | — | 0.72 | 0.74 | * | — | — | −0.60 | 0.68 |
| Glu | 117 | A | A | — | — | — | — | — | 0.43 | 0.71 | * | — | — | −0.45 | 1.57 |
| Tyr | 118 | A | — | — | — | — | T | — | 0.30 | 0.94 | * | * | — | −0.05 | 1.63 |
| Tyr | 119 | — | — | — | — | T | T | — | 1.30 | 0.87 | * | * | — | 0.35 | 1.63 |
| Asn | 120 | — | — | — | — | T | T | — | 1.19 | 0.26 | * | * | — | 0.65 | 1.84 |
| Trp | 121 | — | — | — | — | T | T | — | 1.49 | 1.04 | * | * | — | 0.35 | 1.02 |
| Gly | 122 | — | — | — | — | T | — | — | 1.53 | 0.67 | * | — | — | 0.00 | 0.87 |
| Arg | 123 | — | — | — | — | T | — | — | 1.57 | −0.09 | * | — | — | 1.05 | 1.08 |
| Phe | 124 | — | — | — | — | T | — | — | 1.60 | −0.06 | * | — | F | 1.20 | 1.59 |
| Ser | 125 | — | — | — | — | — | — | C | 1.60 | −0.54 | * | — | F | 1.64 | 2.49 |
| Lys | 126 | — | — | — | — | — | — | C | 1.89 | −0.97 | * | * | F | 1.98 | 2.20 |
| Pro | 127 | — | — | — | — | — | T | C | 2.23 | −0.97 | * | * | F | 2.52 | 4.25 |
| Pro | 128 | — | — | — | — | — | T | C | 2.12 | −1.76 | * | * | F | 2.86 | 5.29 |
| Glu | 129 | — | — | — | — | T | T | — | 2.23 | −2.14 | — | — | F | 3.40 | 4.42 |
| Asp | 130 | A | — | — | — | — | T | — | 2.53 | −1.64 | — | * | F | 2.66 | 2.89 |
| Asp | 131 | A | — | — | — | — | — | — | 2.19 | −1.67 | — | * | F | 2.12 | 3.00 |
| Asp | 132 | A | — | — | — | — | T | — | 2.16 | −1.71 | — | — | F | 1.98 | 2.32 |
| Ala | 133 | A | — | — | — | — | T | — | 2.37 | −0.96 | — | — | F | 1.64 | 2.18 |
| Asn | 134 | A | — | — | — | — | T | — | 2.37 | −0.96 | — | — | F | 1.30 | 2.26 |
| Ser | 135 | A | — | — | — | — | T | — | 1.51 | −0.56 | * | — | F | 1.30 | 2.18 |
| Tyr | 136 | A | — | — | — | — | — | — | 0.70 | 0.09 | * | — | F | 0.20 | 1.60 |
| Glu | 137 | A | — | — | — | — | — | — | −0.19 | 0.27 | — | * | — | −0.10 | 0.82 |
| Asn | 138 | A | — | — | B | — | — | — | −0.27 | 0.56 | — | — | — | −0.60 | 0.43 |
| Val | 139 | A | — | — | B | — | — | — | −0.22 | 0.74 | — | — | — | −0.60 | 0.15 |
| Leu | 140 | A | — | — | B | — | — | — | 0.08 | −0.01 | — | — | — | 0.30 | 0.17 |
| Ile | 141 | A | — | — | B | — | — | — | 0.37 | 0.39 | — | — | — | −0.30 | 0.18 |
| Cys | 142 | A | — | — | B | — | — | — | 0.06 | −0.01 | — | — | — | 0.56 | 0.49 |
| Lys | 143 | A | — | — | B | — | — | — | −0.26 | −0.17 | — | — | F | 0.97 | 0.86 |
| Gln | 144 | A | — | — | — | — | — | — | 0.60 | −0.37 | — | — | F | 1.58 | 1.77 |
| Lys | 145 | — | — | — | — | — | — | C | 1.10 | −1.06 | — | — | F | 2.34 | 5.73 |
| Thr | 146 | — | — | — | — | — | — | C | 1.64 | −1.14 | — | — | F | 2.60 | 4.13 |
| Thr | 147 | — | — | — | — | — | — | C | 1.72 | −0.71 | — | * | F | 2.34 | 2.36 |
| Glu | 148 | — | — | — | — | — | — | C | 1.68 | −0.61 | — | — | F | 2.08 | 1.19 |
| Thr | 149 | — | — | — | — | — | — | C | 1.68 | −0.21 | — | — | F | 1.52 | 1.43 |
| Gly | 150 | — | A | — | — | — | — | C | 1.63 | −0.30 | — | — | F | 1.06 | 1.72 |
| Ala | 151 | A | A | — | — | — | — | — | 1.60 | −0.79 | — | — | F | 0.90 | 1.72 |
| Gln | 152 | A | A | — | — | — | — | — | 1.02 | −0.36 | — | — | F | 0.60 | 1.18 |
| Gln | 153 | A | A | — | — | — | — | — | 0.68 | −0.16 | — | — | F | 0.45 | 0.83 |
| Glu | 154 | — | A | — | — | T | — | — | 0.64 | −0.16 | — | — | F | 0.85 | 0.82 |

TABLE 3-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 155 | — | — | — | — | T | T | — | 0.18 | −0.23 | — | — | F | 1.25 | 0.47 |
| Ile | 156 | — | — | — | — | T | T | — | 0.10 | 0.06 | * | * | F | 0.65 | 0.22 |
| Gly | 157 | — | — | — | — | T | T | — | 0.21 | 0.23 | * | * | F | 0.90 | 0.07 |
| Gly | 158 | — | — | — | — | T | T | — | −0.13 | 0.23 | * | * | F | 1.15 | 0.14 |
| Leu | 159 | — | — | — | — | — | — | C | −0.13 | 0.23 | * | * | — | 0.85 | 0.19 |
| Cys | 160 | — | — | B | — | — | T | — | −0.60 | −0.46 | * | * | — | 1.70 | 0.32 |
| Arg | 161 | — | — | — | — | T | T | — | −0.01 | −0.20 | * | * | F | 2.50 | 0.27 |
| Gly | 162 | — | — | — | — | T | T | — | −0.48 | −0.24 | — | * | F | 2.25 | 0.44 |
| Asp | 163 | — | — | — | — | T | T | — | −0.43 | −0.24 | — | * | F | 2.00 | 0.68 |
| Leu | 164 | A | A | — | — | — | — | — | −0.43 | −0.43 | — | * | F | 0.95 | 0.46 |
| Ser | 165 | A | A | — | — | — | — | — | −0.36 | 0.26 | — | * | — | −0.05 | 0.39 |
| Leu | 166 | A | A | — | — | — | — | — | −1.28 | 0.33 | * | * | — | −0.30 | 0.23 |
| Ser | 167 | A | A | — | — | — | — | — | −0.89 | 1.01 | — | * | — | −0.60 | 0.23 |
| Leu | 168 | A | A | — | — | — | — | — | −1.20 | 0.33 | — | * | — | −0.30 | 0.35 |
| Ala | 169 | A | A | — | — | — | — | — | −0.73 | 0.43 | — | * | — | −0.60 | 0.61 |
| Leu | 170 | A | A | — | — | — | — | — | −0.64 | 0.17 | * | * | — | −0.05 | 0.45 |
| Lys | 171 | — | A | — | — | T | — | — | −0.14 | 0.21 | * | * | F | 0.75 | 0.84 |
| Thr | 172 | — | A | — | — | T | — | — | −0.14 | 0.01 | — | * | F | 1.15 | 1.20 |
| Gly | 173 | — | — | — | — | — | T | C | 0.32 | −0.10 | — | * | F | 2.20 | 1.96 |
| Pro | 174 | — | — | — | — | T | T | — | 0.10 | −0.36 | — | — | F | 2.50 | 0.97 |
| Thr | 175 | — | — | — | — | T | T | — | 0.24 | 0.33 | — | * | F | 1.65 | 0.55 |
| Ser | 176 | — | — | — | — | T | T | — | −0.01 | 0.41 | — | — | F | 1.10 | 0.30 |
| Gly | 177 | — | — | — | — | T | — | — | 0.00 | 0.41 | — | — | F | 0.65 | 0.30 |
| Leu | 178 | — | — | — | — | — | — | C | −0.24 | 0.37 | — | — | F | 0.50 | 0.28 |
| Cys | 179 | — | — | — | — | — | T | C | −0.33 | 0.39 | — | — | F | 0.75 | 0.21 |
| Pro | 180 | — | — | — | — | — | T | C | −0.23 | 0.39 | — | — | F | 1.05 | 0.28 |
| Ser | 181 | — | — | — | — | — | T | C | 0.07 | 0.39 | — | — | F | 1.35 | 0.53 |
| Ala | 182 | — | — | — | — | — | T | C | 0.41 | −0.30 | — | * | F | 2.40 | 1.72 |
| Ser | 183 | — | — | — | — | — | T | C | 1.22 | −0.87 | — | * | F | 3.00 | 1.93 |
| Pro | 184 | — | — | — | — | — | T | C | 1.89 | −1.30 | — | — | F | 2.70 | 2.40 |
| Glu | 185 | A | — | — | — | — | T | — | 1.76 | −1.69 | — | — | F | 2.20 | 4.12 |
| Glu | 186 | A | — | — | — | — | T | — | 1.17 | −1.76 | — | — | F | 1.90 | 3.04 |
| Asp | 187 | A | — | — | — | — | T | — | 1.37 | −1.46 | — | — | F | 1.60 | 1.38 |
| Glu | 188 | A | — | — | — | — | T | — | 1.28 | −1.46 | — | — | — | 1.15 | 1.02 |
| Gly | 189 | A | — | — | — | — | T | — | 1.10 | −1.03 | — | — | — | 1.00 | 0.75 |
| Ile | 190 | A | — | — | — | — | T | — | 0.71 | −0.60 | — | — | — | 1.00 | 0.58 |

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated protein comprising amino acid residues 26 to 190 of SEQ ID NO:161.

2. The isolated protein of claim 1 which comprises amino acid residues 2 to 190 of SEQ ID NO:161.

3. The isolated protein of claim 1 which comprises amino acid residues 1 to 190 of SEQ ID NO:161.

4. The protein of claim 1 which comprises a polypeptide sequence heterologous to SEQ ID NO:161.

5. A composition comprising the protein of claim 1 and a pharmaceutically acceptable carrier.

6. An isolated protein produced by the method comprising:

(a) expressing the protein of claim 1 by a cell; and (b) recovering said protein.

7. An isolated protein comprising the amino acid sequence of the secreted portion of the polypeptide encoded by the HT5GJ57 cDNA contained in ATCC Deposit No. 209889.

8. The isolated protein of claim 7 which comprises the amino acid sequence of the complete polypeptide encoded by the HT5GJ57 cDNA contained in ATCC Deposit No. 209889, excepting the N-terminal methionine.

9. The isolated protein of claim 7 which comprises the amino acid sequence of the complete polypeptide encoded by the HT5GJ57 cDNA contained in ATCC Deposit No. 209889.

10. The protein of claim 7 which comprises a polypeptide sequence heterologous to SEQ ID NO: 161.

11. A composition comprising the protein of claim 7 and a pharmaceutically acceptable carrier.

12. An isolated protein produced by the method comprising:

(a) expressing the protein of claim 7 by a cell; and (b) recovering said protein.

* * * * *

SEQUENCE LISTING

<160> NUMBER OF SEQ ID NOS: 267

<210> SEQ ID NO 1
<211> LENGTH: 733
<212> TYPE: DNA
<213> ORGANISM: Homo sapiens

<400> SEQUENCE: 1
gggatccgga gcccaaatct tctgacaaaa ctcacacatg cccaccgtgc ccagcacctg 60
aattcgaggg tgcaccgtca gtcttcctct tcccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360

-continued

```
agaaaaccat ctccaaagcc aaagggcagc cccgagaacc acaggtgtac accctgcccc    420

catcccggga tgagctgacc aagaaccagg tcagcctgac ctgcctggtc aaaggcttct    480

atccaagcga catcgccgtg gagtgggaga gcaatgggca gccggagaac aactacaaga    540

ccacgcctcc cgtgctggac tccgacggct ccttcttcct ctacagcaag ctcaccgtgg    600

acaagagcag gtggcagcag gggaacgtct tctcatgctc cgtgatgcat gaggctctgc    660

acaaccacta cacgcagaag agcctctccc tgtctccggg taaatgagtg cgacggccgc    720

gactctagag gat                                                       733
```

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring L-amino acids

<400> SEQUENCE: 2

```
Trp Ser Xaa Trp Ser
  1               5
```

<210> SEQ ID NO 3
<211> LENGTH: 86
<212> TYPE: DNA
<213> ORGANISM: Homo sapiens

<400> SEQUENCE: 3

```
gcgcctcgag atttccccga aatctagatt tccccgaaat gatttccccg aaatgatttc     60

cccgaaatat ctgccatctc aattag                                          86
```

<210> SEQ ID NO 4
<211> LENGTH: 27
<212> TYPE: DNA
<213> ORGANISM: Homo sapiens

<400> SEQUENCE: 4

```
gcggcaagct ttttgcaaag cctaggc                                         27
```

<210> SEQ ID NO 5
<211> LENGTH: 271
<212> TYPE: DNA
<213> ORGANISM: Homo sapiens

<400> SEQUENCE: 5

```
ctcgagattt ccccgaaatc tagatttccc cgaaatgatt tccccgaaat gatttccccg     60

aaatatctgc catctcaatt agtcagcaac catagtcccg cccctaactc cgcccatccc    120

gcccctaact ccgcccagtt ccgcccattc tccgccccat ggctgactaa ttttttttat    180

ttatgcagag gccgaggccg cctcggcctc tgagctattc cagaagtagt gaggaggctt    240

ttttggaggc ctaggctttt gcaaaaagct t                                   271
```

<210> SEQ ID NO 6
<211> LENGTH: 32
<212> TYPE: DNA
<213> ORGANISM: Homo sapiens

<400> SEQUENCE: 6

-continued

```
gcgctcgagg gatgacagcg atagaacccc gg                                32


<210> SEQ ID NO 7
<211> LENGTH: 31
<212> TYPE: DNA
<213> ORGANISM: Homo sapiens

<400> SEQUENCE: 7

gcgaagcttc gcgactcccc ggatccgcct c                                 31


<210> SEQ ID NO 8
<211> LENGTH: 12
<212> TYPE: DNA
<213> ORGANISM: Homo sapiens

<400> SEQUENCE: 8

ggggactttc cc                                                      12


<210> SEQ ID NO 9
<211> LENGTH: 73
<212> TYPE: DNA
<213> ORGANISM: Homo sapiens

<400> SEQUENCE: 9

gcggcctcga ggggactttc ccggggactt tccggggact ttccgggact ttccatcctg    60

ccatctcaat tag                                                       73


<210> SEQ ID NO 10
<211> LENGTH: 256
<212> TYPE: DNA
<213> ORGANISM: Homo sapiens

<400> SEQUENCE: 10

ctcgagggga ctttcccggg gactttccgg ggactttccg ggactttcca tctgccatct    60

caattagtca gcaaccatag tcccgcccct aactccgccc atcccgcccc taactccgcc   120

cagttccgcc cattctccgc cccatggctg actaattttt tttatttatg cagaggccga   180

ggccgcctcg gcctctgagc tattccagaa gtagtgagga ggcttttttg gaggcctagg   240

cttttgcaaa aagctt                                                   256


<210> SEQ ID NO 11
<211> LENGTH: 1113
<212> TYPE: DNA
<213> ORGANISM: Homo sapiens
<220> FEATURE:
<221> NAME/KEY: SITE
<222> LOCATION: (393)
<223> OTHER INFORMATION: n equals a,t,g, or c

<400> SEQUENCE: 11

gatgctcctt tagcttggag gagtttgtta ttacccacct tctgaagcct acttctgtca    60

attcatccaa ctcattctca gtccagtttt gtttccttgc tggtgaggag ttgtgatcct   120

ttggaggaga agaggcattc tggtttttgg aatttttagc cattttgctc tggtttcttc   180

ccatctttgt ggatttatct acctttcatc ttcaatgtta gtgacctatg gatggggtct   240

ctgagtggat gtgctcttcc tttctgtttg twagttttct ttctaacagt tagcccctct   300

gctgtaggtc tgctggaktt tgctggaggt ccactccaga ccctgtttgc ctgggtatca   360

ccagtggagg ctgcagaaca gcaaagattg ctncctgttc tttcctctgg aagcttcgtc   420

tcagagggca cctgccagat gccagccaga gctctcctgt atgaggtgtc tgttggccca   480
```

-continued

```
tactgggaga ttcctcccag tcaggataca aggaggtcag ggacctactt gaggaggcag     540

tctgaccctt agcagaggtt gaacactgtg ctaggaggtc ctctgctctt ttcagagctg     600

tcaggcgggg cgtataagtc tgctgaatct gtgtccgcag ccacccettc ccccaggtgc     660

tctgtcccag ggagatgggg gttttatttt taagtcccca actggggctg ctgccttttt     720

ttcagagatg ccctgcccag agaggagaaa tctggcagtc tggcctcaga ggccttgctg     780

agctgccgtt ggctccaccc agttcaaact tcccaagggg ctttgtttat actgtaaggg     840

gaaaaccgcc tactcgagcc tcatcaatgg cagacacccc tccccgcgcc aagcttaagt     900

gtcccaggtt gatctcagac tgctgctgtg ctggcagtga gaatttcaag ccagtggatc     960

ttagtttgct gtgctctgtg gggtgggac ccattgaacc agactactcg gctccctggc     1020

ttcagccccc tttccaggag agtgaagggt tctgtctcat tggcattcca ggagtcactg    1080

gtgtatggaa aaaaaaaaaa aaagggcggc cgc                                 1113
```

<210> SEQ ID NO 12
<211> LENGTH: 983
<212> TYPE: DNA
<213> ORGANISM: Homo sapiens

<400> SEQUENCE: 12

```
ggcacgaggg cagctgcaga gctccaggtt tctctgccca caagggcagg ggctgcccct      60

cgcccaggat gactctgcct tccagagcct tggcctccct gggggtggga gtgtggggga     120

tgctaaggtt aaatcaggtc acagtaagtt gtgggggcag caggtggagc agcagagtgg     180

cactgggagc tttctcttgg gtgtgcggtg tggccttggt tctgcagcca tcaggtgggg     240

gcttgggact gacttctcct tctgaaggat gctgggaagg tgagctggct ttggcagtgc     300

ttagagctcc ggggggttcc ccctcctaga acatgcaagc tctcacaccg gtgcgtcatc     360

atcacaccca tcatcaagcc cacagtggta tactgaacac ctgccccaca aagacggtgg     420

actgctctca gaggagcccc atgaaccacc gatggttaca actatccaat gcctgatggc     480

agacagccag gccaacctcg gcttccactc tctcttcctc accctacaat cagccaaagt     540

gacctgagtc atgtagtgtg aagttgcttt ctgctttctc ttgtttgtgc ttttgctgtt     600

tcttctgccc catactttgt taactccatg agttaaatgc tacccatttt cccagacaag     660

tgctgcttct gcaaggaaac ccttcctgat cccccaccta tctgaaaagt acctctccag     720

cttgcttctt cagggtgctg agcgttcctt cccagcctgt catcaccttc ctccatacgc     780

tatggtgtgt tcctgtcttc tctagtcttg tcctcttttt tctgttagat tgtagctcct     840

tgctgacagg aaccacgcct gctccagctt catacctccc actgctacag cacagaacct     900

gcttctcaga cttacagcaa atgtttgttt gctgaatgaa ttaattaaag ataaagcaaa     960

aaaaaaaaaa aaaaaaactc gag                                             983
```

<210> SEQ ID NO 13
<211> LENGTH: 973
<212> TYPE: DNA
<213> ORGANISM: Homo sapiens

<400> SEQUENCE: 13

```
ggcacgagcc cagcggaagc caagccacca ggccccccag cgtccacgcg gagcatgaac      60

attgaggatg gcgcgtgccc gcggctcccc gtgccccccg ctgccgcccg gtaggatgtc     120

ctggccccac ggggcattgc tcttcctctg gctcttctcc ccacccctgg gggccggtgg     180
```

-continued

```
aggtggagtg gccgtgacgt ctgccgccgg agggggctcc ccgccggcca cctcctgccc    240

cgtggcctgc tcctgcagca accaggccag ccgggtgatc tgcacacgga gagacctggc    300

cgaggtccca gccagcatcc cggtcaacac gcggtacctg aacctgcaag agaacggcat    360

ccaggtgatc cggacggaca cgttcaagca cctgcggcac ctggagattc tgcagctgag    420

caagaacctg gtgcgcaaga tcgaggtggg cgccttcaac gggctgccca gcctcaacac    480

gctggagctt tttgacaacc ggctgaccac ggtgcccacg caggccttcg agtacctgtc    540

caagctgcgg gagctctggc tgcggaacaa ccccatcgag agcatcccct cctacgcctt    600

caaccgcgtg ccctcgctgc ggcgcctgga cctgggcgag ctcaagcggc tggaatacat    660

ctcggaggcg gccttcgagg ggctggtcaa cctgcgctac ctcaacctgg gcatgtgcaa    720

cctcaaggac atccccaacc tgacggccct ggtgcgcctg gaggagctgg agctgtcggg    780

caaccggctg gacctgatcc gcccgggctc cttccagggt ctcaccagcc tgcgcaagct    840

gtggctcatg cacgcccagg tagccaccat cgagcgcaac gccttcgacg acctcaagtc    900

gctggaggag ctcaacctgt cccacaacaa cctgatgtcg ctgccccacg acctcttcac    960

gcccctgcac cgc                                                        973
```

<210> SEQ ID NO 14
<211> LENGTH: 1458
<212> TYPE: DNA
<213> ORGANISM: Homo sapiens

<400> SEQUENCE: 14

```
ccacgcgtcc gggaattttc aaaagatcca aacagagact tcctgcatct tctgcctttc     60

caacagaagc ggtgatcgtc taagtatgag cctgtggctt cctttgtgca tttgagcatg    120

ctgtaattaa gatgagatca gtttcttaga aaaagctttc ctgaatccct ctgacgttgc    180

ctgggatctt tctgttgatt cgtcttttct ggagattggg acagagcatc tgtggtccag    240

ggaagttagt cctctggcct caattctgtt gtggatgtgc agtgataagc gggcattgcg    300

tgcctcgggg gatgcctagt tcgtggcttc ctggctgttt tgtccttctg tgtcttgtag    360

ctgtagggtg ccagctcagg gagtggggtg ttggcggcgt ttccgcggtt ggcctccttg    420

ctttgccgca cctccaggtt ctgggcatga gaggccgtgg cctcatttct ggtggataac    480

ctttttagtt taatagcatc tttaattaga tcacagcatt gaattcaaaa tttcttctgc    540

aaagaaagtt gtggggcata agacaccggg aatgagggag gaggaagaca gttgtgtttt    600

ctctttaaac cttgagctct agccgatgca tttgtcagga aatacagcac tttgtcttaa    660

gaaaacaagg aaggaggccg ggcgcagtgg ctcacgcctg taatcccagc actttgggag    720

gccgaggcgg gcggatcacc tgaggtgggg agtatgagac caccctgact aacatggaga    780

gaccctgtct ctactaaaag tacagaatta gccgggcgtg gttgcgcatg cccataatcc    840

cagctactga ggagacttga ggtaggagaa tcacttgaac ctcagcggcg gaggttgcag    900

tgagtcgaga tcgcgccagt gcactccagc ctgggcaaga agagcgaaac tgggtctcaa    960

gttaaaaaaa gaaagcaagg aaagagtaat ttacaacgaa ggaaaaaaac ccacagcaca   1020

cccttcgcgg ctgtcagcgc tctcctgatg tcacagtggc tgcgtgtcct tggggtgggt   1080

gaggtgtggg gagcccagcc cctggccctg cctcccgcgc cccgctcccc ttctctctct   1140

tactcggtta agccatagcg aggcctccgc tcgtttcaga tatgaatttg ttttatagat   1200

tataaatatg catatacagt gtatgtataa agcagaatgc ctgcctttcc tggttatttt   1260

ttgtaccata ttgtaaatta tattatttat tctttaccaa ttttgggaat aaaaggtgtt   1320
```

-continued ttggttattt aatataataa gagctgttaa acttctgttt aaatttccag ttcaacttgt 1380
aaatgttttt attgtgcata aatacatact aatgttgatc taaaaaaaaa aaaaaaaaaa 1440
aaaaaaaaaa aaaaaaa 1458

<210> SEQ ID NO 15
<211> LENGTH: 2005
<212> TYPE: DNA
<213> ORGANISM: Homo sapiens

<400> SEQUENCE: 15
ggttgctggc ccaggtgagc gggcgcgctg gtccaggtga gcgggcgcgt ccccgcgacg 60
gcgctgcctg cccgaggcgg ttcacgtaaa gacagcgaga tcctgagggc cagccgggaa 120
ggaggcgtgg atatggagct ggctgctgcc aagtccgggg cccgcgccgc tgcctagcgc 180
gtcctgggga ctctgtgggg acgcgccccg cgccgcggct cggggacccg tagagcccgg 240
cgctgcgcgc atggccctgc tctcgcgccc cgcgctcacc ctcctgctcc tcctcatggc 300
cgctgttgtc aggtgccagg agcaggccca gaccaccgac tggagagcca ccctgaagac 360
catccggaac ggcgttcata agatagacac gtacctgaac gccgccttgg acctcctggg 420
aggcgaggac ggtctctgcc agtataaatg cagtgacgga tctaagcctt tcccacgtta 480
tggttataaa ccctccccac cgaatggatg tggctctcca ctgtttggtg ktcatcttaa 540
cattggtatc ccttccctga caaagtgttg caaccaacac gacaggtgct atgaracctg 600
tggcaaaagc aagaatgact gtgatgaaga attccagtat tgcctctcca agatctgccg 660
agatgtacag aaaacactag gactaactca gcatgttcag gcatgtgaaa caacagtgga 720
gctcttgttt gacagtgtta tacatttagg ttgtaaacca tatctggaca gccaacgagc 780
cgcatgcagg tgtcattatg aagaaaaaac tgatctttaa aggagatgcc gacagctagt 840
gacagatgaa gatggaagaa cataaccttt gacaaataac taatgttttt acaacataaa 900
actgtcttat ttttgtgaaa ggattatttt gagaccttaa aataatttat atcttgatgt 960
taaaacctca aagcaaaaaa agtgagggag atagtgaggg gagggcacgc ttgtcttctc 1020
aggtatcttc cccagcattg ctcccttact tagtatgcca aatgtcttga ccaatatcaa 1080
aaacaagtgc ttgtttagcg gagaattttg aaaagaggaa tatataactc aattttcaca 1140
accacattta ccaaaaaaag agatcaaata taaaattcat cataatgtct gttcaacatt 1200
atcttatttg gaaaatgggg aaattatcac ttacaagtat ttgtttacta tgaaatttta 1260
aatacacatt tatgcctaga aggaacggac tttttttttc tattttaatt acacataata 1320
tgtaattaaa gtmcaacata atatgttgtt tctctgtagc ccgttgagca tatgagtaag 1380
tcacatttct attaggacta cttmcaagga caaggtttcc atttttccag ttgtaaaatt 1440
ggaaccatca gctgataacc tcgtagggag caaccccagg atagctaagt gttatgtaat 1500
atgcctagaa ggtgatgtga atgcgattca gaagcatagc cactcccatt ttatgagcta 1560
ctcacatgac aaatgtcatc ttttgctata acctttgcca agttagagaa aagatggatt 1620
taatgagata aatgaaaaga tatttamcct aatatatcaa ggcactattt gctgttatgc 1680
tttgttattt atttcccagc acttgttcct tattgtagat tttttaaaga ctgtaacctt 1740
ttactaactg tggtcttact aaaatttgtg cttgatactg cttttcaaaa agcctttaat 1800
tagagccaaa aggatggaaa aggcaagata taaatgcctt ttatagatct cttatttaca 1860
ttgaaaatta ttaccatatg tttagagcaa atccaagaaa acttcaacag cttctgaaga 1920

-continued tgtctatgaa tgttgaaaac ttttcaatst cttggratgc tcakttaatt cgcagaccgg 1980
cttaacggat taaacgcccc ccccc 2005

<210> SEQ ID NO 16
<211> LENGTH: 943
<212> TYPE: DNA
<213> ORGANISM: Homo sapiens

<400> SEQUENCE: 16
ggcacgagct ccgcccggcc ccgaggggct ctccccggag gctcagcccc ctctgctccc 60
catgggcaac tgccaggcag ggcacaacct gcacctgtgt ctggcccacc acccacctct 120
ggtctgtgcc actttgatcc tgctgctcct tggcctctct ggcctgggcc ttggcagctt 180
cctcctcacc cacaggactg gcctgcgcac cctgacatcc cccaggactg ggtctctttt 240
ttgagatctt ttggccagct gaccctgtgt cccaggaatg ggacagtcac agggaagtgg 300
cgagggtctc acgtcgtggg cttgctgacc accttgaact tcggagacgg tccagacagg 360
aacaagaccc ggacattcca ggccacagtc ctgggaagtc agatgggatt gaaaggatct 420
tctgcaggac aactggtcct tatcacagcc agggtgacca cagaaaggac tgcaggaacc 480
tgcctatatt ttagtgctgt tccaggaatc ctaccctcca gccagccacc catatcctgc 540
tcagaggagg gggctggaaa tgccaccctg agccctagaa tgggtgagga atgtgttagt 600
gtctggagcc atgaaggcct tgtgctgacc aagctgctca cctcggagga gctggctctg 660
tgtggctcca ggctgctggt cttgggctcc ttcctgcttc tcttctgtgg ccttctctgc 720
tgtgtcactg ctatgtgctt ccacccgcgc cgggagtccc actggtctag aacccggctc 780
tgagggcact ggcctagttc ccgacttgtt tctcaggtgt gaatcaactt cttgggcctt 840
ggctctgagt tggaaaaggt tttagaaaaa gtgaagagct ggaatgtggg ggaaaataaa 900
aagctttttt gcccaaaaaa aaaaaaaaaa aaaaaaaaaa aaa 943

<210> SEQ ID NO 17
<211> LENGTH: 1503
<212> TYPE: DNA
<213> ORGANISM: Homo sapiens

<400> SEQUENCE: 17
caggttcctc tcagtamarc ctcarsccga ggttcccttc ctcttgcatc catgtgtgtg 60
tttcaraggc ggccatcctt ccctacttcc agatccttgt agggcagttg gtggagggtg 120
ggaggcaccc cggtgttgcc tccatgaagc cctgtgccag tcactgggct gcaaggctga 180
ggaaattgtg tccgtgtcag aaagctcctc agctcagagg tgctggtacc tcctgcgtgg 240
taggaaggca gggggaagag gccctgcttc tcctgttctc tttgccctta tgagacttga 300
gagtctgtgt catctgtgcc ttgcatgtct ttttttcaga ctccctgcga caaggactgt 360
gtactgcatg aatgaggctg agatagttga tgttgctctg ggaatcctga ttgagagccg 420
yaaacaggam aaggcctgcg agcagccggc cctggcgggg gctgataacc cagagcactc 480
ccctccctgc tccgtgtcgc ctcacacaag ttctgggagc agcagtgagg aagaggacag 540
tgggaaacag gcactgrctc caggcctcag cccttcccag aggccggggg gttccagctc 600
tgcctgtagc aggagccctg aggaggagga ggaagaggat gtgctgaaat acgtccggga 660
gatctttttc agctagggca taaactgtgc actgaactgt ctgccgagag cagctggagg 720
acagctgagc ttccactggt gctgctgggc cgcccgcctg tgggaatggg gctctctgtg 780
ctcctacctt tgtgccttct tgggcctggc agattcacct caggccagaa gcccctggac 840

-continued

```
actccgggcc ttggggctgc cgttctgagt gtgcggaagg caggactcaa aatgagatcc    900

catttgactc cctctgtatg tactgtgccc tctcctggct cttgaggctc tggagtccca    960

attgtctgtg ttagtcagtg accaggttcc agggaaaatg atgtcatgtg gtggtccaac   1020

ttactggaac caaagagaca gtactttgca aagaaaagga tcactgccag gtgcactgga   1080

attgctacag tttagtccgc atgatctctc ctgaaggagg aagcctgttt caaaaatagt   1140

ttccatcatg agtctatcaa tgagctccca cctctccagc cagcctagaa agcaaacgag   1200

ctgcccacag ttctctgccc tgtctgggag gttgaggcca cagtgtatag actggtaagc   1260

cagacaggcc tcctcccgca agctgctacc ttgctttcac ctgtaccttg gtccccgggc   1320

agctagctat aaagcaagag ggacaggagc ccagaagaga cactgaggac aagagatcac   1380

accagagtac atgtctctgc ctctgttttc agtgtggctt tggacaggaa tatatgaata   1440

aatcactgcc atacaggttt tccaatacac aagtgctaga aaatacacac aattccccaa   1500

tga                                                                 1503
```

```
<210> SEQ ID NO 18
<211> LENGTH: 1512
<212> TYPE: DNA
<213> ORGANISM: Homo sapiens
<220> FEATURE:
<221> NAME/KEY: SITE
<222> LOCATION: (207)
<223> OTHER INFORMATION: n equals a,t,g, or c
<220> FEATURE:
<221> NAME/KEY: SITE
<222> LOCATION: (209)
<223> OTHER INFORMATION: n equals a,t,g, or c
<220> FEATURE:
<221> NAME/KEY: SITE
<222> LOCATION: (521)
<223> OTHER INFORMATION: n equals a,t,g, or c

<400> SEQUENCE: 18

gcagagcccc tgggtgtgag aagctcgtct cccgtgggtt gcattggctc tgccctatct     60

ctgcctccag cacccagggc ggccgcagat ggcagtgtct ctggggacag cagctgcgaa    120

tgagtccacg ggccaacgct gagctgctca ggctgaggcg gtgtgctcag cacagagccc    180

ccggaactgg catctgcagg gcgtgancna aggccgccgc gatgccgcac ttcctggact    240

ggttcgtgcc ggtctacttg gtcatctcgg tcctcattct ggtgggcttc ggcgcctgca    300

tctactactt cgagccgggc ctgcaggagg cgcacaagtg gcgcatgcag cgcccccctgg    360

tggaccgcsa cctccgcaag acgctaatgg tgcgcgacaa cctggccttc ggcggcccgg    420

aggtctgagc cgacttgcaa aggggatagg csggcggcac cgggcgccct cccccagccc    480

gccccgcccg cccagcccgg agacccccaa ggcagaggga ngccggcctg ttggccctcc    540

acgctatccc tctgcagcct gggccctccc gacagaggcc ccaggtgcgc tgscagtgra    600

ggtggggcac ttaggtgcct ggctggccca gggcttgctc tccgtgtcaa gccgactcac    660

ccagagccca ccctcccaag ctcaggggca tcctccgctg ggccccagtg cctttgcrct    720

gcgcagcact ctgccctcca ctggactcag gcatgtctat ggctgcctgt cctgaggctc    780

cggagccctc atttcttcgt gaagtcccca gctcccctgc ctccactcaa tggcaccggc    840

cctgcaactt taggcaggtc gaagccaacc caaggaaaga acctaagaac ctcgtttgga    900

gggatgtcag cttgggccag mccagccgca ccccgcgggg ctcaggcttg gaactggtga    960

gggtgtgtgg tgggggtatg cagagggata agaccgtggt agaggagagg gttggtgagg   1020
```

-continued

```
agagagagag agagagagag agagagagtc tggggggagc gggcaagcat ggggagatga   1080

gatgtgtata tgtgagagag agtgtggggg ccccaggcag ggcaggaggt ggtggaaacg   1140

gggtgaactc cgtgggctgt gtgaggactg tccatagtgg gtccmaaccc cctccctctg   1200

ctggagtttc ctagcccttc cccctcccya agactgwggc agcaggcagg agcccctgcc   1260

ctccctccct gtcctgtgcc acacttctgg ggccaaaccc agccccccttg agccaggccc  1320

tgccagactc caagcccacc ctagaaccct cctcctgtgt ggagactctg ttgccccact   1380

ttggacacag attggcaacc tgcctcaccm ckcccccctw cgctggggct tccatcttaa   1440

tttattctca ataataaaga cttcatgatg amaaaaaaaa aaaaaaaaaa aaaaaaaaaa   1500

aaaaaaaaaa aa                                                       1512
```

<210> SEQ ID NO 19
<211> LENGTH: 1655
<212> TYPE: DNA
<213> ORGANISM: Homo sapiens

<400> SEQUENCE: 19

```
ccacgcgtcc gggcaaagaa ttaaacctgg tgtttggact tcaacttagc atggctagaa     60

ttggaagtac agtaaacatg aacctcatgg gatggctgta ttctaagatt gaagctttgt    120

taggttctgc tggtcacaca accctcggga tcacacttat gattgggggt ataacgtgta    180

ttctttcact aatctgtgcc ttggctcttg cctacttgga tcagagagca gagagaatcc    240

ttcataaaga acaaggaaaa acaggtgaag ttattaaatt aactgatgta aaggacttct    300

ccttacccct gtggcttata tttatcatct gtgtctgcta ttatgttgct gtgttccctt    360

ttattggact tgggaaagtt ttctttacag agaaatttgg attttcttcc caggcagcaa    420

gtgcaattaa cagtgttgta tatgtcatat cagctcccat gtccccggtg tttgggctcc    480

tggtggataa aacagggaag aacatcatct gggttctttg cgcatagcag ccactcttgt    540

gtcccacatg atgctggcct ttacgatgtg gaacccttgg attgctatgt gtcttctggg    600

actctcctac tcattgcttg cctgtgcatt gtggccaatg gtggcatttg tagttcctga    660

acatcagctg ggaactgcat atggcttcat gcagtccatt cagaatcttg ggttggccat    720

catttccatc attgctggta tgatactgga ttctcggggg tatttgtttt tggaagtgtt    780

cttcattgcc tgtgtttctt tgtcactttt atctgtggtc ttactctatt ggtgaatcgt    840

gcccagggtg ggaacctaaa ttattctgca agacaaagga agaaataaaa tttcccatac    900

tgaatgagaa gttaaaatga atgtgtcaga gaatgggctt aacacatcgt tggtttgaaa    960

acttccattt taaaaattta gagtttagtc attagaaaaa ataatggact ggaaagttat   1020

atttatatcc aaatatacct atttcaaagt gtatttgtga ggcctgtttt agcctgtgtc   1080

ttttgtattg tgtgttgcta aagaattcta cttttagtag gctaatcaac aatgaaaggg   1140

ttagaaaatt gctgtggaac atccaggtga acttcaggaa agacagtgaa aaatggaaaa   1200

cgttggagct tctgttgaga taatcttcat taggtatata tcttagggat acagcctttt   1260

ctttatctta tagcaggaaa aaaaaacttt tgagggaaat agaagggctg cgttacacaa   1320

aataaacaat ggcattgtca taggccttcc ttttactagt agggcataat gctagggaat   1380

atgtgaagat gtttttttga agtctctttc tgatcacgaa caatagcttg cgctctactc   1440

tgtagttatg tggattgccg agcaatgacc cttttcaatt tcttatttct gtgttactga   1500

ggaccctaat cacttaggga tgtaatttta tagtataaac tttctgtaca gtttttctta   1560

tagtctaata agtaaaaagt gtccttcaaa ttatgataat tgcctatgta catggataaa   1620
```

-continued ttaaaacact gcacacggaa aaaaaaaaaa aaaaa 1655

<210> SEQ ID NO 20
<211> LENGTH: 2525
<212> TYPE: DNA
<213> ORGANISM: Homo sapiens
<220> FEATURE:
<221> NAME/KEY: SITE
<222> LOCATION: (5)
<223> OTHER INFORMATION: n equals a,t,g, or c
<220> FEATURE:
<221> NAME/KEY: SITE
<222> LOCATION: (10)
<223> OTHER INFORMATION: n equals a,t,g, or c
<220> FEATURE:
<221> NAME/KEY: SITE
<222> LOCATION: (1354)
<223> OTHER INFORMATION: n equals a,t,g, or c

<400> SEQUENCE: 20
tgacnctatn gtaaggtacg cctgcaggta ccggtccgga attcccgggt cgacccacgc 60
gtccggtctg ccaacaaggt cgttcatgaa agtgtttttc tctttaaggt aattaaaaaa 120
cagtggaatg gaaaaacagt gctgtagtca tcctgtaata tgctccttgt caacaatgta 180
tacattcctg ctaggtgcca tattcattgc tttaagctca agtcgcatct tactagtgaa 240
gtattctgcc aatgaaggta agttaagact tggtatatgc atggagcact tccatctaat 300
cacacatctc tctcttgcct ttggttctgt tatatataac atggaaataa taatgccttt 360
tgcttcatgt gagtgataaa gcatatttaa atttgattat ttaaccttgc attcctcaac 420
aagaaaaaat gtttgataat ggatgaaatg tgagtcaatc agatacaaaa atcaaaccct 480
ttggtgaaga accagtcgta acatttgact gttaattcaa tcaacaggtg tttctggacc 540
tatagcaaaa tgtgtaattg cgccttattt tgaagtagaa ggatatattt gtttggtcac 600
ttggcatttg tgaggtactt actattgtaa ttattgtatc aatggtaagg tgtcagcatt 660
atattgtgcg gtcatattgt atcaacagta taaattataa gctttgataa gtatgtattt 720
aagaaatctt tttttatgta gggatttaag caaacacttt aattccacca aactgtattg 780
agtacttctt actagttatt gagtgaaggg gtgggttgcc cctccacatc tgtgggtgtt 840
tctcgttagg tggaacgaga gacttggaaa agaaagggac atagacaaag tatagagaaa 900
gaaaaaaggg ggcccagggg accggcgctc agcacacgga ggatctctgc cagcctctga 960
gttccmttag tatttattga tcattattgg gtgtttctcg gagagtggga tgtggcagga 1020
tcataggata gtagtggaga gagggtcaac aggtaaacac gtgaacaaag gtctttgcat 1080
cataracaak gtaaagratt aagtgctktg cttttagata tgcatacaca taaacatctc 1140
aatgctttac aaagcagtat tgctgcccgc akgtcccacc tccagcccta aggcggtttt 1200 ycccctatctc agtagatgga gcatacaatc gggttttata ccgagacatt ccattgccca 1260
gggacrggca ggagacagat gccttcctct tgtctcaact gcaagaggcr ttccttcctc 1320
ttttactaat cctcctcagc acagaccctt tacngggtgt cgggctgggg gacggtcagg 1380
tctttccctt cccacgaggc catatttcag actatcacat ggggagaaac cttggacaat 1440
acctggcttt cctaggcaga ggtcsctgcg gcyttccrca gtgttttgtg tccctgsgta 1500
cttgagatta gggagtggtg atgactctta asgagcatgc tgccttcaag catctgttta 1560
acaaagcaca tcttgcaccg cccttaatcc atttaaccct gagtkgacac agcacatgtt 1620
tcagagagca crgggttggg ggtaaggtta cagattgcag aacaaaatgg agtctcctat 1680

-continued gtctacttct ttctamacag acacagtaac aatctgatct ctcttttccc cacaattgag 1740
gacacataca atcatgatat gacctttaat ggtctactac ttggagagtc agatgtgtac 1800
ccaagtctct actgcagtta acatttacct gccaggcact aggctaagta ttagcagcag 1860
gttcaaagtg cataagatat agaccttgtc ctcaagactt agtttattag gagagacatg 1920
aatgtaaaca catcatgaaa atccattata ataactgcaa taattgatat atcctgaaga 1980
tgcagagatt gtctagagga taaagttata tattctgttt ggtaggggat gatgtggagt 2040
tcaaatggat cagagaacac ttcgctgatt agaagtcagt tgatccacta gaagtcaagg 2100
tgaacaaggg gattcaaaac agaggcaaca gcctgtaaaa gggaacagag gcataaaaaa 2160
gcaggatatg ttgtgagaac atgtagtttg aaattaccaa gcaaaaagtt taaggactcg 2220
tagccaggca cagtggctca tgctgtaatc ccagcacttt aggaggccaa ggccggcgga 2280
tcacttgagg tcaggaattt gagaccaggc tggccaacat ggtgaaaccc atctctacta 2340
gaaatacaaa aaattagctg ggtttgttgg cgtgtgcctg taatcccagc tatgagggag 2400
actgaagcag gagaatgaac ccgggaggca gagattgcag tgagccgaga tcatgccact 2460
gcactccagc ctgggcaaca gagcaaaact gtctcaagaa aaaaaaaaaa aaaaagggcg 2520
gccgc 2525

<210> SEQ ID NO 21
<211> LENGTH: 1396
<212> TYPE: DNA
<213> ORGANISM: Homo sapiens

<400> SEQUENCE: 21
aagtctcgta tcgcgcccgg gaggcgccgg agcccagcgg ctggcgccag atccaggctc 60
ctggaagaac catgtccggc agctactggt catgccaggc acacactgct gcccaagagg 120
agctgctgtt tgaattatct gtgaatgttg ggaagaggaa tgccagagct gccggctgaa 180
aattacccaa ccaagagaaa tctgcaggat ggactttctg gtcctcttct tgttctacct 240
ggcttcggtg ctgatgggtc ttgttcttat ctgcgtctgc tcgaaaaccc atagcttgaa 300
aggcctggcc aggggaggag cacagatatt ttcctgtata attccagaat gtcttcagag 360
agccrtgcat ggattgcttc attacctttt ccatacgaga aaccacacct tcattgtcct 420
gcacctggtc ttgcaaggga tggtttatac tgagtacacc tgggaagtat ttggctactg 480
tcaggagctg gagttgtcct tgcattacct tcttctgccc tatctgctgc taggtgtaaa 540
cctgtttttt ttcaccctga cttgtggaac caatcctggc attataacaa aagcaaatga 600
attattattt cttcatgttt atgaatttga tgaagtgatg tttccaaaga acgtgaggtg 660
ctctacttgt gatttaagga aaccagctcg atccaagcac tgcagtgtgt gtaactggtg 720
tgtgcaccgt ttcgaccatc actgtgtttg ggtgaacaac tgcatcgggg cctggaacat 780
caggtacttc ctcatctacg tcttgacctt gacggcctcg gctgccaccg tcgccattgt 840
gagcaccact tttctggtcc acttggtggt gatgtcagat ttataccagg agacttacat 900
cgatgacctt ggacacctcc atgttatgga cacggtcttt cttattcagt acctgttcct 960
gacttttcca cggattgtct tcatgctggg ctttgtcgtg gttctgagct tcctcctggg 1020
tggctacctg ttgtttgtcc tgtatctggc ggccaccaac cagactacta acgagtggta 1080
cagaggtgac tgggcctggt gccagcgttg tccccttgtg gcctggcctc cgtcagcaga 1140
gccccaagtc caccggaaca ttcactccca tgggcttcgg agcaaccttc aagagatctt 1200
tctacctgcc tttccatgtc atgagaggaa gaaacaagaa tgacaagtgt atgactgcct 1260

-continued ttgagctgta gttcccgttt atttacacat gtggatcctc gttttccaaa aaaaaaaaaa 1320
aaaaaaaaaa aaaaaaaaaa aaaactcgag ggggggcccg gtacccaatt cgccctggag 1380
ttcaagtaga catcaa 1396

<210> SEQ ID NO 22
<211> LENGTH: 1069
<212> TYPE: DNA
<213> ORGANISM: Homo sapiens
<220> FEATURE:
<221> NAME/KEY: SITE
<222> LOCATION: (508)
<223> OTHER INFORMATION: n equals a,t,g, or c

<400> SEQUENCE: 22
ggcacgagca cagcctcagg ccctgcccca gacctgcaga atcagaaact ctggggtgag 60
gcctggttat ctgctgtaac agaccttcca gtgggttctg atgccctcta gagcaggaga 120
accactagct tagaggttgc agtatgtttg gcatcttgcc atttgtgtta gttcagagga 180
atggctgacc cccatgtctc atttctaagc ttcaggcagc ttttctcctg ggcagctgtc 240
attctgttga ggggaatcct ggggactgtg gctcctcctc cctgtccgtg tgtccttgat 300
ctggcagtct accccttca tctccccgtg gaggctccat gcctagaggt ggtcttcaaa 360
cagaagaatg gcaaagataa ttgtctcgtg ttttaccctg accccattcc tttaagaggg 420
tcacttcttg gcccattcat taaaaaccaa tgtcatagtt ctgtgattcc actatcagac 480
agtgccacgt ccaaggcgcg ggctcttnac ctccctggaa gagagactgt gctgtctgtg 540
cttcctgtgt tctccagtcc cacgctccca cggacccacg cccttggaga ctccctcggt 600
gtcccagggc ttctggtgtg ttcagagacc tccacactca acgaccactg gtgctgcaga 660
agggccggtg cttacattcc aattaacaga cgcttttccc atctaatgcc tcttgccttc 720
tcctaacacc acctcgggag tgtttatgtc tattctaagt gaatttcact gtgtgaaaaa 780
attcacacct gttgtcccag cgatttggga ggccggggcg ggtgtatcat ttgagcccag 840
gagtttgagg ctagcctggg caggatggtg aaaccccgtc tctataaaga aattttaaaa 900
attagctggg catagtggca cgtgcctgta gttccatcta ctggggaggc tggggtggga 960
ggatcgcatg agcccgggag tttgaggctg cagtgagctg tgatcgcagc actgcactcc 1020
agtctgggca acagagcaag accctgtctc ttaaaaaaaa aaaaaaaaa 1069

<210> SEQ ID NO 23
<211> LENGTH: 1658
<212> TYPE: DNA
<213> ORGANISM: Homo sapiens

<400> SEQUENCE: 23
ggcacgagcc ggcctgccag agccatgccc ctgactcctc agcttcaaaa tcaggggtct 60
caggacagag gatgctgggt gggctcagag ctcatcaggg gggctgtgtg tgagagggga 120
tgccttctgg atgccctcat cctcctcggg gctggggtct ccctcaaggc cacccagctc 180
cttcctttgt ttgctgctgc tactcctgcc gcctgctgcc ttggccctgc tgctcttctt 240
cttggacttc ttccctccca gggcagctgt gtctcccttc ttgccggacc actgctctgc 300
caggcaacct agggtgtgga ggagagagac cctcaacaga agtgcctcag ggctggggtg 360
ctgggcaagg agcactgagc agggagccgt gggagtagca actgggactg tgcttgacat 420
cagcctccct gcctcctgcc tctcgctgtg gccaccaggc ccctctgggg gcatctgact 480

-continued

```
tgtctgccca tcattctgca cctggtttca gtgactctta cttcaccatg tcttgccaat    540
caagcctttc aagggcagag atcctacaat gccctctggt gccctctgtt tctcctccta    600
cccacctccc ccaagggaga gcaaacaaat catccagagc cagcctgccc ttgcttcccc    660
aaactcactg gtgtcttttc ccttcagcac gtggttggcg cagaggaatt cagtcaggtc    720
ttcctcctgg tggatcctgt accagtcctc gatcacctcc tcaaactctt caccagcaca    780
tcacacttgt taatcataat acctcatatt ggcaaagccc cagcacctga ctcgctccta    840
gaggagctca gcctaagcct cgcaacccac tgcaaggtag cagtggcacg gttcacctaa    900
ggaaactgag gccagagagg tgaaatgacc tgaccaaagc caccccggcc tgggtggact    960
tcctcagagc agacccaatc cccaccagcc cttcactggg cacagcaacc cttccaaggg   1020
ctgaagggcc tgtacctgct tcttgaggtc agccacttct gcagaagtct cgttcaacag   1080
ctcatagggg atgtccatca ccaccttgac ccctttgtgt accaggttgt gtaatgtctc   1140
aaaggtctct gacatgccct ggaagaagcg accagatatg gcaggcggag ctcccttctc   1200
tccctcccac cctcgtctcc cagtggtggc taagaaccca gctataagac caatgctcaa   1260
cgccctctaa ggatcctcat cctttttttt ttgagaagga gtctcactct gtcgcccagg   1320
ttggagcgtc tcagctcact gcaacctctg cctcccaggt tcaagcgatt ttcctgcctc   1380
agcctcccaa gcagctggga ctacaaaggc gtgccaccat acccggctaa tttttgtaga   1440
gttggggttt tgtcatgttg gtcaggctgg tctcgaactc ctagcatcaa gttttccact   1500
cacctcagcc tcccaaagtg ctgagattac aggcgtgagc caccgcacct ggcctcatcc   1560
ttgacctgac cttcctcttc cctcttttag gcctgcttcc cacaacccct gcacatatac   1620
cccctgatct gcctctgcac acctcatcgc ttcaaaaa                            1658
```

```
<210> SEQ ID NO 24
<211> LENGTH: 1077
<212> TYPE: DNA
<213> ORGANISM: Homo sapiens
<220> FEATURE:
<221> NAME/KEY: SITE
<222> LOCATION: (1036)
<223> OTHER INFORMATION: n equals a,t,g, or c
<220> FEATURE:
<221> NAME/KEY: SITE
<222> LOCATION: (1038)
<223> OTHER INFORMATION: n equals a,t,g, or c

<400> SEQUENCE: 24

ggcacgaggg gaaagccatg ctcccaggac tccttccttg cagccttaaa tcggtctgta     60
cggaaaattc cgcgccttag aaacccacgc ttgggtgtaa cttattattg ttcttcctga    120
cctacttcct gtttatcact tccgggttca tcattttggc atttcggtga tcgggttgga    180
actattgaag cccgctttca ggttcttttc cccattttcc ctttgaaagg aagacttctg    240
gcttctccta aatctccgtt ctctgggtaa ggggagtcca agcctctgtc atgaggaacg    300
gaaatgcgag ggcctcgggt gttactctaa aatccgccct cagcttgcac gccggaagct    360
gcgattcctg cagcggaaga ggcgtgatct ggccttcgac tcgctatgtc cactaacaat    420
atgtcggacc cacggaggcc gaacaaagtg ctgaggtaca agccccccgcc gagcgaatgt    480
aacccggcct tggacgaccc gacgccggac tacatgaacc tgctgggcat gatcttcagc    540
atgtgcggcc tcatgcttaa gctgaagtgg tgtgcttggg tcgctgtcta ctgctccttc    600
atcagctttg ccaactctcg gagctcggag gacacgaagc aaatgatgag tagcttcatg    660
ctgtccatct ctgccgtggt gatgtcctat ctgcagaatc ctcagcccat gacgccccca    720
```

-continued tggtgatacc agcctagaag ggtcacattt tggaccctgt ctatccacta ggcctgggct 780
ttggctgcta aacctgctgc cttcagctgc catcctggac ttccctgaat gaggccgtct 840
cggtgccccc agctggatag agggaacctg gccctttcct agggaacacc ctaggcttac 900
ccctcctgcc tcccttcccc tgcctgctgc tgggggagat gctgtccatg tttctagggg 960
tattcatttg ctttctcgtt gaaacctgtt gttaataaag tttttcactc tgaaaaaaaa 1020
aaaaaaaaaa aaaaancncg aggggggcc cggaacccaa ttcsccggat agtgagt 1077

<210> SEQ ID NO 25
<211> LENGTH: 1205
<212> TYPE: DNA
<213> ORGANISM: Homo sapiens

<400> SEQUENCE: 25
cccacgcgtc cgcagaggca gggcaatagt ggagttctgg cttggccaag cagcctagaa 60
ctcaaagtcc atggcccctt ctgggcctgg agaaattgga tggttatagc accaggcagc 120
ccttgtgggt gggggacagc aaatgaggga cctctcttt ctctacactc tcctttggct 180
cccggagatc tggcaggccc tggctggagg cataagatta gatgaggttg agctgttgga 240
gaatgaagct gtgttgggag aagaaatgag gttgtaccgg aagatcaacg aggttgtgct 300
gtcagggaat gaggtggtac ttgggggcaa gtgaggctgc attattagat aaatgaggtt 360
gtactgtcag gggatgaagt gtacttgtag tagagatgac gtcctgctgg atcagtcggc 420
ttttgctcca tcagagaaca cagccacacc acaggaggaa ggagagtgtc cgactcagag 480
gataaatgag ggtgtcctgc tggataaatg agggggcccg tcaggtgaat ggagtgctgt 540
tagcaaatga ggttgtactt gctggataaa tgggactggt gtgctggata aatggggttg 600
tgctgtcagg tgaatgcatt actgctcgtg ggtgaagggc atcctgggaa taatgagggt 660
gtcctgctgg atagatgagc tgccaccacc aaatggatca gaccctgtcc atgaaggagg 720
caccatcagc aacgacgagg ttatcctgtt cccactgggg ctcctggagc gtcttctggc 780
ccaggggaaa ctcggtgtgt gccaccctgg gttatccaag tctctctggg gagcagggtg 840
gggggctggg gagggcaggc agctgcattg tgcaccgtgg gacctctcct tcaccccccaa 900 tggatgccct actcctctcc ctggcacccc tcagtgggtc agactgcttc ggacattctc 960
accccactgc ctgcttctca tcctgcctgt gtcttctttc tgcccagttt ggaaaagccc 1020
ctattatgtg tcagccactc tgcccagtct tatttaatct ccctataaca cagtattact 1080
cctccttgca catacacact ttctcttatt cattcatcca ttcattcatt tgacaaacat 1140
ttaagtgtct agtatgtacc aaacacatga ggtacagttt taaaaagaat aaaaaaaaaa 1200
aaaaa 1205

<210> SEQ ID NO 26
<211> LENGTH: 1674
<212> TYPE: DNA
<213> ORGANISM: Homo sapiens
<220> FEATURE:
<221> NAME/KEY: SITE
<222> LOCATION: (1663)
<223> OTHER INFORMATION: n equals a,t,g, or c

<400> SEQUENCE: 26
cccgagcagc tgagtccctt ccctgtcttt cactcttctg gcatcggtgg ttttacttct 60
tcgattgaac cctgcttcct cgaccccccct gggaggccgc cttcttcagg cgcctccctt 120

-continued

```
ctctccacga gctcgctctg acagctgagg aactggcaag atcctgctac ccagagggtg    180

aatgggtatc tttcccggaa taatcctaat ttttctaagg gtgaagtttg caacggcggc    240

cgtgattgta agcggagtaa gcaaacacct ccattgtatt agtcaccaga aaagtaccac    300

tgtaagtcat gagatgtctg gtctgaattg gaaacccttt gtatatggcg gccttgcctc    360

tatcgtggct gagtttggga ctttccctgt ggaccttacc aaaacacgac ttcaggttca    420

aggccaaagc attgatgccc gtttcaaaga gataaaatat agagggatgt tccatgcgct    480

gtttcgcatc tgtaaagagg aaggtgtatt ggctctctat tcaggaattg ctcctgcgtt    540

gctaagacaa gcatcatatg gcaccattaa aattgggatt taccaaagct tgaagcgctt    600

attcgtagaa cgtttagaag atgaaactct tttaattaat atgatctgtg ggtagtgtc    660

aggagtgata tcttccacta tagccaatcc caccgatgtt ctaaagattc gaatgcaggc    720

tcaaggaagc ttgttccaag ggagcatgat tggaagcttt atcgatatat accaacaaga    780

aggcaccagg ggtctgtgga ggggtgtggt tccaactgct cagcgtgctg ccatcgttgt    840

aggagtagag ctaccagtct atgatattac taagaagcat ttaatattgt caggaatgat    900

gggcgataca attttaactc acttcgtttc cagctttaca tgtggtttgg ctggggctct    960

ggcctccaac ccggttgatg tggttcgaac tcgcatgatg aaccagaggg caatcgtggg   1020

acatgtggat ctctataagg gcactgttga tggtatttta aagatgtgga aacatgaggg   1080

ctttttgca ctctataaag gattttggcc aaactggctt cggcttggac cctggaacat   1140

catttttttt attacatacg agcagctaaa gaggcttcaa atctaagaac tgaattatat   1200

gtgagcccag ccctgccagc ctttctactc ctttgccctt ttcccgtgtt ctaatgtatt   1260

ttgacaatgt tgtaagtgtt taccaagccg ttggtctcct aagggcctcc tgatggaaga   1320

acagtggggt ggttcaaagt tatttctatg tttgtgttac catgttaact tttccccgag   1380

agaaagtgtt aacattgaga ctctggcccc agattggtat cttctatgaa gatggatact   1440

gatgggtgac attgaaaacg gcctgctttc caaatgtggt taaatgtaat tggttagccc   1500

cagacttggg ctagagcaga aggcataggc cagggtggtt attgctatat gtgttacaga   1560

cctcggttct cattaaagta tttattggca gaatcaaaaa aaaaaaaaaa aaaaaaaaaa   1620

aaactcgagg gggggcccgg tacccaattc gccctatggt gantcgaatg ggct         1674
```

<210> SEQ ID NO 27
<211> LENGTH: 1965
<212> TYPE: DNA
<213> ORGANISM: Homo sapiens
<220> FEATURE:
<221> NAME/KEY: SITE
<222> LOCATION: (333)
<223> OTHER INFORMATION: n equals a,t,g, or c
<220> FEATURE:
<221> NAME/KEY: SITE
<222> LOCATION: (1961)
<223> OTHER INFORMATION: n equals a,t,g, or c

<400> SEQUENCE: 27

```
ggatcctcgc ggcggcggcg gtgcttacag cctgagaaga gcgtctcgcc cgggagcggc     60

ggcggccatc gagacccacc caaggcgcgt ccccctcggc ctcccagcgc tcccaagccg    120

cagcggccgc gcccccttcag ctagctcgct cgctcgctct gcttccctgc tgccggctgc    180

gcatggcgtt ggcgttggcg gcgctggcgg cggtcgagcc ggcctgcggc agccggtacc    240

agcagttgca gaatgaagaa gagtctggag aacctgaaca ggctgcaggt gatgctcctc    300

caccttacag cagcatttct gcagagagcg cancatattt tgactacaag gatgagtctg    360
```

-continued

```
ggtttccaaa gcccccatct tacaatgtag ctacaacact gcccagttat gatgaagcgg    420
agaggaccaa ggctgaagct actatccctt tggttcctgg gagagatgag gattttgtgg    480
gtcgggatga ttttgatgat gctgaccagc tgaggatagg aaatgatggg attttcatgt    540
taactttttt catggcattc ctctttaact ggattgggtt tttcctgtct ttttgcctga    600
ccacttcagc tgcaggaagg tatggggcca tttcaggatt tggtctctct ctaattaaat    660
ggatcctgat tgtcaggttt tccacctatt tccctggata ttttgatggt cagtactggc    720
tctggtgggt gttccttgtt ttaggctttc tcctgtttct cagaggattt atcaattatg    780
caaaagttcg gaagatgcca gaaactttct caaatctccc caggaccaga gttctcttta    840
tttattaaag atgttttctg gcaaaggcct tcctgcattt atgaattctc tctcaagaag    900
caagagaaca cctgcaggaa gtgaatcaag atgcagaaca cagaggaata atcacctgct    960
ttaaaaaaat aaagtactgt tgaaaagatc atttctctct atttgttcct aggtgtaaaa   1020
ttttaatagt taatgcagaa ttctgtaatc attgaatcat tagtggttaa tgtttgaaaa   1080
agctcttgca atcaagtctg tgatgtatta ataatgcctt atatattgtt tgtagtcatt   1140
ttaagtagca tgagccatgt ccctgtagtc ggtagggggc agtcttgctt tattcatcct   1200
ccatctcaaa atgaacttgg aattaaatat tgtaagatat gtataatgct ggccatttta   1260
aaggggtttt ctcaaaagtt aaacttttgt tatgactgtg tttttgcaca taatccatat   1320
ttgctgttca agttaatcta gaaatttatt caattctgta tgaacacctg gaagcaaaat   1380
catagtgcaa aaatacattt aaggtgtggt caaaaataag tctttaattg gtaaataata   1440
agcattaatt ttttatagcc tgtattcaca attctgcggt accttattgt acctaaggga   1500
ttctaaaggt gttgtcactg tataaaacag aaagcactag gatacaaatg aagcttaatt   1560
actaaaatgt aattcttgac actctttcta taattagcgt tcttcacccc cacccccacc   1620
cccacccccc ttattttcct tttgtctcct ggtgattagg ccaaagtctg ggagtaagga   1680
gaggattagg tacttaggag caaagaaaga agtagcttgg aactttgag atgatcccta    1740
acatactgta ctacttgctt ttacaatgtg ttagcagaaa ccagtgggtt ataatgtaga   1800
atgatgtgct ttctgcccaa gtggtaattc atcttggttt gctatgttaa aactgtaaat   1860
acaacagaac attaataaat atctcttgtg tagcaccttt aaaaaaaaaa aaaaaaaaaa   1920
aaaaaaaaaa aaaaaaaaaa aaaaaaaaaa aaaaaaaaaa naaaa                   1965
```

```
<210> SEQ ID NO 28
<211> LENGTH: 1863
<212> TYPE: DNA
<213> ORGANISM: Homo sapiens

<400> SEQUENCE: 28

gactaggccg cgagcttagt cctgggagcc gcctccgtcg ccgccgtcag agccgcccta     60
tcagattatc ttaacaagaa aaccaactgg aaaaaaaaat gaaattcctt atcttcgcat    120
ttttcggtgg tgttcacctt ttatccctgt gctctgggaa agctatatgc aagaatggca    180
tctctaagag gacttttgaa gaaataaaag aagaaatagc cagctgtgga gatgttgcta    240
aagcaatcat caacctagct gtttatggta aagcccagaa cagatcctat gagcgattgg    300
cacttctggt tgatactgtt ggacccagac tgagtggctc caagaaccta gaaaaagcca    360
tccaaattat gtaccaaaac ctgcagcaag atgggctgga gaaagttcac ctggagccag    420
tgagaatacc ccactgggag aggggagaag aatcagctgt gatgctggag ccaagaattc    480
```

-continued

```
ataagatagc catcctgggt cttggcagca gcattgggac tcctccagaa ggcattacag    540
cagaagttct ggtggtgacc tctttcgatg aactgcagag aagggcctca gaagcaagag    600
ggaagattgt tgtttataac caaccttaca tcaactactc aaggacggtg caataccgaa    660
cgcaggggc ggtggaagct gccaaggttg gggctttggc atctctcatt cgatccgtgg    720
cctccttctc catctacagt cctcacacag gtattcagga ataccaggat ggcgtgccca    780
agattccaac agcctgtatt acggtggaag atgcagaaat gatgtcaaga atggcttctc    840
atgggatcaa aattgtcatt cagctaaaga tgggggcaaa gacctaccca gatactgatt    900
ccttcaacac tgtagcagag atcactggga gcaaatatcc agaacaggtt gtactggtca    960
gtggacatct ggacagctgg gatgttgggc agggtgccat ggatgatggc ggtggagcct   1020
ttatatcatg ggaagcactc tcacttatta aagatcttgg gctgcgtcca aagaggactc   1080
tgcggctggt gctctggact gcagaagaac aaggtggagt tggtgccttc cagtattatc   1140
agttacacaa ggtaaatatt tccaactaca gtctggtgat ggagtctgac gcaggaacct   1200
tcttacccac tgggctgcaa ttcactggca gtgaaaaggc cagggccatc atggaggagg   1260
ttatgagcct gctgcagccc ctcaatatca ctcaggtcct gagccatgga gaagggacag   1320
acatcaactt ttggatccaa gctggagtgc ctggagccag tctacttgat gacttataca   1380
agtatttctt cttccatcac tcccacggag acaccatgac tgtcatggat ccaaagcaga   1440
tgaatgttgc tgctgctgtt tgggctgttg tttcttatgt tgttgcagac atggaagaaa   1500
tgctgcctag gtcctagaaa cagtaagaaa gaaacgtttt catgcttctg gccaggaatc   1560
ctgggtctgc aactttggaa aactcctctt cacataacaa tttcatccaa ttcatcttca   1620
aagcacaact ctatttcatg ctttctgtta ttatctttct tgatactttc caaattctct   1680
gattctagaa aaaggaatca ttctcccctc cctcccacca catagaatca acatatggta   1740
gggattacag tgggggcatt tctttatatc acctcttaaa aacattgttt ccactttaaa   1800
agtaaacact taataaattt ttggaagatc tctgaaaaaa aaaaaaaaaa aaagggcggc   1860
cgc                                                                 1863
```

<210> SEQ ID NO 29
<211> LENGTH: 1626
<212> TYPE: DNA
<213> ORGANISM: Homo sapiens

<400> SEQUENCE: 29

```
cccacgcgtc cggagccggg agccggtcgc gggggctccg ggctgtggga ccgctgggcc     60
cccagcgatg gcgaccctgt ggggaggcct tcttcggctt ggctccttgc tcagcctgtc    120
gtgcctggcg ctttccgtgc tgctgctggc gcactgtcag acgccgccaa gtgattgcct    180
tcatgttgtg gagcccatgc ctgtgcgggg gcctgatgta gaagcatact gtctacgctg    240
tgaatgcaaa tatgaagaaa gaagctctgt cacaatcaag gttaccatta taatttatct    300
ctccattttg ggccttctac ttctgtacat ggtatatctt actctggttg agcccatact    360
gaagaggcgc ctctttggac atgcacagtt gatacagagt gatgatgata ttggggatca    420
ccagcctttt gcaaatgcac acgatgtgct agcccgctcc cgcagtcgag ccaacgtgct    480
gaacaaggta gaatatgcac agcagcgctg gaagcttcaa gtccaagagc agcgaaagtc    540
tgtctttgac cggcatgttg tcctcagcta attgggaatt gaattcaagg tgactagaaa    600
gaaacaggca gacaactgga aagaactgac tgggttttgc tgggtttcat tttaatacct    660
tgttgatttc accaactgtt gctggaaatt caaaactgga agcaaaaact tgcttgattt    720
```

-continued tttttttcttg ttaacgtaat aatagagaca tttttaaaag cacacagctc aaatcagcca 780
ataatctttt cctattgtga cttttactaa taaaaataaa tctgcctgta aattatcttg 840
aagtccttta cctggaacaa gcactctctt tttcaccaca tagttttaac ttgactttca 900
agataatttt cagggttttt gttgttgttg ttttttgttt gtttgttttg gtgggagagg 960
ggagggatgc ctgggaagtg gttaacaact tttttcaagt cactttacta aacaaacttt 1020
tgtaaataga ccttaccttc tattttcgag tttcatttat attttgcagt gtagccagcc 1080
tcatcaaaga gctgacttac tcatttgact tttgcactga ctgtattatc tgggtatctg 1140
ctgtgtctgc acttcatggt aaacgggatc taaaatgcct ggtggctttt cacaaaaagc 1200
agattttctt catgtactgt gatgtctgat gcaatgcatc ctagaacaaa ctggccattt 1260
gctagtttac tctaaagact aaacatagtc ttggtgtgtg tggtcttact catcttctag 1320
tacctttaag gacaaatcct aaggacttgg acacttgcaa taaagaaatt ttattttaaa 1380
cccaagcctc cctggattga taatatatac acatttgtca gcatttccgg tcgtggtgag 1440
aggcagctgt ttgagctcca atgtgtgcag ctttgaacta gggctggggt tgtgggtgcc 1500
tcttctgaaa ggtctaacca ttattggata actggctttt ttcttcctct ttggaatgta 1560
acaataaaaa taatttttga aacatcaaaa aaaaaaaaaa aaaaaaaaaa aaaaaaaaaa 1620
aaaaaa 1626

<210> SEQ ID NO 30
<211> LENGTH: 605
<212> TYPE: DNA
<213> ORGANISM: Homo sapiens

<400> SEQUENCE: 30
ccacgcgtcc gcccacgcgt ccgggaaatg accttggaga ttgtagcaga gagtgagcat 60
gaggagcggc ctgctggcca gggccgggat gagcccaaca tgaaccctaa gcttgaggac 120
ccaaggcgcc ccgacacctc cttcctgtgg tttacctccc catacaagac catgaagttc 180
atcctgtggc ggcgtttccg gtgggccatc atcctcttca tcatcctctt catcctgctg 240
ctgttcctgg ccatcttcat ctacgccttc ccgaactatg ctgccatgaa gctggtgaag 300
cccttcagct gaggactctc ctgccctgta gaaggggccg tggggtcccc tccagcatgg 360
gactggcctg cctcctccgc ccagctcggc gagctcctcc agacctccta ggcctgattg 420
tcctgccagg gtgggcagac agacagatgg accggcccac actcccagag ttgctaacat 480
ggagctctga gatcacccca cttccatcat ttccttctcc cccaacccaa cgctttttttg 540 gatcagctca gacatatttc agtataaaac agttggaacc acaaaaaaaa aaaaaaaaaa 600
aaaaa 605

<210> SEQ ID NO 31
<211> LENGTH: 931
<212> TYPE: DNA
<213> ORGANISM: Homo sapiens

<400> SEQUENCE: 31
gagagtgcct aagcgggggt gaaagaggac gtgttaccca ctgccatgca ccaggactgg 60
ctgtgtaacc ttgggtggcc cctgctgtct ctctgggctg cagagtctgc cccacatgtg 120
gccatggcct ctgcaactgc tcagctctgg tccaggccct gtggcaggac acacatggtg 180
agcctagccc tgggacatca ggagactggg ctctggctct gttcggcctt tgggtgtgtg 240

-continued

```
gtggattctc cctgggcctc agtgtgccca tctgtaaagg ggcagctgac agtttgtggc    300

atcttgccaa gggtccctgt gtgtgtgtat gtgtgtgcat gtgtgcgtgt ctccatgtgc    360

gtccatattt aacatgtaaa aatgtccscc crckcgtccg cccaaacatg ttgtacattt    420

caccatggcc ccctcatcat agcaataaca ttcccactgc caggggttct tgagccagcc    480

aggccctgcc agtggggaag gaggccaagc agtgcctgcc tatgaaattt caacttttcc    540

tttcatacgt ctttattacc caagtcttct cccgtccatt ccagtcaaat ctgggctcac    600

tcaccccagc gagctctcaa atccctctcc aactgcctaa ggccctttgt gtaaggtgtc    660

ttaatactgt cctttttttt tttttaacag tgttttgtag atttcagatg actatgcaga    720

ggcctggggg acccctggct ctgggccggg cctggggctc cgaaattcca aggcccagac    780

ttgcgggggg tgggggggta tccagaattg gttgtaaata ctttgcatat tgtctgatta    840

aacacaaaca gacctcaaaa aaaaaaaaaa aaaaaaaaaa aaaaaaaaaa aaaaaaaaaa    900

aaaaaaaaaa aaaaaaaaaa aaagggcggc c                                   931
```

<210> SEQ ID NO 32
<211> LENGTH: 1407
<212> TYPE: DNA
<213> ORGANISM: Homo sapiens

<400> SEQUENCE: 32

```
gaattcggca cgagggcagg ctcagaagac gatgcggggc tgtgtgccgg ccttcttgct     60

gcatgtactc agcctcagga gagcttgctg cacccaggcc gcccaggtct tcacagcaca    120

actgcctgga aggcaggttg cgagaaggag aggcggatgg catgagcagc aaggggggacc    180

gatgctgtgc agctcacacc actccagaac ctgacaaggc accagcagga ccccttgcca    240

ggagcatgtc tgtgcagcag tgtttttgcc cctgcacatt ccagaagccc tcatgggaag    300

ggatgcagcc aggcagactc ctgccagatg gggcaggtag tttattcaaa gagaactctg    360

tatcccatag gcccaggctc tcctttcgct tggcgtgggc tttgctggcc cagtgtgtgc    420

tcctggctca gcagaaacat ccatttgagt tggcatccct gtagggatcc cagagcgttg    480

taagccttct tgtgattggt agggatggct gtggggtggc ttccaggagg gggccaccat    540

tgccgcatct acttctagac tcccaaagga gcccaggctc aggcaggcct ggcccagagt    600

cacgctggca accacgagtt tgggaagcag tcgtattctc tctctctctc tctctctctc    660

agtatccatg acaggtatga aacatattgt ctctttataa atgtcatttt acaaattatg    720

tgattatctg gaagctctaa gatgagagca aatgcctgat cactctggcc aaatgtcaga    780

tactaaagcc cattcttggc cggcatgtt ggctcccgcc kgtaatccca gcactttggg    840

aagcccaagt gggtgaatca cctgaggtca ggagttcaag accagcctga ccaacatggg    900

gataccccgt ctctactaaa aatacaagcc gggcgtggtg gcgcatgcct gtaatcccag    960

ctactcagga ggctgaggca ggaaaatcac ttgaactcgg gaggcagagg ttgcagtgag   1020

ctgagatcgc gccattgcac tccagcctgg gtgacagagc aagactctgt ctcataaata   1080

aatacaaagc ccattcttcc agagtcttgt gccttaaata aaacacacct ctctgctgtg   1140

ggaagactgt gcaatggcac agccgcagag cttggtttgg gaggttgaag tgctctgggg   1200

agaattcgta gatcatcctc agaaaagcct tgccctggtg ttctaccaga aaaacgtctc   1260

ccaatcaccc aggaaagctg tccacagtag tccccccttta tccacggtgt cactttccat   1320

gggttcagtt atctgcggtc aaccacggtc tgacaatatt aaatggaaaa ttcttcaaac   1380

agttaaaaaa aaaaaaaaaa aactcga                                       1407
```

-continued

<210> SEQ ID NO 33
<211> LENGTH: 1526
<212> TYPE: DNA
<213> ORGANISM: Homo sapiens

<400> SEQUENCE: 33

```
ggcacgagaa aaaaccttca ggcggcccat gggtatgccc aagaggacag agaacgaatg     60
cacagaaata ttgtcagcct tgcacagaat ctcctgaact ttatgattgg ctctatcttg    120
gatttatggc aatgcttcct ctggttttac attggttctt cattgaatgg tactcgggga    180
aaaagagttc cagcgcactt ttccaacaca tcactgcatt atttgaatgc agcatggcag    240
ctattatcac cttacttgtg agtgatccag ttggtgttct ttatattcgt tcatgtcgag    300
tattgatgct ttctgactgg tacacgatgc tttacaaccc aagtccagat tacgttacca    360
cagtacactg tactcatgaa gccgtctacc cactatatac cattgtattt atctattacg    420
cattctgctt ggtattaatg atgctgctcc gacctcttct ggtgaagaag attgcatgtg    480
ggttagggaa atctgatcga tttaaaagta tttatgctgc actttacttc ttcccaattt    540
taaccgtgct tcaggcagtt ggtggaggcc ttttatatta cgccttccca tacattatat    600
tagtgttatc tttggttact ctggctgtgt acatgtctgc ttctgaaata gagaactgct    660
atgatcttct ggtcagaaag aaaagactta ttgttctctt cagccactgg ttacttcatg    720
cctatggaat aatctccatt tccagagtgg ataaacttga gcaagatttg ccccctttgg    780
ctttggtacc tacaccagcc ctttttttact tgttcactgc aaaatttacc gaaccttcaa    840
ggatactctc agaaggagcc aatggacact gagtgtagac atgtgaaatg ccaaaaacct    900
gagaagtgct cctaataaaa aagtaaatca atcttaacag tgtatgagaa ctattctatc    960
atatatggga acaagattgt cagtatatct taatgtttgg gtttgtcttt gttttgttta   1020
tggttagact tacagacttg gaaaatgcaa aactctgtaa tactctgtta cacagggtaa   1080
tattatctgc tacactggaa ggccgctagg aagcccttgc ttctctcaac agttcagctg   1140
ttctttaggg caaaatcatg tttctgtgta cctagcaatg tgttcccatt ttattaagaa   1200
aagctttaac acgtgtaatc tgcagtcctt aacagtggcg taattgtacg tacctgttgt   1260
gtttcagttt gtttttcacc tataatgaat tgtaaaaaca aacatacttg tggggtctga   1320
tagcaaacat agaaatgatg tatattgttt tttgttatct atttattttc atcaatacag   1380
tattttgatg tattgcaaaa atagataata atttatataa caggttttct gtttatagat   1440
tggttcaaga tttgtttgga ttattgttcc tgtaaagaaa acaataataa aaagcttacc   1500
tacataaaaa aaaaaaaaaa aaaaaa                                         1526
```

<210> SEQ ID NO 34
<211> LENGTH: 1737
<212> TYPE: DNA
<213> ORGANISM: Homo sapiens
<220> FEATURE:
<221> NAME/KEY: SITE
<222> LOCATION: (1674)
<223> OTHER INFORMATION: n equals a,t,g, or c
<220> FEATURE:
<221> NAME/KEY: SITE
<222> LOCATION: (1731)
<223> OTHER INFORMATION: n equals a,t,g, or c

<400> SEQUENCE: 34

```
gtcgacccac gcgtccgccc acgcgtccgc ccacgcgtcc ggtttataaa cagaagttta     60
```

-continued

```
aacttgtaag cttaagcttc cgtttataaa cagaagttta aaattatagg tcctgtttaa    120

cattcagctc tgttaactca ctcatctttt tgtgttttta cactttgtca agatttcttt    180

acatattcat caatgtctga agaagttact tatgcagatc ttcaattcca gaactccagt    240

gagatggaaa aaatcccaga aattggcaaa tttggggaaa aagcacctcc agctccctct    300

catgtatggc gtccagcagc cttgtttctg actcttctgt gccttctgtt gctcattgga    360

ttgggagtct tggcaagcat gtttcatgta actttgaaga tagaaatgaa aaaaatgaac    420

aaactacaaa acatcagtga agagctccag agaaatattt ctctacaact gatgagtaac    480

atgaatatct ccaacaagat caggaacctc tccaccacac tgcaaacaat agccaccaaa    540

ttatgtcgtg agctatatag caaagaacaa gagcacaaat gtaagccttg tccaaggaga    600

tggatttggc ataaggacag ctgttatttc ctaagtgatg atgtccaaac atggcaggag    660

agtaaaatgg cctgtgctgc tcagaatgcc agcctgttga agataaacaa caaaaatgca    720

ttggaattta taaaatccca gagtagatca tatgactatt ggctgggatt atctcctgaa    780

gaagattcca ctcgtggtat gagagtggat aatataatca actcctctgc ctgggttata    840

agaaacgcac ctgacttaaa taacatgtat tgtggatata taaatagact atatgttcaa    900

tattatcact gcacttataa acaaagaatg atatgtgaga agatggccaa tccagtgcag    960

cttggttcta catattttag ggaggcatga ggcatcaatc aaatacattg aaggagtgta   1020

kggggtgggg gttctaggct ataggtaaat ttaaatattt tctggttgac aattagttga   1080

gtttgtctga agacctggga ttttatcatg cagatgaaac atccaggtag caagcttcag   1140

agagaataga ctgtgaatgt taatgccaga gaggtataat gaagcatgtc ccacctccca   1200

ctttccatca tggcctgaac cctggaggaa gaggaagtcc attcagatag tgtgggggggc   1260

cttcgaattt tcattttcat ttacgttctt ccccttctgg ccaagatttg ccagaggcaa   1320

catcaaaaac cagcaaattt taattttgtc ccacagcgtt gctagggtgg catggctccc   1380

catctcgggt ccatcctata cttccatggg actccctatg gctgaaggcc ttatgagtca   1440

aaggacttat agccaattga ttgttctagg ccaggtaaga atggatatgg acatgcattt   1500

attacctctt aaaattatta ttttaagtaa aagccaataa acaaaaacga aaaggcaagt   1560

tacgagactg acttattttt aacttctgtg tgttgagcta ctgtaagctt ggcttttgtt   1620

aaagacatac agcaattagc tatgcaaaca taagcattgt tctgaaaaaa aatntataga   1680

tagatatgtt tatctcccat aactcataac tggggagtat tataccccgg nggcttt      1737
```

<210> SEQ ID NO 35
<211> LENGTH: 2242
<212> TYPE: DNA
<213> ORGANISM: Homo sapiens

<400> SEQUENCE: 35

```
tcgacccacg cgtccgggct gccatggcgg cggcgggccg gctcccgagc tcctgggccc     60

tcttctcgcc gctcctcgca gggcttgcac tactgggagt cgggccggtc ccagcgcggg    120

cgctgcacaa cgtcacggcc gagctctttg gggccgaggc ctggggcacc cttgcggctt    180

tcggggacct caactccgac aagcagacgg atctcttcgt gctgcgggaa agaaatgact    240

taatcgtctt tttggcagac cagaatgcac cctattttaa acccaaagta aaggtatctt    300

tcaagaatca cagtgcattg ataacaagtg tagtccctgg ggattatgat ggagattctc    360

aaatggatgt ccttctgaca tatcttccca aaaattatgc caagagtgaa ttaggagctg    420

ttatcttctg ggacaaaat caaacattag atcctaacaa tatgaccata ctcaatagga    480
```

-continued

```
cttttcaaga tgagccacta attatggatt tcaatggtga tctaattcct gatatttttg    540
gtatcacaaa tgaatccaac cagccacaga tactattagg agggaattta tcatggcatc    600
cagcattgac cactacaagt aaaatgcgaa ttccacattc tcatgcattt attgatctga    660
ctgaagattt tacagcagat ttattcctga cgacattgaa tgccaccact agtaccttcc    720
agtttgaaat atgggaaaat ttggatggaa acttytstgw magtacymta ttggaaaaac    780
ctcaaaatat gatggtggtt ggacagtcag catttgcaga ctttgatgga gatggacaca    840
tggatcattt actgccaggc tgtgaagata aaaattgcca aaagagtacc atctacttag    900
tgagatctgg gatgaagcag tgggttccag tcctacaaga tttcagcaat aagggcacac    960
tctggggctt tgtgccattt gtggatgaac agcaaccaac tgaaatacca attccaatta   1020
cccttcatat tggagactac aatatggatg gctatccaga cgctctggtc atactaaaga   1080
acacatctgg aagcaaccag caggcctttt tactggagaa cgtcccttgt aataatgcaa   1140
gctgtgaaga ggcgcgtcga atgtttaaag tctactggga gctgacagac ctaaatcaaa   1200
ttaaggatgc catggttgcc accttctttg acatttacga agatggaatc ttggacattg   1260
tagtgctaag taaaggatat acaaagaatg attttgccat tcatacacta aaaaataact   1320
ttgaagcaga tgcttatttt gttaaagtta ttgttcttag tggtctgtgt tctaatgact   1380
gtcctcgtaa gataacaccc tttggagtga atcaacctgg accttatatc atgtatacaa   1440
ctgtagatgc aaatgggtat ctgaaaaatg gatcagctgg ccaactcagc caatccgcac   1500
atttagctct ccaactacca tacaacgtgc ttggtttagg tcggagcgca aattttcttg   1560
accatctcta cgttggtatt ccccgtccat ctggagaaaa atctatacga aaacaagagt   1620
ggactgcaat cattccaaat tcccagctaa ttgtcattcc ataccctcac aatgtccctc   1680
gaagttggag tgccaaactg tatcttacac caagtaatat tgttctgctt actgctatag   1740
ctctcatcgg tgtctgtgtt ttcatcttgg caataattgg cattttacat tggcaggaaa   1800
agaaagcaga tgatagagaa aaacgacaag aagcccaccg gtttcatttt gatgctatgt   1860
gacttgcctt taatattaca taatggaatg gctgttcact tgattagttg aaacacaaat   1920
tctggcttga aaaaataggg gagattaaat attatttata aatgatgtat cccatggtaa   1980
ttattggaaa gtattcaaat aaatatggtt tgaatatgtc acaaggtctt ttttttttaaa   2040
gcactttgta tataaaaatt tggttctctct attctgtagt gctgtacatt tttgttcctt   2100
tgtggaatgt gttgcatgta ctccagtgtt tgtgtattta taatcttatt tgcatcatga   2160
tgatggaaaa agttgtgtaa ataaaaataa ttaaatgagc aggaaaaaaa aaaaaaaaaa   2220
aaaaaaaaaa aagggcggcc gc                                            2242
```

<210> SEQ ID NO 36
<211> LENGTH: 2235
<212> TYPE: DNA
<213> ORGANISM: Homo sapiens

<400> SEQUENCE: 36

```
gtaattcggc acgagggttc caccaacatg gagctctcgc agatgtcgsa gctcatgggg     60
ctgtcggtgt tgcttgggct gctggccctg atggcgacgg cggcggtasc gcgggggtgg    120
ctgcgcgcgg gggaggagag gagcggccgg cccgcctgcc aaaaagcaaa tggatttcca    180
cctgacaaat cttcgggatc caagaagcag aaacaatatc agcggattcg gaaggagaag    240
cctcaacaac acaacttcac ccaccgcctc ctggctgcag ctctgaagag ccacagcggg    300
```

-continued aacatatctt gcatggactt tagcagcaat ggcaaatacc tggctacctg tgcagatgat 360
cgcaccatcc gcatctggag caccaaggac ttcctgcagc gagagcaccg cagcatgaga 420
gccaacgtgg agctggacca cgccaccctg gtgcgcttca gccctgactg cagagccttc 480
atcgtctggc tggccaacgg ggacaccctc cgtgtcttca agatgaccaa gcgggaggat 540
gggggctaca ccttcacagc caccccagag gacttcccta aaaagcacaa ggcgcctgtc 600
atcgacattg gcattgctaa cacagggaag tttatcatga ctgcctccag tgacaccact 660
gtcctcatct ggagcctgaa gggtcaagtg ctgtctacca tcaacaccaa ccagatgaac 720
aacacacacg ctgctgtatc tccctgtggc agatttgtag cctcgtgtgg cttcacccca 780
gatgtgaagg tttgggaagt ctgctttgga aagaaggggg agttccagga ggtggtgcga 840
gccttcgaac taaagggcca ctccgcggct gtgcactcgt ttgctttctc caacgactca 900
cggaggatgg cttctgtctc caaggatggt acatggaaac tgtgggacac aratgtggaa 960
tacaagaaga agcaggaccc ctacttgctg aagacaggcc gctttgaaga ggcggcgggt 1020
gccgmgccgt gccgcctggc cctctccccc aacgcccagg tcttggcctt ggccagtggc 1080
agtagtattc atctctacaa tacccggcgg ggcgagaagg aggagtgctt tgagcgggtc 1140
catggcgagt gtatcgccaa cttgtccttt gacatcactg gccgctttct ggcctcctgt 1200
ggggaccggg cggtgcggct gtttcacaac actcctggcc accgagccat ggtggaggag 1260
atgcagggcc acctgaagcg ggcctccaac gagagcaccc gccagaggct gcagcagcag 1320
ctgacccagg cccaagagac cctgaagagc ctgggtgccc tgaagaagtg actctgggag 1380
ggcccggcgc agaggattga ggaggaggga tctggcctcc tcatggcact gctgccatct 1440
ttcctcccag gtggaagcct ttcagaagga gtctcctggt tttyttactg gtggccctgc 1500
ttcttcccat tgaaactact cttgtctact taggtctctc tcttcttgct ggctgtgact 1560
cctccctgac tagtggccaa ggtgcttttc ttcctcccag gcccagtggg tggaatctgt 1620
ccccacctgg cactgaggag aatggtagag aggagaggag agagagagag aatgtgattt 1680
ttggccttgt ggcagcacat cctcacaccc aaagaagttt gtaaatgttc cagaacaacc 1740
tagagaacac ctgagtacta agcagcagtt ttgcaaggat gggagactgg gatagcttcc 1800
catcacagaa ctgtgttcca tcaaaaagac actaagggat ttccttctgg gcctcagttc 1860
tatttgtaag atggagaata atcctctctg tgaactcctt gcaaagatga tatgaggcta 1920
agagaatatc aagtccccag gtctggaaga aaagtagaaa agagtagtac tattgtccaa 1980
tgtcatgaaa gtggtaaaag tgggaaccag tgtgctttga aaccaaatta gaaacacatt 2040
ccttgggaag gcaaagtttt ctgggacttg atcatacatt ttatatggtt gggacttctc 2100
tcttcgggag atgatatctt gtttaaggag acctcttttc agttcatcaa gttcatcaga 2160
tatttgagtg cccactctgt gcccaaataa atatgagctg gggattaaaa aaaaaaaaaa 2220
aaaaaaaaaa ctcga 2235

<210> SEQ ID NO 37
<211> LENGTH: 2971
<212> TYPE: DNA
<213> ORGANISM: Homo sapiens

<400> SEQUENCE: 37
gacgtgagga gcgttccatt tggccagtgg tgggcggttg ccacagctgg tttagggccc 60
cgaccactgg ggccccttgt caggaggaga cagcctcccg gcccggggag gacaagtcgc 120
tgccaccttt ggctgccgac gtgattccct gggacggtcc gtttcctgcc gtcagctgcc 180

-continued

```
ggccgagttg ggtctccgtg gttcaggccg gctcccctt cctggtctcc cttctcccgc    240
tgggccggtt tatcgggagg agattgtctt ccagggctag caattggact tttgatgatg    300
tttgacccag cggcaggaat agcaggcaac gtgatttcaa agctgggctc agcctctgtt    360
tcttctctcg tgtaatcgca aaacccattt tggagcagga attccaatca tgtctgtgat    420
ggtggtgaga aagaaggtga cacggaaatg ggagaaactc ccaggcagga acaccttttg    480
ctgtgatggc cgcgtcatga tggcccggca aaagggcatt ttctacctga ccctttttcct   540
catcctgggg acatgtacac tcttcttcgc ctttgagtgc cgctacctgg ctgttcagct    600
gtctcctgcc atccctgtat ttgctgccat gctcttcctt ttctccatgg ctacactgtt    660
gaggaccagc ttcagtgacc ctggagtgat tcctcgggcg ctaccagatg aagcagcttt    720
catagaaatg gagatagaag ctaccaatgg tgcggtgccc cagggccagc gaccaccgcc    780
tcgtatcaag aatttccaga taaacaacca gattgtgaaa ctgaaatact gttacacatg    840
caagatcttc cggcctcccc gggcctccca ttgcagcatc tgtgacaact gtgtggagcg    900
cttcgaccat cactgcccct gggtggggaa ttgtgttgga aagaggaact accgctactt    960
ctacctcttc atcctttctc tctccctcct cacaatctat gtcttcgcct tcaacatcgt   1020
ctatgtggcc ctcaaatctt tgaaaattgg cttcttggag acattgaaag aaactcctgg   1080
aactgttcta gaagtcctca tttgcttctt tacactctgg tccgtcgtgg gactgactgg   1140
atttcatact ttcctcgtgg ctctcaacca gacaaccaat gaagacatca aaggatcatg   1200
gacagggaag aatcgcgtcc agaatcccta cagccatggc aatattgtga agaactgctg   1260
tgaagtgctg tgtggcccct tgccccccag tgtgctggat cgaaggggta ttttgccact   1320
ggaggaaagt ggaagtcgac ctcccagtac tcaagagacc agtagcagcc tcttgccaca   1380
gagcccagcc cccacagaac acctgaactc aaatgagatg ccggaggaca gcagcactcc   1440
cgaagagatg ccacctccag agcccccaga gccaccacag gaggcagctg aagctgagaa   1500
gtagcctatc tatggaagag acttttgttt gtgtttaatt agggctatga gagatttcag   1560
gtgagaagtt aaacctgaga cagagagcaa gtaagctgtc ccttttaact gtttttcttt   1620
ggtctttagt cacccagttg cacactggca ttttcttgct gcaagctttt ttaaatttct   1680
gaactcaagg cagtggcaga agatgtcagt cacctctgat aactggaaaa atgggtctct   1740
tgggccctgg cactggttct ccatggcctc agccacaggg tcccccttgga cccccctctct  1800
tccctccaga tcccagccct cctgcttggg gtcactggtc tcattctggg gctaaaagtt   1860
tttgagactg gctcaaatcc tcccaagctg ctgcacgtgc tgagtccaga ggcagtcaca   1920
gagacctctg gccaggggat cctaactggg ttcttggggt cttcaggact gaagaggagg   1980
gagagtgggg tcagaagatt ctcctggcca ccaagtgcca gcattgccca caaatccttt   2040
taggaatggg acaggtacct tccacttgtt gtatttatta gtgtagcttc tcctttgtct   2100
cccatccact ctgacaccta agccccactc ttttcccatt agatatatgt aagtagttgt   2160
agtagagata ataattgaca tttctcgtag actacccaga aactttttta atacctgtgc   2220
cattctcaat aagaatttat gagatgccag cggcatagcc cttcacactc tctgtctcat   2280
ctctcctcct ttctcattag cccctttttaa tttgtttttc cttttgactc ctgctcccat  2340
taggagcagg aatggcagta ataaaagtct gcactttggt catttctttt cctcagagga   2400
agcctgagtg ctcacttaaa cactatcccc tcagactccc tgtgtgaggc ctgcagaggc   2460
cctgaatgca caaatgggaa accaaggcac agagaggctc tcctctcctc tcctctcccc   2520
```

-continued cgatgtaccc tcaaaaaaaa aaaaaatgct aaccagttct tccattaagc ctcggctgag 2580
tgagggaaag cccagcactg ctgccctctc gggtaactca ccctaaggcc tcggcccacc 2640
tctggctatg gtaaccacac tgggggcttc ctccaagccc cgctcttcca gcacttccac 2700
cggcagagtc ccagagccac ttcaccctgg gggtgggctg tggcccccag tcagctctgc 2760
tcaggacctg ctctatttca gggaagaaga tttatgtatt atatgtggct atatttccta 2820
gagcacctgt gttttcctct ttctaagcca gggtcctgtc tggatgactt atgcggtggg 2880
ggagtgtaaa ccggaacttt tcatctattt gaaggcgatt aaactgtgtc taatgcaaaa 2940
aaaaaaaaaa aaaaaaaaaa aaaaaaaaaa a 2971

<210> SEQ ID NO 38
<211> LENGTH: 1163
<212> TYPE: DNA
<213> ORGANISM: Homo sapiens

<400> SEQUENCE: 38
ccacgcgtcc gccaagggtg ctgattaggg aatggttatg gactaggagt atcagtaaca 60
atggttagaa agtggctaac atttgttgag cacctgctgt gtgcctggcc ccggctggga 120
gccttcgtgc ccagagtgac cccgtctgaa tgcagttctt tgcctcattc aaactgggga 180
gtgggaggca gagctgcaca actcacaggt gccgagctca agactcactc ctgggtctgc 240
ctgggctggg ctgtgcttgt tgcccctgtg gccaacacac gcgcaccttt cacctgaaag 300
ccaggatccg cagaacgttc cccgaggagg tcattgtttg gcactatgat ttgtctcttc 360
ctaaaaaggt gatagagtta cactggagag agcagcatcc aggtgcagca gggatgggcc 420
tggggctcac gggcaggggc tctgtgtccg gctggggcct ggggtcctgc gctgcacctg 480
tgtgtcagaa gcactcagta aatctttgct gatgaaggat gacaggatat aggacatgat 540
gcttgctgct gcattgcctg caatcctgga tgaatgccca ggttggcttt gctccccgtc 600
gggtggatgt gacgttagct gtgatgttag gtccctggct ttaaaatacg acggaactgg 660
gaattgaggg agcagttggg gcagaaagga cagccccgca gaggcctgga gctgagcagt 720
gcgggcgacc caggagcagt gagtgcttcc gtcacagcct tcatcgcacc ctgtggtcct 780
cataaagggg atggaatcta cgaatttagt tttcccagcc tccttaaaaa ctcattcatg 840
ccaggggcag tggctcacac ctgaaatccc accactttgg gaggctgagg caggctgatt 900
acttgaggtc aggagtttga gaccagccta gccaacatgg tgaaaccccg tgtctactca 960
aagtacaaaa aaaaaaatta gtcagacgtg gtgtcacgca cctgtaatcc cagctctttg 1020
ggaggctgag gcaggagaat cacttgaacc caggaggcag aggttatagt gagccagtat 1080
tgcgccactg acctccatct gggcaataga gtgagaccct gtctcaaaaa aaaaaaaaaa 1140
aaaaaaaaaa aaaaaaaaaa aaa 1163

<210> SEQ ID NO 39
<211> LENGTH: 1932
<212> TYPE: DNA
<213> ORGANISM: Homo sapiens
<220> FEATURE:
<221> NAME/KEY: SITE
<222> LOCATION: (1624)
<223> OTHER INFORMATION: n equals a,t,g, or c

<400> SEQUENCE: 39
ggcacgagcc aggcccctgg gccgggcgct gaggcgggcc cctctgggca gggcccgggc 60
ggggctgggt gggccgcccc tgctgctgcc gtccatgctg atgtttgcgg tgatcgtggc 120

-continued

```
ctccagcggg ctgctgctca tgatcgagcg gggcatcctg gccgaratga agcccctgcc    180
cctgcacccg cccggccgcg arggcacagc ctggcgcggg aaagccccca agcctggggg    240
cctgtccctc agggctgggg acgcggactt gcaagtgcgg caggacgtcc ggaacaggac    300
cctgcgggcg gtgtgcggac agccaggcat gccccgggac ccctgggact tgccggtggg    360
gcagcggcgc accctgctgc gccamatcct cgtaagtgac cgttaccgct tcctctactg    420
ctacgtcccc aaggtggcct gctctaactg gaagcgggtg atgaaggtgc tggcaggcgt    480
cctggacagc gtggacgtcc gcctcaagat ggaccaccgc agtgacctgg tgttcctggc    540
cgacctgcgg cctgaggaga ttcgctaccg cctgcagcac tactttaagt tcctgtttgt    600
gcgggagccc ttggaacgcc tcctctctgc ctaccgcaac aagtttggcg agatccgaga    660
gtaccagcaa cgctatgggg ctgagatagt gaggcggtac agggctggag cggggcccag    720
ccctgcaggc gacgatgtca cattccccga gttcctgaga tacctggtgg atgaggaccc    780
tgagcgcatg aatgagcatt ggatgcccgt gtaccacctg tgccagcctt gtgccgtgca    840
ctatgacttt gtgggctcct atgagaggct ggaggctgat gcaaatcagg tgctggagtg    900
ggtacgggca ccacctcacg tccgatttcc agctcgccag gcctggtacc ggccagccag    960
ccccgaaagc ctgcattacc acttgtgcag tgcccccggg gccctgctgc aggatgtgct   1020
gcctaagtat atcctggayt tytccctctt tgcctaccca ctgcctaatg tcaccaagga   1080
ggcgtgtcag cagtgaccat gggtgtgggg ccagcagctg gtggggactg gtttcaacgc   1140
cagctttctg tgcttctgcc tgtcattcgg agaaactctg gctctggggc ttggggcttc   1200
tcaggatcct ggatggcaga gactgccctc agaarttcct tgtccagggt gggcacccac   1260
agtgactcag aggacagggc taggcaggag acctgctgct cctcattggg gggatctctt   1320
ggggggcaga caccagtttg ccaatgaagc aacacatctg atctaaagac tggctccaga   1380
ccccgggctg ccaggattat gcagtccact tggtctacct taatttaacc tgtggccaaa   1440
ctcagagatg gtaccagcca ggggcaagca tgaccagagc cagggaccct gtggctctga   1500
tcccccattt atccacccca tgtgcctcag gactagagtg agcaatcata ccttataaat   1560
gacttttgtg cctttctgct ccagtctcaa aatttcctac acctgccagt tctttacatt   1620
tttnccaagg aaaggaaaac ggaagcaggg ttcttgcctg gtagctccag gacccagctc   1680
tgcaggcacc caaagaccct ctgtgcccag cctcttcctt gagttctcgg aacctcctcc   1740
ctaattctcc cttccttccc cacaaggcmt ttgaggttgt gactgtggct ggtatatctg   1800
gctgccattt ttctgatgca tttatttaaa atttgtactt tttgatagaa cccttgtaag   1860
ggctttgttt tcctaatagc tgactttttta ataaagcagt tttatataaa aaaaaaaaaa   1920
aaaaaaaaaa aa                                                       1932
```

<210> SEQ ID NO 40
<211> LENGTH: 881
<212> TYPE: DNA
<213> ORGANISM: Homo sapiens

<400> SEQUENCE: 40

```
gaattcggca cgagggaacc cagaagatgc tgcctctcct gatcatctgt ctcctgcctg     60
ccattgaagg gaagaactgc ctccgctgct ggccagaact gtctgccttg atagactatg    120
acctgcagat cctctgggtg accccagggc cacccacaga actttctcaa agtattcact    180
ccttgttcct agaggataat aattttctca aaccctggta ccttgatcgt gaccatttgg    240
```

-continued

```
aagaagaaac agccaaattc ttcactcaag tacaccaagc cattaaaacg ttacgagatg    300

ataaaacagt acttctggaa gagatctaca cgcacaagaa tctctttact gagaggctga    360

ataagatatc tgatgggctg aaggagaagg gagccccacc cytctccatg aatgccttcc    420

cggctccatc tcctacttgc accccagaac cccttggctc tgtctgcctc cccagcacct    480

cagtttctct accttctcac ctccctggca gcctgcaatg agtcctgtgc caggaaccgg    540

cggacctccc tgtgggctgt gagtctcagc agtgctctac tcctggccat agctggagat    600

gtttctttta ctggcaaagg aagaaggagg cagtaaagga acagggcagc ccgcatgtct    660

tccagaagtg aacagaggcc gcagctacca ccgtcacaaa gttcactcat ctctgggtcc    720

cggtgacccc atccccccat accctccatc ctgggtcctg gggccccaaa gctctgaggc    780

ctaggagact gcgctgtctc gtggtttgcc tactcctaca cctttgtaaa gagtctcttc    840

attaaaaccc ctcttcataa aaaaaaaaaa aaaaaactcg a                        881
```

```
<210> SEQ ID NO 41
<211> LENGTH: 1932
<212> TYPE: DNA
<213> ORGANISM: Homo sapiens
<220> FEATURE:
<221> NAME/KEY: SITE
<222> LOCATION: (2)
<223> OTHER INFORMATION: n equals a,t,g, or c
<220> FEATURE:
<221> NAME/KEY: SITE
<222> LOCATION: (1022)
<223> OTHER INFORMATION: n equals a,t,g, or c

<400> SEQUENCE: 41

cncggcgcgg ctcggctcat gcccccgggc gcggggcaca caggccggcc ggcagccgct     60

gggaaatagg cccccggggg cggtggcggc ggcggggcca tggcgcggag accccgggcg    120

ccggccgcct ccggggagga gttctccttc gtcagcccgc tggtgaaata cctgctcttc    180

ttcttcaaca tgctcttctg ggtgatttcc atggtgatgg tggctgtggg tgtctacgct    240

cggctaatga agcatgcaga agcagcccta gcctgcctgg cagtggaccc tgccatcctg    300

ctgatcgtgg tgggtgtcct catgttcctg ctcaccttct gtggctgcat tgggtccctc    360

cgcgagaaca tctgcctcct gcagacgttc tccctctgcc tcaccgctgt gttcctgctg    420

cagctggccg ctgggatcct gggcttcgtc ttctcagaca aggctcgagg gaaagtgagt    480

gagatcatca acaatgccat tgtgcactac cgagatgact tggatctgca gaacctcatt    540

gattttggcc agaaaaagtt tagctgctgt ggagggattt cctacaagga ctggtctcag    600

aacatgtatt tcaactgctc agaagacaac cccagtcgag agcgctgctc tgtgccttac    660

tcctgttgct tgcctactcc tgaccaggca gtgatcaaca ctatgtgtgg ccaaggtatg    720

caggcctttg actacttgga agctagcaaa gtcatctaca ccaatggctg tattgacaag    780

ttggtcaact ggatacacag caacctattc ttacttggtg gtgtggctct aggcctggcc    840

atcccccagc tggtgggaat tctgctgtcc cagatcctag tgaatcagat caaagatcag    900

atcaagctac agctctacaa ccagcagcac cgggctgacc catggtactg agaatccatc    960

ctgcacctcc tcaccatgga aactggcaag cctcataaac gaacagcagt gggtgctgaa   1020

ancagcacca aatggagatt tggattccag ccccccagtg acagcccagt gggaagaagc   1080

aaactccaga tgggcagaag gcagggtgca caggtggctc cagtctcagg aggatgcgcc   1140

tcctctcccc catcccagcc ctcagcattg tgccagagtg atacccttaa gtgtttgggt   1200

ttatgttttc agttttgttt gggaaacagc agttgcacag agagttgggg gtactgctgc   1260
```

-continued

```
tgccttttca ccgaggcact gccaccacca gctctascag ggatgctcct gagcttggcg   1320

gacatactta gatcctaacg tgccagtgag acctggctgt ggagagtagc actggcagcc   1380

ctgcctggac tccacttggc atgataccag ctccagaagg gaagggagtg gagcaggcag   1440

tgaggagaga gcctgggggt cggctgggga cagccgtatg tgctaggtag gagtggaggg   1500

agatatgttt accaaatgcc tgtcctgcca tcctcccagg tagtcagagt gagctacatc   1560

ctgccccgcc ttcatttcca tggaaacatg gcagctagga cacggggtac aacagcagcc   1620

aaattcttcc ccacctccct tacttcgaaa aaaagtttgg aaccctggtc cctatactct   1680

gcagtcagaa gtgggactga gccatacatg cccttgaatt cctccctgtc tggccctccc   1740

tctccagcaa gcagggtttt ctttaacttg gcagtgtgca gaggagaagt ggtaacaccc   1800

ccaccccatt cccctgcatc ggagctcagt attcctacag ggtaagaggt aggaatcttg   1860

ctgggacgag gggagccaga agtggcaata aaagcgtgtt gacctggaaa aaaaaaaaaa   1920

aagggcggcc gc                                                       1932


<210> SEQ ID NO 42
<211> LENGTH: 1164
<212> TYPE: DNA
<213> ORGANISM: Homo sapiens
<220> FEATURE:
<221> NAME/KEY: SITE
<222> LOCATION: (582)
<223> OTHER INFORMATION: n equals a,t,g, or c
<220> FEATURE:
<221> NAME/KEY: SITE
<222> LOCATION: (592)
<223> OTHER INFORMATION: n equals a,t,g, or c

<400> SEQUENCE: 42

ggcacgagct tgtgtgtcac cagcctcctg atctgccagg gtctgctctg ggttggcact     60

gaccagggtg tcatcgtcct gctgcccgtg cctcggctgg aaggcatccc caagatcaca    120

gggaaaggca tggtctcact caatgggcac tgtgggcctg tggccttcct ggctgtggct    180

accagcatcc tggcccctga catcctgcgg agtgaccagg aggaggctga ggggccccgg    240

gctgaggagg acaagccaga cgggcaggca cacgagccca tgcccgacag ccacgtgggc    300

cgagagctga cccgcaagaa gggcatcctc ttgcagtacc gcctgcgctc caccgcacac    360

ctcccgggcc cgctgctctc catgcgggag ccggcgcctg ctgatggcgc agctttggag    420

cacagcgagg aggacggctc catttacgag atggccgacg accccgacgt ctgggtgcgc    480

agccggccct gcgcccgcga cgcccaccgc aaggagattt gctctgtggc catcatctcg    540

gcgggcaggg ctaccgcaac tttggcagcg ctctgggcac antgggaagc angccccgtg    600

tggggagacg gacagcaccc tcctcatctg gcagtgccct tgatgctata gcgcctcccc    660

tctcccctca gagggcacag ctgcaggcct gaccaaggcc acgcccggct ctcgtgctct    720

aggacctgca cgggacttgt ggatgggcct ggactctcca gaaactactt gggccagagc    780

aaaggaaaac ctcttgtttt aaaaaaattt ttttcagagt gttttgggga ggagttttag    840

ggcttgggga gagggaggac acatctggag gaaatggcct tctttttaaa agcaaaaaac    900

acaaaacctc acaactgcct ggcaagccca gtatcacttg tttgggccct agcgggactc    960

caaggcagcc acacgcccct cctggaaggg tgtgtgcgtg tgagtgtgtg cgagtgtgtg   1020

ggctggtgtg tgaatatcta taaataagta tatatggtgt atattatatg tgtataaata   1080

aagtctgtac atattggagc tctgggagat gctggaataa aagacaagag ttacatctgg   1140
```

-continued

```
acttggaaaa aaaaaaaaaa aaaa                                          1164


<210> SEQ ID NO 43
<211> LENGTH: 1105
<212> TYPE: DNA
<213> ORGANISM: Homo sapiens

<400> SEQUENCE: 43

gaattcggca cgagaacaaa ttgaaaccat ctggtcatga acttttattt gttaagaggt     60

tttctaatat tgattcaatc tctttgctta ttctaaatgt gttcagattt tccacttctt    120

gagtcaattt ggtaatttat ttgtttctag gaatttgtcc atttcatcta gtttacctaa    180

tttttgacat ataaaattat atatggaaat ttctaaaata tttaaaaatt tctgtaatgt    240

caatagtaat gtcccctctt ttgttaccaa tttgttattt gaatcttctc cttttttttg    300

tcaatctagc taaaaatttg tcaattttgt tcgtctcttc aaaaaaatat acgtttgtct    360

tcatgatttc tctawtgttt ttccatcyat atttcatttg aatacatttt taaacyttay    420

ctttattatt tcattccttc tgggagcttt gggtctcatt tttttttcct gataatctag    480

ttgtttattg tataagatta agtatttatt tgaaatctgt atgttcttta atgtaggcat    540

tcactactat aaatttactt ctcaggagca tctctgccgc attccatgtt ttagtatgtt    600

gtgttttaat ttgtattcat aactagaggg aaacagaggt gacggagaaa aagacgtaca    660

aatatcatcc acttgcaaag tatagatttg tttgtattgk ratatgaatr aaaatattac    720

gagacagata agaaaatttg aacactgacc attgatgcag ttacagttaa ttttaaaatc    780

aaggttaata acattttagt tattttaaag aatgatagta atttagagat gtattctgaa    840

tgtttttaaa tgaaaagata tgcctgggat ttcttccaaa atgaatcttg taggttggga    900

agaaaatgag aacatagtgg aaacaagact gacaatgagt tgttgaggtt gggcaatgcg    960

tacactaaag cttattttat cttattttac tgtatatact gttaaagctt gcattatttt   1020

cataaatgca tttgctaagt gcaactgtta tcaaataaag tggattgggc tctaaaaaaa   1080

aaaaaaaaaa aaactcgagg ggggg                                         1105


<210> SEQ ID NO 44
<211> LENGTH: 1262
<212> TYPE: DNA
<213> ORGANISM: Homo sapiens

<400> SEQUENCE: 44

cagcatgtac ccagttgttc tttctcctga gaaagcaaaa tgcctgatat ttcttataat     60

ccaggctgcc acgtttacct tgtaaaatca atacttaatt tttagatttt tatattatct    120

tttctcgtga agcaagactt ctaaattatg gctataatat cttttgaatt gttgttctta    180

atgaatcttc caactgtaaa ctcatctaat ttcaaactta tcatacctga ggatgtaaca    240

ttgtcctttg tttctcatct tgatattacc gtcaatcatt ttgtatttct gagtacattt    300

gaacttgctg gagtaataga gggaaaacct ctgcctgatt ctaaatcaga tctttgtcct    360

atactcggac aattatggtt tcatatttta ttatttttta ttttctgggt ttaacaaatg    420

agataacatt ttagacataa tatttgtaaa catcttgact tatttcagca ttttcctttt    480

ttgtgtatct tcagagagtt tgttgaaagt agcaatttcc aagtaatttt aaattattga    540

agtctactag cacgaaaggt caaattctta ggatatttaa aaaatgttgt ttaataatca    600

aactcatctt aaaaaatgtt catcagactc tgtctttgat gcacattttg ccaaaagaga    660

gccttatttc tgtgaaagaa atacagtatg tactttggga tttactaaag taaaactgtt    720
```

-continued actttaaggc acagagcaga tatagaatcc ccctctctcc ccactcctag tgactggtat 780
tctacattaa tatttatctt ccatgcatag tgtacttgag ggaaaaaaac aataactctt 840
aattgtttaa tatcaaacaa taaaatcctg tgtatcagtg actgtcaata gatggctttc 900
tgtttaaaaa ctgaagctac tccagaagta ggaattaatt tatttagtaa acaaagtcag 960
tcaaaccaga gccatgtcct ggggaactgt caaaagaatg gttcctaagg gccagaggcc 1020
acatccactg gtagatgaca gaacaaccat acttcagatg gcaaaaccgg tcagtttggt 1080
ttgcgttgtg tgcctatcct ctttctgtgt gcttcagctg aattaagtgc ttggagagct 1140
caaatagttc aagatagcca agatgaccaa ttctgccagg tggcaagcct gatcttgcaa 1200
ttttgattaa aataaagaac attccccaag aacagtttgt tgcaaaaaaa aaaaaaaaaa 1260
aa 1262

<210> SEQ ID NO 45
<211> LENGTH: 517
<212> TYPE: DNA
<213> ORGANISM: Homo sapiens

<400> SEQUENCE: 45
gaattcggca cgagtgcact tccaccagct atgtatgaga cttcccattg ctccacatct 60
ccagtatttt atgtggtcag tccttttgtt tttggtcatt ttggtggata tgaaatggca 120
tctcagtgtg gcttttcatt atatttcctt gatgactaat ggtattcttt caccctttca 180
gtgcttattg gccattcatg tatctttgtt ttttgtgtag cacttcaggt cttttgccca 240
tagatttagt gggttgattg ctctttatta atgatttgta gggatgttat atatattctg 300
gacacaagat tattgttaga gatacgtact tcagatattt tctcccagtc tgtagcttgc 360
ctaattatta ttattattat tatttgagat gaagtctcac tctgtcgccc aggcagaggt 420
tgcagtgggc cgagatagca ccactacact caagcctggc tgacagagtg agactctgtc 480
tcaaaaaaaa aaaaaaaaaa aaaaaaaaaa aactcga 517

<210> SEQ ID NO 46
<211> LENGTH: 858
<212> TYPE: DNA
<213> ORGANISM: Homo sapiens

<400> SEQUENCE: 46
agaaaaaatc ctacatggat attggtagga aagagagaaa ggaagtggcc agtgtcccgt 60
ggcctcttcc accttctgga ttgttgaagc tggggcctgg aggggatggt cctgccactc 120
agcagggggc actaatggga ccaagctaac ctgtccagtg agaatcctgc agggagacct 180
gagggtacca ggaaagtgca ggggaaggcc cgggaaatgg agagagctgg tctggagggg 240
aggagcaagc cgcgtggggc aggccatgtg ccttttgcct gggggagtat tactcatttg 300
gagctgtgcg tctggaacgc ctgcctcaca cacaaaggac tggggcagat gtaagttctc 360
tgcagcaacg aagcgcacag ctgagagtaa cttagaaagc acccagctaa tgctggcatc 420
ccagatcgac cccctcctcg ctgaatgttg gcatctctgt gcctcagttt cctcatctgt 480
aaatgggggt gataagaaat gtgtacacac ctcccgggca gtggggagga ttaaactgtg 540
ctctgacacg atccgggcat gttcagggtg gtatctgcag taaaccgcgc tcggaaaatg 600
gcggcgcatc agggccagcg gtgggagctc tccgtgcttg gcttgacgcc attgtggagg 660
tggaggaggg gctgcaagac tctgagcagg aagaccccgc aaagcaggaa agcagagcca 720

-continued

```
gagttggggg ccagccgcag aaacgagagc ccccgtgact ttgaggcacc ctttggagag    780

ggcaggaagc aggaagggta aattttctcc aaaacccaag aggcagagtg accccacatg    840

ataactgagt ttctcgag                                                  858
```

<210> SEQ ID NO 47
<211> LENGTH: 6107
<212> TYPE: DNA
<213> ORGANISM: Homo sapiens
<220> FEATURE:
<221> NAME/KEY: SITE
<222> LOCATION: (5749)
<223> OTHER INFORMATION: n equals a,t,g, or c
<220> FEATURE:
<221> NAME/KEY: SITE
<222> LOCATION: (5892)
<223> OTHER INFORMATION: n equals a,t,g, or c
<220> FEATURE:
<221> NAME/KEY: SITE
<222> LOCATION: (5896)
<223> OTHER INFORMATION: n equals a,t,g, or c
<220> FEATURE:
<221> NAME/KEY: SITE
<222> LOCATION: (5906)
<223> OTHER INFORMATION: n equals a,t,g, or c
<220> FEATURE:
<221> NAME/KEY: SITE
<222> LOCATION: (5957)
<223> OTHER INFORMATION: n equals a,t,g, or c
<220> FEATURE:
<221> NAME/KEY: SITE
<222> LOCATION: (5966)
<223> OTHER INFORMATION: n equals a,t,g, or c

<400> SEQUENCE: 47

```
gcagttagtt ccttgatgtc agtagtgggc taaaggcagc ttactgtgtg tttgctggag     60

ctttcactca gccaagtgtt agagtcagga aacccattga ggcaatggcg tcaaatggtg    120

tttcacaaga atgagccatt cagtctttgc tcactatata tttaatattt tattattgtt    180

gttattgtta ttattaattg gctttctgta ttctatgcct tttatttata aagacactaa    240

gaaaacccat gtttgtaatt ttaataacat ttttcccatc ttgtaatatc cagagctact    300

ttataaattc tctgaaccaa aagtattttc ctcagtgtat ctcttctccc ccagccccta    360

ttgggaaaaa ttacccagta tagttcaggt tatgaggagg atcagccaca caatccagtg    420

cttcagtttg aaaatgtaaa attctaaccc taaagtaggg ttggttgaaa tttcagacaa    480

agcaaaccca gcaggtataa aaagtagtat aaatacaaat ctgtaagtta tttttgaatt    540

ttctgaactt ttttctaaga gattacatag gagactaaag aaatctatct gttcaagttc    600

taattaggat gattgttaat actgcactgt ggatgaagtg gcgactggct tgtgtgctga    660

cttctgtggt ttagcaagag gtttattgtt atcaaatgct aattggcaat gccaagtcac    720

tgggaccaat tttctgtttt ataatatcta agtttagaac agaatatata cctgaactgt    780

agtggtttga tcggatggag acagaaaacc cgatttttat tctcataaat tttgtggtta    840

tttatacaag ggctgtgcta tgctaccata ttcttgttca ataataatag gtttgttgtt    900

ttttttacat tgttaaatgt tccttacccc taaaggtcaa tgttaagtac aacattctga    960

aaatacaatt tggctacgaa gagtattcat cttctttgaa gctcagtggt tgatatttgt   1020

gctaataatg caatttcctg attcctgtta caagttatag ctacatatgg gagagactca   1080

gtgagccagc aaaggccata gaaacaacaa tttattaaat gtatttatgg cagaaggacc   1140

taaataaact gtgagccacc ttttcttctt tatattgtta catttaagtg ttcttgcttt   1200

cagcaactca cattaatgct tggagcttat ctctttctct ctctctctct ctctctctct   1260
```

-continued

```
ctgtgtgtgt gtgtgtatgt gtgtgtgtgt gtgtgtgtgt ttccttattg tcattccatt   1320
atatatccac accaacatgg gtgacgataa ttcaaagtca tattttgcct ctaagcttga   1380
tcatgttacc tttatgatta aagtatcatg ttatttagcc aatgcaaatc tgttttaaaa   1440
caaatagttt aaaaaaagaa caagttttta agggctttat tatagaagaa gtattaatga   1500
aggactttcc ttcctccctc cctttcctcc cctccctgcc tcccttcttc ccttccatct   1560
ccccctcctc cctgccttct ttgtttctcc ttcccttatt cctccctccc tcctttctcc   1620
cttccttcct ttcttccatt catccttcct tgccttttat ttttattttt tgtaatatca   1680
catgtgctgt agtttggaat tttattctag tgcatttctt gctcatcaga acctcagcta   1740
atctacctag gaaaaatagt atcaaaggaa atgagaaagt tgtatctgag tccctccaga   1800
actaagataa ttctttttga ccatttaagc ctttataaat gcgttttgac catttaagcc   1860
tttataaatg cttgttttag gaaagtgaat ctgttagatg catcaacaaa taatgaccag   1920
gacaaaacga tttaataatt aaagtctcaa atcaccatgg ttatacattt tcaccagaaa   1980
tagtaatctt acaatttttc atttttctga tgaagatttc tgttccaata tctgtttcct   2040
aatagatttt ttaaattaat tagctttcct ctgctttatg accacaggtt ttatccctaa   2100
ccgagacagc tgtcttatat ctgcatgcct tagactgtgt ggagggactc catgaagaaa   2160
gaccataggt tagaaaaata actcatagta tataccctag taagtgggtt agtagaatct   2220
cataacatgt attaaaaaga ggttttcttc tctgcttgtt tgtgtcacta gagcaaaatt   2280
gtagagataa tgctcataat gcagtaaata tcagaataat ctacaatatc atttgtggat   2340
ggtcccaggt cccagtgctc tagttacttt acttcttttt ttttttttga gatggagtct   2400
tgctctgtct ctcaggctag agcagtgtgc gatctcagct cactgcagcc tccacctccc   2460
aggttcaagc gattctcctg cctcagcctc ccaagtagcc aggattacag gcaccctcca   2520
ctaggcccgg ctaatttttt ttgtattttt ttagtagaga tggggttttg ccatgttggc   2580
caggctggtt tcgaactcct aacctccagt gatccacctg cctcggcgtc ccaaagtgct   2640
aggattacag gcatgagcca ccacatccgg cctaattact tctttaatcc ccatttattt   2700
ttatgccatt ctagcctcat ttattaataa aattatgttt ttactttctc tttcaggaaa   2760
ttttttaaat taatatttta tatctagatc taatgctatg gaaaagtgcc tttttatcat   2820
ttataatttc atttttcact atttccaaaa acacataaac aaatagtttc agtaggtccc   2880
agcttttact ttttccattt aaaccttctt ttctccattt cttccctttg gcttaagaat   2940
aaaagaaaag gtacattgct agaattgttt ctttgggaga gggtaaaaga ttacagaatt   3000
agactgttca gcctttatat aaactaaatt tgtcttcatc tcaaccagct aatggtaggt   3060
cttatctgaa tactcatgag aattttagca tctgtgaaac tccatgcacc agatgtgtgt   3120
aaatttcagg aagaaagtgt tgaaagcatt ttctctgatg ttaattagat ggaaataaat   3180
cactaaaaca tagtttaggt aaagcctgat tatgccactt ttttttaact agacagggca   3240
aagttgttta tgttagtgta cttcttgtct atcctcagtt aatttaccta gacaaaaagt   3300
gtcaaaggaa atgagaaaaa ggttatatct gactccctcc agacctaaga taattccttt   3360
tgatcagata cagtcagatg gagtgccttg gtttttgtta attttgcctc tattccagct   3420
ccttaccaca gcggtggtgc ttaaagaaag gatcatcagc aacaggtcag gatagttcta   3480
cctttgggat agggctgctt tccccgtgct agtatttctg tgactgttag tggcactgag   3540
gactgcaaac ttttatgcaa tattcttaat accctattga tattatgcac tttaatcatt   3600
```

-continued

```
ccaaagaagc caagaatgct gtatagtgat gattccttcc taatgaattc atcttaacta   3660
tttagaatgt tatgtccctt ttcttttgga tagccaactt ggtataaatg ttatatggat   3720
ttttctaaaa tgactatata ggacttaaga ctttgaaatg taatttactt ataaggggaa   3780
ataattatgc tttagcacat cattttagaa acgtcacatt ttagaaacat tcagcttgct   3840
aacctacatg tttgggaatt cattaaaacc agttgtctat atattttgtg ccatgtatat   3900
aagaacatta caatatatct ttttctacat atgtagtatg tgcaaccagt ggttctcaga   3960
gtatggttct cagcccacca gctagtatca gtatcacctg ggaactagtt agaaatgtaa   4020
attctttggc cccatcccag acatactgag tcagaaattc tggaataggg cccccgcaat   4080
ctgttttcac aagccctcca ggtgattctg atgcacactt taaagtttag gaaccactgg   4140
gctaagactc tgttgagata tagagttttt cttccactca gactgatata gttatacatt   4200
gttcttcatg taaattcagc ttaacctggt tatctataat cttttattgg caaaagttaa   4260
ttctcagtac tgcctataga gatacagtgt attttatgta catacacaat tagtctaatt   4320
cttgataatt cagttaattt agtttggcat tttcctacca cttactaaaa ggtttacatt   4380
aaatgactga tttaaatata taggtgcaat gttctatgtt tattttaatt gttatgacat   4440
ttaagtagct aatataattg accggtgcta aagtctcctg tttatccata aaatgggtac   4500
attatgggca gtgtaataca agctttcttt tcattgccta gtactttacc agcagaccac   4560
agttttgccc tggctagacc aaccctcaga acaaaatcat cattccttgt atttatattt   4620
gtatctgaga tagtaaacaa gatggctggc caggtcaaca tggcacctta acttattttt   4680
ttaataggta aaacttcttc aaaagtagct tgctttgtat aagaactaag ctatcagtat   4740
agatatagct atccttggag cttatgtttc agacaagaat tatttactaa aataaataat   4800
aaacaagata atgcattata caatttgggc atttctcgtt tctcaagtgt atgcatcatg   4860
gtaaatataa actaaccaca agataggtag attgattcat ttcattttaa tctccttgtg   4920
taattcagta cctccataat tgttctaatc ttcttcccac tgtttacaaa ttaccagtta   4980
attaactcgt gaaagaaaaa ttcacatatc agaataaaaa taaatgtata ctcactttat   5040
aaaaatcacc actgctgtct ttccttaata ctagcagtgg aaatgtaagt ggcttactct   5100
acaaattttg gtgctggcaa atacataggc aaactgttgg gagctgctct agttacattc   5160
ctcccttctt attccctttt tctcttcctc actttattgc ataacatatt cctgtaccca   5220
aagcattcta ccacagttct atttgactcc cacttgtaat aactccttta aaaaattcca   5280
tgtttaacca tatgaccctg cttgcttact catattctcc ctccctctcc ccttcctttc   5340
tctctcttcc agaagtcatt tgcctggttt gaaatatttt gtagggattg cttattatat   5400
tattttagct gatgaacctc aggacaacgt ctacacacac acacatacat acacgcacac   5460
aaaatctcag ctgttgaaga gtgggcttgg aatcagactt ctgtgtccag taaaaaactc   5520
ctgcactgaa gtcattgtga cttgagtagt tacagactga ttccagtgaa cttgatctaa   5580
tttcttttga tctaatgaat gtgtctgctt accttgtttc cttttaattg ataagctcca   5640
agtagttgct aattttttga caactttaaa tgagtttcat tcacttcttt tacttaatgt   5700
tttaagtata gtaccaataa tttcattaac ctgttctcaa gtggtttanc taccattctg   5760
ccatttttaa tttttattta attttatttg cttgagcaca ctgatcaacc actgaactgc   5820
cttcttccat tgtcctgcaa tgatataagg gttacatttt tgtgtatatg gctttcatag   5880
ttgggatttc anagcnctga taccanatat tttcagtttg ttctctgggg gaatttcatt   5940
tgcatctatg tttttancta tctgtnataa cttgttaaat attaaaaaga tattttgctt   6000
```

-continued ctattggaac atttgtatac tcgcaactat atttctgtaa acagctgcag tcaaaaataa 6060
aacactgaaa gttttcaaaa aaaaaaaaaa aaaaaaaaaa aaaaaaa 6107

<210> SEQ ID NO 48
<211> LENGTH: 703
<212> TYPE: DNA
<213> ORGANISM: Homo sapiens

<400> SEQUENCE: 48
ccacgcgtcc gcaggacatc gttttctaca tggtggctgt gttcctgacc ttcctcatgc 60
tcttccgtgg cagggtcacc ctggcatggg ctctgggtta cctgggcttg tatgtgttct 120
atgtggtcac tgtgattctc tgcacctgga tctaccaacg gcaacggaga ggatctctgt 180
tctgccccat gccagttact ccagagatcc tctcagactc cgaggaggac cgggtatctt 240
ctaataccaa cagctatgac tacggtgatg agtaccggcc gctgttcttc taccaggaga 300
ccacggctca gatcctggtc cgggccctca atcccctgga ttacatgaag tggagaagga 360
aatcagcata ctggaaagcc ctcaaggtgt tcaagctgcc tgtggagttc ctgctgctcc 420
tcacagtccc cgtcgtggac ccggacaagg atgaccagaa ctggaaacgg cccctcaact 480
gtctgcatct ggttatcagc cccctggttg tggtcctgac cctgcagtcg gggacctatg 540
gtgtctatga gataggcggc ctcgttcccg tctgggtcgt ggtggtgatc gcaggcacag 600
ccttggcttc agtgaccttt tttgccacat ctgacagcca gcccccccagg cttcactggc 660 tctttgcttt cctgggcttt ctgaccagcg ccctgtggat caa 703

<210> SEQ ID NO 49
<211> LENGTH: 639
<212> TYPE: DNA
<213> ORGANISM: Homo sapiens

<400> SEQUENCE: 49
ggcacgagca ttcacaggtt acaaatgctg ctgccaactg tcctggccaa atgactctgc 60
atcacaaacc tttccttgca tgtggagggg atggatttac tcagtccaac tttgatggct 120
gcatcacttc tgccctatgt gttctggaag ctttaaagaa ttatatttag tgcctatatc 180
cttattctct acatgtgtat tgggttttta ttttcacaat tttctgttat tgattatttt 240
gttttctatt ttgctaagaa aaattactgg aaaattgttc ttcacttatt atcatttttc 300
atgtggagta taaaatcaat tttgtaattt tgatagttac aacccatgct agaatggaaa 360
ttcctcacac cttgcacctt ccctactttt ctgaattgct atgactactc cttgttggag 420
gaaaagtggt acttaaaaaa taacaaacga ctctctcaaa aaaattacat taaatcacaa 480
taacagtttg tatgccaaaa acttgattat ccttatgaaa atttcaattc tgaataaaga 540
ataatcacat tatcaaagcc ccaaaaaaaa aaaaaaaaaa aaaaaaaaaa aaaaaaaaaa 600
aaaaaaaaaa aaaaaaaaaa aaaaaaaaaa aaaaaaaaa 639

<210> SEQ ID NO 50
<211> LENGTH: 867
<212> TYPE: DNA
<213> ORGANISM: Homo sapiens

<400> SEQUENCE: 50
ggcacgagca ggtactgggt gactgcctgg ctgaggaaaa gttaactaga cacttgggga 60
aaggagatcc aagggagtaa gaggcaaaat gcctttgcat gcttttcttc ctatctcttt 120

-continued

```
ttctttctct ccttctcact ctctcccttc cttcctttct tcctttctct ttcttttttt    180

tttctctttt cccccacctc tctgcctgcc tccttccttc cctcccctcc cctcccttcc    240

ccctccctcc ctccctccct tccttccttc cttccttcct tccttccttc cttccctccc    300

tcctctctcc ctccttccct gccttctttc cttcgttctg ccaacttgcc agaaggagcc    360

caagaaaaag cacccagatg cttcagtcaa cttcttagaa ttcttctttt ttttatgttc    420

agaaaagatg gaaattcatt tctgctaaag agaaagaaaa aattggaaga cagggtgaag    480

gtgaacaggc ccattataag aaagaaacaa aaatctatat tctgtctaca aggaagcgag    540

agagagaaag agagagaaga aagaagttcc aggattctaa tgtaccaaag ggatctcctt    600

tttcttgttt tgttctgaaa atttcaccaa aagagcacag gagaacatct tggctaattc    660

attggcgatg atgtaagaaa actgagagaa atgaaagaaa tgaagaatta ctgctgcaga    720

taatatacag ccttgaggaa agaaaggctt ttaagattat agatataaag gctattgctg    780

tattctggga taaaagaaag tctgatgtca gggaaagggg aagttggaaa aactggaaaa    840

agaaaaaaga aaaaaaaaaa aaaaaaa                                          867
```

<210> SEQ ID NO 51
<211> LENGTH: 1569
<212> TYPE: DNA
<213> ORGANISM: Homo sapiens
<220> FEATURE:
<221> NAME/KEY: SITE
<222> LOCATION: (341)
<223> OTHER INFORMATION: n equals a,t,g, or c

<400> SEQUENCE: 51

```
gtattggcca ggctggtctc aaactcctga cctcgtgatc cacccacctt ggcctcccaa     60

agtgcagaga ttacaggcat gagccactgc acctggcctc aagaaaaatt atatatcacg    120

tggaatagga tagtagtctc tgcactgatt ttcgttgata atggctgttc ttcttatcac    180

cattttgcta tttctttgtc tgggctatta cagggttatt acagaaattt ccagaaagac    240

ccctgcctgt cgaatgttta cttcaagctt gagctcctgg tatattatga ggaaattata    300

tgatacccca ggagaggtct tcctttccca tgccattgta naattcctaa agtaaaatta    360

atttgccttc ttgtcaaaga aggagccaat gttgttttaa aattttagct tgagagatag    420

gtggggaaga aattaaatag acaagtaatc mctattcaga agagaaggga gagtcattgt    480

acgaggccca agatacttgc ccaaaaatat cgcagagaaa aactagtctt tggggtccta    540

ttttttgagt ggaacatttg agttatttaa aattagaatt ttattttggt cagattagaa    600

tttctagggt atgtcatatg tgtttttaaa ttgaaagctc ttaaaactcc tattgtagtt    660

taatgtcatt atccattaat ttacataaat ctgatttgga tctctatttt catcgtagac    720

tgtgtagggg caatttttcc taaaggttct gtgacatagt gctacctttt ttttaaaacc    780

tgtcttgccc aggcattatt gagtgccccc tggtgccagc atgtgtattt cacgactgta    840

tcaacaaatc atgatcatct tctctggcca ttgtgccctt tcagattcca aacttgttac    900

ctctcagtcc ttcctacaaa cttagaaagt ctaatatctt aatgtttact tatgtagcaa    960

cctccctttc tcccatccct aaatcctctt gtaattaatt attttccttt ggaacttttt   1020

aaatctacaa tttccttata atatggtaac caatattaat tttcttgttc tgcgccaagt   1080

ttgattttat acaaattgtt tccagtttgg gtcatgagca caaaaccagg tatttttaaa   1140

aatctatata acccttcaat gaggcagtat taattttatt aactcattaa ttcaaccaat   1200

aattcttgat tgtttactgt gttagatatt ggggtatccc caatacctga cagctgtgag   1260
```

-continued caaaacaaat gccctacaca catgaggtgt acagtccagt agaaaagata aacaataagc 1320
aaattaatag ataatatgat gtccaataag gacttcaaag gaaaataaag cagagtaaag 1380
agccagagaa tgacagtgag ctgtttttca catgagtcat cagaaaaggc ctctttaaag 1440
aattgacatt tgaacagaaa aacgaatcaa gggcgtcaac tgtttattgc ttttattgct 1500
taccatttga ccaagcaatt ctacacatag gattcaccct aaaaaaaaaa aaaaaaaaaa 1560
aaactcgag 1569

<210> SEQ ID NO 52
<211> LENGTH: 1196
<212> TYPE: DNA
<213> ORGANISM: Homo sapiens
<220> FEATURE:
<221> NAME/KEY: SITE
<222> LOCATION: (590)
<223> OTHER INFORMATION: n equals a,t,g, or c

<400> SEQUENCE: 52
gattggttct gtttatgtga tagattactt ttattgattt gtatgttgaa ccagccttgc 60
atcctaggga tgaagccgac ttggttgtgg tggataagct tttgatgtg ctgctgggtt 120 tggcttgcca gtgttttatt agggattttt gcgtcaatat tcatcaggga tattggcctg 180
gaattttctt tttttgttat gtgtctgcca ggttttggta tcagggtgat gctggcctca 240
taaaataagt tagggagggc tccctctttt tctttcattt ggaagaattt cagaaggaat 300
ggtaccagat ccyctttgta cctctggtag aatttggctg tgaatccatc tggtcckgag 360
cttttttttt gttggtaggc tattaattac tgcctcaatt tcagaacttg ttattggtct 420
attcagggat ttgacttctt cctggtttag tcttgggagg ttgtatgtgt gcaggaattt 480
attcatttct tctagatttt ctcgtttatt tgtgtagagg tgtttatagc atyctctgat 540
ggtagtttgt attctgtggg atcagtggtg atctcccctt tatcattttn attgtgtcta 600
tttgattctt ctctcttktc ttctttatta ttctygctaa tggtctatgt attttgttaa 660
tctyttacaa aaacaggctt ctagattcat ggatgttttg aaaggttytt cgtgtctcta 720
tctccttcag ttcttccctg atcttagcta tttcttgtct tctgctagct tttgaaattg 780
tttgcttttg cttctctagt tcttttaacc gtgatgtcca gtgtgtcaat ttcagatctt 840
tccagccttc tgatatgggc atttaatgct ataaatttcc ctcttaacac tgctttagct 900
gtgtcctaga gattctggta cgttgtctct ttgttctcat tggtttcaaa taacttcatt 960
atttctgcct taattttgtt atttacccag cagtcattca agagcaggtt gttcaatttc 1020
catgtagttg tgtggttttg agtgaatttc ttaatcttga gttctaattt gattgcactg 1080
tggtctgaga gacggttaca atttccattc ttttgcattt gctgagaagt gttttacttc 1140
caattgtgtc tcgtgccgaa ttcgatatca agcttatcga taccgtcgac ctcgag 1196

<210> SEQ ID NO 53
<211> LENGTH: 945
<212> TYPE: DNA
<213> ORGANISM: Homo sapiens
<220> FEATURE:
<221> NAME/KEY: SITE
<222> LOCATION: (295)
<223> OTHER INFORMATION: n equals a,t,g, or c
<220> FEATURE:
<221> NAME/KEY: SITE
<222> LOCATION: (875)
<223> OTHER INFORMATION: n equals a,t,g, or c
<220> FEATURE:

-continued

<221> NAME/KEY: SITE
<222> LOCATION: (914)
<223> OTHER INFORMATION: n equals a,t,g, or c

<400> SEQUENCE: 53
gaatggtgaa atattaagtg ctttctcccc caggttcagg attatgacag ctatgtccat 60
tcacctcttc tgtacagcat tgtcctgtgg aagttctggc cagtgcaata aggcaattaa 120
aagaaataaa atatcaaacg attggaaaga tgttaatgtg tcatcattca tagaaaacat 180
gattcataga tatacataca cgaatgcttt gaattcataa gtagattcag ccagttgctg 240
gatataaagt caatatacaa aaactatttt tatagacatg aaacacgcaa tgagnaaaaa 300
aatttaacca tttttagtag catcaaaaaa cccccatacc taggaatatg aatttgtagt 360
actatttggg atatgttgat ggatatttat catttccagt ttgggattat tataaagaaa 420
atagccctga acatttgtaa tatatgactt ttggtgaatg tagcattcat ttctgttgat 480
tacaaactca ggggtgaaat tgttgagtcc taagggagct atagatgtat tcaacttcag 540
ctgatatggc taaataaatt tgcgaaaaag attgcatcaa gttatgctcc catcagcaat 600
atgagagttc ctgtttttcc acattgtcag caacactttg tactgttact ccttttaatt 660
ttagccgatt tggctgaagg tgtggtaata tctcattgta gtggccaggc gtggtgctca 720
cgcctgtaat cccagcactg tgggaagcca aggtgggccg atcacgaggt caggagatcc 780
agaccatcct ggctaacatg atgaaaccct gttgcctgta gtcccaacta cttgggaggc 840
tgaggcagga gaatggcatg aactcgggag gcggngcttg cagtgagcct ccagcctggg 900
caacagagtg agantctctc aaaaaaaaaa aaaaaaaaac tcgag 945

<210> SEQ ID NO 54
<211> LENGTH: 488
<212> TYPE: DNA
<213> ORGANISM: Homo sapiens

<400> SEQUENCE: 54
ggcacgagga gagtagaggc tattcatgta atgtctataa aaaaataaca ccaaggctgg 60
gattacaggc atgagccact gcacctggcc agtttgctta ttttgtttgg tgcctcctcc 120
catgggagac ctcaaggagg tatgcctgcc ccacagatgc cctggaagga cagcttgctg 180
ctcctactca gaaccacacc tgcagacaga ggaggacaga cggacactca tttgctgagc 240
acccatgtaa catgaactaa gagctgggtg gagacaatga acggtggagc catcgttccc 300
gatgtggagg gagaacagct caagaccacg gaacagcctg ctctcccgct tcctggcttc 360
cgtgcgcttt tgtccaatca ggctttttga ccaatcggcc aggcgcgcta tgtaaatttc 420
tgacattttc aaagctgtct ttttaataaa cctttcagtg taaaaataaa aaaaaaaaaa 480
aaaaaaaa 488

<210> SEQ ID NO 55
<211> LENGTH: 2860
<212> TYPE: DNA
<213> ORGANISM: Homo sapiens
<220> FEATURE:
<221> NAME/KEY: SITE
<222> LOCATION: (753)
<223> OTHER INFORMATION: n equals a,t,g, or c

<400> SEQUENCE: 55
ggcacacagg gctggcaggc ccgcggtggc tggtgttgag gcatgaacaa attgtaccgg 60
gtatccccca ccccactctg accaccagtt cctccttgga tatcactccc cctgacaggc 120

-continued

```
agcccaccca ggcctggatt tgtccctgtc tccccctttt gcttttcccc catgactaat    180
gggcaccagg tcttgctgct cctgcttctc acctctgcag tggcagcagg cccctggccc    240
caggtgcatg ccggtcagtg gggttggatg tgccttcctc caggcctgcc ctctgtccaa    300
gcccggagtg ggcttggtgg gctccctggt ggcccccagt gggtgccagg tggtgcccgg    360
ggttattgag gggtggttgt atcactgtag ggacaggctt cttgccccag cctggagagc    420
tgttttcttc aggaaggttc tggagatgga gacttgtttg cgaattcacc acaactccag    480
gctgggaggc tgggtctctg ctctcagagc cgagacacca gggaggatag ccaggctgcc    540
ctgcctggga attctgctgg gccgtcaaat tcaacccgca ccaacgtggg caggaggcca    600
cagtgtcctg ccaggagcag agggctgaag gtctgcagga ggaagaccct atcctggtgg    660
ggggcacctg ctgcccaccc tgcccccagc gtgcctgggg ggagcacacc tgggcatgga    720
ggagtccagg gtgctgggcc acacaagaga ggngggggag aggcctggac agtaggaaga    780
tcttgcccag ggtcctggat ccgccactct gggggtgacc ttggacaaac ctctgccttg    840
gccctcagtc tccccatcaa ggtttttcca ttcaggaggg tttgggccat cttcagccac    900
cctaccagcc ctgaaaagga tgtgactcct gtttctggga agtgtgtggt gtgttaggtg    960
ggcctacagc cctggttgtg gggagggaag gatggagaga cagcacagtg acagagccca   1020
gactgcaggc tggagtgagg gttccacttc cccgctgctg tgtgtcctgg accagtgcct   1080
ctgaaccttg gcacttgggg cagtggatat taacatcttt ccaagcccaa ttcttggggc   1140
atcagggcct ccggtcctct gggaggtggc aggtcctcag attggagatg ccatgggggg   1200
gggaggtgcc tctcctttgg agggtatgga agtggagaca ggagtggcct ggcgcagctg   1260
ccgtggttct taggggctgg gcccggggag cccatggggc ttgtgcctag aaagcctggg   1320
ctcctcactg ggtctagat gtgcagactt catgtctccc cagctccagc tctgttctct   1380
ataggtcaag cctccacaat gccagaggcc cagggctagc cccctccacg tccctcctag   1440
atctacagct gccccctttga tgacagcgcc attgagtccc ctgggctggg ggggtcatgc   1500
aggggtgagg cagctgcctg ccgccggtac tcattgcctg gccaggcagg acacaggctg   1560
gcgggcactg agagtgggcc ccacgaaatc cattgtcagg ttaccaggat gaagaaccca   1620
ggctggtcgt ggagtgcagg gcggggcctg ccggaagaat tatgggcact gcagcaggag   1680
ggcagcctgg gccattagct cctgatgtca tcgatttggg tgaggggaca gggaagtcag   1740
aggaagctgg ccagtggctc tcacgcagac ttacagcagt ggagtggtgc ctgattcctg   1800
gtacagctgc tcccactgag tctccaggga tctgtggttc aggacccccct gcaacccccct   1860
cccagacccc tgtactggtg ggaggagagg acctagagga aaggtgctgg gcagataagc   1920
agctgaggga ggccctgggt ttagcttatc agtcttctgg gccctcctgc cccaggaagg   1980
gcagcgagga ccatggtgtt gcccctgtca tcgttatcgt cctggccatg agcttgcagg   2040
actgggaggg ccggagtcag ccaggcagac ggcagcacag catttgcctg ttggcaggtg   2100
gccttggtgg cttcccaaag gcaatcgctc cacgcagaac aaaactcact tttttggggg   2160
gtgaagcacc ttggttcatt tgtttagttc gttaattcca gcagtctgtt tctaagggaa   2220
acatggctgc agccggtcct gcgcctccca ccctcccacc aggtgcccag tgttcccaag   2280
ggccccgaat cccaacctta ttcaggcgtc agcatctctg caccccaaat gcctgttagg   2340
gaggatagtg aaggctgagc cctcctgggc ccatcaaaag ccagcagtga gagaacaccc   2400
ccatctctct gaggtgacct tgtagggcag tccgtgctgt ctggctggcc tgggtgaggt   2460
```

-continued

```
gggcagggac caaggcctgg cgcctgggcc tcgctggcct tgctctgcgt gctgacttca   2520

tcctgatagt accttgattt tcctactgtg acttcccctt ctgtcgactt cctcaccaac   2580

tttaaaattc cgtattgaga gcagtttcct aagttacctc aaatcctatt cagaagaagg   2640

ttcttcctgg aagttgggag ggcggaaaac aagtttagtc acagaagact actccatgtt   2700

tgagcttctg tttcaaggga agtgagtaac tgccggagga gccctgcccc tctgcagtgt   2760

gtggtgttgc cctgatactt ttcagattga ggtgttactt acatgtaata aaatgcacag   2820

acttaagtgt aaaaaaaaaa aaaaaaaaaa aaaaaaaaaa                          2860


<210> SEQ ID NO 56
<211> LENGTH: 1559
<212> TYPE: DNA
<213> ORGANISM: Homo sapiens
<220> FEATURE:
<221> NAME/KEY: SITE
<222> LOCATION: (1445)
<223> OTHER INFORMATION: n equals a,t,g, or c
<220> FEATURE:
<221> NAME/KEY: SITE
<222> LOCATION: (1551)
<223> OTHER INFORMATION: n equals a,t,g, or c

<400> SEQUENCE: 56

atccagcagt ggggagacag cgtgctgggc aggcgctgcc gagaccttct cctgcagctc     60

tacctacagc ggccggagct gcgggtgccc gtgcctgagg tcctactgca cagcgaaggg    120

gctgccagca gcagcgtctg caagctggac ggactcatcc accgcttcat cacgctcctt    180

gcggacacca gcgactcccg ggcgttggag aaccgagggg cggatgccag catggcctgc    240

cggaagctgg cggtggcgca cccgctgctg ctgctcaggc acctgcccat gatcgcggcg    300

ctcctgcacg gccgcaccca cctcaacttc caggagttcc ggcagcagaa ccacctgagc    360

tgcttcctgc acgtgctggg cctgctggag ctgctgcagc cgcacgtgtt ccgcagcgag    420

caccaggggg cgctgtggga ctgccttctg tccttcatcc gcctgctgct gaattacagg    480

aagtcctccc gccatctggc tgccttcatc aacaagtttg tgcagttcat ccataagtac    540

attacctaca atgccccagc agccatctcc ttcctgcaga agcacgccga cccgctccac    600

gacctgtcct tcgacaacag tgacctggtg atgctgaaat ccctccttgc agggctcagc    660

ctgcccagca gggacgacag gaccgaccga ggcctggacg aagagggcga ggaggagagc    720

tcagccggct ccttgcccct ggtcagcgtc tccctgttca cccctctgac cgcggccgag    780

atggccccct acatgaaacg gctttcccgg ggccaaacgg tggaggatct gctggaggtt    840

ctgagtgaca tagacgagat gtcccggcgg agacccgaga tcctgagctt cttctcgacc    900

aacctgcagc ggctgatgag ctcggccgag gagtgttgcc gcaacctcgc cttcagcctg    960

gccctgcgct ccatgcagaa cagccccagc attgcagccg ctttcctgcc cacgttcatg   1020

tactgcctgg gcagccagga ctttgaggtg gtgcagacgg ccctccggaa cctgcctgag   1080

tacgctctcc tgtgccaaga gcacgcggct gtgctgctcc accgggcctt cctggtgggc   1140

atgtacggcc agatggaccc cagcgcgcag atctccgagg ccctgaggat cctgcatatg   1200

gaggccgtga tgtgagcctg tggcagccga cccccctcca agccccggcc cgtcccgtcc   1260

ccggggatcc tcgaggcaaa gcccaggaag cgtgggcgtt gctggtctgt ccgaggaggt   1320

gagggcgccg agccctgagg ccaggcaggc ccaggagcaa tactccgagc cctggggtgg   1380

ctccgggccg gccgctggca tcaggggccg tccagcaagc cctcattcac cttctgggcc   1440

acagncctgc gcggagcggc ggatcccccc gggcatggcc tgggctggtt ttgaatgaaa   1500
```

-continued

```
cgacctgaac tgtcaaaaaa aaaaaaaaaa aaacccgrgg gggggcccgg nacccaatt    1559


<210> SEQ ID NO 57
<211> LENGTH: 2064
<212> TYPE: DNA
<213> ORGANISM: Homo sapiens
<220> FEATURE:
<221> NAME/KEY: SITE
<222> LOCATION: (2001)
<223> OTHER INFORMATION: n equals a,t,g, or c
<220> FEATURE:
<221> NAME/KEY: SITE
<222> LOCATION: (2024)
<223> OTHER INFORMATION: n equals a,t,g, or c
<220> FEATURE:
<221> NAME/KEY: SITE
<222> LOCATION: (2049)
<223> OTHER INFORMATION: n equals a,t,g, or c

<400> SEQUENCE: 57

atgggcgagg ctgcggggcc ccggcgcgca cgcccgcacc tctccccagc cctggcgtgg      60

gcccagcccg gcccaggcag caatggggtt cctgcagctg ctggtcgtar cggtgctggy     120

atccgaacac cgggtggctg gtgcagccga ggtcttcggg aattccagcg arggtcttat     180

tgaattttct gtggggaaat ttagatactt cgagctcaat aggccctttc cagaggaagc     240

tattttgcat gatatttcaa gcaatgtgac ttttcttatt ttccaaatac actcacagta     300

tcagaataca actgtttcct tttctccgag gcgtagatcc cccaccatgt gacgctggga     360

cagaccagga ctccaggtgg aggttgcagt atgatgtcta tcagtatttt ctgcctgaga     420

atgacctcac tgaggagatg ttgctgaagc atctgcagag gatggtcagt gtgccccagg     480

tgaaggccag tgctctcaag gtggttaccc taacagctaa tgataagaca agtgtttcct     540

tctcctccct cccgggacaa ggtgtcatat acaatgtcat tgtttgggac ccgtttctaa     600

atacatctgc tgcctacatt cctgctcaca catacgcttg cagctttgag gcaggagagg     660

gtagttgtgc ttccctagga agagtgtctt ccaaagtgtt cttcactctt tttgccctgc     720

ttggtttctt catttgtttc tttggacaca gattctggaa aacagaatta ttcttcatag     780

gctttatcat catgggattc ttcttttata tactgattac aagactgaca cctatcaagt     840

atgatgtgaa tctgattctg acagctgtca ctggaagcgt cggtggaatg ttcttggtag     900

ctgtgtggtg gcgatttgga atcctctcga tctgcatgct ctgtgttgga ctagtgctgg     960

ggttcctcat ctcgtcagtg actttcttta ctccactggg aaacctaaag atttttcatg    1020

atgatggtgt attctgggtc actttctctt gcatagctat cctcattcca gtagttttca    1080

tgggctgcct aagaatactg aacatactga cttgtggagt cattggctcc tattcggtgg    1140

ttttagccat tgacagttac tggtccacaa gcctttccta catcactttg aacgtactca    1200

agagagcgct caacaaggat ttccacagag ctttcacaaa tgtgcctttt caaactaatg    1260

acttcattat cctggcagta tggggcatgc tggctgtaag tggaattacg ttacagattc    1320

gaagagagag aggacgaccg ttcttccctc cccacccata caagttatgg aagcaagaga    1380

gagagcgccg agtgacaaac attctggacc ctagctacca cattcctcca ttgagagaga    1440

ggctctatgg ccgattaacc cagattaaag ggctcttcca gaaggagcag ccagctggag    1500

agagaacgcc tttgcttctg tagatgccca ggggcttggt cagtgtgcct cagctttgga    1560

gttcatgcct ggagtggttc aacagtctct ggtgcaagtc taataagaga tcaggcatat    1620

atatctgttc tttgcataat attatggtgc ccttattgat atatggtaag ggtgtactag    1680
```

-continued

```
gggattagga tgattgtaag agaatgagaa agatgaccaa aaggttggtg gtagggaggc   1740

tttttcttat ttccaaatac ttgagaaatt accttttggt ttacaaatct atgatcaact   1800

tattccatta aatagataca ttaaaaaaat taaaaactga ttcttctgca gagcactggt   1860

gtttcttttt ataacccctt gaaacaagtc tctcacctga gcctgtctaa actttcggag   1920

ggagtttatt attgagtctt tatctgtgac agtatttgga gatttaggga tttgatactt   1980

aggcctttga attttagaat ncaaaaaggg gagccagcca gacngggggg ccaacccgga   2040

tccccaacng ggaccagggg ggtc                                          2064
```

<210> SEQ ID NO 58
<211> LENGTH: 1050
<212> TYPE: DNA
<213> ORGANISM: Homo sapiens

<400> SEQUENCE: 58

```
ccacgcgtcc ggccagccag tccgcccgtc cggagcccgg ctcgctgggg cagcatggcg     60

gggtcgccgc tgctctgggg gccgcgggcc gggggcgtcg gccttttggt gctgctgctg    120

ctcggcctgt ttcggccgcc ccccgcgctc tgcgcgcggc cggtaaagga gccccgcggc    180

ctaagcgcag cgtctccgcc cttggctaga ctggcgctcc tcgccgcttc cggcggtcag    240

tgccccgagg tgaggcggcg ggggcggtgc agacctggcg cgggcgctgg cgcatctgct    300

ggagccgaac gtcaggagcg ggcgcgggcc gaggcgcaga ggctgaggat cagcaggcgc    360

gcgtcctggc gcagctgctg cgcgtctggg gcgccccccg caactctgat ccggctctgg    420

gcctggacga cgaccccgac gcgcctgcag cgcagctcgc tcgcgctctg ctccgcgccc    480

gccttgaccc tgccgcccta gcagcccagc ttgtccccgc gcccgtcccc gccgcggcgc    540

tccgaccccg gcccccggtc tacgacgacg gccccgcggg cccggatgct gaggaggcag    600

gcgacgagac acccgacgtg gaccccgagc tgttgaggta cttgctggga cggattcttg    660

cgggaagcgc ggactccgag ggggtggcag ccccgcgccg cctccgccgt gccgccgacc    720

acgatgtggg ctctgagctg ccccctgagg gcgtgctggg ggcgctgctg cgtgtgaaac    780

gcctagagac cccggcgccc caggtgcctg cacgccgcct cttgccaccc tgagcactgc    840

ccggatcccg tgcaccctgg gacccagaag tgcccccgcc atcccgccac caggactgct    900

ccccgccagc acgtccagag caacttaccc cggccagcca gccctctcac ccgaggatcc    960

ctaccccctg gccccacaat aaacatgatc tgaagcagca aaaaaaaaaa aaaaaaaaaa   1020

aaaaaaaaaa aaaaaaaaaa aaaaaaaaaa                                    1050
```

<210> SEQ ID NO 59
<211> LENGTH: 2533
<212> TYPE: DNA
<213> ORGANISM: Homo sapiens

<400> SEQUENCE: 59

```
ccacgcgtcc gcctggcaac ccctaatatt tgggatctct caatgctatt tgccttcatt     60

agcttgctcg ttatgcttcc cacttggtgg attgtgtctt cctggctggt atggggagtg    120

attctatttg tgtatctggt cataagagct ttgagattat ggaggacagc caaactacaa    180

gtgaccctaa aaaaatacag cgttcatttg gaagatatgg ccacaaacag ccgagctttt    240

actaacctcg tgagaaaagc tttacgtctc attcaagaaa ccgaagtgat ttccagagga    300

tttacactgg tcagtgctgc ttgcccattt aataaagctg gacagcatcc aagtcagcat    360

ctcatcggtc ttcggaaagc tgtctaccga actctaagag ccaacttcca agcagcaagg    420
```

-continued

```
ctagctaccc tatatatgct gaaaaactac cccctgaact ctgagagtga caatgtaacc    480
aactacatct gtgtggtgcc ttttaaagag ctgggccttg gacttagtga agagcagatt    540
tcagaagagg aagcacataa ctttacagat ggcttcagcc tgcctgcatt gaaggttttg    600
ttccaactct gggtggcaca gagttcagag ttcttcagac ggttagccct attactttct    660
acagccaatt cacctcctgg gcccttactt actccagcac ttctgcctca tcgtatctta    720
tctgatgtga ctcaaggtct acctcatgct cattctgcct gtttggaaga gcttaagcgc    780
agctatgagt tctatcggta ctttgaaact cagcaccagt cagtaccgca gtgtttatcc    840
aaaactcaac agaagtcaag agaactgaat aatgttcaca cagcagtgcg tagcttgcag    900
ctccatctga aagcattact gaatgaggta ataattcttg aagatgaact tgaaaagctt    960
gtttgtacta aagaaacaca agaactagtg tcagaggctt atcccatcct agaacagaaa   1020
ttaaagttga ttcagcccca cgttcaagca agcaacaatt gctgggaaga ggccatttct   1080
caggtcgaca aactgctacg aagaaataca gataaaaaag gcaagcctga aatagcatgt   1140
gaaaacccac attgtacagt aagtaccttt gaagcagcct actctacaca ttgcagacaa   1200
agatccaatc ccagaggagc aggaattaga agcttatgta gatgatatag atattgatag   1260
tgatttcaga aaggatgatt tttattactt gtctcaagaa gacaaagaga gacagaagcg   1320
tgagcatgaa gaatccaaga gggtgctcca agaattaaaa tctgtgctgg gatttaaagc   1380
ttcagaggca gaaaggcaga agtggaagca acttctattt agtgatcatg tgtttcttca   1440
tatagcttta aaattatgct attgacatta tgggaaagat ttatcaatga gagaaatgtg   1500
tctctttttc agccgtgttg aaatccttgt ctcctgtaga cccagtggaa cccataagta   1560
attcagaacc atcaatgaat tcagatatgg gaaaagtcag taaaaatgat actgaagagg   1620
aaagtaataa atccgccaca acagacaatg aaataagtag gactgagtat ttatgtgaaa   1680
actctctaga aggtaaaaat aaagataatt cttcaaatga agtcttcccc caaggagcag   1740
aagaaagaat gtgttaccaa tgtgagagtg aagatgaacc acaagcagat ggaagtggtc   1800
tgaccactgc cctccaact cccagggact cattacagcc ctccattaag cagaggctgg    1860
cacggctaca gctgtcacca gattttacct tcactgctgg ccttgctgca gaagtggctg   1920
ctagatctct ctcctttacc accatgcagg aacagacttt tggtgatgag gaggaagaac   1980
aaataataga agaaaataaa aatgagatag aagaaaagta agaaccaaga ttcatatgaa   2040
gtgatattag attgttcctt ttacaaaagt gtttagcttc aagactggaa agggaatatg   2100
agtgtaagtt tactatatat aaagctaaga tgtggattta caggaagaac cctggtttga   2160
ataactgatc tgaaattagt agttacctgt aaatggcaga tcttttagga aaataagaga   2220
aaggtaaggg ctcttttgaa taaactgctg ttttatttgt ggcacaactg atcaatcttg   2280
gaaattcttt aagtattttt aataagaaat gaattatcat ttcttgccag aatttgctac   2340
cttaaggtga ttgggaaaat tctgttgcaa gaacattaac atttagtatg actccttttt   2400
actgtattct tgcagttaat aactgcagct attatgttaa taacaagttg tttgtatttt   2460
atttttgttt ataccagtct taaagatcca ggttctgaat aaaaaaatta attgatacaa   2520
aaaaaaaaaa aaa                                                      2533
```

<210> SEQ ID NO 60
<211> LENGTH: 899
<212> TYPE: DNA
<213> ORGANISM: Homo sapiens -continued

<400> SEQUENCE: 60
ggcagatttc ccggcacctt cgtgggcacc acagagcccg cctccccacc cctgagcagc 60
acctcaccca ccactgctgc ggccactatg cctgtggtgc cctctgtggc cagcctggcc 120
cctccggggg aggcctcgct ctgcctggaa gaggtggccc cccctgccag tgggacccgc 180
aaagctcggg tgctctatga ctacgaggca gccgacagca gtgagctggc cctgctggct 240
gatgagctca tcactgtcta cagcctgcct ggcatggacc ctgactggct cattggcgag 300
agaggcaaca agaagggcaa ggtccctgtc acctacttgg aactgctcag ctaggcaggt 360
gcccccatcc cccccgcatt ctggcctagg caggagagga tgggcgcact gccacttaac 420
ttgtttgttg gtgacacagt tgttcagagt ggggagaatt caccccattc tgtccctgcc 480
cctagtcacc tagctgtgag ggtgcctgag gctgaatggc tccaccctcc cccagccctg 540
cttctgacct gtggctctgg agcccctgcc cctgcctgca tccccgagca ccccaccctc 600
caggctccac taaggaggga ggggctgtct gcagcagctg cactcagcac ctaggccagg 660
gtggggccgc cgcagatggg ctcaggaagc cccaggtgca ctcagcgaga gccctgcctt 720
tcagttgcca aaagctgcat caggggaatg cggcaaggca cacagggctc tggcagcccc 780
tggggactgg gcgctgcccc tgggagggga gagcctggcc agggctggtg ttgggcccgg 840
agcagcatct tccggtgcta tcctcccctc ccacccctca cagctcaagc caagtccag 899

<210> SEQ ID NO 61
<211> LENGTH: 1079
<212> TYPE: DNA
<213> ORGANISM: Homo sapiens

<400> SEQUENCE: 61
tcgacccacg cgtccgggtt tcaccacgtt ggccaggctg gtctcaaact cctgacttca 60
gttggcctcc caaagtgctg ggattaaagg catgagccac tgcgcccggc ctacctttct 120
aactctactt ctagcttctt gcttctgggc tgctgctata ccaaacagga atgtaatact 180
ttctgtcagc ttcaggcctt tgcacatgca gttcactttg tctatcttgg tttttattct 240
taggatttta attctcctaa gaagctttct ctgaccagcc taaaacttac gtaagccctg 300
ggttaggtgc tatgcttatg tcctcccata gcattttgca tttgcatgtg ttgtaactct 360
taatgtacag catcatgatt gcctatttta actttcctgt ttgttacagt agactttaat 420
ctctttaagg acaggaactg tgtcttgttt agaatcccca gagcttattt agtacaatgg 480
ctatgcttat aatttaagta tttattgaac aaatgaaatt ttcctaagcc ctaaaacctt 540
gcaagatgtt ttagtgcagg aaactggcct cggtggagtt gaataactag cacgaggtca 600
ctcacctaaa aagtggtgag gagggattaa aatctaaatc tgtttagctg taaagattgg 660 gctttttyc ttgctgctgc acatgactgc yctctctcat gttgcctgta cacatccctg 720
tcaagtgttc aaacagcccg tgcctaacaa ccccatccat agcttctgag gaaagttgtg 780
tcatctttgg acagctctga gagctgaagc gagtctttgc agaataattt cccatctatt 840
ggtcttaatt tatgctttgg agaatataac ttattttcaa aaaacaaatg attcagaatt 900
tgtcatctcc ttaaggtccg tttattagtt tatttcattc cttcattcac tgataaccat 960
ttactgagca ccagcctggg caacatggtg agaacccatc tctaccaatt taaaaaaaaa 1020
aaaaaagggc ggccgctcta gaggatccaa gcttacgtac gcgtgcatgc gacgtcata 1079

<210> SEQ ID NO 62
<211> LENGTH: 1928

-continued

<212> TYPE: DNA
<213> ORGANISM: Homo sapiens

<400> SEQUENCE: 62
ggcacgagag taggtctgcc ggcgatggag tggtgggcta gctcgccgct tcggctctgg 60
ctgctgttgt tcctcctgcc ctcagcgcag ggccgccaga aggagtcagg ttcaaaatgg 120
aaagtattta ttgaccaaat taacaggtct ttggagaatt acgaaccatg ttcaagtcaa 180
aactgcagct gctaccatgg tgtcatagaa gaggatctaa ctcctttccg aggaggcatc 240
tccaggaaga tgatggcaga ggtagtcaga cggaagctag ggacccacta tcagatcact 300
aagaacagac tgtaccggga aaatgactgc atgttcccct caaggtgtag tggtgttgag 360
cactttattt tggaagtgat cgggcgtctc cctgacatgg agatggtgat caatgtacga 420
gattatcctc aggttcctaa atggatggag cctgccatcc cagtcttctc cttcagtaag 480
acatcagagt accatgatat catgtatcct gcttggacat tttgggaagg gggacctgct 540
gtttggccaa tttatcctac aggtcttgga cggtgggacc tcttcagaga agatctggta 600
aggtcagcag cacagtggcc atggaaaaag aaaaactcta cagcatattt ccgaggatca 660
aggacaagtc cagaacgaga tcctctcatt cttctgtctc ggaaaaaccc aaaacttgtt 720
gatgcagaat acaccaaaaa ccaggcctgg aaatctatga aagatacctt aggaaagcca 780
gctgctaagg atgtccatct tgtggatcac tgcaaataca agtatctgtt taattttcga 840
ggcgtagctg caagtttccg gtttaaacac ctcttcctgt gtggctcact tgttttccat 900
gttggtgatg agtggctaga attcttctat ccacagctga agccatgggt tcactatatc 960
ccagtcaaaa cagatctctc caatgtccaa gagctgttac aatttgtaaa agcaaatgat 1020
gatgtagctc aagagattgc tgaaagggga agccagttta ttaggaacca tttgcagatg 1080
gatgacatca cctgttactg ggagaacctc ttgagtgaat actctaaatt cctgtcttat 1140
aatgtaacga gaaggaaagg ttatgatcaa attattccca aaatgttgaa aactgaacta 1200
tagtagtcat cataggacca tagtcctctt tgtggcaaca gatctcagat atcctacggt 1260
gagaagctta ccataagctt ggcacctata ccttgaatat ctgctatcaa gccaaatacc 1320
tggttttcct tatcatgctg cacccagagc aactcttgag aaagatttaa aatgtgtcta 1380
atacactgat atgaagcagt tcaacttttt ggatgaataa ggaccagaaa tcgtgagatg 1440
tggattttga acccaactct acctttcatt ttcttaagac caatcacagc ttgtgcctca 1500
gatcatccac ctgtgtgagt ccatcactgt gaaattgact gtgtccatgt gatgatgccc 1560
tttgtcccat tatttggagc agaaaattcg tcatttggaa gtagtacaac tcattgctgg 1620
aattgtgaaa ttattcaagg cgtgatctct gtcactttat tttaatgtag gaaaccctat 1680
ggggtttatg aaaaatactt ggggatcatt ctctgaatgg tctaaggaag cggtagccat 1740
gccatgcaat gatgtaggag ttctcttttg taaaaccata aactctgtta ctcaggaggt 1800
ttctataatg ccacatagaa agaggccaat tgcatgagta attattgcaa ttggatttca 1860
ggttcccttt ttgtgccttc atgccctact tcttaatgcc tctctaaagc caaaaaaaaa 1920
aaaaaaaa 1928

<210> SEQ ID NO 63
<211> LENGTH: 781
<212> TYPE: DNA
<213> ORGANISM: Homo sapiens

<400> SEQUENCE: 63

-continued

```
ggcacgagat tttcagcctt tttggactgg tttctccaca tcttcgtgga tttatctaac     60

tttggtcttt gatgttggtg accttcagat tgggtctctg agtgaacatc ctttttgttg    120

atgttgatac tattcctttc tgtttgtttg tttgttttcc ttctaacagt cagggccctc    180

tgctgcaggt ctgctggagt ttggttgagg tccactccag accctgtttg tctgggtttt    240

gccagaggag gctgcagaat agcaatgatt gctgcctgtt tttcctctgg aagctttgtc    300

ccagaggggc acccaccaga tgccagccag agctctcctg tatgaggtgt ctgttggccc    360

atacttggag gtgccttcca gtcaggatac acaggtgtca ggtacccact tgaggaggca    420

ctctgtcccc tatcagagct cgaacactgt gctgggagat ccactgttct cttcagagct    480

gtcagacagg gacgtttaag tctgctgaag ctatgcccac agctgcccct ttccccagat    540

gctctgtccc agggagaagg gagttttatc tataagtctc tgactggggc tgctgccttt    600

tcttcagaga tgccctgccc caagacgggg actctagaga ggcagtctgg ctgcagtggc    660

cttgctgaac tgtggtgggc ttcacccagt tggaccttcc ctgagccttt tttttaccc    720

tgtgagggta aaaatgccta atcaagcctc agcaatggtg gatgcccttc cccccaccaa    780

g                                                                    781
```

```
<210> SEQ ID NO 64
<211> LENGTH: 1194
<212> TYPE: DNA
<213> ORGANISM: Homo sapiens
<220> FEATURE:
<221> NAME/KEY: SITE
<222> LOCATION: (1172)
<223> OTHER INFORMATION: n equals a,t,g, or c

<400> SEQUENCE: 64

ggcacgagaa gacatggagt cttaagtgtg atcagtggga gggggctgga atcatttaga     60

ggcatcttca ttcacaaaac caggagctga tactggctgt cagccaggac ttcaactgac    120

ctatgtagaa cctgtccatg tggcccctcc ttgcagtctc cccatttggg ctggtttggg    180

cttcatcaca gtccggcagc ttacttctaa gggcaagcat tccacgacaa cacagcagaa    240

gggcatggca tttttacagt gaagtttggc aatctcatag cgtcgcttct gtcctacttt    300

atttattggt cagggcaatc acaaagatgt gcataggctc aaagaaaaga gacataaccc    360

cgaccacgcg atggaagaag tgacacggtc atgttatgag aggagtgtgt gggatgggag    420

atagggctgt ggccacctgc agaaaacagc atctgctata ggctgtcatg gaagcgcagg    480

atggggattt agcctacctg aggggtcagt cagcaaaggc ctctgggagg aagtgagatc    540

ttcggctgag gatgtgaagg gctaaaagga gaatgaggaa gagtttcagg gagaggaatc    600

aatgaaacga gtccagagac gctggtgagt tggatggttt gcttcagtat gatgacaata    660

cagaggggca aggagactgg tgcaggagaa gagagaaggt gccatgtgct ctgggtcgtg    720

tcttctatgc cagactccct tagaagagga gcagcctcca gtcagcggtg tcccaggaac    780

acggaggcta gacaggacaa tggcagccaa tccctgctcc caaactggtg acagtgggga    840

aaagctgcat ggtctagatc caccctgctc cctggcccca gtatagaaga tcaaattcaa    900

tctgcccaat cttatccaga taaagtaaag gaagactgga aaaaagaact aatccacggc    960

tccatctgcc catgactttc tctgctgatg ccggaggcag ctatggataa agagacggca   1020

cacggcatgt cccgacgctg tggaggtggg gagaccccgc aagtccacag gaaaagagtt   1080

aagttgctgc cacctgggca tccgctattc tctgctcttc tgcctcatcc tcaattcaga   1140

ccatgatgga gctgattgtc tcccatttta tnccttggat tgaatggtct cgag         1194
```

-continued

<210> SEQ ID NO 65
<211> LENGTH: 1677
<212> TYPE: DNA
<213> ORGANISM: Homo sapiens
<220> FEATURE:
<221> NAME/KEY: SITE
<222> LOCATION: (1012)
<223> OTHER INFORMATION: n equals a,t,g, or c

<400> SEQUENCE: 65

```
ggtgcagtgg tgccatcaca gttcactgca gccttgacct cccgggctca agcaatcctc     60
ccacctcagc cacttgagta gctgagacct cagatatgtg ccatcacacc cagctgattt    120
tttaaaatta attttttgta gagatagggt ctcatatgtt gcccatgctg gtctcaaact    180
actgggttca aatgatcctc ctgcctcagc cttccaaagt actgggatta caggcatgag    240
ccaccatgcc gggctgggag gcggaatttt gttcagtcta aagataagct ttttcatagc    300
tctggctgta gtgggaggga gcagaggagt gaatgattgt cagttgggag ggtgcagagt    360
gggctcctgc cctagggtgr aggtragggt ggcttaggtg asmcamcaca gaggccctgt    420
tcagccccac gtcccctccc tgtgctccct cctcctctct cctctcctgc aggcgtggra    480
ggtatcatca ttcagcagat ttcaccagag gcagtggagg aggcaggtac ctgagccaga    540
attcagaatg tcttattctc cacttgactc tgccactaac ttgttgtgca actttgggcc    600
tttccccagg ccttcatttt cttttctttt ctttttcttt yttttttttt gaggcggagt    660
ctcgctatgt tgcccaggct ggagtgcagt ggcgcagcat catctcggct cactgcaagc    720
tccaccttct gagttcacgc cattctactg cctcagcctc ccgagtagcc gggactgcag    780
gcrcccacca ccacgcccgg cttatttttt gtatttttag tagagacagg gtttcaccac    840
gttagccaag atggtctcga tctcctgacc tcgtgatcca cccgcctggg cttcccaaag    900
tgctgggatt acaggcgtga gccactgcgc ccggccattt tcttaaatat ctaataaaaa    960
atatatagca aatgcagttt ttaaactacg acaatatgac cacgcaaaag antattatct   1020
tccaagactg ctggtccaag gaaaagtcag taataaagtg gaagcattgt agcttatgga   1080
atgactggtt asatttggga gaagccttag caataatcta gaatctgcat agataataca   1140
tctgaggatt gggctttgtg gtttacaaag cattttttttt tcctcttttg atcccagccg   1200
tttgtctgga ctgatacaaa gcatttttat tagtttgtct tattcaatcc tcacaccacc   1260
tcaaatttac agaggatatg gatctggtta atttgtatga ctatgtaacc tcatgtcagt   1320
ccacagcact gcctggaggt gggtagaggt ggtcctgggc tggaatccca gccccagtgg   1380
gaccttgagc aagttacttt agctgtctgc acctaaattt cctcactggc aaaacaggaa   1440
tactggtggt tcacacctgc aattccagca ctttgggagg ctgaggtggg aggattgctt   1500
gagtccagaa gttcaaaacc agactgggca acatagcaag accatctcta caaaaattaa   1560
ataaataaaa catttacaag ggttgtggtg aagattaaat gagatcactc acgaaaaagc   1620
tcagcagacc ctgatgtgca gtaggtgctc aataaatgtt agccagcaaa aaaaaag      1677
```

<210> SEQ ID NO 66
<211> LENGTH: 1237
<212> TYPE: DNA
<213> ORGANISM: Homo sapiens

<400> SEQUENCE: 66

```
agcaaaccca ggaaggtgtg gcgtccccgc ttcgcgccaa gatggtgctg gtgctgcgcc     60
```

-continued

```
atcctttgtg tgcccgggaa agggcgttcc gggagccggg tcgggggctc ctgactcgca    120

ctgggcagca tgacggtgcg ccggctgtca ctgctgtgcc gggacctctg ggcgctgtgg    180

ctgctgctga aggccggcgc agtgcgtggg gcgcgggcgg gtcctcgcct ccccggaagg    240

tgttgtgggg cgacatgcgg ggacgccggg cgggggtgga cgttctgggc ccagccctgt    300

cctcagaagc tgctggggca gaagcccggg gctgggggat gccggggatg ggtgttgggg    360

tgggtgcctc cgagaccaga ggagccctgt tccttggcag ggaaggtgtg cacgggcctt    420

gcccgatgga tggtttaggg ccatggccct ggggtccctg gtgagcagtg gggccgcctc    480

tgcccttggc ctgtgaggga ctgtctgtgc tggtcccaga aggctgggat cacctttcca    540

ctggctcctt tgttcgaggt ttttcataga caggctatgt ggacaaatga gggcagcgcc    600

cacgtctggc tggtggaggg gctgcggctc ctccttggag gggacgcctg gccactgctg    660

tccccacaat ggggccaccc gtggtgcaag gcgtgacaag ctgccctctc taggtaagca    720

ggacttggga ggcccctggc caagcctgtg gacccggctg ggcggcctct gtggtctcag    780

gtttgggtgt gtttggtctg gtcagggctc aggggctgct ggtccacact ggccccatcc    840

tgacaattgg agctttgggg caaggtccct ggagaagggg tcacgtcggg aggaaacagc    900

ctgggttttg ttgatgcttt tctaagaatg gagtactcgt tttcaagaga tttgtcctaa    960

ttatattttc cagcgggtac ttatgccaag tattgatgaa taattcataa aataagcatc   1020

tttgtgaatt ttagtgaatc agaccttaac tatcaacggc aatgaatgaa catctaaagt   1080

ttccaatttt aaagtaaaga actggctggg tacagcagtt cacgcctgta atcccagcac   1140

tttgggaggc caaggctaga ggatcgcttg agcccaggag tttgagatca gcctgggcaa   1200

cataccaaga cctcatctgt taaaaaaaaa aaaaaaa                            1237
```

```
<210> SEQ ID NO 67
<211> LENGTH: 1934
<212> TYPE: DNA
<213> ORGANISM: Homo sapiens

<400> SEQUENCE: 67

ccacgcgtcc ggggcgttcc tggtcgtgag aggggagccc caggggagct ggggcagcat     60

gactggggtg ataaatggcc ggaaatttgg cgtggccaca ctcaacacca gcgtgatgca    120

ggaggcacac tccggggtca gcagcatcca cagcagcatc cgccatgtcc cagcaaacgt    180

ggggcctctg atgcgggtgc tcgtggtcac catcgccccc atctactggg ccctggccag    240

agagagtggg gaagccctga atggccactc tctgactggg ggcaagttcc ggcaggagtc    300

acacgtggag tttgctacag gggagctgct cacgatgacc cagtggcccg gggtctggat    360

cccgatggcc tcctgctcct cgacgtggtg gtcaatggcg ttgtccccgg acagcctggc    420

tgacgcagat cttcaagtgc aggactttga ggagcactac gtgcaaacag ggcctggcca    480

gctgttcgtg ggctccacac agcgcttctt ccagggcggc ctcccctcgt tcctacgctg    540

caaccacagc atccagtaca acgcggcccg gggcccccag ccccagctgg tgcagcacct    600

gcgggcctca gctatcagct cggcctttga tccagaggcc gaggccctgc gcttccagct    660

cgctacagcc ctgcaggcgg aggagaacga ggtcggctgc cccgagggct ttgagctgga    720

ctcccaggga gcgttttgtg tggatgtgga cgagtgtgcg tgggatgctc acctctgccg    780

agagggacag cgctgtgtga acctgctcgg gtcctaccgc tgcctccccg actgtgggcc    840

tggcttccgg gtggctgatg gggccggctg tgaagatgtg gacgaatgcc tggaggggtt    900

ggacgactgt cactacaacc agctctgcga gaacacccca ggcggtcacc gctgcagctg    960
```

-continued

```
ccccaggggt taccggatgc agggccccag cctgccctgc ctagatgtca atgagtgcct   1020

gcagctgccc aaggcctgcg cctaccagtg ccacaacctc cagggcagct accgctgcct   1080

gtgcccccca ggccagaccc tccttcgcga cggcaaggcc tgcacctcac tggagcggaa   1140

tggacaaaat gtgaccaccg tcagccaccg aggccctcta ttgccctggc tgcggccctg   1200

ggcctcgatc cccggtacct cctaccacgc ctgggtctct ctccgtccgg gtcccatggc   1260

cctgagcagt gtgggccggg cctggtgccc tcctggtttc atcaggcaga acggagtctg   1320

cacagacctt gacgagtgcc gcgtgaggaa cctgtgtcag cacgcctgcc gcaacactga   1380

gggcagctac cagtgcctgt gccccgccgg ctaccgtctg ctccccagcg ggaagaactg   1440

ccaggacatc aacgagtgcg aggaggagag catcgagtgt ggacccggcc agatgtgctt   1500

caacacccgt ggcagctacc agtgtgtgga cacaccctgt cctgccacct accggcaggg   1560

ccccagccct gggacgtgct tccggcgctg ctcgcaggac tgcggcacgg gcggcccttc   1620

tacgctgcag taccggctgc tgccgctgcc cctgggcgtg cgcgcccacc acgacgtggc   1680

ccgcctcacc gccttctccg aggtcggcgt ccccgccaac cgcaccgagc tcagcatgct   1740

ggagcccgac ccccgcagcc ccttcgcgct gcgtccgctg cgcgcgggcc ttggcgcggt   1800

ctacacccgt cgcgcgctca cccgcgccgg cctctaccgg ctcaccgtgc gtgctgcggc   1860

accgcgccac caaagcgtct tcgtcttgct catcgccgtg tccccctacc cctactaaac   1920

gggagagggc attg                                                     1934
```

<210> SEQ ID NO 68
<211> LENGTH: 3300
<212> TYPE: DNA
<213> ORGANISM: Homo sapiens
<220> FEATURE:
<221> NAME/KEY: SITE
<222> LOCATION: (1)
<223> OTHER INFORMATION: n equals a,t,g, or c
<220> FEATURE:
<221> NAME/KEY: SITE
<222> LOCATION: (3)
<223> OTHER INFORMATION: n equals a,t,g, or c
<220> FEATURE:
<221> NAME/KEY: SITE
<222> LOCATION: (15)
<223> OTHER INFORMATION: n equals a,t,g, or c

<400> SEQUENCE: 68

```
ncngcagccg gacgnccgag cgcagcgagt cagtgagcga ggaagcggaa gagcgcccaa     60

tacgcaaacc gcctctcccc gcgcgttggc cgattcatta atgcagctgg cacgacaggt    120

ttcccgactg gaaagcgggc agtgagcgca acgcaattaa tgtgagttag ctcactcatt    180

aggcacccca ggctttacac tttatgcttc cggctcgtat gttgtgtgga attgtgagcg    240

gataacaatt tcacacagga aacagctatg accatgatta cgccaagctc gaaattaacc    300

ctcactaaag ggaacaaaag ctggagctcc accgcggtgg cggccgctct agaactagtg    360

gatcccccgg gctgcaggaa ttcggcacga gaacacatct taagggaacc aagtctcaag    420

agaaatcaag taattatgaa tgaacagctc taaaaaagag agagagaata ttttcttaaa    480

tcaacttagt tgctgttatg accaaagaac agatgttgtg gtgttcaccc cagagaagca    540

agagattttc ccttaaacct cagcttataa tgaatggaag tgaatgacag ggagagagtt    600

tttctctcgt ttcccagaac tctatccttt tcttctcaaa cagttggaaa ctgtagccaa    660

tacagtagac agtgatatgg gagaaccaaa tcgtcatcca agcatgtttc tcttactttt    720
```

-continued

```
ggtgttggag agactctacg cttccccgat ggatggtact tcttctgctc tcagcatggg    780
accttttgtt cccttcatta tgaggtgtgg tcactcacct gtctaccact cccgtgaaat    840
ggcagctcgt gccttggtcc catttgttat gatagatcac attcctaata ccattcgaac    900
tctgttgtcc acactcccca gctgcactga ccagtgtttc cggcaaaacc acattcatgg    960
gacacttctc caggtttttc atttgttgca agcctactca gactccaaac acggaacgaa   1020
ttcagacttc cagcacgagc tgactgacat cactgtttgt accaaagcca aactctggct   1080
ggccaagagg caaaatccat gtttggtgac cagagctgta tatattgata ttctcttcct   1140
attgacttgc tgcctcaaca gatctgcaaa ggacaaccag ccagttctgg agagtcttgg   1200
cttctgggag gaagtcagag ggattatctc aggatcagag ctgataacgg gattcccttg   1260
ggccttcaag gtgccaggcc tgccccagta cctccagagc ctcaccagac tagccattgc   1320
tgcagtgtgg gccgcggcag ccaagagtgg agagcgggag acgaatgtcc ccatctcttt   1380
ctctcagctg ttagaatctg ccttccctga agtgcgctca ctaacactgg aagccctctt   1440
ggaaaagttc ttagcagcag cctctggact tggagagaag ggcgtgccac ccttgctgtg   1500
caacatggga gagaagttct tattgttggc catgaaggaa aatcacccag aatgcttctg   1560
caagatactg aaaattctcc actgcatgga ccctggtgag tggcttcccc agacggagca   1620
ctgtgtccat ctgaccccaa aggagttctt gatctggacg atggatattg cttccaatga   1680
aagatctgaa attcagagtg tagctctgag acttgcttcc aaagtcattt cccaccacat   1740
gcagacatgt gtggagaaca gggaattgat agctgctgag ctgaagcagt gggttcagct   1800
ggtcatcttg tcatgtgaag accatcttcc tacagagtct aggctggccg tcgttgaagt   1860
cctcaccagt actacaccac ttttcctcac caacccccat cctattcttg agttgcagga   1920
tacacttgct ctctggaagt gtgtccttac ccttctgcag agtgaggagc aagctgttag   1980
agatgcagcc acggaaaccg tgacaactgc catgtcacaa gaaaatacct gccagtcaac   2040
agagtttgcc ttctgccagg tggatgcctc catcgctctg gccctggccc tggccgtcct   2100
gtgtgatctg ctccagcagt gggaccagtt ggcccctgga ctgcccatcc tgctgggatg   2160
gctgttggga gagagtgatg acctcgtggc ctgtgtggag agcatgcatc aggtggaaga   2220
agactacctg tttgaaaaag cagaagtcaa cttttgggcc gagaccctga tctttgtgaa   2280
atacctctgc aagcacctct tctgtctcct ctcaaagtcc ggctggcgtc cccaagccc    2340
tgagatgctc tgtcaccttc aaaggatggt gtcagagcag tgccacctcc tgtctcagtt   2400
cttcagagag cttccaccag ctgctgagtt tgtgaagaca gtggagttca caagactacg   2460
cattcaagag gaaaggactt tggcttgctt gaggctgctg gcctttttgg aaggaaagga   2520
aggggaagac accctagttc tcagtgtttg ggactcttat gcagaatcga ggcagttaac   2580
tcttccaaga acagaagcgg catgttgaag aaaatctggg ggattgggat gggggtatgt   2640
gtggattttt cctccactaa atctgcagga aacatgttga acataaattc aaaaatttta   2700
tcccaaaaaa aaaaaaaaaa aaactcgagg gggggcccgg tacccaattc gccctatagt   2760
gagtcgtatt acaattcact ggccgtcgtt ttacaacgtc gtgactggga aaaccctggc   2820
gttacccaac ttaatcgcct tgcagcacat ccccctttcg ccagctggcg taatagcgaa   2880
gaggcccgca ccgatcgccc ttcccaacag ttgcgcagcc tgaatggcga atggcaaatt   2940
gtaagcgtta atattttgtt aaaattcgcg ttaaattttt gttaaatcag ctcatttttt   3000
aaccaatagg ccgaaatcgg caaaatccct tataaatcaa aagaatagac cgagataggg   3060
ttgagtgttg ttccagtttg gaacaagagt ccactattaa agaacgtgga ctccaacgtc   3120
```

-continued aaagggcgaa aaaccgtcta tcagggcgat ggcccactac gtgaaccatc accctaatca 3180
agttttttgg ggtcgaggtg ccgtaaagca ctaaatcgga accctaaagg gagcccccga 3240
tttagagctt gacggggaaa gccggcgaac gtggcgagaa aggaagggaa gctgtctctt 3300

<210> SEQ ID NO 69
<211> LENGTH: 1797
<212> TYPE: DNA
<213> ORGANISM: Homo sapiens

<400> SEQUENCE: 69
ggtcgacggt atcgataagc ttgatatcga attcctgcaa cagttcttgg aaacccactc 60
gagagggcca cgcctccatt caccaggcca cgcatcacaa gaggcaacac caggagccaa 120
catgagctcg gggactgaac tgctgtggcc cggagcagcg ctgctggtgc tgttgggggt 180
ggcagccagt ctgtgtgtgc gctgctcacg cccaggtgca aagaggtcag agaaaatcta 240
ccagcagaga agtctgcgtg aggaccaaca gagctttacg gggtcccgga cctactcctt 300
ggtcgggcag gcatggccag gacccctggc ggacatggca cccacaagga aggacaagct 360
gttgcaattc taccccagcc tggaggatcc agcatcttcc aggtaccaga acttcagcaa 420
aggaagcaga cacgggtcgg aggaagccta catagacccc attgccatgg agtattacaa 480
ctgggggcgg ttctcgaagc cccagaaga tgatgatgcc aattcctacg agaatgtgct 540
catttgcaag cagaaaacca cagagacagg tgcccagcag gagggcatag gtggcctctg 600
cagaggggac ctcagcctgt cactggccct gaagactggc cccacttctg gtctctgtcc 660
ctctgcctcc ccggaagaag atgaaggaat ctgaggatta tcagaacttc agcattccat 720
ccattcagtg gcgcgagtcc aggaaggtca tggggcaact ccagagaaga aagcatcccc 780
tggcccggtg ggaagcccag acgaggagga cggggaaccg gattacgtga atggggaggt 840
ggcagccaca gaagcctagg gcagaccaag aagaaaggag ccaaggcaaa gagggaccac 900
tgtgctcatg gacccatcgc tgccttccaa ggaccatttc ccagagctac tcaactttta 960
agcccctgcc atggttgctc ctggaaggag aaccagccac cctgaggacc acctggccat 1020
gcgtgcacag cctgggaaaa gacagttact cacgggagct gcaggccccg tcaccaagcc 1080
ctctcccgac ccaggctttg tggggcaggc acctggtacc aagggtaacc cggctcctgg 1140
tatggacgga tgcgcaggat ttaggataag ctgtcaccca gtccccataa caaaaccact 1200
gtccaacact ggtatctgtg ttcttttgtg ctatgaattt ggattcctaa ttgctattgt 1260
tggttgctgg ggttttaaat gattgataag cttgtacagt taacttatag agggggagcc 1320
atatttaaca ttctggattt cagagtagag atttctgtgt tgtctcctag aaagcattac 1380
atgtagttta tttcagcatc cttgttgggt ggggccctgg ctctcttccc ctttggtggg 1440
acctcccctt tctttgggct tcagttcact caggaagaaa tgaggctgtc gccatcttta 1500
tgtgcttcca gtggaaatgt cacttgctac agacaatagt gcatgagagt ctagagaagt 1560
agtgaccaga acagggcaga gtaggtcccc tccatggccc tgaatcctcc tctgctccag 1620
ggctggcctc tgcagagctg attaaacagt gttgtgactg tctcatggga agagctgggg 1680
cccagaggga ccttgagtca gaaatgttgc cagaaaaagt atctcctcca accaaaacat 1740
ctcaataaaa ccattttagt tgaaaaaaaa aaaaaaaaaa aaaaaaaaaa aaaaaaa 1797

<210> SEQ ID NO 70
<211> LENGTH: 1373
<212> TYPE: DNA

-continued

<213> ORGANISM: Homo sapiens

<400> SEQUENCE: 70
ggcacgaggg ctgacggcgc ttttgtctcc ggtgagtttt gtggcgggaa gcttctgcgc 60
tggtgcttag taaccgactt tcctccggac tcctgcacga cctgctccta cagccggcga 120
tccactcccg gctgttcccc cggaggtcca gaggcctttc agaaggagaa ggcagctctg 180
tttctctgca gaggagtagg gtcctttcag ccatgaagca tgtgttgaac ctctacctgt 240
taggtgtggt actgacccta ctctccatct tcgttagagt gatggagtcc ctagagggct 300
tactagagag cccatcgcct gggacctcct ggaccaccag aagccaacta gccaacacag 360
agcccaccaa gggccttcca gaccatccat ccagaagcat gtgataagac ctccttccat 420
actggccata ttttggaaca ctgacctaga catgtccaga tgggagtccc attcctagca 480
gacaagctga gcaccgttgt aaccagagaa ctattactag gccttgaaaa acctgtctaa 540
ctggatgctc attgcctggg caaggcctgt ttaggccggt tgcggtggct catgcctgta 600
atcctagcac tttgggaggc tgatgtgggt ggatcacctg aggtcaggag ttcagaccag 660
cctcgccaac atggcgaaac cccatctcta ctaaaaatac aaaagttagc tgggtgtggt 720
ggcagaggcc tgtaatccca gctccttggg aggctgaggc gggagaattg cttgaacccg 780
gggacggagg ttgcagtgag ccgagatcgc actgctgtac ccagcctggg ccacagtgca 840
agactccatc tcaaaaaaaa aagaaaagaa aaagcctgtt taatgcacag gtgtgagtgg 900
attgcttatg gctatgagat aggttgatct cgcccttacc ccggggtctg gtgtatgctg 960
tgctttcctc agcagtatgg ctctgacatc tcttagatgt cccaacttca gctgttggga 1020
gatggtgata ttttcaaccc tacttcctaa acatctgtct ggggttcctt tagtcttgaa 1080
tgtcttatgc tcaattattt ggtgttgagc ctctcttcca caagagctcc tccatgtttg 1140
gatagcagtt gaagagtgtg tgggtgggct gttgggatga gatggagtgt tcagtgccca 1200
tttctcattt tacattttaa agtcgttcct ccaacatagt gtgtattggt ctgaaggggg 1260
tggtgggatg ccaaagcctg ctcaagttat ggacattgtg gccaccatgt ggcttaaatg 1320
atttttttcta actaataaag tgggatatat atttaaaaaa aaaaaaaaaa aaa 1373

<210> SEQ ID NO 71
<211> LENGTH: 1579
<212> TYPE: DNA
<213> ORGANISM: Homo sapiens

<400> SEQUENCE: 71
ggcacgagga tttggagggg acaaacatcc aaaccattta agtcacagca ctttactccg 60
cagtgtgaat aacacaggca ttctcctaca taatcacagt acagttatca tactctggaa 120
attgaatatc atctaatata ctttccatac ccagattttc ttagatttcc caatgatatt 180
tcttactgtc ctccctttag ccttcctctt tctccattca ggattctacc attacatttc 240
attttcatgt ctcttcagtc tctctttagc tttgtttttc tttcttgatg ttgccacttt 300
taggaggcca ggccagttgt tttgtgaaag atctgttctc tttgatatgt ttcattttgg 360
atttgtttca ttgtttttgc atgaatggat tcaggctaaa catttttggg caggactgtt 420
tattgtatta cctagtgatg tgttcttttc agtccatcat ctggaggcac ctgatggcag 480
ttttcccaat attgcgaaat taagtttgat tattttgtta aggtagtgtc caccagatct 540
ctccatttta aagacatcct tttctctaat tactcagtgg actgtagagt gatgctttga 600
aactgaataa ctaacactcc ctaactcagt gatttagcac ccgttgattt ttttttttg 660

-continued

```
cctgaatcaa atattattat agtagtttta aatggtgatt ttccatttct attcttttgt    720
tagctgccat tcttctataa ttttgtcttt atattttact gggtgttaag attgctattc    780
cagctttcct ttgtctttta caccttttcc cattctttta tttttttcca tcccttttttg   840
tcctgttttc caatagatgg atagaatttt ctttctctgg tttaaaggtt atacatttgt    900
gtgtgtgtgt gtattctaaa ccatttgccc ttaaaacata gagatggtta ttcctgttga    960
ttaaaaaaaa ctcagtaatg ttactatctt ctctttaata agataggtac tttatttcat   1020
tctgtgttct tgggtgaggt ctcccctcac ccagtcaagt tgatgttaat ctagaatttt   1080
tagtttttta aattatcgat atactttctg tcttttcctt tttttttcac tctctctgta   1140
tttgtgcttt cccccttac tctctttccc ttcattcctt ctttctcact ttcttcttct    1200
atttttcact cttgggtaga ttatctttta gaaaacagca agatattata taatttactt   1260
tatattctct ttccaaatga ttaaagtaat aattaaaaat ttttgatatg tgtgtatgca   1320
aggataggaa tcctcttgta agtggaagaa ctctaccaca tgcatgagtc attagtgtgt   1380
taaacactgg gaagtggctt taggtccagc tgggtgctct gaagaaggta ggtttcttca   1440
gttctttatg ttaactgtct ccttacctta aaaaaggagt gaagaatact gactgcagag   1500
gttttgtgag gattccggta acacagaagc atagaactgg aaaagaatat taatatttgc   1560
caaaaaaaaa aaaaaaaaa                                                1579
```

<210> SEQ ID NO 72
<211> LENGTH: 1028
<212> TYPE: DNA
<213> ORGANISM: Homo sapiens

<400> SEQUENCE: 72

```
gcacgacaat tgaactgaac cctaaaaatg ctacttcaat tcaccttatg ggtatttggt     60
gctatacatt tcccgaaatg ccttggtatc aaagaagaat tgctaaaatg ctgtttgcaa    120
ctgcctccta gttccaccta tgagaaggta gtatgatgtc ctttgttaag ttagtacgga    180
tttcttgaac cacagcgccc attctaccat gtgttccaca cattgtggag ctctggattc    240
agtgaagggg acttgaggca atttccttaa cgatccaatt caactgtgtt atcacaaggc    300
ttaacactta ttatccttga ctggtgagtg gttttctttt tccccgttag gtgagtggct    360
ggtaattctg gaatactgtc atctaaaatg gctcgtggct aaaatctacc ttcattttct    420
gtttgaaatc taaactatat tgaagtcata aaatagaaca agaaatacag catctgttac    480
ccagcatgtt ttagctgtat tacacacaat aacagaaaag taaagcagat gcttaagttg    540
ataaaagaag aacactcatt ataacttcta ttttaaaaag catatgaaag gttcatattc    600
tctcatattt tcaaggcctt ttgcttttct tgttaaaaat aagatttgag aggaatttct    660
ggttaaactt tgggtttact catcacaagc ttttcagagt aagaaaacag gcaatcgaaa    720
aagctgtact tgtattattt acattataac aaggagcctt tttttctttc tgggaagcta    780
tagtgtagaa attgatgtaa aaaatactta gttgtattct ttacacacag ttgagaaata    840
ttattaaaat aatgcaccaa tattttataa tggtattatt aaaataatgc ccatttgctg    900
gacacggtgg ctcatgcctg taatgccagc attttggaag gccaaggttg gtggatcagt    960
tgagcctggg agtttgagac cagcctgggc aacgtggcaa aacccctgca aaaaaaaaaa   1020
aaaaaaaa                                                            1028
```

<210> SEQ ID NO 73

-continued

<211> LENGTH: 3674
<212> TYPE: DNA
<213> ORGANISM: Homo sapiens

<400> SEQUENCE: 73
ggcacgagct caaaagaaat agggtgattt ttaaaggatt aataaaattc tgaaatgtta 60
agtagaagat tacattgtct agtcttgtat ttcctccttc tgttgctctc tttcattcac 120
acactctcag tttctcatat ttgtagctca tttatttggt tatttcctaa gaatattgaa 180
agtgaagcaa ctatgtgact gtattcttca ggtaaacact gactgcgctt gttggatttt 240
ccctattttt gtgacttcaa gaataatatg ccctgctgaa tacatgccat ttcacattct 300
gaaactgggt agagtggttg ggtgttctgc caacaattgc tagtggtgtg aattcattca 360
tatttgccag tattgctcac ttcaaagaaa ctccttcatc aagcagtcca gagctaggcc 420
agatcaatgc tacaatcatg aagttctcat tgcatgcaat tgtgtaggat tgacaaggaa 480
ctcagataaa aatttccagg gtgcacttcc agaaccagct tcaacatatg tctacattgc 540
ccccaagtta ataaagtgcc aaccctttac tctctcatac agccagaaat gttagaaatc 600
caaaatcttg gtgcattatt ttttcataaa cgctaaaaca tttgaagaaa caatttaatt 660
atttaaaatt caagtatttt attcacatta tttgcaatat ccaaatgttt aaaaattccc 720
agataattaa ctagctatta cagatctcac ctagagggtt gatgttatga agactccagt 780
ggactgtact cacaaattga ctggacaccc tatgaaagtg ggtagacctc tcagcggaaa 840
ataagaaggg cttttaccta cagggcagga cagggtccca tgagagcagt tctgtggaga 900
tataaaaaga atggaagaag gaatgcctta tagtgatatt gtgacattat atctatatat 960
ctacatatat ctatctatct atatctacat ctatataatc ttacatttaa aattgtattc 1020
ctacacatat tagaaactct tctaataaat gaagtaaaaa aattaaaaag aatacaaata 1080
ttccagcccc aaatgagaaa tcaaacatat taaaattgtt caagaaaatt tctttgaaca 1140
cttctgaaag tttttggaaa cttagaaaag agggaaaaaa atccagtgtt actagtaatt 1200
tccatggtaa tacagataaa atacattctt ttaattctgg gaaattagaa aaagtggggt 1260
gatctttcca ggaaaaacat gtgtaacatc tgcttatcac tccagctccc tcctcctcct 1320
cctctccacg ttcccttgag taaatgtctg ggaaagcatg aagcttgatg caagaaccct 1380
gttgtactgg cgttttcctc ccctgtgaaa acgtaactac tgttgggagt gaattgagga 1440
tgtagaaagg tggtggaacc aaattgtggt caatggaaat aggagaatat ggttctcact 1500
cttgagaaaa aaacctaaga ttagcccagg tagttgcctg taacttcagt ttttctgcct 1560
gggtttgata tagtttaggg ttggggttag attaagatct aaattacatc aggacaaaga 1620
gacagactat taactccaca gttaattaag gacgtatgtt ccatgtttat ttgttaaagc 1680
agtgtgaata gccttcaagc atgtgaataa tcttccatct tccccgccac acatacacac 1740
acacactttt tgtttctttc aggtagacac cttttaaaat gcagaactaa ctgaggcatt 1800
tcagtaactt tgctttcaaa tcaataaagt caaatgtatg gaaacatttt gtgccctact 1860
ctccataccc cgtgtactca aattctctac tgtatgaatt atgctttaag tagaattcag 1920
tgccaaggag aacttggtga aataaattat tttaattttt tttttatcct ttacaaagcc 1980
atggatttta tttggttgat gtgtgctctg tacacaagcc atttcaatag gatggagctg 2040
ttaattattt tccaaagagt aatagacatg caaaagtttc aataaaaact gggccattaa 2100
caagtaaatt aataaactaa taagcattcc cttctaggtt tttgccaaac tgcctatcca 2160
ataacaaatt tgagaatcgt tgtaaaagct agttatattt cagagaaatg attttcatta 2220

-continued

```
ttgaaactgt tctccctagc aggccatttt cccttttttcc tgggagttta gcaagtttag   2280
gagagaatag tcatgaaaag aaagggaaga aaggggagaa gggaagaggt taaaaagtaa   2340
gtgctcagac ctatgaacgt aatccctttg ctacaaatat ttaagagcag ctcagcttgg   2400
ttgaaactga gttttgtcat cttccatatt tgcaggaagg tattttctga cttgcaatgc   2460
agctagatgt aaaattttat tttatcatcc tagaaagcct tgactagaaa aatgaataaa   2520
tattgagggt ttcctgtcca tatctggctt gcatgtgcca gaaagcagag aatagaaaat   2580
gtaatctcca acatccaagc atcgaaaccc aaggggtagg caattctatg taggttttgg   2640
acatgaagtt tggtgcatct tggtttatgc tggctcaact gctattaaac ctctctggct   2700
tatagtctct tcattctatt agacaagcac gtatcgaaca cttgcttcgc acaaggctct   2760
ttagttaaca atttagcagc tactgtttgt gttaaacaca cttttcacca aataggttct   2820
gaggcaaacg agagcaatga ctatttaaag aaaggctttc ccagcatcac ttacacatcc   2880
caaaactaaa aagatcaact cttccaactg agaaaagact cctggctttg aatggaaact   2940
tacagcagag agtcacaggc cacggcaaca acaacgacaa caacaaacat ttggaatatt   3000
attctcaact cacgttttaa taatacatct tattattttt ctagtagaga aactacaaat   3060
cagcctcttc aacatttata tacagtttaa taagcctctt gcaagttact tgttctctca   3120
cctgaggtat ttttttcctc cccaccttgc ccctgttcct cccttcctct tctccctttg   3180
caagaggaaa tatttaacat atttgggtcc aacttcaata atgtaataat taatacatta   3240
aaagcattta acttcctttc tagaaaaatg cacaggctaa ggcatagaca aaacaaagag   3300
aaatgctgag aaatttgcca ctggagacaa gcaatctgaa taaatatttg ccaaaagttc   3360
tttttatgtc atatagtgtc aggatttgaa ggagctattt ttttttaatg ttgcaactag   3420
caactcatct tcggaagaca cagccaggag aatgaagtag aagtgaaagg tttataaatc   3480
catttgtaag catttatccc atatatttta aattcaagaa aaattgtgtt tatctttaga   3540
attttgtatt caatacttta tgtactatgt gactcatgct tctggataaa taaagcacca   3600
aatatgtatc tgtaaccaca atcacacata ttatattaaa tatatatcta tataacaaaa   3660
aaaaaaaaaa aaaa                                                      3674
```

<210> SEQ ID NO 74
<211> LENGTH: 2797
<212> TYPE: DNA
<213> ORGANISM: Homo sapiens
<220> FEATURE:
<221> NAME/KEY: SITE
<222> LOCATION: (853)
<223> OTHER INFORMATION: n equals a,t,g, or c

<400> SEQUENCE: 74

```
ggcacgagag agcagacaga attatatgta gaggacacag gagatattta cattgtggat     60
ggagatggag gattgaataa cagattgatc aaactgtccc aagatttcat gatcctttgg    120
ctgcatggag aaaatgggac agggcctgct aagttcaaca tacctcacag tgttacactt    180
gattcagctg gtcgggtgtg ggttgctgac cgaggaaata aaagaatcca agtatttgat    240
aaagacactg gggagtggtt aggagcatgg aataattgtt tcacagaaga ggaccttctt    300
cagtcagttt actcctgatg ggaagtactt gattgtggcc cagctgaatc ttagcaggct    360
ctcagtcgta gcagcacccc cagtgggaag cattggggag tgttctgtga tcagcacaat    420
ccaactagca gatcaagttt tgccacatct cctagaagtc gacagaaaag actggagcag    480
```

-continued

```
tctatgtagc agaaattgga gcaaaacaag tacaaaaata tgtccctttg aatagctatg    540

ttccttcatt tggttcataa tgtttctttc ccgggaatat ttcaagtggc agttcagatt    600

ctcaattcac taagtgctta aaaatgatgt tcaagcacaa gaatttattt ttctagtata    660

aaagatctag tatcagaaag atttgttttt gtatcattaa gaatcttata ttttgttgcc    720

ctcttgggac ttagttttat ttgtaagtgc ataaggatat tttaatgaaa ggaaagtaac    780

taaaaaatgg ggttgggaag agggactaag gtggtaacct cattatttgc cctggtagac    840

tgattctccc tgngtaaaaa aaatgggaat aaaaatgagc ttgcatgata atttattaaa    900

tttcatgtga agaactccag acctccagat tgtgcaacta acataaagtg agctgcttga    960

gagattgtaa ataagatgaa ctattgatta atttgagtac ccacagagtg ctgtgtcttg   1020

acgacttaaa aatgaaaaag catgattgcc ttttgagtag cttgcagtct agtggggaga   1080

caagcaggca aacagtcaca acacagcaaa agcgaccttg gagcatagtg ggacttttgg   1140

agtaggagtg ctgcatttga ctgagggaat catggatact tcgcaggaga agtgaatttg   1200

agctcagact tgaaaactga ggaggagctt accaagggac aaggaggaga aaacaataat   1260

ttccaagtaa agaaggtata aaaagttaga agtgtactgt aaactttgat aggcttttag   1320

gcctttttta aagcccaact tggcttctgt ccattaccta taagatattt aatgtcagtc   1380

agcctttaaa tgtaggaata aaatggctgg catctaagca ctttagtaaa agaggttttt   1440

acaaataact aaggattgta gagcttcctt ctcttttttt ttctttttct ttcttttgtt   1500

ttacatgaac tcaacttatt cctaacattt gtctacctca aagaaatttc aagattattt   1560

agataacatg gatatgtgcc aaatcctttg agctgttaag atgataattt cctgctttcc   1620

tcctacatct tctcctccca ctccctcctt tggtgtgaat attggcttcc caattaagac   1680

cttttttttt tccagtttgt tttagcttat tataggtttt ggaggaactt tgccattttg   1740

taatctttca aatcattctt caccccttcct cacatcagct tcctgctttt cccagtgttt   1800

tactgtaaat tgtgtagcat atgacaaatc ttgagctgac tttcctcttc acctgttatg   1860

gctggagtat tttccagacc tgaagggact cacacttgtt ttgatacttg gatcacatct   1920

ccgtgaggtt aggaaggtaa atctaccaac aggaagccct gtactctgta ttccaaggcc   1980

attggtaaat gtgttggtgc cactgatcgg actgtatgac cttaaacaag tcaccttagt   2040

tttcagtgaa atgggaatat cattgtctcc tctttcatga atgctgtgag aatcagatgt   2100

gcaacaggta catacttgcc ctttggaaat ctaatacctc tgggatacca ttaagaggca   2160

ttttaattaa acaaaagggc ccttctaaat gtgctattta tttgacaata actatcagat   2220

ttgccttaat tttgtgttta tagcatttat caaaacgtat cctcatagac tttatgcaga   2280

ttaatatggt caattgattt ggataaaaga aagtaatttc agggtttgtt tttaagccag   2340

gacaagaagt gcaaatgcct ctttgaagca atttaggcta aactgatttt gaaatttcaa   2400

aatgttttat tttactttgt tttattaagc caggacaaga agtgcaaatg cctctttgaa   2460

gcaattcagg ctaggtaaac cgattttgcc atttcaaaac gttttatttt actttgwttt   2520

rtrtcagagt yttawaarvc ctgctgcaaa tatttctgaa tgtctttgta aaagtgtttg   2580

ttagtgtacc tgtgattata gtacttcact tttttccttt ggattaattg gttaaatgaa   2640

tgagaaatgt gttatgtttt ttactaaaaa gtataaatta aaattttgga aagaaaaggc   2700

aatattatct ggctccccaa ttaaagtttg attttattgt cacaaaaaaa aaaaaaaaaa   2760

aaaaaaaaaa aaaaaaaaaa aaaaaaaaaa aaaaaaa                            2797
```

-continued

<210> SEQ ID NO 75
<211> LENGTH: 2703
<212> TYPE: DNA
<213> ORGANISM: Homo sapiens

<400> SEQUENCE: 75
ggcacgagat ttcctacagg tgaaacgcca tcattaggat tcactgtaac gttagtgcta 60
ttaaactcac tagcattttt attaatggcc gttatctaca ctaagctata ctgcaacttg 120
gaaaaagagg acctctcaga aaactcacaa tctagcatga ttaagcatgt cgcttggcta 180
atcttcacca attgcatctt tttctgccct gtggcgtttt tttcatttgc accattgatc 240
actgcaatct ctatcagccc cgaaataatg aagtctgtta ctctgatatt ttttccattg 300
cctgcttgcc tgaatccagt cctgtatgtt ttcttcaacc caaagtttaa agaagactgg 360
aagttactga agcgacgtgt taccaagaaa agtggatcag tttcagtttc catcagtagc 420
caaggtggtt gtctggaaca ggatttctac tacgactgtg gcatgtactc acatttgcag 480
ggcaacctga ctgtttgcga ctgctgcgaa tcgtttcttt taacaaagcc agtatcatgc 540
aaacacttga taaaatcaca cagctgtcct gcattggcag tggcttcttg ccaaagacct 600
gagggctact ggtccgactg tggcacacag tcggcccact ctgattatgc agatgaagaa 660
gattcctttg tctcagacag ttctgaccag gtgcaggcct gtggacgagc ctgcttctac 720
cagagtagag gattcccttt ggtgcgctat gcttacaatc taccaagagt taaagactga 780
actactgtgt gtgtaaccgt ttcccccgtc aaccaaaatc agtgtttata gagtgaaccc 840
tattctcatc tttcatctgg gaagcacttc tgtaatcact gcctggtgtc acttagaaga 900
aggagaggtg gcagtttatt tctcaaacca gtcattttca aagaacaggt gcctaaatta 960
taaattggtg aaaaatgcaa tgtccaagca atgtatgatc tgtttgaaac aaatatatga 1020
cttgaaaagg atcttaggtg tagtagagca atataatgtt agtttttttct gatccataag 1080 aagcaaattt atacctattt gtgtattaag cacaagataa agaacagctg ttaatatttt 1140
ttaaaaatct attttaaaat gtgattttct ataactgaag aaaatatctt gctaatttta 1200
cctaatgttt catccttaat ctcaggacaa cttactgcag ggccaaaaaa gggactgtcc 1260
cagctagaac tgtgagagta tacataggca ttactttatt atgttttcac ttgccatcct 1320
tgacataaga gaactataaa ttttgtttaa gcaatttata aatctaaaac ctgaagatgt 1380
ttttaaaaca atattaacag ctgttaggtt aaaaaaatag ctggacattt gttttcagtc 1440
attatacatt gctttggtcc aatcagtaat tttttcttaa gtgttttgtg attacactac 1500
tagaaaaaaa gtaaaaggct aattgctgtg tgggtttagt cgatttggct aaactactaa 1560
ctaatgtggg ggtttaatag tatctgaggg atttggtggc ttcatgtaat gttctcatta 1620
atgaatactt cctaatatcg ttggctctac taatattttc caatttgctg ggatgtcacc 1680
tagcaatagc ttggattata tagaaagtaa actgtggtca atacttgcat ttaattagac 1740
gaaacgggga gtaattatga cacgaagtac ttatgtttat ttcttagtga gctggattat 1800
cttgaacctg tgctattaaa tggaaatttc catacatctt ccccatacta tttttttataa 1860 aagagcctat tcaatagctc agaggttgaa ctctggttaa acaagataat atgttattaa 1920
taaaaataga agaagaaaga ataaagctta gtcctgtgtc tttaaaaatt aaaaatttta 1980
cttgattccc atctatgggc tttagaccta ttactgggtg gagtcttaaa gttataattg 2040
ttcaatatgt tttttgaaca gtgtgctaaa tcaatagcaa acccactgcc atattagtta 2100
ttctgaatat actaaaaaaa tccagctaga ttgcagttta ataattaaac tgtacatact 2160

-continued

```
gtgcatataa tgaattttta tcttatgtaa attattttta gaacacaagt tgggaaatgt   2220

ggcttctgtt catttcgttt aattaaagct acctcctaaa ctatagtggc tgccagtagc   2280

agactgttaa attgtggttt atatactttt tgcattgtaa atagtctttg ttgtacattg   2340

tcagtgtaat aaaaacagaa tctttgtata tcaaaatcat gtagtttgta taaaatgtgg   2400

gaaggattta tttacagtgt gttgtaattt tgtaaggcca actatttaca agttttaaaa   2460

attgctatca tgtatattta cacatctgat aaatattaaa tcataacttg gtaagaaact   2520

cctaattaaa aggtttttc caaaattcag gttattgaaa atttttcatt ttattcattt   2580

aaaaactaga ataacagata tataaaagtg ttaatctttg tgctatatgg tatgaaatac   2640

aatattgtac tcagtgtttt gaattattaa agtttctaga aagcaaaaaa aaaaaaaaaa   2700

aaa                                                                 2703
```

```
<210> SEQ ID NO 76
<211> LENGTH: 742
<212> TYPE: DNA
<213> ORGANISM: Homo sapiens
<220> FEATURE:
<221> NAME/KEY: SITE
<222> LOCATION: (707)
<223> OTHER INFORMATION: n equals a,t,g, or c
<220> FEATURE:
<221> NAME/KEY: SITE
<222> LOCATION: (724)
<223> OTHER INFORMATION: n equals a,t,g, or c
<220> FEATURE:
<221> NAME/KEY: SITE
<222> LOCATION: (726)
<223> OTHER INFORMATION: n equals a,t,g, or c

<400> SEQUENCE: 76

gcgctcgaga atagtgggtc ccccggrctg caggattcgg cacgagctca cttcaatyct     60

tctttgagaa gtttttcctt tctccgcaac cagatgtaca tatttgaact ctctttgtac    120

ttggagggca cttctttcgt ggtagttctt ttatttttat taatctctgt atccttagat    180

agtcctccaa caaccaaagg ttgggactct gtcttacata tctgggtgcc cctcatagtg    240

cagtaataag taagttgatt atatacgagc tatgtaactt atattttttta atggttggat    300

atcactgagt tttttttttt aagaattttt ttattgaggt aaacttcaca taacataaaa    360

ttaactattt taaagtgaga agttcagtgc cacttagtat tgttaacaat gttgcataac    420

caccaccttt atttaaagtt ccaaaaaaaa tgttctcctc taaaaggaaa ccccatccca    480

ttaagcagat actctccatt ccttccttcc tccagccccc agcaaccacc aatctgcttt    540

ctgtctctat ggatttatct attcttgcta ttttatataa atcgaattgt atgagacctt    600

ttgtgtctgg cttctttcac ttagtacaag tttttgagat ttatttacat agtagcatgt    660

atcaacactt catttttatg gccaaataaa attgtattat gtgtttntag cacaaaaaaa    720

aaananaaaa atgaccctcg ag                                             742
```

```
<210> SEQ ID NO 77
<211> LENGTH: 1825
<212> TYPE: DNA
<213> ORGANISM: Homo sapiens

<400> SEQUENCE: 77

ggcacgagca tgtcacatgt atacctatgt aacacacctg cacattctgc acatgtatcc     60

cagaacttaa attataataa taaaaaaaga ataattgggt gatggcacat ccaggtttgc    120

caaagacagt cccagtttat gctgttgtcc tggcattatt aataatgaca ctgcctttaa    180
```

-continued

```
ctctcacaat taatttggat gataacttat atggtaactc tgctaaataa aaaaaataaa    240
aattaccata gtaacaggaa cctacttgaa atgatgcctc tgtttctatt ctggcttgaa    300
ttctgcattc tttgaggatt tgtagcctca tgacagaatc ctatctacag gtgatgtatt    360
tcatatgatt tttggctatt tttttaacaa tctcaagccc aataatagcc agtgatataa    420
ggaatgtagt tactttctcc ccactttctg gcaagttaag tttagccacc tgattacaag    480
aagggacatt cagaggtagg atggcacaaa gacacagggt ccactggaga tcactggaag    540
cagctgcagc agggttaaga gaagggagtc ccagcgagtc ttcagtcacc acacactaac    600
atcatcagtg aaaagttcct gggcctgaag atccagctat gttgtttcta gttgactatt    660
ttaagtgaca gaacttggcc caagcattga ccattttggt tcctcaataa gcctgattca    720
accagggtca cctttgaatc tgtcctccac ctttccaata aacctatttt atgcatcatt    780
cagtgagtta tttatttatt tactttttttg ctgagaaaca tgactagatt taggaaaaat    840
gtagaatttt actttttttt caatattttc tgggttttcc agagttttca cgtgtttcac    900
accttccttt gcttcccacc attccccttt ctatttggaa ctagagagac atgagtttga    960
attctagctg tgtaacctga gtcagttatt taacctcttt ttgtttctgt ttctttgtct   1020
gtaaatagca aaaactacaa ttaactttag tccctgctgt acaccaaatg ttatcttgaa   1080
atattataca tattatatgt aattactact gaaatgctct aagatgccta tgtgtgaatg   1140
gcattgttgt aaagattaaa taatataagg gaagtgtctg cttcagtgtc tggcatataa   1200
taaaagctat tatttttacg attattttcc atcttataga agaattatcg ttcttccctt   1260
ccaaagctaa taaatggaca tgtgtttatc agacagaacg taagagctgc caaataaata   1320
gggaataggt gctttcggga gtctagggaa ataaaggtca gggaattgtt cataaaattt   1380
agtacccata aatagcctat aagtagattc cctagtttat tctatgcagg aaaataaagt   1440
tctacggagc acagattcca aaactaattg gtcataaata tcacctgaaa gtttagaaaa   1500
tgtagcatca tggacctctt ttcataggtt ctaaatctta atatctgtgg gatggtgcag   1560
gaatctagct ttgctaagtg ccctcagatg actcttgctg ttctaggcta aaatacatgt   1620
ggtttggctt caatggacat gttcctgaag aatgtttgga tgtcacacat tcatatttag   1680
tatgagagat gaggtcctcc tctcatcatt ttcttaggtt ctcttctctc cactccttac   1740
cctcccatca cttacaataa atcttttaga aaattagcta tacatttgtt tcattataaa   1800
aaagaaagaa gataaaaaaa aaaaa                                         1825
```

<210> SEQ ID NO 78
<211> LENGTH: 1674
<212> TYPE: DNA
<213> ORGANISM: Homo sapiens

<400> SEQUENCE: 78

```
ggccacgaga gtatctgcgg cagctgcagg tcctggattt atttctcgat tcgctgtcgg     60
aggagaatga gaccctggtg gagtttgcta ttggaggcct gtgcaacctg tgcccagaca    120
gggccaacaa ggagcacatc ctgcacgcag gaggtgtccc actcatcatc aactgcctat    180
ccagccccaa tgaggagacg gtgctgtctg ccatcaccac gctcatgcac ctgagcccgc    240
cgggccgcag ctttctccca gagctgaccg ccacgcccgt ggtgcagtgc atgcttcgct    300
tctccctctc ggccagcgcc aggttccgga acctggcaca gatcttcctg gaggacttct    360
gctccccccg ccaagtggcc gaggcccgca gccggcaggc gcaattttgc cctgggtatc    420
```

-continued

```
ccactgccga ggagcgtggc cccacggcag cgctgatcca tggagactgc gagaccgtgg    480

caccccctact gctggggacc acagtcctga tgtggacgca gggaacgggg agcacatact    540

gccccattgg tgccttttca gccatctgaa aggcgggttc tttcagcagg acaggcattt    600

acactgatga aacgccactg ggagtgagga agccagactc cagagacacg gagaagatca    660

aactggagct gcgttcatag gctggcactc tcaatcctac atcaggtgcc accaccacca    720

gactcaggcc ctggtgtaag aagcggccaa gtgcctggac ccagaggctt tgcaggacag    780

tgttctcagg agctgggcct gaggcttagg agagctgcct tcgctgcagg aaatcaggga    840

ttatccctta acagaagtgt ctggagtagt tttcaggtat aggaatgaga tgcctcgtgg    900

tgaaaggatc tcaccctggg aagatgtggt gccccctcca gggctctgga ggatggatgc    960

ctcccccagg ggctctccaa gctgggcatt tgggcctggt ggatgccaac ctggataacc   1020

tgtggcccag cattgactgt ccacccagcc ttgctgttag gcaccatgac tccaaagatg   1080

aagatgtggt ccctgccctt gagtgacagc cccagggact taatgtggcc atcgggcatc   1140

aagcacaagg ccatgcaggt gatgatacgt cggaatagag gcaccagccc tggtaactgc   1200

atcttctccc cttgccaccc catggccccg gctgaaagct tcggccctcc tctgctgtca   1260

ctcaatgatg gggagcccta ccccagaagt gtatcccacg agggcatcag ggacgcagtg   1320

agtgttgctc aagggagtca ggaagagacg gcaacgtaaa ggatgtggct ccatgtccat   1380

ggtgcccccct ggtcaacata aggagcgtgg gatccgatgg aaaggtggag ctcagggaaa   1440

atgggggtcc ttgcctctcg tgtacccccct caaggctgac cccttagatg gcccaggaat   1500

ggcaggtgct acaaaaatgg tacccacgtg ggcatggaaa tggggcagat taggggacca   1560

ctggactcag aggggaggga agggctcatc agcacccgct cagggagcct gtccctttat   1620

gttcccaaat aaagggtcct agaagactaa aaaaaaaaaa aaaaaaaaaa aaaa         1674
```

<210> SEQ ID NO 79
<211> LENGTH: 2191
<212> TYPE: DNA
<213> ORGANISM: Homo sapiens
<220> FEATURE:
<221> NAME/KEY: SITE
<222> LOCATION: (1327)
<223> OTHER INFORMATION: n equals a,t,g, or c
<220> FEATURE:
<221> NAME/KEY: SITE
<222> LOCATION: (1334)
<223> OTHER INFORMATION: n equals a,t,g, or c

<400> SEQUENCE: 79

```
ccttctctaa aaaagcaaac aggcaaaact tcatgagaat cttgatcatg ttaaaatttt     60

atgtccttcg atttctccct acacacacac acacacacac acacacacac acacacacac    120

tcaacatttc ctccacccat atcatcactc cttagcatct ttattccatc aaaactttct    180

accccttgac attctctgtg cagttttgaa aattaccctc tcagcattct ctgttcaccc    240

ccacacctag accctgacct ctagtcaatt ctactaccca ggggtgtcca cggttccagc    300

ctcctccatg aagcccagtt ctatgggctc actcctctgg gtaagtggga gcccccagct    360

atcatcctca ttgtatagaa aaccaactct gtgatgctac ctgcccctct tccccttctc    420

tcctgaaaga gggctggggt agaggtggga ggactggtta tggccctggc cgggtctgta    480

ttcgtactgg gaggagtatt ggtactctgt gtagaaagaa atggggaggg ggaaatgggg    540

tggcctcagc atctccctaa gtcccagcct ttaagtcctc ctgttgcagt tcgtcgctgc    600

agcttcgaga ggagttggat cgatcttctt gtggaaacgt cctcttcaat ggttacctgc    660
```

-continued

```
cgccaacagg taggcactcc caatggaatg gaggggcgcg gaggtgggcc aaagactaca    720
tttcccataa ggctgcagct ctcgggtgcc tgtgctgtgc gtcctgagat acagtgggaa    780
gtgtagttcc ctatcagatg cttgggctga tgcttggaaa ggaagttgga cacagcattt    840
cccatgaaac aatgggccaa ctaactcttg aagctcaaaa agatgtcctt ggaaccccat    900
ggggaatttg ttatcccggg tttgggtttc ttttgttagg gggggctttg ggaaaaactg    960
gggattcctc cgtatggaag gggaaaaaat attaaatagg aagttattga cattaatgcc   1020
catgatagcc accccactgg gccatggaag gtatgcccca gtgggtattg gaactaggct   1080
tttctgattg gtagaagtaa cagagtaggg aaatttcatc tacagcttta tttccctaac   1140
tgcagtcagc acctgtacct tcatgaaagt tgccagatat aaagatctgt agtagtactt   1200
ttccaactta gttttatcct gttttcccga aaaacaatca tttatttatt tatttattta   1260
tttaatttta tgagacaggg tctggctttg tcacccaggc tggagtgcag tggtgcgatc   1320
ttggctncac tgcnacctct gcctctcaga ttcaagccat ccttccacct cagctctgcc   1380
actgagtagc tgagactaca agcactcgcc accatgcccg gctaattaaa aaaataataa   1440
tcattttaaa tgcaagcttt atattataaa tacaaagtaa acatgaaaat aaaacccaaa   1500
catagcagtg ttattaaact ctggcctgta gcagtggctc acacctgtaa tcctagcagt   1560
ttggaggccg agacaggtgg attacttgag acctggagtt tgagaccagc ccaggtgaca   1620
cagcaagacc tcatctctac taaaaataaa aaaaaattag ccaggtgtgg tggtatgcac   1680
ctgtggtccc agctacttag gatgctggag tgcgaggatc gcttgagccc aggaggtcaa   1740
ggctgcagtg aactatgatc actcattaca ccccagcctg ggtgacagag cgagatgctg   1800
tctcaaaaca aaacaaaacg aaaaacaact ctggctagat gctattgctt gccaagggtg   1860
cagtcttcca tttattaaaa gtgaaaatta gggccaggca cattggctca tgcctgtaat   1920
cccagcactt tgggaggctg aggtgggtgg atcacctgag gtcaggagtt cgagaccagc   1980
ctggccaaca tggtgaaacc ttatctctgc caaaaatata aaagattagc catgtgtcgt   2040
ggtgggtgct tgtaatctca gctacttggg aggctgaggc aggagaatca cttgaaccca   2100
ggaggcagag gttgcagtga gccaagattg tgccattgca ctccagcctg tgcaacgagc   2160
gaaactccaa ctcaaaaaaa aaaaaaaaaa a                                  2191
```

<210> SEQ ID NO 80
<211> LENGTH: 1335
<212> TYPE: DNA
<213> ORGANISM: Homo sapiens
<220> FEATURE:
<221> NAME/KEY: SITE
<222> LOCATION: (1287)
<223> OTHER INFORMATION: n equals a,t,g, or c

<400> SEQUENCE: 80

```
ggatatatcc agggctgcgg attttccccc cttcaggttt aaatgttcct gtttttctac     60
ctttccctcg cagtatacgc tcaacggcaa gawagtggaa gttgccgtca aacagatcat    120
cgctggaaaa gccgtggagc aaggaggtgc tttctcgaac cccgagaccc tggatctgta    180
ccgggacatc cctgagctgc agggcttctg agtcagactg gctggcgtgt cactcagccg    240
cacccgtgtg cactgtaact tttgtgtgct caagaaatta tacagaaacc tacagctgtt    300
gtaaaaggat gctcgcacca agtgttctgt aggcttgggg agggatcgtt tctctgtttt    360
gttaaatctg gtgggtacct ggatcttcca cacgagtggg attctggcct tcagagacca    420
```

-continued

```
ggagggagtg tctgggccgc agtgtggcac tgtggtgaga gtgtgtgtct ttgcacacac     480
agtgcagcgg gaacggtggg gctggctggt gctgaagaca gacacactcc tgagccaagg     540
tcttgtcttc aacctccccg tcccgttgtc ccattttgct ctgtgaaggt gcaaatccct     600
ttcttccctt cccatctcag gctctcctgt tttccctcag ggtccagtat gcctttgagc     660
tttagctgtt agaaaggaac ccccgtgact tgacacagct ttcacagctg gctgctagga     720
ccggcgggct gggtgttcac gtgtgtctgt gtcatggatg caatgcaggc cctggaggac     780
tgtgcgtcac ccgtcaacca gagcgtgcct ccgggccagc ttccctccaa ggaatgagtg     840
gatttcatac aggatctctt tattgcacag actgaatggc tttacatgtt tctaatgtga     900
attaggcatg tgaagcagtg ggtgtccacc cgtgtccctc atgggtgagc cctccagctg     960
tgagcccagg cagtgtggtc accgagtgag gaccctcctc accaggaacc gcatccctgt    1020
gctgcctcca cctgagagtt gctagggggt tcttgtcgag atcatgtcat cagcacccct    1080
aagtcaagtc acgggtttcc atagccaggc agttggtatg tacaattcag ttcagcgtat    1140
gaacttgtat ctctaatctg atgtccattt ttatattttt tgaaactgag cacaatgaaa    1200
tcctttcttg aatcattttc cttttggatt ataaaaatat gggggaaagt gctatgatga    1260
attttatgca ataaatgtat acatgtntgc acatgcaccc atgctgaaaa aaaaaaaaaa    1320
aaaaaaaaaa aaaaa                                                      1335
```

<210> SEQ ID NO 81
<211> LENGTH: 1867
<212> TYPE: DNA
<213> ORGANISM: Homo sapiens

<400> SEQUENCE: 81

```
cccacgcgtc cgggccacag cagagacagt ggagggcagt ggagaggacc gcgctgtcct      60
gctgtcacca agagctggag acaccatctc ccaccgagag tcatggcccc attggccctg     120
cacctcctcg tcctcgtccc catcctcctc agcctggtgg cctcccagga ctggaaggct     180
gaacgcagcc aagacccctt cgagaaatgc atgcaggatc ctgactatga gcagctgctc     240
aaggtggtga cctgggggct caatcggacc ctgaagcccc agagggtgat tgtggttggc     300
gctggtgtgg ccgggctggt ggccgccaag gtgctcagcg atgctggaca caaggtcacc     360
atcctggagg cagataacag gatcgggggc cgcatcttca cctaccggga ccagaacacg     420
ggctggattg gggagctggg agccatgcgc atgcccagct ctcacaggat cctccacaag     480
ctctgccagg gcctggggct caacctgacc aagttcaccc agtacgacaa gaacacgtgg     540
acggaggtgc acgaagtgaa gctgcgcaac tatgtggtgg agaaggtgcc cgagaagctg     600
ggctacgcct tgcgtcccca ggaaaagggc cactcgcccg aagacatcta ccagatggct     660
ctcaaccagg ccctcaaaga cctcaaggca ctgggctgca gaaaggcgat gaagaagttt     720
gaaaggcaca cgctcttgga atatcttctc ggggagggga acctgagccg gccggccgtg     780
cagcttctgg gagacgtgat gtccgaggat ggcttcttct atctcagctt cgccgaggcc     840
ctccgggccc acagctgcct cagcgacaga ctccagtaca gccgcatcgt gggtggctgg     900
gacctgctgc cgcgcgcgct gctgagctcg ctgtccgggc ttgtgctgtt gaacgcgccc     960
gtggtggcga tgacccaggg accgcacgat gtgcacgtgc agatcgagac ctctcccccg    1020
gcgcggaatc tgaaggtgct gaaggccgac gtggtgctgc tgacggcgag cggaccggcg    1080
gtgaagcgca tcaccttctc gccgccgctg ccccgccaca tgcaggaggc gctgcggagg    1140
ctgcactacg tgccggccac caaggtgttc ctaagcttcc gcaggccctt ctggcgcgag    1200
```

gagcacattg aaggcggcca ctcaaacacc gatcgcccgt cgcgcatgat tttctacccg 1260
ccgccgcgcg agggcgcgct gctgctggcc tcgtacacgt ggtcggacgc ggcggcagcg 1320
ttcgccggct tgagccggga agaggcgttg cgcttggcgc tcgacgacgt ggcggcattg 1380
cacgggcctg tcgtgcgcca gctctgggac ggcaccggcg tcgtcaagcg ttgggcggag 1440
gaccagcaca gccagggtgg ctttgtggta cagccgccgg cgctctggca aaccgaaaag 1500
gatgactgga cggtccctta tggccgcatc tactttgccg gcgagcacac cgcctacccg 1560
cacggctggg tggagacggc ggtcaagttg ctgcgcgccg ccatcaagat caacagccgg 1620
aaggggcctg catcggacac ggccagcccc gaggggcacg catctgacat ggaggggcag 1680
gggcatgtgc atggggtggc cagcagcccc tcgcatgacc tggcaaagga agaaggcagc 1740
caccctccag tccaaggcca gttatctctc caaaacacga cccacacgag gacctcgcat 1800
taaagtattt tcggaaaaaa aaaaaaaaaa aaaaaaaaaa aaaaaaaaaa aaaaaaaaaa 1860
aaaaaaa 1867

<210> SEQ ID NO 82
<211> LENGTH: 984
<212> TYPE: DNA
<213> ORGANISM: Homo sapiens

<400> SEQUENCE: 82
gaattcggca cgagcccagc ggaagccaag ccaccaggcc ccccagcgtc cacgcggagc 60
atgaacattg aggatggcgc gtgcccgcgg ctccccgtgc cccccgctgc cgcccggtag 120
gatgtcctgg ccccacgggg cattgctctt cctctggctc ttctccccac ccctgggggc 180
cggtggaggt ggagtggccg tgacgtctgc cgccggaggg ggctccccgc cggccacctc 240
ctgccccgtg gcctgctcct gcagcaacca ggccagccgg gtgatctgca cacggagaga 300
mctggccgag gtcccagcca gcatcccggt caacacgcgg tacctgaacc tgcaagagaa 360
cggcatccag gtgatccgga cggacacgtt caagcacctg cggcacctgg agattctgca 420
gctgagcaag aacctggtgc gcaagatcga ggtgggcgcc ttcaacgggc tgcccagcct 480
caacacgctg gagctttttg acaaccggct gaccacggtg cccacgcagg ccttcgagta 540
cctgtccaag ctgcgggagc tctggctgcg gaacaacccc atcgagagca tcccctccta 600
cgccttcaac cgcgtgccct cgctgcggcg cctggacctg ggcgagctca agcggctgga 660
atacatctcg gaggcggcct tcgargggct ggtcaacctg cgctacctca acctgggcat 720
gtgcaacctc aaggacatcc ccaactgacg gccctggtgc gcctggagga gctggagctg 780
tcgggcaacc ggctggacct gatccgcccg ggctccttcc agggtctcac cagcctgcgc 840
aagctgtggc tcatgcacgc ccaggtagcc accatcgagc gcaacgcctt cgacgacctc 900
aagtcgctgg aggagctcaa cctgtcccac aacaacctga tgtcgctgcc ccacgacctc 960
ttcacgcccc tgcaccgcct cgta 984

<210> SEQ ID NO 83
<211> LENGTH: 2664
<212> TYPE: DNA
<213> ORGANISM: Homo sapiens

<400> SEQUENCE: 83
ggttgctggc ccaggtgagc gggcgcgctg gtccaggtga gcgggcgcgt ccccgcgacg 60
gcgctgcctg cccgaggcgg ttcacgtaaa gacagcgaga tcctgagggc cagccgggaa 120

-continued

```
ggaggcgtgg atatggagct ggctgctgcc aagtccgggg cccgcgccgc tgcctagcgc    180
gtcctgggga ctctgtgggg acgcgccccg cgccgcggct cggggacccg tagagcccgg    240
cgctgcgcgc atggccctgc tctcgcgccc cgcgctcacc ctcctgctcc tcctcatggc    300
cgctgttgtc aggtgccagg agcaggccca gaccaccgac tggagagcca ccctgaagac    360
catccggaac ggcgttcata agatagacac gtacctgaac gccgccttgg acctcctggg    420
aggcgaggac ggtctctgcc agtataaatg catgacggat ctaagccttt cccacgttat    480
ggttataaac cctccccacc gaatggatgt ggctctccac tgtttggtgt tcatcttaac    540
attggtatcc cttccctgac aaagtgttgc aaccaacacg acaggtgcta tgaracctgt    600
ggcaaaagca agaatgactg tgatgaagaa ttccagtatt gcctctccaa gatctgccga    660
gatgtacaga aaacactagg actaactcag catgttcagg catgtgaaac aacagtggag    720
ctcttgtttg acagtgttat acatttaggt tgtaaaccat atctggacag ccaacgagcc    780
gcatgcaggt gtcattatga agaaaaaact gatctttaaa ggagatgccg acagctagtg    840
acagatgaag atggaagaac ataacctttg acaaataact aatgttttta caacataaaa    900
ctgtcttatt tttgtgaaag gattattttg agaccttaaa ataatttata tcttgatgtt    960
aaaacctcaa agcaaaaaaa gtgagggaga tagtgagggg agggcacgct tgtcttctca   1020
ggtatcttcc ccagcattgc tcccttactt agtatgccaa atgtcttgac caatatcaaa   1080
aacaagtgct tgtttagcgg agaattttga aaagaggaat atataactca attttcacaa   1140
ccacatttac caaaaaaaga gatcaaatat aaaattcatc ataatgtctg ttcaacatta   1200
tcttatttgg aaaatgggga aattatcact tacaagtatt tgtttactat gaaattttaa   1260
atacacattt atgcctagaa ggaacggact tttttttct attttaatta cacataatat   1320
gtaattaaag tacaacataa tatgttgttt ctctgtagcc cgttgagcat atgagtaagt   1380
cacatttcta ttaggactac ttmcaaggac aaggtttcca tttttccagt tgtaaaattg   1440
gaaccatcag ctgataacct cgtagggagc aaccccagga tagctaagtg ttatgtaata   1500
tgcctagaag gtgatgtgaa tgcgattcag aagcatagcc actcccattt tatgagctac   1560
tcacatgaca aatgtcatct tttgctataa cctttgccaa gttagagaaa agatggattt   1620
aatgagataa atgaaaagat atttamccta atatatcaag gcactatttg ctgttatgct   1680
ttgttattta tttcccagca cttgttcctt attgtagatt ttttaaagac tgtaaccttt   1740
tactaactgt ggtcttacta aaatttgtgc ttgatactgc ttttcaaaaa gcctttaatt   1800
agagccaaaa ggatggaaaa ggcaagatat aaatgccttt tatagatctc ttatttacat   1860
tgaaaattat taccatatgt ttagagcaaa tccaagaaaa cttcaacagc ttctgaagat   1920
gtctatgaat gttgaaaact tttcaatctc ttggaatgct cagttatgtt cctagaccgg   1980
tctttgctga ctactggttg ttaacctttc cctagcctgg gacctcaagc catatatatc   2040
ctttgggtga cccatggcca aagttattaa gatgaactga ctttcaaagt cagagaagga   2100
cagcataggg agaggcggtt atttgtaagt cattacaggt agaacagggc agaaggaaaa   2160
gtatgttctg gagaaagggc catgttccta actttggaga tatgtcattg ccgggaacct   2220
agtatcttcc aacttgaatt ggtggcagct gttccagtga gacaaggcac atgtatgcct   2280
tgtggctaag tgagcaaact gggtttccac ttaaatgttt gggaccctca attgattctt   2340
tatttcaaac ctttataaaa ggtacagttt tgtaagccat tattaataat taatgcttat   2400
cggctgggca cagtggctca cacctataat cccagcactt gggaggctga ggcggttgga   2460
tcacttgagg tcaggagttt gagaccagct ggccaacatg gtgaaacagc gtctctacta   2520
```

-continued

```
aaaatacaaa aatttgccgg gcgtggtggc gcatgcttat agtctcagct actcaggaag    2580

ctgaggtacg agaatcactt gaacccagga ggtggaggtt gcagtgagct gagattgtgc    2640

cactgcactg cagcctggct cgag                                            2664
```

<210> SEQ ID NO 84
<211> LENGTH: 1328
<212> TYPE: DNA
<213> ORGANISM: Homo sapiens

<400> SEQUENCE: 84

```
cccacgcgtc cgggccagtg gaggtccgca gagtttgggc gccaggcgag acggcagggc     60

ttaaagttcc gggaatcaaa gatcaactcc cactgaggac aaatggacct gtaattccgg    120

gtgtgacgag agaacgagat ttaccttcct gaattaaaaa wcwgactccc tgcgacaagg    180

actgtgtact gcatgaatga ggctgagata gttgatgttg ctctgggaat cctgattgag    240

agccgcaaac aggaaaaggc ctgcgagcag ccggccctgg cgggggctga taacccagar    300

cactcccctc cctgctccgt gtcgcctcac acaagttctg ggagcagcag tgaggaagag    360

gacagtggga aacaggcact grctccaggc ctcagccctt cccagaggcc gggggttcc    420

agctctgcct gtagcaggag ccctgaggag gaggaggaag aggatgtgct gaaatacgtc    480

cgggagatct ttttcagcta gggcataaac tgtgcactga actgtctgcc gagagcagct    540

ggaggacagc tgagcttcca ctggtgctgc tgggccgccc gcctgtggga atggggctct    600

ctgtgctcct acctttgtgc cttcttgggc ctggcagatt cacctcaggc cagaagcccc    660

tggacactcc gggccttggg gctgccgttc tgagtgtgcg gaaggcagga ctcaaaatga    720

gatcccattt gactccctct gtatgtactg tgccctctcc tggctcttga ggctctggag    780

tcccaattgt ctgtgttagt cagtgaccag gttccaggga aaatgatgtc atgtggtggt    840

ccaacttact ggaaccaaag agacagtact ttgcaaagaa aaggatcact gccaggtgca    900

ctggaattgc tacagtttag tccgcatgat ctctcctgaa ggaggaagcc tgtttcaaaa    960

atagtttcca tcatgagtct atcaatgagc tcccacctct ccagccagcc tagaaagcaa   1020

acgagctgcc cacagttctc tgccctgtct gggaggttga ggccacagtg tatagactgg   1080

taagccagac aggcctcctc ccgcaagctg ctaccttgct ttcacctgta ccttggtccc   1140

cgggcagcta gctataaagc aagagggaca ggagcccaga agagacactg aggacaagag   1200

atcacaccag agtacatgtc tctgcctctg ttttcagtgt ggctttggac aggaatatat   1260

gaataaatca ctgccataca ggttttccaa tacacaagtg ctagaaaata cacacaattc   1320

cccaatga                                                            1328
```

<210> SEQ ID NO 85
<211> LENGTH: 1342
<212> TYPE: DNA
<213> ORGANISM: Homo sapiens

<400> SEQUENCE: 85

```
ggcccgccca ggaggtattc tgcctttgac tgcaactctt gtcgtcttat gtgggtgttg     60

aattgatctg tctctgcagc cagatccagg ctcctggaag aaccatgtcc ggcagctact    120

ggtcatgcca ggcacacact gctgcccaag aggagctgct gtttgaatta tctgtgaatg    180

ttgggaagag gaatgccaga gctgccggct gaaaattacc caaccaagag aaatctgcag    240

gatggacttt ctggtcctct tcttgttcta cctggcttcg gtgctgatgg gtcttgttct    300
```

-continued

```
tatctgcgtc tgctcgaaaa cccatagctt gaaaggcctg gccaggggag gagcacagat    360

attttcctgt ataattccag aatgtcttca gagagccrtg catggattgc ttcattacct    420

tttccatacg agaaaccaca ccttcattgt cctgcacctg gtcttgcaag ggatggttta    480

tactgagtac acctggggaa gtatttggct actgtcagga gctggagttg tccttgcatt    540

accttcttct gccctatctg ctgctaggtg taaacctgtt ttttttcacc ctgacttgtg    600

gaaccaatcc tggcattata acaaaagcaa atgaattatt atttcttcat gtttatgaat    660

ttgatgaagt gatgtttcca aagaacgtga ggtgctctac ttgtgattta aggaaaccag    720

ctcgatccaa gcactgcagt gtgtgtaact ggtgtgtgca ccgtttcgac catcactgtg    780

tttgggtgaa caactgcatc ggggcctgga acatcaggta cttcctcatc tacgtcttga    840

ccttgacggc ctcggctgcc accgtcgcca ttgtgagcac cacttttctg gtccacttgg    900

tggtgatgtc agatttatac caggagactt acatcgatga ccttggacac ctccatgtta    960

tggacacggt ctttcttatt cagtacctgt tcctgacttt tccacggatt gtcttcatgc   1020

tgggctttgt cgtggttctg agcttcctcc tgggtggcta cctgttgttt gtcctgtatc   1080

tggcggccac caaccagact actaacgagt ggtacagagg tgactgggcc tggtgccagc   1140

gttgtcccct tgtggcctgg cctccgtcag cagagcccca agtccaccgg aacattcact   1200

cccatgggct tcggagcaac cttcaagaga tctttctacc tgcctttcca tgtcatgaga   1260

ggaagaaaca agaatgacaa gtgtatgact gcctttgagc tgtagttccc gtttatttac   1320

acatgtggat cctcgttttc ca                                            1342
```

<210> SEQ ID NO 86
<211> LENGTH: 1154
<212> TYPE: DNA
<213> ORGANISM: Homo sapiens

<400> SEQUENCE: 86

```
aagacaggaa aagctccagg ccgtggttct caaagtgtgg tccctggaca gcagcaacat     60

cacctaggag cctgttaggg aaggcacagc ctcaggccct gccccagacc tgcagaatca    120

gaaactctgg ggtgaggcct ggttatctgc tgtaacagac cttccagtgg gttctgatgc    180

cctctagagc aggagaacca ctagcttaga ggttgcagta tgtttggcat cttgccattt    240

gtgttagttc agaggaatgg ctgaccccca tgtctcattt ctaagcttca ggcagctttt    300

ctcctgggca gctgtcattc tgttgagggg aatcctgggg actgtggctc ctcctccctg    360

tccgtgtgtc cttgatctgg cagtctaccc ccttcatctc cccgtggagg ctccatgcct    420

agaggtggtc ttcaaacaga agaatggcaa agataattgt ctcgtgtttt accctgaccc    480

cattccttta agagggtcac ttcttggccc attcatttaa aaaccaatgt catagttctg    540

tgattccacc tatcagacag tgccacgtcc aaaggcgggg ctctyacctc cctggraaga    600

gagactgttg ctgtctgtgc ttcctgtgtt ctccagtccc acgctcccac ggacccacgc    660

ccttggagac tccctcrgtg tcccagggct tctggtgtgt tcagagacct ccacactcaa    720

cgaccactgg tgctgcagaa gggccggtgc ttacattcca attaacagac gcttttccca    780

tctaatgcct cttgccttct cctaacacca cctcgggagt gtttatgtct attctaagtg    840

aatttcactg tgtgaaaaaa ttcacacctg ttgtcccagc gatttgggag gccggggcgg    900

gtgtatcatt tgagcccagg agtttgaggc tagcctgggc aggatggtga aaccccgtct    960

ctataaagaa attttaaaaa ttagctgggc atagtggcac gtgcctgtag ttccatctac   1020

tggggaggct ggggtgggag gatcgcatga gcccgggagt ttgaggctgc agtgagctgt   1080
```

-continued gatcgcagca ctgcactcca gtctgggcaa cagagcaaga ccctgtctct taaaaaaaaa 1140
aaaaaaaact cgag 1154

<210> SEQ ID NO 87
<211> LENGTH: 1197
<212> TYPE: DNA
<213> ORGANISM: Homo sapiens
<220> FEATURE:
<221> NAME/KEY: SITE
<222> LOCATION: (573)
<223> OTHER INFORMATION: n equals a,t,g, or c
<220> FEATURE:
<221> NAME/KEY: SITE
<222> LOCATION: (1177)
<223> OTHER INFORMATION: n equals a,t,g, or c
<220> FEATURE:
<221> NAME/KEY: SITE
<222> LOCATION: (1185)
<223> OTHER INFORMATION: n equals a,t,g, or c

<400> SEQUENCE: 87
aagacaggaa aagctccagg ccgtggttct caaagtgtgg tccctggaca gcagcaacat 60
cacctaggag cctgttaggg aaggcacagc ctcaggccct gccccagacc tgcagaatca 120
gaaactctgg ggtgaggcct ggttatctgc tgtaacagac cttccagtgg gttctgatgc 180
cctctagagc aggagaacca ctagcttaga ggttgcagta tgtttggcat cttgccattt 240
gtgttagttc agaggaatgg ctgaccccca tgtctcattt ctaagcttca ggcagctttt 300
ctcctgggca gctgtcattc tgttgagggg aatcctgggg actgtggctc ctcctccctg 360
tccgtgtgtc cttgatctgg cagtctaccc ccttcatctc cccgtggagg ctccatgccw 420
agaggtggtc ttcaaacaga agaatggcaa arataattgt ctcgtgtttt accctgaccc 480
cattccttta agagggtcac ttcttggccc attcatttaa aaaccaatgt catagttctg 540
tgattccacc tatcagacag tgccacgtcc aangcggggc tctcacctcc ctgggaagag 600
agactgttgc tgtctgtgct tcctgtgttc tccagtccca cgctcccacg gacccacgcc 660
cttggagact ccctcagtgt cccagggctt ctggtgtgtt cagagacctc cacactcaac 720
gaccactggt gctgcagaag ggccggtgct tacattccaa ttaacagacg cttttcccat 780
ctaatgcctc ttgccttctc ctaacaccac ctcgggagtg tttatgtcta ttctaagtga 840
atttcactgt gtgaaaaaat tcacacctgt tatcccagca atttgggagg ccgaggcggg 900
tgtatcattt gggcccagga gtttgagact agcctgggca agatggtgaa accccgtctc 960
tataaagaaa ttttaaaaat tggctgggca tagtggcgcg tgcctgtagt tccatctgct 1020
ggggaggctg ggtgggaggg atcgcatgag cccgggagtt tgaggctgca gtgagctgtg 1080
atcgcggcac tgcactccag tctgggcaac agagcaaaac cctgtctctt aaaaaaaaaa 1140
aaaactcgag ggggggcccg gtacccaatt cgccctnats agtgnagtcg tattaca 1197

<210> SEQ ID NO 88
<211> LENGTH: 910
<212> TYPE: DNA
<213> ORGANISM: Homo sapiens

<400> SEQUENCE: 88
ggcagagctg gccttcgact cgctatgtcc actaacaata tgtcggaccc acggaggccg 60
aacaaagtgc tgaggtgagg accccagcgt cgtgggcacg ggttcgggtt gtgggtgtgg 120
atcggggccc tgggaagcgc ctgtctatcc cgggggcagg acctgagcgc ccctgaccct 180

-continued

```
cgagcctgtc gcaggtacaa gcccccgccg agcgaatgta acccggcctt ggacgacccg    240

acgccggact acatgaacct gctgggcatg atcttcagca tgtgcggcct catgcttaag    300

ctgaagtggt gtgcttgggt cgctgtctac tgctccttca tcagctttgc caactctcgg    360

agctcggagg acacgaagca aatgatgagt agcttcatgt gagacttgcc ctacagaaca    420

agtgactctt gagtaagggg tggggggacc ccagcctggc catcctagac tgacacctct    480

ctcctgtctt catgctgtcc atctctgccg tggtgatgtc ctatctgcag aatcctcagc    540

ccatgacgcc cccatggtga taccagccta gaagggtcac attttggacc ctgtctatcc    600

actaggcctg ggctttggct gctaaacctg ctgccttcag ctgccatcct ggacttccct    660

gaatgaggcc gtctcggtgc ccccagctgg atagagggaa cctggccctt tcctagggaa    720

caccctaggc ttacccctcc tgcctccctt cccctgcctg ctgctggggg agatgctgtc    780

catgtttcta ggggtattca tttgctttct cgttgaaacc tgttgttaat aaagtttttc    840

actctgaaaa aaaaaaaaaa aaaaaaaaac tygrgggggg gcccggaacc caattcsccg    900

gatagtgagt                                                           910
```

```
<210> SEQ ID NO 89
<211> LENGTH: 1076
<212> TYPE: DNA
<213> ORGANISM: Homo sapiens
<220> FEATURE:
<221> NAME/KEY: SITE
<222> LOCATION: (1029)
<223> OTHER INFORMATION: n equals a,t,g, or c
<220> FEATURE:
<221> NAME/KEY: SITE
<222> LOCATION: (1037)
<223> OTHER INFORMATION: n equals a,t,g, or c
<220> FEATURE:
<221> NAME/KEY: SITE
<222> LOCATION: (1040)
<223> OTHER INFORMATION: n equals a,t,g, or c

<400> SEQUENCE: 89

ggcacgaggg gaaagccatg ctcccaggac tccttccttg cagccttaaa tcggtctgta     60

cggaaaattc cgcgccttag aaacccacgc ttgggtgtaa cttattattg ttcttcctga    120

cctacttcct gtttatcact tccgggttca tcattttggc atttcggtga tcgggttgga    180

actattgaag cccgctttca ggttcttttc cccattttcc ctttgaaagg aagacttctg    240

gcttctccta aatctccgtt ctctgggtaa ggggagtcca agcctctgtc atgaggaacg    300

gaaatgcgag ggcctcgggt gttactctaa aatccgccct cagcttgcac gccggaagct    360

gcgattcctg cagcggaaga ggcgtgatct ggccttcgac tcgctatgtc cactaacaat    420

atgtcggacc cacggaggcc gaacaaagtg ctgaggtaca agcccccgcc gagcgaatgt    480

aacccggcct tggacgaccc gacgccggac tacatgaacc tgctgggcat gatcttcagc    540

atgtgcggcc tcatgcttaa gctgaagtgg tgtgcttggg tcgctgtcta ctgctccttc    600

atcagctttg ccaactctcg gagctcggag gacacgaagc aaatgatgag tagcttcatg    660

ctgtccatct ctgccgtggt gatgtcctat ctgcagaatc ctcagcccat gacgccccca    720

tggtgatacc agcctagaag ggtcacattt tggaccctgt ctatccacta ggcctgggct    780

ttggctgcta aacctgctgc cttcagctgc catcctggac ttccctgaat gaggccgtct    840

cggtgccccc agctggatag agggaacctg gccctttcct agggaacacc ctaggcttac    900

ccctcctgcc tcccttcccc tgcctgctgc tgggggagat gctgtccatg tttctagggg    960

tattcatttg ctttctcgtt gaaacctgtt gttaataaag tttttcactc tgaaaaaaaa   1020
```

-continued

```
aaaaaaaana raaaacncgn ggggggg ccc ggaacccaat tcsccggata gtgagt      1076
```

```
<210> SEQ ID NO 90
<211> LENGTH: 1842
<212> TYPE: DNA
<213> ORGANISM: Homo sapiens
<220> FEATURE:
<221> NAME/KEY: SITE
<222> LOCATION: (67)
<223> OTHER INFORMATION: n equals a,t,g, or c
<220> FEATURE:
<221> NAME/KEY: SITE
<222> LOCATION: (98)
<223> OTHER INFORMATION: n equals a,t,g, or c
<220> FEATURE:
<221> NAME/KEY: SITE
<222> LOCATION: (212)
<223> OTHER INFORMATION: n equals a,t,g, or c
<220> FEATURE:
<221> NAME/KEY: SITE
<222> LOCATION: (1838)
<223> OTHER INFORMATION: n equals a,t,g, or c

<400> SEQUENCE: 90

gcgaccgcgc ccttcagcta gctcgctcgc tcgctctgct tccctgctgc cggctgcgca     60

tggcttnggc gttggcggcg ctggcggcgg ctcgagcngc ctgcgsagcc ggtaccagca    120

gttgcagaat gaagaagagt ctggagaacc tgaacaggct gcaggtgatg ctcctccacc    180

ttacagcagc atttctgcag agagcgcaca tnattttgac tacaaggatg agtctgggtt    240

tccaaagccc ccatcttaca atgtagctac aacactgccc agttatgatg aagcggagag    300

gaccaaggct gaagctacta tccctttggt tcctgggaga gatgaggatt ttgtgggtcg    360

ggatgatttt gatgatgctg accagctgag gataggaaat gatgggattt tcatgttaac    420

ttttttcatg gcattcctct ttaactggat tgggtttttc ctgtcttttt gcctgaccac    480

ttcagctgca ggaaggtatg gggccatttc aggatttggt ctctctctaa ttaaatggat    540

cctgattgtc aggttttcca cctatttccc tggatatttt gatggtcagt actggctctg    600

gtgggtgttc cttgttttag gctttctcct gtttctcaga ggatttatca attatgcaaa    660

agttcggaag atgccagaaa ctttctcaaa tctccccagg accagagttc tctttattta    720

ttaaagatgt tttctggcaa aggccttcct gcatttatga attctctctc aagaagcaag    780

agaacacctg caggaagtga atcaagatgc agaacacaga ggaataatca cctgctttaa    840

aaaaataaag tactgttgaa aagatcattt ctctctattt gttcctaggt gtaaaatttt    900

aatagttaat gcagaattct gtaatcattg aatcattagt ggttaatgtt tgaaaaagct    960

cttgcaatca agtctgtgat gtattaataa tgccttatat attgtttgta gtcattttaa   1020

gtagcatgag ccatgtccct gtagtcggta gggggcagtc ttgctttatt catcctccat   1080

ctcaaaatga acttggaatt aaatattgta agatatgtat aatgctggcc attttaaagg   1140

ggttttctca aaagttaaac ttttgttatg actgtgtttt tgcacataat ccatatttgc   1200

tgttcaagtt aatctagaaa tttattcaat tctgtatgaa cacctggaag caaaatcata   1260

gtgcaaaaat acatttaagg tgtggtcaaa aataagtctt taattggtaa ataataagca   1320

ttaatttttt atagcctgta ttcacaattc tgcggtacct tattgtacct aagggattct   1380

aaaggtgttg tcactgtata aaacagaaag cactaggata caaatgaagc ttaattacta   1440

aaatgtaatt cttgacactc tttctataat tagcgttctt cacccccacc cccaccccca   1500

ccccccttat tttcctttg tctcctggtg attaggccaa agtctgggag taaggagagg   1560
```

-continued

```
attaggtact taggagcaaa gaaagaagta gcttggaact tttgagatga tccctaacat   1620

actgtactac ttgcttttac aatgtgttag cagaaaccag tgggttataa tgtagaatga   1680

tgtgctttct gcccaagtgg taattcatct tggtttgcta tgttaaaact gtaaatacaa   1740

cagaacatta ataaatatct cttgtgtagc accttttaaa aaaaaaaaaa aaaaaaaaaa   1800

aaaaaaaaaa aaaaaaaaaa aaaaaaaaaa aaaaaaanaa aa                       1842
```

```
<210> SEQ ID NO 91
<211> LENGTH: 1963
<212> TYPE: DNA
<213> ORGANISM: Homo sapiens
<220> FEATURE:
<221> NAME/KEY: SITE
<222> LOCATION: (335)
<223> OTHER INFORMATION: n equals a,t,g, or c
<220> FEATURE:
<221> NAME/KEY: SITE
<222> LOCATION: (1959)
<223> OTHER INFORMATION: n equals a,t,g, or c

<400> SEQUENCE: 91

ggatcctcgc ggcggcggcg gtgcttacag cctgagaaga gcgtctcgcc cgggagcggc     60

ggcggccatc gagacccacc caaggcgcgt ccccctcggc ctcccagcgc tcccaagccg    120

cagcggccgc gccccttcag ctagctcgct cgctcgctct gcttccctgc tgccggctgc    180

gcatggcktt ggcgttggcg gcgctggcgg cggtcgagcc gcctgcgcag ccggtaccag    240

cagttgcaga atgaagaaga gtctggagaa cctgaacagg ctgcaggtga tgctcctcca    300

ccttacagca gcatttctgc agagagcgca gcatnatttt gactacaagg atgagtctgg    360

gtttccaaag cccccatctt acaatgtagc tacaacactg cccagttatg atgaagcgga    420

gaggaccaag gctgaagcta ctatcccttt ggttcctggg agagatgagg attttgtggg    480

tcgggatgat tttgatgatg ctgaccagct gaggatagga aatgatggga ttttcatgtt    540

aactttttttc atggcattcc tctttaactg gattgggttt ttcctgtctt tttgcctgac    600

cacttcagct gcaggaaggt atggggccat ttcaggattt ggtctctctc taattaaatg    660

gatcctgatt gtcaggtttt ccacctattt ccctggatat tttgatggtc agtactggct    720

ctggtgggtg ttccttgttt taggctttct cctgtttctc agaggattta tcaattatgc    780

aaaagttcgg aagatgccag aaactttctc aaatctcccc aggaccagag ttctctttat    840

ttattaaaga tgttttctgg caaaggcctt cctgcattta tgaattctct ctcaagaagc    900

aagagaacac ctgcaggaag tgaatcaaga tgcagaacac agaggaataa tcacctgctt    960

taaaaaaata aagtactgtt gaaaagatca tttctctcta tttgttccta ggtgtaaaat   1020

tttaatagtt aatgcagaat tctgtaatca ttgaatcatt agtggttaat gtttgaaaaa   1080

gctcttgcaa tcaagtctgt gatgtattaa taatgcctta tatattgttt gtagtcattt   1140

taagtagcat gagccatgtc cctgtagtcg gtagggggca gtcttgcttt attcatcctc   1200

catctcaaaa tgaacttgga attaaatatt gtaagatatg tataatgctg gccattttaa   1260

aggggttttc tcaaaagtta aacttttgtt atgactgtgt ttttgcacat aatccatatt   1320

tgctgttcaa gttaatctag aaatttattc aattctgtat gaacacctgg aagcaaaatc   1380

atagtgcaaa aatacattta aggtgtggtc aaaaataagt ctttaattgg taaataataa   1440

gcattaattt tttatagcct gtattcacaa ttctgcggta ccttattgta cctaagggat   1500

tctaaaggtg ttgtcactgt ataaaacaga aagcactagg atacaaatga agcttaatta   1560

ctaaaatgta attcttgaca ctctttctat aattagcgtt cttcaccccc acccccaccc   1620
```

-continued ccacccccct tattttcctt ttgtctcctg gtgattaggc caaagtctgg gagtaaggag 1680
aggattaggt acttaggagc aaagaaagaa gtagcttgga acttttgaga tgatccctaa 1740
catactgtac tacttgcttt tacaatgtgt tagcagaaac cagtgggtta taatgtagaa 1800
tgatgtgctt tctgcccaag tggtaattca tcttggtttg ctatgttaaa actgtaaata 1860
caacagaaca ttaataaata tctcttgtgt agcaccttta aaaaaaaaaa aaaaaaaaaa 1920
aaaaaaaaaa aaaaaaaaaa aaaaaaaaaa aaaaaaaana aaa 1963

<210> SEQ ID NO 92
<211> LENGTH: 1487
<212> TYPE: DNA
<213> ORGANISM: Homo sapiens
<220> FEATURE:
<221> NAME/KEY: SITE
<222> LOCATION: (1470)
<223> OTHER INFORMATION: n equals a,t,g, or c
<220> FEATURE:
<221> NAME/KEY: SITE
<222> LOCATION: (1487)
<223> OTHER INFORMATION: n equals a,t,g, or c

<400> SEQUENCE: 92
gcgaccgcgc ccctttcagc tagctcgctc gctcgctctg cttccctgct gccggctgcg 60
catggckwtg gcgttggcgg cgctggcggc ggtcgagccg gcctgcgcag ccggtaccag 120
cagttgcaga atgaagaaga gtctggagaa cctgaacagg ctgcaggtga tgctcctcca 180
ccttacagca gcatttctgc agagagcgca gttttccacc tatttccctg gatattttga 240
tggtcagtac tggctctggt gggtgttcct tgttttaggc tttctcctgt ttctcagagg 300
atttatcaat tatgcaaaag ttcggaagat gccagaaact ttctcaaatc tccccaggac 360
cagagttctc tttatttatt aaagatgttt tctggcaaag gccttcctgc atttatgaat 420
tctctctcaa gaagcaagag aacacctgca ggaagtgaat caagatgcag aacacagagg 480
aataatcacc tgctttaaaa aaataaagta ctgttgaaaa gatcatttct ctctatttgt 540
tcctaggtgt aaaattttaa tagttaatgc agaattctgt aatcattgaa tcattagtgg 600
ttaatgtttg aaaaagctct tgcaatcaag tctgtgatgt attaataatg ccttatatat 660
tgtttgtagt cattttaagt agcatgagcc atgtccctgt agtcggtagg gggcagtctt 720
gctttattca tcctccatct caaaatgaac ttggaattaa atattgtaag atatgtataa 780
tgctggccat tttaaagggg ttttctcaaa agttaaactt ttgttatgac tgtgtttttg 840
cacataatcc atatttgctg ttcaagttaa tctagaaatt tattcaattc tgtatgaaca 900
cctggaagca aaatcatagt gcaaaaatac atttaaggtg tggtcaaaaa taagtcttta 960
attggtaaat aataagcatt aattttttat agcctgtatt cacaattctg cggtacctta 1020
ttgtacctaa gggattctaa aggtgttgtc actgtataaa acagaaagca ctaggataca 1080
aatgaagctt aattactaaa atgtaattct tgacactctt tctataatta gcgttcttca 1140
cccccacccc cacccccacc cccctattt tccttttgtc tcctggtgat taggccaaag 1200
tctgggagta aggagaggat taggtactta ggagcaaaga aagaagtagc ttggaacttt 1260
tgagatgatc cctaacatac tgtactactt gcttttacaa tgtgttagca gaaaccagtg 1320
ggttataatg tagaatgatg tgctttctgc ccaagtggta attcatcttg gtttgctatg 1380
ttaaaactgt aaatacaaca gaacattaat aaatatctct tgtgtagcac ctttaaaaaa 1440
aaaaaaaaaa aaaaaaaaaa aaaaaaaaan cccggggggg ggccccn 1487

-continued

<210> SEQ ID NO 93
<211> LENGTH: 1653
<212> TYPE: DNA
<213> ORGANISM: Homo sapiens
<220> FEATURE:
<221> NAME/KEY: SITE
<222> LOCATION: (67)
<223> OTHER INFORMATION: n equals a,t,g, or c
<220> FEATURE:
<221> NAME/KEY: SITE
<222> LOCATION: (212)
<223> OTHER INFORMATION: n equals a,t,g, or c
<220> FEATURE:
<221> NAME/KEY: SITE
<222> LOCATION: (1636)
<223> OTHER INFORMATION: n equals a,t,g, or c
<220> FEATURE:
<221> NAME/KEY: SITE
<222> LOCATION: (1653)
<223> OTHER INFORMATION: n equals a,t,g, or c

<400> SEQUENCE: 93
gcgaccgcgc ccttcagcta gctcgctcgc tcgctctgct tccctgctgc cggctgcgca 60
tggcttnggc gttggcggcg ctggcggcgg ctcgagccgc ctgcgsagcc ggtaccagca 120
gttgcagaat gaagaagagt ctggagaacc tgaacaggct gcaggtgatg ctcctccacc 180
ttacagcagc atttctgcag agagcgcaca tnattttgac tacaaggatg agtctgggtt 240
tccaaagccc ccatcttaca atgtagctac aacactgccc agttatgatg aagcggagag 300
gaccaaggct gaagctacta tccctttggt tcctgggaga gatgaggatt ttgtgggtcg 360
ggatgatttt gatgatgctg accagctgag gataggaaat gatgggattt tcatgttaac 420
ttttttcatg gcattcctct ttaactggat tgggtttttc ctgtcttttt gcctgaccac 480
ttcagctgca ggaaggtatg ggccatttc aggatttggt ctctctctaa ttaaatggat 540
cctgattgtc aggttttcca cctatttccc tgcatttatg aattctctct caagaagcaa 600
gagaacacct gcaggaagtg aatcaagatg cagaacacag aggaataatc acctgcttta 660
aaaaaataaa gtactgttga aaagatcatt tctctctatt tgttcctagg tgtaaaattt 720
taatagttaa tgcagaattc tgtaatcatt gaatcattag tggttaatgt ttgaaaaagc 780
tcttgcaatc aagtctgtga tgtattaata atgccttata tattgtttgt agtcatttta 840
agtagcatga gccatgtccc tgtagtcggt agggggcagt cttgctttat tcatcctcca 900
tctcaaaatg aacttggaat taaatattgt aagatatgta taatgctggc cattttaaag 960
gggttttctc aaaagttaaa cttttgttat gactgtgttt ttgcacataa tccatatttg 1020
ctgttcaagt taatctagaa atttattcaa ttctgtatga acacctggaa gcaaaatcat 1080
agtgcaaaaa tacatttaag gtgtggtcaa aaataagtct ttaattggta aataataagc 1140
attaattttt tatagcctgt attcacaatt ctgcggtacc ttattgtacc taagggattc 1200
taaaggtgtt gtcactgtat aaaacagaaa gcactaggat acaaatgaag cttaattact 1260
aaaatgtaat tcttgacact ctttctataa ttagcgttct tcacccccac ccccaccccc 1320
acccccctta ttttcctttt gtctcctggt gattaggcca aagtctggga gtaaggagag 1380
gattaggtac ttaggagcaa agaaagaagt agcttggaac ttttgagatg atccctaaca 1440
tactgtacta cttgctttta caatgtgtta gcagaaacca gtgggttata atgtagaatg 1500
atgtgctttc tgcccaagtg gtaattcatc ttggtttgct atgttaaaac tgtaaataca 1560
acagaacatt aataaatatc tcttgtgtag caccttttaw aaaaaaaaaa aaaaaaaaaa 1620
aaaaaaaaaa aaaaancccg gggggggcc ccn 1653

-continued

<210> SEQ ID NO 94
<211> LENGTH: 1830
<212> TYPE: DNA
<213> ORGANISM: Homo sapiens
<220> FEATURE:
<221> NAME/KEY: SITE
<222> LOCATION: (67)
<223> OTHER INFORMATION: n equals a,t,g, or c
<220> FEATURE:
<221> NAME/KEY: SITE
<222> LOCATION: (97)
<223> OTHER INFORMATION: n equals a,t,g, or c
<220> FEATURE:
<221> NAME/KEY: SITE
<222> LOCATION: (211)
<223> OTHER INFORMATION: n equals a,t,g, or c
<220> FEATURE:
<221> NAME/KEY: SITE
<222> LOCATION: (1813)
<223> OTHER INFORMATION: n equals a,t,g, or c
<220> FEATURE:
<221> NAME/KEY: SITE
<222> LOCATION: (1830)
<223> OTHER INFORMATION: n equals a,t,g, or c

<400> SEQUENCE: 94
gcgaccgcgc ccttcagcta gctcgctcgc tcgctctgct tccctgctgc cggctgcgca 60
tggcttnggc gttggcggcg ctggcggcgg tcgagcngcc tgcgsagccg gtaccagcag 120
ttgcagaatg aagaagagtc tggagaacct gaacaggctg caggtgatgc tcctccacct 180
tacagcagca tttctgcaga gagcgcacat nattttgact acaaggatga gtctgggttt 240
ccaaagcccc catcttacaa tgtagctaca acactgccca gttatgatga agcggagagg 300
accaaggctg aagctactat ccctttggtt cctgggagag atgaggattt tgtgggtcgg 360
gatgattttg atgatgctga ccagctgagg ataggaaatg atgggatttt catgttaact 420
tttttcatgg cattcctctt taactggatt gggtttttcc tgtctttttg cctgaccact 480
tcagctgcag gaaggtatgg ggccatttca ggatttggtc tctctctaat taaatggatc 540
ctgattgtca ggttttccac ctatttccct ggatattttg atggtcagta ctggctctgg 600
tgggtgttcc ttgttttagg ctttctcctg tttctcagag gatttatcaa ttatgcaaaa 660
gttcggaaga tgccagaaac tttctcaaat ctccccagga ccagagttct ctttatttat 720
taaagatgtt ttctggcaaa ggccttcctg catttatgaa ttctctctca agaagcaaga 780
gaacacctgc aggaagtgaa tcaagatgca gaacacagag gaataatcac ctgctttaaa 840
aaaataaagt actgttgaaa agatcatttc tctctatttg ttcctaggtg taaaatttta 900
atagttaatg cagaattctg taatcattga atcattagtg gttaatgttt gaaaaagctc 960
ttgcaatcaa gtctgtgatg tattaataat gccttatata ttgtttgtag tcattttaag 1020
tagcatgagc catgtccctg tagtcggtag gggcagtct tgctttattc atcctccatc 1080
tcaaaatgaa cttggaatta aatattgtaa gatatgtata atgctggcca ttttaaaggg 1140
gttttctcaa aagttaaact tttgttatga ctgtgttttt gcacataatc catatttgct 1200
gttcaagtta atctagaaat ttattcaatt ctgtatgaac acctggaagc aaaatcatag 1260
tgcaaaaata catttaaggt gtggtcaaaa ataagtcttt aattggtaaa taataagcat 1320 taattttta tagcctgtat tcacaattct gcggtacctt attgtaccta agggattcta 1380
aaggtgttgt cactgtataa aacagaaagc actaggatac aaatgaagct taattactaa 1440
aatgtaattc ttgacactct ttctataatt agcgttcttc acccccaccc ccaccccac 1500

-continued cccccttatt ttccttttgt ctcctggtga ttaggccaaa gtctgggagt aaggagagga 1560
ttaggtactt aggagcaaag aaagaagtag cttggaactt ttgagatgat ccctaacata 1620
ctgtactact tgcttttaca atgtgttagc agaaaccagt gggttataat gtagaatgat 1680
gtgctttctg cccaagtggt aattcatctt ggtttgctat gttaaaactg taaatacaac 1740
agaacattaa taaatatctc ttgtgtagca ccttttaaaa aaaaaaaaaa aaaaaaaaaa 1800
aaaaaaaaaa aancccgggg gggggccccn 1830

<210> SEQ ID NO 95
<211> LENGTH: 1134
<212> TYPE: DNA
<213> ORGANISM: Homo sapiens

<400> SEQUENCE: 95
tccatctaca gtcctcacac aggtattcag gaataccagg atggcgtgcc caagattcca 60
acagcctgta ttacggtgga agatgcagaa atgatgtcaa gaatggcttc tcatgggatc 120
aaaattgtca ttcagctaaa gatgggggca aagacctacc cagatactga ttccttcaac 180
actgtagcag agatcactgg gagcaaatat ccagaacagg ttgtactggt cagtggacat 240
ctggacagct gggatgttgg gcagggtgcc atggatgatg gcggtggagc ctttatatca 300
tgggaagcac tctcacttat taaagatctt gggctgcgtc caaagaggac tctgcggctg 360
gtgctctgga ctgcagaaga acaaggtgga gttggtgcct tccagtatta tcagttacac 420
aaggtaaata tttccaacta cagtctggtg atggagtctg acgcaggaac cttcttaccc 480
actgggctgc aattcactgg cagtgaaaag gccagggcat catggaggag gttatgagcc 540
tgctgcagcc cctcaatatc actcaggtcc tgagccatgg agaagggaca gacatcaact 600
tttggatcca agctggagtg cctggagcca gtctacttga tgacttatac aagtatttct 660
tcttccatca ctcccacgga gacaccatga ctgtcatgga tccaaagcag atgaatgttg 720
ctgctgctgt ttgggctgtt gtttcttatg ttgttgcaga catggaagaa atgctgccta 780
ggtcctagaa acagtaagaa agaaacgttt tcatgcttct ggccaggaat cctgggtctg 840
caactttgga aaactcctct tcacataaca atttcatcca attcatcttc aaagcacaac 900
tctatttcat gctttctgtt attatctttc ttgatacttt ccaaattctc tgcattctag 960
aaaaaggaat cattctcccc tccctcccac cacatagaat caacatatgg tagggattac 1020
agtgggggca tttctttata tcacctctta aaaacattgt ttccacttta aaagtaaaca 1080
cttaataaat ttttggaaga tctctgaaaa aaaaaaaaaa aaaaaaaaaa aaaa 1134

<210> SEQ ID NO 96
<211> LENGTH: 1772
<212> TYPE: DNA
<213> ORGANISM: Homo sapiens

<400> SEQUENCE: 96
tcgacccacg cgtccgggag gatccccagc cgggtcccaa gcctgtgcct gagcctgagc 60
ctgagcctga gccgagccgg gagccggtcg cgggggctcc gggctgtggg accgctgggc 120
ccccagcgat ggcgaccctg tggggaggcc ttcttcggct tggctccttg ctcagcctgt 180
cgtgcctggc gctttccgtg ctgctgctgg cgcactgtca gacgccgcca agaatttcga 240
ggatgtcaga tgtaaatgta tctgccctcc ctataaagaa aaattctggg catatttata 300
ataagaacat atctcagaaa gattgtgatt gccttcatgt tgtggagccc atgcctgtgc 360
gggggcctga tgtagaagca tactgtctac gctgtgaatg caaatatgaa gaaagaagct 420

-continued

```
ctgtcacaat caaggttacc attataattt atctctccat tttgggcctt ctacttctgt    480
acatggtata tcttactctg gttgagccca tactgaagag gcgcctcttt ggacatgcac    540
agttgataca gagtgatgat gatattgggg atcaccagcc ttttgcaaat gcacacgatg    600
tgctagcccg ctcccgcagt cgagccaacg tgctgaacaa ggtagaatat ggcacagcag    660
cgctggaagc ttcaagtcca agagcagcga aaagtctgtc tttgaccggc atgttgtcct    720
cagctaattg gggaattgaa ttcaaggtga ctagaaagaa acaggcagac aactggaaag    780
gaactgactg ggttttgctg ggtttcattt taataccttg ttgatttcac caactgttgc    840
tggaagattc aaaactggaa gkaaaaactt gcttgatttt tttttcttgt taacgtaata    900
atagagacat ttttaaaagc acacagctca aagtcagcca ataagtcttt tcctatttgt    960
gacttttact aataaaaata aatctgcctg taaaataaat taaaaaatcc tttacctgga   1020
acaagcactc tctttttcac cacatagttt taacttgact ttccaagata attttcaggg   1080
tttttgttgt tgttgttttt tgtttgtttg ttttggtggg agaggggagg gatgcctggg   1140
aagtggttaa caactttttt caagtcactt tactaaacaa acttttgtaa atagacctta   1200
ccttctattt tcgagtttca tttatatttt gcagtgtagc cagcctcatc aaagagctga   1260
cttactcatt tgacttttgc actgactgta ttatctgggt atctgctgtg tctgcacttc   1320
atggtaaacg ggatctaaaa tgcctggtgg cttttcacaa aaagcagatt ttcttcatgt   1380
actgtgatgt ctgatgcaat gcatcctaga acaaactggc catttgctag tttactctaa   1440
agactaaaca tagtcttggt gtgtgtggtc ttactcatct tctagtacct ttaaggacaa   1500
atcctaagga cttggacact tgcaataaag aaattttatt ttaaacccaa gcctccctgg   1560
attgataata tatacacatt tgtcagcatt tccggtcgtg gtgagaggca gctgtttgag   1620
ctccaatgtg tgcagctttg aactagggct ggggttgtgg gtgcctcttc tgaaaggtct   1680
aaccattatt ggataactgg cttttttttct tcctctttgg aatgtaacaa taaaaataat   1740
ttttgaaaca tcaaaaaaaa aaaaaaaaaa aa                                 1772
```

<210> SEQ ID NO 97
<211> LENGTH: 2381
<212> TYPE: DNA
<213> ORGANISM: Homo sapiens

<400> SEQUENCE: 97

```
ccacgcgtcc cgcaaggcca gttctagtgt agagagaaaa aggagccggc agcggctctt     60
acgcgtcccg gggctgcgcg ccactctctc ggccggtaac gcggtgcttt gcggctgtcg    120
tcaagcgcgg cgttgggccg gcgggcgggg gctgaggggc tgccatggcg gcggcgggcc    180
ggctcccgag ctcctgggcc ctcttctcgc cgctcctcgc agggcttgca ctactgggag    240
tcgggccggt cccagcgcgg gcgctgcaca acgtcacggc cgagctcttt ggggccgagg    300
cctggggcac ccttgcggct ttcggggacc tcaactccga caagcagacg gatctcttcg    360
tgctgcggga aagaaatgac ttaatcgtct ttttggcaga ccagaatgca ccctatttta    420
aacccaaagt aaaggtatct ttcaagaatc acagtgcatt gataacaagt gtagtccctg    480
gggattatga tggagattct caaatggatg tccttctgac atatcttccc aaaaattatg    540
ccaagagtga attaggagct gttatcttct ggggacaaaa tcaaacatta gatcctaaca    600
atatgaccat actcaatagg acttttcaag atgagccact aattatggat ttcaatggtg    660
atctaattcc tgatattttt ggtatcacaa atgaatccaa ccagccacag atactattag    720
```

-continued

```
gagggaattt atcatggcat ccagcattga ccactacaag taaaatgcga attccacatt    780
ctcatgcatt tattgatctg actgaagatt ttacagcaga tttattcctg acgacattga    840
atgccaccac tagtaccttc cagtttgaaa tatgggaaaa tttggatgga aacttctctg    900
tcagtactat attggaaaaa cctcaaaata tgatggtggt tggacagtca gcatttgcag    960
actttgatgg agatggacac atggatcatt tactgccagg ctgtgaagat aaaaattgcc   1020
aaaagagtac catctactta gtgagatctg ggatgaagca gtgggttcca gtcctacaag   1080
atttcagcaa taagggcaca ctctggggct ttgtgccatt tgtggatgaa cagcaaccaa   1140
ctgaaatacc aattccaatt acccttcata ttggagacta caatatggat ggctatccag   1200
acgctctggt catactaaag aacacatctg gaagcaacca gcaggccttt ttactggaga   1260
acgtcccttg taataatgca agctgtgaag aggcgcgtcg aatgtttaaa gtctactggg   1320
agctgacaga cctaaatcaa attaaggatg ccatggttgc caccttcttt gacatttacg   1380
aagatggaat cttggacatt gtagtgctaa gtaaaggata tacaaagaat gattttgcca   1440
ttcatacact aaaaaataac tttgaagcag atgcttattt tgttaaagtt attgttctta   1500
gtggtctgtg ttctaatgac tgtcctcgta gataacaccc tttggagtga atcaacctgg   1560
accttatatc atgtatacaa ctgtagatgc aaatgggtat ctgaaaaatg gatcagctgg   1620
ccaactcagc caatccgcac atttagctct ccaactacca tacaacgtgc ttggtttagg   1680
tcggagcgca aattttcttg accatctcta cgttggtatt ccccgtccat ctggagaaaa   1740
atctatacga aaacaagagt ggactgcaat cattccaaat tcccagctaa ttgtcattcc   1800
ataccctcac aatgtccctc gaagttggag tgccaaactg tatcttacac caagtaatat   1860
tgttctgctt actgctatag ctctcatcgg tgtctgtgtt ttcatcttgg caataattgg   1920
cattttacat tggcaggaaa agaaagcaga tgatagagaa aaacgacaag aagcccaccg   1980
gtttcatttt gatgctatgt gacttgcctt taatattaca taatggaatg gctgttcact   2040
tgattagttg aaacacaaat tctggcttga aaaaataggg gagattaaat attatttata   2100
aatgatgtat cccatggtaa ttattggaaa gtattcaaat aaatatggtt tgaatatgtc   2160
acaaggtctt ttttttaaa gcactttgta tataaaaatt tgggttctct attctgtagt   2220
gctgtacatt tttgttcctt tgtggaatgt gttgcatgta ctccagtgtt tgtgtattta   2280
taatcttatt tgcatcatga tgatggaaaa agttgtgtaa ataaaaataa ttaaatgagc   2340
aggaaaaaaa aaaaaaaaaa aaaaaaaaaa aaaaaaaaaa a                        2381
```

<210> SEQ ID NO 98
<211> LENGTH: 1955
<212> TYPE: DNA
<213> ORGANISM: Homo sapiens

<400> SEQUENCE: 98

```
ggcacgagtg ccatccctgt atttgctgcc atgctcttcc ttttctccat ggctacactg     60
ttgaggacca gcttcagtga ccctggagtg attcctcggg cgctaccaga tgaagcagct    120
ttcatagaaa tggagataga agctaccaat ggtgcggtgc cccagggcca gcgaccaccg    180
cctcgtatca agaatttcca gataaacaac cagattgtga aactgaaata ctgttacaca    240
tgcaagatct tccggcctcc ccgggcctcc cattgcagca tctgtgacaa ctgtgtggag    300
cgcttcgacc atcactgccc ctgggtgggg aattgtgttg gaaagaggaa ctaccgctac    360
ttctacctct tcatcctttc tctctccctc ctcacaatct atgtcttcgc cttcaacatc    420
gtctatgtgg ccctcaaatc tttgaaaatt ggcttcttgg agacattgaa aggaaactcc    480
```

-continued tggaactgtt ctagaagtcc tcatttgctt ctttacactc tggtccgtcg tgggactgac 540
tggatttcat actttcctcg tggctctcaa ccagacaacc aatgaaagac atcaaaggat 600
catggacagg gaagaatcgc gtccagaatc cctacagcca tggcaatatt gtgaagaact 660
gctgtgaagt gctgtgtggc cccttgcccc ccagtgtgct ggatcgaagg ggtattttgc 720
cactggagga aagtggaagt cgacctccca gtactcaaga gaccagtagc agcctcttgc 780
cacagagccc agcccccaca gaacacctga actcaaatga gatgccggag gacagcagca 840
ctcccgaaga gatgccacct ccagagcccc cagagccacc acaggaggca gctgaagctg 900
agaagtagcc tatctatgga agagactttt gtttgtgttt aattagggct atgagagatt 960
tcaggtgaga agttaaacct gagacagaga gcaagtaagc tgtccctttt aactgttttt 1020
ctttggtctt tagtcaccca gttgcacact ggcattttct tgctgcaagc ttttttaaat 1080
ttctgaactc aaggcagtgg cagaagatgt cagtcacctc tgataactgg aaaaatgggt 1140
ctcttgggcc ctggcactgg ttctccatgg cctcagccac agggtcccct tggacccccct 1200 ctcttccctc cagatcccag ccctcctgct tggggtcact ggtctcattc tggggctaaa 1260
agttttcgag actggctcaa atcctcccaa gctgctgcac gtgctgagtc cagaggcagt 1320
cacagagacc tctggccagg ggatcctaac tgggttcttg ggtcttcag gactgaagag 1380 gagggagagt ggggtcagaa gattctcctg gccaccaagt gccagcattg cccacaaatc 1440
cttttaggaa tgggacaggt accttccact agttgtattt attagtgtag cttctccttt 1500
gtctcccatc cactctgaca ccttaagccc cactcttttc ccattagata tatgtaagta 1560
gttgtagtag agataataat tgacatttct cgtagactac ccagaaactt ttttaatacc 1620
tgtgccattc tcaataagaa tttatgagat gccagcggca tagcccttca cactctctgt 1680
ctcatctctc ctcctttctc attagcccct tttaatttgt ttttcctttt gactcctgct 1740
cccattagga gcaggaatgg cagtaataaa agtctgcact ttggtcattt cttttcctca 1800
gaggaagcct gagtgctcac ttaaacacta tcccctcaga ctccctgtgt gaggcctgca 1860
gaggccctga atgcacaaat gggaaaccaa ggcacagaga ggctctcctc tcctctcctc 1920
tcccccgatg taccctcaaa aaaaaaaaaa aaaaa 1955

<210> SEQ ID NO 99
<211> LENGTH: 1958
<212> TYPE: DNA
<213> ORGANISM: Homo sapiens

<400> SEQUENCE: 99
ccacgcgtcc ggggcgttcc tggtcgtgag aggggagccc caggggagct ggggcagcat 60
gactggggtg ataaatggcc ggaaatttgg cgtggccaca ctcaacacca gcgtgatgca 120
ggaggcacac tccggggtca gcagcatcca cagcagcatc cgccatgtcc cagcaaacgt 180
ggggcctctg atgcgggtgc tcgtggtcac catcgccccc atctactggg ccctggccag 240
agagagtggg gaagccctga atggccactc tctgactggg ggcaagttcc ggcagagtca 300
cacgtggagt ttgctacagg gagctgctca cgatgaccca gtggcccggg gtctggatcc 360
cgatggcctc ctgctcctcg acgtggtggt caatggcgtt gtccccggac gagcctggct 420
gacgcagatc ttcaagtgca ggactttgaa gaagcactac gtgcaaacaa gggcctggcc 480
agctgttcgt gggctccaca cagcgcttct tccagggcgg cctcccctcg ttcctacgct 540
gcaaccacag catccagtac aacgcggccc ggggccccca gccccagctg gtgcagcacc 600

-continued

```
tgcgggcctc agctatcagc tcggcctttg atccagaggc cgaggccctg cgcttccagc    660

tcgctacagc cctgcaggcg gaggagaacg aggtcggctg ccccgagggc tttgagctgg    720

actcccaggg agcgttttgt gtggatgtgg acgagtgtgc gtgggatgct cacctctgcc    780

gagagggaca gcgctgtgtg aacctgctcg ggtcctaccg ctgcctcccc gactgtgggc    840

ctggcttccg ggtggctgat ggggccggct gtgaaaatgt ggacgaatgc ctggaagggg    900

ttggacgact gtcactacaa ccagctctgc gagaacaccc caggcggtca ccgctgcagc    960

tgccccaggg gttaccggat gcagggcccc agcctgccct gcctagatgt caatgagtgc   1020

ctgcagctgc ccaaggcctg cgcctaccag tgccacaacc tccagggcag ctaccgctgc   1080

ctgtgccccc caggccagac cctccttcgc gacggcaagg cctgcacctc actggagcgg   1140

aatggacaaa atgtgaccac cgtcagccac cgaggccctc tattgccctg gctgcggccc   1200

tgggcctcga tccccggtac ctcctaccac gcctgggtct ctctccgtcc gggtcccatg   1260

gccctgagca gtgtgggccg ggcctggtgc cctcctggtt tcatcaggca gaacggagtc   1320

tgcacagacc ttgacgagtg ccgcgtgagg aacctgtgtc agcacgcctg ccgcaacact   1380

gagggcagct accagtgcct gtgccccgcc ggctaccgtc tgctccccag cgggaagaac   1440

tgccaggaca tcaacgagtg cgaggaggag agcatcgagt gtggacccgg ccagatgtgc   1500

ttcaacaccc gtggcagcta ccagtgtgtg gacacaccct gtcctgccac ctaccggcag   1560

ggccccagcc ctgggacgtg cttccggcgc tgctcgcagg actgcggcac gggcggccct   1620

tctacgctgc agtaccggct gctgccgctg cccctgggcg tgcgcgccca ccacgacgtg   1680

gcccgcctca ccgccttctc cgaggtcggc gtccccgcca accgcaccga gctcagcatg   1740

ctggagcccg acccccgcag ccccttcgcg ctgcgtccgc tgcgcgcggg ccttggcgcg   1800

gtctacaccc gtcgcgcgct cacccgcgcc ggcctctacc ggctcaccgt gcgtgctgcg   1860

gcaccgcgcc accaaagcgt cttcgtcttg ctcatcgccg tgtcccccta cccctactaa   1920

acgggagagg gcattggcgg ccgctctaga ggatccct                           1958
```

<210> SEQ ID NO 100
<211> LENGTH: 2444
<212> TYPE: DNA
<213> ORGANISM: Homo sapiens

<400> SEQUENCE: 100

```
ttacgccaag ctggcacgag caatgaaaga gttaatctct ttggctgggc ctacagatga     60

catacagagt acagtccccc aggttcatgc tttaaatatc cttagagcat tgttcagaga    120

tacgcgcctg ggagaaaata ttattcctta tgttgctgat ggagctaagg ctgcaattct    180

gggttttaca tcaccggtct gggcagtgcg aaattcatcc acacttctct ttagtgcctt    240

gatcacaaga atttttggag ttaaaagggc aaaggatgaa cattccaaaa caaatagaat    300

gacagggaga gagtttttct ctcgtttccc agaactctat ccttttcttc tcaaacagtt    360

ggaaactgta gccaatacag tagacagtga tatgggagaa ccaaatcgtc atccaagcat    420

gtttctctta cttttggtgt tggagagact ctacgcttcc ccgatggatg gtacttcttc    480

tgctctcagc atgggacctt ttgttccctt cattatgagg tgtggtcact cacctgtcta    540

ccactcccgt gaaatggcag ctcgtgcctt ggtcccattt gttatgatag atcacattcc    600

taataccatt cgaactctgt tgtccacact ccccagctgc actgaccagt gtttccgggc    660

aaaaccacat tcatggggac acttctccag gtttttccat ttgttgcaag cctactcaga    720

ctccaaaaca cggaacgaat tcagacttcc agcacgagct gactgacatc actgtttgta    780
```

-continued ccaaagccaa actctggctg gccaagaggc aaaatccatg tttggtgacc agagctgtat 840
atattgatat tctcttccta ttgacttgct gcctcaacag atctgcaaag gacaaccagc 900
cagttctgga gagtcttggc ttctgggaag aaattcaaag ggaattatct caggatcaga 960
agctgataac gggattccct tgggccttca aggtgccagg cctgccccag tacctccaga 1020
gcctcaccag actagccatt gctgcagtgt gggccgcggc agccaagagt ggagagcggg 1080
agacgaatgt ccccatctct ttctctcagc tgttagaatc tgccttccct gaagtgcgct 1140
cactaacact ggaagccctc ttggaaaagt tcttagcagc agactctgga cttggagaga 1200
agggcgtgcc acccttgctg tgcaacatgg gagagaagtt cttattgttg gccatgaagg 1260
aaaatcaccc agaatgcttc tgcaagatac tgaaaattct acactgcatg gaccctggtg 1320
agtggcttcc ccagacggag cactgtgtcc atctgacccc aaaggagttc ttgatctgga 1380
cgatggatat tgcttccaat gaaagatctg aaattcagag tgtagctctg agacttgctt 1440
ccaaagtcat ttcccaccac atgcagacat gtgtggagaa cagggaattg atagctgctg 1500
agctgaagca gtgggttcag ctggtcatct tgtcatgtga agaccatctt cctacagagt 1560
ctaggctggc cgtcgttgaa gtcctcacca gtactacacc acttttcctc accaaccccc 1620
atcctattct tgagttgcag gatacacttg ctctctggaa gtgtgtcctt acccttctgc 1680
agagtgagga gcaagctgtt agagatgcag ccacggaaac cgtgacaact gccatgtcac 1740
aagaaaatac ctgccagtca acagagtttg ccttctgcca ggtggatgcc tccatcgctc 1800
tggccctggc cctggccgtc ctgtgtgatc tgctccagca gtgggaccag ttggcccctg 1860
gactgcccat cctgctggga tggctgttgg gagagagtga tgacctcgtg gcctgtgtgg 1920
agagcatgca tcaggtggaa gaagactacc tgtttgaaaa agcagaagtc aacttttggg 1980
ccgagaccct gatctttgtg aaatacctct gcaagcacct cttctgtctc ctctcaaagt 2040
ccggctggcg tcccccaagc cctgagatgc tctgtcacct tcaaaggatg gtgtcagagc 2100
agtgccacct cctgtctcag ttcttcagag agcttccacc agctgctgag tttgtgaaga 2160
cagtggagtt cacaagacta cgcattcaag aggaaaggac tttggcttgc ttgaggctgc 2220
tggccttttt ggaaggaaag gaaggggaag acaccctagt tctcagtgtt tgggactctt 2280
atgcagaatc gaggcagtta actcttccaa gaacagaagc ggcatgttga agaaaatctg 2340
ggggattggg atgggggtat gtgtggattt ttcctccact aaatctgcag gaaacatgtt 2400
gaacataaat tcaaaaattt tatcccaaaa aaaaaaaaaa aaaa 2444

<210> SEQ ID NO 101
<211> LENGTH: 2709
<212> TYPE: DNA
<213> ORGANISM: Homo sapiens

<400> SEQUENCE: 101
ggcacgagat ttcctacagg tgaaacgcca tcattaggat tcactgtaac gttagtgcta 60
ttaaactcac tagcattttt attaatggcc gttatctaca ctaagctata ctgcaacttg 120
gaaaaagagg acctctcaga aaactcacaa tctagcatga ttaagcatgt cgcttggcta 180
atcttcacca attgcatctt tttctgccct gtggcgtttt tttcatttgc accattgatc 240
actgcaatct ctatcagccc cgaaataatg aagtctgtta ctctgatatt ttttccatgc 300
ctgcttgcct gaatccagtc ctgtatgttt tcttcaaccc aaagtttaaa gaagactgga 360
agttactgaa gcgacgtgtt accaagaaaa gtggatcagt ttcagtttcc atcagtagcc 420

-continued

```
aaggtggttg tctggaacag gatttctact acgactgtgg catgtactca catttgcagg    480
gcaacctgac tgtttgcgac tgctgcgaat cgtttctttt aacaaagcca gtatcatgca    540
aacacttgat aaaatcacac agctgtcctg cattggcagt ggcttcttgc caaagacctg    600
agggctactg gtccgactgt ggcacacatt cggcccactc tgattatgca gatgaagaag    660
attcctttgt ctcagacagt tctgaccagg tgcaggcctg tggacgagcc tgcttctacc    720
agagtagagg attccctttg gtgcgctatg cttacaatct accaagagtt aaagactgaa    780
ctactgtgtg tgtaaccgtt tcccccgtca accaaaatca gtgtttatag agtgaaccct    840
attctcatct ttcatctggg aagcacttct gtaatcactg cctggtgtca cttagaagaa    900
ggagaggtgg cagtttattt ctcaaaccag tcattttcaa agaacaggtg cctaaattat    960
aaattggtga aaaatgcaat gtccaagcaa tgtatgatct gtttgaaaca aatatatgac   1020
ttgaaaagga tcttaggtgt agtagagcaa tataatgtta gttttttctg atccataaga   1080
agcaaattta tacctatttg tgtattaagc acaagataaa gaacagctgt taatattttt   1140
taaaaattct atttttaaaa tgtgattttc tataactgaa gaaaaatatc ttgctaattt   1200
tacctaatgt ttcatccttt aatctcagga caacttactg cagggccaaa aaagggactg   1260
tcccagctag acctgtgaga gtatacatag gcattacttt attatgtttt cacttgccat   1320
ccttgacata agagaactat aaattttgtt taagcaattt ataaatctaa aacctgaaga   1380
tgtttttaaa acaatattaa cagctgttag gttaaaaaaa tagctggaca tttgttttca   1440
gtcattatac attgctttgg tccaatcagt aattttttct taagtgtttt gtgattacac   1500
tactagaaaa aaagtaaaag gctaattgct gtgtgggttt agtcgatttg gctaaactac   1560
taactaatgt gggggtttaa tagtatctga gggatttggt ggcttcatgt aatgttctca   1620
ttaatgaata cttcctaata tcgttggctc tactaatatt ttccaatttg ctgggatgtc   1680
acctagcaat agcttggatt atatagaaag taaactgtgg tcaatacttg catttaatta   1740
gacgaaacgg ggagtaatta tgacacgaag tacttaatgt ttatttctta gtgagctgga   1800
ttatcttgaa cctgtgctat taaatggaaa tttccataca tcttccccat actatttttt   1860
ataaaagagc ctattcaata gctcagaggt tgaactctgg ttaaacaaga taatatgtta   1920
ttaataaaaa tagaagaaga aagaataaag cttagtcctg tgtcttttaa aaattaaaaa   1980
ttttacttga ttccccatct atgggcttta gacctattac tgggtggagt cttaaagtta   2040
taattgttca atatgttttt tgaacagtgt gctaaatcaa tagcaaaccc actgccatat   2100
tagttattct gaatatacta aaaaaatcca gctagattgc agtttaataa ttaaactgta   2160
catactgtgc atataatgaa tttttatctt atgtaaatta tttttagaac acaagttggg   2220
aaatgtggct tctgttcatt tcgtttaatt aaagctacct cctaaactat agtggctgcc   2280
agtagcagac tgttaaattg tggtttatat actttttgca ttgtaaatag tctttgttgt   2340
acattgtcag tgtaataaaa acagaatctt tgtatatcaa aatcatgtag tttgtataaa   2400
atgtgggaag gatttattta cagtgtgttg taattttgta aggccaacta tttacaagtt   2460
ttaaaaattg ctatcatgta tatttacaca tctgataaat attaaatcat aacttggtaa   2520
gaaactccta attaaaaggt tttttccaaa attcaggtta ttgaaaactt ttcattttat   2580
tcatttaaaa actagaataa cagatatata aaagtgttaa tctttgtgct atatggtatg   2640
aaatacaata ttgtactcag tgttttgaat tattaaagtt tctagaaagc aaaaaaaaaa   2700
aaaaaaaaa                                                           2709
```

-continued

<210> SEQ ID NO 102
<211> LENGTH: 1722
<212> TYPE: DNA
<213> ORGANISM: Homo sapiens
<220> FEATURE:
<221> NAME/KEY: SITE
<222> LOCATION: (401)
<223> OTHER INFORMATION: n equals a,t,g, or c
<220> FEATURE:
<221> NAME/KEY: SITE
<222> LOCATION: (695)
<223> OTHER INFORMATION: n equals a,t,g, or c

<400> SEQUENCE: 102
gggaccgcgc tgtcctgctg tcaccaagag ctggagacac catctcccac cgagagtcat 60
ggccccattg gccctgcacc tcctcgtcct cgtccccatc ctcctcagcc tggtggcctc 120
ccaggactgg aaggctgaac gcagccaaga ccccttcgag aaatgcatgc aggatcctga 180
ctatgagcag ctgctcaagg tcaccatcct ggaggcagat aacaggatcg gggccgcat 240 cttcacctac cgggaccaga wyacgggctg gattggggag ctgggagcca tgcgcatgcc 300
cagctctcac aggatcctcc acaagctctg ccagggcctg ggctcaacc tgaccaagtt 360 cacccagtac gacaagaaca cgtggacgga ggtgcacgaa ntgaagctgc gcaactatgt 420
ggtggagaag gtgcccgaga agctgggcta cgccttgcgt ccccaggaaa agggccactc 480
gcccgaagac atctaccaga tggctctcaa ccaggccctc aaagacctca aggcactggg 540
ctgcagaaag gcgatgaaga agtttgaaag gcacacgctc ttggaatatc ttctcgggga 600
ggggaacctg agccggccgg ccgtgcagct tctgggagac gtgatgtccg aggatggctt 660
cttctatctc agcttcgccg aggccctccg ggccnacagc tgcctcagcg acagactcca 720
gtacagccgc atcgtgggtg gctgggacct gctgccgcgc gcgctgctga gctcgctgtc 780
cgggcttgtg ctgttgaacg cgcccgtggt ggcgatgacc cagggaccgc acgatgtgca 840
cgtgcagatc gagacctctc cccggcgcg gaatctgaag gtgctgaagg ccgacgtggt 900
gctgctgacg gcgagcggac cggcggtgaa gcgcatcacc ttctcgccgc gctgccccgc 960
cacatgcagg aggcgctgcg gaggctgcac tacgtgccgg ccaccaaggt gttcctaagc 1020
ttccgcaggc ccttctggcg cgaggagcac attgaaggcg gccactcaaa caccgatcgc 1080
ccgtcgcgca tgattttcta cccgccgccg cgcgagggcg cgctgctgct ggcctcgtac 1140
acgtggtcgg acgcggcggc agcgttcgcc ggcttgagcc gggaagaggc gttgcgcttg 1200
gcgctcgacg acgtggcggc attgcacggg cctgtcgtgc gccagctctg ggacggcacc 1260
ggcgtcgtca agcgttgggc ggaggaccag cacagccagg gtggctttgt ggtacagmcg 1320
ccggcgctct ggcaaaccga aaaggatgac tggacggtcc cttatggccg catctacttt 1380
gccggcgagc acaccgccta cccgcacggc tgggtggaga cggcggtcaa gtcggcgctg 1440
cgcgccgcca tcaagatcaa cagccggaag ggcctgcat cggacacggc cagccccgag 1500
gggcacgcat ctgacatgga ggggcagggg catgtgcatg ggtggccag cagcccctcg 1560 catgacctgg caaaggaaga aggcagccac cctccagtcc aaggccagtt atctctccaa 1620
aacacgaccc acacgaggac ctcgcattaa agtattttcg gaaaaaaaaa aaaaaaaaaa 1680
aaaaaaaaaa aaaaaaaaaa aaaaaaaaaa aaaagggcgg cc 1722

<210> SEQ ID NO 103
<211> LENGTH: 106
<212> TYPE: PRT
<213> ORGANISM: Homo sapiens
<220> FEATURE:

-continued

<221> NAME/KEY: SITE
<222> LOCATION: (14)
<223> OTHER INFORMATION: Xaa equals any of the naturally occurring L-amino acids
<220> FEATURE:
<221> NAME/KEY: SITE
<222> LOCATION: (29)
<223> OTHER INFORMATION: Xaa equals any of the naturally occurring L-amino acids

<400> SEQUENCE: 103

```
Met Gly Ser Leu Ser Gly Cys Ala Leu Pro Phe Cys Leu Xaa Val Phe
  1               5                  10                  15

Phe Leu Thr Val Ser Pro Ser Ala Val Gly Leu Leu Xaa Phe Ala Gly
             20                  25                  30

Gly Pro Leu Gln Thr Leu Phe Ala Trp Val Ser Pro Val Glu Ala Ala
         35                  40                  45

Glu Gln Gln Arg Leu Leu Pro Val Leu Ser Ser Gly Ser Phe Val Ser
     50                  55                  60

Glu Gly Thr Cys Gln Met Pro Ala Arg Ala Leu Leu Tyr Glu Val Ser
 65                  70                  75                  80

Val Gly Pro Tyr Trp Glu Ile Pro Pro Ser Gln Asp Thr Arg Arg Ser
                 85                  90                  95

Gly Thr Tyr Leu Arg Arg Gln Ser Asp Pro
            100                 105
```

<210> SEQ ID NO 104
<211> LENGTH: 86
<212> TYPE: PRT
<213> ORGANISM: Homo sapiens

<400> SEQUENCE: 104

```
Met Thr Leu Pro Ser Arg Ala Leu Ala Ser Leu Gly Val Gly Val Trp
  1               5                  10                  15

Gly Met Leu Arg Leu Asn Gln Val Thr Val Ser Cys Gly Gly Ser Arg
             20                  25                  30

Trp Ser Ser Arg Val Ala Leu Gly Ala Phe Ser Trp Val Cys Gly Val
         35                  40                  45

Ala Leu Val Leu Gln Pro Ser Gly Gly Gly Leu Gly Leu Thr Ser Pro
     50                  55                  60

Ser Glu Gly Cys Trp Glu Gly Glu Leu Ala Leu Ala Val Leu Arg Ala
 65                  70                  75                  80

Pro Gly Gly Ser Pro Ser
                 85
```

<210> SEQ ID NO 105
<211> LENGTH: 302
<212> TYPE: PRT
<213> ORGANISM: Homo sapiens

<400> SEQUENCE: 105

```
Met Ala Arg Ala Arg Gly Ser Pro Cys Pro Pro Leu Pro Pro Gly Arg
  1               5                  10                  15

Met Ser Trp Pro His Gly Ala Leu Leu Phe Leu Trp Leu Phe Ser Pro
             20                  25                  30

Pro Leu Gly Ala Gly Gly Gly Gly Val Ala Val Thr Ser Ala Ala Gly
         35                  40                  45

Gly Gly Ser Pro Pro Ala Thr Ser Cys Pro Val Ala Cys Ser Cys Ser
     50                  55                  60
```

-continued

```
Asn Gln Ala Ser Arg Val Ile Cys Thr Arg Arg Asp Leu Ala Glu Val
 65                  70                  75                  80

Pro Ala Ser Ile Pro Val Asn Thr Arg Tyr Leu Asn Leu Gln Glu Asn
                 85                  90                  95

Gly Ile Gln Val Ile Arg Thr Asp Thr Phe Lys His Leu Arg His Leu
            100                 105                 110

Glu Ile Leu Gln Leu Ser Lys Asn Leu Val Arg Lys Ile Glu Val Gly
        115                 120                 125

Ala Phe Asn Gly Leu Pro Ser Leu Asn Thr Leu Glu Leu Phe Asp Asn
    130                 135                 140

Arg Leu Thr Thr Val Pro Thr Gln Ala Phe Glu Tyr Leu Ser Lys Leu
145                 150                 155                 160

Arg Glu Leu Trp Leu Arg Asn Asn Pro Ile Glu Ser Ile Pro Ser Tyr
                165                 170                 175

Ala Phe Asn Arg Val Pro Ser Leu Arg Arg Leu Asp Leu Gly Glu Leu
            180                 185                 190

Lys Arg Leu Glu Tyr Ile Ser Glu Ala Ala Phe Glu Gly Leu Val Asn
        195                 200                 205

Leu Arg Tyr Leu Asn Leu Gly Met Cys Asn Leu Lys Asp Ile Pro Asn
    210                 215                 220

Leu Thr Ala Leu Val Arg Leu Glu Glu Leu Glu Leu Ser Gly Asn Arg
225                 230                 235                 240

Leu Asp Leu Ile Arg Pro Gly Ser Phe Gln Gly Leu Thr Ser Leu Arg
                245                 250                 255

Lys Leu Trp Leu Met His Ala Gln Val Ala Thr Ile Glu Arg Asn Ala
            260                 265                 270

Phe Asp Asp Leu Lys Ser Leu Glu Glu Leu Asn Leu Ser His Asn Asn
        275                 280                 285

Leu Met Ser Leu Pro His Asp Leu Phe Thr Pro Leu His Arg
    290                 295                 300
```

<210> SEQ ID NO 106
<211> LENGTH: 56
<212> TYPE: PRT
<213> ORGANISM: Homo sapiens
<220> FEATURE:
<221> NAME/KEY: SITE
<222> LOCATION: (56)
<223> OTHER INFORMATION: Xaa equals stop translation

<400> SEQUENCE: 106

```
Met Pro Ser Ser Trp Leu Pro Gly Cys Phe Val Leu Leu Cys Leu Val
  1               5                  10                  15

Ala Val Gly Cys Gln Leu Arg Glu Trp Gly Val Gly Gly Val Ser Ala
             20                  25                  30

Val Gly Leu Leu Ala Leu Pro His Leu Gln Val Leu Gly Met Arg Gly
         35                  40                  45

Arg Gly Leu Ile Ser Gly Gly Xaa
     50                  55
```

<210> SEQ ID NO 107
<211> LENGTH: 189
<212> TYPE: PRT
<213> ORGANISM: Homo sapiens
<220> FEATURE:
<221> NAME/KEY: SITE
<222> LOCATION: (94)
<223> OTHER INFORMATION: Xaa equals any of the naturally occurring
      L-amino acids -continued

<400> SEQUENCE: 107

```
Met Ala Leu Leu Ser Arg Pro Ala Leu Thr Leu Leu Leu Leu Leu Met
  1               5                  10                  15

Ala Ala Val Val Arg Cys Gln Glu Gln Ala Gln Thr Thr Asp Trp Arg
             20                  25                  30

Ala Thr Leu Lys Thr Ile Arg Asn Gly Val His Lys Ile Asp Thr Tyr
         35                  40                  45

Leu Asn Ala Ala Leu Asp Leu Leu Gly Gly Glu Asp Gly Leu Cys Gln
     50                  55                  60

Tyr Lys Cys Ser Asp Gly Ser Lys Pro Phe Pro Arg Tyr Gly Tyr Lys
 65                  70                  75                  80

Pro Ser Pro Pro Asn Gly Cys Gly Ser Pro Leu Phe Gly Xaa His Leu
                 85                  90                  95

Asn Ile Gly Ile Pro Ser Leu Thr Lys Cys Cys Asn Gln His Asp Arg
            100                 105                 110

Cys Tyr Glu Thr Cys Gly Lys Ser Lys Asn Asp Cys Asp Glu Glu Phe
        115                 120                 125

Gln Tyr Cys Leu Ser Lys Ile Cys Arg Asp Val Gln Lys Thr Leu Gly
    130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
            180                 185
```

<210> SEQ ID NO 108
<211> LENGTH: 61
<212> TYPE: PRT
<213> ORGANISM: Homo sapiens
<220> FEATURE:
<221> NAME/KEY: SITE
<222> LOCATION: (61)
<223> OTHER INFORMATION: Xaa equals stop translation

<400> SEQUENCE: 108

```
Met Gly Asn Cys Gln Ala Gly His Asn Leu His Leu Cys Leu Ala His
  1               5                  10                  15

His Pro Pro Leu Val Cys Ala Thr Leu Ile Leu Leu Leu Leu Gly Leu
             20                  25                  30

Ser Gly Leu Gly Leu Gly Ser Phe Leu Leu Thr His Arg Thr Gly Leu
         35                  40                  45

Arg Thr Leu Thr Ser Pro Arg Thr Gly Ser Leu Phe Xaa
     50                  55                  60
```

<210> SEQ ID NO 109
<211> LENGTH: 128
<212> TYPE: PRT
<213> ORGANISM: Homo sapiens
<220> FEATURE:
<221> NAME/KEY: SITE
<222> LOCATION: (47)
<223> OTHER INFORMATION: Xaa equals any of the naturally occurring L-amino acids
<220> FEATURE:
<221> NAME/KEY: SITE
<222> LOCATION: (90)
<223> OTHER INFORMATION: Xaa equals any of the naturally occurring L-amino acids -continued

<400> SEQUENCE: 109

```
Met Arg Leu Glu Ser Leu Cys His Leu Cys Leu Ala Cys Leu Phe Phe
  1               5                  10                  15

Arg Leu Pro Ala Thr Arg Thr Val Tyr Cys Met Asn Glu Ala Glu Ile
             20                  25                  30

Val Asp Val Ala Leu Gly Ile Leu Ile Glu Ser Arg Lys Gln Xaa Lys
         35                  40                  45

Ala Cys Glu Gln Pro Ala Leu Ala Gly Ala Asp Asn Pro Glu His Ser
     50                  55                  60

Pro Pro Cys Ser Val Ser Pro His Thr Ser Ser Gly Ser Ser Ser Glu
 65                  70                  75                  80

Glu Glu Asp Ser Gly Lys Gln Ala Leu Xaa Pro Gly Leu Ser Pro Ser
                 85                  90                  95

Gln Arg Pro Gly Gly Ser Ser Ser Ala Cys Ser Arg Ser Pro Glu Glu
            100                 105                 110

Glu Glu Glu Glu Asp Val Leu Lys Tyr Val Arg Glu Ile Phe Phe Ser
        115                 120                 125
```

<210> SEQ ID NO 110
<211> LENGTH: 69
<212> TYPE: PRT
<213> ORGANISM: Homo sapiens
<220> FEATURE:
<221> NAME/KEY: SITE
<222> LOCATION: (50)
<223> OTHER INFORMATION: Xaa equals any of the naturally occurring L-amino acids
<220> FEATURE:
<221> NAME/KEY: SITE
<222> LOCATION: (69)
<223> OTHER INFORMATION: Xaa equals stop translation

<400> SEQUENCE: 110

```
Met Pro His Phe Leu Asp Trp Phe Val Pro Val Tyr Leu Val Ile Ser
  1               5                  10                  15

Val Leu Ile Leu Val Gly Phe Gly Ala Cys Ile Tyr Tyr Phe Glu Pro
             20                  25                  30

Gly Leu Gln Glu Ala His Lys Trp Arg Met Gln Arg Pro Leu Val Asp
         35                  40                  45

Arg Xaa Leu Arg Lys Thr Leu Met Val Arg Asp Asn Leu Ala Phe Gly
     50                  55                  60

Gly Pro Glu Val Xaa
 65
```

<210> SEQ ID NO 111
<211> LENGTH: 123
<212> TYPE: PRT
<213> ORGANISM: Homo sapiens
<220> FEATURE:
<221> NAME/KEY: SITE
<222> LOCATION: (123)
<223> OTHER INFORMATION: Xaa equals stop translation

<400> SEQUENCE: 111

```
Met Ile Gly Gly Ile Thr Cys Ile Leu Ser Leu Ile Cys Ala Leu Ala
  1               5                  10                  15

Leu Ala Tyr Leu Asp Gln Arg Ala Glu Arg Ile Leu His Lys Glu Gln
             20                  25                  30

Gly Lys Thr Gly Glu Val Ile Lys Leu Thr Asp Val Lys Asp Phe Ser
         35                  40                  45
```

-continued

```
Leu Pro Leu Trp Leu Ile Phe Ile Ile Cys Val Cys Tyr Tyr Val Ala
     50                  55                  60

Val Phe Pro Phe Ile Gly Leu Gly Lys Val Phe Phe Thr Glu Lys Phe
 65                  70                  75                  80

Gly Phe Ser Ser Gln Ala Ala Ser Ala Ile Asn Ser Val Val Tyr Val
                 85                  90                  95

Ile Ser Ala Pro Met Ser Pro Val Phe Gly Leu Leu Val Asp Lys Thr
            100                 105                 110

Gly Lys Asn Ile Ile Trp Val Leu Cys Ala Xaa
        115                 120


<210> SEQ ID NO 112
<211> LENGTH: 83
<212> TYPE: PRT
<213> ORGANISM: Homo sapiens
<220> FEATURE:
<221> NAME/KEY: SITE
<222> LOCATION: (83)
<223> OTHER INFORMATION: Xaa equals stop translation

<400> SEQUENCE: 112

Met Glu Lys Gln Cys Cys Ser His Pro Val Ile Cys Ser Leu Ser Thr
  1               5                  10                  15

Met Tyr Thr Phe Leu Leu Gly Ala Ile Phe Ile Ala Leu Ser Ser Ser
             20                  25                  30

Arg Ile Leu Leu Val Lys Tyr Ser Ala Asn Glu Gly Lys Leu Arg Leu
         35                  40                  45

Gly Ile Cys Met Glu His Phe His Leu Ile Thr His Leu Ser Leu Ala
     50                  55                  60

Phe Gly Ser Val Ile Tyr Asn Met Glu Ile Ile Met Pro Phe Ala Ser
 65                  70                  75                  80

Cys Glu Xaa


<210> SEQ ID NO 113
<211> LENGTH: 345
<212> TYPE: PRT
<213> ORGANISM: Homo sapiens
<220> FEATURE:
<221> NAME/KEY: SITE
<222> LOCATION: (53)
<223> OTHER INFORMATION: Xaa equals any of the naturally occurring
      L-amino acids
<220> FEATURE:
<221> NAME/KEY: SITE
<222> LOCATION: (345)
<223> OTHER INFORMATION: Xaa equals stop translation

<400> SEQUENCE: 113

Met Asp Phe Leu Val Leu Phe Leu Phe Tyr Leu Ala Ser Val Leu Met
  1               5                  10                  15

Gly Leu Val Leu Ile Cys Val Cys Ser Lys Thr His Ser Leu Lys Gly
             20                  25                  30

Leu Ala Arg Gly Gly Ala Gln Ile Phe Ser Cys Ile Ile Pro Glu Cys
         35                  40                  45

Leu Gln Arg Ala Xaa His Gly Leu Leu His Tyr Leu Phe His Thr Arg
     50                  55                  60

Asn His Thr Phe Ile Val Leu His Leu Val Leu Gln Gly Met Val Tyr
 65                  70                  75                  80

Thr Glu Tyr Thr Trp Glu Val Phe Gly Tyr Cys Gln Glu Leu Glu Leu
                 85                  90                  95
```

-continued

Ser Leu His Tyr Leu Leu Leu Pro Tyr Leu Leu Leu Gly Val Asn Leu
            100                 105                 110

Phe Phe Phe Thr Leu Thr Cys Gly Thr Asn Pro Gly Ile Ile Thr Lys
        115                 120                 125

Ala Asn Glu Leu Leu Phe Leu His Val Tyr Glu Phe Asp Glu Val Met
    130                 135                 140

Phe Pro Lys Asn Val Arg Cys Ser Thr Cys Asp Leu Arg Lys Pro Ala
145                 150                 155                 160

Arg Ser Lys His Cys Ser Val Cys Asn Trp Cys Val His Arg Phe Asp
                165                 170                 175

His His Cys Val Trp Val Asn Asn Cys Ile Gly Ala Trp Asn Ile Arg
            180                 185                 190

Tyr Phe Leu Ile Tyr Val Leu Thr Leu Thr Ala Ser Ala Ala Thr Val
        195                 200                 205

Ala Ile Val Ser Thr Thr Phe Leu Val His Leu Val Val Met Ser Asp
    210                 215                 220

Leu Tyr Gln Glu Thr Tyr Ile Asp Asp Leu Gly His Leu His Val Met
225                 230                 235                 240

Asp Thr Val Phe Leu Ile Gln Tyr Leu Phe Leu Thr Phe Pro Arg Ile
                245                 250                 255

Val Phe Met Leu Gly Phe Val Val Val Leu Ser Phe Leu Leu Gly Gly
            260                 265                 270

Tyr Leu Leu Phe Val Leu Tyr Leu Ala Ala Thr Asn Gln Thr Thr Asn
        275                 280                 285

Glu Trp Tyr Arg Gly Asp Trp Ala Trp Cys Gln Arg Cys Pro Leu Val
    290                 295                 300

Ala Trp Pro Pro Ser Ala Glu Pro Gln Val His Arg Asn Ile His Ser
305                 310                 315                 320

His Gly Leu Arg Ser Asn Leu Gln Glu Ile Phe Leu Pro Ala Phe Pro
                325                 330                 335

Cys His Glu Arg Lys Lys Gln Glu Xaa
            340                 345

<210> SEQ ID NO 114
<211> LENGTH: 181
<212> TYPE: PRT
<213> ORGANISM: Homo sapiens
<220> FEATURE:
<221> NAME/KEY: SITE
<222> LOCATION: (110)
<223> OTHER INFORMATION: Xaa equals any of the naturally occurring
      L-amino acids

<400> SEQUENCE: 114

Met Ala Asp Pro His Val Ser Phe Leu Ser Phe Arg Gln Leu Phe Ser
  1               5                  10                  15

Trp Ala Ala Val Ile Leu Leu Arg Gly Ile Leu Gly Thr Val Ala Pro
             20                  25                  30

Pro Pro Cys Pro Cys Val Leu Asp Leu Ala Val Tyr Pro Leu His Leu
         35                  40                  45

Pro Val Glu Ala Pro Cys Leu Glu Val Val Phe Lys Gln Lys Asn Gly
     50                  55                  60

Lys Asp Asn Cys Leu Val Phe Tyr Pro Asp Pro Ile Pro Leu Arg Gly
 65                  70                  75                  80

Ser Leu Leu Gly Pro Phe Ile Lys Asn Gln Cys His Ser Ser Val Ile
                 85                  90                  95

-continued

```
Pro Leu Ser Asp Ser Ala Thr Ser Lys Ala Arg Ala Leu Xaa Leu Pro
            100                 105                 110

Gly Arg Glu Thr Val Leu Ser Val Leu Pro Val Phe Ser Ser Pro Thr
        115                 120                 125

Leu Pro Arg Thr His Ala Leu Gly Asp Ser Leu Gly Val Pro Gly Leu
    130                 135                 140

Leu Val Cys Ser Glu Thr Ser Thr Leu Asn Asp His Trp Cys Cys Arg
145                 150                 155                 160

Arg Ala Gly Ala Tyr Ile Pro Ile Asn Arg Arg Phe Ser His Leu Met
                165                 170                 175

Pro Leu Ala Phe Ser
            180
```

<210> SEQ ID NO 115
<211> LENGTH: 116
<212> TYPE: PRT
<213> ORGANISM: Homo sapiens
<220> FEATURE:
<221> NAME/KEY: SITE
<222> LOCATION: (116)
<223> OTHER INFORMATION: Xaa equals stop translation

<400> SEQUENCE: 115

```
Met Pro Ser Ser Ser Ser Gly Leu Gly Ser Pro Ser Arg Pro Pro Ser
  1               5                  10                  15

Ser Phe Leu Cys Leu Leu Leu Leu Leu Leu Pro Pro Ala Ala Leu Ala
             20                  25                  30

Leu Leu Leu Phe Phe Leu Asp Phe Phe Pro Pro Arg Ala Ala Val Ser
         35                  40                  45

Pro Phe Leu Pro Asp His Cys Ser Ala Arg Gln Pro Arg Val Trp Arg
     50                  55                  60

Arg Glu Thr Leu Asn Arg Ser Ala Ser Gly Leu Gly Cys Trp Ala Arg
 65                  70                  75                  80

Ser Thr Glu Gln Gly Ala Val Gly Val Ala Thr Gly Thr Val Leu Asp
                 85                  90                  95

Ile Ser Leu Pro Ala Ser Cys Leu Ser Leu Trp Pro Pro Gly Pro Ser
            100                 105                 110

Gly Gly Ile Xaa
        115
```

<210> SEQ ID NO 116
<211> LENGTH: 71
<212> TYPE: PRT
<213> ORGANISM: Homo sapiens
<220> FEATURE:
<221> NAME/KEY: SITE
<222> LOCATION: (71)
<223> OTHER INFORMATION: Xaa equals stop translation

<400> SEQUENCE: 116

```
Met Asn Leu Leu Gly Met Ile Phe Ser Met Cys Gly Leu Met Leu Lys
  1               5                  10                  15

Leu Lys Trp Cys Ala Trp Val Ala Val Tyr Cys Ser Phe Ile Ser Phe
             20                  25                  30

Ala Asn Ser Arg Ser Ser Glu Asp Thr Lys Gln Met Met Ser Ser Phe
         35                  40                  45

Met Leu Ser Ile Ser Ala Val Val Met Ser Tyr Leu Gln Asn Pro Gln
     50                  55                  60

Pro Met Thr Pro Pro Trp Xaa
```

-continued

```
 65                  70


<210> SEQ ID NO 117
<211> LENGTH: 64
<212> TYPE: PRT
<213> ORGANISM: Homo sapiens
<220> FEATURE:
<221> NAME/KEY: SITE
<222> LOCATION: (64)
<223> OTHER INFORMATION: Xaa equals stop translation

<400> SEQUENCE: 117

Met Arg Asp Leu Ser Phe Leu Tyr Thr Leu Leu Trp Leu Pro Glu Ile
  1               5                  10                  15

Trp Gln Ala Leu Ala Gly Gly Ile Arg Leu Asp Glu Val Glu Leu Leu
             20                  25                  30

Glu Asn Glu Ala Val Leu Gly Glu Glu Met Arg Leu Tyr Arg Lys Ile
         35                  40                  45

Asn Glu Val Val Leu Ser Gly Asn Glu Val Val Leu Gly Gly Lys Xaa
     50                  55                  60


<210> SEQ ID NO 118
<211> LENGTH: 335
<212> TYPE: PRT
<213> ORGANISM: Homo sapiens
<220> FEATURE:
<221> NAME/KEY: SITE
<222> LOCATION: (335)
<223> OTHER INFORMATION: Xaa equals stop translation

<400> SEQUENCE: 118

Met Gly Ile Phe Pro Gly Ile Ile Leu Ile Phe Leu Arg Val Lys Phe
  1               5                  10                  15

Ala Thr Ala Ala Val Ile Val Ser Gly Val Ser Lys His Leu His Cys
             20                  25                  30

Ile Ser His Gln Lys Ser Thr Thr Val Ser His Glu Met Ser Gly Leu
         35                  40                  45

Asn Trp Lys Pro Phe Val Tyr Gly Gly Leu Ala Ser Ile Val Ala Glu
     50                  55                  60

Phe Gly Thr Phe Pro Val Asp Leu Thr Lys Thr Arg Leu Gln Val Gln
 65                  70                  75                  80

Gly Gln Ser Ile Asp Ala Arg Phe Lys Glu Ile Lys Tyr Arg Gly Met
                 85                  90                  95

Phe His Ala Leu Phe Arg Ile Cys Lys Glu Glu Gly Val Leu Ala Leu
            100                 105                 110

Tyr Ser Gly Ile Ala Pro Ala Leu Leu Arg Gln Ala Ser Tyr Gly Thr
        115                 120                 125

Ile Lys Ile Gly Ile Tyr Gln Ser Leu Lys Arg Leu Phe Val Glu Arg
    130                 135                 140

Leu Glu Asp Glu Thr Leu Leu Ile Asn Met Ile Cys Gly Val Val Ser
145                 150                 155                 160

Gly Val Ile Ser Ser Thr Ile Ala Asn Pro Thr Asp Val Leu Lys Ile
                165                 170                 175

Arg Met Gln Ala Gln Gly Ser Leu Phe Gln Gly Ser Met Ile Gly Ser
            180                 185                 190

Phe Ile Asp Ile Tyr Gln Gln Glu Gly Thr Arg Gly Leu Trp Arg Gly
        195                 200                 205

Val Val Pro Thr Ala Gln Arg Ala Ala Ile Val Val Gly Val Glu Leu
    210                 215                 220
```

```
Pro Val Tyr Asp Ile Thr Lys Lys His Leu Ile Leu Ser Gly Met Met
225                 230                 235                 240

Gly Asp Thr Ile Leu Thr His Phe Val Ser Ser Phe Thr Cys Gly Leu
                245                 250                 255

Ala Gly Ala Leu Ala Ser Asn Pro Val Asp Val Val Arg Thr Arg Met
            260                 265                 270

Met Asn Gln Arg Ala Ile Val Gly His Val Asp Leu Tyr Lys Gly Thr
        275                 280                 285

Val Asp Gly Ile Leu Lys Met Trp Lys His Glu Gly Phe Phe Ala Leu
    290                 295                 300

Tyr Lys Gly Phe Trp Pro Asn Trp Leu Arg Leu Gly Pro Trp Asn Ile
305                 310                 315                 320

Ile Phe Phe Ile Thr Tyr Glu Gln Leu Lys Arg Leu Gln Ile Xaa
                325                 330                 335


<210> SEQ ID NO 119
<211> LENGTH: 221
<212> TYPE: PRT
<213> ORGANISM: Homo sapiens
<220> FEATURE:
<221> NAME/KEY: SITE
<222> LOCATION: (51)
<223> OTHER INFORMATION: Xaa equals any of the naturally occurring
      L-amino acids

<400> SEQUENCE: 119

Met Ala Leu Ala Leu Ala Ala Leu Ala Ala Val Glu Pro Ala Cys Gly
  1               5                  10                  15

Ser Arg Tyr Gln Gln Leu Gln Asn Glu Glu Glu Ser Gly Glu Pro Glu
            20                  25                  30

Gln Ala Ala Gly Asp Ala Pro Pro Pro Tyr Ser Ser Ile Ser Ala Glu
        35                  40                  45

Ser Ala Xaa Tyr Phe Asp Tyr Lys Asp Glu Ser Gly Phe Pro Lys Pro
     50                  55                  60

Pro Ser Tyr Asn Val Ala Thr Thr Leu Pro Ser Tyr Asp Glu Ala Glu
 65                  70                  75                  80

Arg Thr Lys Ala Glu Ala Thr Ile Pro Leu Val Pro Gly Arg Asp Glu
                 85                  90                  95

Asp Phe Val Gly Arg Asp Asp Phe Asp Asp Ala Asp Gln Leu Arg Ile
            100                 105                 110

Gly Asn Asp Gly Ile Phe Met Leu Thr Phe Phe Met Ala Phe Leu Phe
        115                 120                 125

Asn Trp Ile Gly Phe Phe Leu Ser Phe Cys Leu Thr Thr Ser Ala Ala
    130                 135                 140

Gly Arg Tyr Gly Ala Ile Ser Gly Phe Gly Leu Ser Leu Ile Lys Trp
145                 150                 155                 160

Ile Leu Ile Val Arg Phe Ser Thr Tyr Phe Pro Gly Tyr Phe Asp Gly
                165                 170                 175

Gln Tyr Trp Leu Trp Trp Val Phe Leu Val Leu Gly Phe Leu Leu Phe
            180                 185                 190

Leu Arg Gly Phe Ile Asn Tyr Ala Lys Val Arg Lys Met Pro Glu Thr
        195                 200                 205

Phe Ser Asn Leu Pro Arg Thr Arg Val Leu Phe Ile Tyr
    210                 215                 220


<210> SEQ ID NO 120
```

-continued

<211> LENGTH: 473
<212> TYPE: PRT
<213> ORGANISM: Homo sapiens
<220> FEATURE:
<221> NAME/KEY: SITE
<222> LOCATION: (473)
<223> OTHER INFORMATION: Xaa equals stop translation

<400> SEQUENCE: 120

```
Met Lys Phe Leu Ile Phe Ala Phe Phe Gly Gly Val His Leu Leu Ser
  1               5                  10                  15

Leu Cys Ser Gly Lys Ala Ile Cys Lys Asn Gly Ile Ser Lys Arg Thr
             20                  25                  30

Phe Glu Glu Ile Lys Glu Glu Ile Ala Ser Cys Gly Asp Val Ala Lys
         35                  40                  45

Ala Ile Ile Asn Leu Ala Val Tyr Gly Lys Ala Gln Asn Arg Ser Tyr
     50                  55                  60

Glu Arg Leu Ala Leu Leu Val Asp Thr Val Gly Pro Arg Leu Ser Gly
 65                  70                  75                  80

Ser Lys Asn Leu Glu Lys Ala Ile Gln Ile Met Tyr Gln Asn Leu Gln
                 85                  90                  95

Gln Asp Gly Leu Glu Lys Val His Leu Glu Pro Val Arg Ile Pro His
            100                 105                 110

Trp Glu Arg Gly Glu Glu Ser Ala Val Met Leu Glu Pro Arg Ile His
        115                 120                 125

Lys Ile Ala Ile Leu Gly Leu Gly Ser Ser Ile Gly Thr Pro Pro Glu
    130                 135                 140

Gly Ile Thr Ala Glu Val Leu Val Val Thr Ser Phe Asp Glu Leu Gln
145                 150                 155                 160

Arg Arg Ala Ser Glu Ala Arg Gly Lys Ile Val Val Tyr Asn Gln Pro
                165                 170                 175

Tyr Ile Asn Tyr Ser Arg Thr Val Gln Tyr Arg Thr Gln Gly Ala Val
            180                 185                 190

Glu Ala Ala Lys Val Gly Ala Leu Ala Ser Leu Ile Arg Ser Val Ala
        195                 200                 205

Ser Phe Ser Ile Tyr Ser Pro His Thr Gly Ile Gln Glu Tyr Gln Asp
    210                 215                 220

Gly Val Pro Lys Ile Pro Thr Ala Cys Ile Thr Val Glu Asp Ala Glu
225                 230                 235                 240

Met Met Ser Arg Met Ala Ser His Gly Ile Lys Ile Val Ile Gln Leu
                245                 250                 255

Lys Met Gly Ala Lys Thr Tyr Pro Asp Thr Asp Ser Phe Asn Thr Val
            260                 265                 270

Ala Glu Ile Thr Gly Ser Lys Tyr Pro Glu Gln Val Val Leu Val Ser
        275                 280                 285

Gly His Leu Asp Ser Trp Asp Val Gly Gln Gly Ala Met Asp Asp Gly
    290                 295                 300

Gly Gly Ala Phe Ile Ser Trp Glu Ala Leu Ser Leu Ile Lys Asp Leu
305                 310                 315                 320

Gly Leu Arg Pro Lys Arg Thr Leu Arg Leu Val Leu Trp Thr Ala Glu
                325                 330                 335

Glu Gln Gly Gly Val Gly Ala Phe Gln Tyr Tyr Gln Leu His Lys Val
            340                 345                 350

Asn Ile Ser Asn Tyr Ser Leu Val Met Glu Ser Asp Ala Gly Thr Phe
        355                 360                 365
```

-continued

```
Leu Pro Thr Gly Leu Gln Phe Thr Gly Ser Glu Lys Ala Arg Ala Ile
    370                 375                 380

Met Glu Glu Val Met Ser Leu Leu Gln Pro Leu Asn Ile Thr Gln Val
385                 390                 395                 400

Leu Ser His Gly Glu Gly Thr Asp Ile Asn Phe Trp Ile Gln Ala Gly
                405                 410                 415

Val Pro Gly Ala Ser Leu Leu Asp Asp Leu Tyr Lys Tyr Phe Phe Phe
            420                 425                 430

His His Ser His Gly Asp Thr Met Thr Val Met Asp Pro Lys Gln Met
        435                 440                 445

Asn Val Ala Ala Ala Val Trp Ala Val Val Ser Tyr Val Val Ala Asp
    450                 455                 460

Met Glu Glu Met Leu Pro Arg Ser Xaa
465                 470


<210> SEQ ID NO 121
<211> LENGTH: 168
<212> TYPE: PRT
<213> ORGANISM: Homo sapiens
<220> FEATURE:
<221> NAME/KEY: SITE
<222> LOCATION: (168)
<223> OTHER INFORMATION: Xaa equals stop translation

<400> SEQUENCE: 121

Met Ala Thr Leu Trp Gly Gly Leu Leu Arg Leu Gly Ser Leu Leu Ser
  1               5                  10                  15

Leu Ser Cys Leu Ala Leu Ser Val Leu Leu Leu Ala His Cys Gln Thr
            20                  25                  30

Pro Pro Ser Asp Cys Leu His Val Val Glu Pro Met Pro Val Arg Gly
        35                  40                  45

Pro Asp Val Glu Ala Tyr Cys Leu Arg Cys Glu Cys Lys Tyr Glu Glu
     50                  55                  60

Arg Ser Ser Val Thr Ile Lys Val Thr Ile Ile Ile Tyr Leu Ser Ile
 65                  70                  75                  80

Leu Gly Leu Leu Leu Leu Tyr Met Val Tyr Leu Thr Leu Val Glu Pro
                 85                  90                  95

Ile Leu Lys Arg Arg Leu Phe Gly His Ala Gln Leu Ile Gln Ser Asp
            100                 105                 110

Asp Asp Ile Gly Asp His Gln Pro Phe Ala Asn Ala His Asp Val Leu
        115                 120                 125

Ala Arg Ser Arg Ser Arg Ala Asn Val Leu Asn Lys Val Glu Tyr Ala
    130                 135                 140

Gln Gln Arg Trp Lys Leu Gln Val Gln Glu Gln Arg Lys Ser Val Phe
145                 150                 155                 160

Asp Arg His Val Val Leu Ser Xaa
                165


<210> SEQ ID NO 122
<211> LENGTH: 47
<212> TYPE: PRT
<213> ORGANISM: Homo sapiens
<220> FEATURE:
<221> NAME/KEY: SITE
<222> LOCATION: (47)
<223> OTHER INFORMATION: Xaa equals stop translation

<400> SEQUENCE: 122

Met Lys Phe Ile Leu Trp Arg Arg Phe Arg Trp Ala Ile Ile Leu Phe
```

-continued

```
  1               5                  10                  15

Ile Ile Leu Phe Ile Leu Leu Leu Phe Leu Ala Ile Phe Ile Tyr Ala
             20                  25                  30

Phe Pro Asn Tyr Ala Ala Met Lys Leu Val Lys Pro Phe Ser Xaa
         35                  40                  45


<210> SEQ ID NO 123
<211> LENGTH: 108
<212> TYPE: PRT
<213> ORGANISM: Homo sapiens

<400> SEQUENCE: 123

Met His Gln Asp Trp Leu Cys Asn Leu Gly Trp Pro Leu Leu Ser Leu
  1               5                  10                  15

Trp Ala Ala Glu Ser Ala Pro His Val Ala Met Ala Ser Ala Thr Ala
             20                  25                  30

Gln Leu Trp Ser Arg Pro Cys Gly Arg Thr His Met Val Ser Leu Ala
         35                  40                  45

Leu Gly His Gln Glu Thr Gly Leu Trp Leu Cys Ser Ala Phe Gly Cys
     50                  55                  60

Val Val Asp Ser Pro Trp Ala Ser Val Cys Pro Ser Val Lys Gly Gln
 65                  70                  75                  80

Leu Thr Val Cys Gly Ile Leu Pro Arg Val Pro Val Cys Val Tyr Val
                 85                  90                  95

Cys Ala Cys Val Arg Val Ser Met Cys Val His Ile
            100                 105


<210> SEQ ID NO 124
<211> LENGTH: 60
<212> TYPE: PRT
<213> ORGANISM: Homo sapiens

<400> SEQUENCE: 124

Met Arg Gly Cys Val Pro Ala Phe Leu Leu His Val Leu Ser Leu Arg
  1               5                  10                  15

Arg Ala Cys Cys Thr Gln Ala Ala Gln Val Phe Thr Ala Gln Leu Pro
             20                  25                  30

Gly Arg Gln Val Ala Arg Arg Arg Gly Gly Trp His Glu Gln Gln Gly
         35                  40                  45

Gly Pro Met Leu Cys Ser Ser His His Ser Arg Thr
     50                  55                  60


<210> SEQ ID NO 125
<211> LENGTH: 248
<212> TYPE: PRT
<213> ORGANISM: Homo sapiens

<400> SEQUENCE: 125

Met Ala Met Leu Pro Leu Val Leu His Trp Phe Phe Ile Glu Trp Tyr
  1               5                  10                  15

Ser Gly Lys Lys Ser Ser Ser Ala Leu Phe Gln His Ile Thr Ala Leu
             20                  25                  30

Phe Glu Cys Ser Met Ala Ala Ile Ile Thr Leu Leu Val Ser Asp Pro
         35                  40                  45

Val Gly Val Leu Tyr Ile Arg Ser Cys Arg Val Leu Met Leu Ser Asp
     50                  55                  60

Trp Tyr Thr Met Leu Tyr Asn Pro Ser Pro Asp Tyr Val Thr Thr Val
 65                  70                  75                  80
```

-continued

```
His Cys Thr His Glu Ala Val Tyr Pro Leu Tyr Thr Ile Val Phe Ile
                 85                  90                  95

Tyr Tyr Ala Phe Cys Leu Val Leu Met Met Leu Leu Arg Pro Leu Leu
            100                 105                 110

Val Lys Lys Ile Ala Cys Gly Leu Gly Lys Ser Asp Arg Phe Lys Ser
        115                 120                 125

Ile Tyr Ala Ala Leu Tyr Phe Phe Pro Ile Leu Thr Val Leu Gln Ala
    130                 135                 140

Val Gly Gly Gly Leu Leu Tyr Tyr Ala Phe Pro Tyr Ile Ile Leu Val
145                 150                 155                 160

Leu Ser Leu Val Thr Leu Ala Val Tyr Met Ser Ala Ser Glu Ile Glu
                165                 170                 175

Asn Cys Tyr Asp Leu Leu Val Arg Lys Lys Arg Leu Ile Val Leu Phe
            180                 185                 190

Ser His Trp Leu Leu His Ala Tyr Gly Ile Ile Ser Ile Ser Arg Val
        195                 200                 205

Asp Lys Leu Glu Gln Asp Leu Pro Pro Leu Ala Leu Val Pro Thr Pro
    210                 215                 220

Ala Leu Phe Tyr Leu Phe Thr Ala Lys Phe Thr Glu Pro Ser Arg Ile
225                 230                 235                 240

Leu Ser Glu Gly Ala Asn Gly His
                245


<210> SEQ ID NO 126
<211> LENGTH: 248
<212> TYPE: PRT
<213> ORGANISM: Homo sapiens

<400> SEQUENCE: 126

Met Glu Lys Ile Pro Glu Ile Gly Lys Phe Gly Glu Lys Ala Pro Pro
  1               5                  10                  15

Ala Pro Ser His Val Trp Arg Pro Ala Ala Leu Phe Leu Thr Leu Leu
             20                  25                  30

Cys Leu Leu Leu Leu Ile Gly Leu Gly Val Leu Ala Ser Met Phe His
         35                  40                  45

Val Thr Leu Lys Ile Glu Met Lys Lys Met Asn Lys Leu Gln Asn Ile
     50                  55                  60

Ser Glu Glu Leu Gln Arg Asn Ile Ser Leu Gln Leu Met Ser Asn Met
 65                  70                  75                  80

Asn Ile Ser Asn Lys Ile Arg Asn Leu Ser Thr Thr Leu Gln Thr Ile
                 85                  90                  95

Ala Thr Lys Leu Cys Arg Glu Leu Tyr Ser Lys Glu Gln Glu His Lys
            100                 105                 110

Cys Lys Pro Cys Pro Arg Arg Trp Ile Trp His Lys Asp Ser Cys Tyr
        115                 120                 125

Phe Leu Ser Asp Asp Val Gln Thr Trp Gln Glu Ser Lys Met Ala Cys
    130                 135                 140

Ala Ala Gln Asn Ala Ser Leu Leu Lys Ile Asn Asn Lys Asn Ala Leu
145                 150                 155                 160

Glu Phe Ile Lys Ser Gln Ser Arg Ser Tyr Asp Tyr Trp Leu Gly Leu
                165                 170                 175

Ser Pro Glu Glu Asp Ser Thr Arg Gly Met Arg Val Asp Asn Ile Ile
            180                 185                 190

Asn Ser Ser Ala Trp Val Ile Arg Asn Ala Pro Asp Leu Asn Asn Met
```

-continued

```
        195                 200                 205

Tyr Cys Gly Tyr Ile Asn Arg Leu Tyr Val Gln Tyr Tyr His Cys Thr
    210                 215                 220

Tyr Lys Gln Arg Met Ile Cys Glu Lys Met Ala Asn Pro Val Gln Leu
225                 230                 235                 240

Gly Ser Thr Tyr Phe Arg Glu Ala
                245


<210> SEQ ID NO 127
<211> LENGTH: 612
<212> TYPE: PRT
<213> ORGANISM: Homo sapiens
<220> FEATURE:
<221> NAME/KEY: SITE
<222> LOCATION: (245)
<223> OTHER INFORMATION: Xaa equals any of the naturally occurring
      L-amino acids
<220> FEATURE:
<221> NAME/KEY: SITE
<222> LOCATION: (246)
<223> OTHER INFORMATION: Xaa equals any of the naturally occurring
      L-amino acids
<220> FEATURE:
<221> NAME/KEY: SITE
<222> LOCATION: (249)
<223> OTHER INFORMATION: Xaa equals any of the naturally occurring
      L-amino acids

<400> SEQUENCE: 127

Met Ala Ala Ala Gly Arg Leu Pro Ser Ser Trp Ala Leu Phe Ser Pro
  1               5                  10                  15

Leu Leu Ala Gly Leu Ala Leu Leu Gly Val Gly Pro Val Pro Ala Arg
             20                  25                  30

Ala Leu His Asn Val Thr Ala Glu Leu Phe Gly Ala Glu Ala Trp Gly
         35                  40                  45

Thr Leu Ala Ala Phe Gly Asp Leu Asn Ser Asp Lys Gln Thr Asp Leu
     50                  55                  60

Phe Val Leu Arg Glu Arg Asn Asp Leu Ile Val Phe Leu Ala Asp Gln
 65                  70                  75                  80

Asn Ala Pro Tyr Phe Lys Pro Lys Val Lys Val Ser Phe Lys Asn His
                 85                  90                  95

Ser Ala Leu Ile Thr Ser Val Val Pro Gly Asp Tyr Asp Gly Asp Ser
            100                 105                 110

Gln Met Asp Val Leu Leu Thr Tyr Leu Pro Lys Asn Tyr Ala Lys Ser
        115                 120                 125

Glu Leu Gly Ala Val Ile Phe Trp Gly Gln Asn Gln Thr Leu Asp Pro
    130                 135                 140

Asn Asn Met Thr Ile Leu Asn Arg Thr Phe Gln Asp Glu Pro Leu Ile
145                 150                 155                 160

Met Asp Phe Asn Gly Asp Leu Ile Pro Asp Ile Phe Gly Ile Thr Asn
                165                 170                 175

Glu Ser Asn Gln Pro Gln Ile Leu Leu Gly Gly Asn Leu Ser Trp His
            180                 185                 190

Pro Ala Leu Thr Thr Thr Ser Lys Met Arg Ile Pro His Ser His Ala
        195                 200                 205

Phe Ile Asp Leu Thr Glu Asp Phe Thr Ala Asp Leu Phe Leu Thr Thr
    210                 215                 220

Leu Asn Ala Thr Thr Ser Thr Phe Gln Phe Glu Ile Trp Glu Asn Leu
225                 230                 235                 240
```

-continued

```
Asp Gly Asn Phe Xaa Xaa Ser Thr Xaa Leu Glu Lys Pro Gln Asn Met
                245                 250                 255

Met Val Val Gly Gln Ser Ala Phe Ala Asp Phe Asp Gly Asp Gly His
            260                 265                 270

Met Asp His Leu Leu Pro Gly Cys Glu Asp Lys Asn Cys Gln Lys Ser
        275                 280                 285

Thr Ile Tyr Leu Val Arg Ser Gly Met Lys Gln Trp Val Pro Val Leu
    290                 295                 300

Gln Asp Phe Ser Asn Lys Gly Thr Leu Trp Gly Phe Val Pro Phe Val
305                 310                 315                 320

Asp Glu Gln Gln Pro Thr Glu Ile Pro Ile Pro Ile Thr Leu His Ile
                325                 330                 335

Gly Asp Tyr Asn Met Asp Gly Tyr Pro Asp Ala Leu Val Ile Leu Lys
            340                 345                 350

Asn Thr Ser Gly Ser Asn Gln Gln Ala Phe Leu Leu Glu Asn Val Pro
        355                 360                 365

Cys Asn Asn Ala Ser Cys Glu Glu Ala Arg Arg Met Phe Lys Val Tyr
    370                 375                 380

Trp Glu Leu Thr Asp Leu Asn Gln Ile Lys Asp Ala Met Val Ala Thr
385                 390                 395                 400

Phe Phe Asp Ile Tyr Glu Asp Gly Ile Leu Asp Ile Val Val Leu Ser
                405                 410                 415

Lys Gly Tyr Thr Lys Asn Asp Phe Ala Ile His Thr Leu Lys Asn Asn
            420                 425                 430

Phe Glu Ala Asp Ala Tyr Phe Val Lys Val Ile Val Leu Ser Gly Leu
        435                 440                 445

Cys Ser Asn Asp Cys Pro Arg Lys Ile Thr Pro Phe Gly Val Asn Gln
    450                 455                 460

Pro Gly Pro Tyr Ile Met Tyr Thr Thr Val Asp Ala Asn Gly Tyr Leu
465                 470                 475                 480

Lys Asn Gly Ser Ala Gly Gln Leu Ser Gln Ser Ala His Leu Ala Leu
                485                 490                 495

Gln Leu Pro Tyr Asn Val Leu Gly Leu Gly Arg Ser Ala Asn Phe Leu
            500                 505                 510

Asp His Leu Tyr Val Gly Ile Pro Arg Pro Ser Gly Glu Lys Ser Ile
        515                 520                 525

Arg Lys Gln Glu Trp Thr Ala Ile Ile Pro Asn Ser Gln Leu Ile Val
    530                 535                 540

Ile Pro Tyr Pro His Asn Val Pro Arg Ser Trp Ser Ala Lys Leu Tyr
545                 550                 555                 560

Leu Thr Pro Ser Asn Ile Val Leu Leu Thr Ala Ile Ala Leu Ile Gly
                565                 570                 575

Val Cys Val Phe Ile Leu Ala Ile Ile Gly Ile Leu His Trp Gln Glu
            580                 585                 590

Lys Lys Ala Asp Asp Arg Glu Lys Arg Gln Glu Ala His Arg Phe His
        595                 600                 605

Phe Asp Ala Met
    610
```

<210> SEQ ID NO 128
<211> LENGTH: 447
<212> TYPE: PRT
<213> ORGANISM: Homo sapiens
<220> FEATURE:
<221> NAME/KEY: SITE -continued

```
<222> LOCATION: (8)
<223> OTHER INFORMATION: Xaa equals any of the naturally occurring
      L-amino acids
<220> FEATURE:
<221> NAME/KEY: SITE
<222> LOCATION: (28)
<223> OTHER INFORMATION: Xaa equals any of the naturally occurring
      L-amino acids
<220> FEATURE:
<221> NAME/KEY: SITE
<222> LOCATION: (309)
<223> OTHER INFORMATION: Xaa equals any of the naturally occurring
      L-amino acids
<220> FEATURE:
<221> NAME/KEY: SITE
<222> LOCATION: (333)
<223> OTHER INFORMATION: Xaa equals any of the naturally occurring
      L-amino acids

<400> SEQUENCE: 128

Met Glu Leu Ser Gln Met Ser Xaa Leu Met Gly Leu Ser Val Leu Leu
  1               5                  10                  15

Gly Leu Leu Ala Leu Met Ala Thr Ala Ala Val Xaa Arg Gly Trp Leu
             20                  25                  30

Arg Ala Gly Glu Glu Arg Ser Gly Arg Pro Ala Cys Gln Lys Ala Asn
         35                  40                  45

Gly Phe Pro Pro Asp Lys Ser Ser Gly Ser Lys Lys Gln Lys Gln Tyr
     50                  55                  60

Gln Arg Ile Arg Lys Glu Lys Pro Gln Gln His Asn Phe Thr His Arg
 65                  70                  75                  80

Leu Leu Ala Ala Ala Leu Lys Ser His Ser Gly Asn Ile Ser Cys Met
                 85                  90                  95

Asp Phe Ser Ser Asn Gly Lys Tyr Leu Ala Thr Cys Ala Asp Asp Arg
            100                 105                 110

Thr Ile Arg Ile Trp Ser Thr Lys Asp Phe Leu Gln Arg Glu His Arg
        115                 120                 125

Ser Met Arg Ala Asn Val Glu Leu Asp His Ala Thr Leu Val Arg Phe
    130                 135                 140

Ser Pro Asp Cys Arg Ala Phe Ile Val Trp Leu Ala Asn Gly Asp Thr
145                 150                 155                 160

Leu Arg Val Phe Lys Met Thr Lys Arg Glu Asp Gly Gly Tyr Thr Phe
                165                 170                 175

Thr Ala Thr Pro Glu Asp Phe Pro Lys Lys His Lys Ala Pro Val Ile
            180                 185                 190

Asp Ile Gly Ile Ala Asn Thr Gly Lys Phe Ile Met Thr Ala Ser Ser
        195                 200                 205

Asp Thr Thr Val Leu Ile Trp Ser Leu Lys Gly Gln Val Leu Ser Thr
    210                 215                 220

Ile Asn Thr Asn Gln Met Asn Asn Thr His Ala Ala Val Ser Pro Cys
225                 230                 235                 240

Gly Arg Phe Val Ala Ser Cys Gly Phe Thr Pro Asp Val Lys Val Trp
                245                 250                 255

Glu Val Cys Phe Gly Lys Lys Gly Glu Phe Gln Glu Val Val Arg Ala
            260                 265                 270

Phe Glu Leu Lys Gly His Ser Ala Ala Val His Ser Phe Ala Phe Ser
        275                 280                 285

Asn Asp Ser Arg Arg Met Ala Ser Val Ser Lys Asp Gly Thr Trp Lys
    290                 295                 300

Leu Trp Asp Thr Xaa Val Glu Tyr Lys Lys Lys Gln Asp Pro Tyr Leu
```

-continued 305 310 315 320

Leu Lys Thr Gly Arg Phe Glu Glu Ala Ala Gly Ala Xaa Pro Cys Arg
325 330 335

Leu Ala Leu Ser Pro Asn Ala Gln Val Leu Ala Leu Ala Ser Gly Ser
340 345 350

Ser Ile His Leu Tyr Asn Thr Arg Arg Gly Glu Lys Glu Glu Cys Phe
355 360 365

Glu Arg Val His Gly Glu Cys Ile Ala Asn Leu Ser Phe Asp Ile Thr
370 375 380

Gly Arg Phe Leu Ala Ser Cys Gly Asp Arg Ala Val Arg Leu Phe His
385 390 395 400

Asn Thr Pro Gly His Arg Ala Met Val Glu Glu Met Gln Gly His Leu
405 410 415

Lys Arg Ala Ser Asn Glu Ser Thr Arg Gln Arg Leu Gln Gln Gln Leu
420 425 430

Thr Gln Ala Gln Glu Thr Leu Lys Ser Leu Gly Ala Leu Lys Lys
435 440 445

<210> SEQ ID NO 129
<211> LENGTH: 291
<212> TYPE: PRT
<213> ORGANISM: Homo sapiens

<400> SEQUENCE: 129

Met Leu Phe Leu Phe Ser Met Ala Thr Leu Leu Arg Thr Ser Phe Ser
1 5 10 15

Asp Pro Gly Val Ile Pro Arg Ala Leu Pro Asp Glu Ala Ala Phe Ile
20 25 30

Glu Met Glu Ile Glu Ala Thr Asn Gly Ala Val Pro Gln Gly Gln Arg
35 40 45

Pro Pro Pro Arg Ile Lys Asn Phe Gln Ile Asn Asn Gln Ile Val Lys
50 55 60

Leu Lys Tyr Cys Tyr Thr Cys Lys Ile Phe Arg Pro Pro Arg Ala Ser
65 70 75 80

His Cys Ser Ile Cys Asp Asn Cys Val Glu Arg Phe Asp His His Cys
85 90 95

Pro Trp Val Gly Asn Cys Val Gly Lys Arg Asn Tyr Arg Tyr Phe Tyr
100 105 110

Leu Phe Ile Leu Ser Leu Ser Leu Leu Thr Ile Tyr Val Phe Ala Phe
115 120 125

Asn Ile Val Tyr Val Ala Leu Lys Ser Leu Lys Ile Gly Phe Leu Glu
130 135 140

Thr Leu Lys Glu Thr Pro Gly Thr Val Leu Glu Val Leu Ile Cys Phe
145 150 155 160

Phe Thr Leu Trp Ser Val Val Gly Leu Thr Gly Phe His Thr Phe Leu
165 170 175

Val Ala Leu Asn Gln Thr Thr Asn Glu Asp Ile Lys Gly Ser Trp Thr
180 185 190

Gly Lys Asn Arg Val Gln Asn Pro Tyr Ser His Gly Asn Ile Val Lys
195 200 205

Asn Cys Cys Glu Val Leu Cys Gly Pro Leu Pro Pro Ser Val Leu Asp
210 215 220

Arg Arg Gly Ile Leu Pro Leu Glu Glu Ser Gly Ser Arg Pro Pro Ser
225 230 235 240

-continued

```
Thr Gln Glu Thr Ser Ser Ser Leu Leu Pro Gln Ser Pro Ala Pro Thr
                245                 250                 255

Glu His Leu Asn Ser Asn Glu Met Pro Glu Asp Ser Ser Thr Pro Glu
            260                 265                 270

Glu Met Pro Pro Pro Glu Pro Pro Glu Pro Pro Gln Glu Ala Ala Glu
        275                 280                 285

Ala Glu Lys
    290


<210> SEQ ID NO 130
<211> LENGTH: 78
<212> TYPE: PRT
<213> ORGANISM: Homo sapiens

<400> SEQUENCE: 130

Met Val Arg Lys Trp Leu Thr Phe Val Glu His Leu Leu Cys Ala Trp
  1               5                  10                  15

Pro Arg Leu Gly Ala Phe Val Pro Arg Val Thr Pro Ser Glu Cys Ser
             20                  25                  30

Ser Leu Pro His Ser Asn Trp Gly Val Gly Gly Arg Ala Ala Gln Leu
         35                  40                  45

Thr Gly Ala Glu Leu Lys Thr His Ser Trp Val Cys Leu Gly Trp Ala
     50                  55                  60

Val Leu Val Ala Pro Val Ala Asn Thr Arg Ala Pro Phe Thr
 65                  70                  75


<210> SEQ ID NO 131
<211> LENGTH: 333
<212> TYPE: PRT
<213> ORGANISM: Homo sapiens
<220> FEATURE:
<221> NAME/KEY: SITE
<222> LOCATION: (97)
<223> OTHER INFORMATION: Xaa equals any of the naturally occurring
      L-amino acids

<400> SEQUENCE: 131

Met Leu Met Phe Ala Val Ile Val Ala Ser Ser Gly Leu Leu Leu Met
  1               5                  10                  15

Ile Glu Arg Gly Ile Leu Ala Glu Met Lys Pro Leu Pro Leu His Pro
             20                  25                  30

Pro Gly Arg Glu Gly Thr Ala Trp Arg Gly Lys Ala Pro Lys Pro Gly
         35                  40                  45

Gly Leu Ser Leu Arg Ala Gly Asp Ala Asp Leu Gln Val Arg Gln Asp
     50                  55                  60

Val Arg Asn Arg Thr Leu Arg Ala Val Cys Gly Gln Pro Gly Met Pro
 65                  70                  75                  80

Arg Asp Pro Trp Asp Leu Pro Val Gly Gln Arg Arg Thr Leu Leu Arg
                 85                  90                  95

Xaa Ile Leu Val Ser Asp Arg Tyr Arg Phe Leu Tyr Cys Tyr Val Pro
            100                 105                 110

Lys Val Ala Cys Ser Asn Trp Lys Arg Val Met Lys Val Leu Ala Gly
        115                 120                 125

Val Leu Asp Ser Val Asp Val Arg Leu Lys Met Asp His Arg Ser Asp
    130                 135                 140

Leu Val Phe Leu Ala Asp Leu Arg Pro Glu Glu Ile Arg Tyr Arg Leu
145                 150                 155                 160

Gln His Tyr Phe Lys Phe Leu Phe Val Arg Glu Pro Leu Glu Arg Leu
```

-continued

```
                165                 170                 175

Leu Ser Ala Tyr Arg Asn Lys Phe Gly Glu Ile Arg Glu Tyr Gln Gln
            180                 185                 190

Arg Tyr Gly Ala Glu Ile Val Arg Arg Tyr Arg Ala Gly Ala Gly Pro
        195                 200                 205

Ser Pro Ala Gly Asp Asp Val Thr Phe Pro Glu Phe Leu Arg Tyr Leu
    210                 215                 220

Val Asp Glu Asp Pro Glu Arg Met Asn Glu His Trp Met Pro Val Tyr
225                 230                 235                 240

His Leu Cys Gln Pro Cys Ala Val His Tyr Asp Phe Val Gly Ser Tyr
                245                 250                 255

Glu Arg Leu Glu Ala Asp Ala Asn Gln Val Leu Glu Trp Val Arg Ala
            260                 265                 270

Pro Pro His Val Arg Phe Pro Ala Arg Gln Ala Trp Tyr Arg Pro Ala
        275                 280                 285

Ser Pro Glu Ser Leu His Tyr His Leu Cys Ser Ala Pro Arg Ala Leu
    290                 295                 300

Leu Gln Asp Val Leu Pro Lys Tyr Ile Leu Asp Phe Ser Leu Phe Ala
305                 310                 315                 320

Tyr Pro Leu Pro Asn Val Thr Lys Glu Ala Cys Gln Gln
                325                 330


<210> SEQ ID NO 132
<211> LENGTH: 164
<212> TYPE: PRT
<213> ORGANISM: Homo sapiens
<220> FEATURE:
<221> NAME/KEY: SITE
<222> LOCATION: (126)
<223> OTHER INFORMATION: Xaa equals any of the naturally occurring
      L-amino acids

<400> SEQUENCE: 132

Met Leu Pro Leu Leu Ile Ile Cys Leu Leu Pro Ala Ile Glu Gly Lys
  1               5                  10                  15

Asn Cys Leu Arg Cys Trp Pro Glu Leu Ser Ala Leu Ile Asp Tyr Asp
             20                  25                  30

Leu Gln Ile Leu Trp Val Thr Pro Gly Pro Pro Thr Glu Leu Ser Gln
         35                  40                  45

Ser Ile His Ser Leu Phe Leu Glu Asp Asn Asn Phe Leu Lys Pro Trp
     50                  55                  60

Tyr Leu Asp Arg Asp His Leu Glu Glu Glu Thr Ala Lys Phe Phe Thr
 65                  70                  75                  80

Gln Val His Gln Ala Ile Lys Thr Leu Arg Asp Asp Lys Thr Val Leu
                 85                  90                  95

Leu Glu Glu Ile Tyr Thr His Lys Asn Leu Phe Thr Glu Arg Leu Asn
            100                 105                 110

Lys Ile Ser Asp Gly Leu Lys Glu Lys Gly Ala Pro Pro Xaa Ser Met
        115                 120                 125

Asn Ala Phe Pro Ala Pro Ser Pro Thr Cys Thr Pro Glu Pro Leu Gly
    130                 135                 140

Ser Val Cys Leu Pro Ser Thr Ser Val Ser Leu Pro Ser His Leu Pro
145                 150                 155                 160

Gly Ser Leu Gln


<210> SEQ ID NO 133
```

-continued

<211> LENGTH: 245
<212> TYPE: PRT
<213> ORGANISM: Homo sapiens
<220> FEATURE:
<221> NAME/KEY: SITE
<222> LOCATION: (245)
<223> OTHER INFORMATION: Xaa equals stop translation

<400> SEQUENCE: 133

```
Met Val Ala Val Gly Val Tyr Ala Arg Leu Met Lys His Ala Glu Ala
  1               5                  10                  15

Ala Leu Ala Cys Leu Ala Val Asp Pro Ala Ile Leu Leu Ile Val Val
             20                  25                  30

Gly Val Leu Met Phe Leu Leu Thr Phe Cys Gly Cys Ile Gly Ser Leu
         35                  40                  45

Arg Glu Asn Ile Cys Leu Leu Gln Thr Phe Ser Leu Cys Leu Thr Ala
     50                  55                  60

Val Phe Leu Leu Gln Leu Ala Ala Gly Ile Leu Gly Phe Val Phe Ser
 65                  70                  75                  80

Asp Lys Ala Arg Gly Lys Val Ser Glu Ile Ile Asn Asn Ala Ile Val
                 85                  90                  95

His Tyr Arg Asp Asp Leu Asp Leu Gln Asn Leu Ile Asp Phe Gly Gln
            100                 105                 110

Lys Lys Phe Ser Cys Cys Gly Gly Ile Ser Tyr Lys Asp Trp Ser Gln
        115                 120                 125

Asn Met Tyr Phe Asn Cys Ser Glu Asp Asn Pro Ser Arg Glu Arg Cys
    130                 135                 140

Ser Val Pro Tyr Ser Cys Cys Leu Pro Thr Pro Asp Gln Ala Val Ile
145                 150                 155                 160

Asn Thr Met Cys Gly Gln Gly Met Gln Ala Phe Asp Tyr Leu Glu Ala
                165                 170                 175

Ser Lys Val Ile Tyr Thr Asn Gly Cys Ile Asp Lys Leu Val Asn Trp
            180                 185                 190

Ile His Ser Asn Leu Phe Leu Leu Gly Gly Val Ala Leu Gly Leu Ala
        195                 200                 205

Ile Pro Gln Leu Val Gly Ile Leu Leu Ser Gln Ile Leu Val Asn Gln
    210                 215                 220

Ile Lys Asp Gln Ile Lys Leu Gln Leu Tyr Asn Gln Gln His Arg Ala
225                 230                 235                 240

Asp Pro Trp Tyr Xaa
                245
```

<210> SEQ ID NO 134
<211> LENGTH: 56
<212> TYPE: PRT
<213> ORGANISM: Homo sapiens
<220> FEATURE:
<221> NAME/KEY: SITE
<222> LOCATION: (56)
<223> OTHER INFORMATION: Xaa equals stop translation

<400> SEQUENCE: 134

```
Met Gly Thr Val Gly Leu Trp Pro Ser Trp Leu Trp Leu Pro Ala Ser
  1               5                  10                  15

Trp Pro Leu Thr Ser Cys Gly Val Thr Arg Arg Arg Leu Arg Gly Pro
             20                  25                  30

Gly Leu Arg Arg Thr Ser Gln Thr Gly Arg His Thr Ser Pro Cys Pro
         35                  40                  45
```

-continued

```
Thr Ala Thr Trp Ala Glu Ser Xaa
     50                  55


<210> SEQ ID NO 135
<211> LENGTH: 55
<212> TYPE: PRT
<213> ORGANISM: Homo sapiens
<220> FEATURE:
<221> NAME/KEY: SITE
<222> LOCATION: (47)
<223> OTHER INFORMATION: Xaa equals any of the naturally occurring
      L-amino acids
<220> FEATURE:
<221> NAME/KEY: SITE
<222> LOCATION: (51)
<223> OTHER INFORMATION: Xaa equals any of the naturally occurring
      L-amino acids
<220> FEATURE:
<221> NAME/KEY: SITE
<222> LOCATION: (55)
<223> OTHER INFORMATION: Xaa equals stop translation

<400> SEQUENCE: 135

Met Ser Ile Val Met Ser Pro Leu Leu Leu Pro Ile Cys Tyr Leu Asn
  1               5                  10                  15

Leu Leu Leu Phe Phe Val Asn Leu Ala Lys Asn Leu Ser Ile Leu Phe
             20                  25                  30

Val Ser Ser Lys Lys Tyr Thr Phe Val Phe Met Ile Ser Leu Xaa Phe
         35                  40                  45

Phe His Xaa Tyr Phe Ile Xaa
     50                  55


<210> SEQ ID NO 136
<211> LENGTH: 89
<212> TYPE: PRT
<213> ORGANISM: Homo sapiens
<220> FEATURE:
<221> NAME/KEY: SITE
<222> LOCATION: (89)
<223> OTHER INFORMATION: Xaa equals stop translation

<400> SEQUENCE: 136

Met Ala Ile Ile Ser Phe Glu Leu Leu Phe Leu Met Asn Leu Pro Thr
  1               5                  10                  15

Val Asn Ser Ser Asn Phe Lys Leu Ile Ile Pro Glu Asp Val Thr Leu
             20                  25                  30

Ser Phe Val Ser His Leu Asp Ile Thr Val Asn His Phe Val Phe Leu
         35                  40                  45

Ser Thr Phe Glu Leu Ala Gly Val Ile Glu Gly Lys Pro Leu Pro Asp
     50                  55                  60

Ser Lys Ser Asp Leu Cys Pro Ile Leu Gly Gln Leu Trp Phe His Ile
 65                  70                  75                  80

Leu Leu Phe Phe Ile Phe Trp Val Xaa
                 85


<210> SEQ ID NO 137
<211> LENGTH: 62
<212> TYPE: PRT
<213> ORGANISM: Homo sapiens
<220> FEATURE:
<221> NAME/KEY: SITE
<222> LOCATION: (62)
<223> OTHER INFORMATION: Xaa equals stop translation

<400> SEQUENCE: 137
```

-continued

Met Arg Leu Pro Ile Ala Pro His Leu Gln Tyr Phe Met Trp Ser Val
1 5 10 15

Leu Leu Phe Leu Val Ile Leu Val Asp Met Lys Trp His Leu Ser Val
20 25 30

Ala Phe His Tyr Ile Ser Leu Met Thr Asn Gly Ile Leu Ser Pro Phe
35 40 45

Gln Cys Leu Leu Ala Ile His Val Ser Leu Phe Phe Val Xaa
50 55 60

<210> SEQ ID NO 138
<211> LENGTH: 106
<212> TYPE: PRT
<213> ORGANISM: Homo sapiens
<220> FEATURE:
<221> NAME/KEY: SITE
<222> LOCATION: (106)
<223> OTHER INFORMATION: Xaa equals stop translation

<400> SEQUENCE: 138

Met Cys Leu Leu Pro Gly Gly Val Leu Leu Ile Trp Ser Cys Ala Ser
1 5 10 15

Gly Thr Pro Ala Ser His Thr Lys Asp Trp Gly Arg Cys Lys Phe Ser
20 25 30

Ala Ala Thr Lys Arg Thr Ala Glu Ser Asn Leu Glu Ser Thr Gln Leu
35 40 45

Met Leu Ala Ser Gln Ile Asp Pro Leu Leu Ala Glu Cys Trp His Leu
50 55 60

Cys Ala Ser Val Ser Ser Ser Val Asn Gly Gly Asp Lys Lys Cys Val
65 70 75 80

His Thr Ser Arg Ala Val Gly Arg Ile Lys Leu Cys Ser Asp Thr Ile
85 90 95

Arg Ala Cys Ser Gly Trp Tyr Leu Gln Xaa
100 105

<210> SEQ ID NO 139
<211> LENGTH: 52
<212> TYPE: PRT
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 139

Met Ser His Ser Val Phe Ala His Tyr Ile Phe Asn Ile Leu Leu Leu
1 5 10 15

Leu Leu Leu Leu Leu Leu Ile Gly Phe Leu Tyr Ser Met Pro Phe Ile
20 25 30

Tyr Lys Asp Thr Lys Lys Thr His Val Cys Asn Phe Asn Asn Ile Phe
35 40 45

Pro Ile Leu Xaa
50

<210> SEQ ID NO 140
<211> LENGTH: 119
<212> TYPE: PRT
<213> ORGANISM: Homo sapiens

<400> SEQUENCE: 140

Met Lys Trp Arg Arg Lys Ser Ala Tyr Trp Lys Ala Leu Lys Val Phe
1 5 10 15

-continued

```
Lys Leu Pro Val Glu Phe Leu Leu Leu Leu Thr Val Pro Val Val Asp
            20                  25                  30

Pro Asp Lys Asp Asp Gln Asn Trp Lys Arg Pro Leu Asn Cys Leu His
        35                  40                  45

Leu Val Ile Ser Pro Leu Val Val Val Leu Thr Leu Gln Ser Gly Thr
    50                  55                  60

Tyr Gly Val Tyr Glu Ile Gly Gly Leu Val Pro Val Trp Val Val Val
 65                  70                  75                  80

Val Ile Ala Gly Thr Ala Leu Ala Ser Val Thr Phe Phe Ala Thr Ser
                85                  90                  95

Asp Ser Gln Pro Pro Arg Leu His Trp Leu Phe Ala Phe Leu Gly Phe
            100                 105                 110

Leu Thr Ser Ala Leu Trp Ile
        115
```

```
<210> SEQ ID NO 141
<211> LENGTH: 59
<212> TYPE: PRT
<213> ORGANISM: Homo sapiens
<220> FEATURE:
<221> NAME/KEY: SITE
<222> LOCATION: (59)
<223> OTHER INFORMATION: Xaa equals stop translation

<400> SEQUENCE: 141

Met Cys Ser Gly Ser Phe Lys Glu Leu Tyr Leu Val Pro Ile Ser Leu
  1               5                  10                  15

Phe Ser Thr Cys Val Leu Gly Phe Tyr Phe His Asn Phe Leu Leu Leu
            20                  25                  30

Ile Ile Leu Phe Ser Ile Leu Leu Arg Lys Ile Thr Gly Lys Leu Phe
        35                  40                  45

Phe Thr Tyr Tyr His Phe Ser Cys Gly Val Xaa
    50                  55
```

```
<210> SEQ ID NO 142
<211> LENGTH: 100
<212> TYPE: PRT
<213> ORGANISM: Homo sapiens
<220> FEATURE:
<221> NAME/KEY: SITE
<222> LOCATION: (100)
<223> OTHER INFORMATION: Xaa equals stop translation

<400> SEQUENCE: 142

Met Leu Phe Phe Leu Ser Leu Phe Leu Ser Leu Leu Leu Thr Leu Ser
  1               5                  10                  15

Leu Pro Ser Phe Leu Pro Phe Ser Phe Phe Phe Phe Ser Leu Phe Pro
            20                  25                  30

His Leu Ser Ala Cys Leu Leu Pro Ser Leu Pro Ser Pro Pro Phe Pro
        35                  40                  45

Leu Pro Pro Ser Leu Pro Ser Phe Leu Pro Ser Phe Leu Pro Ser Phe
    50                  55                  60

Leu Pro Ser Leu Leu Ser Pro Ser Phe Pro Ala Phe Phe Pro Ser Phe
 65                  70                  75                  80

Cys Gln Leu Ala Arg Arg Ser Pro Arg Lys Ser Thr Gln Met Leu Gln
                85                  90                  95

Ser Thr Ser Xaa
            100
```

-continued

<210> SEQ ID NO 143
<211> LENGTH: 65
<212> TYPE: PRT
<213> ORGANISM: Homo sapiens
<220> FEATURE:
<221> NAME/KEY: SITE
<222> LOCATION: (61)
<223> OTHER INFORMATION: Xaa equals any of the naturally occurring L-amino acids
<220> FEATURE:
<221> NAME/KEY: SITE
<222> LOCATION: (65)
<223> OTHER INFORMATION: Xaa equals stop translation

<400> SEQUENCE: 143

```
Met Ala Val Leu Leu Ile Thr Ile Leu Leu Phe Leu Cys Leu Gly Tyr
  1               5                  10                  15

Tyr Arg Val Ile Thr Glu Ile Ser Arg Lys Thr Pro Ala Cys Arg Met
             20                  25                  30

Phe Thr Ser Ser Leu Ser Ser Trp Tyr Ile Met Arg Lys Leu Tyr Asp
         35                  40                  45

Thr Pro Gly Glu Val Phe Leu Ser His Ala Ile Val Xaa Phe Leu Lys
     50                  55                  60

Xaa
 65
```

<210> SEQ ID NO 144
<211> LENGTH: 67
<212> TYPE: PRT
<213> ORGANISM: Homo sapiens
<220> FEATURE:
<221> NAME/KEY: SITE
<222> LOCATION: (67)
<223> OTHER INFORMATION: Xaa equals stop translation

<400> SEQUENCE: 144

```
Met Leu Asn Gln Pro Cys Ile Leu Gly Met Lys Pro Thr Trp Leu Trp
  1               5                  10                  15

Trp Ile Ser Phe Leu Met Cys Cys Trp Val Trp Leu Ala Ser Val Leu
             20                  25                  30

Leu Gly Ile Phe Ala Ser Ile Phe Ile Arg Asp Ile Gly Leu Glu Phe
         35                  40                  45

Ser Phe Phe Val Met Cys Leu Pro Gly Phe Gly Ile Arg Val Met Leu
     50                  55                  60

Ala Ser Xaa
 65
```

<210> SEQ ID NO 145
<211> LENGTH: 59
<212> TYPE: PRT
<213> ORGANISM: Homo sapiens
<220> FEATURE:
<221> NAME/KEY: SITE
<222> LOCATION: (59)
<223> OTHER INFORMATION: Xaa equals stop translation

<400> SEQUENCE: 145

```
Met Thr Ala Met Ser Ile His Leu Phe Cys Thr Ala Leu Ser Cys Gly
  1               5                  10                  15

Ser Ser Gly Gln Cys Asn Lys Ala Ile Lys Arg Asn Lys Ile Ser Asn
             20                  25                  30

Asp Trp Lys Asp Val Asn Val Ser Ser Phe Ile Glu Asn Met Ile His
         35                  40                  45
```

-continued

```
Arg Tyr Thr Tyr Thr Asn Ala Leu Asn Ser Xaa
     50                  55


<210> SEQ ID NO 146
<211> LENGTH: 56
<212> TYPE: PRT
<213> ORGANISM: Homo sapiens
<220> FEATURE:
<221> NAME/KEY: SITE
<222> LOCATION: (56)
<223> OTHER INFORMATION: Xaa equals stop translation

<400> SEQUENCE: 146

Met Ser His Cys Thr Trp Pro Val Cys Leu Phe Cys Leu Val Pro Pro
  1               5                  10                  15

Pro Met Gly Asp Leu Lys Glu Val Cys Leu Pro His Arg Cys Pro Gly
             20                  25                  30

Arg Thr Ala Cys Cys Ser Tyr Ser Glu Pro His Leu Gln Thr Glu Glu
         35                  40                  45

Asp Arg Arg Thr Leu Ile Cys Xaa
     50                  55


<210> SEQ ID NO 147
<211> LENGTH: 66
<212> TYPE: PRT
<213> ORGANISM: Homo sapiens
<220> FEATURE:
<221> NAME/KEY: SITE
<222> LOCATION: (66)
<223> OTHER INFORMATION: Xaa equals stop translation

<400> SEQUENCE: 147

Met Thr Asn Gly His Gln Val Leu Leu Leu Leu Leu Leu Thr Ser Ala
  1               5                  10                  15

Val Ala Ala Gly Pro Trp Pro Gln Val His Ala Gly Gln Trp Gly Trp
             20                  25                  30

Met Cys Leu Pro Pro Gly Leu Pro Ser Val Gln Ala Arg Ser Gly Leu
         35                  40                  45

Gly Gly Leu Pro Gly Gly Pro Gln Trp Val Pro Gly Gly Ala Arg Gly
     50                  55                  60

Tyr Xaa
 65


<210> SEQ ID NO 148
<211> LENGTH: 328
<212> TYPE: PRT
<213> ORGANISM: Homo sapiens
<220> FEATURE:
<221> NAME/KEY: SITE
<222> LOCATION: (328)
<223> OTHER INFORMATION: Xaa equals stop translation

<400> SEQUENCE: 148

Met Ala Cys Arg Lys Leu Ala Val Ala His Pro Leu Leu Leu Leu Arg
  1               5                  10                  15

His Leu Pro Met Ile Ala Ala Leu Leu His Gly Arg Thr His Leu Asn
             20                  25                  30

Phe Gln Glu Phe Arg Gln Gln Asn His Leu Ser Cys Phe Leu His Val
         35                  40                  45

Leu Gly Leu Leu Glu Leu Leu Gln Pro His Val Phe Arg Ser Glu His
     50                  55                  60
```

-continued

```
Gln Gly Ala Leu Trp Asp Cys Leu Leu Ser Phe Ile Arg Leu Leu Leu
 65                  70                  75                  80

Asn Tyr Arg Lys Ser Ser Arg His Leu Ala Ala Phe Ile Asn Lys Phe
                 85                  90                  95

Val Gln Phe Ile His Lys Tyr Ile Thr Tyr Asn Ala Pro Ala Ala Ile
            100                 105                 110

Ser Phe Leu Gln Lys His Ala Asp Pro Leu His Asp Leu Ser Phe Asp
        115                 120                 125

Asn Ser Asp Leu Val Met Leu Lys Ser Leu Leu Ala Gly Leu Ser Leu
    130                 135                 140

Pro Ser Arg Asp Asp Arg Thr Asp Arg Gly Leu Asp Glu Glu Gly Glu
145                 150                 155                 160

Glu Glu Ser Ser Ala Gly Ser Leu Pro Leu Val Ser Val Ser Leu Phe
                165                 170                 175

Thr Pro Leu Thr Ala Ala Glu Met Ala Pro Tyr Met Lys Arg Leu Ser
            180                 185                 190

Arg Gly Gln Thr Val Glu Asp Leu Leu Glu Val Leu Ser Asp Ile Asp
        195                 200                 205

Glu Met Ser Arg Arg Arg Pro Glu Ile Leu Ser Phe Phe Ser Thr Asn
    210                 215                 220

Leu Gln Arg Leu Met Ser Ser Ala Glu Glu Cys Cys Arg Asn Leu Ala
225                 230                 235                 240

Phe Ser Leu Ala Leu Arg Ser Met Gln Asn Ser Pro Ser Ile Ala Ala
                245                 250                 255

Ala Phe Leu Pro Thr Phe Met Tyr Cys Leu Gly Ser Gln Asp Phe Glu
            260                 265                 270

Val Val Gln Thr Ala Leu Arg Asn Leu Pro Glu Tyr Ala Leu Leu Cys
        275                 280                 285

Gln Glu His Ala Ala Val Leu Leu His Arg Ala Phe Leu Val Gly Met
    290                 295                 300

Tyr Gly Gln Met Asp Pro Ser Ala Gln Ile Ser Glu Ala Leu Arg Ile
305                 310                 315                 320

Leu His Met Glu Ala Val Met Xaa
                325


<210> SEQ ID NO 149
<211> LENGTH: 90
<212> TYPE: PRT
<213> ORGANISM: Homo sapiens
<220> FEATURE:
<221> NAME/KEY: SITE
<222> LOCATION: (10)
<223> OTHER INFORMATION: Xaa equals any of the naturally occurring
      L-amino acids
<220> FEATURE:
<221> NAME/KEY: SITE
<222> LOCATION: (13)
<223> OTHER INFORMATION: Xaa equals any of the naturally occurring
      L-amino acids
<220> FEATURE:
<221> NAME/KEY: SITE
<222> LOCATION: (90)
<223> OTHER INFORMATION: Xaa equals stop translation

<400> SEQUENCE: 149

Met Gly Phe Leu Gln Leu Leu Val Val Xaa Val Leu Xaa Ser Glu His
  1               5                  10                  15

Arg Val Ala Gly Ala Ala Glu Val Phe Gly Asn Ser Ser Glu Gly Leu
             20                  25                  30
```

-continued

```
Ile Glu Phe Ser Val Gly Lys Phe Arg Tyr Phe Glu Leu Asn Arg Pro
        35                  40                  45

Phe Pro Glu Glu Ala Ile Leu His Asp Ile Ser Ser Asn Val Thr Phe
    50                  55                  60

Leu Ile Phe Gln Ile His Ser Gln Tyr Gln Asn Thr Thr Val Ser Phe
 65                  70                  75                  80

Ser Pro Arg Arg Arg Ser Pro Thr Met Xaa
                85                  90


<210> SEQ ID NO 150
<211> LENGTH: 149
<212> TYPE: PRT
<213> ORGANISM: Homo sapiens
<220> FEATURE:
<221> NAME/KEY: SITE
<222> LOCATION: (149)
<223> OTHER INFORMATION: Xaa equals stop translation

<400> SEQUENCE: 150

Met Ala Gly Ser Pro Leu Leu Trp Gly Pro Arg Ala Gly Gly Val Gly
  1               5                  10                  15

Leu Leu Val Leu Leu Leu Leu Gly Leu Phe Arg Pro Pro Pro Ala Leu
             20                  25                  30

Cys Ala Arg Pro Val Lys Glu Pro Arg Gly Leu Ser Ala Ala Ser Pro
        35                  40                  45

Pro Leu Ala Arg Leu Ala Leu Leu Ala Ala Ser Gly Gly Gln Cys Pro
    50                  55                  60

Glu Val Arg Arg Arg Gly Arg Cys Arg Pro Gly Ala Gly Ala Gly Ala
 65                  70                  75                  80

Ser Ala Gly Ala Glu Arg Gln Glu Arg Ala Arg Ala Glu Ala Gln Arg
                85                  90                  95

Leu Arg Ile Ser Arg Arg Ala Ser Trp Arg Ser Cys Cys Ala Ser Gly
            100                 105                 110

Ala Pro Pro Ala Thr Leu Ile Arg Leu Trp Ala Trp Thr Thr Thr Pro
        115                 120                 125

Thr Arg Leu Gln Arg Ser Ser Leu Ala Leu Cys Ser Ala Pro Ala Leu
    130                 135                 140

Thr Leu Pro Pro Xaa
145


<210> SEQ ID NO 151
<211> LENGTH: 391
<212> TYPE: PRT
<213> ORGANISM: Homo sapiens
<220> FEATURE:
<221> NAME/KEY: SITE
<222> LOCATION: (391)
<223> OTHER INFORMATION: Xaa equals stop translation

<400> SEQUENCE: 151

Met Leu Pro Thr Trp Trp Ile Val Ser Ser Trp Leu Val Trp Gly Val
  1               5                  10                  15

Ile Leu Phe Val Tyr Leu Val Ile Arg Ala Leu Arg Leu Trp Arg Thr
             20                  25                  30

Ala Lys Leu Gln Val Thr Leu Lys Lys Tyr Ser Val His Leu Glu Asp
        35                  40                  45

Met Ala Thr Asn Ser Arg Ala Phe Thr Asn Leu Val Arg Lys Ala Leu
    50                  55                  60

Arg Leu Ile Gln Glu Thr Glu Val Ile Ser Arg Gly Phe Thr Leu Val
```

-continued

```
65                  70                  75                  80

Ser Ala Ala Cys Pro Phe Asn Lys Ala Gly Gln His Pro Ser Gln His
                85                  90                  95

Leu Ile Gly Leu Arg Lys Ala Val Tyr Arg Thr Leu Arg Ala Asn Phe
            100                 105                 110

Gln Ala Ala Arg Leu Ala Thr Leu Tyr Met Leu Lys Asn Tyr Pro Leu
        115                 120                 125

Asn Ser Glu Ser Asp Asn Val Thr Asn Tyr Ile Cys Val Val Pro Phe
    130                 135                 140

Lys Glu Leu Gly Leu Gly Leu Ser Glu Glu Gln Ile Ser Glu Glu Glu
145                 150                 155                 160

Ala His Asn Phe Thr Asp Gly Phe Ser Leu Pro Ala Leu Lys Val Leu
                165                 170                 175

Phe Gln Leu Trp Val Ala Gln Ser Ser Glu Phe Phe Arg Arg Leu Ala
            180                 185                 190

Leu Leu Leu Ser Thr Ala Asn Ser Pro Pro Gly Pro Leu Leu Thr Pro
        195                 200                 205

Ala Leu Leu Pro His Arg Ile Leu Ser Asp Val Thr Gln Gly Leu Pro
    210                 215                 220

His Ala His Ser Ala Cys Leu Glu Glu Leu Lys Arg Ser Tyr Glu Phe
225                 230                 235                 240

Tyr Arg Tyr Phe Glu Thr Gln His Gln Ser Val Pro Gln Cys Leu Ser
                245                 250                 255

Lys Thr Gln Gln Lys Ser Arg Glu Leu Asn Asn Val His Thr Ala Val
            260                 265                 270

Arg Ser Leu Gln Leu His Leu Lys Ala Leu Leu Asn Glu Val Ile Ile
        275                 280                 285

Leu Glu Asp Glu Leu Glu Lys Leu Val Cys Thr Lys Glu Thr Gln Glu
    290                 295                 300

Leu Val Ser Glu Ala Tyr Pro Ile Leu Glu Gln Lys Leu Lys Leu Ile
305                 310                 315                 320

Gln Pro His Val Gln Ala Ser Asn Asn Cys Trp Glu Glu Ala Ile Ser
                325                 330                 335

Gln Val Asp Lys Leu Leu Arg Arg Asn Thr Asp Lys Lys Gly Lys Pro
            340                 345                 350

Glu Ile Ala Cys Glu Asn Pro His Cys Thr Val Ser Thr Phe Glu Ala
        355                 360                 365

Ala Tyr Ser Thr His Cys Arg Gln Arg Ser Asn Pro Arg Gly Ala Gly
    370                 375                 380

Ile Arg Ser Leu Cys Arg Xaa
385                 390


<210> SEQ ID NO 152
<211> LENGTH: 99
<212> TYPE: PRT
<213> ORGANISM: Homo sapiens
<220> FEATURE:
<221> NAME/KEY: SITE
<222> LOCATION: (99)
<223> OTHER INFORMATION: Xaa equals stop translation

<400> SEQUENCE: 152

Met Thr Thr Arg Gln Pro Thr Ala Val Ser Trp Pro Cys Trp Leu Met
  1               5                  10                  15

Ser Ser Ser Leu Ser Thr Ala Cys Leu Ala Trp Thr Leu Thr Gly Ser
             20                  25                  30
```

-continued

```
Leu Ala Arg Glu Ala Thr Arg Arg Ala Arg Ser Leu Ser Pro Thr Trp
         35                  40                  45

Asn Cys Ser Ala Arg Gln Val Pro Pro Ser Pro Pro His Ser Gly Leu
     50                  55                  60

Gly Arg Arg Gly Trp Ala His Cys His Leu Thr Cys Leu Leu Val Thr
 65                  70                  75                  80

Gln Leu Phe Arg Val Gly Arg Ile His Pro Ile Leu Ser Leu Pro Leu
                 85                  90                  95

Val Thr Xaa


<210> SEQ ID NO 153
<211> LENGTH: 61
<212> TYPE: PRT
<213> ORGANISM: Homo sapiens
<220> FEATURE:
<221> NAME/KEY: SITE
<222> LOCATION: (61)
<223> OTHER INFORMATION: Xaa equals stop translation

<400> SEQUENCE: 153

Met Ser His Cys Ala Arg Pro Thr Phe Leu Thr Leu Leu Leu Ala Ser
  1               5                  10                  15

Cys Phe Trp Ala Ala Ala Ile Pro Asn Arg Asn Val Ile Leu Ser Val
             20                  25                  30

Ser Phe Arg Pro Leu His Met Gln Phe Thr Leu Ser Ile Leu Val Phe
         35                  40                  45

Ile Leu Arg Ile Leu Ile Leu Leu Arg Ser Phe Leu Xaa
     50                  55                  60


<210> SEQ ID NO 154
<211> LENGTH: 393
<212> TYPE: PRT
<213> ORGANISM: Homo sapiens
<220> FEATURE:
<221> NAME/KEY: SITE
<222> LOCATION: (393)
<223> OTHER INFORMATION: Xaa equals stop translation

<400> SEQUENCE: 154

Met Glu Trp Trp Ala Ser Ser Pro Leu Arg Leu Trp Leu Leu Leu Phe
  1               5                  10                  15

Leu Leu Pro Ser Ala Gln Gly Arg Gln Lys Glu Ser Gly Ser Lys Trp
             20                  25                  30

Lys Val Phe Ile Asp Gln Ile Asn Arg Ser Leu Glu Asn Tyr Glu Pro
         35                  40                  45

Cys Ser Ser Gln Asn Cys Ser Cys Tyr His Gly Val Ile Glu Glu Asp
     50                  55                  60

Leu Thr Pro Phe Arg Gly Gly Ile Ser Arg Lys Met Met Ala Glu Val
 65                  70                  75                  80

Val Arg Arg Lys Leu Gly Thr His Tyr Gln Ile Thr Lys Asn Arg Leu
                 85                  90                  95

Tyr Arg Glu Asn Asp Cys Met Phe Pro Ser Arg Cys Ser Gly Val Glu
            100                 105                 110

His Phe Ile Leu Glu Val Ile Gly Arg Leu Pro Asp Met Glu Met Val
        115                 120                 125

Ile Asn Val Arg Asp Tyr Pro Gln Val Pro Lys Trp Met Glu Pro Ala
    130                 135                 140

Ile Pro Val Phe Ser Phe Ser Lys Thr Ser Glu Tyr His Asp Ile Met
```

-continued

```
145                 150                 155                 160

Tyr Pro Ala Trp Thr Phe Trp Glu Gly Gly Pro Ala Val Trp Pro Ile
                165                 170                 175

Tyr Pro Thr Gly Leu Gly Arg Trp Asp Leu Phe Arg Glu Asp Leu Val
            180                 185                 190

Arg Ser Ala Ala Gln Trp Pro Trp Lys Lys Lys Asn Ser Thr Ala Tyr
        195                 200                 205

Phe Arg Gly Ser Arg Thr Ser Pro Glu Arg Asp Pro Leu Ile Leu Leu
    210                 215                 220

Ser Arg Lys Asn Pro Lys Leu Val Asp Ala Glu Tyr Thr Lys Asn Gln
225                 230                 235                 240

Ala Trp Lys Ser Met Lys Asp Thr Leu Gly Lys Pro Ala Ala Lys Asp
                245                 250                 255

Val His Leu Val Asp His Cys Lys Tyr Lys Tyr Leu Phe Asn Phe Arg
            260                 265                 270

Gly Val Ala Ala Ser Phe Arg Phe Lys His Leu Phe Leu Cys Gly Ser
        275                 280                 285

Leu Val Phe His Val Gly Asp Glu Trp Leu Glu Phe Phe Tyr Pro Gln
    290                 295                 300

Leu Lys Pro Trp Val His Tyr Ile Pro Val Lys Thr Asp Leu Ser Asn
305                 310                 315                 320

Val Gln Glu Leu Leu Gln Phe Val Lys Ala Asn Asp Asp Val Ala Gln
                325                 330                 335

Glu Ile Ala Glu Arg Gly Ser Gln Phe Ile Arg Asn His Leu Gln Met
            340                 345                 350

Asp Asp Ile Thr Cys Tyr Trp Glu Asn Leu Leu Ser Glu Tyr Ser Lys
        355                 360                 365

Phe Leu Ser Tyr Asn Val Thr Arg Arg Lys Gly Tyr Asp Gln Ile Ile
    370                 375                 380

Pro Lys Met Leu Lys Thr Glu Leu Xaa
385                 390
```

<210> SEQ ID NO 155
<211> LENGTH: 75
<212> TYPE: PRT
<213> ORGANISM: Homo sapiens
<220> FEATURE:
<221> NAME/KEY: SITE
<222> LOCATION: (75)
<223> OTHER INFORMATION: Xaa equals stop translation

<400> SEQUENCE: 155

```
Met Leu Ile Leu Phe Leu Ser Val Cys Leu Phe Val Phe Leu Leu Thr
  1               5                  10                  15

Val Arg Ala Leu Cys Cys Arg Ser Ala Gly Val Trp Leu Arg Ser Thr
             20                  25                  30

Pro Asp Pro Val Cys Leu Gly Phe Ala Arg Gly Gly Cys Arg Ile Ala
         35                  40                  45

Met Ile Ala Ala Cys Phe Ser Ser Gly Ser Phe Val Pro Glu Gly His
     50                  55                  60

Pro Pro Asp Ala Ser Gln Ser Ser Pro Val Xaa
 65                  70                  75
```

<210> SEQ ID NO 156
<211> LENGTH: 82
<212> TYPE: PRT
<213> ORGANISM: Homo sapiens -continued
<220> FEATURE:
<221> NAME/KEY: SITE
<222> LOCATION: (82)
<223> OTHER INFORMATION: Xaa equals stop translation

<400> SEQUENCE: 156

Met Trp Pro Leu Leu Ala Val Ser Pro Phe Gly Leu Val Trp Ala Ser
1 5 10 15

Ser Gln Ser Gly Ser Leu Leu Leu Arg Ala Ser Ile Pro Arg Gln His
20 25 30

Ser Arg Arg Ala Trp His Phe Tyr Ser Glu Val Trp Gln Ser His Ser
35 40 45

Val Ala Ser Val Leu Leu Tyr Leu Leu Val Arg Ala Ile Thr Lys Met
50 55 60

Cys Ile Gly Ser Lys Lys Arg Asp Ile Thr Pro Thr Thr Arg Trp Lys
65 70 75 80

Lys Xaa

<210> SEQ ID NO 157
<211> LENGTH: 54
<212> TYPE: PRT
<213> ORGANISM: Homo sapiens
<220> FEATURE:
<221> NAME/KEY: SITE
<222> LOCATION: (49)
<223> OTHER INFORMATION: Xaa equals any of the naturally occurring L-amino acids
<220> FEATURE:
<221> NAME/KEY: SITE
<222> LOCATION: (54)
<223> OTHER INFORMATION: Xaa equals stop translation

<400> SEQUENCE: 157

Met Ser His His Ala Gly Leu Gly Gly Gly Ile Leu Phe Ser Leu Lys
1 5 10 15

Ile Ser Phe Phe Ile Ala Leu Ala Val Val Gly Gly Ser Arg Gly Val
20 25 30

Asn Asp Cys Gln Leu Gly Gly Cys Arg Val Gly Ser Cys Pro Arg Val
35 40 45

Xaa Val Arg Val Ala Xaa
50

<210> SEQ ID NO 158
<211> LENGTH: 103
<212> TYPE: PRT
<213> ORGANISM: Homo sapiens
<220> FEATURE:
<221> NAME/KEY: SITE
<222> LOCATION: (103)
<223> OTHER INFORMATION: Xaa equals stop translation

<400> SEQUENCE: 158

Met Thr Val Arg Arg Leu Ser Leu Leu Cys Arg Asp Leu Trp Ala Leu
1 5 10 15

Trp Leu Leu Leu Lys Ala Gly Ala Val Arg Gly Ala Arg Ala Gly Pro
20 25 30

Arg Leu Pro Gly Arg Cys Cys Gly Ala Thr Cys Gly Asp Ala Gly Arg
35 40 45

Gly Trp Thr Phe Trp Ala Gln Pro Cys Pro Gln Lys Leu Leu Gly Gln
50 55 60

Lys Pro Gly Ala Gly Gly Cys Arg Gly Trp Val Leu Gly Trp Val Pro
65 70 75 80

-continued

```
Pro Arg Pro Glu Glu Pro Cys Ser Leu Ala Gly Lys Val Cys Thr Gly
                85                  90                  95

Leu Ala Arg Trp Met Val Xaa
            100


<210> SEQ ID NO 159
<211> LENGTH: 575
<212> TYPE: PRT
<213> ORGANISM: Homo sapiens

<400> SEQUENCE: 159

Met Arg Val Leu Val Val Thr Ile Ala Pro Ile Tyr Trp Ala Leu Ala
  1               5                  10                  15

Arg Glu Ser Gly Glu Ala Leu Asn Gly His Ser Leu Thr Gly Gly Lys
             20                  25                  30

Phe Arg Gln Glu Ser His Val Glu Phe Ala Thr Gly Glu Leu Leu Thr
         35                  40                  45

Met Thr Gln Trp Pro Gly Val Trp Ile Pro Met Ala Ser Cys Ser Ser
     50                  55                  60

Thr Trp Trp Ser Met Ala Leu Ser Pro Asp Ser Leu Ala Asp Ala Asp
 65                  70                  75                  80

Leu Gln Val Gln Asp Phe Glu Glu His Tyr Val Gln Thr Gly Pro Gly
                 85                  90                  95

Gln Leu Phe Val Gly Ser Thr Gln Arg Phe Phe Gln Gly Gly Leu Pro
            100                 105                 110

Ser Phe Leu Arg Cys Asn His Ser Ile Gln Tyr Asn Ala Ala Arg Gly
        115                 120                 125

Pro Gln Pro Gln Leu Val Gln His Leu Arg Ala Ser Ala Ile Ser Ser
    130                 135                 140

Ala Phe Asp Pro Glu Ala Glu Ala Leu Arg Phe Gln Leu Ala Thr Ala
145                 150                 155                 160

Leu Gln Ala Glu Glu Asn Glu Val Gly Cys Pro Glu Gly Phe Glu Leu
                165                 170                 175

Asp Ser Gln Gly Ala Phe Cys Val Asp Val Asp Glu Cys Ala Trp Asp
            180                 185                 190

Ala His Leu Cys Arg Glu Gly Gln Arg Cys Val Asn Leu Leu Gly Ser
        195                 200                 205

Tyr Arg Cys Leu Pro Asp Cys Gly Pro Gly Phe Arg Val Ala Asp Gly
    210                 215                 220

Ala Gly Cys Glu Asp Val Asp Glu Cys Leu Glu Gly Leu Asp Asp Cys
225                 230                 235                 240

His Tyr Asn Gln Leu Cys Glu Asn Thr Pro Gly Gly His Arg Cys Ser
                245                 250                 255

Cys Pro Arg Gly Tyr Arg Met Gln Gly Pro Ser Leu Pro Cys Leu Asp
            260                 265                 270

Val Asn Glu Cys Leu Gln Leu Pro Lys Ala Cys Ala Tyr Gln Cys His
        275                 280                 285

Asn Leu Gln Gly Ser Tyr Arg Cys Leu Cys Pro Pro Gly Gln Thr Leu
    290                 295                 300

Leu Arg Asp Gly Lys Ala Cys Thr Ser Leu Glu Arg Asn Gly Gln Asn
305                 310                 315                 320

Val Thr Thr Val Ser His Arg Gly Pro Leu Leu Pro Trp Leu Arg Pro
                325                 330                 335

Trp Ala Ser Ile Pro Gly Thr Ser Tyr His Ala Trp Val Ser Leu Arg
```

-continued

```
            340                 345                 350

Pro Gly Pro Met Ala Leu Ser Ser Val Gly Arg Ala Trp Cys Pro Pro
        355                 360                 365

Gly Phe Ile Arg Gln Asn Gly Val Cys Thr Asp Leu Asp Glu Cys Arg
    370                 375                 380

Val Arg Asn Leu Cys Gln His Ala Cys Arg Asn Thr Glu Gly Ser Tyr
385                 390                 395                 400

Gln Cys Leu Cys Pro Ala Gly Tyr Arg Leu Leu Pro Ser Gly Lys Asn
                405                 410                 415

Cys Gln Asp Ile Asn Glu Cys Glu Glu Glu Ser Ile Glu Cys Gly Pro
            420                 425                 430

Gly Gln Met Cys Phe Asn Thr Arg Gly Ser Tyr Gln Cys Val Asp Thr
        435                 440                 445

Pro Cys Pro Ala Thr Tyr Arg Gln Gly Pro Ser Pro Gly Thr Cys Phe
    450                 455                 460

Arg Arg Cys Ser Gln Asp Cys Gly Thr Gly Gly Pro Ser Thr Leu Gln
465                 470                 475                 480

Tyr Arg Leu Leu Pro Leu Pro Leu Gly Val Arg Ala His His Asp Val
                485                 490                 495

Ala Arg Leu Thr Ala Phe Ser Glu Val Gly Val Pro Ala Asn Arg Thr
            500                 505                 510

Glu Leu Ser Met Leu Glu Pro Asp Pro Arg Ser Pro Phe Ala Leu Arg
        515                 520                 525

Pro Leu Arg Ala Gly Leu Gly Ala Val Tyr Thr Arg Arg Ala Leu Thr
    530                 535                 540

Arg Ala Gly Leu Tyr Arg Leu Thr Val Arg Ala Ala Ala Pro Arg His
545                 550                 555                 560

Gln Ser Val Phe Val Leu Leu Ile Ala Val Ser Pro Tyr Pro Tyr
                565                 570                 575


<210> SEQ ID NO 160
<211> LENGTH: 643
<212> TYPE: PRT
<213> ORGANISM: Homo sapiens

<400> SEQUENCE: 160

Met Gly Glu Pro Asn Arg His Pro Ser Met Phe Leu Leu Leu Leu Val
  1               5                  10                  15

Leu Glu Arg Leu Tyr Ala Ser Pro Met Asp Gly Thr Ser Ser Ala Leu
             20                  25                  30

Ser Met Gly Pro Phe Val Pro Phe Ile Met Arg Cys Gly His Ser Pro
         35                  40                  45

Val Tyr His Ser Arg Glu Met Ala Ala Arg Ala Leu Val Pro Phe Val
     50                  55                  60

Met Ile Asp His Ile Pro Asn Thr Ile Arg Thr Leu Leu Ser Thr Leu
 65                  70                  75                  80

Pro Ser Cys Thr Asp Gln Cys Phe Arg Gln Asn His Ile His Gly Thr
                 85                  90                  95

Leu Leu Gln Val Phe His Leu Leu Gln Ala Tyr Ser Asp Ser Lys His
            100                 105                 110

Gly Thr Asn Ser Asp Phe Gln His Glu Leu Thr Asp Ile Thr Val Cys
        115                 120                 125

Thr Lys Ala Lys Leu Trp Leu Ala Lys Arg Gln Asn Pro Cys Leu Val
    130                 135                 140
```

-continued

```
Thr Arg Ala Val Tyr Ile Asp Ile Leu Phe Leu Leu Thr Cys Cys Leu
145                 150                 155                 160

Asn Arg Ser Ala Lys Asp Asn Gln Pro Val Leu Glu Ser Leu Gly Phe
                165                 170                 175

Trp Glu Glu Val Arg Gly Ile Ile Ser Gly Ser Glu Leu Ile Thr Gly
            180                 185                 190

Phe Pro Trp Ala Phe Lys Val Pro Gly Leu Pro Gln Tyr Leu Gln Ser
        195                 200                 205

Leu Thr Arg Leu Ala Ile Ala Ala Val Trp Ala Ala Ala Ala Lys Ser
    210                 215                 220

Gly Glu Arg Glu Thr Asn Val Pro Ile Ser Phe Ser Gln Leu Leu Glu
225                 230                 235                 240

Ser Ala Phe Pro Glu Val Arg Ser Leu Thr Leu Glu Ala Leu Leu Glu
                245                 250                 255

Lys Phe Leu Ala Ala Ala Ser Gly Leu Gly Glu Lys Gly Val Pro Pro
            260                 265                 270

Leu Leu Cys Asn Met Gly Glu Lys Phe Leu Leu Leu Ala Met Lys Glu
        275                 280                 285

Asn His Pro Glu Cys Phe Cys Lys Ile Leu Lys Ile Leu His Cys Met
    290                 295                 300

Asp Pro Gly Glu Trp Leu Pro Gln Thr Glu His Cys Val His Leu Thr
305                 310                 315                 320

Pro Lys Glu Phe Leu Ile Trp Thr Met Asp Ile Ala Ser Asn Glu Arg
                325                 330                 335

Ser Glu Ile Gln Ser Val Ala Leu Arg Leu Ala Ser Lys Val Ile Ser
            340                 345                 350

His His Met Gln Thr Cys Val Glu Asn Arg Glu Leu Ile Ala Ala Glu
        355                 360                 365

Leu Lys Gln Trp Val Gln Leu Val Ile Leu Ser Cys Glu Asp His Leu
    370                 375                 380

Pro Thr Glu Ser Arg Leu Ala Val Val Glu Val Leu Thr Ser Thr Thr
385                 390                 395                 400

Pro Leu Phe Leu Thr Asn Pro His Pro Ile Leu Glu Leu Gln Asp Thr
                405                 410                 415

Leu Ala Leu Trp Lys Cys Val Leu Thr Leu Leu Gln Ser Glu Glu Gln
            420                 425                 430

Ala Val Arg Asp Ala Ala Thr Glu Thr Val Thr Thr Ala Met Ser Gln
        435                 440                 445

Glu Asn Thr Cys Gln Ser Thr Glu Phe Ala Phe Cys Gln Val Asp Ala
    450                 455                 460

Ser Ile Ala Leu Ala Leu Ala Leu Ala Val Leu Cys Asp Leu Leu Gln
465                 470                 475                 480

Gln Trp Asp Gln Leu Ala Pro Gly Leu Pro Ile Leu Leu Gly Trp Leu
                485                 490                 495

Leu Gly Glu Ser Asp Asp Leu Val Ala Cys Val Glu Ser Met His Gln
            500                 505                 510

Val Glu Glu Asp Tyr Leu Phe Glu Lys Ala Glu Val Asn Phe Trp Ala
        515                 520                 525

Glu Thr Leu Ile Phe Val Lys Tyr Leu Cys Lys His Leu Phe Cys Leu
    530                 535                 540

Leu Ser Lys Ser Gly Trp Arg Pro Pro Ser Pro Glu Met Leu Cys His
545                 550                 555                 560

Leu Gln Arg Met Val Ser Glu Gln Cys His Leu Leu Ser Gln Phe Phe
```

-continued

```
                565                 570                 575

Arg Glu Leu Pro Pro Ala Ala Glu Phe Val Lys Thr Val Glu Phe Thr
            580                 585                 590

Arg Leu Arg Ile Gln Glu Glu Arg Thr Leu Ala Cys Leu Arg Leu Leu
        595                 600                 605

Ala Phe Leu Glu Gly Lys Glu Gly Glu Asp Thr Leu Val Leu Ser Val
    610                 615                 620

Trp Asp Ser Tyr Ala Glu Ser Arg Gln Leu Thr Leu Pro Arg Thr Glu
625                 630                 635                 640

Ala Ala Cys


<210> SEQ ID NO 161
<211> LENGTH: 191
<212> TYPE: PRT
<213> ORGANISM: Homo sapiens
<220> FEATURE:
<221> NAME/KEY: SITE
<222> LOCATION: (191)
<223> OTHER INFORMATION: Xaa equals stop translation

<400> SEQUENCE: 161

Met Ser Ser Gly Thr Glu Leu Leu Trp Pro Gly Ala Ala Leu Leu Val
  1               5                  10                  15

Leu Leu Gly Val Ala Ala Ser Leu Cys Val Arg Cys Ser Arg Pro Gly
             20                  25                  30

Ala Lys Arg Ser Glu Lys Ile Tyr Gln Gln Arg Ser Leu Arg Glu Asp
         35                  40                  45

Gln Gln Ser Phe Thr Gly Ser Arg Thr Tyr Ser Leu Val Gly Gln Ala
     50                  55                  60

Trp Pro Gly Pro Leu Ala Asp Met Ala Pro Thr Arg Lys Asp Lys Leu
 65                  70                  75                  80

Leu Gln Phe Tyr Pro Ser Leu Glu Asp Pro Ala Ser Ser Arg Tyr Gln
                 85                  90                  95

Asn Phe Ser Lys Gly Ser Arg His Gly Ser Glu Glu Ala Tyr Ile Asp
            100                 105                 110

Pro Ile Ala Met Glu Tyr Tyr Asn Trp Gly Arg Phe Ser Lys Pro Pro
        115                 120                 125

Glu Asp Asp Asp Ala Asn Ser Tyr Glu Asn Val Leu Ile Cys Lys Gln
    130                 135                 140

Lys Thr Thr Glu Thr Gly Ala Gln Gln Glu Gly Ile Gly Gly Leu Cys
145                 150                 155                 160

Arg Gly Asp Leu Ser Leu Ser Leu Ala Leu Lys Thr Gly Pro Thr Ser
                165                 170                 175

Gly Leu Cys Pro Ser Ala Ser Pro Glu Glu Asp Glu Gly Ile Xaa
            180                 185                 190


<210> SEQ ID NO 162
<211> LENGTH: 64
<212> TYPE: PRT
<213> ORGANISM: Homo sapiens
<220> FEATURE:
<221> NAME/KEY: SITE
<222> LOCATION: (64)
<223> OTHER INFORMATION: Xaa equals stop translation

<400> SEQUENCE: 162

Met Lys His Val Leu Asn Leu Tyr Leu Leu Gly Val Val Leu Thr Leu
  1               5                  10                  15
```

-continued

```
Leu Ser Ile Phe Val Arg Val Met Glu Ser Leu Glu Gly Leu Leu Glu
            20                  25                  30

Ser Pro Ser Pro Gly Thr Ser Trp Thr Thr Arg Ser Gln Leu Ala Asn
        35                  40                  45

Thr Glu Pro Thr Lys Gly Leu Pro Asp His Pro Ser Arg Ser Met Xaa
    50                  55                  60


<210> SEQ ID NO 163
<211> LENGTH: 118
<212> TYPE: PRT
<213> ORGANISM: Homo sapiens
<220> FEATURE:
<221> NAME/KEY: SITE
<222> LOCATION: (118)
<223> OTHER INFORMATION: Xaa equals stop translation

<400> SEQUENCE: 163

Met Ile Phe Leu Thr Val Leu Pro Leu Ala Phe Leu Phe Leu His Ser
  1               5                  10                  15

Gly Phe Tyr His Tyr Ile Ser Phe Ser Cys Leu Phe Ser Leu Ser Leu
            20                  25                  30

Ala Leu Phe Phe Phe Leu Asp Val Ala Thr Phe Arg Arg Pro Gly Gln
        35                  40                  45

Leu Phe Cys Glu Arg Ser Val Leu Phe Asp Met Phe His Phe Gly Phe
    50                  55                  60

Val Ser Leu Phe Leu His Glu Trp Ile Gln Ala Lys His Phe Trp Ala
 65                  70                  75                  80

Gly Leu Phe Ile Val Leu Pro Ser Asp Val Phe Phe Ser Val His His
                 85                  90                  95

Leu Glu Ala Pro Asp Gly Ser Phe Pro Asn Ile Ala Lys Leu Ser Leu
            100                 105                 110

Ile Ile Leu Leu Arg Xaa
        115


<210> SEQ ID NO 164
<211> LENGTH: 43
<212> TYPE: PRT
<213> ORGANISM: Homo sapiens
<220> FEATURE:
<221> NAME/KEY: SITE
<222> LOCATION: (43)
<223> OTHER INFORMATION: Xaa equals stop translation

<400> SEQUENCE: 164

Met Leu Leu Gln Phe Thr Leu Trp Val Phe Gly Ala Ile His Phe Pro
  1               5                  10                  15

Lys Cys Leu Gly Ile Lys Glu Glu Leu Leu Lys Cys Cys Leu Gln Leu
            20                  25                  30

Pro Pro Ser Ser Thr Tyr Glu Lys Val Val Xaa
        35                  40


<210> SEQ ID NO 165
<211> LENGTH: 48
<212> TYPE: PRT
<213> ORGANISM: Homo sapiens
<220> FEATURE:
<221> NAME/KEY: SITE
<222> LOCATION: (48)
<223> OTHER INFORMATION: Xaa equals stop translation

<400> SEQUENCE: 165

Met Leu Ser Arg Arg Leu His Cys Leu Val Leu Tyr Phe Leu Leu Leu
```

-continued 1 5 10 15

Leu Leu Ser Phe Ile His Thr Leu Ser Val Ser His Ile Cys Ser Ser
20 25 30

Phe Ile Trp Leu Phe Pro Lys Asn Ile Glu Ser Glu Ala Thr Met Xaa
35 40 45

<210> SEQ ID NO 166
<211> LENGTH: 46
<212> TYPE: PRT
<213> ORGANISM: Homo sapiens
<220> FEATURE:
<221> NAME/KEY: SITE
<222> LOCATION: (46)
<223> OTHER INFORMATION: Xaa equals stop translation

<400> SEQUENCE: 166

Met Glu Lys Met Gly Gln Gly Leu Leu Ser Ser Thr Tyr Leu Thr Val
1 5 10 15

Leu His Leu Ile Gln Leu Val Gly Cys Gly Leu Leu Thr Glu Glu Ile
20 25 30

Lys Glu Ser Lys Tyr Leu Ile Lys Thr Leu Gly Ser Gly Xaa
35 40 45

<210> SEQ ID NO 167
<211> LENGTH: 207
<212> TYPE: PRT
<213> ORGANISM: Homo sapiens

<400> SEQUENCE: 167

Met Ile Lys His Val Ala Trp Leu Ile Phe Thr Asn Cys Ile Phe Phe
1 5 10 15

Cys Pro Val Ala Phe Phe Ser Phe Ala Pro Leu Ile Thr Ala Ile Ser
20 25 30

Ile Ser Pro Glu Ile Met Lys Ser Val Thr Leu Ile Phe Phe Pro Leu
35 40 45

Pro Ala Cys Leu Asn Pro Val Leu Tyr Val Phe Phe Asn Pro Lys Phe
50 55 60

Lys Glu Asp Trp Lys Leu Leu Lys Arg Arg Val Thr Lys Lys Ser Gly
65 70 75 80

Ser Val Ser Val Ser Ile Ser Ser Gln Gly Gly Cys Leu Glu Gln Asp
85 90 95

Phe Tyr Tyr Asp Cys Gly Met Tyr Ser His Leu Gln Gly Asn Leu Thr
100 105 110

Val Cys Asp Cys Cys Glu Ser Phe Leu Leu Thr Lys Pro Val Ser Cys
115 120 125

Lys His Leu Ile Lys Ser His Ser Cys Pro Ala Leu Ala Val Ala Ser
130 135 140

Cys Gln Arg Pro Glu Gly Tyr Trp Ser Asp Cys Gly Thr Gln Ser Ala
145 150 155 160

His Ser Asp Tyr Ala Asp Glu Glu Asp Ser Phe Val Ser Asp Ser Ser
165 170 175

Asp Gln Val Gln Ala Cys Gly Arg Ala Cys Phe Tyr Gln Ser Arg Gly
180 185 190

Phe Pro Leu Val Arg Tyr Ala Tyr Asn Leu Pro Arg Val Lys Asp
195 200 205

<210> SEQ ID NO 168
<211> LENGTH: 51

-continued

<212> TYPE: PRT
<213> ORGANISM: Homo sapiens
<220> FEATURE:
<221> NAME/KEY: SITE
<222> LOCATION: (51)
<223> OTHER INFORMATION: Xaa equals stop translation

<400> SEQUENCE: 168

Met Tyr Ile Phe Glu Leu Ser Leu Tyr Leu Glu Gly Thr Ser Phe Val
1 5 10 15

Val Val Leu Leu Phe Leu Leu Ile Ser Val Ser Leu Asp Ser Pro Pro
20 25 30

Thr Thr Lys Gly Trp Asp Ser Val Leu His Ile Trp Val Pro Leu Ile
35 40 45

Val Gln Xaa
50

<210> SEQ ID NO 169
<211> LENGTH: 43
<212> TYPE: PRT
<213> ORGANISM: Homo sapiens
<220> FEATURE:
<221> NAME/KEY: SITE
<222> LOCATION: (43)
<223> OTHER INFORMATION: Xaa equals stop translation

<400> SEQUENCE: 169

Met Ala His Pro Gly Leu Pro Lys Thr Val Pro Val Tyr Ala Val Val
1 5 10 15

Leu Ala Leu Leu Ile Met Thr Leu Pro Leu Thr Leu Thr Ile Asn Leu
20 25 30

Asp Asp Asn Leu Tyr Gly Asn Ser Ala Lys Xaa
35 40

<210> SEQ ID NO 170
<211> LENGTH: 56
<212> TYPE: PRT
<213> ORGANISM: Homo sapiens
<220> FEATURE:
<221> NAME/KEY: SITE
<222> LOCATION: (56)
<223> OTHER INFORMATION: Xaa equals stop translation

<400> SEQUENCE: 170

Met Arg Pro Trp Trp Ser Leu Leu Leu Glu Ala Cys Ala Thr Cys Ala
1 5 10 15

Gln Thr Gly Pro Thr Arg Ser Thr Ser Cys Thr Gln Glu Val Ser His
20 25 30

Ser Ser Ser Thr Ala Tyr Pro Ala Pro Met Arg Arg Arg Cys Cys Leu
35 40 45

Pro Ser Pro Arg Ser Cys Thr Xaa
50 55

<210> SEQ ID NO 171
<211> LENGTH: 109
<212> TYPE: PRT
<213> ORGANISM: Homo sapiens
<220> FEATURE:
<221> NAME/KEY: SITE
<222> LOCATION: (109)
<223> OTHER INFORMATION: Xaa equals stop translation

<400> SEQUENCE: 171

Met Ala Leu Ala Gly Ser Val Phe Val Leu Gly Gly Val Leu Val Leu

-continued

```
  1               5                  10                  15

Cys Val Glu Arg Asn Gly Glu Gly Glu Met Gly Trp Pro Gln His Leu
            20                  25                  30

Pro Lys Ser Gln Pro Leu Ser Pro Pro Val Ala Val Arg Arg Cys Ser
        35                  40                  45

Phe Glu Arg Ser Trp Ile Asp Leu Leu Val Glu Thr Ser Ser Ser Met
     50                  55                  60

Val Thr Cys Arg Gln Gln Val Gly Thr Pro Asn Gly Met Glu Gly Arg
 65                  70                  75                  80

Gly Gly Gly Pro Lys Thr Thr Phe Pro Ile Arg Leu Gln Leu Ser Gly
                85                  90                  95

Ala Cys Ala Val Arg Pro Glu Ile Gln Trp Glu Val Xaa
            100                 105


<210> SEQ ID NO 172
<211> LENGTH: 51
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally occurring
      L-amino acids
<220> FEATURE:
<221> NAME/KEY: SITE
<222> LOCATION: (51)
<223> OTHER INFORMATION: Xaa equals stop translation

<400> SEQUENCE: 172

Met Phe Leu Phe Phe Tyr Leu Ser Leu Ala Val Tyr Ala Gln Arg Gln
  1               5                  10                  15

Xaa Ser Gly Ser Cys Arg Gln Thr Asp His Arg Trp Lys Ser Arg Gly
            20                  25                  30

Ala Arg Arg Cys Phe Leu Glu Pro Arg Asp Pro Gly Ser Val Pro Gly
        35                  40                  45

His Pro Xaa
     50


<210> SEQ ID NO 173
<211> LENGTH: 566
<212> TYPE: PRT
<213> ORGANISM: Homo sapiens

<400> SEQUENCE: 173

Met Ala Pro Leu Ala Leu His Leu Leu Val Leu Val Pro Ile Leu Leu
  1               5                  10                  15

Ser Leu Val Ala Ser Gln Asp Trp Lys Ala Glu Arg Ser Gln Asp Pro
            20                  25                  30

Phe Glu Lys Cys Met Gln Asp Pro Asp Tyr Glu Gln Leu Leu Lys Val
        35                  40                  45

Val Thr Trp Gly Leu Asn Arg Thr Leu Lys Pro Gln Arg Val Ile Val
     50                  55                  60

Val Gly Ala Gly Val Ala Gly Leu Val Ala Ala Lys Val Leu Ser Asp
 65                  70                  75                  80

Ala Gly His Lys Val Thr Ile Leu Glu Ala Asp Asn Arg Ile Gly Gly
                85                  90                  95

Arg Ile Phe Thr Tyr Arg Asp Gln Asn Thr Gly Trp Ile Gly Glu Leu
            100                 105                 110

Gly Ala Met Arg Met Pro Ser Ser His Arg Ile Leu His Lys Leu Cys
```

-continued

```
        115                 120                 125

Gln Gly Leu Gly Leu Asn Leu Thr Lys Phe Thr Gln Tyr Asp Lys Asn
    130                 135                 140

Thr Trp Thr Glu Val His Glu Val Lys Leu Arg Asn Tyr Val Val Glu
145                 150                 155                 160

Lys Val Pro Glu Lys Leu Gly Tyr Ala Leu Arg Pro Gln Glu Lys Gly
                165                 170                 175

His Ser Pro Glu Asp Ile Tyr Gln Met Ala Leu Asn Gln Ala Leu Lys
            180                 185                 190

Asp Leu Lys Ala Leu Gly Cys Arg Lys Ala Met Lys Lys Phe Glu Arg
        195                 200                 205

His Thr Leu Leu Glu Tyr Leu Leu Gly Glu Gly Asn Leu Ser Arg Pro
    210                 215                 220

Ala Val Gln Leu Leu Gly Asp Val Met Ser Glu Asp Gly Phe Phe Tyr
225                 230                 235                 240

Leu Ser Phe Ala Glu Ala Leu Arg Ala His Ser Cys Leu Ser Asp Arg
                245                 250                 255

Leu Gln Tyr Ser Arg Ile Val Gly Gly Trp Asp Leu Leu Pro Arg Ala
            260                 265                 270

Leu Leu Ser Ser Leu Ser Gly Leu Val Leu Leu Asn Ala Pro Val Val
        275                 280                 285

Ala Met Thr Gln Gly Pro His Asp Val His Val Gln Ile Glu Thr Ser
    290                 295                 300

Pro Pro Ala Arg Asn Leu Lys Val Leu Lys Ala Asp Val Val Leu Leu
305                 310                 315                 320

Thr Ala Ser Gly Pro Ala Val Lys Arg Ile Thr Phe Ser Pro Pro Leu
                325                 330                 335

Pro Arg His Met Gln Glu Ala Leu Arg Arg Leu His Tyr Val Pro Ala
            340                 345                 350

Thr Lys Val Phe Leu Ser Phe Arg Arg Pro Phe Trp Arg Glu Glu His
        355                 360                 365

Ile Glu Gly Gly His Ser Asn Thr Asp Arg Pro Ser Arg Met Ile Phe
    370                 375                 380

Tyr Pro Pro Pro Arg Glu Gly Ala Leu Leu Leu Ala Ser Tyr Thr Trp
385                 390                 395                 400

Ser Asp Ala Ala Ala Ala Phe Ala Gly Leu Ser Arg Glu Glu Ala Leu
                405                 410                 415

Arg Leu Ala Leu Asp Asp Val Ala Ala Leu His Gly Pro Val Val Arg
            420                 425                 430

Gln Leu Trp Asp Gly Thr Gly Val Val Lys Arg Trp Ala Glu Asp Gln
        435                 440                 445

His Ser Gln Gly Gly Phe Val Val Gln Pro Pro Ala Leu Trp Gln Thr
    450                 455                 460

Glu Lys Asp Asp Trp Thr Val Pro Tyr Gly Arg Ile Tyr Phe Ala Gly
465                 470                 475                 480

Glu His Thr Ala Tyr Pro His Gly Trp Val Glu Thr Ala Val Lys Leu
                485                 490                 495

Leu Arg Ala Ala Ile Lys Ile Asn Ser Arg Lys Gly Pro Ala Ser Asp
            500                 505                 510

Thr Ala Ser Pro Glu Gly His Ala Ser Asp Met Glu Gly Gln Gly His
        515                 520                 525

Val His Gly Val Ala Ser Ser Pro Ser His Asp Leu Ala Lys Glu Glu
    530                 535                 540
```

-continued

Gly Ser His Pro Pro Val Gln Gly Gln Leu Ser Leu Gln Asn Thr Thr
545 550 555 560

His Thr Arg Thr Ser His
565

<210> SEQ ID NO 174
<211> LENGTH: 224
<212> TYPE: PRT
<213> ORGANISM: Homo sapiens
<220> FEATURE:
<221> NAME/KEY: SITE
<222> LOCATION: (76)
<223> OTHER INFORMATION: Xaa equals any of the naturally occurring
L-amino acids

<400> SEQUENCE: 174

Met Ala Arg Ala Arg Gly Ser Pro Cys Pro Pro Leu Pro Pro Gly Arg
1 5 10 15

Met Ser Trp Pro His Gly Ala Leu Leu Phe Leu Trp Leu Phe Ser Pro
20 25 30

Pro Leu Gly Ala Gly Gly Gly Gly Val Ala Val Thr Ser Ala Ala Gly
35 40 45

Gly Gly Ser Pro Pro Ala Thr Ser Cys Pro Val Ala Cys Ser Cys Ser
50 55 60

Asn Gln Ala Ser Arg Val Ile Cys Thr Arg Arg Xaa Leu Ala Glu Val
65 70 75 80

Pro Ala Ser Ile Pro Val Asn Thr Arg Tyr Leu Asn Leu Gln Glu Asn
85 90 95

Gly Ile Gln Val Ile Arg Thr Asp Thr Phe Lys His Leu Arg His Leu
100 105 110

Glu Ile Leu Gln Leu Ser Lys Asn Leu Val Arg Lys Ile Glu Val Gly
115 120 125

Ala Phe Asn Gly Leu Pro Ser Leu Asn Thr Leu Glu Leu Phe Asp Asn
130 135 140

Arg Leu Thr Thr Val Pro Thr Gln Ala Phe Glu Tyr Leu Ser Lys Leu
145 150 155 160

Arg Glu Leu Trp Leu Arg Asn Asn Pro Ile Glu Ser Ile Pro Ser Tyr
165 170 175

Ala Phe Asn Arg Val Pro Ser Leu Arg Arg Leu Asp Leu Gly Glu Leu
180 185 190

Lys Arg Leu Glu Tyr Ile Ser Glu Ala Ala Phe Glu Gly Leu Val Asn
195 200 205

Leu Arg Tyr Leu Asn Leu Gly Met Cys Asn Leu Lys Asp Ile Pro Asn
210 215 220

<210> SEQ ID NO 175
<211> LENGTH: 123
<212> TYPE: PRT
<213> ORGANISM: Homo sapiens

<400> SEQUENCE: 175

Met His Asp Gly Ser Lys Pro Phe Pro Arg Tyr Gly Tyr Lys Pro Ser
1 5 10 15

Pro Pro Asn Gly Cys Gly Ser Pro Leu Phe Gly Val His Leu Asn Ile
20 25 30

Gly Ile Pro Ser Leu Thr Lys Cys Cys Asn Gln His Asp Arg Cys Tyr
35 40 45

-continued

```
Glu Thr Cys Gly Lys Ser Lys Asn Asp Cys Asp Glu Glu Phe Gln Tyr
     50                  55                  60

Cys Leu Ser Lys Ile Cys Arg Asp Val Gln Lys Thr Leu Gly Leu Thr
 65                  70                  75                  80

Gln His Val Gln Ala Cys Glu Thr Thr Val Glu Leu Leu Phe Asp Ser
                 85                  90                  95

Val Ile His Leu Gly Cys Lys Pro Tyr Leu Asp Ser Gln Arg Ala Ala
            100                 105                 110

Cys Arg Cys His Tyr Glu Glu Lys Thr Asp Leu
        115                 120


<210> SEQ ID NO 176
<211> LENGTH: 60
<212> TYPE: PRT
<213> ORGANISM: Homo sapiens
<220> FEATURE:
<221> NAME/KEY: SITE
<222> LOCATION: (60)
<223> OTHER INFORMATION: Xaa equals stop translation

<400> SEQUENCE: 176

Met Gly Leu Ser Val Leu Leu Pro Leu Cys Leu Leu Gly Pro Gly Arg
  1               5                  10                  15

Phe Thr Ser Gly Gln Lys Pro Leu Asp Thr Pro Gly Leu Gly Ala Ala
             20                  25                  30

Val Leu Ser Val Arg Lys Ala Gly Leu Lys Met Arg Ser His Leu Thr
         35                  40                  45

Pro Ser Val Cys Thr Val Pro Ser Pro Gly Ser Xaa
     50                  55                  60


<210> SEQ ID NO 177
<211> LENGTH: 105
<212> TYPE: PRT
<213> ORGANISM: Homo sapiens

<400> SEQUENCE: 177

Met Asp Thr Val Phe Leu Ile Gln Tyr Leu Phe Leu Thr Phe Pro Arg
  1               5                  10                  15

Ile Val Phe Met Leu Gly Phe Val Val Val Leu Ser Phe Leu Leu Gly
             20                  25                  30

Gly Tyr Leu Leu Phe Val Leu Tyr Leu Ala Ala Thr Asn Gln Thr Thr
         35                  40                  45

Asn Glu Trp Tyr Arg Gly Asp Trp Ala Trp Cys Gln Arg Cys Pro Leu
     50                  55                  60

Val Ala Trp Pro Pro Ser Ala Glu Pro Gln Val His Arg Asn Ile His
 65                  70                  75                  80

Ser His Gly Leu Arg Ser Asn Leu Gln Glu Ile Phe Leu Pro Ala Phe
                 85                  90                  95

Pro Cys His Glu Arg Lys Lys Gln Glu
            100                 105


<210> SEQ ID NO 178
<211> LENGTH: 88
<212> TYPE: PRT
<213> ORGANISM: Homo sapiens
<220> FEATURE:
<221> NAME/KEY: SITE
<222> LOCATION: (88)
<223> OTHER INFORMATION: Xaa equals stop translation

<400> SEQUENCE: 178
```

-continued

```
Met Ala Asp Pro His Val Ser Phe Leu Ser Phe Arg Gln Leu Phe Ser
  1               5                  10                  15

Trp Ala Ala Val Ile Leu Leu Arg Gly Ile Leu Gly Thr Val Ala Pro
             20                  25                  30

Pro Pro Cys Pro Cys Val Leu Asp Leu Ala Val Tyr Pro Leu His Leu
         35                  40                  45

Pro Val Glu Ala Pro Cys Leu Glu Val Val Phe Lys Gln Lys Asn Gly
     50                  55                  60

Lys Asp Asn Cys Leu Val Phe Tyr Pro Asp Pro Ile Pro Leu Arg Gly
 65                  70                  75                  80

Ser Leu Leu Gly Pro Phe Ile Xaa
                 85
```

```
<210> SEQ ID NO 179
<211> LENGTH: 88
<212> TYPE: PRT
<213> ORGANISM: Homo sapiens
<220> FEATURE:
<221> NAME/KEY: SITE
<222> LOCATION: (55)
<223> OTHER INFORMATION: Xaa equals any of the naturally occurring
      L-amino acids
<220> FEATURE:
<221> NAME/KEY: SITE
<222> LOCATION: (66)
<223> OTHER INFORMATION: Xaa equals any of the naturally occurring
      L-amino acids
<220> FEATURE:
<221> NAME/KEY: SITE
<222> LOCATION: (88)
<223> OTHER INFORMATION: Xaa equals stop translation

<400> SEQUENCE: 179

Met Ala Asp Pro His Val Ser Phe Leu Ser Phe Arg Gln Leu Phe Ser
  1               5                  10                  15

Trp Ala Ala Val Ile Leu Leu Arg Gly Ile Leu Gly Thr Val Ala Pro
             20                  25                  30

Pro Pro Cys Pro Cys Val Leu Asp Leu Ala Val Tyr Pro Leu His Leu
         35                  40                  45

Pro Val Glu Ala Pro Cys Xaa Glu Val Val Phe Lys Gln Lys Asn Gly
     50                  55                  60

Lys Xaa Asn Cys Leu Val Phe Tyr Pro Asp Pro Ile Pro Leu Arg Gly
 65                  70                  75                  80

Ser Leu Leu Gly Pro Phe Ile Xaa
                 85


<210> SEQ ID NO 180
<211> LENGTH: 49
<212> TYPE: PRT
<213> ORGANISM: Homo sapiens

<400> SEQUENCE: 180

Met Asn Leu Leu Gly Met Ile Phe Ser Met Cys Gly Leu Met Leu Lys
  1               5                  10                  15

Leu Lys Trp Cys Ala Trp Val Ala Val Tyr Cys Ser Phe Ile Ser Phe
             20                  25                  30

Ala Asn Ser Arg Ser Ser Glu Asp Thr Lys Gln Met Met Ser Ser Phe
         35                  40                  45

Met
```

-continued

<210> SEQ ID NO 181
<211> LENGTH: 23
<212> TYPE: PRT
<213> ORGANISM: Homo sapiens

<400> SEQUENCE: 181

```
Leu Gly Ser Leu Ser Thr Ala Pro Ser Ser Ala Leu Pro Thr Leu Gly
  1               5                  10                  15

Ala Arg Arg Thr Arg Ser Lys
             20
```

<210> SEQ ID NO 182
<211> LENGTH: 104
<212> TYPE: PRT
<213> ORGANISM: Homo sapiens
<220> FEATURE:
<221> NAME/KEY: SITE
<222> LOCATION: (104)
<223> OTHER INFORMATION: Xaa equals stop translation

<400> SEQUENCE: 182

```
Met Leu Thr Phe Phe Met Ala Phe Leu Phe Asn Trp Ile Gly Phe Phe
  1               5                  10                  15

Leu Ser Phe Cys Leu Thr Thr Ser Ala Ala Gly Arg Tyr Gly Ala Ile
             20                  25                  30

Ser Gly Phe Gly Leu Ser Leu Ile Lys Trp Ile Leu Ile Val Arg Phe
         35                  40                  45

Ser Thr Tyr Phe Pro Gly Tyr Phe Asp Gly Gln Tyr Trp Leu Trp Trp
     50                  55                  60

Val Phe Leu Val Leu Gly Phe Leu Leu Phe Leu Arg Gly Phe Ile Asn
 65                  70                  75                  80

Tyr Ala Lys Val Arg Lys Met Pro Glu Thr Phe Ser Asn Leu Pro Arg
                 85                  90                  95

Thr Arg Val Leu Phe Ile Tyr Xaa
            100
```

<210> SEQ ID NO 183
<211> LENGTH: 198
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids

<400> SEQUENCE: 183

```
Met Lys Lys Ser Leu Glu Asn Leu Asn Arg Leu Gln Val Met Leu Leu
  1               5                  10                  15

His Leu Thr Ala Ala Phe Leu Gln Arg Ala Gln His Xaa Phe Asp Tyr
             20                  25                  30

Lys Asp Glu Ser Gly Phe Pro Lys Pro Pro Ser Tyr Asn Val Ala Thr
         35                  40                  45

Thr Leu Pro Ser Tyr Asp Glu Ala Glu Arg Thr Lys Ala Glu Ala Thr
     50                  55                  60

Ile Pro Leu Val Pro Gly Arg Asp Glu Asp Phe Val Gly Arg Asp Asp
 65                  70                  75                  80

Phe Asp Asp Ala Asp Gln Leu Arg Ile Gly Asn Asp Gly Ile Phe Met
                 85                  90                  95

Leu Thr Phe Phe Met Ala Phe Leu Phe Asn Trp Ile Gly Phe Phe Leu
            100                 105                 110
```

-continued

```
Ser Phe Cys Leu Thr Thr Ser Ala Ala Gly Arg Tyr Gly Ala Ile Ser
        115                 120                 125

Gly Phe Gly Leu Ser Leu Ile Lys Trp Ile Leu Ile Val Arg Phe Ser
    130                 135                 140

Thr Tyr Phe Pro Gly Tyr Phe Asp Gly Gln Tyr Trp Leu Trp Trp Val
145                 150                 155                 160

Phe Leu Val Leu Gly Phe Leu Leu Phe Leu Arg Gly Phe Ile Asn Tyr
                165                 170                 175

Ala Lys Val Arg Lys Met Pro Glu Thr Phe Ser Asn Leu Pro Arg Thr
            180                 185                 190

Arg Val Leu Phe Ile Tyr
        195


<210> SEQ ID NO 184
<211> LENGTH: 70
<212> TYPE: PRT
<213> ORGANISM: Homo sapiens

<400> SEQUENCE: 184

Met Leu Leu His Leu Thr Ala Ala Phe Leu Gln Arg Ala Gln Phe Ser
  1               5                  10                  15

Thr Tyr Phe Pro Gly Tyr Phe Asp Gly Gln Tyr Trp Leu Trp Trp Val
             20                  25                  30

Phe Leu Val Leu Gly Phe Leu Leu Phe Leu Arg Gly Phe Ile Asn Tyr
         35                  40                  45

Ala Lys Val Arg Lys Met Pro Glu Thr Phe Ser Asn Leu Pro Arg Thr
     50                  55                  60

Arg Val Leu Phe Ile Tyr
 65                  70


<210> SEQ ID NO 185
<211> LENGTH: 82
<212> TYPE: PRT
<213> ORGANISM: Homo sapiens

<400> SEQUENCE: 185

Met Leu Thr Phe Phe Met Ala Phe Leu Phe Asn Trp Ile Gly Phe Phe
  1               5                  10                  15

Leu Ser Phe Cys Leu Thr Thr Ser Ala Ala Gly Arg Tyr Gly Ala Ile
             20                  25                  30

Ser Gly Phe Gly Leu Ser Leu Ile Lys Trp Ile Leu Ile Val Arg Phe
         35                  40                  45

Ser Thr Tyr Phe Pro Ala Phe Met Asn Ser Leu Ser Arg Ser Lys Arg
     50                  55                  60

Thr Pro Ala Gly Ser Glu Ser Arg Cys Arg Thr Gln Arg Asn Asn His
 65                  70                  75                  80

Leu Leu


<210> SEQ ID NO 186
<211> LENGTH: 45
<212> TYPE: PRT
<213> ORGANISM: Homo sapiens
<220> FEATURE:
<221> NAME/KEY: SITE
<222> LOCATION: (28)
<223> OTHER INFORMATION: Xaa equals any of the naturally occurring
      L-amino acids

<400> SEQUENCE: 186
```

-continued

```
Met Lys Lys Ser Leu Glu Asn Leu Asn Arg Leu Gln Val Met Leu Leu
  1               5                  10                  15

His Leu Thr Ala Ala Phe Leu Gln Arg Ala His Xaa Ile Leu Thr Thr
             20                  25                  30

Arg Met Ser Leu Gly Phe Gln Ser Pro His Leu Thr Met
         35                  40                  45


<210> SEQ ID NO 187
<211> LENGTH: 34
<212> TYPE: PRT
<213> ORGANISM: Homo sapiens
<220> FEATURE:
<221> NAME/KEY: SITE
<222> LOCATION: (34)
<223> OTHER INFORMATION: Xaa equals stop translation

<400> SEQUENCE: 187

Met Thr Val Met Asp Pro Lys Gln Met Asn Val Ala Ala Ala Val Trp
  1               5                  10                  15

Ala Val Val Ser Tyr Val Val Ala Asp Met Glu Glu Met Leu Pro Arg
             20                  25                  30

Ser Xaa


<210> SEQ ID NO 188
<211> LENGTH: 232
<212> TYPE: PRT
<213> ORGANISM: Homo sapiens
<220> FEATURE:
<221> NAME/KEY: SITE
<222> LOCATION: (232)
<223> OTHER INFORMATION: Xaa equals stop translation

<400> SEQUENCE: 188

Met Ala Thr Leu Trp Gly Gly Leu Leu Arg Leu Gly Ser Leu Leu Ser
  1               5                  10                  15

Leu Ser Cys Leu Ala Leu Ser Val Leu Leu Leu Ala His Cys Gln Thr
             20                  25                  30

Pro Pro Arg Ile Ser Arg Met Ser Asp Val Asn Val Ser Ala Leu Pro
         35                  40                  45

Ile Lys Lys Asn Ser Gly His Ile Tyr Asn Lys Asn Ile Ser Gln Lys
     50                  55                  60

Asp Cys Asp Cys Leu His Val Val Glu Pro Met Pro Val Arg Gly Pro
 65                  70                  75                  80

Asp Val Glu Ala Tyr Cys Leu Arg Cys Glu Cys Lys Tyr Glu Glu Arg
                 85                  90                  95

Ser Ser Val Thr Ile Lys Val Thr Ile Ile Ile Tyr Leu Ser Ile Leu
            100                 105                 110

Gly Leu Leu Leu Leu Tyr Met Val Tyr Leu Thr Leu Val Glu Pro Ile
        115                 120                 125

Leu Lys Arg Arg Leu Phe Gly His Ala Gln Leu Ile Gln Ser Asp Asp
    130                 135                 140

Asp Ile Gly Asp His Gln Pro Phe Ala Asn Ala His Asp Val Leu Ala
145                 150                 155                 160

Arg Ser Arg Ser Arg Ala Asn Val Leu Asn Lys Val Glu Tyr Gly Thr
                165                 170                 175

Ala Ala Leu Glu Ala Ser Ser Pro Arg Ala Ala Lys Ser Leu Ser Leu
            180                 185                 190

Thr Gly Met Leu Ser Ser Ala Asn Trp Gly Ile Glu Phe Lys Val Thr
```

-continued

```
        195                 200                 205

Arg Lys Lys Gln Ala Asp Asn Trp Lys Gly Thr Asp Trp Val Leu Leu
    210                 215                 220

Gly Phe Ile Leu Ile Pro Cys Xaa
225                 230


<210> SEQ ID NO 189
<211> LENGTH: 457
<212> TYPE: PRT
<213> ORGANISM: Homo sapiens
<220> FEATURE:
<221> NAME/KEY: SITE
<222> LOCATION: (457)
<223> OTHER INFORMATION: Xaa equals stop translation

<400> SEQUENCE: 189

Met Ala Ala Ala Gly Arg Leu Pro Ser Ser Trp Ala Leu Phe Ser Pro
  1               5                  10                  15

Leu Leu Ala Gly Leu Ala Leu Leu Gly Val Gly Pro Val Pro Ala Arg
             20                  25                  30

Ala Leu His Asn Val Thr Ala Glu Leu Phe Gly Ala Glu Ala Trp Gly
         35                  40                  45

Thr Leu Ala Ala Phe Gly Asp Leu Asn Ser Asp Lys Gln Thr Asp Leu
     50                  55                  60

Phe Val Leu Arg Glu Arg Asn Asp Leu Ile Val Phe Leu Ala Asp Gln
 65                  70                  75                  80

Asn Ala Pro Tyr Phe Lys Pro Lys Val Lys Val Ser Phe Lys Asn His
                 85                  90                  95

Ser Ala Leu Ile Thr Ser Val Val Pro Gly Asp Tyr Asp Gly Asp Ser
            100                 105                 110

Gln Met Asp Val Leu Leu Thr Tyr Leu Pro Lys Asn Tyr Ala Lys Ser
        115                 120                 125

Glu Leu Gly Ala Val Ile Phe Trp Gly Gln Asn Gln Thr Leu Asp Pro
    130                 135                 140

Asn Asn Met Thr Ile Leu Asn Arg Thr Phe Gln Asp Glu Pro Leu Ile
145                 150                 155                 160

Met Asp Phe Asn Gly Asp Leu Ile Pro Asp Ile Phe Gly Ile Thr Asn
                165                 170                 175

Glu Ser Asn Gln Pro Gln Ile Leu Leu Gly Gly Asn Leu Ser Trp His
            180                 185                 190

Pro Ala Leu Thr Thr Thr Ser Lys Met Arg Ile Pro His Ser His Ala
        195                 200                 205

Phe Ile Asp Leu Thr Glu Asp Phe Thr Ala Asp Leu Phe Leu Thr Thr
    210                 215                 220

Leu Asn Ala Thr Thr Ser Thr Phe Gln Phe Glu Ile Trp Glu Asn Leu
225                 230                 235                 240

Asp Gly Asn Phe Ser Val Ser Thr Ile Leu Glu Lys Pro Gln Asn Met
                245                 250                 255

Met Val Val Gly Gln Ser Ala Phe Ala Asp Phe Asp Gly Asp Gly His
            260                 265                 270

Met Asp His Leu Leu Pro Gly Cys Glu Asp Lys Asn Cys Gln Lys Ser
        275                 280                 285

Thr Ile Tyr Leu Val Arg Ser Gly Met Lys Gln Trp Val Pro Val Leu
    290                 295                 300

Gln Asp Phe Ser Asn Lys Gly Thr Leu Trp Gly Phe Val Pro Phe Val
305                 310                 315                 320
```

-continued

```
Asp Glu Gln Gln Pro Thr Glu Ile Pro Ile Pro Ile Thr Leu His Ile
                325                 330                 335

Gly Asp Tyr Asn Met Asp Gly Tyr Pro Asp Ala Leu Val Ile Leu Lys
            340                 345                 350

Asn Thr Ser Gly Ser Asn Gln Gln Ala Phe Leu Leu Glu Asn Val Pro
        355                 360                 365

Cys Asn Asn Ala Ser Cys Glu Glu Ala Arg Arg Met Phe Lys Val Tyr
    370                 375                 380

Trp Glu Leu Thr Asp Leu Asn Gln Ile Lys Asp Ala Met Val Ala Thr
385                 390                 395                 400

Phe Phe Asp Ile Tyr Glu Asp Gly Ile Leu Asp Ile Val Val Leu Ser
                405                 410                 415

Lys Gly Tyr Thr Lys Asn Asp Phe Ala Ile His Thr Leu Lys Asn Asn
            420                 425                 430

Phe Glu Ala Asp Ala Tyr Phe Val Lys Val Ile Val Leu Ser Gly Leu
        435                 440                 445

Cys Ser Asn Asp Cys Pro Arg Arg Xaa
    450                 455


<210> SEQ ID NO 190
<211> LENGTH: 185
<212> TYPE: PRT
<213> ORGANISM: Homo sapiens
<220> FEATURE:
<221> NAME/KEY: SITE
<222> LOCATION: (185)
<223> OTHER INFORMATION: Xaa equals stop translation

<400> SEQUENCE: 190

Met Leu Phe Leu Phe Ser Met Ala Thr Leu Leu Arg Thr Ser Phe Ser
  1               5                  10                  15

Asp Pro Gly Val Ile Pro Arg Ala Leu Pro Asp Glu Ala Ala Phe Ile
             20                  25                  30

Glu Met Glu Ile Glu Ala Thr Asn Gly Ala Val Pro Gln Gly Gln Arg
         35                  40                  45

Pro Pro Pro Arg Ile Lys Asn Phe Gln Ile Asn Asn Gln Ile Val Lys
     50                  55                  60

Leu Lys Tyr Cys Tyr Thr Cys Lys Ile Phe Arg Pro Pro Arg Ala Ser
 65                  70                  75                  80

His Cys Ser Ile Cys Asp Asn Cys Val Glu Arg Phe Asp His His Cys
                 85                  90                  95

Pro Trp Val Gly Asn Cys Val Gly Lys Arg Asn Tyr Arg Tyr Phe Tyr
            100                 105                 110

Leu Phe Ile Leu Ser Leu Ser Leu Leu Thr Ile Tyr Val Phe Ala Phe
        115                 120                 125

Asn Ile Val Tyr Val Ala Leu Lys Ser Leu Lys Ile Gly Phe Leu Glu
    130                 135                 140

Thr Leu Lys Gly Asn Ser Trp Asn Cys Ser Arg Ser Pro His Leu Leu
145                 150                 155                 160

Leu Tyr Thr Leu Val Arg Arg Gly Thr Asp Trp Ile Ser Tyr Phe Pro
                165                 170                 175

Arg Gly Ser Gln Pro Asp Asn Gln Xaa
            180                 185


<210> SEQ ID NO 191
<211> LENGTH: 147
```

-continued

<212> TYPE: PRT
<213> ORGANISM: Homo sapiens
<220> FEATURE:
<221> NAME/KEY: SITE
<222> LOCATION: (147)
<223> OTHER INFORMATION: Xaa equals stop translation

<400> SEQUENCE: 191

```
Met Arg Val Leu Val Val Thr Ile Ala Pro Ile Tyr Trp Ala Leu Ala
  1               5                  10                  15

Arg Glu Ser Gly Glu Ala Leu Asn Gly His Ser Leu Thr Gly Gly Lys
             20                  25                  30

Phe Arg Gln Ser His Thr Trp Ser Leu Leu Gln Gly Ala Ala His Asp
         35                  40                  45

Asp Pro Val Ala Arg Gly Leu Asp Pro Asp Gly Leu Leu Leu Leu Asp
     50                  55                  60

Val Val Val Asn Gly Val Val Pro Gly Arg Ala Trp Leu Thr Gln Ile
 65                  70                  75                  80

Phe Lys Cys Arg Thr Leu Lys Lys His Tyr Val Gln Thr Arg Ala Trp
                 85                  90                  95

Pro Ala Val Arg Gly Leu His Thr Ala Leu Leu Pro Gly Arg Pro Pro
            100                 105                 110

Leu Val Pro Thr Leu Gln Pro Gln His Pro Val Gln Arg Gly Pro Gly
        115                 120                 125

Pro Pro Ala Pro Ala Gly Ala Ala Pro Ala Gly Leu Ser Tyr Gln Leu
    130                 135                 140

Gly Leu Xaa
145
```

<210> SEQ ID NO 192
<211> LENGTH: 125
<212> TYPE: PRT
<213> ORGANISM: Homo sapiens
<220> FEATURE:
<221> NAME/KEY: SITE
<222> LOCATION: (125)
<223> OTHER INFORMATION: Xaa equals stop translation

<400> SEQUENCE: 192

```
Met Gly Glu Pro Asn Arg His Pro Ser Met Phe Leu Leu Leu Leu Val
  1               5                  10                  15

Leu Glu Arg Leu Tyr Ala Ser Pro Met Asp Gly Thr Ser Ser Ala Leu
             20                  25                  30

Ser Met Gly Pro Phe Val Pro Phe Ile Met Arg Cys Gly His Ser Pro
         35                  40                  45

Val Tyr His Ser Arg Glu Met Ala Ala Arg Ala Leu Val Pro Phe Val
     50                  55                  60

Met Ile Asp His Ile Pro Asn Thr Ile Arg Thr Leu Leu Ser Thr Leu
 65                  70                  75                  80

Pro Ser Cys Thr Asp Gln Cys Phe Arg Ala Lys Pro His Ser Trp Gly
                 85                  90                  95

His Phe Ser Arg Phe Phe His Leu Leu Gln Ala Tyr Ser Asp Ser Lys
            100                 105                 110

Thr Arg Asn Glu Phe Arg Leu Pro Ala Arg Ala Asp Xaa
        115                 120                 125
```

<210> SEQ ID NO 193
<211> LENGTH: 52
<212> TYPE: PRT

-continued

```
<213> ORGANISM: Homo sapiens
<220> FEATURE:
<221> NAME/KEY: SITE
<222> LOCATION: (52)
<223> OTHER INFORMATION: Xaa equals stop translation

<400> SEQUENCE: 193

Met Ile Lys His Val Ala Trp Leu Ile Phe Thr Asn Cys Ile Phe Phe
  1               5                  10                  15

Cys Pro Val Ala Phe Phe Ser Phe Ala Pro Leu Ile Thr Ala Ile Ser
             20                  25                  30

Ile Ser Pro Glu Ile Met Lys Ser Val Thr Leu Ile Phe Phe Pro Cys
         35                  40                  45

Leu Leu Ala Xaa
     50


<210> SEQ ID NO 194
<211> LENGTH: 320
<212> TYPE: PRT
<213> ORGANISM: Homo sapiens
<220> FEATURE:
<221> NAME/KEY: SITE
<222> LOCATION: (68)
<223> OTHER INFORMATION: Xaa equals any of the naturally occurring
      L-amino acids
<220> FEATURE:
<221> NAME/KEY: SITE
<222> LOCATION: (115)
<223> OTHER INFORMATION: Xaa equals any of the naturally occurring
      L-amino acids
<220> FEATURE:
<221> NAME/KEY: SITE
<222> LOCATION: (213)
<223> OTHER INFORMATION: Xaa equals any of the naturally occurring
      L-amino acids
<220> FEATURE:
<221> NAME/KEY: SITE
<222> LOCATION: (320)
<223> OTHER INFORMATION: Xaa equals stop translation

<400> SEQUENCE: 194

Met Ala Pro Leu Ala Leu His Leu Leu Val Leu Val Pro Ile Leu Leu
  1               5                  10                  15

Ser Leu Val Ala Ser Gln Asp Trp Lys Ala Glu Arg Ser Gln Asp Pro
             20                  25                  30

Phe Glu Lys Cys Met Gln Asp Pro Asp Tyr Glu Gln Leu Leu Lys Val
         35                  40                  45

Thr Ile Leu Glu Ala Asp Asn Arg Ile Gly Gly Arg Ile Phe Thr Tyr
     50                  55                  60

Arg Asp Gln Xaa Thr Gly Trp Ile Gly Glu Leu Gly Ala Met Arg Met
 65                  70                  75                  80

Pro Ser Ser His Arg Ile Leu His Lys Leu Cys Gln Gly Leu Gly Leu
                 85                  90                  95

Asn Leu Thr Lys Phe Thr Gln Tyr Asp Lys Asn Thr Trp Thr Glu Val
            100                 105                 110

His Glu Xaa Lys Leu Arg Asn Tyr Val Val Glu Lys Val Pro Glu Lys
        115                 120                 125

Leu Gly Tyr Ala Leu Arg Pro Gln Glu Lys Gly His Ser Pro Glu Asp
    130                 135                 140

Ile Tyr Gln Met Ala Leu Asn Gln Ala Leu Lys Asp Leu Lys Ala Leu
145                 150                 155                 160

Gly Cys Arg Lys Ala Met Lys Lys Phe Glu Arg His Thr Leu Leu Glu
                165                 170                 175
```

-continued

Tyr Leu Leu Gly Glu Gly Asn Leu Ser Arg Pro Ala Val Gln Leu Leu
180 185 190

Gly Asp Val Met Ser Glu Asp Gly Phe Phe Tyr Leu Ser Phe Ala Glu
195 200 205

Ala Leu Arg Ala Xaa Ser Cys Leu Ser Asp Arg Leu Gln Tyr Ser Arg
210 215 220

Ile Val Gly Gly Trp Asp Leu Leu Pro Arg Ala Leu Leu Ser Ser Leu
225 230 235 240

Ser Gly Leu Val Leu Leu Asn Ala Pro Val Val Ala Met Thr Gln Gly
245 250 255

Pro His Asp Val His Val Gln Ile Glu Thr Ser Pro Pro Ala Arg Asn
260 265 270

Leu Lys Val Leu Lys Ala Asp Val Val Leu Leu Thr Ala Ser Gly Pro
275 280 285

Ala Val Lys Arg Ile Thr Phe Ser Pro Arg Cys Pro Ala Thr Cys Arg
290 295 300

Arg Arg Cys Gly Gly Cys Thr Thr Cys Arg Pro Pro Arg Cys Ser Xaa
305 310 315 320

<210> SEQ ID NO 195
<211> LENGTH: 130
<212> TYPE: PRT
<213> ORGANISM: Homo sapiens
<220> FEATURE:
<221> NAME/KEY: SITE
<222> LOCATION: (38)
<223> OTHER INFORMATION: Xaa equals any of the naturally occurring
L-amino acids
<220> FEATURE:
<221> NAME/KEY: SITE
<222> LOCATION: (53)
<223> OTHER INFORMATION: Xaa equals any of the naturally occurring
L-amino acids

<400> SEQUENCE: 195

Pro Phe Cys Ser Gly Phe Phe Pro Ser Leu Trp Ile Tyr Leu Pro Phe
1 5 10 15

Ile Phe Asn Val Ser Asp Leu Trp Met Gly Ser Leu Ser Gly Cys Ala
20 25 30

Leu Pro Phe Cys Leu Xaa Val Phe Phe Leu Thr Val Ser Pro Ser Ala
35 40 45

Val Gly Leu Leu Xaa Phe Ala Gly Gly Pro Leu Gln Thr Leu Phe Ala
50 55 60

Trp Val Ser Pro Val Glu Ala Ala Glu Gln Gln Arg Leu Leu Pro Val
65 70 75 80

Leu Ser Ser Gly Ser Phe Val Ser Glu Gly Thr Cys Gln Met Pro Ala
85 90 95

Arg Ala Leu Leu Tyr Glu Val Ser Val Gly Pro Tyr Trp Glu Ile Pro
100 105 110

Pro Ser Gln Asp Thr Arg Arg Ser Gly Thr Tyr Leu Arg Arg Gln Ser
115 120 125

Asp Pro
130

<210> SEQ ID NO 196
<211> LENGTH: 108
<212> TYPE: PRT
<213> ORGANISM: Homo sapiens

<400> SEQUENCE: 196

His Glu Gly Ser Cys Arg Ala Pro Gly Phe Ser Ala His Lys Gly Arg
1 5 10 15

Gly Cys Pro Ser Pro Arg Met Thr Leu Pro Ser Arg Ala Leu Ala Ser
20 25 30

Leu Gly Val Gly Val Trp Gly Met Leu Arg Leu Asn Gln Val Thr Val
35 40 45

Ser Cys Gly Gly Ser Arg Trp Ser Ser Arg Val Ala Leu Gly Ala Phe
50 55 60

Ser Trp Val Cys Gly Val Ala Leu Val Leu Gln Pro Ser Gly Gly Gly
65 70 75 80

Leu Gly Leu Thr Ser Pro Ser Glu Gly Cys Trp Glu Gly Glu Leu Ala
85 90 95

Leu Ala Val Leu Arg Ala Pro Gly Gly Ser Pro Ser
100 105

<210> SEQ ID NO 197
<211> LENGTH: 104
<212> TYPE: PRT
<213> ORGANISM: Homo sapiens

<400> SEQUENCE: 197

Ile Pro Leu Thr Leu Pro Gly Ile Phe Leu Leu Ile Arg Leu Phe Trp
1 5 10 15

Arg Leu Gly Gln Ser Ile Cys Gly Pro Gly Lys Leu Val Leu Trp Pro
20 25 30

Gln Phe Cys Cys Gly Cys Ala Val Ile Ser Gly His Cys Val Pro Arg
35 40 45

Gly Met Pro Ser Ser Trp Leu Pro Gly Cys Phe Val Leu Leu Cys Leu
50 55 60

Val Ala Val Gly Cys Gln Leu Arg Glu Trp Gly Val Gly Gly Val Ser
65 70 75 80

Ala Val Gly Leu Leu Ala Leu Pro His Leu Gln Val Leu Gly Met Arg
85 90 95

Gly Arg Gly Leu Ile Ser Gly Gly
100

<210> SEQ ID NO 198
<211> LENGTH: 237
<212> TYPE: PRT
<213> ORGANISM: Homo sapiens
<220> FEATURE:
<221> NAME/KEY: SITE
<222> LOCATION: (142)
<223> OTHER INFORMATION: Xaa equals any of the naturally occurring
L-amino acids

<400> SEQUENCE: 198

Gly Pro Ala Gly Lys Glu Ala Trp Ile Trp Ser Trp Leu Leu Pro Ser
1 5 10 15

Pro Gly Pro Ala Pro Leu Pro Ser Ala Ser Trp Gly Leu Cys Gly Asp
20 25 30

Ala Pro Arg Ala Ala Ala Arg Gly Pro Val Glu Pro Gly Ala Ala Arg
35 40 45

Met Ala Leu Leu Ser Arg Pro Ala Leu Thr Leu Leu Leu Leu Leu Met
50 55 60

Ala Ala Val Val Arg Cys Gln Glu Gln Ala Gln Thr Thr Asp Trp Arg
65 70 75 80

-continued

```
Ala Thr Leu Lys Thr Ile Arg Asn Gly Val His Lys Ile Asp Thr Tyr
                 85                  90                  95

Leu Asn Ala Ala Leu Asp Leu Leu Gly Gly Glu Asp Gly Leu Cys Gln
            100                 105                 110

Tyr Lys Cys Ser Asp Gly Ser Lys Pro Phe Pro Arg Tyr Gly Tyr Lys
        115                 120                 125

Pro Ser Pro Pro Asn Gly Cys Gly Ser Pro Leu Phe Gly Xaa His Leu
    130                 135                 140

Asn Ile Gly Ile Pro Ser Leu Thr Lys Cys Cys Asn Gln His Asp Arg
145                 150                 155                 160

Cys Tyr Glu Thr Cys Gly Lys Ser Lys Asn Asp Cys Asp Glu Glu Phe
                165                 170                 175

Gln Tyr Cys Leu Ser Lys Ile Cys Arg Asp Val Gln Lys Thr Leu Gly
            180                 185                 190

Leu Thr Gln His Val Gln Ala Cys Glu Thr Thr Val Glu Leu Leu Phe
        195                 200                 205

Asp Ser Val Ile His Leu Gly Cys Lys Pro Tyr Leu Asp Ser Gln Arg
    210                 215                 220

Ala Ala Cys Arg Cys His Tyr Glu Glu Lys Thr Asp Leu
225                 230                 235


<210> SEQ ID NO 199
<211> LENGTH: 8
<212> TYPE: PRT
<213> ORGANISM: Homo sapiens

<400> SEQUENCE: 199

Cys Cys Asn Gln His Asp Arg Cys
  1               5


<210> SEQ ID NO 200
<211> LENGTH: 15
<212> TYPE: PRT
<213> ORGANISM: Homo sapiens

<400> SEQUENCE: 200

Ser Leu Thr Lys Cys Cys Asn Gln His Asp Arg Cys Tyr Glu Thr
  1               5                  10                  15


<210> SEQ ID NO 201
<211> LENGTH: 16
<212> TYPE: PRT
<213> ORGANISM: Homo sapiens

<400> SEQUENCE: 201

Leu Thr Lys Cys Cys Asn Gln His Asp Arg Cys Tyr Glu Thr Cys Gly
  1               5                  10                  15


<210> SEQ ID NO 202
<211> LENGTH: 260
<212> TYPE: PRT
<213> ORGANISM: Homo sapiens

<400> SEQUENCE: 202

Gly Thr Ser Ser Ala Arg Pro Arg Gly Ala Leu Pro Gly Gly Ser Ala
  1               5                  10                  15

Pro Ser Ala Pro His Gly Gln Leu Pro Gly Arg Ala Gln Pro Ala Pro
             20                  25                  30

Val Ser Gly Pro Pro Pro Thr Ser Gly Leu Cys His Phe Asp Pro Ala
```

-continued

```
        35                  40                  45

Ala Pro Trp Pro Leu Trp Pro Gly Pro Trp Gln Leu Pro Pro His Pro
     50                  55                  60

Gln Asp Trp Pro Ala His Pro Asp Ile Pro Gln Asp Trp Val Ser Phe
 65                  70                  75                  80

Leu Arg Ser Phe Gly Gln Leu Thr Leu Cys Pro Arg Asn Gly Thr Val
                 85                  90                  95

Thr Gly Lys Trp Arg Gly Ser His Val Val Gly Leu Leu Thr Thr Leu
            100                 105                 110

Asn Phe Gly Asp Gly Pro Asp Arg Asn Lys Thr Arg Thr Phe Gln Ala
        115                 120                 125

Thr Val Leu Gly Ser Gln Met Gly Leu Lys Gly Ser Ser Ala Gly Gln
    130                 135                 140

Leu Val Leu Ile Thr Ala Arg Val Thr Thr Glu Arg Thr Ala Gly Thr
145                 150                 155                 160

Cys Leu Tyr Phe Ser Ala Val Pro Gly Ile Leu Pro Ser Ser Gln Pro
                165                 170                 175

Pro Ile Ser Cys Ser Glu Glu Gly Ala Gly Asn Ala Thr Leu Ser Pro
            180                 185                 190

Arg Met Gly Glu Glu Cys Val Ser Val Trp Ser His Glu Gly Leu Val
        195                 200                 205

Leu Thr Lys Leu Leu Thr Ser Glu Glu Leu Ala Leu Cys Gly Ser Arg
    210                 215                 220

Leu Leu Val Leu Gly Ser Phe Leu Leu Leu Phe Cys Gly Leu Leu Cys
225                 230                 235                 240

Cys Val Thr Ala Met Cys Phe His Pro Arg Arg Glu Ser His Trp Ser
                245                 250                 255

Arg Thr Arg Leu
            260
```

<210> SEQ ID NO 203
<211> LENGTH: 80
<212> TYPE: PRT
<213> ORGANISM: Homo sapiens

<400> SEQUENCE: 203

```
Ala Arg Ala Pro Pro Gly Pro Glu Gly Leu Ser Pro Glu Ala Gln Pro
  1               5                  10                  15

Pro Leu Leu Pro Met Gly Asn Cys Gln Ala Gly His Asn Leu His Leu
             20                  25                  30

Cys Leu Ala His His Pro Pro Leu Val Cys Ala Thr Leu Ile Leu Leu
        35                  40                  45

Leu Leu Gly Leu Ser Gly Leu Gly Leu Gly Ser Phe Leu Leu Thr His
     50                  55                  60

Arg Thr Gly Leu Arg Thr Leu Thr Ser Pro Arg Thr Gly Ser Leu Phe
 65                  70                  75                  80
```

<210> SEQ ID NO 204
<211> LENGTH: 224
<212> TYPE: PRT
<213> ORGANISM: Homo sapiens
<220> FEATURE:
<221> NAME/KEY: SITE
<222> LOCATION: (6)
<223> OTHER INFORMATION: Xaa equals any of the naturally occurring
L-amino acids
<220> FEATURE:
<221> NAME/KEY: SITE

```
<222> LOCATION: (9)
<223> OTHER INFORMATION: Xaa equals any of the naturally occurring
      L-amino acids
<220> FEATURE:
<221> NAME/KEY: SITE
<222> LOCATION: (22)
<223> OTHER INFORMATION: Xaa equals any of the naturally occurring
      L-amino acids
<220> FEATURE:
<221> NAME/KEY: SITE
<222> LOCATION: (143)
<223> OTHER INFORMATION: Xaa equals any of the naturally occurring
      L-amino acids
<220> FEATURE:
<221> NAME/KEY: SITE
<222> LOCATION: (186)
<223> OTHER INFORMATION: Xaa equals any of the naturally occurring
      L-amino acids

<400> SEQUENCE: 204

Arg Phe Leu Ser Val Xaa Pro Gln Xaa Glu Val Pro Phe Leu Leu His
  1               5                  10                  15

Pro Cys Val Cys Phe Xaa Gly Gly His Pro Ser Leu Leu Pro Asp Pro
             20                  25                  30

Cys Arg Ala Val Gly Gly Gly Trp Glu Ala Pro Arg Cys Cys Leu His
         35                  40                  45

Glu Ala Leu Cys Gln Ser Leu Gly Cys Lys Ala Glu Glu Ile Val Ser
     50                  55                  60

Val Ser Glu Ser Ser Ser Ala Gln Arg Cys Trp Tyr Leu Leu Arg Gly
 65                  70                  75                  80

Arg Lys Ala Gly Gly Arg Gly Pro Ala Ser Pro Val Leu Phe Ala Leu
                 85                  90                  95

Met Arg Leu Glu Ser Leu Cys His Leu Cys Leu Ala Cys Leu Phe Phe
            100                 105                 110

Arg Leu Pro Ala Thr Arg Thr Val Tyr Cys Met Asn Glu Ala Glu Ile
        115                 120                 125

Val Asp Val Ala Leu Gly Ile Leu Ile Glu Ser Arg Lys Gln Xaa Lys
    130                 135                 140

Ala Cys Glu Gln Pro Ala Leu Ala Gly Ala Asp Asn Pro Glu His Ser
145                 150                 155                 160

Pro Pro Cys Ser Val Ser Pro His Thr Ser Ser Gly Ser Ser Ser Glu
                165                 170                 175

Glu Glu Asp Ser Gly Lys Gln Ala Leu Xaa Pro Gly Leu Ser Pro Ser
            180                 185                 190

Gln Arg Pro Gly Gly Ser Ser Ser Ala Cys Ser Arg Ser Pro Glu Glu
        195                 200                 205

Glu Glu Glu Glu Asp Val Leu Lys Tyr Val Arg Glu Ile Phe Phe Ser
    210                 215                 220


<210> SEQ ID NO 205
<211> LENGTH: 199
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids
<220> FEATURE:
<221> NAME/KEY: SITE
<222> LOCATION: (103)
<223> OTHER INFORMATION: Xaa equals any of the naturally occurring
      L-amino acids
<220> FEATURE:
```

-continued

<221> NAME/KEY: SITE
<222> LOCATION: (191)
<223> OTHER INFORMATION: Xaa equals any of the naturally occurring
L-amino acids

<400> SEQUENCE: 205

```
Val Pro Gly Trp Pro Arg Ala Cys Ser Pro Cys Gln Ala Asp Ser Pro
  1               5                  10                  15

Arg Ala His Pro Pro Lys Leu Arg Gly Ile Leu Arg Trp Ala Pro Val
             20                  25                  30

Pro Leu Xaa Cys Ala Ala Leu Cys Pro Pro Leu Asp Ser Gly Met Ser
         35                  40                  45

Met Ala Ala Cys Pro Glu Ala Pro Glu Pro Ser Phe Leu Arg Glu Val
     50                  55                  60

Pro Ser Ser Pro Ala Ser Thr Gln Trp His Arg Pro Cys Asn Phe Arg
 65                  70                  75                  80

Gln Val Glu Ala Asn Pro Arg Lys Glu Pro Lys Asn Leu Val Trp Arg
                 85                  90                  95

Asp Val Ser Leu Gly Gln Xaa Ser Arg Thr Pro Arg Gly Ser Gly Leu
            100                 105                 110

Glu Leu Val Arg Val Cys Gly Gly Gly Met Gln Arg Asp Lys Thr Val
        115                 120                 125

Val Glu Glu Arg Val Gly Glu Glu Arg Glu Arg Glu Arg Glu Arg Glu
    130                 135                 140

Ser Leu Gly Gly Ala Gly Lys His Gly Glu Met Arg Cys Val Tyr Val
145                 150                 155                 160

Arg Glu Ser Val Gly Ala Pro Gly Arg Ala Gly Gly Gly Gly Asn Gly
                165                 170                 175

Val Asn Ser Val Gly Cys Val Arg Thr Val His Ser Gly Ser Xaa Pro
            180                 185                 190

Pro Pro Ser Ala Gly Val Ser
        195
```

<210> SEQ ID NO 206
<211> LENGTH: 174
<212> TYPE: PRT
<213> ORGANISM: Homo sapiens

<400> SEQUENCE: 206

```
Thr Arg Pro Gly Lys Glu Leu Asn Leu Val Phe Gly Leu Gln Leu Ser
  1               5                  10                  15

Met Ala Arg Ile Gly Ser Thr Val Asn Met Asn Leu Met Gly Trp Leu
             20                  25                  30

Tyr Ser Lys Ile Glu Ala Leu Leu Gly Ser Ala Gly His Thr Thr Leu
         35                  40                  45

Gly Ile Thr Leu Met Ile Gly Gly Ile Thr Cys Ile Leu Ser Leu Ile
     50                  55                  60

Cys Ala Leu Ala Leu Ala Tyr Leu Asp Gln Arg Ala Glu Arg Ile Leu
 65                  70                  75                  80

His Lys Glu Gln Gly Lys Thr Gly Glu Val Ile Lys Leu Thr Asp Val
                 85                  90                  95

Lys Asp Phe Ser Leu Pro Leu Trp Leu Ile Phe Ile Ile Cys Val Cys
            100                 105                 110

Tyr Tyr Val Ala Val Phe Pro Phe Ile Gly Leu Gly Lys Val Phe Phe
        115                 120                 125

Thr Glu Lys Phe Gly Phe Ser Ser Gln Ala Ala Ser Ala Ile Asn Ser
```

-continued

```
    130                 135                 140

Val Val Tyr Val Ile Ser Ala Pro Met Ser Pro Val Phe Gly Leu Leu
145                 150                 155                 160

Val Asp Lys Thr Gly Lys Asn Ile Ile Trp Val Leu Cys Ala
                165                 170


<210> SEQ ID NO 207
<211> LENGTH: 31
<212> TYPE: PRT
<213> ORGANISM: Homo sapiens

<400> SEQUENCE: 207

Cys Lys Asp Leu Cys Ser Arg Val Tyr Leu Leu Thr Leu Ser Pro Leu
  1               5                  10                  15

Leu Ser Tyr Asp Pro Ala Thr Ser His Ser Pro Arg Asn Thr Gln
            20                  25                  30


<210> SEQ ID NO 208
<211> LENGTH: 369
<212> TYPE: PRT
<213> ORGANISM: Homo sapiens
<220> FEATURE:
<221> NAME/KEY: SITE
<222> LOCATION: (78)
<223> OTHER INFORMATION: Xaa equals any of the naturally occurring
      L-amino acids

<400> SEQUENCE: 208

Ile Ile Cys Glu Cys Trp Glu Glu Glu Cys Gln Ser Cys Arg Leu Lys
  1               5                  10                  15

Ile Thr Gln Pro Arg Glu Ile Cys Arg Met Asp Phe Leu Val Leu Phe
            20                  25                  30

Leu Phe Tyr Leu Ala Ser Val Leu Met Gly Leu Val Leu Ile Cys Val
        35                  40                  45

Cys Ser Lys Thr His Ser Leu Lys Gly Leu Ala Arg Gly Gly Ala Gln
     50                  55                  60

Ile Phe Ser Cys Ile Ile Pro Glu Cys Leu Gln Arg Ala Xaa His Gly
 65                  70                  75                  80

Leu Leu His Tyr Leu Phe His Thr Arg Asn His Thr Phe Ile Val Leu
                 85                  90                  95

His Leu Val Leu Gln Gly Met Val Tyr Thr Glu Tyr Thr Trp Glu Val
            100                 105                 110

Phe Gly Tyr Cys Gln Glu Leu Glu Leu Ser Leu His Tyr Leu Leu Leu
        115                 120                 125

Pro Tyr Leu Leu Leu Gly Val Asn Leu Phe Phe Phe Thr Leu Thr Cys
    130                 135                 140

Gly Thr Asn Pro Gly Ile Ile Thr Lys Ala Asn Glu Leu Leu Phe Leu
145                 150                 155                 160

His Val Tyr Glu Phe Asp Glu Val Met Phe Pro Lys Asn Val Arg Cys
                165                 170                 175

Ser Thr Cys Asp Leu Arg Lys Pro Ala Arg Ser Lys His Cys Ser Val
            180                 185                 190

Cys Asn Trp Cys Val His Arg Phe Asp His His Cys Val Trp Val Asn
        195                 200                 205

Asn Cys Ile Gly Ala Trp Asn Ile Arg Tyr Phe Leu Ile Tyr Val Leu
    210                 215                 220

Thr Leu Thr Ala Ser Ala Ala Thr Val Ala Ile Val Ser Thr Thr Phe
225                 230                 235                 240
```

-continued

```
Leu Val His Leu Val Val Met Ser Asp Leu Tyr Gln Glu Thr Tyr Ile
            245                 250                 255

Asp Asp Leu Gly His Leu His Val Met Asp Thr Val Phe Leu Ile Gln
            260                 265                 270

Tyr Leu Phe Leu Thr Phe Pro Arg Ile Val Phe Met Leu Gly Phe Val
        275                 280                 285

Val Val Leu Ser Phe Leu Leu Gly Gly Tyr Leu Leu Phe Val Leu Tyr
    290                 295                 300

Leu Ala Ala Thr Asn Gln Thr Thr Asn Glu Trp Tyr Arg Gly Asp Trp
305                 310                 315                 320

Ala Trp Cys Gln Arg Cys Pro Leu Val Ala Trp Pro Pro Ser Ala Glu
                325                 330                 335

Pro Gln Val His Arg Asn Ile His Ser His Gly Leu Arg Ser Asn Leu
            340                 345                 350

Gln Glu Ile Phe Leu Pro Ala Phe Pro Cys His Glu Arg Lys Lys Gln
        355                 360                 365

Glu
```

<210> SEQ ID NO 209
<211> LENGTH: 147
<212> TYPE: PRT
<213> ORGANISM: Homo sapiens

<400> SEQUENCE: 209

```
Leu Leu Ser Phe Lys Ile Arg Gly Leu Arg Thr Glu Asp Ala Gly Trp
  1               5                  10                  15

Ala Gln Ser Ser Ser Gly Gly Leu Cys Val Arg Gly Asp Ala Phe Trp
             20                  25                  30

Met Pro Ser Ser Ser Ser Gly Leu Gly Ser Pro Ser Arg Pro Pro Ser
         35                  40                  45

Ser Phe Leu Cys Leu Leu Leu Leu Leu Leu Pro Pro Ala Ala Leu Ala
     50                  55                  60

Leu Leu Leu Phe Phe Leu Asp Phe Phe Pro Pro Arg Ala Ala Val Ser
 65                  70                  75                  80

Pro Phe Leu Pro Asp His Cys Ser Ala Arg Gln Pro Arg Val Trp Arg
                 85                  90                  95

Arg Glu Thr Leu Asn Arg Ser Ala Ser Gly Leu Gly Cys Trp Ala Arg
            100                 105                 110

Ser Thr Glu Gln Gly Ala Val Gly Val Ala Thr Gly Thr Val Leu Asp
        115                 120                 125

Ile Ser Leu Pro Ala Ser Cys Leu Ser Leu Trp Pro Pro Gly Pro Ser
    130                 135                 140

Gly Gly Ile
145
```

<210> SEQ ID NO 210
<211> LENGTH: 143
<212> TYPE: PRT
<213> ORGANISM: Homo sapiens

<400> SEQUENCE: 210

```
Gln Leu Gly Leu Cys Leu Thr Ser Ala Ser Leu Pro Pro Ala Ser Arg
  1               5                  10                  15

Cys Gly His Gln Ala Pro Leu Gly Ala Ser Asp Leu Ser Ala His His
             20                  25                  30
```

-continued

```
Ser Ala Pro Gly Phe Ser Asp Ser Tyr Phe Thr Met Ser Cys Gln Ser
        35                  40                  45

Ser Leu Ser Arg Ala Glu Ile Leu Gln Cys Pro Leu Val Pro Ser Val
    50                  55                  60

Ser Pro Pro Thr His Leu Pro Gln Gly Arg Ala Asn Lys Ser Ser Arg
65                  70                  75                  80

Ala Ser Leu Pro Leu Leu Pro Gln Thr His Trp Cys Leu Phe Pro Ser
                85                  90                  95

Ala Arg Gly Trp Arg Arg Gly Ile Gln Ser Gly Leu Pro Pro Gly Gly
            100                 105                 110

Ser Cys Thr Ser Pro Arg Ser Pro Pro Gln Thr Leu His Gln His Ile
        115                 120                 125

Thr Leu Val Asn His Asn Thr Ser Tyr Trp Gln Ser Pro Ser Thr
    130                 135                 140


<210> SEQ ID NO 211
<211> LENGTH: 160
<212> TYPE: PRT
<213> ORGANISM: Homo sapiens

<400> SEQUENCE: 211

His Gln Pro Pro Cys Leu Leu Pro Leu Ala Val Ala Thr Arg Pro Leu
  1               5                  10                  15

Trp Gly His Leu Thr Cys Leu Pro Ile Ile Leu His Leu Val Ser Val
            20                  25                  30

Thr Leu Thr Ser Pro Cys Leu Ala Asn Gln Ala Phe Gln Gly Gln Arg
        35                  40                  45

Ser Tyr Asn Ala Leu Trp Cys Pro Leu Phe Leu Leu Leu Pro Thr Ser
    50                  55                  60

Pro Lys Gly Glu Gln Thr Asn His Pro Glu Pro Ala Cys Pro Cys Phe
65                  70                  75                  80

Pro Lys Leu Thr Gly Val Phe Ser Leu Gln His Val Val Gly Ala Glu
                85                  90                  95

Glu Phe Ser Gln Val Phe Leu Leu Val Asp Pro Val Pro Val Leu Asp
            100                 105                 110

His Leu Leu Lys Leu Phe Thr Ser Thr Ser His Leu Leu Ile Ile Ile
        115                 120                 125

Pro His Ile Gly Lys Ala Pro Ala Pro Asp Ser Leu Leu Glu Glu Leu
    130                 135                 140

Ser Leu Ser Leu Ala Thr His Cys Lys Val Ala Val Ala Arg Phe Thr
145                 150                 155                 160


<210> SEQ ID NO 212
<211> LENGTH: 157
<212> TYPE: PRT
<213> ORGANISM: Homo sapiens

<400> SEQUENCE: 212

Met Ala Ala Glu Gly Ser Arg Phe Ser Ser Gln Ser Pro Gly Leu Val
  1               5                  10                  15

Asp Arg Gln Gly Pro Lys Cys Asp Pro Ser Arg Leu Val Ser Pro Trp
            20                  25                  30

Gly Arg His Gly Leu Arg Ile Leu Gln Ile Gly His His His Gly Arg
        35                  40                  45

Asp Gly Gln His Glu Ala Thr His His Leu Leu Arg Val Leu Arg Ala
    50                  55                  60
```

-continued

```
Pro Arg Val Gly Lys Ala Asp Glu Gly Ala Val Asp Ser Asp Pro Ser
 65                  70                  75                  80

Thr Pro Leu Gln Leu Lys His Glu Ala Ala His Ala Glu Asp His Ala
                 85                  90                  95

Gln Gln Val His Val Val Arg Arg Arg Val Val Gln Gly Arg Val Thr
            100                 105                 110

Phe Ala Arg Arg Gly Leu Val Pro Gln His Phe Val Arg Pro Pro Trp
        115                 120                 125

Val Arg His Ile Val Ser Gly His Ser Glu Ser Lys Ala Arg Ser Arg
    130                 135                 140

Leu Phe Arg Cys Arg Asn Arg Ser Phe Arg Arg Ala Ser
145                 150                 155


<210> SEQ ID NO 213
<211> LENGTH: 38
<212> TYPE: PRT
<213> ORGANISM: Homo sapiens

<400> SEQUENCE: 213

Arg Leu Val Ser Pro Trp Gly Arg His Gly Leu Arg Ile Leu Gln Ile
  1               5                  10                  15

Gly His His His Gly Arg Asp Gly Gln His Glu Ala Thr His His Leu
             20                  25                  30

Leu Arg Val Leu Arg Ala
         35


<210> SEQ ID NO 214
<211> LENGTH: 12
<212> TYPE: PRT
<213> ORGANISM: Homo sapiens

<400> SEQUENCE: 214

Pro Thr Asp Val Leu Lys Ile Arg Met Gln Ala Gln
  1               5                  10


<210> SEQ ID NO 215
<211> LENGTH: 7
<212> TYPE: PRT
<213> ORGANISM: Homo sapiens

<400> SEQUENCE: 215

Thr Tyr Glu Gln Leu Lys Arg
  1               5


<210> SEQ ID NO 216
<211> LENGTH: 137
<212> TYPE: PRT
<213> ORGANISM: Homo sapiens
<220> FEATURE:
<221> NAME/KEY: SITE
<222> LOCATION: (22)
<223> OTHER INFORMATION: Xaa equals any of the naturally occurring
      L-amino acids
<220> FEATURE:
<221> NAME/KEY: SITE
<222> LOCATION: (33)
<223> OTHER INFORMATION: Xaa equals any of the naturally occurring
      L-amino acids
<220> FEATURE:
<221> NAME/KEY: SITE
<222> LOCATION: (71)
<223> OTHER INFORMATION: Xaa equals any of the naturally occurring
      L-amino acids

<400> SEQUENCE: 216
```

-continued

```
Arg Pro Arg Pro Ser Ala Ser Ser Leu Ala Arg Ser Ala Ser Leu Leu
  1               5                  10                  15

Pro Ala Ala His Gly Xaa Gly Val Gly Gly Ala Gly Gly Gly Ser Ser
             20                  25                  30

Xaa Leu Arg Ser Arg Tyr Gln Gln Leu Gln Asn Glu Glu Glu Ser Gly
         35                  40                  45

Glu Pro Glu Gln Ala Ala Gly Asp Ala Pro Pro Pro Tyr Ser Ser Ile
     50                  55                  60

Ser Ala Glu Ser Ala His Xaa Phe Asp Tyr Lys Asp Glu Ser Gly Phe
 65                  70                  75                  80

Pro Lys Pro Pro Ser Tyr Asn Val Ala Thr Thr Leu Pro Ser Tyr Asp
                 85                  90                  95

Glu Ala Glu Arg Thr Lys Ala Glu Ala Thr Ile Pro Leu Val Pro Gly
            100                 105                 110

Arg Asp Glu Asp Phe Val Gly Arg Asp Asp Phe Asp Asp Ala Asp Gln
        115                 120                 125

Leu Arg Ile Gly Asn Asp Gly Ile Phe
    130                 135
```

<210> SEQ ID NO 217
<211> LENGTH: 20
<212> TYPE: PRT
<213> ORGANISM: Homo sapiens

<400> SEQUENCE: 217

```
Arg Tyr Gln Gln Leu Gln Asn Glu Glu Glu Ser Gly Glu Pro Glu Gln
  1               5                  10                  15

Ala Ala Gly Asp
             20
```

<210> SEQ ID NO 218
<211> LENGTH: 22
<212> TYPE: PRT
<213> ORGANISM: Homo sapiens

<400> SEQUENCE: 218

```
Pro Gly Arg Asp Glu Asp Phe Val Gly Arg Asp Asp Phe Asp Asp Ala
  1               5                  10                  15

Asp Gln Leu Arg Ile Gly
             20
```

<210> SEQ ID NO 219
<211> LENGTH: 103
<212> TYPE: PRT
<213> ORGANISM: Homo sapiens

<400> SEQUENCE: 219

```
Met Leu Thr Phe Phe Met Ala Phe Leu Phe Asn Trp Ile Gly Phe Phe
  1               5                  10                  15

Leu Ser Phe Cys Leu Thr Thr Ser Ala Ala Gly Arg Tyr Gly Ala Ile
             20                  25                  30

Ser Gly Phe Gly Leu Ser Leu Ile Lys Trp Ile Leu Ile Val Arg Phe
         35                  40                  45

Ser Thr Tyr Phe Pro Gly Tyr Phe Asp Gly Gln Tyr Trp Leu Trp Trp
     50                  55                  60

Val Phe Leu Val Leu Gly Phe Leu Leu Phe Leu Arg Gly Phe Ile Asn
 65                  70                  75                  80
```

-continued

```
Tyr Ala Lys Val Arg Lys Met Pro Glu Thr Phe Ser Asn Leu Pro Arg
                 85                  90                  95

Thr Arg Val Leu Phe Ile Tyr
            100


<210> SEQ ID NO 220
<211> LENGTH: 198
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
      L-amino acids

<400> SEQUENCE: 220

Met Lys Lys Ser Leu Glu Asn Leu Asn Arg Leu Gln Val Met Leu Leu
  1               5                  10                  15

His Leu Thr Ala Ala Phe Leu Gln Arg Ala Gln His Xaa Phe Asp Tyr
             20                  25                  30

Lys Asp Glu Ser Gly Phe Pro Lys Pro Pro Ser Tyr Asn Val Ala Thr
         35                  40                  45

Thr Leu Pro Ser Tyr Asp Glu Ala Glu Arg Thr Lys Ala Glu Ala Thr
     50                  55                  60

Ile Pro Leu Val Pro Gly Arg Asp Glu Asp Phe Val Gly Arg Asp Asp
 65                  70                  75                  80

Phe Asp Asp Ala Asp Gln Leu Arg Ile Gly Asn Asp Gly Ile Phe Met
                 85                  90                  95

Leu Thr Phe Phe Met Ala Phe Leu Phe Asn Trp Ile Gly Phe Phe Leu
            100                 105                 110

Ser Phe Cys Leu Thr Thr Ser Ala Ala Gly Arg Tyr Gly Ala Ile Ser
        115                 120                 125

Gly Phe Gly Leu Ser Leu Ile Lys Trp Ile Leu Ile Val Arg Phe Ser
    130                 135                 140

Thr Tyr Phe Pro Gly Tyr Phe Asp Gly Gln Tyr Trp Leu Trp Trp Val
145                 150                 155                 160

Phe Leu Val Leu Gly Phe Leu Leu Phe Leu Arg Gly Phe Ile Asn Tyr
                165                 170                 175

Ala Lys Val Arg Lys Met Pro Glu Thr Phe Ser Asn Leu Pro Arg Thr
            180                 185                 190

Arg Val Leu Phe Ile Tyr
        195


<210> SEQ ID NO 221
<211> LENGTH: 70
<212> TYPE: PRT
<213> ORGANISM: Homo sapiens

<400> SEQUENCE: 221

Met Leu Leu His Leu Thr Ala Ala Phe Leu Gln Arg Ala Gln Phe Ser
  1               5                  10                  15

Thr Tyr Phe Pro Gly Tyr Phe Asp Gly Gln Tyr Trp Leu Trp Trp Val
             20                  25                  30

Phe Leu Val Leu Gly Phe Leu Leu Phe Leu Arg Gly Phe Ile Asn Tyr
         35                  40                  45

Ala Lys Val Arg Lys Met Pro Glu Thr Phe Ser Asn Leu Pro Arg Thr
     50                  55                  60

Arg Val Leu Phe Ile Tyr
```

-continued

```
 65                  70


<210> SEQ ID NO 222
<211> LENGTH: 82
<212> TYPE: PRT
<213> ORGANISM: Homo sapiens

<400> SEQUENCE: 222

Met Leu Thr Phe Phe Met Ala Phe Leu Phe Asn Trp Ile Gly Phe Phe
  1               5                  10                  15

Leu Ser Phe Cys Leu Thr Thr Ser Ala Ala Gly Arg Tyr Gly Ala Ile
             20                  25                  30

Ser Gly Phe Gly Leu Ser Leu Ile Lys Trp Ile Leu Ile Val Arg Phe
         35                  40                  45

Ser Thr Tyr Phe Pro Ala Phe Met Asn Ser Leu Ser Arg Ser Lys Arg
     50                  55                  60

Thr Pro Ala Gly Ser Glu Ser Arg Cys Arg Thr Gln Arg Asn Asn His
 65                  70                  75                  80

Leu Leu


<210> SEQ ID NO 223
<211> LENGTH: 45
<212> TYPE: PRT
<213> ORGANISM: Homo sapiens
<220> FEATURE:
<221> NAME/KEY: SITE
<222> LOCATION: (28)
<223> OTHER INFORMATION: Xaa equals any of the naturally occurring
      L-amino acids

<400> SEQUENCE: 223

Met Lys Lys Ser Leu Glu Asn Leu Asn Arg Leu Gln Val Met Leu Leu
  1               5                  10                  15

His Leu Thr Ala Ala Phe Leu Gln Arg Ala His Xaa Ile Leu Thr Thr
             20                  25                  30

Arg Met Ser Leu Gly Phe Gln Ser Pro His Leu Thr Met
         35                  40                  45


<210> SEQ ID NO 224
<211> LENGTH: 33
<212> TYPE: PRT
<213> ORGANISM: Homo sapiens

<400> SEQUENCE: 224

Met Thr Val Met Asp Pro Lys Gln Met Asn Val Ala Ala Ala Val Trp
  1               5                  10                  15

Ala Val Val Ser Tyr Val Val Ala Asp Met Glu Glu Met Leu Pro Arg
             20                  25                  30

Ser


<210> SEQ ID NO 225
<211> LENGTH: 189
<212> TYPE: PRT
<213> ORGANISM: Homo sapiens

<400> SEQUENCE: 225

Pro Arg Val Arg Ser Arg Glu Pro Val Ala Gly Ala Pro Gly Cys Gly
  1               5                  10                  15

Thr Ala Gly Pro Pro Ala Met Ala Thr Leu Trp Gly Gly Leu Leu Arg
             20                  25                  30
```

-continued

Leu Gly Ser Leu Leu Ser Leu Ser Cys Leu Ala Leu Ser Val Leu Leu
35 40 45

Leu Ala His Cys Gln Thr Pro Pro Ser Asp Cys Leu His Val Val Glu
50 55 60

Pro Met Pro Val Arg Gly Pro Asp Val Glu Ala Tyr Cys Leu Arg Cys
65 70 75 80

Glu Cys Lys Tyr Glu Glu Arg Ser Ser Val Thr Ile Lys Val Thr Ile
85 90 95

Ile Ile Tyr Leu Ser Ile Leu Gly Leu Leu Leu Leu Tyr Met Val Tyr
100 105 110

Leu Thr Leu Val Glu Pro Ile Leu Lys Arg Arg Leu Phe Gly His Ala
115 120 125

Gln Leu Ile Gln Ser Asp Asp Asp Ile Gly Asp His Gln Pro Phe Ala
130 135 140

Asn Ala His Asp Val Leu Ala Arg Ser Arg Ser Arg Ala Asn Val Leu
145 150 155 160

Asn Lys Val Glu Tyr Ala Gln Gln Arg Trp Lys Leu Gln Val Gln Glu
165 170 175

Gln Arg Lys Ser Val Phe Asp Arg His Val Val Leu Ser
180 185

<210> SEQ ID NO 226
<211> LENGTH: 231
<212> TYPE: PRT
<213> ORGANISM: Homo sapiens

<400> SEQUENCE: 226

Met Ala Thr Leu Trp Gly Gly Leu Leu Arg Leu Gly Ser Leu Leu Ser
1 5 10 15

Leu Ser Cys Leu Ala Leu Ser Val Leu Leu Leu Ala His Cys Gln Thr
20 25 30

Pro Pro Arg Ile Ser Arg Met Ser Asp Val Asn Val Ser Ala Leu Pro
35 40 45

Ile Lys Lys Asn Ser Gly His Ile Tyr Asn Lys Asn Ile Ser Gln Lys
50 55 60

Asp Cys Asp Cys Leu His Val Val Glu Pro Met Pro Val Arg Gly Pro
65 70 75 80

Asp Val Glu Ala Tyr Cys Leu Arg Cys Glu Cys Lys Tyr Glu Glu Arg
85 90 95

Ser Ser Val Thr Ile Lys Val Thr Ile Ile Ile Tyr Leu Ser Ile Leu
100 105 110

Gly Leu Leu Leu Leu Tyr Met Val Tyr Leu Thr Leu Val Glu Pro Ile
115 120 125

Leu Lys Arg Arg Leu Phe Gly His Ala Gln Leu Ile Gln Ser Asp Asp
130 135 140

Asp Ile Gly Asp His Gln Pro Phe Ala Asn Ala His Asp Val Leu Ala
145 150 155 160

Arg Ser Arg Ser Arg Ala Asn Val Leu Asn Lys Val Glu Tyr Gly Thr
165 170 175

Ala Ala Leu Glu Ala Ser Ser Pro Arg Ala Ala Lys Ser Leu Ser Leu
180 185 190

Thr Gly Met Leu Ser Ser Ala Asn Trp Gly Ile Glu Phe Lys Val Thr
195 200 205

Arg Lys Lys Gln Ala Asp Asn Trp Lys Gly Thr Asp Trp Val Leu Leu
210 215 220

-continued

```
Gly Phe Ile Leu Ile Pro Cys
225                 230


<210> SEQ ID NO 227
<211> LENGTH: 456
<212> TYPE: PRT
<213> ORGANISM: Homo sapiens

<400> SEQUENCE: 227

Met Ala Ala Ala Gly Arg Leu Pro Ser Ser Trp Ala Leu Phe Ser Pro
  1               5                  10                  15

Leu Leu Ala Gly Leu Ala Leu Leu Gly Val Gly Pro Val Pro Ala Arg
             20                  25                  30

Ala Leu His Asn Val Thr Ala Glu Leu Phe Gly Ala Glu Ala Trp Gly
         35                  40                  45

Thr Leu Ala Ala Phe Gly Asp Leu Asn Ser Asp Lys Gln Thr Asp Leu
     50                  55                  60

Phe Val Leu Arg Glu Arg Asn Asp Leu Ile Val Phe Leu Ala Asp Gln
 65                  70                  75                  80

Asn Ala Pro Tyr Phe Lys Pro Lys Val Lys Val Ser Phe Lys Asn His
                 85                  90                  95

Ser Ala Leu Ile Thr Ser Val Val Pro Gly Asp Tyr Asp Gly Asp Ser
            100                 105                 110

Gln Met Asp Val Leu Leu Thr Tyr Leu Pro Lys Asn Tyr Ala Lys Ser
        115                 120                 125

Glu Leu Gly Ala Val Ile Phe Trp Gly Gln Asn Gln Thr Leu Asp Pro
    130                 135                 140

Asn Asn Met Thr Ile Leu Asn Arg Thr Phe Gln Asp Glu Pro Leu Ile
145                 150                 155                 160

Met Asp Phe Asn Gly Asp Leu Ile Pro Asp Ile Phe Gly Ile Thr Asn
                165                 170                 175

Glu Ser Asn Gln Pro Gln Ile Leu Leu Gly Gly Asn Leu Ser Trp His
            180                 185                 190

Pro Ala Leu Thr Thr Thr Ser Lys Met Arg Ile Pro His Ser His Ala
        195                 200                 205

Phe Ile Asp Leu Thr Glu Asp Phe Thr Ala Asp Leu Phe Leu Thr Thr
    210                 215                 220

Leu Asn Ala Thr Thr Ser Thr Phe Gln Phe Glu Ile Trp Glu Asn Leu
225                 230                 235                 240

Asp Gly Asn Phe Ser Val Ser Thr Ile Leu Glu Lys Pro Gln Asn Met
                245                 250                 255

Met Val Val Gly Gln Ser Ala Phe Ala Asp Phe Asp Gly Asp Gly His
            260                 265                 270

Met Asp His Leu Leu Pro Gly Cys Glu Asp Lys Asn Cys Gln Lys Ser
        275                 280                 285

Thr Ile Tyr Leu Val Arg Ser Gly Met Lys Gln Trp Val Pro Val Leu
    290                 295                 300

Gln Asp Phe Ser Asn Lys Gly Thr Leu Trp Gly Phe Val Pro Phe Val
305                 310                 315                 320

Asp Glu Gln Gln Pro Thr Glu Ile Pro Ile Pro Ile Thr Leu His Ile
                325                 330                 335

Gly Asp Tyr Asn Met Asp Gly Tyr Pro Asp Ala Leu Val Ile Leu Lys
            340                 345                 350

Asn Thr Ser Gly Ser Asn Gln Gln Ala Phe Leu Leu Glu Asn Val Pro
```

-continued

```
        355                 360                 365

Cys Asn Asn Ala Ser Cys Glu Glu Ala Arg Arg Met Phe Lys Val Tyr
    370                 375                 380

Trp Glu Leu Thr Asp Leu Asn Gln Ile Lys Asp Ala Met Val Ala Thr
385                 390                 395                 400

Phe Phe Asp Ile Tyr Glu Asp Gly Ile Leu Asp Ile Val Val Leu Ser
                405                 410                 415

Lys Gly Tyr Thr Lys Asn Asp Phe Ala Ile His Thr Leu Lys Asn Asn
            420                 425                 430

Phe Glu Ala Asp Ala Tyr Phe Val Lys Val Ile Val Leu Ser Gly Leu
        435                 440                 445

Cys Ser Asn Asp Cys Pro Arg Arg
    450                 455


<210> SEQ ID NO 228
<211> LENGTH: 282
<212> TYPE: PRT
<213> ORGANISM: Homo sapiens
<220> FEATURE:
<221> NAME/KEY: SITE
<222> LOCATION: (144)
<223> OTHER INFORMATION: Xaa equals any of the naturally occurring
      L-amino acids
<220> FEATURE:
<221> NAME/KEY: SITE
<222> LOCATION: (168)
<223> OTHER INFORMATION: Xaa equals any of the naturally occurring
      L-amino acids

<400> SEQUENCE: 228

Met Thr Lys Arg Glu Asp Gly Gly Tyr Thr Phe Thr Ala Thr Pro Glu
  1               5                  10                  15

Asp Phe Pro Lys Lys His Lys Ala Pro Val Ile Asp Ile Gly Ile Ala
             20                  25                  30

Asn Thr Gly Lys Phe Ile Met Thr Ala Ser Ser Asp Thr Thr Val Leu
        35                  40                  45

Ile Trp Ser Leu Lys Gly Gln Val Leu Ser Thr Ile Asn Thr Asn Gln
     50                  55                  60

Met Asn Asn Thr His Ala Ala Val Ser Pro Cys Gly Arg Phe Val Ala
 65                  70                  75                  80

Ser Cys Gly Phe Thr Pro Asp Val Lys Val Trp Glu Val Cys Phe Gly
                 85                  90                  95

Lys Lys Gly Glu Phe Gln Glu Val Val Arg Ala Phe Glu Leu Lys Gly
            100                 105                 110

His Ser Ala Ala Val His Ser Phe Ala Phe Ser Asn Asp Ser Arg Arg
        115                 120                 125

Met Ala Ser Val Ser Lys Asp Gly Thr Trp Lys Leu Trp Asp Thr Xaa
    130                 135                 140

Val Glu Tyr Lys Lys Lys Gln Asp Pro Tyr Leu Leu Lys Thr Gly Arg
145                 150                 155                 160

Phe Glu Glu Ala Ala Gly Ala Xaa Pro Cys Arg Leu Ala Leu Ser Pro
                165                 170                 175

Asn Ala Gln Val Leu Ala Leu Ala Ser Gly Ser Ser Ile His Leu Tyr
            180                 185                 190

Asn Thr Arg Arg Gly Glu Lys Glu Glu Cys Phe Glu Arg Val His Gly
        195                 200                 205

Glu Cys Ile Ala Asn Leu Ser Phe Asp Ile Thr Gly Arg Phe Leu Ala
    210                 215                 220
```

-continued

```
Ser Cys Gly Asp Arg Ala Val Arg Leu Phe His Asn Thr Pro Gly His
225                 230                 235                 240

Arg Ala Met Val Glu Glu Met Gln Gly His Leu Lys Arg Ala Ser Asn
                245                 250                 255

Glu Ser Thr Arg Gln Arg Leu Gln Gln Gln Leu Thr Gln Ala Gln Glu
            260                 265                 270

Thr Leu Lys Ser Leu Gly Ala Leu Lys Lys
        275                 280


<210> SEQ ID NO 229
<211> LENGTH: 456
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally occurring
      L-amino acids
<220> FEATURE:
<221> NAME/KEY: SITE
<222> LOCATION: (37)
<223> OTHER INFORMATION: Xaa equals any of the naturally occurring
      L-amino acids
<220> FEATURE:
<221> NAME/KEY: SITE
<222> LOCATION: (318)
<223> OTHER INFORMATION: Xaa equals any of the naturally occurring
      L-amino acids
<220> FEATURE:
<221> NAME/KEY: SITE
<222> LOCATION: (342)
<223> OTHER INFORMATION: Xaa equals any of the naturally occurring
      L-amino acids

<400> SEQUENCE: 229

Val Ile Arg His Glu Gly Ser Thr Asn Met Glu Leu Ser Gln Met Ser
  1               5                  10                  15

Xaa Leu Met Gly Leu Ser Val Leu Leu Gly Leu Leu Ala Leu Met Ala
            20                  25                  30

Thr Ala Ala Val Xaa Arg Gly Trp Leu Arg Ala Gly Glu Glu Arg Ser
        35                  40                  45

Gly Arg Pro Ala Cys Gln Lys Ala Asn Gly Phe Pro Pro Asp Lys Ser
    50                  55                  60

Ser Gly Ser Lys Lys Gln Lys Gln Tyr Gln Arg Ile Arg Lys Glu Lys
 65                  70                  75                  80

Pro Gln Gln His Asn Phe Thr His Arg Leu Leu Ala Ala Ala Leu Lys
                85                  90                  95

Ser His Ser Gly Asn Ile Ser Cys Met Asp Phe Ser Ser Asn Gly Lys
            100                 105                 110

Tyr Leu Ala Thr Cys Ala Asp Asp Arg Thr Ile Arg Ile Trp Ser Thr
        115                 120                 125

Lys Asp Phe Leu Gln Arg Glu His Arg Ser Met Arg Ala Asn Val Glu
    130                 135                 140

Leu Asp His Ala Thr Leu Val Arg Phe Ser Pro Asp Cys Arg Ala Phe
145                 150                 155                 160

Ile Val Trp Leu Ala Asn Gly Asp Thr Leu Arg Val Phe Lys Met Thr
                165                 170                 175

Lys Arg Glu Asp Gly Gly Tyr Thr Phe Thr Ala Thr Pro Glu Asp Phe
            180                 185                 190

Pro Lys Lys His Lys Ala Pro Val Ile Asp Ile Gly Ile Ala Asn Thr
        195                 200                 205
```

-continued

```
Gly Lys Phe Ile Met Thr Ala Ser Ser Asp Thr Thr Val Leu Ile Trp
    210                 215                 220

Ser Leu Lys Gly Gln Val Leu Ser Thr Ile Asn Thr Asn Gln Met Asn
225                 230                 235                 240

Asn Thr His Ala Ala Val Ser Pro Cys Gly Arg Phe Val Ala Ser Cys
                245                 250                 255

Gly Phe Thr Pro Asp Val Lys Val Trp Glu Val Cys Phe Gly Lys Lys
            260                 265                 270

Gly Glu Phe Gln Glu Val Val Arg Ala Phe Glu Leu Lys Gly His Ser
        275                 280                 285

Ala Ala Val His Ser Phe Ala Phe Ser Asn Asp Ser Arg Arg Met Ala
    290                 295                 300

Ser Val Ser Lys Asp Gly Thr Trp Lys Leu Trp Asp Thr Xaa Val Glu
305                 310                 315                 320

Tyr Lys Lys Lys Gln Asp Pro Tyr Leu Leu Lys Thr Gly Arg Phe Glu
                325                 330                 335

Glu Ala Ala Gly Ala Xaa Pro Cys Arg Leu Ala Leu Ser Pro Asn Ala
            340                 345                 350

Gln Val Leu Ala Leu Ala Ser Gly Ser Ser Ile His Leu Tyr Asn Thr
        355                 360                 365

Arg Arg Gly Glu Lys Glu Glu Cys Phe Glu Arg Val His Gly Glu Cys
    370                 375                 380

Ile Ala Asn Leu Ser Phe Asp Ile Thr Gly Arg Phe Leu Ala Ser Cys
385                 390                 395                 400

Gly Asp Arg Ala Val Arg Leu Phe His Asn Thr Pro Gly His Arg Ala
                405                 410                 415

Met Val Glu Glu Met Gln Gly His Leu Lys Arg Ala Ser Asn Glu Ser
            420                 425                 430

Thr Arg Gln Arg Leu Gln Gln Gln Leu Thr Gln Ala Gln Glu Thr Leu
        435                 440                 445

Lys Ser Leu Gly Ala Leu Lys Lys
    450                 455
```

<210> SEQ ID NO 230
<211> LENGTH: 363
<212> TYPE: PRT
<213> ORGANISM: Homo sapiens

<400> SEQUENCE: 230

```
Met Ser Val Met Val Val Arg Lys Lys Val Thr Arg Lys Trp Glu Lys
  1               5                  10                  15

Leu Pro Gly Arg Asn Thr Phe Cys Cys Asp Gly Arg Val Met Met Ala
             20                  25                  30

Arg Gln Lys Gly Ile Phe Tyr Leu Thr Leu Phe Leu Ile Leu Gly Thr
         35                  40                  45

Cys Thr Leu Phe Phe Ala Phe Glu Cys Arg Tyr Leu Ala Val Gln Leu
     50                  55                  60

Ser Pro Ala Ile Pro Val Phe Ala Ala Met Leu Phe Leu Phe Ser Met
 65                  70                  75                  80

Ala Thr Leu Leu Arg Thr Ser Phe Ser Asp Pro Gly Val Ile Pro Arg
                 85                  90                  95

Ala Leu Pro Asp Glu Ala Ala Phe Ile Glu Met Glu Ile Glu Ala Thr
            100                 105                 110

Asn Gly Ala Val Pro Gln Gly Gln Arg Pro Pro Pro Arg Ile Lys Asn
```

-continued

```
        115                 120                 125

Phe Gln Ile Asn Asn Gln Ile Val Lys Leu Lys Tyr Cys Tyr Thr Cys
    130                 135                 140

Lys Ile Phe Arg Pro Pro Arg Ala Ser His Cys Ser Ile Cys Asp Asn
145                 150                 155                 160

Cys Val Glu Arg Phe Asp His His Cys Pro Trp Val Gly Asn Cys Val
                165                 170                 175

Gly Lys Arg Asn Tyr Arg Tyr Phe Tyr Leu Phe Ile Leu Ser Leu Ser
            180                 185                 190

Leu Leu Thr Ile Tyr Val Phe Ala Phe Asn Ile Val Tyr Val Ala Leu
        195                 200                 205

Lys Ser Leu Lys Ile Gly Phe Leu Glu Thr Leu Lys Glu Thr Pro Gly
    210                 215                 220

Thr Val Leu Glu Val Leu Ile Cys Phe Phe Thr Leu Trp Ser Val Val
225                 230                 235                 240

Gly Leu Thr Gly Phe His Thr Phe Leu Val Ala Leu Asn Gln Thr Thr
                245                 250                 255

Asn Glu Asp Ile Lys Gly Ser Trp Thr Gly Lys Asn Arg Val Gln Asn
            260                 265                 270

Pro Tyr Ser His Gly Asn Ile Val Lys Asn Cys Cys Glu Val Leu Cys
        275                 280                 285

Gly Pro Leu Pro Pro Ser Val Leu Asp Arg Arg Gly Ile Leu Pro Leu
    290                 295                 300

Glu Glu Ser Gly Ser Arg Pro Pro Ser Thr Gln Glu Thr Ser Ser Ser
305                 310                 315                 320

Leu Leu Pro Gln Ser Pro Ala Pro Thr Glu Leu Asn Ser Asn Glu Met
                325                 330                 335

Pro Glu Asp Ser Ser Thr Pro Glu Glu Met Pro Pro Pro Glu Pro Pro
            340                 345                 350

Glu Pro Pro Gln Glu Ala Ala Glu Ala Glu Lys
        355                 360


<210> SEQ ID NO 231
<211> LENGTH: 184
<212> TYPE: PRT
<213> ORGANISM: Homo sapiens

<400> SEQUENCE: 231

Met Leu Phe Leu Phe Ser Met Ala Thr Leu Leu Arg Thr Ser Phe Ser
  1               5                  10                  15

Asp Pro Gly Val Ile Pro Arg Ala Leu Pro Asp Glu Ala Ala Phe Ile
            20                  25                  30

Glu Met Glu Ile Glu Ala Thr Asn Gly Ala Val Pro Gln Gly Gln Arg
        35                  40                  45

Pro Pro Pro Arg Ile Lys Asn Phe Gln Ile Asn Asn Gln Ile Val Lys
    50                  55                  60

Leu Lys Tyr Cys Tyr Thr Cys Lys Ile Phe Arg Pro Pro Arg Ala Ser
 65                  70                  75                  80

His Cys Ser Ile Cys Asp Asn Cys Val Glu Arg Phe Asp His His Cys
                85                  90                  95

Pro Trp Val Gly Asn Cys Val Gly Lys Arg Asn Tyr Arg Tyr Phe Tyr
            100                 105                 110

Leu Phe Ile Leu Ser Leu Ser Leu Leu Thr Ile Tyr Val Phe Ala Phe
        115                 120                 125
```

-continued

```
Asn Ile Val Tyr Val Ala Leu Lys Ser Leu Lys Ile Gly Phe Leu Glu
    130                 135                 140

Thr Leu Lys Gly Asn Ser Trp Asn Cys Ser Arg Ser Pro His Leu Leu
145                 150                 155                 160

Leu Tyr Thr Leu Val Arg Arg Gly Thr Asp Trp Ile Ser Tyr Phe Pro
                165                 170                 175

Arg Gly Ser Gln Pro Asp Asn Gln
            180


<210> SEQ ID NO 232
<211> LENGTH: 52
<212> TYPE: PRT
<213> ORGANISM: Homo sapiens

<400> SEQUENCE: 232

Leu His Glu Cys Leu Pro Gly Ser Ile Ser Tyr Leu His Pro Arg Thr
  1               5                  10                  15

Pro Trp Leu Cys Leu Pro Pro Gln His Leu Ser Phe Ser Thr Phe Ser
             20                  25                  30

Pro Pro Trp Gln Pro Ala Met Ser Pro Val Pro Gly Thr Gly Gly Pro
         35                  40                  45

Pro Cys Gly Leu
     50


<210> SEQ ID NO 233
<211> LENGTH: 177
<212> TYPE: PRT
<213> ORGANISM: Homo sapiens

<400> SEQUENCE: 233

Met Leu Pro Leu Leu Ile Ile Cys Leu Leu Pro Ala Ile Glu Gly Lys
  1               5                  10                  15

Asn Cys Leu Arg Cys Trp Pro Glu Leu Ser Ala Leu Ile Asp Tyr Asp
             20                  25                  30

Leu Gln Ile Leu Trp Val Thr Pro Gly Pro Pro Thr Glu Leu Ser Gln
         35                  40                  45

Ser Ile His Ser Leu Phe Leu Glu Asp Asn Asn Phe Leu Lys Pro Trp
     50                  55                  60

Tyr Leu Asp Arg Asp His Leu Glu Glu Glu Thr Ala Lys Phe Phe Thr
 65                  70                  75                  80

Gln Val His Gln Ala Ile Lys Thr Leu Arg Asp Asp Lys Thr Val Leu
                 85                  90                  95

Leu Glu Glu Ile Tyr Thr His Lys Asn Leu Phe Thr Glu Arg Leu Asn
            100                 105                 110

Lys Ile Ser Asp Gly Leu Lys Glu Lys Gly Ala Pro Pro Leu His Glu
        115                 120                 125

Cys Leu Pro Gly Ser Ile Ser Tyr Leu His Pro Arg Thr Pro Trp Leu
    130                 135                 140

Cys Leu Pro Pro Gln His Leu Ser Phe Ser Thr Phe Ser Pro Pro Trp
145                 150                 155                 160

Gln Pro Ala Met Ser Pro Val Pro Gly Thr Gly Gly Pro Pro Cys Gly
                165                 170                 175

Leu


<210> SEQ ID NO 234
<211> LENGTH: 95
<212> TYPE: PRT
```

-continued

<213> ORGANISM: Homo sapiens

<400> SEQUENCE: 234

Pro Pro Val Pro Pro Trp Ile Ser Leu Pro Leu Thr Gly Ser Pro Pro
1 5 10 15

Arg Pro Gly Phe Val Pro Val Ser Pro Phe Cys Phe Ser Pro Met Thr
20 25 30

Asn Gly His Gln Val Leu Leu Leu Leu Leu Leu Thr Ser Ala Val Ala
35 40 45

Ala Gly Pro Trp Pro Gln Val His Ala Gly Gln Trp Gly Trp Met Cys
50 55 60

Leu Pro Pro Gly Leu Pro Ser Val Gln Ala Arg Ser Gly Leu Gly Gly
65 70 75 80

Leu Pro Gly Gly Pro Gln Trp Val Pro Gly Gly Ala Arg Gly Tyr
85 90 95

<210> SEQ ID NO 235
<211> LENGTH: 404
<212> TYPE: PRT
<213> ORGANISM: Homo sapiens

<400> SEQUENCE: 235

Ile Gln Gln Trp Gly Asp Ser Val Leu Gly Arg Arg Cys Arg Asp Leu
1 5 10 15

Leu Leu Gln Leu Tyr Leu Gln Arg Pro Glu Leu Arg Val Pro Val Pro
20 25 30

Glu Val Leu Leu His Ser Glu Gly Ala Ala Ser Ser Ser Val Cys Lys
35 40 45

Leu Asp Gly Leu Ile His Arg Phe Ile Thr Leu Leu Ala Asp Thr Ser
50 55 60

Asp Ser Arg Ala Leu Glu Asn Arg Gly Ala Asp Ala Ser Met Ala Cys
65 70 75 80

Arg Lys Leu Ala Val Ala His Pro Leu Leu Leu Leu Arg His Leu Pro
85 90 95

Met Ile Ala Ala Leu Leu His Gly Arg Thr His Leu Asn Phe Gln Glu
100 105 110

Phe Arg Gln Gln Asn His Leu Ser Cys Phe Leu His Val Leu Gly Leu
115 120 125

Leu Glu Leu Leu Gln Pro His Val Phe Arg Ser Glu His Gln Gly Ala
130 135 140

Leu Trp Asp Cys Leu Leu Ser Phe Ile Arg Leu Leu Leu Asn Tyr Arg
145 150 155 160

Lys Ser Ser Arg His Leu Ala Ala Phe Ile Asn Lys Phe Val Gln Phe
165 170 175

Ile His Lys Tyr Ile Thr Tyr Asn Ala Pro Ala Ala Ile Ser Phe Leu
180 185 190

Gln Lys His Ala Asp Pro Leu His Asp Leu Ser Phe Asp Asn Ser Asp
195 200 205

Leu Val Met Leu Lys Ser Leu Leu Ala Gly Leu Ser Leu Pro Ser Arg
210 215 220

Asp Asp Arg Thr Asp Arg Gly Leu Asp Glu Glu Gly Glu Glu Glu Ser
225 230 235 240

Ser Ala Gly Ser Leu Pro Leu Val Ser Val Ser Leu Phe Thr Pro Leu
245 250 255

Thr Ala Ala Glu Met Ala Pro Tyr Met Lys Arg Leu Ser Arg Gly Gln

-continued

```
            260                 265                 270

Thr Val Glu Asp Leu Leu Glu Val Leu Ser Asp Ile Asp Glu Met Ser
        275                 280                 285

Arg Arg Arg Pro Glu Ile Leu Ser Phe Phe Ser Thr Asn Leu Gln Arg
    290                 295                 300

Leu Met Ser Ser Ala Glu Glu Cys Cys Arg Asn Leu Ala Phe Ser Leu
305                 310                 315                 320

Ala Leu Arg Ser Met Gln Asn Ser Pro Ser Ile Ala Ala Ala Phe Leu
                325                 330                 335

Pro Thr Phe Met Tyr Cys Leu Gly Ser Gln Asp Phe Glu Val Val Gln
            340                 345                 350

Thr Ala Leu Arg Asn Leu Pro Glu Tyr Ala Leu Leu Cys Gln Glu His
        355                 360                 365

Ala Ala Val Leu Leu His Arg Ala Phe Leu Val Gly Met Tyr Gly Gln
    370                 375                 380

Met Asp Pro Ser Ala Gln Ile Ser Glu Ala Leu Arg Ile Leu His Met
385                 390                 395                 400

Glu Ala Val Met


<210> SEQ ID NO 236
<211> LENGTH: 361
<212> TYPE: PRT
<213> ORGANISM: Homo sapiens

<400> SEQUENCE: 236

Met Leu Leu Lys His Leu Gln Arg Met Val Ser Val Pro Gln Val Lys
  1               5                  10                  15

Ala Ser Ala Leu Lys Val Val Thr Leu Thr Ala Asn Asp Lys Thr Ser
            20                  25                  30

Val Ser Phe Ser Ser Leu Pro Gly Gln Gly Val Ile Tyr Asn Val Ile
        35                  40                  45

Val Trp Asp Pro Phe Leu Asn Thr Ser Ala Ala Tyr Ile Pro Ala His
     50                  55                  60

Thr Tyr Ala Cys Ser Phe Glu Ala Gly Glu Gly Ser Cys Ala Ser Leu
 65                  70                  75                  80

Gly Arg Val Ser Ser Lys Val Phe Phe Thr Leu Phe Ala Leu Leu Gly
                85                  90                  95

Phe Phe Ile Cys Phe Phe Gly His Arg Phe Trp Lys Thr Glu Leu Phe
            100                 105                 110

Phe Ile Gly Phe Ile Ile Met Gly Phe Phe Phe Tyr Ile Leu Ile Thr
        115                 120                 125

Arg Leu Thr Pro Ile Lys Tyr Asp Val Asn Leu Ile Leu Thr Ala Val
    130                 135                 140

Thr Gly Ser Val Gly Gly Met Phe Leu Val Ala Val Trp Trp Arg Phe
145                 150                 155                 160

Gly Ile Leu Ser Ile Cys Met Leu Cys Val Gly Leu Val Leu Gly Phe
                165                 170                 175

Leu Ile Ser Ser Val Thr Phe Phe Thr Pro Leu Gly Asn Leu Lys Ile
            180                 185                 190

Phe His Asp Asp Gly Val Phe Trp Val Thr Phe Ser Cys Ile Ala Ile
        195                 200                 205

Leu Ile Pro Val Val Phe Met Gly Cys Leu Arg Ile Leu Asn Ile Leu
    210                 215                 220

Thr Cys Gly Val Ile Gly Ser Tyr Ser Val Val Leu Ala Ile Asp Ser
```

-continued

```
225                 230                 235                 240

Tyr Trp Ser Thr Ser Leu Ser Tyr Ile Thr Leu Asn Val Leu Lys Arg
                245                 250                 255

Ala Leu Asn Lys Asp Phe His Arg Ala Phe Thr Asn Val Pro Phe Gln
            260                 265                 270

Thr Asn Asp Phe Ile Ile Leu Ala Val Trp Gly Met Leu Ala Val Ser
        275                 280                 285

Gly Ile Thr Leu Gln Ile Arg Arg Glu Arg Gly Arg Pro Phe Phe Pro
    290                 295                 300

Pro His Pro Tyr Lys Leu Trp Lys Gln Glu Arg Glu Arg Arg Val Thr
305                 310                 315                 320

Asn Ile Leu Asp Pro Ser Tyr His Ile Pro Pro Leu Arg Glu Arg Leu
                325                 330                 335

Tyr Gly Arg Leu Thr Gln Ile Lys Gly Leu Phe Gln Lys Glu Gln Pro
            340                 345                 350

Ala Gly Glu Arg Thr Pro Leu Leu Leu
        355                 360


<210> SEQ ID NO 237
<211> LENGTH: 116
<212> TYPE: PRT
<213> ORGANISM: Homo sapiens
<220> FEATURE:
<221> NAME/KEY: SITE
<222> LOCATION: (37)
<223> OTHER INFORMATION: Xaa equals any of the naturally occurring
      L-amino acids
<220> FEATURE:
<221> NAME/KEY: SITE
<222> LOCATION: (40)
<223> OTHER INFORMATION: Xaa equals any of the naturally occurring
      L-amino acids

<400> SEQUENCE: 237

Trp Ala Arg Leu Arg Gly Pro Gly Ala His Ala Arg Thr Ser Pro Gln
  1               5                  10                  15

Pro Trp Arg Gly Pro Ser Pro Ala Gln Ala Ala Met Gly Phe Leu Gln
             20                  25                  30

Leu Leu Val Val Xaa Val Leu Xaa Ser Glu His Arg Val Ala Gly Ala
         35                  40                  45

Ala Glu Val Phe Gly Asn Ser Ser Glu Gly Leu Ile Glu Phe Ser Val
     50                  55                  60

Gly Lys Phe Arg Tyr Phe Glu Leu Asn Arg Pro Phe Pro Glu Glu Ala
 65                  70                  75                  80

Ile Leu His Asp Ile Ser Ser Asn Val Thr Phe Leu Ile Phe Gln Ile
                 85                  90                  95

His Ser Gln Tyr Gln Asn Thr Thr Val Ser Phe Ser Pro Arg Arg Arg
            100                 105                 110

Ser Pro Thr Met
        115


<210> SEQ ID NO 238
<211> LENGTH: 166
<212> TYPE: PRT
<213> ORGANISM: Homo sapiens

<400> SEQUENCE: 238

Pro Arg Val Arg Pro Ala Ser Pro Pro Val Arg Ser Pro Ala Arg Trp
  1               5                  10                  15
```

-continued

Gly Ser Met Ala Gly Ser Pro Leu Leu Trp Gly Pro Arg Ala Gly Gly
20 25 30

Val Gly Leu Leu Val Leu Leu Leu Leu Gly Leu Phe Arg Pro Pro Pro
35 40 45

Ala Leu Cys Ala Arg Pro Val Lys Glu Pro Arg Gly Leu Ser Ala Ala
50 55 60

Ser Pro Pro Leu Ala Arg Leu Ala Leu Leu Ala Ala Ser Gly Gly Gln
65 70 75 80

Cys Pro Glu Val Arg Arg Arg Gly Arg Cys Arg Pro Gly Ala Gly Ala
85 90 95

Gly Ala Ser Ala Gly Ala Glu Arg Gln Glu Arg Ala Arg Ala Glu Ala
100 105 110

Gln Arg Leu Arg Ile Ser Arg Arg Ala Ser Trp Arg Ser Cys Cys Ala
115 120 125

Ser Gly Ala Pro Pro Ala Thr Leu Ile Arg Leu Trp Ala Trp Thr Thr
130 135 140

Thr Pro Thr Arg Leu Gln Arg Ser Ser Leu Ala Leu Cys Ser Ala Pro
145 150 155 160

Ala Leu Thr Leu Pro Pro
165

<210> SEQ ID NO 239
<211> LENGTH: 414
<212> TYPE: PRT
<213> ORGANISM: Homo sapiens

<400> SEQUENCE: 239

Pro Arg Val Arg Leu Ala Thr Pro Asn Ile Trp Asp Leu Ser Met Leu
1 5 10 15

Phe Ala Phe Ile Ser Leu Leu Val Met Leu Pro Thr Trp Trp Ile Val
20 25 30

Ser Ser Trp Leu Val Trp Gly Val Ile Leu Phe Val Tyr Leu Val Ile
35 40 45

Arg Ala Leu Arg Leu Trp Arg Thr Ala Lys Leu Gln Val Thr Leu Lys
50 55 60

Lys Tyr Ser Val His Leu Glu Asp Met Ala Thr Asn Ser Arg Ala Phe
65 70 75 80

Thr Asn Leu Val Arg Lys Ala Leu Arg Leu Ile Gln Glu Thr Glu Val
85 90 95

Ile Ser Arg Gly Phe Thr Leu Val Ser Ala Ala Cys Pro Phe Asn Lys
100 105 110

Ala Gly Gln His Pro Ser Gln His Leu Ile Gly Leu Arg Lys Ala Val
115 120 125

Tyr Arg Thr Leu Arg Ala Asn Phe Gln Ala Ala Arg Leu Ala Thr Leu
130 135 140

Tyr Met Leu Lys Asn Tyr Pro Leu Asn Ser Glu Ser Asp Asn Val Thr
145 150 155 160

Asn Tyr Ile Cys Val Val Pro Phe Lys Glu Leu Gly Leu Gly Leu Ser
165 170 175

Glu Glu Gln Ile Ser Glu Glu Glu Ala His Asn Phe Thr Asp Gly Phe
180 185 190

Ser Leu Pro Ala Leu Lys Val Leu Phe Gln Leu Trp Val Ala Gln Ser
195 200 205

Ser Glu Phe Phe Arg Arg Leu Ala Leu Leu Leu Ser Thr Ala Asn Ser
210 215 220

-continued

Pro Pro Gly Pro Leu Leu Thr Pro Ala Leu Leu Pro His Arg Ile Leu
225 230 235 240

Ser Asp Val Thr Gln Gly Leu Pro His Ala His Ser Ala Cys Leu Glu
245 250 255

Glu Leu Lys Arg Ser Tyr Glu Phe Tyr Arg Tyr Phe Glu Thr Gln His
260 265 270

Gln Ser Val Pro Gln Cys Leu Ser Lys Thr Gln Gln Lys Ser Arg Glu
275 280 285

Leu Asn Asn Val His Thr Ala Val Arg Ser Leu Gln Leu His Leu Lys
290 295 300

Ala Leu Leu Asn Glu Val Ile Ile Leu Glu Asp Glu Leu Glu Lys Leu
305 310 315 320

Val Cys Thr Lys Glu Thr Gln Glu Leu Val Ser Glu Ala Tyr Pro Ile
325 330 335

Leu Glu Gln Lys Leu Lys Leu Ile Gln Pro His Val Gln Ala Ser Asn
340 345 350

Asn Cys Trp Glu Glu Ala Ile Ser Gln Val Asp Lys Leu Leu Arg Arg
355 360 365

Asn Thr Asp Lys Lys Gly Lys Pro Glu Ile Ala Cys Glu Asn Pro His
370 375 380

Cys Thr Val Ser Thr Phe Glu Ala Ala Tyr Ser Thr His Cys Arg Gln
385 390 395 400

Arg Ser Asn Pro Arg Gly Ala Gly Ile Arg Ser Leu Cys Arg
405 410

<210> SEQ ID NO 240
<211> LENGTH: 145
<212> TYPE: PRT
<213> ORGANISM: Homo sapiens

<400> SEQUENCE: 240

Ala Ala Pro His Pro Pro Leu Leu Arg Pro Leu Cys Leu Trp Cys Pro
1 5 10 15

Leu Trp Pro Ala Trp Pro Leu Arg Gly Arg Pro Arg Ser Ala Trp Lys
20 25 30

Arg Trp Pro Pro Leu Pro Val Gly Pro Ala Lys Leu Gly Cys Ser Met
35 40 45

Thr Thr Arg Gln Pro Thr Ala Val Ser Trp Pro Cys Trp Leu Met Ser
50 55 60

Ser Ser Leu Ser Thr Ala Cys Leu Ala Trp Thr Leu Thr Gly Ser Leu
65 70 75 80

Ala Arg Glu Ala Thr Arg Arg Ala Arg Ser Leu Ser Pro Thr Trp Asn
85 90 95

Cys Ser Ala Arg Gln Val Pro Pro Ser Pro Pro His Ser Gly Leu Gly
100 105 110

Arg Arg Gly Trp Ala His Cys His Leu Thr Cys Leu Leu Val Thr Gln
115 120 125

Leu Phe Arg Val Gly Arg Ile His Pro Ile Leu Ser Leu Pro Leu Val
130 135 140

Thr
145

<210> SEQ ID NO 241
<211> LENGTH: 72
<212> TYPE: PRT

-continued

```
<213> ORGANISM: Homo sapiens

<400> SEQUENCE: 241

Leu Gln Leu Ala Ser Gln Ser Ala Gly Ile Lys Gly Met Ser His Cys
  1               5                  10                  15

Ala Arg Pro Thr Phe Leu Thr Leu Leu Leu Ala Ser Cys Phe Trp Ala
             20                  25                  30

Ala Ala Ile Pro Asn Arg Asn Val Ile Leu Ser Val Ser Phe Arg Pro
         35                  40                  45

Leu His Met Gln Phe Thr Leu Ser Ile Leu Val Phe Ile Leu Arg Ile
     50                  55                  60

Leu Ile Leu Leu Arg Ser Phe Leu
 65                  70


<210> SEQ ID NO 242
<211> LENGTH: 140
<212> TYPE: PRT
<213> ORGANISM: Homo sapiens

<400> SEQUENCE: 242

Met Val Leu Val Leu Arg His Pro Leu Cys Ala Arg Glu Arg Ala Phe
  1               5                  10                  15

Arg Glu Pro Gly Arg Gly Leu Leu Thr Arg Thr Gly Gln His Asp Gly
             20                  25                  30

Ala Pro Ala Val Thr Ala Val Pro Gly Pro Leu Gly Ala Val Ala Ala
         35                  40                  45

Ala Glu Gly Arg Arg Ser Ala Trp Gly Ala Gly Gly Ser Ser Pro Pro
     50                  55                  60

Arg Lys Val Leu Trp Gly Asp Met Arg Gly Arg Arg Ala Gly Val Asp
 65                  70                  75                  80

Val Leu Gly Pro Ala Leu Ser Ser Glu Ala Ala Gly Ala Glu Ala Arg
                 85                  90                  95

Gly Trp Gly Met Pro Gly Met Gly Val Gly Val Gly Ala Ser Glu Thr
            100                 105                 110

Arg Gly Ala Leu Phe Leu Gly Arg Glu Gly Val His Gly Pro Cys Pro
        115                 120                 125

Met Asp Gly Leu Gly Pro Trp Pro Trp Gly Pro Trp
    130                 135                 140


<210> SEQ ID NO 243
<211> LENGTH: 353
<212> TYPE: PRT
<213> ORGANISM: Homo sapiens

<400> SEQUENCE: 243

Met Gly Pro Ala Val Lys Met Trp Thr Asn Ala Trp Lys Gly Leu Asp
  1               5                  10                  15

Asp Cys His Tyr Asn Gln Leu Cys Glu Asn Thr Pro Gly Gly His Arg
             20                  25                  30

Cys Ser Cys Pro Arg Gly Tyr Arg Met Gln Gly Pro Ser Leu Pro Cys
         35                  40                  45

Leu Asp Val Asn Glu Cys Leu Gln Leu Pro Lys Ala Cys Ala Tyr Gln
     50                  55                  60

Cys His Asn Leu Gln Gly Ser Tyr Arg Cys Leu Cys Pro Pro Gly Gln
 65                  70                  75                  80

Thr Leu Leu Arg Asp Gly Lys Ala Cys Thr Ser Leu Glu Arg Asn Gly
                 85                  90                  95
```

-continued

```
Gln Asn Val Thr Thr Val Ser His Arg Gly Pro Leu Leu Pro Trp Leu
            100                 105                 110

Arg Pro Trp Ala Ser Ile Pro Gly Thr Ser Tyr His Ala Trp Val Ser
        115                 120                 125

Leu Arg Pro Gly Pro Met Ala Leu Ser Ser Val Gly Arg Ala Trp Cys
    130                 135                 140

Pro Pro Gly Phe Ile Arg Gln Asn Gly Val Cys Thr Asp Leu Asp Glu
145                 150                 155                 160

Cys Arg Val Arg Asn Leu Cys Gln His Ala Cys Arg Asn Thr Glu Gly
                165                 170                 175

Ser Tyr Gln Cys Leu Cys Pro Ala Gly Tyr Arg Leu Leu Pro Ser Gly
            180                 185                 190

Lys Asn Cys Gln Asp Ile Asn Glu Cys Glu Glu Glu Ser Ile Glu Cys
        195                 200                 205

Gly Pro Gly Gln Met Cys Phe Asn Thr Arg Gly Ser Tyr Gln Cys Val
    210                 215                 220

Asp Thr Pro Cys Pro Ala Thr Tyr Arg Gln Gly Pro Ser Pro Gly Thr
225                 230                 235                 240

Cys Phe Arg Arg Cys Ser Gln Asp Cys Gly Thr Gly Gly Pro Ser Thr
                245                 250                 255

Leu Gln Tyr Arg Leu Leu Pro Leu Pro Leu Gly Val Arg Ala His His
            260                 265                 270

Asp Val Ala Arg Leu Thr Ala Phe Ser Glu Val Gly Val Pro Ala Asn
        275                 280                 285

Arg Thr Glu Leu Ser Met Leu Glu Pro Asp Pro Arg Ser Pro Phe Ala
    290                 295                 300

Leu Arg Pro Leu Arg Ala Gly Leu Gly Ala Val Tyr Thr Arg Arg Ala
305                 310                 315                 320

Leu Thr Arg Ala Gly Leu Tyr Arg Leu Thr Val Arg Ala Ala Ala Pro
                325                 330                 335

Arg His Gln Ser Val Phe Val Leu Leu Ile Ala Val Ser Pro Tyr Pro
            340                 345                 350

Tyr


<210> SEQ ID NO 244
<211> LENGTH: 146
<212> TYPE: PRT
<213> ORGANISM: Homo sapiens

<400> SEQUENCE: 244

Met Arg Val Leu Val Val Thr Ile Ala Pro Ile Tyr Trp Ala Leu Ala
  1               5                  10                  15

Arg Glu Ser Gly Glu Ala Leu Asn Gly His Ser Leu Thr Gly Gly Lys
             20                  25                  30

Phe Arg Gln Ser His Thr Trp Ser Leu Leu Gln Gly Ala Ala His Asp
         35                  40                  45

Asp Pro Val Ala Arg Gly Leu Asp Pro Asp Gly Leu Leu Leu Leu Asp
     50                  55                  60

Val Val Val Asn Gly Val Val Pro Gly Arg Ala Trp Leu Thr Gln Ile
 65                  70                  75                  80

Phe Lys Cys Arg Thr Leu Lys Lys His Tyr Val Gln Thr Arg Ala Trp
                 85                  90                  95

Pro Ala Val Arg Gly Leu His Thr Ala Leu Leu Pro Gly Arg Pro Pro
            100                 105                 110
```

```
Leu Val Pro Thr Leu Gln Pro Gln His Pro Val Gln Arg Gly Pro Gly
        115                 120                 125

Pro Pro Ala Pro Ala Gly Ala Ala Pro Ala Gly Leu Ser Tyr Gln Leu
    130                 135                 140

Gly Leu
145


<210> SEQ ID NO 245
<211> LENGTH: 638
<212> TYPE: PRT
<213> ORGANISM: Homo sapiens

<400> SEQUENCE: 245

His Ala Ser Gly Ala Phe Leu Val Val Arg Gly Glu Pro Gln Gly Ser
  1               5                  10                  15

Trp Gly Ser Met Thr Gly Val Ile Asn Gly Arg Lys Phe Gly Val Ala
             20                  25                  30

Thr Leu Asn Thr Ser Val Met Gln Glu Ala His Ser Gly Val Ser Ser
         35                  40                  45

Ile His Ser Ser Ile Arg His Val Pro Ala Asn Val Gly Pro Leu Met
     50                  55                  60

Arg Val Leu Val Val Thr Ile Ala Pro Ile Tyr Trp Ala Leu Ala Arg
 65                  70                  75                  80

Glu Ser Gly Glu Ala Leu Asn Gly His Ser Leu Thr Gly Gly Lys Phe
                 85                  90                  95

Arg Gln Glu Ser His Val Glu Phe Ala Thr Gly Glu Leu Leu Thr Met
            100                 105                 110

Thr Gln Trp Pro Gly Val Trp Ile Pro Met Ala Ser Cys Ser Ser Thr
        115                 120                 125

Trp Trp Ser Met Ala Leu Ser Pro Asp Ser Leu Ala Asp Ala Asp Leu
    130                 135                 140

Gln Val Gln Asp Phe Glu Glu His Tyr Val Gln Thr Gly Pro Gly Gln
145                 150                 155                 160

Leu Phe Val Gly Ser Thr Gln Arg Phe Phe Gln Gly Gly Leu Pro Ser
                165                 170                 175

Phe Leu Arg Cys Asn His Ser Ile Gln Tyr Asn Ala Ala Arg Gly Pro
            180                 185                 190

Gln Pro Gln Leu Val Gln His Leu Arg Ala Ser Ala Ile Ser Ser Ala
        195                 200                 205

Phe Asp Pro Glu Ala Glu Ala Leu Arg Phe Gln Leu Ala Thr Ala Leu
    210                 215                 220

Gln Ala Glu Glu Asn Glu Val Gly Cys Pro Glu Gly Phe Glu Leu Asp
225                 230                 235                 240

Ser Gln Gly Ala Phe Cys Val Asp Val Asp Glu Cys Ala Trp Asp Ala
                245                 250                 255

His Leu Cys Arg Glu Gly Gln Arg Cys Val Asn Leu Leu Gly Ser Tyr
            260                 265                 270

Arg Cys Leu Pro Asp Cys Gly Pro Gly Phe Arg Val Ala Asp Gly Ala
        275                 280                 285

Gly Cys Glu Asp Val Asp Glu Cys Leu Glu Gly Leu Asp Asp Cys His
    290                 295                 300

Tyr Asn Gln Leu Cys Glu Asn Thr Pro Gly Gly His Arg Cys Ser Cys
305                 310                 315                 320

Pro Arg Gly Tyr Arg Met Gln Gly Pro Ser Leu Pro Cys Leu Asp Val
```

-continued

```
                325                 330                 335

Asn Glu Cys Leu Gln Leu Pro Lys Ala Cys Ala Tyr Gln Cys His Asn
            340                 345                 350

Leu Gln Gly Ser Tyr Arg Cys Leu Cys Pro Pro Gly Gln Thr Leu Leu
        355                 360                 365

Arg Asp Gly Lys Ala Cys Thr Ser Leu Glu Arg Asn Gly Gln Asn Val
    370                 375                 380

Thr Thr Val Ser His Arg Gly Pro Leu Leu Pro Trp Leu Arg Pro Trp
385                 390                 395                 400

Ala Ser Ile Pro Gly Thr Ser Tyr His Ala Trp Val Ser Leu Arg Pro
                405                 410                 415

Gly Pro Met Ala Leu Ser Ser Val Gly Arg Ala Trp Cys Pro Pro Gly
            420                 425                 430

Phe Ile Arg Gln Asn Gly Val Cys Thr Asp Leu Asp Glu Cys Arg Val
        435                 440                 445

Arg Asn Leu Cys Gln His Ala Cys Arg Asn Thr Glu Gly Ser Tyr Gln
    450                 455                 460

Cys Leu Cys Pro Ala Gly Tyr Arg Leu Leu Pro Ser Gly Lys Asn Cys
465                 470                 475                 480

Gln Asp Ile Asn Glu Cys Glu Glu Glu Ser Ile Glu Cys Gly Pro Gly
                485                 490                 495

Gln Met Cys Phe Asn Thr Arg Gly Ser Tyr Gln Cys Val Asp Thr Pro
            500                 505                 510

Cys Pro Ala Thr Tyr Arg Gln Gly Pro Ser Pro Gly Thr Cys Phe Arg
        515                 520                 525

Arg Cys Ser Gln Asp Cys Gly Thr Gly Gly Pro Ser Thr Leu Gln Tyr
    530                 535                 540

Arg Leu Leu Pro Leu Pro Leu Gly Val Arg Ala His His Asp Val Ala
545                 550                 555                 560

Arg Leu Thr Ala Phe Ser Glu Val Gly Val Pro Ala Asn Arg Thr Glu
                565                 570                 575

Leu Ser Met Leu Glu Pro Asp Pro Arg Ser Pro Phe Ala Leu Arg Pro
            580                 585                 590

Leu Arg Ala Gly Leu Gly Ala Val Tyr Thr Arg Arg Ala Leu Thr Arg
        595                 600                 605

Ala Gly Leu Tyr Arg Leu Thr Val Arg Ala Ala Ala Pro Arg His Gln
    610                 615                 620

Ser Val Phe Val Leu Leu Ile Ala Val Ser Pro Tyr Pro Tyr
625                 630                 635


<210> SEQ ID NO 246
<211> LENGTH: 367
<212> TYPE: PRT
<213> ORGANISM: Homo sapiens

<400> SEQUENCE: 246

Met Gly Glu Lys Phe Leu Leu Leu Ala Met Lys Glu Asn His Pro Glu
  1               5                  10                  15

Cys Phe Cys Lys Ile Leu Lys Ile Leu His Cys Met Asp Pro Gly Glu
             20                  25                  30

Trp Leu Pro Gln Thr Glu His Cys Val His Leu Thr Pro Lys Glu Phe
         35                  40                  45

Leu Ile Trp Thr Met Asp Ile Ala Ser Asn Glu Arg Ser Glu Ile Gln
     50                  55                  60
```

-continued

Ser Val Ala Leu Arg Leu Ala Ser Lys Val Ile Ser His His Met Gln
65 70 75 80

Thr Cys Val Glu Asn Arg Glu Leu Ile Ala Ala Glu Leu Lys Gln Trp
85 90 95

Val Gln Leu Val Ile Leu Ser Cys Glu Asp His Leu Pro Thr Glu Ser
100 105 110

Arg Leu Ala Val Val Glu Val Leu Thr Ser Thr Thr Pro Leu Phe Leu
115 120 125

Thr Asn Pro His Pro Ile Leu Glu Leu Gln Asp Thr Leu Ala Leu Trp
130 135 140

Lys Cys Val Leu Thr Leu Leu Gln Ser Glu Glu Gln Ala Val Arg Asp
145 150 155 160

Ala Ala Thr Glu Thr Val Thr Thr Ala Met Ser Gln Glu Asn Thr Cys
165 170 175

Gln Ser Thr Glu Phe Ala Phe Cys Gln Val Asp Ala Ser Ile Ala Leu
180 185 190

Ala Leu Ala Leu Ala Val Leu Cys Asp Leu Leu Gln Gln Trp Asp Gln
195 200 205

Leu Ala Pro Gly Leu Pro Ile Leu Leu Gly Trp Leu Leu Gly Glu Ser
210 215 220

Asp Asp Leu Val Ala Cys Val Glu Ser Met His Gln Val Glu Glu Asp
225 230 235 240

Tyr Leu Phe Glu Lys Ala Glu Val Asn Phe Trp Ala Glu Thr Leu Ile
245 250 255

Phe Val Lys Tyr Leu Cys Lys His Leu Phe Cys Leu Leu Ser Lys Ser
260 265 270

Gly Trp Arg Pro Pro Ser Pro Glu Met Leu Cys His Leu Gln Arg Met
275 280 285

Val Ser Glu Gln Cys His Leu Leu Ser Gln Phe Phe Arg Glu Leu Pro
290 295 300

Pro Ala Ala Glu Phe Val Lys Thr Val Glu Phe Thr Arg Leu Arg Ile
305 310 315 320

Gln Glu Glu Arg Thr Leu Ala Cys Leu Arg Leu Leu Ala Phe Leu Glu
325 330 335

Gly Lys Glu Gly Glu Asp Thr Leu Val Leu Ser Val Trp Asp Ser Tyr
340 345 350

Ala Glu Ser Arg Gln Leu Thr Leu Pro Arg Thr Glu Ala Ala Cys
355 360 365

<210> SEQ ID NO 247
<211> LENGTH: 124
<212> TYPE: PRT
<213> ORGANISM: Homo sapiens

<400> SEQUENCE: 247

Met Gly Glu Pro Asn Arg His Pro Ser Met Phe Leu Leu Leu Leu Val
1 5 10 15

Leu Glu Arg Leu Tyr Ala Ser Pro Met Asp Gly Thr Ser Ser Ala Leu
20 25 30

Ser Met Gly Pro Phe Val Pro Phe Ile Met Arg Cys Gly His Ser Pro
35 40 45

Val Tyr His Ser Arg Glu Met Ala Ala Arg Ala Leu Val Pro Phe Val
50 55 60

Met Ile Asp His Ile Pro Asn Thr Ile Arg Thr Leu Leu Ser Thr Leu
65 70 75 80

-continued

Pro Ser Cys Thr Asp Gln Cys Phe Arg Ala Lys Pro His Ser Trp Gly
                85                  90                  95

His Phe Ser Arg Phe Phe His Leu Leu Gln Ala Tyr Ser Asp Ser Lys
            100                 105                 110

Thr Arg Asn Glu Phe Arg Leu Pro Ala Arg Ala Asp
        115                 120

<210> SEQ ID NO 248
<211> LENGTH: 674
<212> TYPE: PRT
<213> ORGANISM: Homo sapiens

<400> SEQUENCE: 248

Met Thr Gly Arg Glu Phe Phe Ser Arg Phe Pro Glu Leu Tyr Pro Phe
  1               5                  10                  15

Leu Leu Lys Gln Leu Glu Thr Val Ala Asn Thr Val Asp Ser Asp Met
             20                  25                  30

Gly Glu Pro Asn Arg His Pro Ser Met Phe Leu Leu Leu Leu Val Leu
         35                  40                  45

Glu Arg Leu Tyr Ala Ser Pro Met Asp Gly Thr Ser Ser Ala Leu Ser
     50                  55                  60

Met Gly Pro Phe Val Pro Phe Ile Met Arg Cys Gly His Ser Pro Val
 65                  70                  75                  80

Tyr His Ser Arg Glu Met Ala Ala Arg Ala Leu Val Pro Phe Val Met
                85                  90                  95

Ile Asp His Ile Pro Asn Thr Ile Arg Thr Leu Leu Ser Thr Leu Pro
            100                 105                 110

Ser Cys Thr Asp Gln Cys Phe Arg Gln Asn His Ile His Gly Thr Leu
        115                 120                 125

Leu Gln Val Phe His Leu Leu Gln Ala Tyr Ser Asp Ser Lys His Gly
    130                 135                 140

Thr Asn Ser Asp Phe Gln His Glu Leu Thr Asp Ile Thr Val Cys Thr
145                 150                 155                 160

Lys Ala Lys Leu Trp Leu Ala Lys Arg Gln Asn Pro Cys Leu Val Thr
                165                 170                 175

Arg Ala Val Tyr Ile Asp Ile Leu Phe Leu Leu Thr Cys Cys Leu Asn
            180                 185                 190

Arg Ser Ala Lys Asp Asn Gln Pro Val Leu Glu Ser Leu Gly Phe Trp
        195                 200                 205

Glu Glu Val Arg Gly Ile Ile Ser Gly Ser Glu Leu Ile Thr Gly Phe
    210                 215                 220

Pro Trp Ala Phe Lys Val Pro Gly Leu Pro Gln Tyr Leu Gln Ser Leu
225                 230                 235                 240

Thr Arg Leu Ala Ile Ala Ala Val Trp Ala Ala Ala Ala Lys Ser Gly
                245                 250                 255

Glu Arg Glu Thr Asn Val Pro Ile Ser Phe Ser Gln Leu Leu Glu Ser
            260                 265                 270

Ala Phe Pro Glu Val Arg Ser Leu Thr Leu Glu Ala Leu Leu Glu Lys
        275                 280                 285

Phe Leu Ala Ala Ala Ser Gly Leu Gly Glu Lys Gly Val Pro Pro Leu
    290                 295                 300

Leu Cys Asn Met Gly Glu Lys Phe Leu Leu Leu Ala Met Lys Glu Asn
305                 310                 315                 320

His Pro Glu Cys Phe Cys Lys Ile Leu Lys Ile Leu His Cys Met Asp

-continued

```
                325                 330                 335

Pro Gly Glu Trp Leu Pro Gln Thr Glu His Cys Val His Leu Thr Pro
            340                 345                 350

Lys Glu Phe Leu Ile Trp Thr Met Asp Ile Ala Ser Asn Glu Arg Ser
        355                 360                 365

Glu Ile Gln Ser Val Ala Leu Arg Leu Ala Ser Lys Val Ile Ser His
    370                 375                 380

His Met Gln Thr Cys Val Glu Asn Arg Glu Leu Ile Ala Ala Glu Leu
385                 390                 395                 400

Lys Gln Trp Val Gln Leu Val Ile Leu Ser Cys Glu Asp His Leu Pro
                405                 410                 415

Thr Glu Ser Arg Leu Ala Val Val Glu Val Leu Thr Ser Thr Thr Pro
            420                 425                 430

Leu Phe Leu Thr Asn Pro His Pro Ile Leu Glu Leu Gln Asp Thr Leu
        435                 440                 445

Ala Leu Trp Lys Cys Val Leu Thr Leu Leu Gln Ser Glu Glu Gln Ala
    450                 455                 460

Val Arg Asp Ala Ala Thr Glu Thr Val Thr Thr Ala Met Ser Gln Glu
465                 470                 475                 480

Asn Thr Cys Gln Ser Thr Glu Phe Ala Phe Cys Gln Val Asp Ala Ser
                485                 490                 495

Ile Ala Leu Ala Leu Ala Leu Ala Val Leu Cys Asp Leu Leu Gln Gln
            500                 505                 510

Trp Asp Gln Leu Ala Pro Gly Leu Pro Ile Leu Leu Gly Trp Leu Leu
        515                 520                 525

Gly Glu Ser Asp Asp Leu Val Ala Cys Val Glu Ser Met His Gln Val
    530                 535                 540

Glu Glu Asp Tyr Leu Phe Glu Lys Ala Glu Val Asn Phe Trp Ala Glu
545                 550                 555                 560

Thr Leu Ile Phe Val Lys Tyr Leu Cys Lys His Leu Phe Cys Leu Leu
                565                 570                 575

Ser Lys Ser Gly Trp Arg Pro Pro Ser Pro Glu Met Leu Cys His Leu
            580                 585                 590

Gln Arg Met Val Ser Glu Gln Cys His Leu Leu Ser Gln Phe Phe Arg
        595                 600                 605

Glu Leu Pro Pro Ala Ala Glu Phe Val Lys Thr Val Glu Phe Thr Arg
    610                 615                 620

Leu Arg Ile Gln Glu Glu Arg Thr Leu Ala Cys Leu Arg Leu Leu Ala
625                 630                 635                 640

Phe Leu Glu Gly Lys Glu Gly Glu Asp Thr Leu Val Leu Ser Val Trp
                645                 650                 655

Asp Ser Tyr Ala Glu Ser Arg Gln Leu Thr Leu Pro Arg Thr Glu Ala
            660                 665                 670

Ala Cys


<210> SEQ ID NO 249
<211> LENGTH: 10
<212> TYPE: PRT
<213> ORGANISM: Homo sapiens

<400> SEQUENCE: 249

Ile Ile Ser Gly Ser Glu Leu Ile Thr Gly
  1               5                  10
```

-continued

<210> SEQ ID NO 250
<211> LENGTH: 230
<212> TYPE: PRT
<213> ORGANISM: Homo sapiens

<400> SEQUENCE: 250

Val Asp Gly Ile Asp Lys Leu Asp Ile Glu Phe Leu Gln Gln Phe Leu
1 5 10 15

Glu Thr His Ser Arg Gly Pro Arg Leu His Ser Pro Gly His Ala Ser
20 25 30

Gln Glu Ala Thr Pro Gly Ala Asn Met Ser Ser Gly Thr Glu Leu Leu
35 40 45

Trp Pro Gly Ala Ala Leu Leu Val Leu Leu Gly Val Ala Ala Ser Leu
50 55 60

Cys Val Arg Cys Ser Arg Pro Gly Ala Lys Arg Ser Glu Lys Ile Tyr
65 70 75 80

Gln Gln Arg Ser Leu Arg Glu Asp Gln Gln Ser Phe Thr Gly Ser Arg
85 90 95

Thr Tyr Ser Leu Val Gly Gln Ala Trp Pro Gly Pro Leu Ala Asp Met
100 105 110

Ala Pro Thr Arg Lys Asp Lys Leu Leu Gln Phe Tyr Pro Ser Leu Glu
115 120 125

Asp Pro Ala Ser Ser Arg Tyr Gln Asn Phe Ser Lys Gly Ser Arg His
130 135 140

Gly Ser Glu Glu Ala Tyr Ile Asp Pro Ile Ala Met Glu Tyr Tyr Asn
145 150 155 160

Trp Gly Arg Phe Ser Lys Pro Pro Glu Asp Asp Asp Ala Asn Ser Tyr
165 170 175

Glu Asn Val Leu Ile Cys Lys Gln Lys Thr Thr Glu Thr Gly Ala Gln
180 185 190

Gln Glu Gly Ile Gly Gly Leu Cys Arg Gly Asp Leu Ser Leu Ser Leu
195 200 205

Ala Leu Lys Thr Gly Pro Thr Ser Gly Leu Cys Pro Ser Ala Ser Pro
210 215 220

Glu Glu Asp Glu Gly Ile
225 230

<210> SEQ ID NO 251
<211> LENGTH: 25
<212> TYPE: PRT
<213> ORGANISM: Homo sapiens

<400> SEQUENCE: 251

Ala Ser Ser Arg Tyr Gln Asn Phe Ser Lys Gly Ser Arg His Gly Ser
1 5 10 15

Glu Glu Ala Tyr Ile Asp Pro Ile Ala
20 25

<210> SEQ ID NO 252
<211> LENGTH: 21
<212> TYPE: PRT
<213> ORGANISM: Homo sapiens

<400> SEQUENCE: 252

Met Glu Tyr Tyr Asn Trp Gly Arg Phe Ser Lys Pro Pro Glu Asp Asp
1 5 10 15

Asp Ala Asn Ser Tyr
20

-continued

<210> SEQ ID NO 253
<211> LENGTH: 27
<212> TYPE: PRT
<213> ORGANISM: Homo sapiens

<400> SEQUENCE: 253

```
Glu Asn Val Leu Ile Cys Lys Gln Lys Thr Thr Glu Thr Gly Ala Gln
  1               5                  10                  15

Gln Glu Gly Ile Gly Gly Leu Cys Arg Gly Asp
             20                  25
```

<210> SEQ ID NO 254
<211> LENGTH: 27
<212> TYPE: PRT
<213> ORGANISM: Homo sapiens

<400> SEQUENCE: 254

```
Leu Ser Leu Ser Leu Ala Leu Lys Thr Gly Pro Thr Ser Gly Leu Cys
  1               5                  10                  15

Pro Ser Ala Ser Pro Glu Glu Asp Glu Gly Ile
             20                  25
```

<210> SEQ ID NO 255
<211> LENGTH: 68
<212> TYPE: PRT
<213> ORGANISM: Homo sapiens

<400> SEQUENCE: 255

```
Val Arg Cys Ser Arg Pro Gly Ala Lys Arg Ser Glu Lys Ile Tyr Gln
  1               5                  10                  15

Gln Arg Ser Leu Arg Glu Asp Gln Gln Ser Phe Thr Gly Ser Arg Thr
             20                  25                  30

Tyr Ser Leu Val Gly Gln Ala Trp Pro Gly Pro Leu Ala Asp Met Ala
         35                  40                  45

Pro Thr Arg Lys Asp Lys Leu Leu Gln Phe Tyr Pro Ser Leu Glu Asp
     50                  55                  60

Pro Ala Ser Ser
 65
```

<210> SEQ ID NO 256
<211> LENGTH: 122
<212> TYPE: PRT
<213> ORGANISM: Homo sapiens

<400> SEQUENCE: 256

```
Val Leu Trp Arg Glu Ala Ser Ala Leu Val Leu Ser Asn Arg Leu Ser
  1               5                  10                  15

Ser Gly Leu Leu His Asp Leu Leu Leu Gln Pro Ala Ile His Ser Arg
             20                  25                  30

Leu Phe Pro Arg Arg Ser Arg Gly Leu Ser Glu Gly Glu Gly Ser Ser
         35                  40                  45

Val Ser Leu Gln Arg Ser Arg Val Leu Ser Ala Met Lys His Val Leu
     50                  55                  60

Asn Leu Tyr Leu Leu Gly Val Val Leu Thr Leu Leu Ser Ile Phe Val
 65                  70                  75                  80

Arg Val Met Glu Ser Leu Glu Gly Leu Leu Glu Ser Pro Ser Pro Gly
                 85                  90                  95

Thr Ser Trp Thr Thr Arg Ser Gln Leu Ala Asn Thr Glu Pro Thr Lys
```

-continued

```
            100                 105                 110

Gly Leu Pro Asp His Pro Ser Arg Ser Met
        115                 120


<210> SEQ ID NO 257
<211> LENGTH: 129
<212> TYPE: PRT
<213> ORGANISM: Homo sapiens

<400> SEQUENCE: 257

Tyr Thr Phe His Thr Gln Ile Phe Leu Asp Phe Pro Met Ile Phe Leu
  1               5                  10                  15

Thr Val Leu Pro Leu Ala Phe Leu Phe Leu His Ser Gly Phe Tyr His
            20                  25                  30

Tyr Ile Ser Phe Ser Cys Leu Phe Ser Leu Ser Leu Ala Leu Phe Phe
        35                  40                  45

Phe Leu Asp Val Ala Thr Phe Arg Arg Pro Gly Gln Leu Phe Cys Glu
     50                  55                  60

Arg Ser Val Leu Phe Asp Met Phe His Phe Gly Phe Val Ser Leu Phe
 65                  70                  75                  80

Leu His Glu Trp Ile Gln Ala Lys His Phe Trp Ala Gly Leu Phe Ile
                 85                  90                  95

Val Leu Pro Ser Asp Val Phe Phe Ser Val His His Leu Glu Ala Pro
            100                 105                 110

Asp Gly Ser Phe Pro Asn Ile Ala Lys Leu Ser Leu Ile Ile Leu Leu
        115                 120                 125

Arg


<210> SEQ ID NO 258
<211> LENGTH: 99
<212> TYPE: PRT
<213> ORGANISM: Homo sapiens

<400> SEQUENCE: 258

Gly Thr Arg Phe Pro Thr Gly Glu Thr Pro Ser Leu Gly Phe Thr Val
  1               5                  10                  15

Thr Leu Val Leu Leu Asn Ser Leu Ala Phe Leu Leu Met Ala Val Ile
            20                  25                  30

Tyr Thr Lys Leu Tyr Cys Asn Leu Glu Lys Glu Asp Leu Ser Glu Asn
        35                  40                  45

Ser Gln Ser Ser Met Ile Lys His Val Ala Trp Leu Ile Phe Thr Asn
     50                  55                  60

Cys Ile Phe Phe Cys Pro Val Ala Phe Phe Ser Phe Ala Pro Leu Ile
 65                  70                  75                  80

Thr Ala Ile Ser Ile Ser Pro Glu Ile Met Lys Ser Val Thr Leu Ile
                 85                  90                  95

Phe Phe Pro


<210> SEQ ID NO 259
<211> LENGTH: 51
<212> TYPE: PRT
<213> ORGANISM: Homo sapiens

<400> SEQUENCE: 259

Met Ile Lys His Val Ala Trp Leu Ile Phe Thr Asn Cys Ile Phe Phe
  1               5                  10                  15

Cys Pro Val Ala Phe Phe Ser Phe Ala Pro Leu Ile Thr Ala Ile Ser
```

-continued

```
            20                  25                  30

Ile Ser Pro Glu Ile Met Lys Ser Val Thr Leu Ile Phe Phe Pro Cys
        35                  40                  45

Leu Leu Ala
    50


<210> SEQ ID NO 260
<211> LENGTH: 259
<212> TYPE: PRT
<213> ORGANISM: Homo sapiens

<400> SEQUENCE: 260

Gly Thr Arg Phe Pro Thr Gly Glu Thr Pro Ser Leu Gly Phe Thr Val
  1               5                  10                  15

Thr Leu Val Leu Leu Asn Ser Leu Ala Phe Leu Leu Met Ala Val Ile
            20                  25                  30

Tyr Thr Lys Leu Tyr Cys Asn Leu Glu Lys Glu Asp Leu Ser Glu Asn
        35                  40                  45

Ser Gln Ser Ser Met Ile Lys His Val Ala Trp Leu Ile Phe Thr Asn
    50                  55                  60

Cys Ile Phe Phe Cys Pro Val Ala Phe Phe Ser Phe Ala Pro Leu Ile
 65                  70                  75                  80

Thr Ala Ile Ser Ile Ser Pro Glu Ile Met Lys Ser Val Thr Leu Ile
                 85                  90                  95

Phe Phe Pro Leu Pro Ala Cys Leu Asn Pro Val Leu Tyr Val Phe Phe
            100                 105                 110

Asn Pro Lys Phe Lys Glu Asp Trp Lys Leu Leu Lys Arg Arg Val Thr
        115                 120                 125

Lys Lys Ser Gly Ser Val Ser Val Ser Ile Ser Ser Gln Gly Gly Cys
    130                 135                 140

Leu Glu Gln Asp Phe Tyr Tyr Asp Cys Gly Met Tyr Ser His Leu Gln
145                 150                 155                 160

Gly Asn Leu Thr Val Cys Asp Cys Cys Glu Ser Phe Leu Leu Thr Lys
                165                 170                 175

Pro Val Ser Cys Lys His Leu Ile Lys Ser His Ser Cys Pro Ala Leu
            180                 185                 190

Ala Val Ala Ser Cys Gln Arg Pro Glu Gly Tyr Trp Ser Asp Cys Gly
        195                 200                 205

Thr Gln Ser Ala His Ser Asp Tyr Ala Asp Glu Glu Asp Ser Phe Val
    210                 215                 220

Ser Asp Ser Ser Asp Gln Val Gln Ala Cys Gly Arg Ala Cys Phe Tyr
225                 230                 235                 240

Gln Ser Arg Gly Phe Pro Leu Val Arg Tyr Ala Tyr Asn Leu Pro Arg
                245                 250                 255

Val Lys Asp


<210> SEQ ID NO 261
<211> LENGTH: 22
<212> TYPE: PRT
<213> ORGANISM: Homo sapiens

<400> SEQUENCE: 261

Cys Asp Cys Cys Glu Ser Phe Leu Leu Thr Lys Pro Val Ser Cys Lys
  1               5                  10                  15

His Leu Ile Lys Ser His
            20
```

-continued

<210> SEQ ID NO 262
<211> LENGTH: 81
<212> TYPE: PRT
<213> ORGANISM: Homo sapiens
<220> FEATURE:
<221> NAME/KEY: SITE
<222> LOCATION: (20)
<223> OTHER INFORMATION: Xaa equals any of the naturally occurring
      L-amino acids

<400> SEQUENCE: 262

```
Ala Leu Glu Asn Ser Gly Ser Pro Gly Leu Gln Asp Ser Ala Arg Ala
  1               5                  10                  15

His Phe Asn Xaa Ser Leu Arg Ser Phe Ser Phe Leu Arg Asn Gln Met
             20                  25                  30

Tyr Ile Phe Glu Leu Ser Leu Tyr Leu Glu Gly Thr Ser Phe Val Val
         35                  40                  45

Val Leu Leu Phe Leu Leu Ile Ser Val Ser Leu Asp Ser Pro Pro Thr
     50                  55                  60

Thr Lys Gly Trp Asp Ser Val Leu His Ile Trp Val Pro Leu Ile Val
 65                  70                  75                  80

Gln
```

<210> SEQ ID NO 263
<211> LENGTH: 77
<212> TYPE: PRT
<213> ORGANISM: Homo sapiens

<400> SEQUENCE: 263

```
Gly His Glu Ser Ile Cys Gly Ser Cys Arg Ser Trp Ile Tyr Phe Ser
  1               5                  10                  15

Ile Arg Cys Arg Arg Arg Met Arg Pro Trp Trp Ser Leu Leu Leu Glu
             20                  25                  30

Ala Cys Ala Thr Cys Ala Gln Thr Gly Pro Thr Arg Ser Thr Ser Cys
         35                  40                  45

Thr Gln Glu Val Ser His Ser Ser Ser Thr Ala Tyr Pro Ala Pro Met
     50                  55                  60

Arg Arg Arg Cys Cys Leu Pro Ser Pro Arg Ser Cys Thr
 65                  70                  75
```

<210> SEQ ID NO 264
<211> LENGTH: 119
<212> TYPE: PRT
<213> ORGANISM: Homo sapiens

<400> SEQUENCE: 264

```
Lys Arg Ala Gly Val Glu Val Gly Gly Leu Val Met Ala Leu Ala Gly
  1               5                  10                  15

Ser Val Phe Val Leu Gly Gly Val Leu Val Leu Cys Val Glu Arg Asn
             20                  25                  30

Gly Glu Gly Glu Met Gly Trp Pro Gln His Leu Pro Lys Ser Gln Pro
         35                  40                  45

Leu Ser Pro Pro Val Ala Val Arg Arg Cys Ser Phe Glu Arg Ser Trp
     50                  55                  60

Ile Asp Leu Leu Val Glu Thr Ser Ser Ser Met Val Thr Cys Arg Gln
 65                  70                  75                  80

Gln Val Gly Thr Pro Asn Gly Met Glu Gly Arg Gly Gly Gly Pro Lys
                 85                  90                  95
```

-continued

```
Thr Thr Phe Pro Ile Arg Leu Gln Leu Ser Gly Ala Cys Ala Val Arg
            100                 105                 110

Pro Glu Ile Gln Trp Glu Val
        115


<210> SEQ ID NO 265
<211> LENGTH: 275
<212> TYPE: PRT
<213> ORGANISM: Homo sapiens
<220> FEATURE:
<221> NAME/KEY: SITE
<222> LOCATION: (47)
<223> OTHER INFORMATION: Xaa equals any of the naturally occurring
      L-amino acids
<220> FEATURE:
<221> NAME/KEY: SITE
<222> LOCATION: (94)
<223> OTHER INFORMATION: Xaa equals any of the naturally occurring
      L-amino acids
<220> FEATURE:
<221> NAME/KEY: SITE
<222> LOCATION: (192)
<223> OTHER INFORMATION: Xaa equals any of the naturally occurring
      L-amino acids

<400> SEQUENCE: 265

Gln Asp Trp Lys Ala Glu Arg Ser Gln Asp Pro Phe Glu Lys Cys Met
  1               5                  10                  15

Gln Asp Pro Asp Tyr Glu Gln Leu Leu Lys Val Thr Ile Leu Glu Ala
             20                  25                  30

Asp Asn Arg Ile Gly Gly Arg Ile Phe Thr Tyr Arg Asp Gln Xaa Thr
         35                  40                  45

Gly Trp Ile Gly Glu Leu Gly Ala Met Arg Met Pro Ser Ser His Arg
     50                  55                  60

Ile Leu His Lys Leu Cys Gln Gly Leu Gly Leu Asn Leu Thr Lys Phe
 65                  70                  75                  80

Thr Gln Tyr Asp Lys Asn Thr Trp Thr Glu Val His Glu Xaa Lys Leu
                 85                  90                  95

Arg Asn Tyr Val Val Glu Lys Val Pro Glu Lys Leu Gly Tyr Ala Leu
            100                 105                 110

Arg Pro Gln Glu Lys Gly His Ser Pro Glu Asp Ile Tyr Gln Met Ala
        115                 120                 125

Leu Asn Gln Ala Leu Lys Asp Leu Lys Ala Leu Gly Cys Arg Lys Ala
    130                 135                 140

Met Lys Lys Phe Glu Arg His Thr Leu Leu Glu Tyr Leu Leu Gly Glu
145                 150                 155                 160

Gly Asn Leu Ser Arg Pro Ala Val Gln Leu Leu Gly Asp Val Met Ser
                165                 170                 175

Glu Asp Gly Phe Phe Tyr Leu Ser Phe Ala Glu Ala Leu Arg Ala Xaa
            180                 185                 190

Ser Cys Leu Ser Asp Arg Leu Gln Tyr Ser Arg Ile Val Gly Gly Trp
        195                 200                 205

Asp Leu Leu Pro Arg Ala Leu Leu Ser Ser Leu Ser Gly Leu Val Leu
    210                 215                 220

Leu Asn Ala Pro Val Val Ala Met Thr Gln Gly Pro His Asp Val His
225                 230                 235                 240

Val Gln Ile Glu Thr Ser Pro Pro Ala Arg Asn Leu Lys Val Leu Lys
                245                 250                 255

Ala Asp Val Val Leu Leu Thr Ala Ser Gly Pro Ala Val Lys Arg Ile
```

-continued

```
            260                 265                 270

Thr Phe Ser
        275


<210> SEQ ID NO 266
<211> LENGTH: 212
<212> TYPE: PRT
<213> ORGANISM: Homo sapiens
<220> FEATURE:
<221> NAME/KEY: SITE
<222> LOCATION: (123)
<223> OTHER INFORMATION: Xaa equals any of the naturally occurring
      L-amino acids

<400> SEQUENCE: 266

Leu Pro Arg His Met Gln Glu Ala Leu Arg Arg Leu His Tyr Val Pro
  1               5                  10                  15

Ala Thr Lys Val Phe Leu Ser Phe Arg Arg Pro Phe Trp Arg Glu Glu
             20                  25                  30

His Ile Glu Gly Gly His Ser Asn Thr Asp Arg Pro Ser Arg Met Ile
         35                  40                  45

Phe Tyr Pro Pro Pro Arg Glu Gly Ala Leu Leu Leu Ala Ser Tyr Thr
     50                  55                  60

Trp Ser Asp Ala Ala Ala Ala Phe Ala Gly Leu Ser Arg Glu Glu Ala
 65                  70                  75                  80

Leu Arg Leu Ala Leu Asp Asp Val Ala Ala Leu His Gly Pro Val Val
                 85                  90                  95

Arg Gln Leu Trp Asp Gly Thr Gly Val Val Lys Arg Trp Ala Glu Asp
            100                 105                 110

Gln His Ser Gln Gly Gly Phe Val Val Gln Xaa Pro Ala Leu Trp Gln
        115                 120                 125

Thr Glu Lys Asp Asp Trp Thr Val Pro Tyr Gly Arg Ile Tyr Phe Ala
    130                 135                 140

Gly Glu His Thr Ala Tyr Pro His Gly Trp Val Glu Thr Ala Val Lys
145                 150                 155                 160

Ser Ala Leu Arg Ala Ala Ile Lys Ile Asn Ser Arg Lys Gly Pro Ala
                165                 170                 175

Ser Asp Thr Ala Ser Pro Glu Gly His Ala Ser Asp Met Glu Gly Gln
            180                 185                 190

Gly His Val His Gly Val Ala Ser Ser Pro Ser His Asp Leu Ala Lys
        195                 200                 205

Glu Glu Gly Ser
    210


<210> SEQ ID NO 267
<211> LENGTH: 319
<212> TYPE: PRT
<213> ORGANISM: Homo sapiens
<220> FEATURE:
<221> NAME/KEY: SITE
<222> LOCATION: (68)
<223> OTHER INFORMATION: Xaa equals any of the naturally occurring
      L-amino acids
<220> FEATURE:
<221> NAME/KEY: SITE
<222> LOCATION: (115)
<223> OTHER INFORMATION: Xaa equals any of the naturally occurring
      L-amino acids
<220> FEATURE:
<221> NAME/KEY: SITE
<222> LOCATION: (213)
<223> OTHER INFORMATION: Xaa equals any of the naturally occurring
```

-continued

```
     L-amino acids

<400> SEQUENCE: 267

Met Ala Pro Leu Ala Leu His Leu Leu Val Leu Val Pro Ile Leu Leu
  1               5                  10                  15

Ser Leu Val Ala Ser Gln Asp Trp Lys Ala Glu Arg Ser Gln Asp Pro
             20                  25                  30

Phe Glu Lys Cys Met Gln Asp Pro Asp Tyr Glu Gln Leu Leu Lys Val
         35                  40                  45

Thr Ile Leu Glu Ala Asp Asn Arg Ile Gly Gly Arg Ile Phe Thr Tyr
     50                  55                  60

Arg Asp Gln Xaa Thr Gly Trp Ile Gly Glu Leu Gly Ala Met Arg Met
 65                  70                  75                  80

Pro Ser Ser His Arg Ile Leu His Lys Leu Cys Gln Gly Leu Gly Leu
                 85                  90                  95

Asn Leu Thr Lys Phe Thr Gln Tyr Asp Lys Asn Thr Trp Thr Glu Val
            100                 105                 110

His Glu Xaa Lys Leu Arg Asn Tyr Val Val Glu Lys Val Pro Glu Lys
        115                 120                 125

Leu Gly Tyr Ala Leu Arg Pro Gln Glu Lys Gly His Ser Pro Glu Asp
    130                 135                 140

Ile Tyr Gln Met Ala Leu Asn Gln Ala Leu Lys Asp Leu Lys Ala Leu
145                 150                 155                 160

Gly Cys Arg Lys Ala Met Lys Lys Phe Glu Arg His Thr Leu Leu Glu
                165                 170                 175

Tyr Leu Leu Gly Glu Gly Asn Leu Ser Arg Pro Ala Val Gln Leu Leu
            180                 185                 190

Gly Asp Val Met Ser Glu Asp Gly Phe Phe Tyr Leu Ser Phe Ala Glu
        195                 200                 205

Ala Leu Arg Ala Xaa Ser Cys Leu Ser Asp Arg Leu Gln Tyr Ser Arg
    210                 215                 220

Ile Val Gly Gly Trp Asp Leu Leu Pro Arg Ala Leu Leu Ser Ser Leu
225                 230                 235                 240

Ser Gly Leu Val Leu Leu Asn Ala Pro Val Val Ala Met Thr Gln Gly
                245                 250                 255

Pro His Asp Val His Val Gln Ile Glu Thr Ser Pro Pro Ala Arg Asn
            260                 265                 270

Leu Lys Val Leu Lys Ala Asp Val Val Leu Leu Thr Ala Ser Gly Pro
        275                 280                 285

Ala Val Lys Arg Ile Thr Phe Ser Pro Arg Cys Pro Ala Thr Cys Arg
    290                 295                 300

Arg Arg Cys Gly Gly Cys Thr Thr Cys Arg Pro Pro Arg Cys Ser
305                 310                 315
```